US012479827B2

(12) United States Patent
Eckhardt et al.

(10) Patent No.: US 12,479,827 B2
(45) Date of Patent: Nov. 25, 2025

(54) HETEROAROMATIC CARBOXAMIDE DERIVATIVES AS PLASMA KALLIKREIN INHIBITORS

(71) Applicant: Boehringer Ingelheim International GmbH, Ingelheim am Rhein (DE)

(72) Inventors: Matthias Eckhardt, Biberach an der Riss (DE); Maude Giroud, Basel (CH); Elke Langkopf, Biberach an der Riss (DE); Camilla Mayer, Warthausen (DE); Holger Wagner, Mettenberg (DE); Dieter Wiedenmayer, Bieberach an der Riss (DE)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 0 days.

(21) Appl. No.: 18/455,865

(22) Filed: Aug. 25, 2023

(65) Prior Publication Data

US 2024/0002363 A1 Jan. 4, 2024

Related U.S. Application Data

(63) Continuation of application No. 17/173,213, filed on Feb. 11, 2021, now Pat. No. 11,760,745.

(30) Foreign Application Priority Data

Feb. 13, 2020 (EP) .................................... 20157259

(51) Int. Cl.

| | |
|---|---|
| ***C07D 401/14*** | (2006.01) |
| ***A61K 31/4439*** | (2006.01) |
| ***A61K 31/501*** | (2006.01) |
| ***A61K 31/506*** | (2006.01) |
| ***A61K 31/519*** | (2006.01) |
| ***A61K 45/06*** | (2006.01) |
| ***C07D 235/02*** | (2006.01) |
| ***C07D 403/14*** | (2006.01) |
| ***C07D 405/14*** | (2006.01) |
| ***C07D 409/14*** | (2006.01) |
| ***C07D 413/14*** | (2006.01) |
| ***C07D 487/04*** | (2006.01) |

(52) U.S. Cl.

CPC ........ *C07D 401/14* (2013.01); *A61K 31/4439* (2013.01); *A61K 31/501* (2013.01); *A61K 31/506* (2013.01); *A61K 31/519* (2013.01); *A61K 45/06* (2013.01); *C07D 235/02* (2013.01); *C07D 403/14* (2013.01); *C07D 405/14* (2013.01); *C07D 409/14* (2013.01); *C07D 413/14* (2013.01); *C07D 487/04* (2013.01)

(58) Field of Classification Search

CPC .................................................... C07D 401/14

See application file for complete search history.

(56) References Cited

U.S. PATENT DOCUMENTS

| | | | |
|---|---|---|---|
| 10,399,961 | B2 | 9/2019 | Frattini et al. |
| 10,501,440 | B2 | 12/2019 | Frattini et al. |
| 10,640,486 | B2 | 5/2020 | Frattini et al. |
| 10,695,334 | B2 | 6/2020 | Eckhardt et al. |
| 11,760,745 | B2 | 9/2023 | Eckhardt et al. |
| 2004/0002424 | A1 | 1/2004 | Minn et al. |
| 2005/0090529 | A1 | 4/2005 | McAlpine et al. |
| 2020/0054617 | A1 | 2/2020 | Eckhardt et al. |
| 2021/0276976 | A1 | 9/2021 | Eckhardt et al. |
| 2021/0292301 | A1 | 9/2021 | Eckhardt et al. |

FOREIGN PATENT DOCUMENTS

| | | | |
|---|---|---|---|
| CN | 1636001 | A | 7/2005 |
| CN | 107973809 | A | 5/2018 |
| DE | 10230012 | A1 | 1/2004 |
| JP | 2005089362 | A | 4/2005 |
| JP | 6828191 | B2 | 2/2021 |
| JP | 2022543494 | A | 10/2022 |
| JP | 2022548696 | A | 11/2022 |
| WO | 2002064545 | A1 | 8/2002 |
| WO | 2009097141 | A1 | 8/2009 |
| WO | 2011100401 | A1 | 8/2011 |

(Continued)

OTHER PUBLICATIONS

Biagetti, Synthesis and structure-activity relationship of N-(3-azabicyclo[3.1.0]hex-6-ylmethyl)-5-(2-pyridinyl)-1,3-thiazol-2-amines derivatives as NPY Y5 antagonists, Bioorganic & Medicinal Chem Letters, 2010, vol. 20, p. 4741-4744.

(Continued)

*Primary Examiner* — Brian E McDowell
(74) *Attorney, Agent, or Firm* — Shelley A. Jones

(57) ABSTRACT

Disclosed are heteroaromatic carboxamides of formula (I), (I)

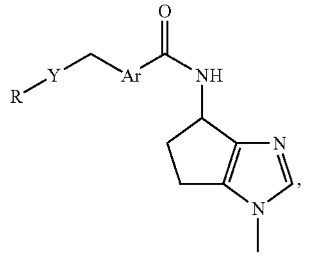

wherein Y, R, and Ar are as defined herein, and pharmaceutically acceptable salts thereof. Also disclosed are the use of the compounds of formula (i) for the treatment of diseases which can be influenced by the inhibition of plasma kallikrein.

21 Claims, No Drawings

(56) References Cited

FOREIGN PATENT DOCUMENTS

| | | | |
|---|---|---|---|
| WO | 2013111107 | A1 | 8/2013 |
| WO | 2013111108 | A1 | 8/2013 |
| WO | 2014108679 | A1 | 7/2014 |
| WO | 2014188211 | A1 | 11/2014 |
| WO | 2017001926 | A2 | 1/2017 |
| WO | 2017072020 | A1 | 5/2017 |
| WO | 2017072021 | A1 | 5/2017 |
| WO | 2017207983 | A1 | 12/2017 |
| WO | 2018011628 | A1 | 1/2018 |
| WO | 2018192866 | A1 | 10/2018 |
| WO | 2018213632 | A1 | 11/2018 |
| WO | 2020035540 | A1 | 2/2020 |
| WO | 2021055621 | A1 | 3/2021 |
| WO | 2021160718 | A1 | 8/2021 |

OTHER PUBLICATIONS

Database Pub Chem, NCBI, No. 8248531, 2014, 1 page.
Feener et al., "Plasma Kallikrein and Diabetic Macular Edema", Curr. Diab. Rep., 2010, p. 270-275.
Hashiguchi, Asymmetric Transfer Hrydogenation of Aromatic Ketones Catalyzed by Chiral Ruthenium (II) Complexes, J. Am. Chem. Soc, 1995, vol. 117, p. 7562-7563.
International Search Report and Written Opinion for PCT/EP2018059633 mailed Jul. 6, 2018.
International Search Report and Written Opinion for PCT/EP2019/071855 mailed Sep. 1, 2019.
International Search Report and Written Opinion for PCTEP2021/053286 mailed May 18, 2021.
International Search Report for PCT/EP2016/075221 mailed Jan. 18, 2017.
International Search Report for PCT/EP2016/075222 mailed Oct. 25, 2016.
International Search Report for PCT/EP2019/077082 mailed Nov. 13, 2019.
Jagtap, "Heck Reaction-State of the Art", Catalysts, 2017, pp. 1-53.
Kim et al., "Asymmetric Reductions involving Borohydrides", Organic Process Research and Development, 2006, vol. 10, p. 949-958.
Li, Enantioselective, Organocataltyic Reduction of Ketones using Bifunctional Thiorea-Amine Catalysts, Organic Letters, 2010, vol. 12, p. 1756-1759.
Mormino et al., "Copper-Mediated Perfluoroalkylation of Heteroaryl Bromides with (phen)CuRf", Organic Letters, 2014, vol. 16, No. 6, pp. 1744-1747.
Nakamura, Recent Developments in asymmetric reduction of ketones with biocatalysts, Tetrahedron: Asymmetry, 2003, vol. 14, p. 2659-2681.
PubChem Substance Record SID 299284535; (2016) 5 pgs.
PubChem Substance Record SID 299284560; (2016) 5 pgs.
Written Opinion for PCT/EP2016/075221 mailed Jan. 18, 2017.
Written Opinion for PCT/EP2016/075222 mailed Oct. 26, 2016.
Written Opinion for PCT/EP2019/077082 mailed Nov. 15, 2019.
Yoshimura, Recent topics in catalytic asymmetric hydrogenation of ketones, Tetrahedron Letters, 2014, vol. 55, p. 3635-3640.
Lee et al., "Advances in drug therapy and delivery for cataract treatment", Curr Opin Ophthalmol, Jan. 1, 2023, 34(1):3-8, doi: 10.1097/ICU.0000000000000910. Epub Nov. 14, 2022. PMID: 36484206.
Thrimawithana et al., "Drug delivery to the lens for the management of cataracts", Adv Drug Deliv Rev, Feb. 15, 2018, 126:185-194, doi: 10.1016/j.addr.2018.03.009. Epub Mar. 28, 2018. PMID: 29604375.
CAS Registry No. 1550999-77-3, dated Feb. 20, 2014, 1 page.
CAS Registry No. 1417724-21-0, dated Jan. 29, 2103, 1 page.
Abdel-Magid et al., "Plasma Kallikrein Inhibitors as Potential Treatment for Diabetic Macular Edema, Retinal Vein Occlusion, Hereditary Angioedema and other Related Diseases", Medicinal Chem. Letters, vol. 14, 2023, p. 129-130.

HETEROAROMATIC CARBOXAMIDE DERIVATIVES AS PLASMA KALLIKREIN INHIBITORS

RELATED APPLICATIONS

This application is a continuation of U.S. patent application Ser. No. 17/173,213, filed Feb. 11, 2021, which is hereby incorporated by reference in its entirety and which claims the benefit of priority to European Patent Application No. 20 157 259.1, filed Feb. 13, 2020.

FIELD OF THE INVENTION

This invention relates to novel heteroaromatic carboxamide derivatives, and pharmaceutically acceptable salts thereof, that are plasma kallikrein inhibitors. In addition, the invention relates to intermediates of the synthesis of said compounds, to pharmaceutical compositions and combinations comprising said compounds and to their use in methods for the treatment of diseases which can be influenced by the inhibition of plasma kallikrein. Particularly, the pharmaceutical compositions of the invention are suitable for the prophylaxis and/or therapy of diabetic complications, ocular diseases and edema-associated diseases, in particular diabetic macular edema, age-related macular degeneration, choroidal neovascularization, hereditary angioedema, and brain edema after stroke.

BACKGROUND OF THE INVENTION

Plasma kallikrein (PKK) is a trypsin-like serine protease secreted by hepatocytes in the liver as an inactive plasma prekallikrein that circulates in plasma either as a free zymogen or as a heterodimer complex bound to high molecular weight kininogen which is activated to give the active PKK that can liberate kinins from kininogens in addition to processing other substrates. Kinins are potent mediators of inflammation that act through G protein-coupled receptors such as bradykinin receptors.

PKK is thought to play a role in a number of inflammatory disorders and may have numerous implications in disorders such as hereditary angioedema (HAE), retinopathy or diabetic retinopathy, proliferative and non-proliferative retinopathy, diabetic macular edema (DME), clinically significant macular edema (CSME), cystoid macular edema (CME), CME following cataract extraction, CME induced by cryotherapy, CME induced by uveitis, endophthalmitis, CME following vascular occlusion (e.g. central retina vein occlusion, branch retinal vein occlusion, or hemiretinal vein occlusion), retinal edema, complications related to cataract surgery in diabetic retinopathy, hypertensive retinopathy, retinal trauma, dry and wet age-related macular degeneration (AMD), polypoidal choroidal vasculopathy (PCV), choroidal neovascularization (CNV; e.g. non-exudative choroidal neovascularization), posterior vitreous detachment (PVD), ischemic reperfusion injuries, e.g. in all kind of contexts associated with tissue and/or organ transplantation, surgically-induced brain injury, focal cerebral ischemia, global cerebral ischemia, glioma-associated edema, spinal cord injury, pain, ischemia, focal brain ischemia, neurological and cognitive deficits, deep vein thrombosis, stroke (including edema in the central nervous system after stroke), myocardial infarction, acquired angioedema, drug-related edema (including ACE-inhibitor induced edema as well as tissue plasminogen activator (tPA)-induced angioedemas), high altitude cerebral edema, cytotoxic cerebral edema, osmotic cerebral edema, obstructive hydrocephalus, radiation induced edema, lymph edema, traumatic brain injury, hemorrhagic stroke (e.g., cerebral stroke or subarachnoid stroke), intracerebral hemorrhage, hemorrhagic transformation of ischemic stroke, cerebral trauma associated with injury or surgery, brain aneurysm, arterio-venous malformation, reduction of blood losses during surgical procedures (e.g. cardiothoracic surgery, such as cardiopulmonary bypass or coronary artery bypass grafting), itch, disorders with an inflammation component (such as multiple sclerosis), epilepsy, encephalitis, Alzheimer's disease, excessive daytime sleepiness, essential hypertension, increased blood pressure associated with diabetes or hyperlipidemia, renal insufficiency, chronic kidney disease, heart failure, microalbuminuria, albuminuria, proteinuria, disorders associated with increased vascular permeability (e.g. increased retinal vascular permeability, increased leg, feet, ankle vascular permeability), cerebral hemorrhage, blood coagulation disorders such as thrombosis, deep vein thrombosis, coagulation from post fibrinolytic treatments, angina, angioedema, sepsis, arthritis (e.g. rheumatoid arthritis, osteoarthritis, infection arthritis), lupus, gout, psoriasis, inflammatory bowel diseases (IBDs, such as ulcerative colitis (UC) and Crohn's disease (CD)), diabetes, diabetic complications, complications arising from metabolic syndrome, infectious diseases, astrocyte-activation related diseases (e.g. Alzheimer's disease or multiple sclerosis), Parkinson's disease, amyotrophic lateral sclerosis, Creutzfeld-Jacob disease, stroke, epilepsy and trauma (e.g. brain trauma), allergic edema e.g. airflow obstruction in chronic allergic sinusitis or perennial rhinitis; airflow obstruction in acute asthma; serositis associated with systemic lupus erythematosus (SLE), acute respiratory distress syndrome (ARDS), coronavirus disease 2019 (COVID-19) related pneumonia, fibrotic disease, hepatic fibrosis, nonalcoholic steatohepatitis (NASH), renal injury, and other diseases. PKK is also thought to play an important role in hypersensitivity reactions and thrombosis during hemodialysis.

PKK inhibitors, like the compounds of the present invention, are considered to be useful in the treatment of a wide range of disorders, e.g. as mentioned hereinbefore; in particular, they should have utility as a treatment to reduce retinal vascular permeability associated with diabetic retinopathy and diabetic macular edema or edema-associated diseases.

PKK inhibitors should be particularly useful in the treatment of edema formation in diseases, e.g. edema formation related to ischemic reperfusion injuries, retinopathy or edema-associated diseases, such as hereditary angioedema, macular edema and brain edema. PKK inhibitors are considered to be especially useful in the treatment of retinopathy, e.g. retinopathy associated with diabetes and/or hypertension, and in the treatment of macular edema, e.g. macular edema associated with diabetes and/or hypertension.

Other complications of diabetes such as cerebral hemorrhage, nephropathy, cardiomyopathy and neuropathy, all of which have associations with PKK, may also be considered as targets for a PKK inhibitor.

PKK inhibitors suitable for therapeutic and/or prophylactic use should bind potently and with high selectivity to PKK. They should be well absorbed from the gastrointestinal tract, be sufficiently metabolically stable and possess favorable pharmacokinetic properties. They should be non-toxic and demonstrate few side-effects.

Low molecular weight PKK inhibitors are known in the art, for example, the compounds disclosed in WO 2009/

097141, WO 2013/111107, WO 2013/111108, WO 2014/188211, WO 2017/072020, WO 2017/072021, and WO 2018/192866.

SUMMARY OF THE INVENTION

In a first aspect, the present invention relates to a compound of formula (I)

(I)

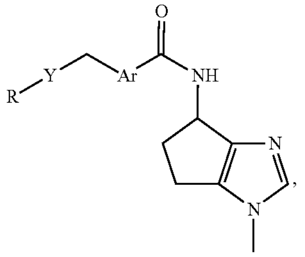

wherein

Y is selected from the group Y-G1 consisting of

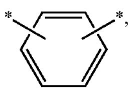
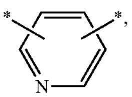
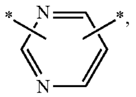
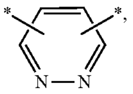
and
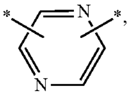

each of which is substituted with 1 or 2 independent substituents $R^1$;

R is selected from the group R-G1 consisting of saturated 6- to 12-membered bicyclic ring systems containing 1 to 2 N atoms as ring members and optionally 1 ring member selected from the group consisting of C═O, O, S, S═O and $SO_2$, provided that the ring systems do not contain any heteroatom-heteroatom bonds between ring members, wherein said ring systems are attached via an N atom to the group Y in formula (I), and wherein said ring systems are optionally substituted with 1 to 6 F and optionally substituted with 1 to 3 substituents selected from the group consisting of $C_{1-3}$-alkyl, CN, HO—$C_{1-3}$-alkylene, OH, and $C_{1-3}$-alkyl-O;

Ar is selected from the group Ar-G1 consisting of 5-membered heteroaryls, containing 1 to 4 N atoms or containing 1 O or S atom or containing 1 to 2 N atoms and 1 O or S atom, and 9-membered heteroaryls, consisting of a 5-membered ring fused to a 6-membered ring and containing 1 to 4 N atoms, wherein said heteroaryls are attached to the carbonyl group in formula (I) via a C atom of the 5-membered ring and to the $CH_2$ group in formula (I) via a non-adjacent C or N atom of the 5-membered ring, and wherein said heteroaryls are optionally substituted with 1 substituent $R^3$;

$R^1$ is selected from the group $R^1$-G1 consisting of

H, halogen, $C_{1-4}$-alkyl optionally substituted with 1 to 5 F, $C_{3-4}$-cycloalkyl optionally substituted with 1 $CH_3$, CN or OH group, CN, O—$C_{1-3}$-alkyl optionally substituted with 1 to 5 F, $C_{1-3}$-alkyl optionally substituted with 1 substituent selected from the group consisting of CN, OH, and O—$C_{1-3}$-alkyl;

$R^3$ is selected from the group $R^3$-G1 consisting of

F, Cl, Br, CN, $C_{1-4}$-alkyl optionally substituted with 1 to 5 F, $C_{3-4}$-cycloalkyl, HO—$C_{1-4}$-alkylene, $C_{1-3}$-alkyl-O—$C_{1-3}$-alkylene, and O—$C_{1-4}$-alkyl optionally substituted with 1 to 5 F;

wherein in any definition mentioned hereinbefore and if not specified otherwise, any alkyl or alkylene group or sub-group may be straight-chained or branched, the isoforms, tautomers, stereoisomers, metabolites, prodrugs, solvates, hydrates, cocrystals and the salts thereof, particularly the pharmaceutically acceptable cocrystals and salts thereof, or the combinations thereof.

In a second aspect, the present invention relates to a pharmaceutical composition comprising one or more compounds of formula (I), as defined hereinbefore or hereinafter, and/or their tautomers or pharmaceutically acceptable salts thereof, optionally together with one or more inert carriers and/or diluents.

In a third aspect, the present invention relates to a pharmaceutical composition comprising one or more compounds of formula (I), as defined hereinbefore or hereinafter, and/or their tautomers or pharmaceutically acceptable salts thereof, and one or more additional therapeutic agents, optionally together with one or more inert carriers and/or diluents.

In a fourth aspect, the present invention relates to a compound of formula (I), as defined hereinbefore or hereinafter, and/or its tautomers or a pharmaceutically acceptable salt thereof for use as a medicament.

In a fifth aspect, the present invention relates to a method for the treatment, i.e. therapy and/or prevention, of diseases or conditions which can be influenced by the inhibition of plasma kallikrein in a patient in need thereof, the method comprising administering to the patient one or more compounds of formula (I), as defined hereinbefore or hereinafter, and/or their tautomers or pharmaceutically acceptable salts thereof.

In addition, the present invention relates to the use of one or more compounds of formula (I), as defined hereinbefore or hereinafter, and/or their tautomers or pharmaceutically acceptable salts thereof in the manufacture of a medicament for the treatment, i.e. therapy and/or prevention, of diseases or conditions which can be influenced by the inhibition of plasma kallikrein.

Furthermore, the present invention relates to a compound of formula (I), as defined hereinbefore or hereinafter, and/or its tautomers or a pharmaceutically acceptable salt thereof for use in a method for the treatment, i.e. therapy and/or prevention, of diseases or conditions which can be influenced by the inhibition of plasma kallikrein, in a patient in need thereof.

In a sixth aspect, the present invention relates to one or more compounds selected from the group consisting of (XVI)

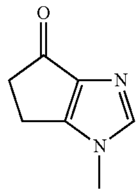

-continued (III)

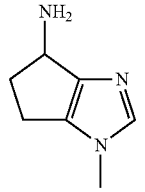

(III.1)

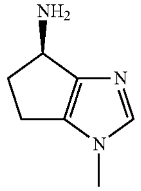

(III.2)

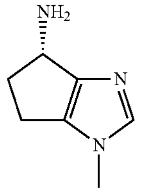

or a salt thereof, which are valuable intermediates in the synthesis of compounds of formula (I).

Further aspects of the present invention will become apparent to the person skilled in the art directly from the foregoing and following description and the examples.

General Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of formula (I) according to the present invention including their tautomers, stereoisomers and mixtures thereof and the salts thereof, in particular the pharmaceutically acceptable salts thereof, and the solvates, hydrates and cocrystals of such compounds, in particular the pharmaceutically acceptable cocrystals thereof, including the solvates, hydrates and cocrystals of such tautomers, stereoisomers and salts thereof.

Also, unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof, and solvates thereof, such as for instance hydrates, including solvates of the free compounds or solvates of a salt of the compound, and cocrystals thereof, including pharmaceutically acceptable cocrystals thereof and cocrystals of the free compounds or of a salt thereof.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include salts from benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartaric acid.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, EtOAc, EtOH, isopropanol, or MeCN, or a mixture thereof.

Salts of other acids than those mentioned above which for example are useful for purifying or isolating the compounds of the present invention (e.g. trifluoro acetate salts) also comprise a part of the invention.

As used herein, "pharmaceutically acceptable cocrystals" refer to derivatives of the disclosed compounds wherein the parent compound is modified by making a cocrystal thereof with the help of one or more coformers. Also, cocrystals of solvates and/or salts of the disclosed compounds are encompassed.

For example, coformers include hydrogen bond donors, such as carboxylic acids, and hydrogen bond acceptors, such as amines and amides.

The pharmaceutically acceptable cocrystals of the present invention can be synthesized from the parent compound by methods known to the one skilled in the art, including solid-based methods, such as solid state grinding, melt extrusion and melt crystallization, and liquid-based methods, such as solution crystallization, solvent evaporation, cooling crystallization, supercritical fluid assisted crystallization, ultrasound assisted crystallization, spray drying, liquid assisted grinding and planetary milling.

In case a compound of the present invention is depicted in form of a chemical name and as a formula, in case of any discrepancy the formula shall prevail.

In the groups, radicals, or moieties defined below, the number of carbon atoms is often specified preceding the group, for example, $C_{1-6}$-alkyl means an alkyl group or radical having 1 to 6 carbon atoms.

An asterisk may be used in sub-formulas to indicate the bond which is connected to the core molecule as defined. In the case of more than one attachment point, i.e. more than one asterisk, in a sub-formula, the asterisks may be further specified by a bracketed designation of the connected part of the core molecule.

The numeration of the atoms of a substituent starts with the atom which is closest to the core or to the group to which the substituent is attached.

For example, the term "3-carboxypropyl-group" represents the following substituent:

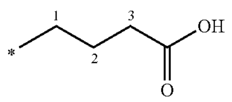

wherein the carboxy group is attached to the third carbon atom of the propyl group. The terms "1-methylpropyl-", "2,2-dimethylpropyl-" or "cyclopropylmethyl-" group represent the following groups:

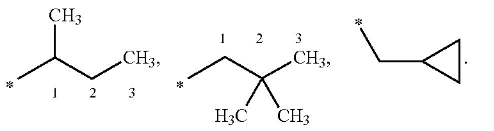

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In a definition of a group, the term "wherein each X, Y and Z group is optionally substituted with" and the like denotes that each group X, each group Y and each group Z either each as a separate group or each as part of a composed group may be substituted as defined. For example a definition "Rex denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$." or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

The term "$C_{1-n}$-alkyl", wherein n is an integer from 1 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{1-n}$-alkylene" wherein n is an integer selected from 2, 3, 4, 5 or 6, preferably 4 or 6, either alone or in combination with another radical, denotes an acyclic, straight or branched chain divalent alkyl radical containing from 1 to n carbon atoms. For example the term $C_{1-4}$-alkylene includes —$CH_2$—, —$CH_2$—$CH_2$—, —$CH(CH_3)$—, —$CH_2$—$CH_2$—$CH_2$—, —$C(CH_3)_2$—, —$CH(CH_2CH_3)$—, —$CH(CH_3)$—$CH_2$—, —$CH_2$—$CH(CH_3)$—, —$CH_2$—$CH_2$—$CH_2$—$CH_2$—, —$CH_2$—$CH_2$—$CH(CH_3)$—, —$CH(CH_3)$—$CH_2$—$CH_2$—, —$CH_2$—$CH(CH_3)$—$CH_2$—, —$CH_2$—$C(CH_3)_2$—, —$C(CH_3)_2$—$CH_2$—, —$CH(CH_3)$—$CH(CH_3)$—, —$CH_2$—$CH(CH_2CH_3)$—, —$CH(CH_2CH_3)$—$CH_2$—, —$CH(CH_2CH_2CH_3)$—, —$CH(CH(CH_3))_2$— and —$C(CH_3)(CH_2CH_3)$—.

The term "$C_{3-n}$-cycloalkyl", wherein n is an integer 3 to n, either alone or in combination with another radical denotes a cyclic, saturated, unbranched hydrocarbon radical with 3 to n C atoms. The cyclic group may be mono-, bi-, tri- or spirocyclic, most preferably monocyclic. Examples of such cycloalkyl groups include cyclopropyl, cyclobutyl, cyclo-pentyl, cyclohexyl, cycloheptyl, cyclooctyl, cyclo-nonyl, cyclododecyl, bicyclo[3.2.1.]octyl, spiro[4.5]decyl, norpinyl, norbonyl, norcaryl, adamantyl, etc.

The term "heteroaryl" means a mono- or polycyclic aromatic ring system containing one or more heteroatoms selected from N, O or $S(O)_r$, wherein r=0, 1 or 2, consisting of 5 to 14 ring atoms wherein at least one of the heteroatoms is part of an aromatic ring. The term "heteroaryl" is intended to include all the possible isomeric forms.

Thus, the term "heteroaryl" includes the following exemplary structures; they are not depicted as radicals as each form is optionally attached through a covalent bond to any atom so long as appropriate valences are maintained:

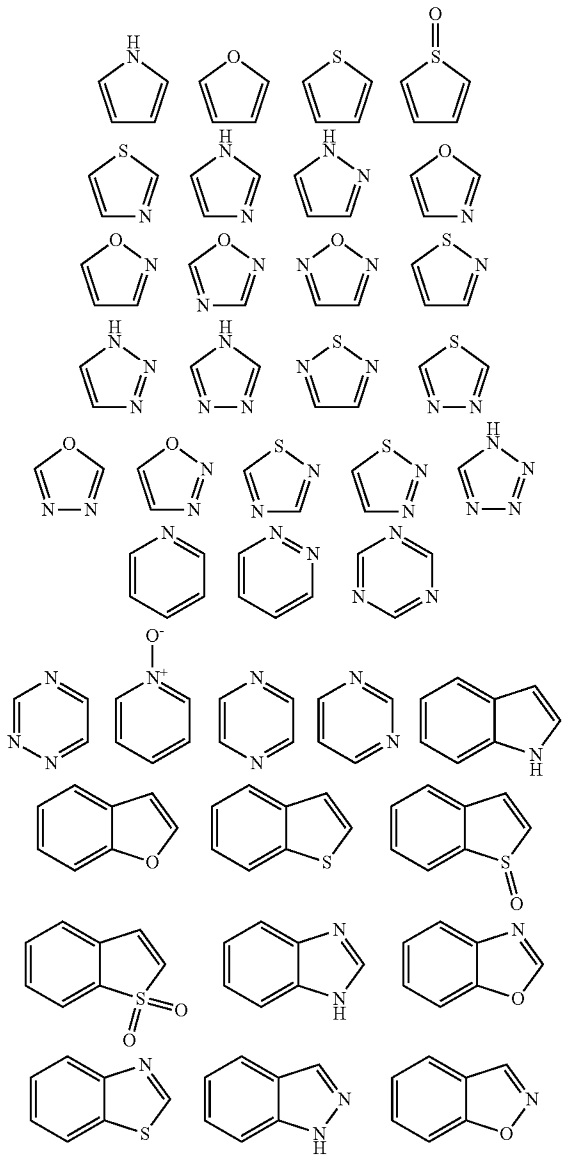

-continued

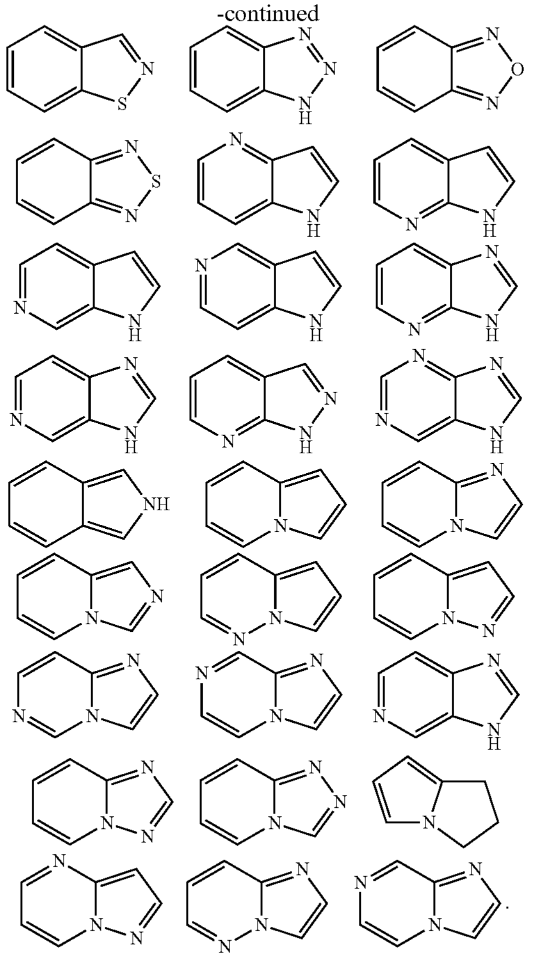

The term "bicyclic ring systems" means groups consisting of 2 joined cyclic substructures including spirocyclic, fused, and bridged ring systems.

The term halogen generally denotes fluorine, chlorine, bromine and iodine.

Many of the terms given above may be used repeatedly in the definition of a formula or group and in each case have one of the meanings given above, independently of one another.

The terms "treatment" and "treating" as used herein embrace both therapeutic, i.e. curative and/or palliative, and preventive, i.e. prophylactic, treatment.

Therapeutic treatment refers to the treatment of patients having already developed one or more of said conditions in manifest, acute or chronic form. Therapeutic treatment may be symptomatic treatment in order to relieve the symptoms of the specific indication or causal treatment in order to reverse or partially reverse the conditions of the indication or to stop or slow down progression of the disease.

Preventive treatment ("prevention") refers to the treatment of patients at risk of developing one or more of said conditions, prior to the clinical onset of the disease in order to reduce said risk.

The terms "treatment" and "treating" include the administration of one or more active compounds in order to prevent or delay the onset of the symptoms or complications and to prevent or delay the development of the disease, condition or disorder and/or in order to eliminate or control the disease, condition or disorder as well as to alleviate the symptoms or complications associated with the disease, condition or disorder.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

DETAILED DESCRIPTION OF THE INVENTION

The present invention discloses novel heteroaromatic carboxamide derivatives, which are effective plasma kallikrein (PKK) inhibitors and possess suitable pharmacological and pharmacokinetic properties to use them as medicaments for the treatment of diseases and/or conditions that may be influenced by PKK inhibition, including but not limited to diabetic complications, ocular diseases and edema-associated diseases, in particular diabetic macular edema, age-related macular degeneration, choroidal neovascularization, hereditary angioedema, and brain edema after stroke.

The compounds of the present invention may provide several advantages, such as enhanced potency, high metabolic and/or chemical stability, high selectivity, safety and tolerability, enhanced solubility, enhanced permeability, desirable plasma protein binding, enhanced bioavailability, improved pharmacokinetic profiles, and the possibility to form stable salts.

Compounds of the Invention

In a first aspect of the present invention, it is found that compounds of formula (I)

(I)

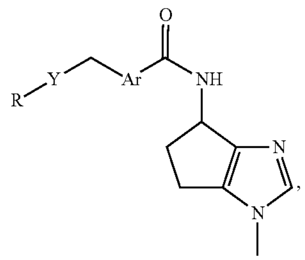

wherein Y, R, and Ar are defined as hereinbefore and hereinafter, are potent inhibitors of PKK and exhibit favorable properties with regard to selectivity, safety and tolerability, metabolic and/or chemical stability, pharmacokinetic and physicochemical characteristics, solubility, permeability, plasma protein binding, bioavailability and/or the possibility to form stable salts. In particular, they provide an advantageous combination of high potency on human PKK and significant selectivity, e.g. vs. various serine proteases, such as human tissue kallikrein 1 (TK1), as well as adequate solubilities at physiologically relevant pH values and high metabolic stabilities. In addition, advantageous safety features, such as low potential of mutagenicity, low inhibition of cytochrome P450 (CYP) enzymes like CYP3A4 and CYP2C8, and low propensity for mechanism based inhibition of CYP3A4, are exhibited.

Therefore, the compounds of formula (I), as defined hereinbefore or hereinafter, or pharmaceutically acceptable salts thereof are expected to be useful in the treatment of diseases and/or conditions that can be influenced by PKK inhibition.

Thus, according to one aspect of the present invention, a compound of formula (I)

(I)

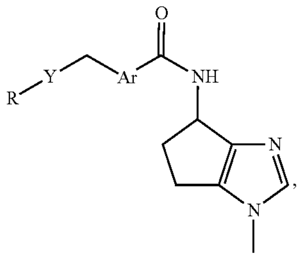

wherein Y, R, and Ar are defined as hereinbefore or hereinafter, is provided as well as the isoforms, tautomers, stereoisomers, metabolites, prodrugs, solvates, hydrates, cocrystals, and the salts thereof, particularly the pharmaceutically acceptable cocrystals and salts thereof.

Unless otherwise stated, the groups, residues and substituents, particularly Y, R, Ar, $R^1$, and $R^3$ are defined as hereinbefore and hereinafter. Some preferred meanings of the substituents Y, R, Ar, $R^1$, and $R^3$ as well as of the stereochemistry of the compounds of formula (I) will be given hereinafter as embodiments of the invention. Any and each of these definitions and embodiments may be combined with one another.

Y:

According to one embodiment, Y is selected from the group Y-G1 consisting of

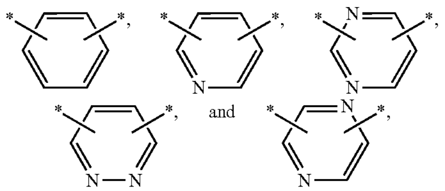

and each of which is substituted with 1 or 2 independent substituents $R^1$.

According to another embodiment, Y is selected from the group Y-G2 consisting of

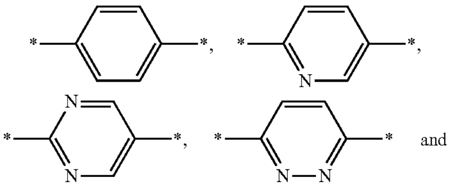

and

-continued

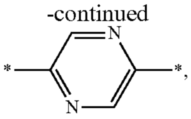

each of which is substituted with 1 or 2 independent substituents $R^1$ and wherein the bonds with asterisk indicate the sites of attachment of R and the $CH_2$ group of formula (I).

According to another embodiment, Y is selected from the group Y-G3 consisting of

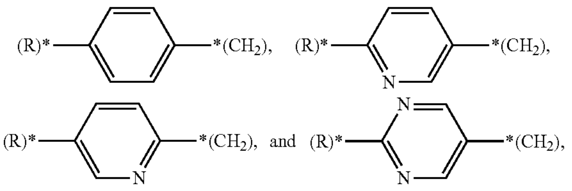

and each of which is substituted with 1 or 2 substituents $R^1$ and wherein the bonds with asterisk and parentheses indicate the sites of attachment of R and the $CH_2$ group of formula (I).

According to another embodiment, Y is selected from the group Y-G4 consisting of

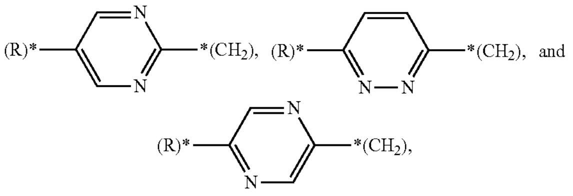

and each of which is substituted with 1 substituent $R^1$ and wherein the bonds with asterisk and parentheses indicate the sites of attachment of R and the $CH_2$ group of formula (I).

According to another embodiment, Y is selected from the group Y-G5 consisting of

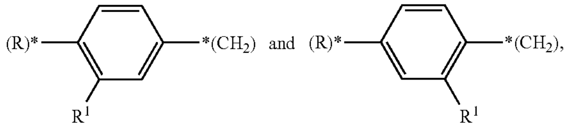

and each of which is optionally substituted with 1 additional substituent $R^1$ and wherein the bonds with asterisk and parentheses indicate the sites of attachment of R and the $CH_2$ group of formula (I).

According to another embodiment, Y is selected from the group Y-G6 consisting of

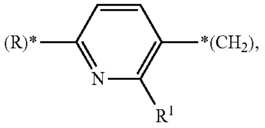

which is optionally substituted with one additional substituent $R^1$ and wherein the bonds with asterisk and parentheses indicate the sites of attachment of R and the $CH_2$ group of formula (I).

According to another embodiment, Y is selected from the group Y-G7 consisting of

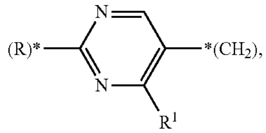

wherein the bonds with asterisk and parentheses indicate the sites of attachment of R and the $CH_2$ group of formula (I).

R:

According to one embodiment, R is selected from the group R-G1 consisting of saturated 6- to 12-membered bicyclic ring systems containing 1 to 2 N atoms as ring members and optionally 1 ring member selected from the group consisting of C═O, O, S, S═O and $SO_2$, provided that the ring systems do not contain any heteroatom-heteroatom bonds between ring members, wherein said ring systems are attached via an N atom to the group Y in formula (I), and wherein said ring systems are optionally substituted with 1 to 6 F and optionally substituted with 1 to 3 substituents selected from the group consisting of $C_{1-3}$-alkyl, CN, HO—$C_{1-3}$-alkylene, OH, and $C_{1-3}$-alkyl-O.

According to another embodiment, R is selected from the group R-G2 consisting of saturated 6- to 10-membered bicyclic ring systems containing 1 N atom and optionally 1 O atom as ring members, wherein the ring systems are attached via the N atom to the group Y in formula (I), and wherein the ring systems are optionally substituted with 1 substituent selected from the group consisting of F, $C_{1-3}$-alkyl (preferably $CH_3$), CN, HO—$C_{1-3}$-alkylene (preferably $HOCH_2$), OH, and $C_{1-3}$-alkyl-O— (preferably $CH_3O$), and wherein the ring system is optionally additionally substituted with one substituent selected from the group consisting of F and $CH_3$.

According to another embodiment, R is selected from the group R-G3 consisting of 5-azaspiro[2.3]hexane, 2-azaspiro[3.3]heptane, 5-azaspiro[2.4]heptane, 6-azaspiro[3.4]octane, 3-azabicyclo[3.1.0]hexane, 3-azabicyclo[3.2.0]heptane, octahydrocyclopenta[c]pyrrole, 6-azaspiro[2.5]octane, 5-azaspiro[2.5]octane, 7-azaspiro[3.5]nonane, 3-azabicyclo[4.1.0]heptane, 3-azabicyclo[3.1.1]heptane, 6-oxa-3-azabicyclo[3.1.1]heptane, and 3-azabicyclo[3.2.1]octane, each of which is attached via the N atom to the group Y in formula (I) and each of which is optionally substituted with one substituent selected from the group consisting of F, $CH_3$, CN, $CH_2OH$, OH, and $OCH_3$, preferably consisting of F and $CH_3$, and each of which is optionally substituted with one additional substituent selected from the group consisting of F and $CH_3$.

According to another embodiment, R is selected from the group R-G4 consisting of

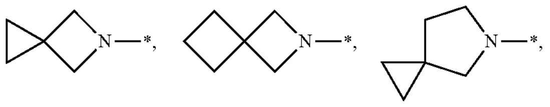

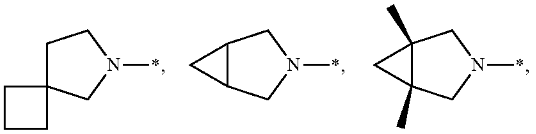

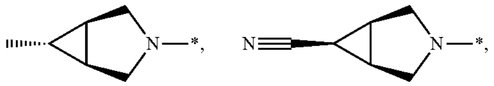

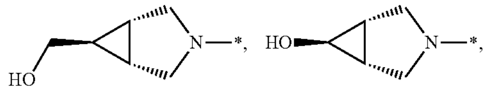

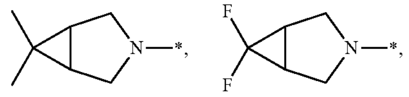

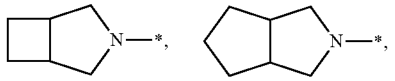

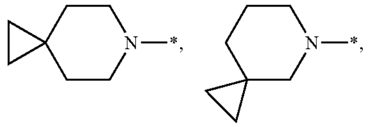

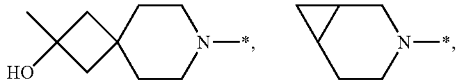

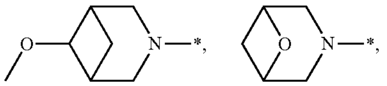

and

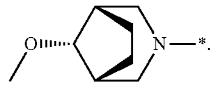

According to another embodiment, R is selected from the group R-G5 consisting of

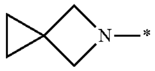

and

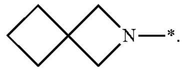

According to another embodiment, R is selected from the group R-G6 consisting of

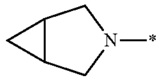

and

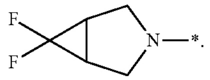

According to another embodiment, R is selected from the group R-G7 consisting of

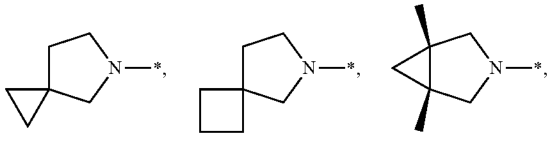

-continued

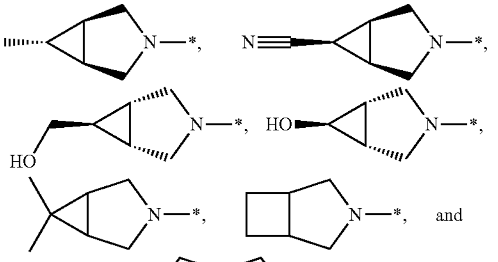

and

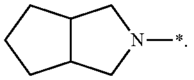

According to another embodiment, R is selected from the group R-G8 consisting of

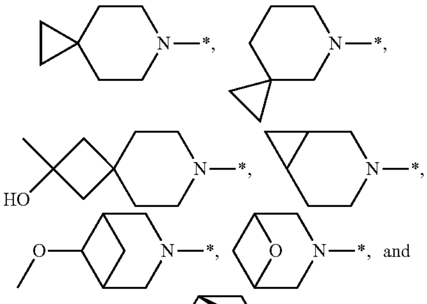

and

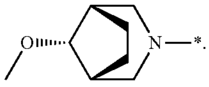

Ar:

According to one embodiment, Ar is selected from the group Ar-G1 consisting of 5-membered heteroaryls, containing 1 to 4 N atoms or containing 1 O or S atom or containing 1 to 2 N atoms and 1 O or S atom, and 9-membered heteroaryls, consisting of a 5-membered ring fused to a 6-membered ring and containing 1 to 4 N atoms, wherein said heteroaryls are attached to the carbonyl group in formula (I) via a C atom of the 5-membered ring and to the $CH_2$ group in formula (I) via a non-adjacent C or N atom of the 5-membered ring, and wherein said heteroaryls are optionally substituted with 1 substituent $R^3$.

According to another embodiment, Ar is selected from the group Ar-G2 consisting of 5-membered heteroaryls, containing 1 to 3 N atoms or containing 1 O or S atom or containing 1 N atom and 1 O or S atom, and 9-membered heteroaryls, consisting of a 5-membered ring fused to a 6-membered ring and containing 1 to 3 N atoms, wherein said heteroaryls are attached to the carbonyl group in formula (I) via a C atom of the 5-membered ring and to the $CH_2$ group in formula (I) via a non-adjacent C or N atom of the 5-membered ring, and wherein said heteroaryls are optionally substituted with 1 substituent $R^3$.

According to another embodiment, Ar is selected from the group Ar-G3 consisting of

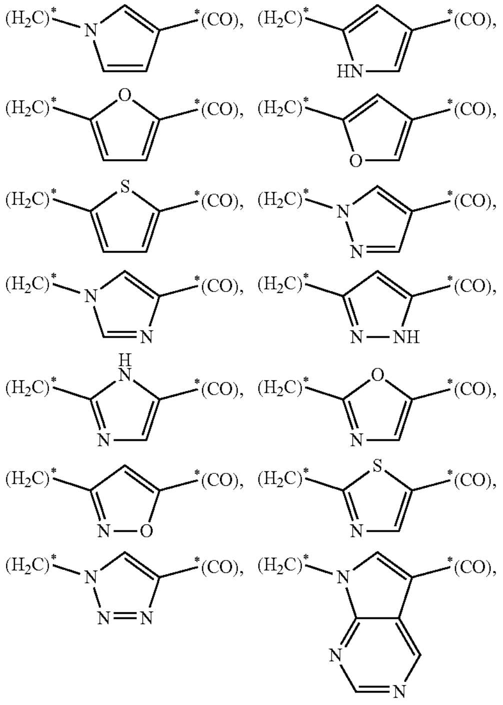

and the tautomers thereof, each of which is optionally substituted with 1 substituent $R^3$ and wherein the bonds with asterisk and parentheses indicate the sites of attachment of the groups C═O and $CH_2$ of formula (I).

According to another embodiment, Ar is selected from the group Ar-G4 consisting of

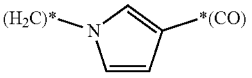

and

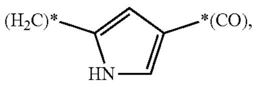

each of which is optionally substituted with 1 substituent $R^3$ and wherein the bonds with asterisk and parentheses indicate the sites of attachment of the groups C═O and $CH_2$ of formula (I).

According to another embodiment, Ar is selected from the group Ar-G5 consisting of

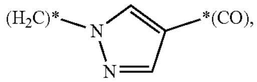

which is optionally substituted with 1 substituent $R^3$ and wherein the bonds with asterisk and parentheses indicate the sites of attachment of the groups C═O and $CH_2$ of formula (I).

According to another embodiment, Ar is selected from the group Ar-G6 consisting of

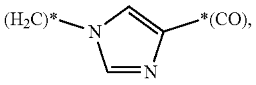

which is optionally substituted with 1 substituent $R^3$ and wherein the bonds with asterisk and parentheses indicate the sites of attachment of the groups C═O and $CH_2$ of formula (I).

According to another embodiment, Ar is selected from the group Ar-G7 consisting of

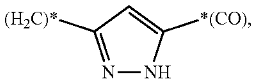

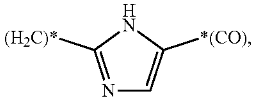

and the tautomers thereof, each of which is optionally substituted with 1 substituent $R^3$ and wherein the bonds with asterisk and parentheses indicate the sites of attachment of the groups C═O and $CH_2$ of formula (I).

According to another embodiment, Ar is selected from the group Ar-G8 consisting of

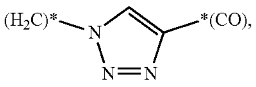

which is optionally substituted with 1 substituent $R^3$ and wherein the bonds with asterisk and parentheses indicate the sites of attachment of the groups C═O and $CH_2$ of formula (I).

According to another embodiment, Ar is selected from the group Ar-G9 consisting of

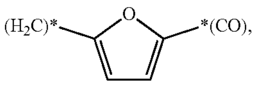 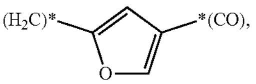 and

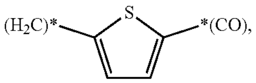

each of which is optionally substituted with 1 substituent $R^3$ and wherein the bonds with asterisk and parentheses indicate the sites of attachment of the groups C═O and $CH_2$ of formula (I).

According to another embodiment, Ar is selected from the group Ar-G10 consisting of

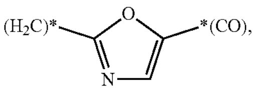 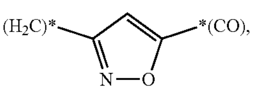 and

-continued

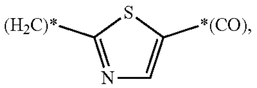

each of which is optionally substituted with 1 substituent $R^3$ and wherein the bonds with asterisk and parentheses indicate the sites of attachment of the groups C═O and $CH_2$ of formula (I).

According to another embodiment, Ar is selected from the group Ar-G11 consisting of

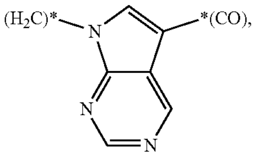

which is optionally substituted with 1 substituent $R^3$ and wherein the bonds with asterisk and parentheses indicate the sites of attachment of the groups C═O and $CH_2$ of formula (I).

$R^1$:

According to one embodiment, $R^1$ is selected from the group $R^1$-G1 consisting of H, halogen, $C_{1-4}$-alkyl optionally substituted with 1 to 5 F, $C_{3-4}$-cycloalkyl optionally substituted with 1 $CH_3$, CN or OH group, CN, O—$C_{1-3}$-alkyl optionally substituted with 1 to 5 F, $C_{1-3}$-alkyl optionally substituted with 1 substituent selected from the group consisting of CN, OH, and O—$C_{1-3}$-alkyl.

According to another embodiment, $R^1$ is selected from the group $R^1$-G2 consisting of H, F, C, Br, $C_{1-2}$-alkyl optionally substituted with 1 to 5 F or with 1 CN, OH or O—$C_{1-2}$-alkyl group, $C_{3-4}$-alkyl optionally substituted with 1 CN or OH group, $C_{3-4}$-cycloalkyl optionally substituted with 1 $CH_3$, CN or OH group, O—$C_{1-2}$-alkyl optionally substituted with 1 to 5 F.

According to another embodiment, $R^1$ is selected from the group $R^1$-G3 consisting of H, F, C, Br, $CH_3$, $CH_2CH_3$, $CH_2CH_2CH_3$, $CH_2CH(CH_3)_2$, cyclopropyl, cyclobutyl, $CHF_2$, $CF_3$, CN, 1-cyanocycloprop-1-yl, $CH_2CN$, $C(CH_3)_2CN$, $CH_2OH$, $CH_2CH_2OH$, $CH(OH)CH_3$, $CH_2CH_2CH_2OH$, $CH(CH_3)CH_2OH$, $C(OH)(CH_3)_2$, $CH_2OCH_3$, $CH_2OCH_2CH_3$, O—$CH_3$, O—$CH_2CH_3$, and O—$CF_3$.

According to another embodiment, $R^1$ is selected from the group $R^1$-G4 consisting of H, F, C, Br, $CH_3$, $CH_2CH_3$, $CHF_2$, CN, $CH_2OH$, and $CH_2OCH_3$.

According to another embodiment, $R^1$ is selected from the group $R^1$-G5 consisting of H.

According to another embodiment, $R^1$ is selected from the group $R^1$-G6 consisting of F, C, and Br.

According to another embodiment, $R^1$ is selected from the group $R^1$-G7 consisting of $CH_3$.

According to another embodiment, $R^1$ is selected from the group $R^1$-G8 consisting of $CH_2CH_3$.

According to another embodiment, $R^1$ is selected from the group $R^1$-G9 consisting of $CH_2CH_2CH_3$, $CH_2CH(CH_3)_2$, cyclopropyl, and cyclobutyl.

According to another embodiment, $R^1$ is selected from the group $R^1$-G10 consisting of $CHF_2$, and $CF_3$.

According to another embodiment, $R^1$ is selected from the group $R^1$-G11 consisting of CN.

According to another embodiment, $R^1$ is selected from the group $R^1$-G12 consisting of 1-cyanocycloprop-1-yl, $CH_2CN$, and $C(CH_3)_2CN$.

According to another embodiment, $R^1$ is selected from the group $R^1$-G13 consisting of $CH_2OH$.

According to another embodiment, $R^1$ is selected from the group $R^1$-G14 consisting of $CH_2CH_2OH$, $CH(OH)CH_3$, $CH_2CH_2CH_2OH$, $CH(CH_3)CH_2OH$, and $C(OH)(CH_3)_2$.

According to another embodiment, $R^1$ is selected from the group $R^1$-G15 consisting of $CH_2OCH_3$, $CH_2OCH_2CH_3$, O—$CH_3$, O—$CH_2CH_3$, and O—$CF_3$.

$R^3$:

According to one embodiment, $R^3$ is selected from the group $R^3$-G1 consisting of F, C, Br, CN, $C_{1-4}$-alkyl optionally substituted with 1 to 5 F, $C_{3-4}$-cycloalkyl, HO—$C_{1-4}$-alkylene, $C_{1-3}$-alkyl-O—$C_{1-3}$-alkylene, and O—$C_{1-4}$-alkyl optionally substituted with 1 to 5 F.

According to another embodiment, $R^3$ is selected from the group $R^3$-G2 consisting of F, Cl, Br, CN, $C_{1-3}$-alkyl optionally substituted with 1 to 3 F, HO—$C_{1-4}$-alkylene, $C_{1-2}$-alkyl-O—$C_{1-2}$-alkylene, and O—$C_{1-2}$-alkyl optionally substituted with 1 to 3 F.

According to another embodiment, $R^3$ is selected from the group $R^3$-G3 consisting of Cl, CN, $CH_3$, $CF_3$, $CH_2CH_3$, $CH(CH_3)_2$, $CH_2OH$, $CH_2CH_2OH$, $C(CH_3)_2OH$, and $CH_2OCH_3$.

According to another embodiment, $R^3$ is selected from the group $R^3$-G4 consisting of Cl and CN.

According to another embodiment, $R^3$ is selected from the group $R^3$-G5 consisting of $CH_3$, $CF_3$, $CH_2CH_3$, and $CH(CH_3)_2$.

According to another embodiment, $R^3$ is selected from the group $R^3$-G6 consisting of $CH_2OH$, $CH_2CH_2OH$, and $C(CH_3)_2OH$.

According to another embodiment, $R^3$ is selected from the group $R^3$-G7 consisting of $CH_2OCH_3$.

Stereochemistry:

According to one embodiment, the stereochemistry of the compound of formula (I) is according to formula (I.1)

(I.1)

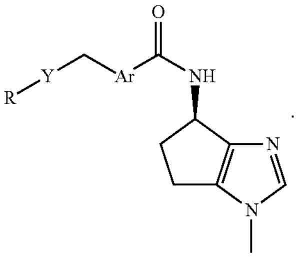

According to another embodiment, the stereochemistry of the compound of formula (I) is according to formula (I.2)

(I.2)

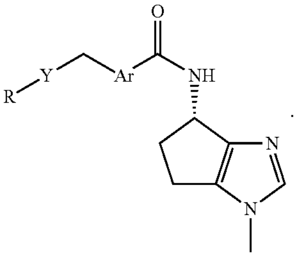

Further preferred subgeneric embodiments of the compounds of formula (I) are set forth as embodiments (I-a) to (I-r) in the following Table 1, wherein the above-mentioned substituent definitions are used. For example, the entry -G1 in column $R^1$ and row (I-a) means that in embodiment (I-a) substituent $R^1$ is selected from the definition designated $R^1$-G1. The same applies analogously to the other variables incorporated in the general formulas.

TABLE 1

| | Substituents | | | | |
|---|---|---|---|---|---|
| Embodiment | Y | R | Ar | $R^1$ | $R^3$ |
| (I-a) | Y-G1 | R-G1 | Ar-G1 | $R^1$-G1 | $R^3$-G1 |
| (I-b) | Y-G2 | R-G2 | Ar-G1 | $R^1$-G1 | $R^3$-G2 |
| (I-c) | Y-G2 | R-G2 | Ar-G2 | $R^1$-G2 | $R^3$-G2 |
| (I-d) | Y-G2 | R-G3 | Ar-G2 | $R^1$-G3 | $R^3$-G2 |
| (I-e) | Y-G2 | R-G4 | Ar-G3 | $R^1$-G3 | $R^3$-G3 |
| (I-f) | Y-G6 | R-G5 | Ar-G5 | $R^1$-G4 | $R^3$-G5 |
| (I-g) | Y-G6 | R-G5 | Ar-G6 | $R^1$-G4 | $R^3$-G5 |
| (I-h) | Y-G6 | R-G5 | Ar-G8 | $R^1$-G4 | $R^3$-G5 |
| (I-i) | Y-G6 | R-G6 | Ar-G5 | $R^1$-G4 | $R^3$-G5 |
| (I-j) | Y-G6 | R-G6 | Ar-G6 | $R^1$-G4 | $R^3$-G5 |
| (I-k) | Y-G6 | R-G6 | Ar-G8 | $R^1$-G4 | $R^3$-G5 |
| (I-m) | Y-G7 | R-G5 | Ar-G5 | $R^1$-G4 | $R^3$-G5 |
| (I-n) | Y-G7 | R-G5 | Ar-G6 | $R^1$-G4 | $R^3$-G5 |
| (I-o) | Y-G7 | R-G5 | Ar-G8 | $R^1$-G4 | $R^3$-G5 |
| (I-p) | Y-G7 | R-G6 | Ar-G5 | $R^1$-G4 | $R^3$-G5 |
| (I-q) | Y-G7 | R-G6 | Ar-G6 | $R^1$-G4 | $R^3$-G5 |
| (I-r) | Y-G7 | R-G6 | Ar-G8 | $R^1$-G4 | $R^3$-G5 |

Particularly preferred are those subgeneric embodiments (I.1-a) to (I.1-r) which, in respect of the definitions of Y, R, Ar, $R^1$, and $R^3$ correspond to the subgeneric embodiments (I-a) to (I-r) of Table 1, but wherein the stereochemistry of the compounds is according to formula (I.1).

According to another preferred embodiment, the stereochemistry of the compounds of the present invention is according to formula (I.1) wherein Ar is selected from the group Ar-G5.

According to another preferred embodiment, the stereochemistry of the compounds of the present invention is according to formula (I.1) wherein Ar is selected from the group Ar-G6.

According to another preferred embodiment, the stereochemistry of the compounds of the present invention is according to formula (I.1) wherein Ar is selected from the group Ar-G8.

Particularly preferred compounds, including their tautomers, the salts thereof, or any solvates, hydrates or cocrystals thereof, are those described in the section Examples and Experimental Data.

Preparation

The compounds according to the invention and their intermediates may be obtained using methods of synthesis which are known to the one skilled in the art and described in the literature of organic synthesis for example using methods described in "Comprehensive Organic Transformations", 2nd Edition, Richard C. Larock, John Wiley & Sons, 2010, and "March's Advanced Organic Chemistry", 7th Edition, Michael B. Smith, John Wiley & Sons, 2013. Preferably the compounds are obtained analogously to the methods of preparation explained more fully hereinafter, in particular as described in the experimental section. In some cases the sequence adopted in carrying out the reaction schemes may be varied. Variants of these reactions that are known to the skilled person but are not described in detail here may also be used. The general processes for preparing the compounds according to the invention will become apparent to the skilled person on studying the schemes that follow. Starting compounds are commercially available or may be prepared by methods that are described in the literature or herein, or may be prepared in an analogous or similar manner. Before the reaction is carried out, any corresponding functional groups in the starting compounds may be protected using conventional protecting groups. These protecting groups may be cleaved again at a suitable stage within the reaction sequence using methods familiar to the skilled person and described in the literature for example in "Protecting Groups", 3rd Edition, Philip J. Kocienski, Thieme, 2005, and "Protective Groups in Organic Synthesis", 4th Edition, Peter G. M. Wuts, Theodora W. Greene, John Wiley & Sons, 2006.

Scheme 1

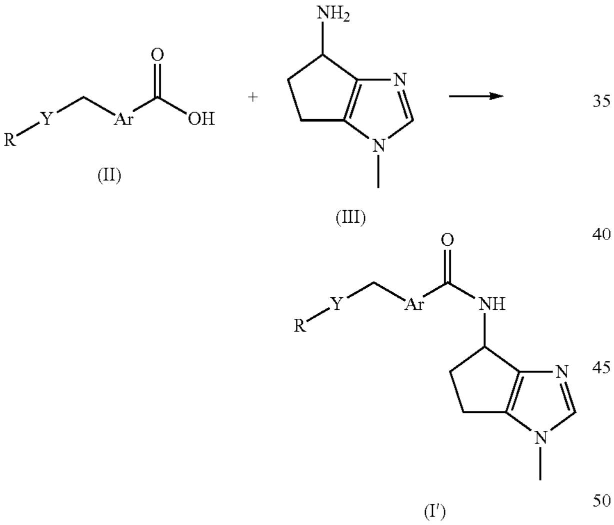

(II) (III) (I')

Scheme 1: Compounds of formula (I') can be prepared by reacting a suitable acid of formula (II) (either as free acid or carboxylate with a suitable metal cation such as $Li^+$, $Na^+$, $K^+$, etc.) and a suitable amine of formula (III) (either as free amine or a salt such as hydrochloride, hydrobromide, etc.) in a suitable solvent (e.g., DCM, THF, 1,4-dioxane, DMF, N,N-dimethylacetamide, and 1-methyl-2-pyrrolidinone) in the presence of a suitable coupling agent (e.g., O-(7-azabenzotriazol-1-yl)-N,N,N',N'-tetramethyluronium-hexafluorophosphate (HATU), O-(benzotriazol-1-yl)-N,N,N',N'-tetramethyluronium tetrafluoroborate (TBTU), (benzotriazol-1-yloxy)tripyrrolidinophosphonium hexafluorophosphate (PyBOP), carbodiimide reagents, etc.) and a base (e.g., triethylamine, N,N-diisopropyl-ethylamine, pyridine, etc.) to form an amide bond; Y, R, and Ar in Scheme 1 have the meanings as defined hereinbefore. Alternatively, the carboxylic acid is transformed into a carboxylic chloride (using, e.g., oxalyl chloride or thionyl chloride in DCM) and coupled as such with amine (III) in the presence of a suited base (e.g., triethylamine, N,N-diisopropyl-ethylamine, pyridine, etc.).

Scheme 2

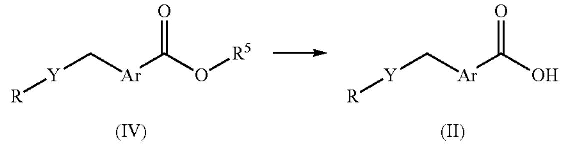

(IV) (II)

$R^5$ = $C_{1-4}$-alkyl or benzyl

Scheme 2: Acids of formula (II), wherein Y, R, and Ar have the meanings as defined hereinbefore, are preferably prepared from the corresponding ester (IV) through hydrolysis or hydrogenolysis depending on the nature of $R^5$. Lower alkyl group esters such as ethyl or methyl esters are preferably cleaved by hydrolysis with a hydroxide salt such as NaOH, LiOH, or KOH in a mixture of water and a suitable miscible solvent (e.g., THF, MeOH, EtOH, 1,4-dioxane, or mixtures of these) at ambient or elevated temperature. The acid may be isolated either as a salt with the metal cation or as free acid. A tert-butyl ester is preferably cleaved by treatment with an acid (e.g., hydrochloric acid or TFA) in a suitable solvent (e.g., DCM, 1,4-dioxane, MeOH, EtOH, THF, water, or mixtures of these). A benzyl ester is preferably cleaved by hydrogenolysis with a suitable catalyst (e.g., palladium on carbon) in a suitable solvent (e.g., EtOH, MeOH, THF, DCM, or EtOAc) under an atmosphere of hydrogen (preferably 1 to 5 bar).

Scheme 3

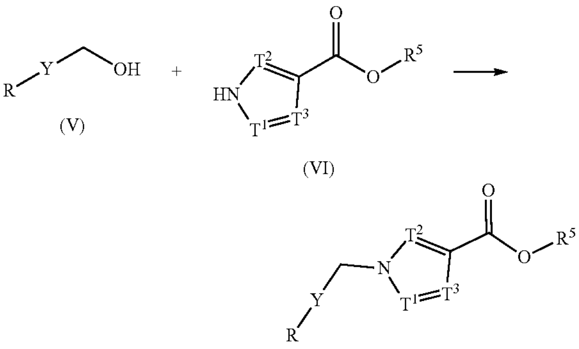

(V) (VI) (II')

$T^1$ and $T^2$ are independently of each other N, C—H, or C—$R^3$; or
$T^1$ and $T^2$ form together an annulated benzo, pyrido, or pyrimido ring, which is optionally monosubstituted with $R^3$;
$T^3$ = CH or N;
$R^5$ = $C_{1-4}$-alkyl or benzyl.

Scheme 3: Some of the compounds (II') can be prepared by reaction of an alcohol (V) with an ester (VI) employing the conditions of the Mitsunobu reaction (e.g., triphenylphosphine or tri-n-butylphosphine combined with, e.g., diethyl azodicarboxylate (DEAD), diisopropyl azodicarboxylate (DIAD), or di-tert-butyl azodicarboxylate (DBAD)

in a solvent such as THF, 1,4-dioxane, toluene, etc.); Y, R, and $R^3$ in Scheme 3 have the meanings as defined hereinbefore. Alcohol (V) may bear the desired residue R on the heteroaromatic ring Y or a leaving group instead to introduce R later on. Alternatively, some of the compounds (II') can be obtained by reacting alcohol (V) and ester (VI) in the presence of a Lewis acid or Brønsted acid (e.g., 4-toluenesulfonic acid) in a suited solvent (e.g., MeCN) at elevated temperature (20 to 120° C.).

Scheme 4

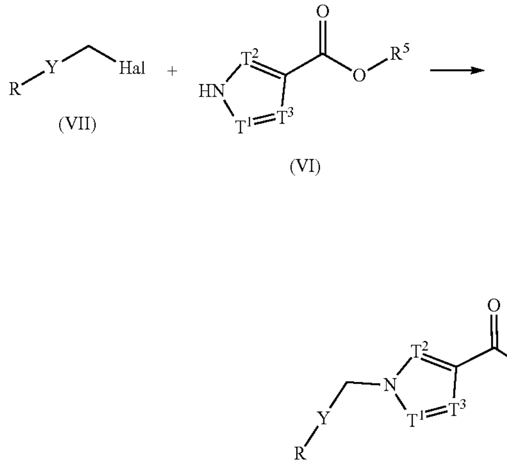

(VII) (VI) (II')

$T^1$ and $T^2$ are independently of each other N, C—H, or C—$R^3$; or $T^1$ and $T^2$ form together an annulated benzo, pyrido, or pyrimido ring, which is optionally monosubstituted with $R^3$;

$T^3$ = CH or N;

$R^5$ = $C_{1-4}$-alkyl or benzyl;

Hal = leaving group such as Cl, Br, I, $OSO_2CH_3$.

Scheme 4: Some of the compounds (II') can also be prepared by reaction of compound (VII), bearing a leaving group at the heteroarylmethyl position such as Cl, Br, or mesyloxy (methanesulfonyloxy), with ester (VI) in the presence of a suitable base (e.g., sodium hydride, cesium carbonate, potassium carbonate, or triethylamine) in a suitable solvent (e.g., THF, DMF); Y, R, and $R^3$ in Scheme 4 have the meanings as defined hereinbefore. Compound (VII) may bear the desired residue R on the heteroaromatic ring Y or a leaving group instead to introduce R later on.

Scheme 5

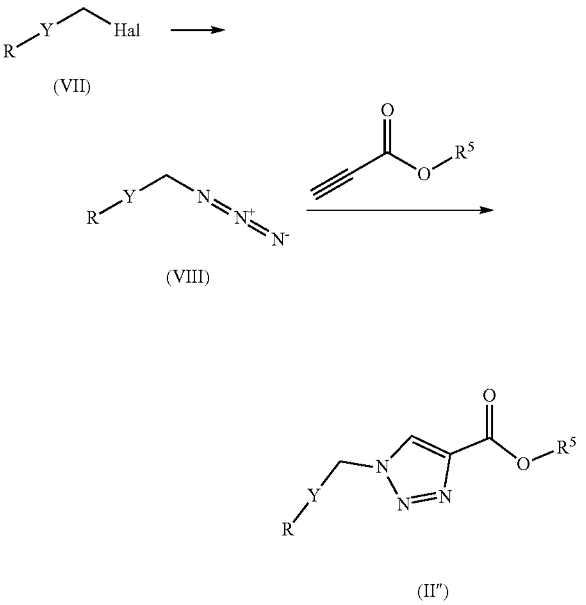

(VII) (VIII) (II")

$R^5$ = $C_{1-4}$-alkyl or benzyl;

Hal = leaving group such as OH, Cl, Br, I, $OSO_2CH_3$

Scheme 5: Some esters of formula (II"), wherein Y and R have the meanings defined hereinbefore, can be prepared by treatment of a corresponding alkyl halide (bromide or chloride) or sulfonate (e.g., mesylate) of formula (VII) with sodium azide in DMF or another suitable solvent to give an intermediate of formula (VIII) which is then reacted with a suitable propiolic acid ester under copper mediated conditions (e.g., ethyl propiolate or tert-butyl propiolate with catalytic copper sulfate and sodium ascorbate in water/tert-butanol) to give compound (II"). Alternatively, azide (VIII) can be obtained from an alcohol of formula (V) (or (VII) wherein Hal is OH) by treatment with diphenylphosphoryl azide in the presence of a suitable base such as DBU in a suitable solvent (e.g., THF or DMF). Compound (VII) may bear the desired residue R on the heteroaromatic ring Y or a leaving group instead to introduce R later on.

Scheme 6

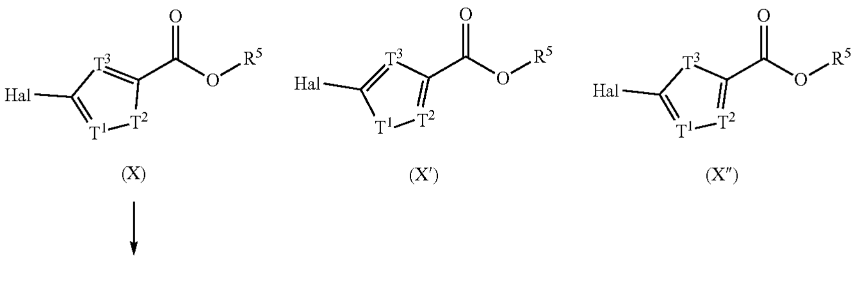

(X) (X') (X")

-continued

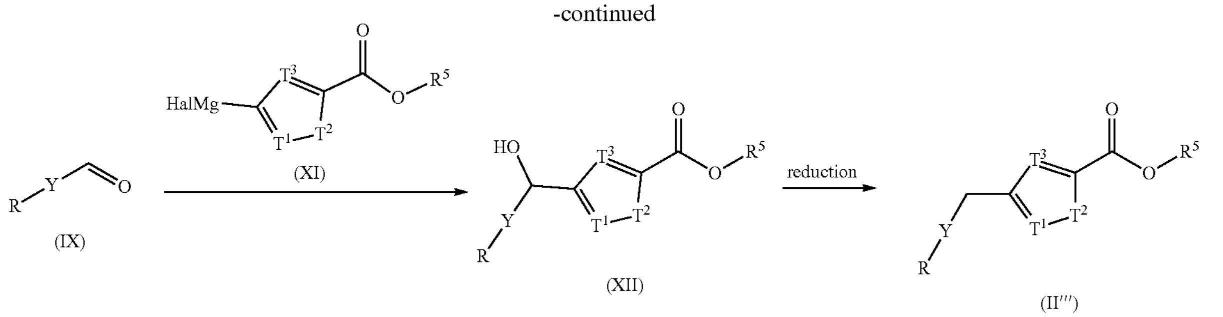

(IX) (XI) (XII) (II'''')

for compound (X), (XI), (XII), and (II''''): $T^1$ and $T^3$ are independently selected from CH, and N, C—$R^3$ and $T^2$ is selected from N—$R^3$, O and S;
for compound (X'): $T^2$ and $T^3$ are independently selected from CH, C—$R^3$ and N, and $T^1$ is selected from N—$R^3$, O and S;
for compound (X''): $T^1$ and $T^2$ are independtly selected from CH, C—$R^3$ and N, and $T^3$ is selected from N—$R^3$, O and S;
$R^5$ = $C_{1-4}$alkyl or benzyl;
Hal = Cl, Br, I Scheme 6: Esters of formula (II''''), wherein Y, R, and $R^3$ have the meanings defined hereinbefore, can be prepared from alcohols (XII) by displacement of the hydroxyl group with hydrogen employing well known methods reported in the literature (e.g., triethylsilane and TFA or borontrifluoride etherate in DCM, or hydrogen in the presence of palladium on carbon in a solvent such as THF or EtOH). Alcohols (XII) may be prepared by adding magnesium halide (XI), or another organometal derivative, to aldehyde (IX), that, in turn, can be obtained from its corresponding alcohol by oxidation (e.g., Dess-Martin oxidation or Swern oxidation) in an inert solvent (e.g., THF, DCM, or diethyl ether) at low to ambient temperature. Magnesium halide (XI) may be obtained after a halogen metal exchange reaction from the corresponding bromide or iodide of (X) using isopropyl magnesium chloride optionally combined with lithium chloride in THF at low temperature. Alternatively, magnesium metal is inserted into the carbon halogen bond to provide magnesium halide (XI). Compounds (IX) and (XII) may bear the desired residue R on the heteroaromatic ring Y or a leaving group instead to introduce R later on.

Starting from the compounds (X') and (X'') the corresponding analogs of compound (II'''') are accessible employing the principle proceeding delineated above (see Scheme 7 for (X')).

Scheme 7

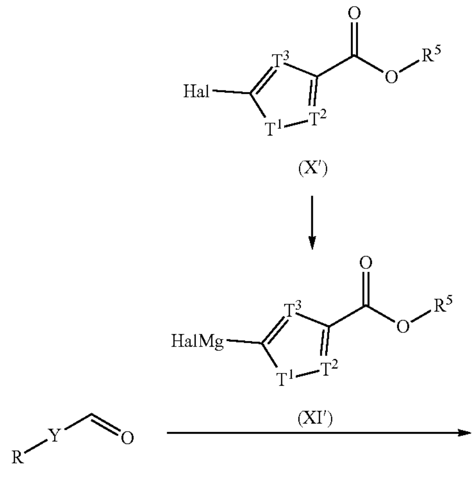

(X') (XI') (IX)

-continued

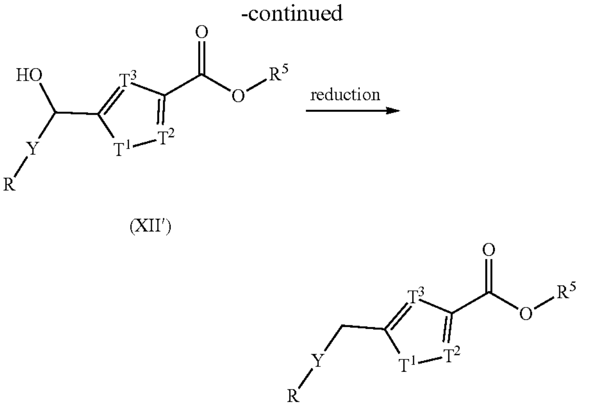

(XII') (II''''')

$T^2$ and $T^3$ are independently selected from CH, C—$R^3$ and N, and $T^1$ is selected from N—$R^3$, O and S;
$R^5$ = $C_{1-4}$alkyl or benzyl;
Hal = Cl, Br, I Scheme 7: Compounds of formula (II'''''), wherein Y, R, and $R^3$ have the meanings defined hereinbefore, can be prepared in an analogous fashion to the compounds delineated in Scheme 6 using the isomeric magnesium halide (XI').

Scheme 8

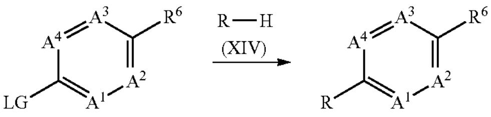

(XIII) (XV)

LG = leaving group such as F, Cl, Br, I; $A^1$, $A^2$, $A^3$, $A^4$ = independently N or C—$R^1$
$R^6$ = $COOR^5$, CHO, $CH_2OH$, $CH_2$—Ar—$COOR^5$;
$R^5$ = $C_{1-4}$-alkyl or benzyl Scheme 8: Intermediates of formula (XV) can be prepared from aromatic compound (XIII) and amine (XIV) via either a nucleophilic substitution reaction on the heteroaromatic ring or a transition metal catalyzed coupling reaction; Ar, R and $R^1$ in Scheme 8 have the meanings defined hereinbefore. The nucleophilic substitution of a leaving group on the heteroaromatic ring in (XIII) with the N in compound (XIV)

can be conducted in the presence of a suitable base (e.g., sodium hydride, cesium carbonate, potassium carbonate, N,N-diisopropyl-ethylamine) in a suitable solvent (e.g., THF, 1,4-dioxane, DMF, DMSO) at ambient or elevated temperature. A transition metal catalyzed coupling reaction is preferably carried out in analogy to procedures reported in the literature of organic chemistry referred to as Ullmann or Buchwald/Hartwig coupling reaction using suitable copper or palladium salts or complexes thereof, optionally combined with additional ligands, in the presence of a base and in a suited solvent.

Scheme 9

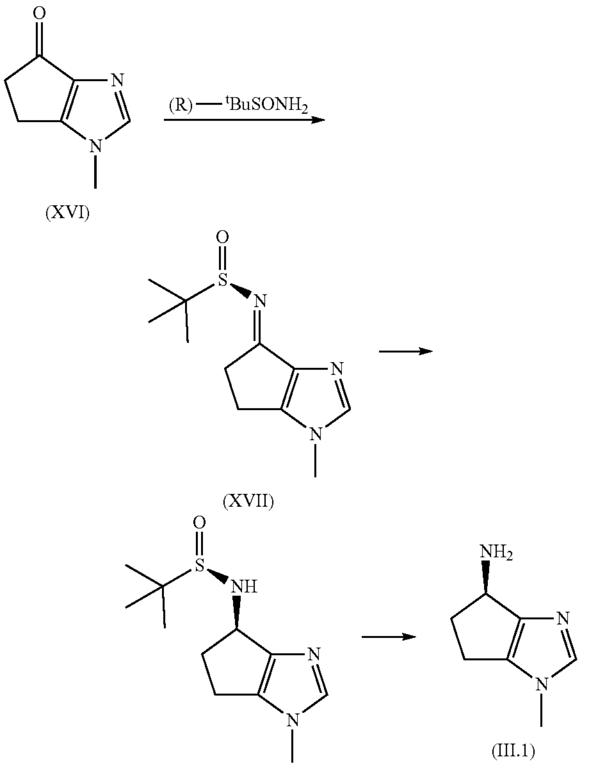

(XVI) (XVII) (XVIII) (III.1)

Scheme 9: Enantiopure amine (III.1) can be prepared from ketone (XVI) as delineated in Scheme 9. The overall synthesis comprises 3 steps and starts with the condensation of the ketone with the enantiopure tert-butanesulfinamide in the presence of a dehydrating agent such as titanium alcoholate (e.g., $Ti(OEt)_4$ or $Ti(OPr)_4$) in a suited solvent (e.g., THF, DCM, toluene, or neat) at ambient or elevated temperature to generate the corresponding enantiopure tert-butylsulfinylated imine (XVII). Imine (XVII) can be diastereoselectively reduced to the corresponding tert-butylsulfinylated amine (XVIII) using a hydride (e.g., lithium or sodium borohydride, L-selectride, diisobutylaluminum hydride, etc.) in a suited solvent (e.g., THF, toluene, MeOH, etc., depending on the hydride source used). The tert-butylsulfinyl group can be cleaved off using an acid (e.g., TFA or hydrochloric acid) in a suitable solvent (e.g., toluene, DCM, dioxane, alcohol, water, etc.) at ambient or elevated temperature.

The racemate (III) and the opposite enantiomer (III.2) are obtained by employing the racemic tert-butanesulfinamine and enantiopure (S)-tert-butanesulfinamine, respectively, in the route described above.

Alternatively, compound (III.1) and its enantiomer (III.2) can be obtained from ketone (XVI) via a 3-step synthesis sequence starting with an enantioselective reduction of the ketone moiety in compound (XVI) using conditions reported in the literature of organic chemistry (e.g., J. Am. Chem. Soc. 1995, 117, 7562-3; Org. Lett. 2010, 12, 1756-9; Org. Proc. Res. Dev. 2006, 10, 949-958; Tetrahedron: Asymmetry 2003, 14, 2659-2681; Tetrahedron Lett. 2014, 55, 3635-40; and references quoted therein) to give the corresponding enantiopure or enantioenriched alcohol. The thus formed hydroxyl group can then be replaced with a protected or masked ammonia group such as phthalimide or (tert-BuOCO)$_2$N employing a stereospecific Mitsunobu or Mitsunobu-type reaction (using, e.g., triphenylphosphine or tri-n-butylphosphine combined with dimethyl azodicarboxylate, DEAD, DIAD, di-(4-chlorobenzyl) azodicarboxylate, dibenzyl azodicarboxylate, DBAD, azodicarboxylic acid bis-(dimethylamide), azodicarboxylic acid dipiperidide, or azodicarboxylic acid dimorpholide in a suitable solvent (e.g., THF, 1,4-dioxane, EtOAc, benzene, toluene, etc.)) leading to inversion of the configuration at the heteroatom bearing C. Alternatively, a phosphoryl azide (e.g., diphenylphosphoryl azide) can be employed to replace the OH group with azide under inversion of the configuration. The amino group can be liberated from the phthalimide group by treatment with, e.g., hydrazine, hydroxylamine, methylamine, n-butylamine, or ethanolamine in a suitable solvent (e.g., EtOH, MeOH, MeCN, THF, dioxane, DMSO, N,N-dimethylacetamide, water, or mixtures of these) with heating if necessary to give compound (III.1). tert-Bu-O—CO is preferably removed under acidic conditions (using, e.g., TFA or hydrochloric acid) to give the same amine (III.1). The azide can be reduced to the amine (III.1) with, e.g., hydrogen in the presence of a transition metal (e.g., Pd on carbon, Raney-Ni, $PtO_2$, etc.) or a phosphine (e.g., triphenylphosphine). The racemate (III) is obtained upon reduction of compound (XVI) with an achiral reducing agent such as sodium borohydride and following the further route described above.

Scheme 10

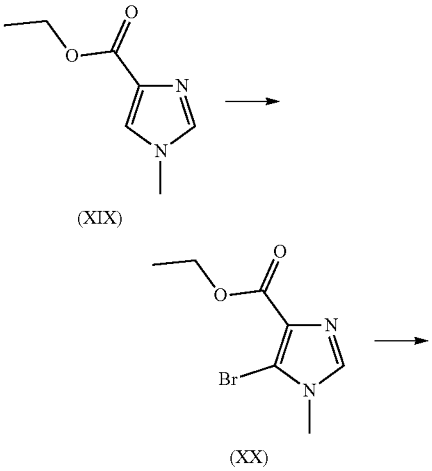

(XIX) (XX)

-continued

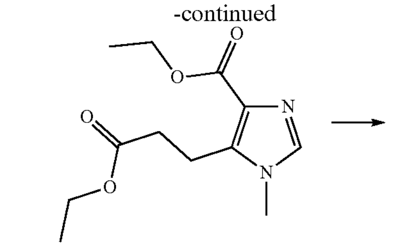

(XXI)

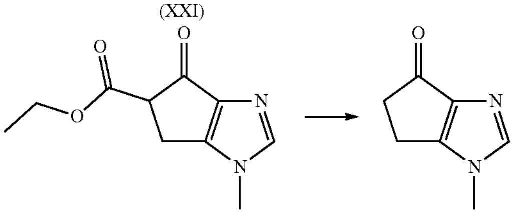

(XXII) (XVI)

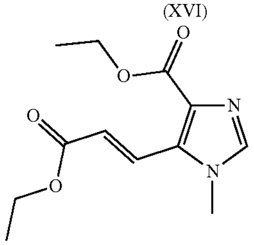

(XXIII)

Scheme 10: Compounds (XVI) can be obtained from ester (XIX) (or the corresponding lower or higher alkyl esters, e.g., methyl, n-propyl, isopropyl, or tert-butyl ester) in a sequence consisting of 3 or 4 reaction steps. Compound (XIX) can be brominated employing a suited electrophilic bromine source (e.g., N-bromosuccinimide (NBS) or $Br_2$) in a suited solvent (e.g., AcOH, DCM, dichloroethane, dioxane, MeCN, DMF, etc.) at ambient or elevated temperature. For example, NBS in acetic acid at ambient temperature or NBS in $HCCl_3$ at 65° C. provide the compound. Alternatively, treatment of compound (XIX) with NBS, sodium persulfate and palladium acetate in trifluoromethanesulfonic acid and 1,2-dichloroethane at 80° C. gives access to (XX) as well. Compound (XX) can then be transformed into ester (XXI) by applying a 1- or 2-step synthesis route encompassing a Heck coupling reaction (broadly covered in the literature of organic chemistry, e.g., in Catalysts 2017, 7, 267 and references quoted therein) with either acrolein dialkyl acetal (e.g., acrolein diethyl acetal, →(XXI)) or an acrylic acid ester (e.g., acrylic ethyl ester, →(XXIII)); using the latter coupling partner requires an additional step to reduce the olefinic bond formed routinely achieved with hydrogen in the presence of a transition metal catalyst (e.g., Pd such as palladium on carbon, Ni such as Raney-Ni, Pt such as platinum oxide, Rh such as rhodium on carbon, etc.) in a suited solvent (e.g., DCM, dioxane, THF, EtOAc, alcohol such as MeOH, water, etc.). Ketoester (XXII) may be produced upon treatment of compound (XXI) with a base (e.g., a hydride such as sodium hydride, an alcoholate such as lithium methoxide or potassium tert-butylate, an organic amine such as DBU, a phosphazene such as $P_2Et$ phosphazene, an amide such as lithium diisopropylamide, lithium, sodium or potassium hexamethyldisilazide, etc.) in a suited solvent (e.g., benzene, toluene, dioxane, THF, alcohol, etc., depending on the base used) at low to elevated temperature (−78° C. to 100° C., depending on the base and solvent employed); potassium hexamethyldisilazide in THF at 20° C. is one of the more preferred conditions for this transformation. Hydrolysis of the ester group in compound (XXII) followed by decarboxylation can be achieved by stirring the compound in a solvent (e.g., dioxane, THF, ACN, DMF, N,N-dimethylacetamide, DMSO, alcohol, water, etc., or mixtures of these), optionally in the presence of a base (e.g., sodium hydroxide), a halide salt such as lithium iodide or chloride, or an acid (e.g., hydrochloric acid) at 0 to 140° C. to give ketone (XVI).

The compounds of formula (I) may be resolved into their enantiomers and/or diastereomers as mentioned below. Thus, for example, cis/trans mixtures may be resolved into their cis and trans isomers and racemic compounds may be separated into their enantiomers.

The cis/trans mixtures may be resolved, for example, by chromatography into the cis and trans isomers thereof. The compounds of formula (I) which occur as racemates may be separated by methods known per se into their optical antipodes and diastereomeric mixtures of compounds of general formula (I) may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned below.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids commonly used for such a purpose as well as optically active alcohols applicable as auxiliary residues are known to those skilled in the art.

As mentioned above, the compounds of formula (I) may be converted into salts, particularly for pharmaceutical use into the pharmaceutically acceptable salts. As used herein, "pharmaceutically acceptable salts" refer to derivatives of the disclosed compounds wherein the parent compound is modified by making acid or base salts thereof.

The compounds according to the invention are advantageously also obtainable using the methods described in the examples that follow, which may also be combined for this purpose with methods known to the skilled person from the literature.

Thus, according to another aspect of the present invention, processes for the synthesis of compounds of formula (I) are provided.

According to another aspect of the present invention, intermediates of the synthesis of compounds of formula (I) are provided.

According to one embodiment, the invention relates to intermediates as depicted and described in Schemes 9 and/or 10.

According to another embodiment, the invention relates to one or more of the following intermediates (XVI)

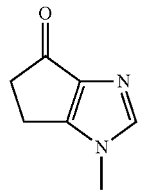

(III)

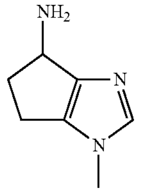

(III.1)

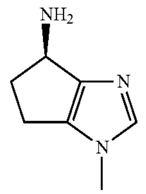

(III.2)

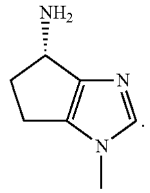

Pharmacological Activity

The activity of the compounds of the invention may be demonstrated using the following assays:

Biological Methods

The ability of compounds of formula (I) to inhibit plasma kallikrein (PKK), Factor XIIa (FXIIa), Factor XIa (FXIa), Factor Xa (FXa), Factor IIa (alpha-thrombin; FIIa), plasmin, trypsin, tissue kallikrein 1 (TK1), Factor VIIa (FVIIa), or FVIIa complexed with Tissue Factor, phospholipids and $CaCl_2$ (FVIIa/TF/PL/$CaCl_2$) is determined using the following biochemical assays in assay buffer (100 mM Tris, 150 mM NaCL, adjusted to a pH of 7.8 with HCl, and containing 0.1% (w/v) BSA and 0.05% (v/v) Tween20) in the presence of 1% (v/v) DMSO:

Evaluation of the Inhibition of Pkk Using an Endpoint Assay

Human PKK (0.01 U/mL; Enzyme Research Laboratories) or rat PKK (0.625 nM; produced in-house) is incubated for 1 h at room temperature with 0.10 μM fluorogenic substrate H-Pro-Phe-Arg-AMC (11295 from Bachem) and various concentrations of the test compound in assay buffer. Subsequently, PPACK II (Calbiochem) is added as a stop solution to achieve a final concentration of 1 μM and fluorescence is measured using an Envision Reader (PerkinElmer) with the wavelength excitation setting of 355 nm and the wavelength emission setting of 460 nm.

$IC_{50}$ values for compounds according to the invention are shown in the following table. The number of the compound corresponds to the number of the Example in the experimental section.

| Example | $IC_{50}$ (nM) |
|---|---|
| 1 | 1.3 |
| 2 | 3.1 |
| 3 | 1.7 |
| 4 | 0.9 |
| 5 | 1.1 |
| 6 | 0.9 |
| 7 | 1.4 |
| 8 | 2.3 |
| 9 | 3.8 |
| 10 | 2.5 |
| 11 | 2.1 |
| 12 | 3.4 |
| 13 | 1.1 |
| 14 | 1.0 |
| 15 | 1.1 |
| 16 | 0.6 |
| 17 | 2.0 |
| 18 | 2.1 |
| 19 | 14.2 |
| 20 | 0.7 |
| 21 | 0.9 |
| 22 | 0.5 |
| 23 | 1.1 |
| 24 | 1.0 |
| 25 | 2.0 |
| 26 | 4.9 |
| 27 | 0.9 |
| 28 | 0.6 |
| 29 | 2.6 |
| 30 | 0.9 |
| 31 | 5.3 |
| 32 | 1.1 |
| 33 | 2.5 |
| 34 | 0.9 |
| 35 | 2.2 |
| 36 | 0.5 |
| 37 | 0.9 |
| 38 | 3.4 |
| 39 | 0.7 |
| 40 | 1.2 |
| 41 | 3.4 |
| 42 | 0.6 |
| 43 | 0.9 |
| 44 | 1.8 |
| 45 | 0.7 |
| 46 | 1.0 |
| 47 | 0.8 |
| 48 | 2.8 |
| 49 | 2.5 |
| 50 | 1.7 |
| 51 | 1.0 |
| 52 | 1.1 |
| 53 | 2.0 |
| 54 | 0.7 |
| 55 | 2.3 |
| 56 | 1.8 |
| 57 | 0.6 |
| 58 | 2.5 |
| 59 | 0.4 |
| 60 | 18.8 |
| 61 | 3.1 |
| 62 | 14.0 |
| 63 | 3.0 |
| 64 | 0.7 |
| 65 | 1.4 |
| 66 | 0.7 |
| 67 | 3.1 |
| 68 | 1.4 |
| 69 | 0.9 |
| 70 | 0.8 |
| 71 | 151 |
| 72 | 3.3 |
| 73 | 9.6 |
| 74 | 6.9 |
| 75 | 0.5 |
| 76 | 0.6 |
| 77 | 3.3 |
| 78 | 6.8 |
| 79 | 5.5 |

-continued

| Example | $IC_{50}$ (nM) |
| --- | --- |
| 80 | 4.7 |
| 81 | 1.3 |
| 82 | 0.8 |
| 83 | 1.7 |
| 84 | 0.7 |
| 85 | 0.8 |
| 86 | 1.2 |
| 87 | 3.3 |
| 88 | 0.9 |
| 89 | 77.5 |
| 90 | 0.7 |
| 91 | 2.1 |
| 92 | 2.8 |
| 93 | 1.4 |
| 94 | 10.8 |
| 95 | 5.5 |
| 96 | 1.5 |
| 97 | 1.4 |
| 98 | 1.5 |
| 99 | 3.7 |
| 100 | 5.6 |
| 101 | 0.6 |
| 102 | 2.1 |
| 103 | 0.7 |
| 104 | 3.2 |
| 105 | 0.5 |
| 106 | 9.8 |
| 107 | 1.0 |
| 108 | 1.7 |
| 109 | 0.8 |
| 110 | 0.9 |
| 111 | 8.6 |
| 112 | 12.6 |
| 113 | 9.9 |
| 114 | 1.8 |
| 115 | 4.1 |
| 116 | 0.4 |
| 117 | 2.2 |
| 118 | 0.3 |
| 119 | 1.2 |
| 120 | 2.4 |
| 121 | 1.6 |
| 122 | 1.5 |
| 123 | 0.9 |
| 124 | 2.4 |
| 125 | 1.1 |
| 126 | 0.6 |
| 127 | 1.2 |
| 128 | 5.1 |
| 129 | 23.7 |
| 130 | 20.0 |
| 131 | 4.3 |
| 132 | 1.9 |
| 133 | 1.6 |
| 134 | 1.7 |
| 135 | 4.2 |
| 136 | 2.0 |
| 137 | 4.4 |
| 138 | 2.2 |
| 139 | 9.6 |
| 140 | 5.8 |
| 141 | 2.0 |
| 142 | 5.8 |
| 143 | 0.6 |
| 144 | 0.8 |
| 145 | 0.7 |
| 146 | 1.1 |
| 147 | 1.4 |
| 148 | 1.4 |
| 149 | 1.6 |
| 150 | 1.0 |
| 151 | 3.6 |
| 152 | 1.2 |
| 153 | 0.5 |
| 154 | 9.9 |
| 155 | 15.4 |
| 156 | 0.8 |
| 157 | 1.2 |
| 158 | 4.6 |
| 159 | 3.5 |
| 160 | 2.2 |
| 161 | 1.5 |
| 162 | 1.1 |
| 163 | 2.2 |
| 164 | 1.8 |
| 165 | 0.8 |
| 166 | 1.0 |
| 167 | 1.3 |
| 168 | 1.5 |
| 169 | 0.6 |
| 170 | 0.8 |
| 171 | 2.6 |
| 172 | 8.1 |
| 173 | 0.6 |
| 174 | 1.9 |
| 175 | 2.9 |
| 176 | 4.2 |
| 177 | 5.5 |
| 178 | 5.0 |
| 179 | 4.2 |
| 180 | 2.6 |
| 181 | 10.9 |
| 182 | 7.1 |
| 183 | 19.4 |
| 184 | 13.5 |
| 185 | 10.9 |
| 186 | 10.9 |
| 187 | 12.2 |
| 188 | 19.8 |
| 189 | 22.1 |
| 190 | 1.5 |
| 191 | 169 |
| 192 | 1890 |
| 193 | 0.4 |
| 194 | 0.3 |
| 195 | 20.3 |
| 196 | 1.5 |
| 197 | 13.4 |
| 198 | 0.8 |
| 199 | 3.1 |
| 200 | 8.6 |
| 201 | 0.6 |
| 202 | 0.5 |
| 203 | 0.7 |
| 204 | 1.5 |
| 205 | 8.3 |
| 206 | 0.4 |
| 207 | 3.2 |
| 208 | 0.6 |
| 209 | 1.5 |
| 210 | 0.4 |
| 211 | 0.8 |
| 212 | 2.1 |
| 213 | 2.3 |
| 214 | 20.3 |
| 215 | 0.7 |
| 216 | 1.2 |
| 217 | 0.9 |
| 218 | 3.5 |
| 219 | 3.6 |
| 220 | 1.9 |
| 221 | 2.8 |
| 222 | 11.6 |
| 223 | 7540 |
| 224 | 302 |
| 225 | 232 |
| 226 | 35.7 |
| 227 | 45.3 |
| 228 | 126 |
| 229 | 110 |
| 230 | 53.7 |
| 231 | 223 |
| 232 | 512 |
| 233 | 81.4 |

-continued

| Example | $IC_{50}$ (nM) |
|---|---|
| 234 | 350 |
| 235 | 214 |
| 236 | 222 |
| 237 | 111 |
| 238 | 123 |
| 239 | 123 |
| 240 | 52 |

Evaluation of the Inhibition of PKK in Kaolin Activated Human PPP

Platelet poor plasma (PPP) obtained from human whole-blood, anticoagulated with Na-Citrate, is incubated with various concentrations of the test compound together with either 25, 75, 250, or 750 µg/mL kaolin in assay buffer for 20 min at 37° C. such that for each kaolin dose used a concentration response is obtained for the test compound. Afterwards 0.25 mM fluorogenic substrate H-Pro-Phe-Arg-AMC (11295 from Bachem) is added to the mixture and measurements are performed in a kinetic interval every 2nd minute for 12 min using a Spectramax MS (Molecular Devices) with the following settings of the wavelength excitation of 350 nm and wavelength emission of 450 nm. pIC50 and pIC90 values are obtained from 4 x/y-plots (x=log M, Compound; y=delta rfu/min) fitted with Graph-Pad prism 7.0 (Equation: log(agonist) vs. response—Find ECanything; the four concentration response curves obtained for the test compound, each obtained using a different kaolin dose, are fitted using a global fitting procedure yielding shared pIC50 or pIC90 values).

$IC_{90}$ values for compounds according to the invention are shown in the following table. The number of the compound corresponds to the number of the Example in the experimental section.

| Example | $IC_{50}$ (nM) |
|---|---|
| 1 | 290 |
| 2 | 253 |
| 3 | 210 |
| 4 | 184 |
| 5 | 278 |
| 6 | 1880 |
| 7 | 151 |
| 8 | 352 |
| 9 | 603 |
| 10 | 789 |
| 11 | 300 |
| 12 | 802 |
| 13 | 451 |
| 14 | 636 |
| 15 | 414 |
| 16 | 280 |
| 17 | 818 |
| 18 | 460 |
| 20 | 99 |
| 21 | 325 |
| 22 | 249 |
| 23 | 233 |
| 24 | 181 |
| 25 | 286 |
| 26 | 343 |
| 27 | 202 |
| 28 | 184 |
| 29 | 336 |
| 30 | 334 |
| 31 | 973 |
| 32 | 548 |
| 33 | 265 |
| 34 | 1190 |

-continued

| Example | $IC_{50}$ (nM) |
|---|---|
| 35 | 259 |
| 36 | 180 |
| 37 | 125 |
| 39 | 380 |
| 40 | 543 |
| 41 | 488 |
| 42 | 195 |
| 43 | 308 |
| 44 | 444 |
| 45 | 151 |
| 46 | 162 |
| 47 | 173 |
| 48 | 612 |
| 49 | 254 |
| 50 | 110 |
| 51 | 213 |
| 52 | 155 |
| 53 | 203 |
| 54 | 109 |
| 55 | 250 |
| 56 | 586 |
| 57 | 166 |
| 62 | 769 |
| 63 | 203 |
| 64 | 221 |
| 65 | 1230 |
| 66 | 839 |
| 67 | 635 |
| 68 | 637 |
| 69 | 328 |
| 70 | 797 |
| 71 | 9310 |
| 72 | 831 |
| 73 | 498 |
| 74 | 321 |
| 75 | 192 |
| 76 | 270 |
| 77 | 197 |
| 78 | 317 |
| 79 | 249 |
| 80 | 495 |
| 81 | 117 |
| 82 | 117 |
| 83 | 594 |
| 84 | 209 |
| 85 | 132 |
| 86 | 597 |
| 87 | 177 |
| 88 | 139 |
| 89 | 3430 |
| 90 | 126 |
| 91 | 439 |
| 92 | 307 |
| 93 | 110 |
| 94 | 1760 |
| 95 | 577 |
| 96 | 134 |
| 97 | 766 |
| 98 | 282 |
| 99 | 2170 |
| 101 | 297 |
| 102 | 1440 |
| 103 | 531 |
| 104 | 706 |
| 105 | 117 |
| 106 | 1970 |
| 107 | 324 |
| 108 | 465 |
| 109 | 414 |
| 110 | 784 |
| 111 | 4150 |
| 112 | 2780 |
| 114 | 14700 |
| 115 | 2660 |
| 116 | 278 |
| 117 | 1540 |
| 118 | 157 |

-continued

| Example | $IC_{50}$ (nM) |
|---|---|
| 119 | 1460 |
| 120 | 934 |
| 121 | 514 |
| 122 | 492 |
| 123 | 1320 |
| 124 | 823 |
| 125 | 2740 |
| 126 | 681 |
| 127 | 1680 |
| 128 | 1390 |
| 131 | 962 |
| 132 | 425 |
| 133 | 560 |
| 134 | 1030 |
| 135 | 909 |
| 136 | 310 |
| 137 | 756 |
| 139 | 774 |
| 140 | 760 |
| 141 | 621 |
| 142 | 731 |
| 143 | 1170 |
| 144 | 248 |
| 145 | 245 |
| 146 | 274 |
| 147 | 149 |
| 148 | 985 |
| 149 | 511 |
| 150 | 373 |
| 151 | 1140 |
| 152 | 430 |
| 153 | 280 |
| 154 | 4270 |
| 155 | 4100 |
| 158 | 2100 |
| 159 | 1140 |
| 160 | 967 |
| 161 | 431 |
| 162 | 231 |
| 163 | 470 |
| 164 | 443 |
| 165 | 342 |
| 166 | 193 |
| 167 | 272 |
| 168 | 1860 |
| 169 | 485 |
| 170 | 469 |
| 171 | 268 |
| 181 | 22300 |
| 182 | 6270 |
| 184 | 2310 |
| 185 | 2270 |
| 186 | 236 |
| 187 | 2450 |
| 188 | 1500 |
| 190 | 1080 |
| 193 | 253 |
| 194 | 183 |
| 196 | 350 |
| 198 | 398 |
| 199 | 808 |
| 201 | 130 |
| 202 | 157 |
| 203 | 202 |
| 204 | 818 |
| 206 | 138 |
| 207 | 745 |
| 208 | 80 |
| 173 | 729 |
| 174 | 1430 |
| 175 | 822 |
| 177 | 1180 |
| 178 | 844 |
| 179 | 389 |
| 180 | 207 |
| 209 | 432 |
| 210 | 128 |

-continued

| Example | $IC_{50}$ (nM) |
|---|---|
| 211 | 590 |
| 212 | 1890 |
| 213 | 621 |
| 214 | 1040 |
| 215 | 194 |
| 216 | >10000 |
| 217 | 624 |
| 218 | 646 |
| 219 | 776 |
| 220 | 525 |

Evaluation of the Inhibition of PKK ($K_i$)

Human PKK (1.78 nM or 0.025 U/mL; Enzyme Research Laboratories) is incubated at 24° C. with 0.25 mM fluorogenic substrate H-Pro-Phe-Arg-AMC (11295 from Bachem) and various concentrations of the test compound in assay buffer. Measurements are performed in a kinetic interval every $2^{nd}$ minute for 16 min using a Spectramax M5 (Molecular Devices) with the following settings of the wavelength excitation of 350 nm and wavelength emission of 450 nm.

Evaluation of the Inhibition of FXIIa ($K_i$)

Human FXIIa (47.5 nM or 1.1 U/mL; Enzyme Research Laboratories) is incubated at 24° C. with 0.5 mM chromogenic Substrate S2302 (Chromogenix) and various concentrations of the test compound in assay buffer. Measurements are performed in a kinetic interval every $2^{nd}$ minute for 16 min using a Spectramax M5 (Molecular Devices) measuring the optical absorbance at 405 nm.

Evaluation of the Inhibition of FXIa ($K_i$)

Human FXIa (0.5 nM or 0,016 U/mL; Enzyme Research Laboratories) is incubated at 24° C. with 0.25 mM fluorogenic substrate Boc-Glu(OBzl)-Ala-Arg-AMC·HCl (11575 from Bachem) and various concentrations of the test compound in assay buffer. Measurements are performed in a kinetic interval every $2^{nd}$ minute for 16 min using a Spectramax M5 (Molecular Devices) with the following settings of the wavelength excitation of 350 nm and wavelength emission of 450 nm.

Evaluation of the Inhibition of FXa ($K_i$)

Human FXa (0.86 nM or 0.01 U/mL; Enzyme Research Laboratories) is incubated at 24° C. with 0.5 mM chromogenic Substrate S2765 (Chromogenix) and various concentrations of the test compound in assay buffer. Measurements are performed in a kinetic interval every $2^{nd}$ minute for 16 min using a Spectramax M5 (Molecular Devices) measuring the optical absorbance at 405 nm.

Evaluation of the Inhibition of FIIa ($K_i$)

Human FIIa (44.6 nM or 5 U/mL; Enzyme Research Laboratories) is incubated at 24° C. with 0.5 mM chromogenic Substrate S2238 (Chromogenix) and various concentrations of the test compound in assay buffer. Measurements are performed in a kinetic interval every $2^{nd}$ minute for 16 min using a Spectramax M5 (Molecular Devices) measuring the optical absorbance at 405 nm.

Evaluation of the Inhibition of Plasmin ($K_i$)

Human plasmin (64.1 nM or 0.0275 U/mL; Enzyme Research Laboratories) is incubated at 24° C. with 0.3 mM chromogenic Substrate S2251 (Chromogenix) and various concentrations of the test compound in assay buffer. Measurements are performed in a kinetic interval every $2^{nd}$ minute for 16 min using a Spectramax M5 (Molecular Devices) measuring the optical absorbance at 405 nm.

Evaluation of the Inhibition of Trypsin ($K_i$)

Human trypsin (4.54 nM or 250 U/mL; Calbiochem) is incubated at 24° C. with 0.5 mM chromogenic Substrate S2222 (Chromogenix) and various concentrations of the test compound in assay buffer. Measurements are performed in a kinetic interval every 2nd minute for 16 min using a Spectramax M5 (Molecular Devices) measuring the optical absorbance at 405 nm.

Evaluation of the Inhibition of Tk1 ($K_i$)

Prior to the assay, human TK1 (R&D Systems) is activated by incubation with human trypsin (Calbiochem) in a 1:10,000 ratio for 15 min at 37° C. For assaying TK1 inhibitory activity, activated TK1 (31.25 nM or 1 U/mL) is incubated at 24° C. with 0.1 mM fluorogenic substrate H-Pro-Phe-Arg-AMC (11295 from Bachem) and various concentrations of the test compound in assay buffer. Measurements are performed in a kinetic interval every 2nd minute for 16 min using a Spectramax M5 (Molecular Devices) with the following settings of the wavelength excitation of 350 nm and wavelength emission of 450 nm.

$K_i$ values for compounds according to the invention are shown in the following table. The number of the compound corresponds to the number of the Example in the experimental section.

| Example | $K_i$ (nM) |
|---|---|
| 4 | >10000 |
| 16 | >10000 |
| 20 | >10000 |
| 22 | >10000 |
| 23 | >10000 |
| 24 | >10000 |
| 27 | >10000 |
| 36 | >10000 |
| 47 | >10000 |
| 49 | >10000 |
| 51 | >10000 |
| 52 | >10000 |
| 75 | >10000 |
| 80 | >10000 |
| 86 | >10000 |
| 90 | >10000 |
| 107 | >10000 |
| 108 | >10000 |
| 110 | >10000 |
| 113 | >10000 |
| 114 | >10000 |
| 115 | >10000 |
| 116 | 871 |
| 117 | >10000 |
| 118 | >10000 |
| 119 | 1060 |
| 120 | >10000 |
| 121 | >10000 |
| 122 | >10000 |
| 123 | >10000 |
| 124 | >10000 |
| 125 | >10000 |
| 126 | >10000 |
| 127 | >10000 |
| 128 | >10000 |
| 131 | >10000 |
| 133 | >10000 |
| 134 | >10000 |
| 135 | >10000 |
| 136 | >10000 |
| 137 | >10000 |
| 169 | >10000 |
| 170 | >10000 |
| 171 | >10000 |
| 173 | >10000 |
| 175 | >10000 |
| 177 | >10000 |
| 178 | >10000 |

-continued

| Example | $K_i$ (nM) |
|---|---|
| 181 | >10000 |
| 190 | >10000 |
| 193 | >10000 |
| 194 | >10000 |
| 196 | >10000 |
| 198 | >10000 |
| 217 | >10000 |
| 218 | >10000 |
| 222 | 7280 |

Evaluation of the Inhibition of FVIIa ($K_i$)

Human FVIIa (0.86 nM or 0.01 U/mL; Enzyme Research Laboratories) is incubated at 24° C. with 1.5 mM chromogenic Pefachrome® FVIIa (Loxo) and various concentrations of the test compound in assay buffer. Measurements are performed in a kinetic interval every 2nd minute for 16 min using a Spectramax M5 (Molecular Devices) measuring the optical absorbance at 405 nm.

Evaluation of the Inhibition of FVIIa/TF/PL/$CaCl_2$) ($K_i$)

Human FVIIa (300 nM or 585 U/mL; Enzyme Research Laboratories) together with 10 mM $CaCl_2$*$2H_2O$ and 13.3% (v/v) Dade®Innovin® (Siemens; OQUMI94E0002(5534), which contains recombinant human tissue factor synthetic phospholipids (thromboplastin), is incubated at 24° C. with 1.5 mM chromogenic Pefachrome® FVIIa (Loxo) and various concentrations of the test compound in assay buffer. Measurements are performed in a kinetic interval every 2nd minute for 16 min using a Spectramax M5 (Molecular Devices) measuring the optical absorbance at 405 nm.

Calculation of $pIC_{50}$ and $pK_i$ Values

The average $V_{max}$ values for the time interval from 2 to 12 min after initiation of the assay (expressed as either delta OD/min for assays using a chromogenic substrate or delta RFU/min for assays using a fluorigenic substrate, respectively) are plotted versus the Log of the concentration in molar of the evaluated inhibitor compound. The $pIC_{50}$ values are then fitted using a four-parametric fitting procedure using GraphPad Prism (version 6; GraphPad Software, Inc.). Respective $K_i$ values are obtained by correction of the $IC_{50}$ values for the respective $K_M$ value of the used substrate (see Table A for the obtained $K_M$ values of the used substrates) using the following formula:

$$K_i = \frac{IC_{50}}{1 + \frac{[\text{Substrate, mM}]}{K_M}}$$

Where the $IC_{50}$ is in molar and the $K_M$ value in mM.

TABLE A $K_M$ values obtained for the substrates used in the enzymatic assays.

| Enzyme | Substrate | $K_M$ (mM) |
|---|---|---|
| PKK | I1295 | 0.16 |
| FXIIa | S2302 | 0.20 |
| FXIa | I1575 | 0.29 |
| FXa | S2765 | 1.31 |
| FIIa | S2238 | 1.25 |
| Plasmin | S2251 | 1.45 |
| Trypsin | S2222 | 2.03 |

TABLE A-continued $K_M$ values obtained for the substrates used in the enzymatic assays.

| Enzyme | Substrate | $K_M$ (mM) |
|---|---|---|
| TK1 | I1295 | 0.07 |
| FVIIa | Pefachrome ® FVIIa | 0.42 |
| FVIIa/TF/PL/$CaCl_2$ | Pefachrome ® FVIIa | 3.92 |

Evaluation of Permeability

Caco-2 cells (1-2×$10^5$ cells/1 $cm^2$ area) are seeded on filter inserts (Costar transwell polycarbonate or PET filters, 0.4 μm pore size) and cultured (DMEM) for 10 to 25 days.

Compounds are dissolved in appropriate solvent (like DMSO, 1-20 mM stock solutions). Stock solutions are diluted with HTP-4 buffer (128.13 mM NaCl, 5.36 mM KCl, 1 mM $MgSO_4$, 1.8 mM $CaCl_2$, 4.17 mM $NaHCO_3$, 1.19 mM $Na_2HPO_4$x$7H_2O$, 0.41 mM $NaH_2PO_4$x$H_2O$, 15 mM HEPES, 20 mM glucose, pH 7.2) containing 0.25% BSA to prepare the transport solutions (0.1-300 μM compound, final DMSO<=0.5%). The transport solution (TL) is applied to the apical or basolateral donor side for measuring A-B or B-A permeability (2 filter replicates), respectively. The receiver side contains HTP-4 buffer supplemented with 0.25% BSA. Samples are collected at the start and end of experiment from the donor and at various time intervals for up to 2 hours also from the receiver side for concentration measurement by HPLC-MS/MS or scintillation counting. Sampled receiver volumes are replaced with fresh receiver solution.

Evaluation of Metabolic Stability in Human or Rat Liver Microsomes

The metabolic degradation of the test compound is assayed at 37° C. with pooled human (HLM) or rat liver microsomes (RLM). The final incubation volume of 60 μl per time point contains TRIS buffer pH 7.6 at RT (0.1 M), magnesium chloride (5 mM), microsomal protein (HLM: 1 mg/mL, RLM: 0.5 mg/mL) and the test compound at a final concentration of 1 μM.

Following a short preincubation period at 37° C., the reactions are initiated by addition of beta-nicotinamide adenine dinucleotide phosphate, reduced form (NADPH, 1 mM) and terminated by transferring an aliquot into solvent after different time points. Additionally, the NADPH-independent degradation is monitored in incubations without NADPH, terminated at the last time point. The quenched incubations are pelleted by centrifugation (10000 g, 5 min). An aliquot of the supernatant is assayed by LC-MS/MS for the amount of parent compound. The half-life (t½ INVITRO) is determined by the slope of the semilogarithmic plot of the concentration-time profile.

Evaluation of Metabolic Stability in Human or Rat Hepatocytes

The metabolic degradation of the test compound is assayed in a hepatocyte suspension. After recovery from cryopreservation, human or rat hepatocytes are incubated in Dulbecco's modified eagle medium supplemented with 3.5 μg glucagon/500 ml, 2.5 mg insulin/500 ml and 3.75 mg/500 ml hydrocortisone) containing 5% or 50% human or rat serum or in absence of serum.

Following a 30 min preincubation in a cell culture incubator (37° C., 10% $CO_2$), test compound solution is spiked into the hepatocyte suspension to obtain a final cell density of 1.0*106 cells/ml, a final test compound concentration of 1 μM, and a final DMSO concentration of 0.05%.

The cells are incubated for six hours (incubator, horizontal shaker) and samples are removed from the incubation after 0, 0.5, 1, 2, 4 and 6 hours. Samples are quenched with acetonitrile and pelleted by centrifugation. The supernatant is transferred to a 96-deepwell plate, and prepared for analysis of decline of parent compound by HPLC-MS/MS.

$CL_{int}$ is calculated as follows:

$$CL_{int}=\text{Dose}/AUC=(C0/CD)/(AUD+\text{clast}/k)\times 1000/60$$

C0: initial concentration in the incubation [μM], CD: cell density of vital cells [10e6 cells/ml], AUD: area under the data [μM×h], clast: concentration of last data point [μM], k: slope of the regression line for parent decline [$h^{-1}$].

The calculated in vitro hepatic intrinsic clearance can be scaled up to the intrinsic in vivo hepatic clearance and used to predict hepatic in vivo blood clearance (CL) by the use of a liver model (well-stirred model).

Evaluation of Plasma Protein Binding

The equilibrium dialysis (ED) technique is used to determine the approximate in vitro fractional binding of test compounds to plasma proteins applying Dianorm Teflon dialysis cells (micro 0.2). Each dialysis cell consists of a donor and an acceptor chamber, separated by an ultrathin semipermeable membrane with a 5 kDa molecular weight cutoff. Stock solutions for each test compound are prepared in DMSO at 1 mM and serially diluted to obtain a final test concentration of 1 μM. The subsequent dialysis solutions are prepared in plasma (supplemented with NaEDTA as anticoagulant), and aliquots of 200 μl test compound dialysis solution in plasma are dispensed into the donor (plasma) chambers. Aliquots of 200 μL dialysis buffer (100 mM potassium phosphate, pH 7.4) are dispensed into the buffer (acceptor) chamber. Incubation is carried out for 2 hours under rotation at 37° C. for establishing equilibrium.

At the end of the dialysis period, aliquots obtained from donor and acceptor chambers, respectively, are transferred into reaction tubes, spiked with Internal Standard solution and processed for HPLC-MS/MS analysis. Analyte concentrations are quantified in aliquots of samples by HPLC-MS/MS against external calibration curves.

Percent bound is calculated using the formula:

$$\%\ \text{bound}=(\text{plasma concentration}-\text{buffer concentration}/\text{plasma concentration})\times 100$$

Evaluation of Solubility

The aqueous solubility of the test compound is determined by comparing the amount dissolved in buffer to the amount in an ACN/water (1/1) solution. Starting from a 10 mM DMSO stock solution aliquots are diluted with acetonitrile/water (1/1) or buffer resp. After 24 h of shaking, the solutions are filtrated and analyzed by LC-UV. The amount dissolved in buffer is compared to the amount in the ACN solution.

Solubility will usually be measured from 0.001 to 0.125 mg/mL at a DMSO concentration of 2.5%. If more than 90% of the compound is dissolved in buffer, the value is marked with ">".

Evaluation of Pharmacokinetic Characteristics in Rodents

The test compound is administered either intravenously to fed rats or orally to fasted rats. Blood samples are taken at several time points post application of the test compound, anticoagulated and centrifuged.

The concentration of analytes—the administered compound and/or metabolites—are quantified in the plasma samples. PK parameters are calculated using non compartment methods. AUC and Cmax are normalized to a dose of 1 μmol/kg.

Evaluation of Inhibition of Cytochrome P450 Isoenzyme-Catalysed Reactions

The inhibition of cytochrome P450 isoenzyme-catalysed reactions by the test compound is assayed at 37° C. with human liver microsomes. All assays are carried out on a robotic system in 384-well plates. Test compounds are directly spotted into incubation plates from DMSO stocks by acoustic liquid dispensing (using the Labyte ECHO® system). The final incubation volume contains TRIS buffer (0.1 M), $MgCl_2$ (5 mM), human liver microsomes, specific cytochrome P450 isoenzyme-substrate and the test compound at five different concentrations or no compound (high control) in duplicate (e.g. highest concentration 50 NM with subsequent serial 1:4 dilutions). Following a short preincubation period, reactions are started with the cofactor (NADPH, 1 mM) and stopped by cooling the incubation down to 8° C. and subsequently by addition of one volume of acetonitrile. An internal standard solution—usually the stable isotope of the formed metabolite—is added after quenching of incubations. Peak area analyte (=metabolite formed) and internal standard is determined by LC-MS/MS. The resulting peak area ratio analyte to internal standard in these incubations is compared to a control activity containing no test compound. Within each of the assay runs, the $IC_{50}$ of a positive control inhibitor is determined. Experimental IC50 values are calculated by least square regression according to the following equation:

$$\%\ \text{control activity}=(100\%\ \text{control activity}/(1+(I/IC_{50})S)))-b$$

with

I=inhibitor concentration

S=slope factor

B=background activity

If the inhibition of the reaction is already >50% at the lowest concentration of the test compound, the $IC_{50}$ is assigned "<lowest concentration tested" (usually <0.2 μM). If the inhibition of the reaction is still <50% at the highest concentration of the test compound, the IC50 is assigned ">highest concentration tested" (usually >50 μM).

Evaluation of Mechanism-Based Inhibition (MBI) of Cytochrome P450 3A4-Catalysed Midazolam Turnover The mechanism-based inhibition towards CYP3A4 is assayed in human liver microsomes (0.02 mg/ml) with Midazolam (15 uM) as a substrate.

The test compounds are preincubated at 37° C. in presence of NADPH with human liver microsomes (0.2 mg/ml) at a concentration of 5 uM and 25 uM for 0 min, 10 min or 30 min. After preincubation, the incubate is diluted 1:10 and the substrate Midazolam is added for the main incubation (15 min). The main incubation is quenched with acetonitrile and the formation of Hydroxy-Midazolam is quantified via LC/MS-MS.

The turnover rates in pmol/min/mg protein are calculated and the activity after 10 and 30 min preincubation time is compared to that of the 0 min preincubation of the respective compound/concentration (% CTRL=% of the 0 min control of the respective compound/concentration). Additionally, the turnover rate is expressed relative to the turnover rate of the substrate reaction without compound added (% TR=% of the turnover rate without compound), in order to recognize competitive inhibition effects.

Methods of Treatment

In another aspect of the present invention, it is found that compounds of formula (I) or pharmaceutically acceptable salts thereof possess suitable properties for use in therapy and/or prevention, i.e. for use as medicaments. In particular, compounds of formula (I) or pharmaceutically acceptable salts thereof, as well as pharmaceutical compositions containing the same, may be useful for the treatment, i.e. therapy and/or prevention (prophylaxis), of diseases or conditions, which can be influenced by the inhibition of plasma kallikrein, e.g. which are mediated by unwanted PKK activity or in which inhibition of PKK is beneficial, in a patient.

Diseases and conditions which can be influenced by the inhibition of PKK, e.g. which are mediated by unwanted PKK activity or in which inhibition of PKK is beneficial, are, for instance, those mentioned in section Background of the Invention, in particular diabetic complications, diabetic retinopathy, proliferative and non-proliferative retinopathy, diabetic macular edema (DME), clinically significant macular edema (CSME), cystoid macular edema (CME), CME following cataract extraction, CME induced by cryotherapy, CME induced by uveitis, endophthalmitis, CME following vascular occlusion (e.g. central retinal vein occlusion, branch retinal vein occlusion, or hemiretinal vein occlusion), retinal edema, complications related to cataract surgery in diabetic retinopathy, hypertensive retinopathy, retinal trauma, dry and wet age-related macular degeneration (AMD), polypoidal choroidal vasculopathy (PCV), choroidal neovascularization (CNV; e.g. non-exudative choroidal neovascularization), hereditary angioedema (HAE), acute respiratory distress syndrome (ARDS), hemorrhage and edema after stroke, e.g. brain edema after stroke, vascular dementia, Alzheimer's disease, fibrotic disease, colitis, arthritis and renal injury.

Thus, the compounds and pharmaceutical compositions of the present invention are particularly suitable for treating ocular diseases including diabetic retinopathy, proliferative and non-proliferative retinopathy, diabetic macular edema (DME), retinal vein occlusion, age-related macular degeneration (AMD), polypoidal choroidal vasculopathy (PCV) and choroidal neovascularization (CNV; e.g. non-exudative choroidal neovascularization).

In addition, the compounds and pharmaceutical compositions according to the invention are particularly suitable for the treatment of edema, such as hereditary angioedema (HAE) and brain edema after stroke.

In particular, the compounds and pharmaceutical compositions according to the invention are suitable for the treatment of diabetic retinopathy, proliferative and non-proliferative retinopathy, diabetic macular edema (DME), age-related macular degeneration (AMD), polypoidal choroidal vasculopathy (PCV), choroidal neovascularization (CNV), hereditary angioedema (HAE), and brain edema after stroke.

The compounds and pharmaceutical compositions according to the invention are most particularly suitable for treating diabetic macular edema (DME), wet age-related macular degeneration (AMD), non-exudative choroidal neovascularization (CNV), hereditary angioedema (HAE), and brain edema after stroke.

For instance, they are particularly suitable for the prevention of diabetic macular edema (DME), wet age-related macular degeneration (AMD), hereditary angioedema (HAE), and brain edema after stroke as well as for the prevention of the conversion from non-exudative choroidal neovascularization (neCNV) to exudative choroidal neovascularization (eCNV).

The dose range of the compounds of formula (I) applicable per day is usually from 0.01 to 10 mg per kg body weight. The actual therapeutically effective amount or therapeutic dosage will of course depend on factors known by those skilled in the art such as age and weight of the patient, route of administration and severity of disease. In any case the compound or composition will be administered at dosages and in a manner which allows a therapeutically effective amount to be delivered based upon patient's unique condition.

The compounds and compositions, including any combinations with one or more additional therapeutic agents, according to the invention may be administered by oral, intravitreal, transdermal, inhalative, parenteral or sublingual route. Of the possible methods of administration, oral or intravitreal administration is preferred. In case of intravitreal injection the preferred dose should not exceed 5 mg per eye.

The patient to be treated is preferably a mammal, most preferably a human patient.

Thus, in another aspect, the present invention provides a compound of formula (I) and its tautomers, including pharmaceutically acceptable salts thereof, for use as a medicament.

In another aspect, the present invention provides a method for the treatment of a disease or condition, which is mediated by unwanted plasma kallikrein activity or in which inhibition of plasma kallikrein is beneficial, in a patient in need thereof.

Likewise, the present invention provides a compound of formula (I) and/or its tautomers or a pharmaceutically acceptable salt thereof for use in a method for the treatment of a disease or condition, which is mediated by unwanted plasma kallikrein activity or in which inhibition of plasma kallikrein is beneficial, in a patient in need thereof.

Likewise, the present invention provides the use of a compound of formula (I) and/or its tautomers or a pharmaceutically acceptable salt thereof, in the manufacture of a medicament for use in a method for the treatment of a disease or condition, which is mediated by unwanted plasma kallikrein activity or in which inhibition of plasma kallikrein is beneficial, in a patient in need thereof.

Likewise, the present invention provides the use of a compound of formula (I) and/or its tautomers or a pharmaceutically acceptable salt thereof, in a method for the treatment of a disease or condition, which is mediated by unwanted plasma kallikrein activity or in which inhibition of plasma kallikrein is beneficial, in a patient in need thereof.

According to one embodiment, the method for the treatment comprises administering to the patient one or more compounds of formula (I) and/or its tautomers or pharmaceutically acceptable salts thereof, preferably administering to the patient a therapeutically effective amount of one or more compounds of formula (I) and/or its tautomers or pharmaceutically acceptable salts thereof.

According to another embodiment, the method for the treatment comprises administering to the patient a pharmaceutical composition according to the present invention.

According to one embodiment, the disease or condition, which is mediated by unwanted plasma kallikrein activity or in which inhibition of plasma kallikrein is beneficial, is selected from ophthalmic indications such as diabetic retinopathy, proliferative and non-proliferative retinopathy, diabetic macular edema (DME), age-related macular degeneration (AMD), polypoidal choroidal vasculopathy (PCV) and choroidal neovascularization (CNV).

According to another embodiment, the disease or condition, which is mediated by unwanted plasma kallikrein activity or in which inhibition of plasma kallikrein is beneficial, is selected from edema-associated diseases such as hereditary angioedema (HAE) and brain edema after stroke.

According to another embodiment, the disease or condition, which is mediated by unwanted plasma kallikrein activity or in which inhibition of plasma kallikrein is beneficial, is selected from diabetic complications such as retinal vascular permeability associated with diabetic retinopathy and diabetic macular edema.

According to one embodiment, the patient is a human patient.

Pharmaceutical Compositions

In another aspect of the present invention, it is described that a compound of the invention or a pharmaceutically acceptable salt thereof may be used as active ingredients in pharmaceutical compositions.

Suitable preparations for administering the compounds of the invention, optionally in combination with one or more further therapeutic agents, will be apparent to those with ordinary skill in the art and include for example tablets, pills, capsules, suppositories, lozenges, troches, solutions, syrups, elixirs, sachets, injectables, inhalatives and powders etc. Oral formulations, particularly solid forms such as e.g. tablets or capsules are preferred. For intravitreal injection, solutions are preferred. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula (I) with known excipients, for example inert diluents, carriers, disintegrants, adjuvants, surfactants, binders and/or lubricants. The tablets may also consist of several layers. The particular excipients, carriers and/or diluents that are suitable for the desired preparations will be familiar to the skilled person on the basis of his specialist knowledge. The preferred ones are those that are suitable for the particular formulation and method of administration that are desired. The preparations or formulations according to the invention may be prepared using methods known per se that are familiar to the skilled person, such as for example by mixing or combining at least one compound of formula (I) according to the invention, or a pharmaceutically acceptable salt of such a compound, and one or more excipients, carriers and/or diluents.

Thus, according to another aspect of the present invention, pharmaceutical compositions comprising one or more compounds of formula (I) and/or their tautomers, or pharmaceutically acceptable salts thereof, optionally together with one or more inert carriers and/or diluents are provided.

Also, a pharmaceutical composition that comprises one or more of the above-mentioned compounds, or pharmaceutically acceptable salts thereof, optionally together with one or more inert carriers and/or diluents is provided for use in a method for the treatment of diseases or conditions which are mediated by unwanted plasma kallikrein activity or in which inhibition of plasma kallikrein is beneficial, in a patient in need thereof.

In particular, the invention provides a pharmaceutical composition according to this invention for use in a method for the treatment of ophthalmic indications such as diabetic retinopathy, proliferative and non-proliferative retinopathy, diabetic macular edema (DME), age-related macular degeneration (AMD), polypoidal choroidal vasculopathy (PCV) and choroidal neovascularization (CNV) and of edema-associated diseases such as hereditary angioedema (HAE) and brain edema after stroke.

Furthermore, the present invention relates to the use of a pharmaceutical composition according to this invention for the treatment of diseases or conditions which are mediated by unwanted plasma kallikrein activity in a patient, preferably in a human.

Also, the present invention relates to the use of a pharmaceutical composition according to this invention for the treatment of diseases or conditions in which inhibition of plasma kallikrein is beneficial in a patient, preferably in a human.

According to another embodiment, a pharmaceutical composition comprising one or more compounds of formula (I) and/or their tautomers, or pharmaceutically acceptable salts thereof, and one or more additional therapeutic agents, optionally together with one or more inert carriers and/or diluents is provided.

Preferably, this composition comprises one compound of formula (I) and/or its tautomers or a pharmaceutically acceptable salt thereof and one or more additional therapeutic agents.

Combination Therapy

The compounds of the invention may further be combined with one or more, preferably one additional therapeutic agent.

According to one embodiment the additional therapeutic agent is selected from the group of therapeutic agents useful in the treatment of diseases or conditions described hereinbefore, in particular associated with metabolic diseases or conditions such as for example diabetes mellitus, obesity, diabetic complications, hypertension, hyperlipidemia, or therapeutic agents useful for the treatment of ocular diseases.

Additional therapeutic agents which are suitable for such combinations include in particular those which for example potentiate the therapeutic effect of one or more active substances with respect to one of the indications mentioned and/or which allow the dosage of one or more active substances to be reduced.

Therefore a compound of the invention may be combined with one or more additional therapeutic agents selected from the group consisting of antidiabetic agents, agents for the treatment of overweight and/or obesity, agents for the treatment of high blood pressure, heart failure and/or atherosclerosis and agents for the treatment of ocular diseases. Antidiabetic agents are for example metformin, sulphonylureas, nateglinide, repaglinide, thiazolidinediones, PPAR-(alpha, gamma or alpha/gamma) agonists or modulators, alpha-glucosidase inhibitors, DPPIV inhibitors, SGLT2-inhibitors, insulin and insulin analogues, GLP-1 and GLP-1 analogues or amylin and amylin analogues, cycloset, 11β-HSD inhibitors. Other suitable combination partners are inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, alpha2-antagonists, CCR-2 antagonists or glucokinase activators. One or more lipid lowering agents are also suitable as combination partners, such as for example HMG-CoA-reductase inhibitors, fibrates, nicotinic acid and the derivatives thereof, PPAR-(alpha, gamma or alpha/gamma) agonists or modulators, PPAR-delta agonists, ACAT inhibitors or cholesterol absorption inhibitors such as, bile acid-binding substances such as, inhibitors of ileac bile acid transport, MTP inhibitors, or HDL-raising compounds such as CETP inhibitors or ABC1 regulators.

Therapeutic agents for the treatment of overweight and/or obesity are for example antagonists of the cannabinoid1 receptor, MCH-1 receptor antagonists, MC4 receptor agonists, NPY5 or NPY2 antagonists, β3-agonists, leptin or leptin mimetics, agonists of the 5HT2c receptor.

Therapeutic agents for the treatment of high blood pressure, chronic heart failure and/or atherosclerosis are for example A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Angiotensin II receptor antagonists are preferably used for the treatment or prevention of high blood pressure and complications of diabetes, often combined with a diuretic such as hydrochlorothiazide.

Therapeutic agents for the treatment of ocular diseases may include for example intravitreally administered corticosteroids, intravitreally administered anti-VEGF therapy, anti-Ang2 inhibitors, dual anti-VEGF/anti-Ang2 inhibitors, anti PDGF, dual anti-VEGF/anti-PDGF, VAP-1 (AOC3) inhibitors, Complement inhibitors (e.g. Complement factors 3, 5, B, and D inhibitors), Bradykinin receptor 1 antagonists, CCR-2 antagonists.

Additional treatments for ocular diseases may include laser coagulation therapy.

Preferably, compounds of the present invention and/or pharmaceutical compositions comprising a compound of the present invention optionally in combination with one or more additional therapeutic agents are administered in conjunction with exercise and/or a diet.

The dosage for the combination partners mentioned above is usually ⅕ of the lowest dose normally recommended up to 1/1 of the normally recommended dose.

The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Thus, according to another aspect, this invention relates to a pharmaceutical composition which comprises one or more compounds according to the invention and one or more additional therapeutic agents described hereinbefore and hereinafter, optionally together with one or more inert carriers and/or diluents.

According to another aspect, the present invention provides a method for the treatment of a disease or condition, which is mediated by unwanted plasma kallikrein activity or in which inhibition of plasma kallikrein is beneficial, in a patient in need thereof, the method comprising administering to the patient one or more compounds of formula (I) and/or its tautomers or pharmaceutically acceptable salts thereof, in combination with one or more additional therapeutic agents described in hereinbefore and hereinafter, preferably administering to the patient a therapeutically effective amount of one or more compounds of formula (I) and/or its tautomers or pharmaceutically acceptable salts thereof, in combination with a therapeutically effective amount of one or more additional therapeutic agents described in hereinbefore and hereinafter.

Likewise, the present invention provides a compound of formula (I) and/or its tautomers or a pharmaceutically acceptable salt thereof in combination with one or more additional therapeutic agents described hereinbefore or hereinafter for use in a method for the treatment of a disease or condition, which is mediated by unwanted plasma kallikrein activity or in which inhibition of plasma kallikrein is beneficial, in a patient in need thereof.

Likewise, the present invention provides the use of a compound of formula (I) and/or its tautomers or a pharmaceutically acceptable salt thereof, in combination with one or more additional therapeutic agents described hereinbefore or hereinafter, in the manufacture of a medicament for use in a method for the treatment of a disease or condition, which is mediated by unwanted plasma kallikrein activity or in which inhibition of plasma kallikrein is beneficial, in a patient in need thereof.

Likewise, the present invention provides the use of a compound of formula (I) and/or its tautomers or a pharmaceutically acceptable salt thereof, in combination with one or more additional therapeutic agents described hereinbefore or hereinafter, in a method for the treatment of a disease or condition, which is mediated by unwanted plasma kallikrein activity or in which inhibition of plasma kallikrein is beneficial, in a patient in need thereof.

According to one embodiment, the method for the treatment comprises administering to the patient one or more compounds of formula (I) and/or its tautomers or pharmaceutically acceptable salts thereof, in combination with one or more additional therapeutic agents described in hereinbefore and hereinafter, preferably administering to the patient a therapeutically effective amount of one or more compounds of formula (I) and/or its tautomers or pharmaceutically acceptable salts thereof, in combination with a therapeutically effective amount of one or more additional therapeutic agents described in hereinbefore and hereinafter.

According to another embodiment, the method for the treatment comprises administering to the patient a pharmaceutical composition comprising one or more compounds according to the invention and one or more additional therapeutic agents described hereinbefore and hereinafter, optionally together with one or more inert carriers and/or diluents.

According to one embodiment, the one or more additional therapeutic agents are selected from antidiabetic agents, agents for the treatment of overweight and/or obesity, agents for the treatment of high blood pressure, heart failure and/or atherosclerosis and agents for the treatment of ocular diseases, in particular from those agents specifically mentioned above.

According to one embodiment, the disease or condition, which is mediated by unwanted plasma kallikrein activity or in which inhibition of plasma kallikrein is beneficial, is selected from ophthalmic indications such as diabetic retinopathy, proliferative and non-proliferative retinopathy, diabetic macular edema (DME), age-related macular degeneration (AMD), polypoidal choroidal vasculopathy (PCV) and choroidal neovascularization (CNV); from edema-associated diseases such as hereditary angioedema (HAE) and brain edema after stroke; or from diabetic complications such as retinal vascular permeability associated with diabetic retinopathy and diabetic macular edema.

According to one embodiment, the patient is a human patient.

Other features and advantages of the present invention will become apparent from the following more detailed Examples which illustrate, by way of example, the principles of the invention.

EXAMPLES AND EXPERIMENTAL DATA

The following examples are for the purpose of illustration of the invention only and are not intended in any way to limit the scope of the present invention.

Abbreviations

Ac acetyl
ACN acetonitrile
AMC 7-amino-4-methylcoumarin
Boc tert-butyloxycarbonyl
BSA bovine serum albumin
Bzl benzyl
d day(s)
DAD diode array detector
DBAD di-tert-butyl azodicarboxylate
DBU 1,8-diazabicyclo[5.4.0]undec-7-ene
DBN 1,5-diazabicyclo[4.3.0]non-5-ene
DCM dichloromethane
DEAD diethyl azodicarboxylate
DIAD diisopropyl azodicarboxylate
DIPEA N,N-diisopropylethylamine
DMEM Dulbecco's modified eagle medium
DMF N,N-dimethylformamide
DMSO dimethyl sulfoxide
EDTA ethylenediaminetetraacetate
ESI electrospray ionization (in MS)
EtOAc ethyl acetate
EtOH ethanol
h hour(s)
HATU O-(7-azabenzotriazol-1-yl)-N,N,N',N'-tetramethyluronium-hexafluorophosphate
HPLC high performance liquid chromatography
HPLC-MS coupled high performance liquid chromatography-mass spectrometry
LC liquid chromatography
LC-MS coupled liquid chromatography—mass spectrometry
LG leaving group
M molar (mol/L)
MeOH methanol
min minute(s)
MS mass spectrometry
NADPH nicotinamide adenine dinucleotide phosphate
NMP N-methyl-2-pyrrolidone
NMR nuclear magnetic resonance
PET polyethylene terephthalate
PyBop (benzotriazol-1-yloxy)tripyrrolidinophosphonium hexafluorophosphate
Rf retardation factor
RFU relative fluorescence units
RP reverse phase
rt room temperature
$t_R$ retention time (in HPLC/LC)
SFC supercritical fluid chromatography
TBTU O-(benzotriazol-1-yl)-N,N,N',N'-tetramethyluronium tetrafluoroborate
TFA trifluoroacetic acid
THF tetrahydrofuran
UV ultraviolet The terms "ambient temperature" and "room temperature" are used interchangeably and designate a temperature of about 20° C., e.g. 15 to 25° C.

As a rule, $^1$H-NMR and/or mass spectra have been obtained for the compounds prepared.

Unless otherwise specified, compounds containing chiral centers have the stereochemistry depicted. The assignment of stereochemistry has been made either by use of a chiral starting material of known stereochemistry, by stereoselective synthesis of known stereochemistry or by biological activity.

Analytical Methods

| | |
|---|---|
| Method: | 1 |
| Device: | Agilent 1200 with DA- and MS-Detector |
| Column: | XBridge C18, 3 × 30 mm, 2.5 μm |
| Column Supplier: | Waters |

| Gradient/ Solvent Time [min] | % Solvent [$H_2O$, 0.1% NH3] | % Solvent [ACN] | Flow [mL/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| | |
|---|---|
| Method: | 2 |
| Device: | Agilent 1200 with DA- and MS-Detector |
| Column: | Sunfire C18, 3 × 30 mm, 2.5 μm |
| Column Supplier: | Waters |

| Gradient/ Solvent Time [min] | % Solvent [$H_2O$, 0.1% TFA] | % Solvent [ACN] | Flow [mL/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| | |
|---|---|
| Method: | 3 |
| Device: | Agilent 1260 SFC with DA- and MS-Detector |
| Column: | CHIRAL ART ® Cellulose SC, 4.6 × 250 mm, 5 μm |
| Column Supplier: | YMC |

| Gradient/ Solvent Time [min] | % Solvent [$scCO_2$] | % Solvent [MeOH, 20 mM $NH_3$] | Flow [mL/min] | Temperature [° C.] | Back pressure [PSI] |
|---|---|---|---|---|---|
| 0.00 | 65.0 | 35.0 | 4.0 | 40.0 | 2175.0 |
| 10.0 | 65.0 | 35.0 | 4.0 | 40.0 | 2175.0 |

| | |
|---|---|
| Method: | 4 |
| Device: | Waters Acquity, QDa Detector |
| Column: | XBridge C18, 3 × 30 mm, 2.5 μm |
| Column Supplier: | Waters |

| Gradient/ Solvent Time [min] | % Solvent [$H_2O$, 0.1% NH3] | % Solvent [ACN] | Flow [mL/min] | Temperature [° C.] |
|---|---|---|---|---|
| 0.00 | 95 | 5 | 1.5 | 60 |
| 1.30 | 0 | 100 | 1.5 | 60 |
| 1.50 | 0 | 100 | 1.5 | 60 |
| 1.60 | 95 | 5 | 1.5 | 60 |

| | |
|---|---|
| Method: | 5 |
| Device: | Waters Acquity, QDa Detector |
| Column: | XBridge C18, 3 × 30 mm, 2.5 μm |
| Column Supplier: | Waters |

| Gradient/ Solvent Time [min] | % Solvent [$H_2O$, 0.1% NH3] | % Solvent [ACN] | Flow [mL/min] | Temperature [° C.] |
|---|---|---|---|---|
| 0.00 | 95 | 5 | 1.5 | 60 |
| 1.30 | 0 | 100 | 1.5 | 60 |
| 1.50 | 0 | 100 | 1.5 | 60 |
| 1.60 | 95 | 5 | 1.5 | 60 |

Synthesis of Intermediates:

The starting materials and intermediates that are used in the processes leading to the compounds according to the invention are either commercially available or they may be prepared by methods (or by analogous or similar methods to those) described in the following or already known to those skilled in the art from the literature, e.g. from WO 2017/072020, WO 2017/072021 and WO 2018/192866 which are hereby incorporated by reference in their entirety.

Intermediate 1

(4R)-1-Methyl-1H,4H,5H,6H-cyclopenta[d]imidazol-4-amine dihydrochloride

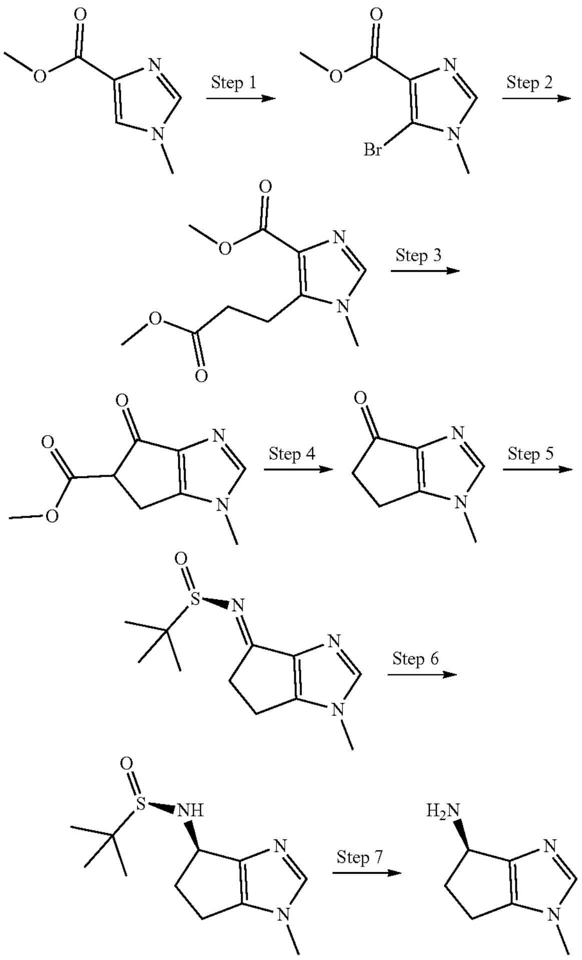

Step 1: Methyl 5-bromo-1-methyl-1H-imidazole-4-carboxylate

Under argon atmosphere methyl 1-methyl-1H-imidazole-4-carboxylate (19.1 g) is dissolved in DCM (230 mL). N-Bromosuccinimide (29.1 g), sodium persulfate ($Na_2S_2O_8$, 64.9 g) and palladium-II-acetate ($Pd(OAc)_2$, 3.1 g) are added successively and the mixture is cooled to 0° C. Trifluoromethanesulfonic acid ($CF_3$—$SO_3H$, 42.2 mL) is added dropwise and thereafter the mixture is heated to 60° C. for 20 h. The mixture is diluted with DCM, cooled to 0° C. and treated carefully with saturated aqueous $Na_2CO_3$ until a pH-value of 8 is reached. The mixture is partitioned between water and DCM. The aqueous phase is extracted with DCM and the combined organic phases are dried ($MgSO_4$) and concentrated in vacuo. The residue is chromatographed on silica gel (EtOAc/MeOH 85:15→70:30). The product thus obtained is triturated with tert.-butyl-methyl-ether (50 mL) to give the title compound.

LC (Method 1): $t_R$=0.69 min; Mass spectrum ($ESI^+$): m/z=219 $[M+H]^+$.

Step 2: Methyl 5-(3-methoxy-3-oxopropyl)-1-methyl-1H-imidazole-4-carboxylate

Methyl 5-bromo-1-methyl-1H-imidazole-4-carboxylate (10.6 g) is dissolved in dimethylacetamide (80 mL) and water (20 mL). 3,3-Dimethoxyprop-1-ene (8.6 mL) and N-methyldicyclohexylamin (15.3 mL) are added and the mixture is purged for 5 minutes with argon. Dichlorobis(tri-o-tolylphosphine)palladium(II) ($PdCl_2[P(o\text{-}Tol)_3]_2$, 1.9 g) is added and the mixture is stirred for 3 h at 120° C. Then the mixture is partitioned between water and EtOAc and filtered over celite. The aqueous phase is mixed with saturated aqueous $NaHCO_3$ and extracted for 4 times with EtOAc. The combined organic phases are dried ($MgSO_4$) and concentrated in vacuo. The residue is chromatographed on silica gel (EtOAc/MeOH 90:10→70:30) to give the title compound.

LC (Method 2): $t_R$=0.55 min; Mass spectrum ($ESI^+$): m/z=227 $[M+H]^+$.

Step 3: Methyl 1-methyl-4-oxo-1H,4H,5H,6H-cyclopenta[d]imidazole-5-carboxylate

Under argon atmosphere methyl 5-(3-methoxy-3-oxopropyl)-1-methyl-1H-imidazole-4-carboxylate (4.5 g) is dissolved in THF (100 mL) and treated with potassium bis (trimethylsilyl)amide (40 mL of a 1 M solution in THF). The mixture is stirred for 30 minutes and then poured into a cooled mixture of EtOAc (800 mL) and acetic acid (7 mL). After stirring for 40 minutes the mixture is filtered. The solvents are evaporated in vacuo to give the title compound.

LC (Method 1): $t_R$=0.25 min; Mass spectrum ($ESI^+$): m/z=195 $[M+H]^+$.

Step 4: 1-Methyl-1H,4H,5H,6H-cyclopenta[d]imidazol-4-one

A solution of methyl 1-methyl-4-oxo-1H,4H,5H,6H-cyclopenta[d]imidazole-5-carboxylate (4.0 g) in 1,4-dioxane (150 mL) and water (15 mL) is heated under reflux for 90 h. The solvents are evaporated in vacuo to give the title compound. LC (Method 1): $t_R$=0.16 min; Mass spectrum ($ESI^+$): m/z=137 $[M+H]^+$.

Alternatively, the reaction can be conducted by heating the starting material in a mixture of hydrogen chloride and acetic acid at 120° C. After completion of the reaction the solvents are evaporated in vacuo. The residue is dissolved in MeOH and treated with $K_2CO_3$ until a pH-value of 8 is reached. The mixture is filtered, concentrated and chromatographed on silica gel (DCM/MeOH 20:1→5:1) to give the title compound.

Step 5: (R)-2-Methyl-N-[(4E)-1-methyl-1H,4H,5H,6H-cyclopenta[d]imidazol-4-ylidene]propane-2-sulfinamide 1-Methyl-1H,4H,5H,6H-cyclopenta[d]imidazol-4-one (2.94 g), toluene (120 mL) and titanium tetraethoxide ($Ti(OEt)_4$, 13.6 mL) are stirred for 15 minutes and then treated with (R)-2-methylpropane-2-sulfinamide (5.25 g). The mixture is heated for 4 h at reflux, cooled to rt and treated with saturated aqueous NaCl (30 mL). The mixture is stirred for 1 h and then filtered over celite. For two times the filter cake is stirred 10 minutes in MeOH (20 mL) and filtered over celite. The combined organic phases are concentrated and the residue is chromatographed on silica gel (DCM/MeOH 95:5). The product thus obtained is triturated from EtOAc to give the title compound.

LC (Method 3): $t_R$=3.69 min; Mass spectrum ($ESI^+$): m/z=240 $[M+H]^+$.

Step 6: (R)-2-Methyl-N-[(4R)-1-methyl-1H,4H,5H,6H-cyclopenta[d]imidazol-4-yl]propane-2-sulfinamide L-Selectride (1 M in THF, 45 mL) is dissolved in THF (75 mL) and treated portionwise with (R)-2-methyl-N-[(4E)-1-methyl-1H,4H,5H,6H-cyclopenta[d]imidazol-4-ylidene] propane-2-sulfinamide (7.2 g). The mixture is stirred for 1 h and then treated dropwise with MeOH (5 mL). The solvents are evaporated in vacuo and the residue is chromatographed on silica gel (DCM/MeOH 95:5→80:20) to give the title compound.

LC (Method 2): $t_R$=0.55 min; Mass spectrum ($ESI^+$): m/z=242 $[M+H]^+$. LC (Method 3): $t_R$=3.71 min.

Step 7: (4R)-1-Methyl-1H,4H,5H,6H-cyclopenta[d]imidazol-4-amine dihydrochloride

A mixture of (R)-2-methyl-N-[(4R)-1-methyl-1H,4H,5H,6H-cyclopenta[d]imidazol-4-yl]propane-2-sulfinamide (7.25 g) in isopropanol (50 mL) is treated with a 1.25 M solution of HCl in isopropanol (50 mL) and stirred for 2 h. The precipitate is collected by filtration, washed successively with isopropanol and diethylether and dried in vacuo to give the title compound. Mass spectrum ($ESI^+$): m/z=138 $[M+H]^+$.

Intermediate 2

5-{3-Azabicyclo[3.1.0]hexan-3-yl}pyridine-2-carbaldehyde

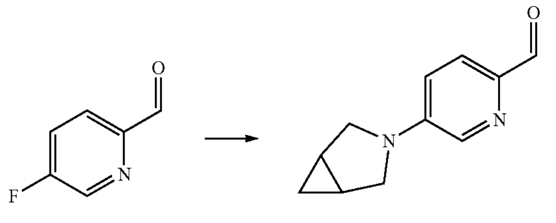 [SMILES: O=Cc1ccc(F)cn1 ; O=Cc1ccc(N2CC3CC3C2)cn1]

5-Fluoropyridine-2-carbaldehyde (1.0 g), 3-azabicyclo[3.1.0]hexane hydrochloride (1.1 g) and $K_2CO_3$ (2.8 g) are suspended in NMP (10 mL) and heated to 120° C. for 2 h. The mixture is cooled to rt, partitioned between water and EtOAc and the phases are separated. The aqueous phase is extracted twice with EtOAc, the combined organic phase are dried ($MgSO_4$) and concentrated. The residue is chromatographed on silica gel (cyclohexane/EtOAc 100:0→60:40) to give the title compound. LC (Method 2): $t_R$=0.68 min; Mass spectrum (ESI+): m/z=189 $[M+H]^+$.

Intermediates 2-1 to 2-4 are prepared in analogy to Intermediate 2:

| Intermediate | Structure | $t_R$ | Mass spectrum (ESI+): m/z $[M + H]^+$ | LC Method |
|---|---|---|---|---|
| 2-1 | 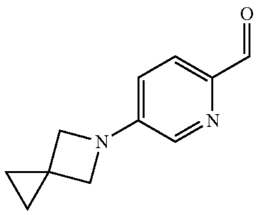 [SMILES: O=Cc1ccc(N2CC3(CC3)C2)cn1] | 0.75 | 189 | Method 2 |
| 2-2 | 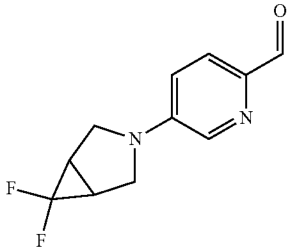 [SMILES: O=Cc1ccc(N2CC3C(C2)C3(F)F)cn1] | 0.73 | 225 | Method 2 |
| 2-3 | 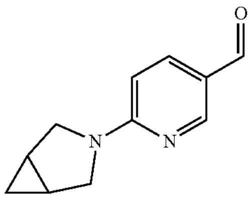 [SMILES: O=Cc1ccc(N2CC3CC3C2)nc1] | 0.82 | 189 | Method 2 |
| 2-4 | 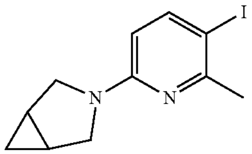 | 1.22 | 301 | Method 1 |

| Intermediate | Reaction comment |
|---|---|
| 2-2 | The reaction is conducted for 12 h at 115° C. |
| 2-3 | The reaction is conducted in DMF for 18 h at rt. |
| 2-4 | The reaction is conducted in DMF for 26 h at 80° C. |

| Intermediate | Name | Name of Starting Material 1 | Name of Starting Material 2 |
|---|---|---|---|
| 2-1 | 5-{5-Azaspiro[2.3]hexan-5-yl}pyridine-2-carbaldehyde | 5-Fluoropyridine-2-carbaldehyde | 5-Azaspiro[2.3]hexane hemioxalate |
| 2-2 | 5-{6,6-Difluoro-3-azabicyclo-[3.1.0]hexan-3-yl}pyridine-2-carbaldehyde | 5-Fluoropyridine-2-carbaldehyde | 6,6-Difluoro-3-azabicyclo-[3.1.0]hexane hydrochloride |
| 2-3 | 6-{3-Azabicyclo[3.1.0]hexan-3-yl}pyridine-3-carbaldehyde | 6-Fluoropyridine-3-carbaldehyde | 3-Azabicyclo[3.1.0]hexane hydrochloride |
| 2-4 | 3-(5-Iodo-6-methylpyridin-2-yl)-3-azabicyclo[3.1.0]hexane | 6-Fluoro-3-iodo-2-methylpyridine | 3-Azabicyclo[3.1.0]hexane hydrochloride |

Intermediate 3

(5-{3-Azabicyclo[3.1.0]hexan-3-yl}pyridin-2-yl) methanol

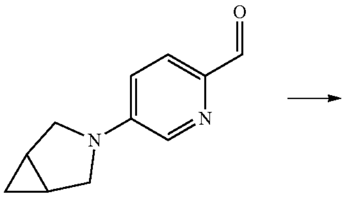

-continued

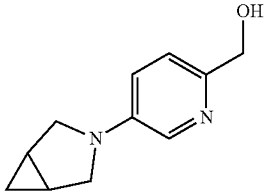

$NaBH_4$ (217 mg) is added portionwise to a ice-cooled mixture of 5-{3-azabicyclo[3.1.0]hexan-3-yl}pyridine-2-carbaldehyde (920 mg) in THF (10 mL) and MeOH (5 mL). The mixture is stirred for 1 h at 0° C., treated with 1 M aqueous HCl (10 mL) and stirred for 30 minutes at rt. Then the mixture is partitioned between saturated aqueous $NaHCO_3$ and EtOAc. The phases are separated. The organic phase is dried ($MgSO_4$) and concentrated to give the title compound. LC (Method 2): $t_R$=0.59 min; Mass spectrum (ESI+): m/z=191 $[M+H]^+$.

Intermediates 3-1 to 3-23 are prepared in analogy to Intermediate 3:

| Intermediate | Structure | $t_R$ | Mass spectrum (ESI+): m/z $[M + H]^+$ | LC Method |
|---|---|---|---|---|
| 3-1 | 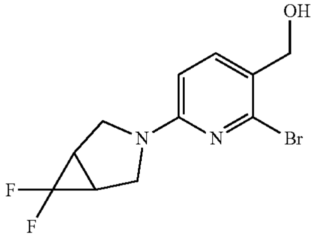 [SMILES: OCc1ccc(N2CC3C(C2)C3(F)F)nc1Br] | 0.94 | 305 | Method 2 |
| 3-2 | 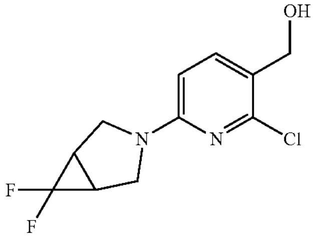 [SMILES: OCc1ccc(N2CC3C(C2)C3(F)F)nc1Cl] | 0.90 | 261 | Method 2 |
| 3-3 | 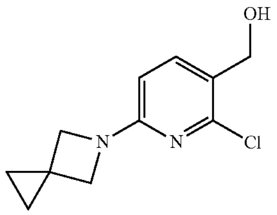 [SMILES: OCc1ccc(N2CC3(CC3)C2)nc1Cl] | 0.87 | 225 | Method 2 |

-continued
| Intermediate | Structure | $t_R$ | Mass spectrum (ESI+): m/z [M + H]$^+$ | LC Method |
|---|---|---|---|---|
| 3-4 | 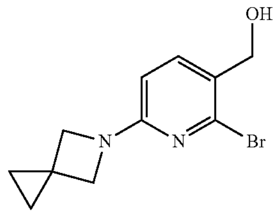 [SMILES: OCc1ccc(N2CC3(CC3)C2)nc1Br] | 0.90 | 269 | Method 2 |
| 3-5 | 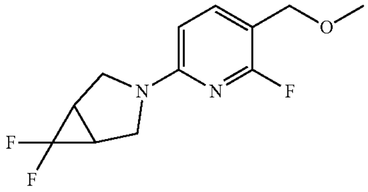 [SMILES: COCc1ccc(N2CC3C(C2)C3(F)F)nc1F] | 1.00 | 259 | Method 2 |
| 3-6 | 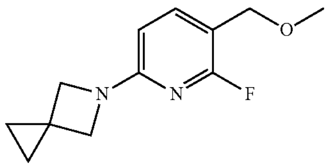 [SMILES: COCc1ccc(N2CC3(CC3)C2)nc1F] | 0.99 | 223 | Method 1 |
| 3-7 | 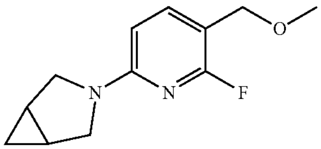 [SMILES: COCc1ccc(N2CC3CC3C2)nc1F] | 1.03 | 223 | Method 2 |
| 3-8 | 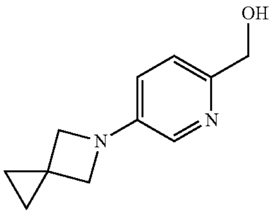 [SMILES: OCc1ccc(N2CC3(CC3)C2)cn1] | 0.60 | 191 | Method 2 |
| 3-9 | 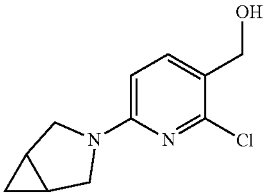 [SMILES: OCc1ccc(N2CC3CC3C2)nc1Cl] | 0.89 | 225 | Method 1 |
| 3-10 | 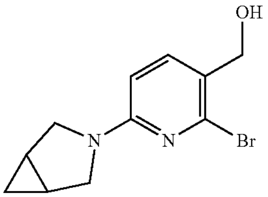 [SMILES: OCc1ccc(N2CC3CC3C2)nc1Br] | 0.94 | 269 | Method 2 |

-continued
| Intermediate | Structure | $t_R$ | Mass spectrum (ESI+): m/z $[M + H]^+$ | LC Method |
|---|---|---|---|---|
| 3-11 | 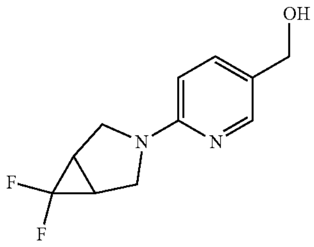 [SMILES: OCc1ccc(N2CC3C(C2)C3(F)F)nc1] | 0.52 | 227 | Method 2 |
| 3-12 | 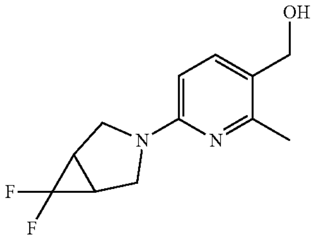 [SMILES: Cc1nc(N2CC3C(C2)C3(F)F)ccc1CO] | 0.59 | 241 | Method 2 |
| 3-13 | 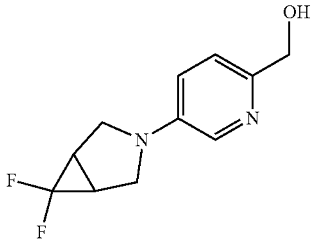 [SMILES: OCc1ccc(N2CC3C(C2)C3(F)F)cn1] | 0.58 | 227 | Method 2 |
| 3-14 | 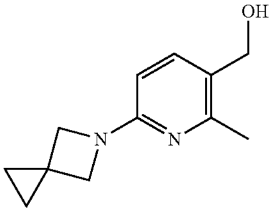 | 0.82 | 205 | Method 1 |
| 3-15 | 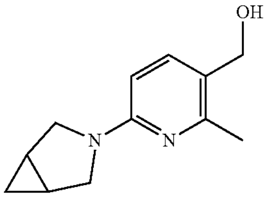 | 0.85 | 205 | Method 1 |
| 3-16 | 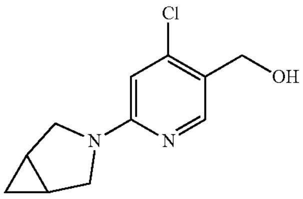 [SMILES: OCc1cnc(N2CC3CC3C2)cc1Cl] | 0.87 | 225 | Method 1 |

-continued
| Intermediate | Structure | $t_R$ | Mass spectrum (ESI+): m/z $[M + H]^+$ | LC Method |
|---|---|---|---|---|
| 3-17 | 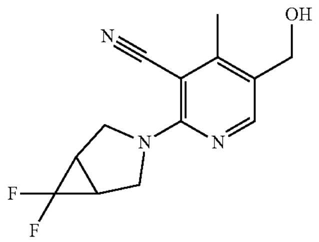 [SMILES: Cc1c(CO)cnc(N2CC3C(C2)C3(F)F)c1C#N] | 0.83 | 266 | Method 2 |
| 3-18 | 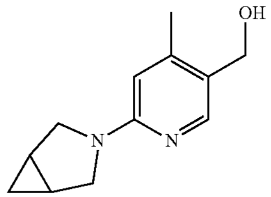 | 0.82 | 205 | Method 1 |
| 3-19 | 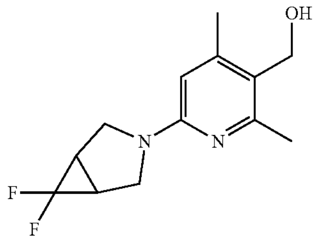 [SMILES: Cc1cc(N2CC3C(C2)C3(F)F)nc(C)c1CO] | 0.62 | 255 | Method 2 |
| 3-20 | 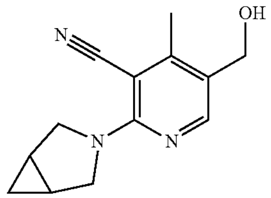 [SMILES: Cc1c(CO)cnc(N2CC3CC3C2)c1C#N] | 0.71 | 230 | Method 2 |
| 3-21 | 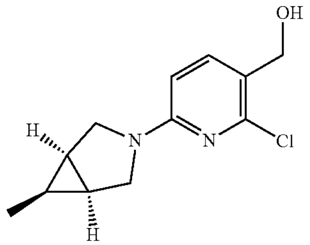 [SMILES: C[C@H]1[C@H]2CN(c3ccc(CO)c(Cl)n3)C[C@@H]12] | 0.96 | 239 | Method 2 |
| 3-22 | 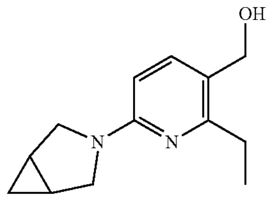 [SMILES: CCc1nc(N2CC3CC3C2)ccc1CO] | 0.60 | 219 | Method 2 |

-continued

| Intermediate | Structure | $t_R$ | Mass spectrum (ESI+): m/z $[M + H]^+$ | LC Method |
| --- | --- | --- | --- | --- |
| 3-23 | 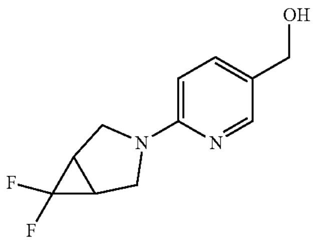 [SMILES: OCc1ccc(N2CC3C(C2)C3(F)F)nc1] | 0.79 | 227 | Method 2 |

| Intermediate | Reaction comment |
| --- | --- |
| 3-1 | The reaction is conducted in EtOH. |
| 3-5 | Methylether is formed during stirring in presence of 1N aqueous HCl. |
| 3-6 | Methylether is formed during stirring in presence of 1N aqueous HCl. |
| 3-7 | Methylether is formed during stirring in presence of 1N aqueous HCl. |
| 3-10 | The reaction is conducted in EtOH. |
| 3-12 | The reaction is conducted in EtOH. |
| 3-14 | The reaction is conducted in THF/EtOH 1:2. |
| 3-15 | The reaction is conducted in EtOH for 2 h at rt. |
| 3-16 | The reaction is conducted for 2 h at 0° C. |
| 3-17 | The reaction is conducted for 30 minutes at rt. |
| 3-18 | The reaction is conducted in EtOH for 1 h at rt. |
| 3-19 | The reaction is conducted for 45 minutes at rt. |
| 3-20 | The reaction is conducted for 45 minutes at 0° C. |
| 3-21 | The reaction is conducted for 1 h at 0° C. |
| 3-22 | The reaction is conducted in EtOH for 1.5 h at rt. |
| 3-23 | The reaction is conducted in EtOH for 1 h at rt. |

| Intermediate | Name | Name of Starting Material |
| --- | --- | --- |
| 3-1 | (2-Bromo-6-{6,6-difluoro-3-azabicyclo-[3.1.0]hexan-3-yl}pyridin-3-yl)methanol | 2-Bromo-6-{6,6-difluoro-3-azabicyclo-[3.1.0]hexan-3-yl}pyridine-3-carbaldehyde |
| 3-2 | (2-Chloro-6-{6,6-difluoro-3-azabicyclo-[3.1.0]hexan-3-yl}pyridin-3-yl)methanol | 2-Chloro-6-{6,6-difluoro-3-azabicyclo-[3.1.0]hexan-3-yl}pyridine-3-carbaldehyde |
| 3-3 | (6-{5-Azaspiro[2.3]hexan-5-yl}-2-chloropyridin-3-yl)methanol | 6-{5-Azaspiro[2.3]hexan-5-yl}-2-chloropyridine-3-carbaldehyde |
| 3-4 | (6-{5-Azaspiro[2.3]hexan-5-yl}-2-bromopyridin-3-yl)methanol | 6-{5-Azaspiro[2.3]hexan-5-yl}-2-bromopyridine-3-carbaldehyde |
| 3-5 | 6,6-Difluoro-3-[6-fluoro-5-(methoxy-methyl)pyridin-2-yl]-3-azabicyclo[3.1.0]hexane | 6-{6,6-Difluoro-3-azabicyclo[3.1.0]hexan-3-yl}-2-fluoropyridine-3-carbaldehyde |
| 3-6 | 5-[6-Fluoro-5-(methoxymethyl)pyridin-2-yl]-5-azaspiro[2.3]hexane | 6-{5-Azaspiro[2.3]hexan-5-yl}-2-fluoropyridine-3-carbaldehyde |
| 3-7 | 3-[6-Fluoro-5-(methoxymethyl)pyridin-2-yl]-3-azabicyclo[3.1.0]hexane | 6-{3-Azabicyclo[3.1.0]hexan-3-yl}-2-fluoropyridine-3-carbaldehyde |
| 3-8 | (5-{5-Azaspiro[2.3]hexan-5-yl}pyridin-2-yl)methanol | 5-{5-Azaspiro[2.3]hexan-5-yl}pyridine-2-carbaldehyde |
| 3-9 | (6-{3-Azabicyclo[3.1.0]hexan-3-yl}-2-chloropyridin-3-yl)methanol | 6-{3-Azabicyclo[3.1.0]hexan-3-yl}-2-chloropyridine-3-carbaldehyde |
| 3-10 | (6-{3-Azabicyclo[3.1.0]hexan-3-yl}-2-bromopyridin-3-yl)methanol | 6-{3-Azabicyclo[3.1.0]hexan-3-yl}-2-bromopyridine-3-carbaldehyde |
| 3-11 | (6-{6,6-Difluoro-3-azabicyclo[3.1.0]hexan-3-yl}pyridin-3-yl)methanol | 6-{6,6-Difluoro-3-azabicyclo[3.1.0]hexan-3-yl}pyridine-3-carbaldehyde |
| 3-12 | (6-{6,6-Difluoro-3-azabicyclo[3.1.0]hexan-3-yl}-2-methylpyridin-3-yl)methanol | 6-{6,6-Difluoro-3-azabicyclo[3.1.0]hexan-3-yl}-2-methylpyridine-3-carbaldehyde |
| 3-13 | (5-{6,6-Difluoro-3-azabicyclo[3.1.0]hexan-3-yl}pyridin-2-yl)methanol | 5-{6,6-Difluoro-3-azabicyclo[3.1.0]hexan-3-yl}pyridine-2-carbaldehyde |
| 3-14 | (6-{5-Azaspiro[2.3]hexan-5-yl}-2-methylpyridin-3-yl)methanol | 6-{5-Azaspiro[2.3]hexan-5-yl}-2-methylpyridine-3-carbaldehyde |
| 3-15 | (6-{3-Azabicyclo[3.1.0]hexan-3-yl}-2-methylpyridin-3-yl)methanol | 6-{3-Azabicyclo[3.1.0]hexan-3-yl}-2-methylpyridine-3-carbaldehyde |

-continued

| Intermediate | Name | Name of Starting Material |
|---|---|---|
| 3-16 | (6-{3-Azabicyclo[3.1.0]hexan-3-yl}-4-chloropyridin-3-yl)methanol | 6-{3-Azabicyclo[3.1.0]hexan-3-yl}-4-chloropyridine-3-carbaldehyde |
| 3-17 | 2-{6,6-Difluoro-3-azabicyclo[3.1.0]hexan-3-yl}-5-(hydroxymethyl)-4-methylpyridine-3-carbonitrile | 2-{6,6-Difluoro-3-azabicyclo[3.1.0]hexan-3-yl}-5-formyl-4-methylpyridine-3-carbonitrile |
| 3-18 | (6-{3-Azabicyclo[3.1.0]hexan-3-yl}-4-methylpyridin-3-yl)methanol | 6-{3-Azabicyclo[3.1.0]hexan-3-yl}-4-methylpyridine-3-carbaldehyde |
| 3-19 | (6-{6,6-Difluoro-3-azabicyclo[3.1.0]hexan-3-yl}-2,4-dimethylpyridin-3-yl)methanol | 6-{6,6-Difluoro-3-azabicyclo[3.1.0]hexan-3-yl}-2,4-dimethylpyridine-3-carbaldehyde |
| 3-20 | 2-{3-Azabicyclo[3.1.0]hexan-3-yl}-5-(hydroxy-methyl)-4-methylpyridine-3-carbonitrile | 2-{3-Azabicyclo[3.1.0]hexan-3-yl}-5-formyl-4-methylpyridine-3-carbonitrile |
| 3-21 | {2-Chloro-6-[(1R,5S,6R)-6-methyl-3-aza-bicyclo[3.1.0]hexan-3-yl]pyridin-3-yl}methanol | 2-Chloro-6-[(1R,5S,6R)-6-methyl-3-azabicyclo[3.1.0]hexan-3-yl]pyridine-3-carbaldehyde |
| 3-22 | (6-{3-Azabicyclo[3.1.0]hexan-3-yl}-2-ethylpyridin-3-yl)methanol | 6-{3-Azabicyclo[3.1.0]hexan-3-yl}-2-ethylpyridine-3-carbaldehyde |
| 3-23 | (6-{6,6-difluoro-3-azabicyclo[3.1.0]hexan-3-yl}pyridin-3-yl)methanol | 6-{6,6-difluoro-3-azabicyclo[3.1.0]hexan-3-yl}-pyridine-3-carbaldehyde |

Intermediate 4

Ethyl 1-[(5-{3-azabicyclo[3.1.0]hexan-3-yl}pyridin-2-yl)methyl]-1H-imidazole-4-carboxylate

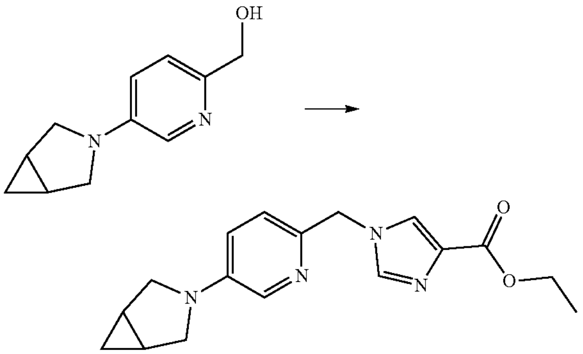

In a microwave vial a mixture of (5-{3-azabicyclo[3.1.0]hexan-3-yl}pyridin-2-yl)methanol (100 mg), ethyl 1H-imidazole-4-carboxylate (77 mg) and p-toluenesulfonic acid (54 mg) in ACN (15 mL) is heated for 5 h to 120° C. After cooling to rt the mixture is partitioned between saturated aqueous $NaHCO_3$ and EtOAc. The aqueous phase is extracted with EtOAc and the combined organic phases are dried ($MgSO_4$) and concentrated. The residue is purified by HPLC on reversed phase (ACN, water) to give the title compound.

LC (Method 2): $t_R$=0.71 min; Mass spectrum (ESI+): m/z=313 $[M+H]^+$.

Intermediates 4-1 to 4-61 are prepared in analogy to Intermediate 4:

| Intermediate | Structure | $t_R$ | Mass spectrum (ESI+): m/z $[M + H]^+$ | LC Method |
|---|---|---|---|---|
| 4-1 | 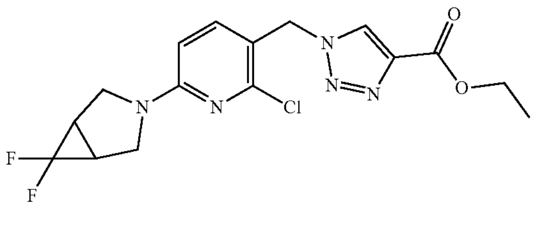 [SMILES: CCOC(=O)c1cn(Cc2ccc(N3CC4C(C3)C4(F)F)nc2Cl)nn1] | 1.02 | 384 | Method 2 |
| 4-2 | 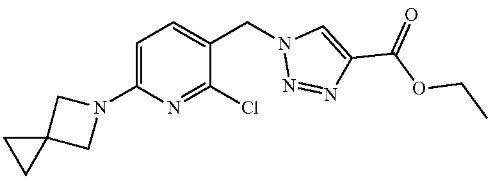 | 1.03 | 348 | Method 2 |

-continued
| Intermediate | Structure | $t_R$ | Mass spectrum (ESI+): m/z $[M + H]^+$ | LC Method |
|---|---|---|---|---|
| 4-3 | 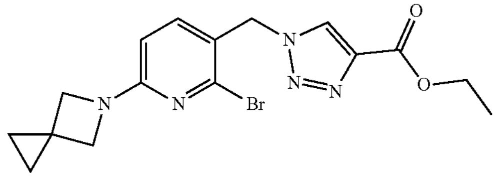 [SMILES: CCOC(=O)c1cn(Cc2ccc(N3CC4(CC4)C3)nc2Br)nn1] | 1.05 | 392 | Method 2 |
| 4-4 | 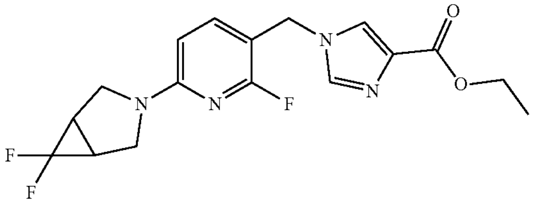 [SMILES: CCOC(=O)c1cn(Cc2ccc(N3CC4C(C3)C4(F)F)nc2F)cn1] | 0.85 | 367 | Method 2 |
| 4-5 | 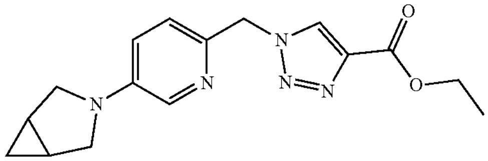 [SMILES: CCOC(=O)c1cn(Cc2ccc(N3CC4CC4C3)cn2)nn1] | 0.94 | 314 | Method 1 |
| 4-6 | 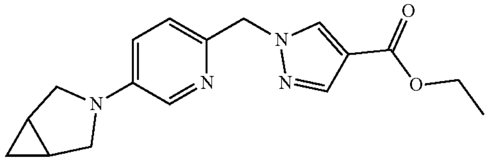 [SMILES: CCOC(=O)c1cnn(Cc2ccc(N3CC4CC4C3)cn2)c1] | 0.76 | 313 | Method 2 |
| 4-7 | 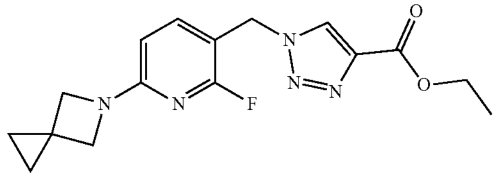 | 1.00 | 332 | Method 2 |
| 4-8 | 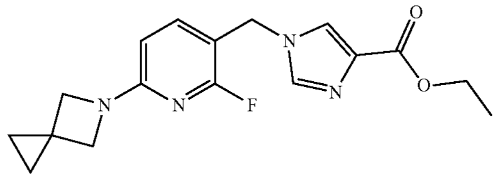 [SMILES: CCOC(=O)c1cn(Cc2ccc(N3CC4(CC4)C3)nc2F)nn1] | 0.95 | 331 | Method 1 |
| 4-9 | 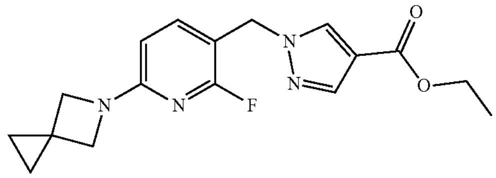 [SMILES: CCOC(=O)c1cnn(Cc2ccc(N3CC4(CC4)C3)nc2F)c1] | 1.06 | 331 | Method 2 |
| 4-10 | 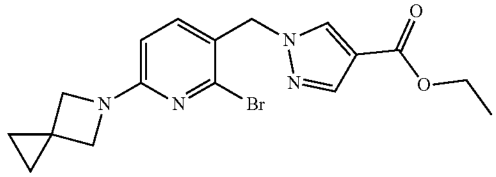 | 1.11 | 391 | Method 2 |

-continued
| Intermediate | Structure | $t_R$ | Mass spectrum (ESI+): m/z $[M + H]^+$ | LC Method |
|---|---|---|---|---|
| 4-11 | 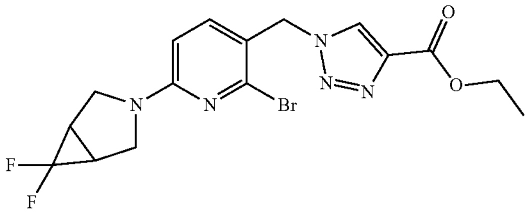 | 1.04 | 428 | Method 2 |
| 4-12 | 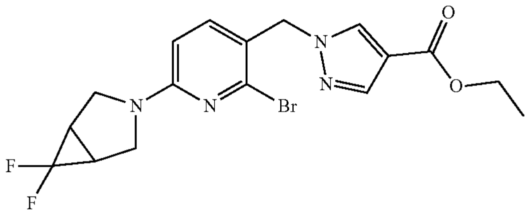 | 1.06 | 427 | Method 2 |
| 4-13 | 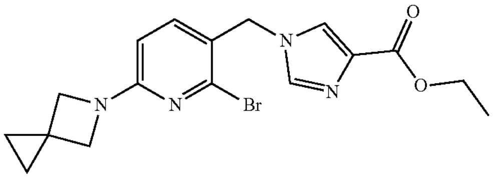 [SMILES: CCOC(=O)c1cn(Cc2ccc(N3CC4(CC4)C3)nc2Br)cn1] | 0.99 | 391 | Method 1 |
| 4-14 | 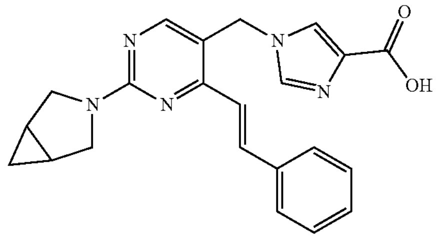 [SMILES: O=C(O)c1cn(Cc2cnc(N3CC4CC4C3)nc2/C=C/c2ccccc2)cn1] | 0.78 | 388 | Method 1 |
| 4-15 | 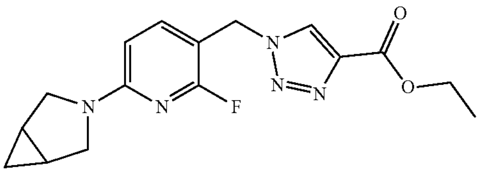 [SMILES: CCOC(=O)c1cn(Cc2ccc(N3CC4CC4C3)nc2F)nn1] | 1.01 | 332 | Method 2 |
| 4-16 | 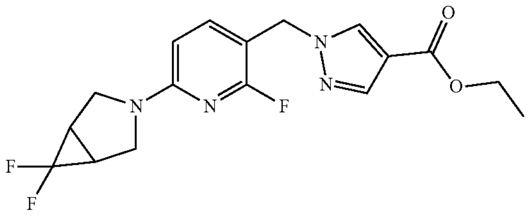 [SMILES: CCOC(=O)c1cnn(Cc2ccc(N3CC4C(C3)C4(F)F)nc2F)c1] | 1.04 | 367 | Method 2 |
| 4-17 | 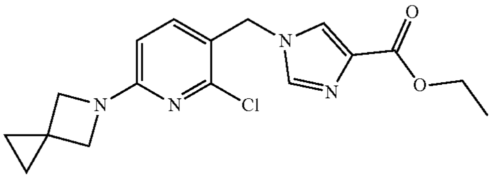 | 0.97 | 347 | Method 1 |

-continued
| Intermediate | Structure | $t_R$ | Mass spectrum (ESI+): m/z $[M + H]^+$ | LC Method |
|---|---|---|---|---|
| 4-18 | 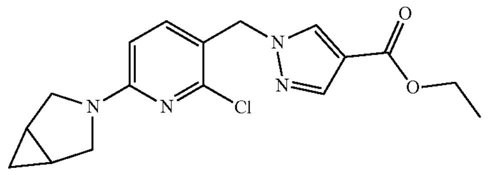 [SMILES: CCOC(=O)c1cnn(Cc2ccc(N3CC4CC4C3)nc2Cl)c1] | 1.08 | 347 | Method 2 |
| 4-19 | 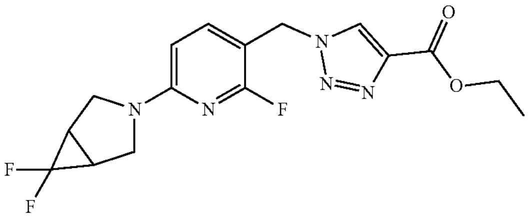 [SMILES: CCOC(=O)c1cn(Cc2ccc(N3CC4C(C3)C4(F)F)nc2F)nn1] | 0.99 | 368 | Method 2 |
| 4-20 | 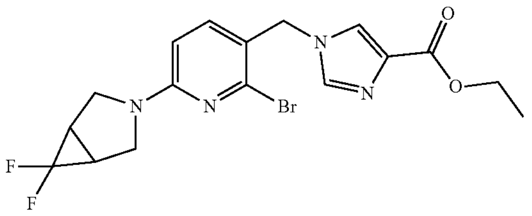 | 0.98 | 427 | Method 1 |
| 4-21 | 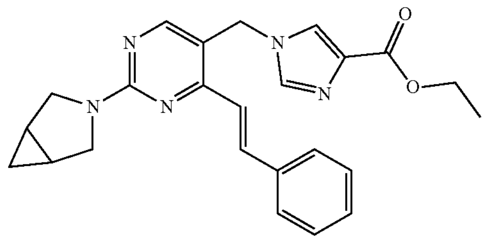 [SMILES: CCOC(=O)c1cn(Cc2cnc(N3CC4CC4C3)nc2/C=C/c2ccccc2)cn1] | 0.93 | 416 | Method 2 |
| 4-22 | 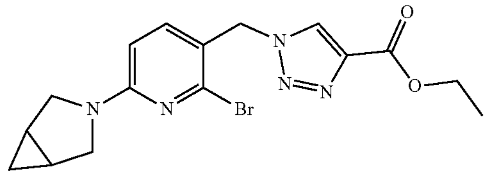 [SMILES: CCOC(=O)c1cn(Cc2ccc(N3CC4CC4C3)nc2Br)nn1] | 1.08 | 392 | Method 2 |
| 4-23 | 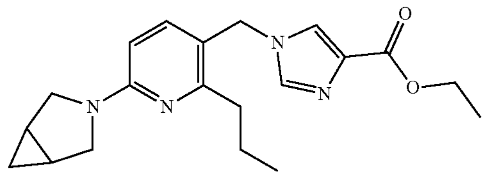 [SMILES: CCCc1nc(N2CC3CC3C2)ccc1Cn1cnc(C(=O)OCC)c1] | 0.83 | 356 | Method 2 |
| 4-24 | 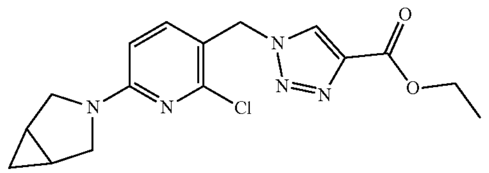 [SMILES: CCOC(=O)c1cn(Cc2ccc(N3CC4CC4C3)nc2Cl)nn1] | 1.07 | 348 | Method 2 |

-continued
| Intermediate | Structure | $t_R$ | Mass spectrum (ESI+): m/z $[M + H]^+$ | LC Method |
| --- | --- | --- | --- | --- |
| 4-25 | 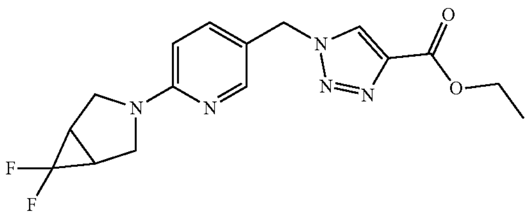 | 0.68 | 350 | Method 2 |
| 4-26 | 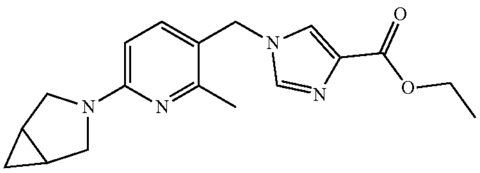 [SMILES: CCOC(=O)c1cn(Cc2ccc(N3CC4CC4C3)nc2C)cn1] | 0.98 | 327 | Method 1 |
| 4-27 | 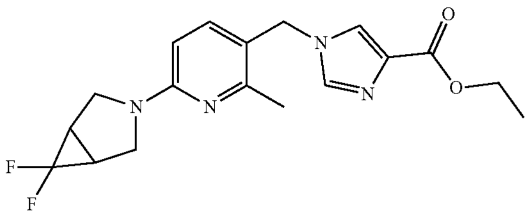 | 0.95 | 363 | Method 1 |
| 4-28 | 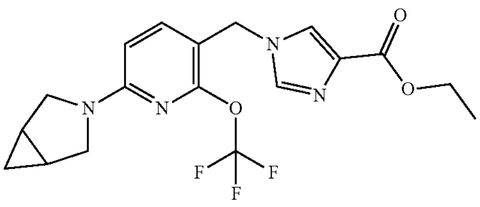 [SMILES: CCOC(=O)c1cn(Cc2ccc(N3CC4CC4C3)nc2OC(F)(F)F)cn1] | 1.01 | 397 | Method 2 |
| 4-29 | 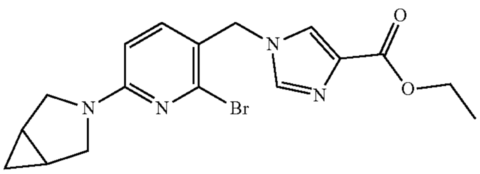 | 0.92 | 391 | Method 2 |
| 4-30 | 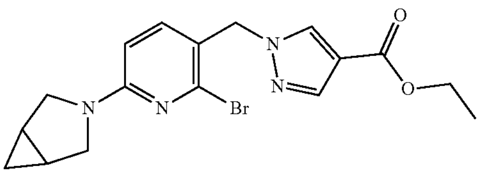 | 1.14 | 391 | Method 2 |
| 4-31 | 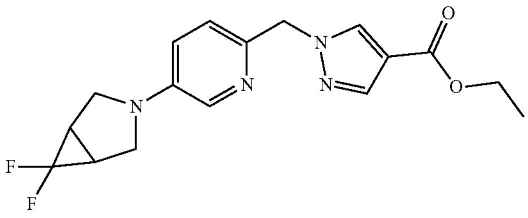 [SMILES: CCOC(=O)c1cnn(Cc2ccc(N3CC4C(C3)C4(F)F)cn2)c1] | 0.78 | 349 | Method 2 |

-continued
| Intermediate | Structure | $t_R$ | Mass spectrum (ESI+): m/z $[M + H]^+$ | LC Method |
|---|---|---|---|---|
| 4-32 | 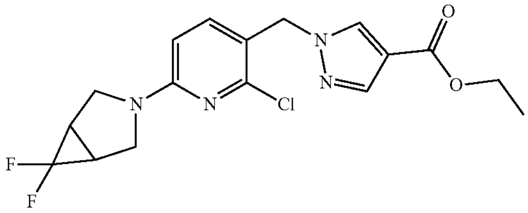 | 1.10 | 383 | Method 2 |
| 4-33 | 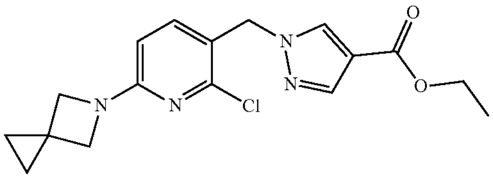 [SMILES: CCOC(=O)c1cnn(Cc2ccc(N3CC4(CC4)C3)nc2Cl)c1] | 1.05 | 347 | Method 2 |
| 4-34 | 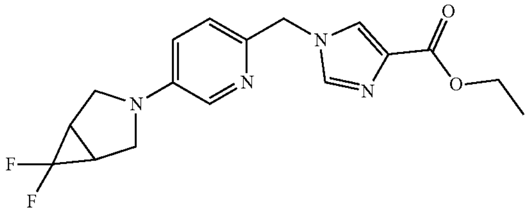 [SMILES: CCOC(=O)c1cn(Cc2ccc(N3CC4C(C3)C4(F)F)cn2)cn1] | 0.72 | 349 | Method 2 |
| 4-35 | 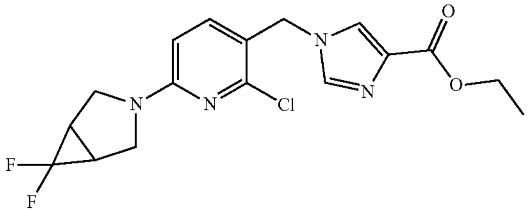 [SMILES: CCOC(=O)c1cn(Cc2ccc(N3CC4C(C3)C4(F)F)nc2Cl)cn1] | 0.97 | 383 | Method 1 |
| 4-36 | 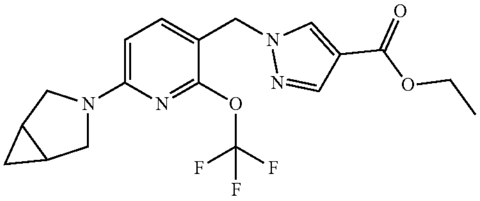 [SMILES: CCOC(=O)c1cnn(Cc2ccc(N3CC4CC4C3)nc2OC(F)(F)F)c1] | 1.21 | 397 | Method 2 |
| 4-37 | 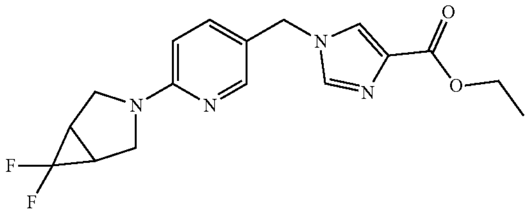 [SMILES: CCOC(=O)c1cn(Cc2ccc(N3CC4C(C3)C4(F)F)nc2)cn1] | 0.90 | | Method 1 |
| 4-38 | 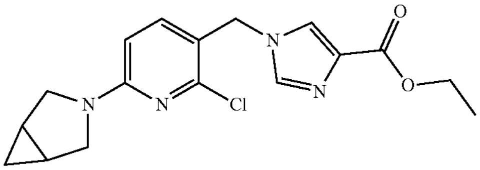 [SMILES: CCOC(=O)c1cn(Cc2ccc(N3CC4CC4C3)nc2Cl)cn1] | 0.91 | 347 | Method 2 |

-continued
| Intermediate | Structure | $t_R$ | Mass spectrum (ESI+): m/z $[M + H]^+$ | LC Method |
|---|---|---|---|---|
| 4-39 | 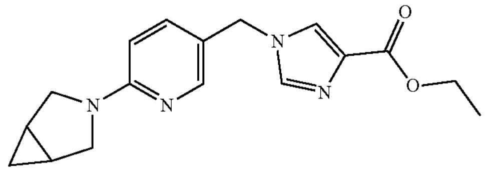 [SMILES: CCOC(=O)c1cn(Cc2ccc(N3CC4CC4C3)nc2)cn1] | 0.92 | 313 | Method 1 |
| 4-40 | 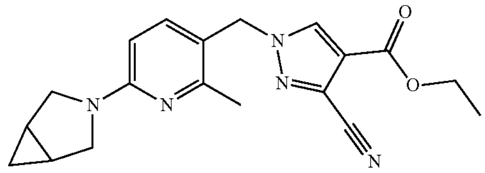 [SMILES: CCOC(=O)c1cn(Cc2ccc(N3CC4CC4C3)nc2C)nc1C#N] | 1.07 | 338 | Method 1 |
| 4-41 | 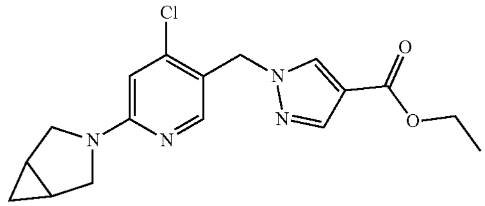 [SMILES: CCOC(=O)c1cnn(Cc2cnc(N3CC4CC4C3)cc2Cl)c1] | 1.05 | 347 | Method 1 |
| 4-42 | 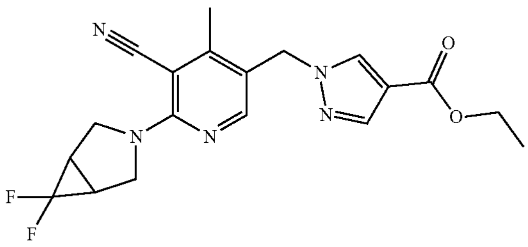 [SMILES: CCOC(=O)c1cnn(Cc2cnc(N3CC4C(C3)C4(F)F)c(C#N)c2C)c1] | 1.02 | 388 | Method 1 |
| 4-43 | 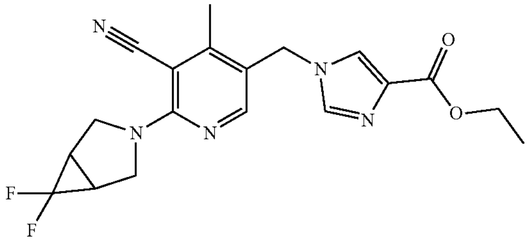 [SMILES: CCOC(=O)c1cn(Cc2cnc(N3CC4C(C3)C4(F)F)c(C#N)c2C)cn1] | 0.92 | 388 | Method 1 |
| 4-44 | 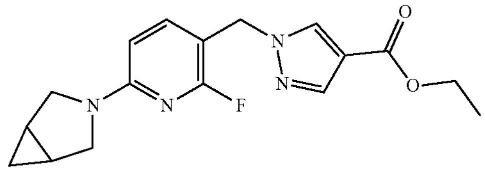 [SMILES: CCOC(=O)c1cnn(Cc2ccc(N3CC4CC4C3)nc2F)c1] | 1.09 | 331 | Method 2 |
| 4-45 | 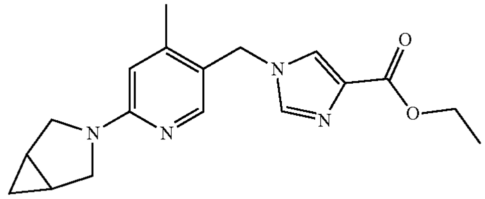 [SMILES: CCOC(=O)c1cn(Cc2cnc(N3CC4CC4C3)cc2C)cn1] | 0.93 | 327 | Method 1 |

-continued
| Intermediate | Structure | $t_R$ | Mass spectrum (ESI+): m/z $[M + H]^+$ | LC Method |
|---|---|---|---|---|
| 4-46 | 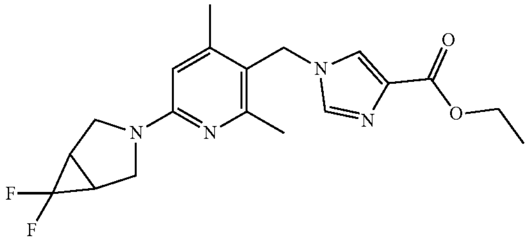 [SMILES: CCOC(=O)c1cn(Cc2c(C)cc(N3CC4C(C3)C4(F)F)nc2C)cn1] | 0.98 | 377 | Method 1 |
| 4-47 | 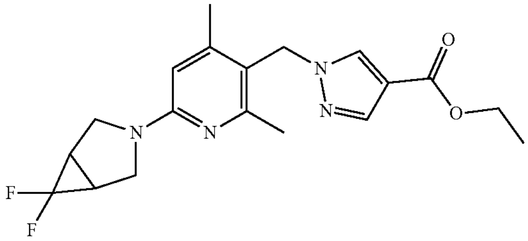 [SMILES: CCOC(=O)c1cnn(Cc2c(C)cc(N3CC4C(C3)C4(F)F)nc2C)c1] | 0.79 | 377 | Method 2 |
| 4-48 | 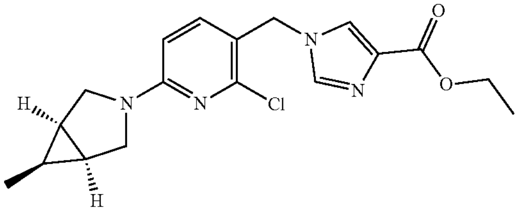 [SMILES: CCOC(=O)c1cn(Cc2ccc(N3C[C@@H]4[C@H](C)[C@@H]4C3)nc2Cl)cn1] | 1.05 | 361 | Method 1 |
| 4-49 | 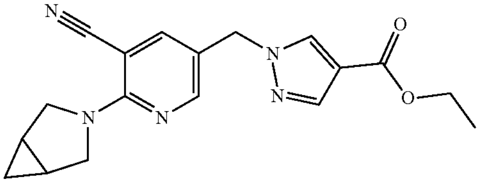 [SMILES: CCOC(=O)c1cnn(Cc2cnc(N3CC4CC4C3)c(C#N)c2)c1] | 1.03 | 338 | Method 2 |
| 4-50 | 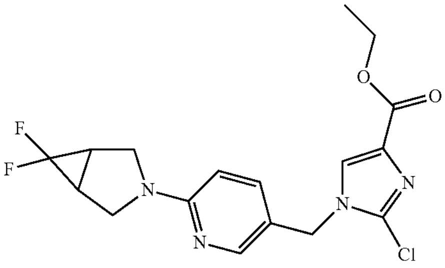 [SMILES: CCOC(=O)c1cn(Cc2ccc(N3CC4C(C3)C4(F)F)nc2)c(Cl)n1] | 0.97 | 383 | Method 1 |
| 4-51 | 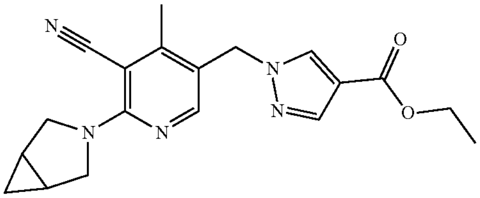 [SMILES: CCOC(=O)c1cnn(Cc2cnc(N3CC4CC4C3)c(C#N)c2C)c1] | 1.04 | 352 | Method 2 |

-continued
| Intermediate | Structure | $t_R$ | Mass spectrum (ESI+): m/z $[M + H]^+$ | LC Method |
|---|---|---|---|---|
| 4-52 | 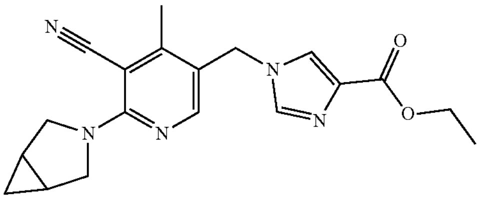 [SMILES: CCOC(=O)c1cn(Cc2cnc(N3CC4CC4C3)c(C#N)c2C)cn1] | 0.94 | 352 | Method 1 |
| 4-53 | 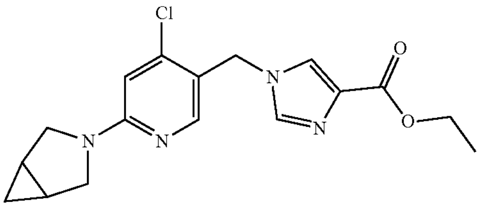 [SMILES: CCOC(=O)c1cn(Cc2cnc(N3CC4CC4C3)cc2Cl)cn1] | 0.96 | 347 | Method 1 |
| 4-54 | 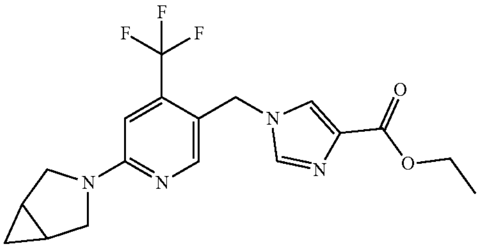 [SMILES: CCOC(=O)c1cn(Cc2cnc(N3CC4CC4C3)cc2C(F)(F)F)cn1] | 1.00 | 381 | Method 1 |
| 4-55 | 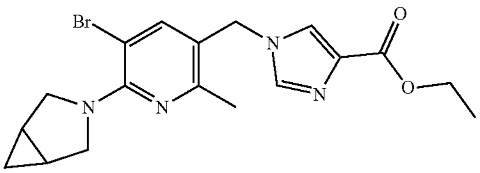 [SMILES: CCOC(=O)c1cn(Cc2cc(Br)c(N3CC4CC4C3)nc2C)cn1] | 1.11 | | Method 1 |
| 4-56 | 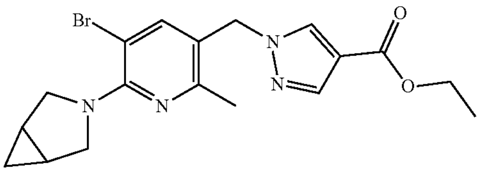 [SMILES: CCOC(=O)c1cnn(Cc2cc(Br)c(N3CC4CC4C3)nc2C)c1] | 1.17 | 405 | Method 2 |
| 4-57 | 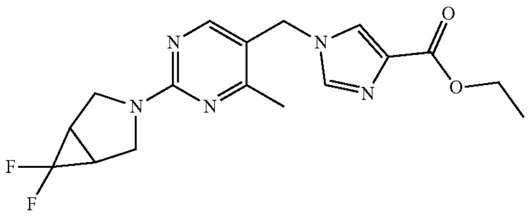 [SMILES: CCOC(=O)c1cn(Cc2cnc(N3CC4C(C3)C4(F)F)nc2C)cn1] | 0.89 | 364 | Method 1 |
| 4-58 | 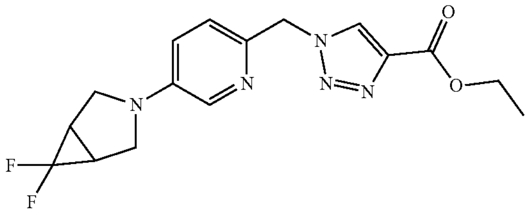 [SMILES: CCOC(=O)c1cn(Cc2ccc(N3CC4C(C3)C4(F)F)cn2)nn1] | 0.90 | 350 | Method 1 |

-continued

| Intermediate | Structure | $t_R$ | Mass spectrum (ESI+): m/z $[M + H]^+$ | LC Method |
|---|---|---|---|---|
| 4-59 | 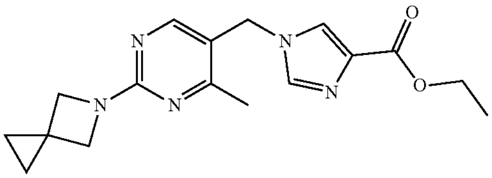 | 0.85 | 328 | Method 2 |
| 4-60 | 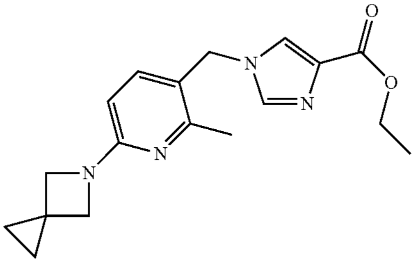 [SMILES: CCOC(=O)c1cn(Cc2ccc(N3CC4(CC4)C3)nc2C)cn1] | 0.93 | 327 | Method 2 |
| 4-61 | 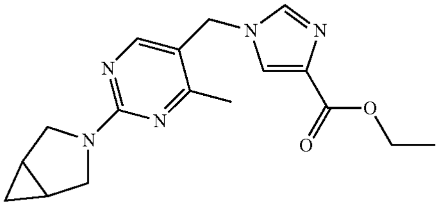 [SMILES: CCOC(=O)c1cn(Cc2cnc(N3CC4CC4C3)nc2C)cn1] | 0.89 | 328 | Method 2 |

| Intermediate | Reaction comment |
|---|---|
| 4-1 | The reaction is conducted for 10 minutes at 70° C. |
| 4-2 | The reaction is conducted for 15 minutes at 70° C. |
| 4-3 | The reaction is conducted for 15 minutes at 70° C. |
| 4-4 | The reaction is conducted for 48 h at 90° C. |
| 4-5 | The reaction is conducted for 10 h at 130° C. |
| 4-6 | The reaction is conducted for 4 h at 120° C. |
| 4-7 | The reaction is conducted for 10 minutes at 70° C. |
| 4-8 | The reaction is conducted for 5 h at 70° C. |
| 4-9 | The reaction is conducted for 1 h at 70° C. |
| 4-10 | The reaction is conducted for 30 minutes at 80° C. |
| 4-11 | The reaction is conducted for 10 minutes at 70° C. |
| 4-12 | The reaction is conducted for 2 h at 80° C. |
| 4-13 | The reaction is conducted for 12 h at 80° C. |
| 4-14 | The reaction is conducted for 4 h at 80° C. |
| 4-15 | The reaction is conducted for 10 minutes at 70° C. |
| 4-16 | The reaction is conducted for 1 h at 70° C. |
| 4-17 | The reaction is conducted for 15 h at 80° C. |
| 4-18 | The reaction is conducted for 1 h at 70° C. |
| 4-19 | The reaction is conducted for 10 minutes at 70° C. |
| 4-20 | The reaction is conducted for 7 h at 80° C. and for 2 h at 90° C. |
| 4-21 | Camphersulfonic acid is used instead of p-toluenesulfonic acid. The reaction is conducted for 4 h at 80° C. |
| 4-22 | The reaction is conducted for 15 minutes at 70° C. |
| 4-23 | The reaction is conducted for 2 h at 90° C. |
| 4-24 | The reaction is conducted for 15 minutes at 70° C. |
| 4-25 | The reaction is conducted for 12 h at 70° C. |
| 4-26 | The reaction is conducted for 5 h at 90° C. |
| 4-27 | The reaction is conducted for 15 h at 90° C. |
| 4-28 | The reaction is conducted for 12 h at 90° C. |
| 4-29 | The reaction is conducted for 5 h at 80° C. |
| 4-30 | The reaction is conducted for 30 minutes at 80° C. |
| 4-31 | The reaction is conducted for 6 h at 120° C. |
| 4-32 | The reaction is conducted for 2 h at 80° C. |
| 4-33 | The reaction is conducted for 2 h at 60° C. |
| 4-34 | The reaction is conducted for 4 h at 120° C. and for 1 h at 130° C. |

-continued

| Intermediate | Reaction comment |
|---|---|
| 4-35 | The reaction is conducted for 15 h at 75° C. and for 12 h at 80° C. |
| 4-36 | The reaction is conducted for 30 minutes at 70° C. |
| 4-37 | The reaction is conducted for 12 h at 70° C. and for 6 h at 80° C. |
| 4-38 | The reaction is conducted for 12 h at 80° C. |
| 4-39 | The reaction is conducted for 12 h at 90° C. |
| 4-40 | The reaction is conducted for 12 h at 80° C. |
| 4-41 | The reaction is conducted for 22 h at 70° C. |
| 4-42 | The reaction is conducted for 12 h at 90° C. |
| 4-43 | The reaction is conducted for 48 h at 80° C. |
| 4-44 | The reaction is conducted for 3 h at 70° C. |
| 4-45 | The reaction is conducted for 20 h at 80° C. |
| 4-46 | The reaction is conducted for 4 h at 80° C. |
| 4-47 | The reaction is conducted for 2 h at 80° C. |
| 4-48 | The reaction is conducted for 20 h at 80° C. |
| 4-49 | The reaction is conducted for 5 h at 70° C. |
| 4-50 | The reaction is conducted for 5 h at 90° C. |
| 4-51 | The reaction is conducted for 16 h at 60° C. |
| 4-52 | The reaction is conducted for 12 h at 90° C. |
| 4-53 | The reaction is conducted for 22 h at 70° C. |
| 4-54 | The reaction is conducted for 22 h at 70° C. |
| 4-55 | The reaction is conducted for 20 h at 70° C. |
| 4-56 | The reaction is conducted for 12 h at 70° C. |
| 4-57 | The reaction is conducted for 4 h at 90° C. |
| 4-58 | The reaction is conducted for 13 h at 130° C. |
| 4-59 | The reaction is conducted for 5 h at 90° C. |
| 4-60 | The reaction is conducted for 5 h at 90° C. |
| 4-61 | The reaction is conducted for 5 h at 90° C. |

| Intermediate | Name | Name of Starting Material 1 | Name of Starting Material 2 |
|---|---|---|---|
| 4-1 | Ethyl 1-[(2-chloro-6-{6,6-difluoro-3-azabicyclo[3.1.0]-hexan-3-yl}pyridin-3-yl)methyl]-1H-1,2,3-triazole-4-carboxylate | 2-Chloro-6-{6,6-difluoro-3-azabicyclo[3.1.0]hexan-3-yl}pyridin-3-yl)methanol | Ethyl 1H-1,2,3-triazole-4-carboxylate |
| 4-2 | Ethyl 1-[(6-{5-azaspiro[2.3]hexan-5-yl}-2-chloropyridin-3-yl)methyl]-1H-1,2,3-triazole-4-carboxylate | (6-{5-Azaspiro[2.3]hexan-5-yl}-2-chloropyridin-3-yl)methanol | Ethyl 1H-1,2,3-triazole-4-carboxylate |
| 4-3 | Ethyl 1-[(6-{5-azaspiro[2.3]hexan-5-yl}-2-bromopyridin-3-yl)methyl]-1H-1,2,3-triazole-4-carboxylate | (6-{5-Azaspiro[2.3]hexan-5-yl}-2-bromopyridin-3-yl)methanol | Ethyl 1H-1,2,3-triazole-4-carboxylate |
| 4-4 | Ethyl 1-[(6-{6,6-difluoro-3-azabicyclo[3.1.0]hexan-3-yl}-2-fluoropyridin-3-yl)methyl]-1H-imidazole-4-carboxylate | 6,6-Difluoro-3-[6-fluoro-5-(methoxymethyl)pyridin-2-yl]-3-azabicyclo[3.1.0]hexane | Ethyl 1H-imidazole-4-carboxylate |
| 4-5 | Ethyl 1-[(5-{3-azabicyclo[3.1.0]-hexan-3-yl}pyridin-2-yl)methyl]-1H-1,2,3-triazole-4-carboxylate | (5-{3-Azabicyclo[3.1.0]hexan-3-yl}pyridin-2-yl)methanol | Ethyl 1H-1,2,3-triazole-4-carboxylate |
| 4-6 | Ethyl 1-[(5-{3-azabicyclo[3.1.0]-hexan-3-yl}pyridin-2-yl)methyl]-1H-pyrazole-4-carboxylate | (5-{3-Azabicyclo[3.1.0]hexan-3-yl}pyridin-2-yl)methanol | Ethyl 1H-pyrazole-4-carboxylate |
| 4-7 | Ethyl 1-[(6-{5-azaspiro[2.3]hexan-5-yl}-2-fluoropyridin-3-yl)methyl]-1H-1,2,3-triazole-4-carboxylate | 5-[6-Fluoro-5-(methoxymethyl)pyridin-2-yl]-5-azaspiro[2.3]hexane | Ethyl 1H-1,2,3-triazole-4-carboxylate |
| 4-8 | Ethyl 1-[(6-{5-azaspiro[2.3]hexan-5-yl}-2-fluoropyridin-3-yl)methyl]-1H-imidazole-4-carboxylate | 5-[6-Fluoro-5-(methoxymethyl)pyridin-2-yl]-5-azaspiro[2.3]hexane | Ethyl 1H-imidazole-4-carboxylate |
| 4-9 | Ethyl 1-[(6-{5-azaspiro[2.3]hexan-5-yl}-2-fluoropyridin-3-yl)methyl]-1H-pyrazole-4-carboxylate | 5-[6-Fluoro-5-(methoxymethyl)pyridin-2-yl]-5-azaspiro[2.3]hexane | Ethyl 1H-pyrazole-4-carboxylate |
| 4-10 | Ethyl 1-[(6-{5-azaspiro[2.3]hexan-5-yl}-2-bromopyridin-3-yl)methyl]-1H-pyrazole-4-carboxylate | (6-{5-Azaspiro[2.3]hexan-5-yl}-2-bromopyridin-3-yl)methanol | Ethyl 1H-pyrazole-4-carboxylate |
| 4-11 | Ethyl 1-[(2-bromo-6-{6,6-difluoro-3-azabicyclo[3.1.0]hexan-3-yl}pyridin-3-yl)methyl]-1H-1,2,3-triazole-4-carboxylate | (2-Bromo-6-{6,6-difluoro-3-azabicyclo[3.1.0]hexan-3-yl}pyridin-3-yl)methanol | Ethyl 1H-1,2,3-triazole-4-carboxylate |
| 4-12 | Ethyl 1-[(2-bromo-6-{6,6-difluoro-3-azabicyclo[3.1.0]hexan-3-yl}pyridin-3-yl)methyl]-1H-pyrazole-4-carboxylate | (2-Bromo-6-{6,6-difluoro-3-azabicyclo[3.1.0]hexan-3-yl}pyridin-3-yl)methanol | Ethyl 1H-pyrazole-4-carboxylate |
| 4-13 | Ethyl 1-[(6-{5-azaspiro[2.3]hexan-5-yl}-2-bromopyridin-3-yl)methyl]-1H-imidazole-4-carboxylate | (6-{5-Azaspiro[2.3]hexan-5-yl}-2-bromopyridin-3-yl)methanol | Ethyl 1H-imidazole-4-carboxylate |
| 4-14 | 1-[(2-{3-Azabicyclo[3.1.0]-hexan-3-yl}-4-[(1E)-2-phenyl-ethenyl]pyrimidin-5-yl)methyl]-1H-imidazole-4-carboxylic acid | (2-{3-Azabicyclo[3.1.0]hexan-3-yl}-4-[(1E)-2-phenylethenyl]-pyrimidin-5-yl)methanol | 1H-imidazole-4-carboxylic acid |
| 4-15 | Ethyl 1-[(6-{3-azabicyclo[3.1.0]-hexan-3-yl}-2-fluoropyridin-3-yl)-methyl]-1H-1,2,3-triazole-4-carboxylate | 3-[6-Fluoro-5-(methoxymethyl)pyridin-2-yl]-3-azabicyclo[3.1.0]hexane | Ethyl 1H-1,2,3-triazole-4-carboxylate |
| 4-16 | Ethyl 1-[(6-{6,6-difluoro-3-azabicyclo[3.1.0]hexan-3-yl}-2-fluoropyridin-3-yl)methyl]-1H-pyrazole-4-carboxylate | 6,6-Difluoro-3-[6-fluoro-5-(methoxymethyl)pyridin-2-yl]-3-azabicyclo[3.1.0]hexane | Ethyl 1H-pyrazole-4-carboxylate |
| 4-17 | Ethyl 1-[(6-{5-azaspiro[2.3]hexan-5-yl}-2-chloropyridin-3-yl)methyl]-1H-imidazole-4-carboxylate | (6-{5-Azaspiro[2.3]hexan-5-yl}-2-chloropyridin-3-yl)methanol | Ethyl 1H-imidazole-4-carboxylate |
| 4-18 | Ethyl 1-[(6-{3-azabicyclo[3.1.0]-hexan-3-yl}-2-chloropyridin-3-yl)-methyl]-1H-pyrazole-4-carboxylate | (6-{3-Azabicyclo[3.1.0]hexan-3-yl}-2-chloropyridin-3-yl)-methanol | Ethyl 1H-pyrazole-4-carboxylate |
| 4-19 | Ethyl 1-[(6-{6,6-difluoro-3-azabicyclo[3.1.0]hexan-3-yl}-2-fluoropyridin-3-yl)methyl]-1H-1,2,3-triazole-4-carboxylate | 6,6-Difluoro-3-[6-fluoro-5-(methoxymethyl)pyridin-2-yl]-3-azabicyclo[3.1.0]hexane | Ethyl 1H-1,2,3-triazole-4-carboxylate |
| 4-20 | Ethyl 1-[(2-bromo-6-{6,6-difluoro-3-azabicyclo[3.1.0]-hexan-3-yl}-pyridin-3-yl)methyl]-1H-imidazole-4-carboxylate | (2-Bromo-6-{6,6-difluoro-3-azabicyclo[3.1.0]hexan-3-yl}-pyridin-3-yl)methanol | Ethyl 1H-imidazole-4-carboxylate |
| 4-21 | Ethyl 1-[(2-{3-azabicyclo[3.1.0]-hexan-3-yl}-4-[(1E)-2-phenyl-ethenyl]pyrimidin-5-yl)methyl]-1H-imidazole-4-carboxylate | (2-{3-Azabicyclo[3.1.0]hexan-3-yl}-4-[(1E)-2-phenylethenyl]-pyrimidin-5-yl)methanol | Ethyl 1H-imidazole-4-carboxylate |
| 4-22 | Ethyl 1-[(6-{3-azabicyclo[3.1.0]-hexan-3-yl}-2-bromopyridin-3-yl)-methyl]-1H-1,2,3-triazole-4-carboxylate | (6-{3-Azabicyclo[3.1.0]hexan-3-yl}-2-bromopyridin-3-yl)-methanol | Ethyl 1H-1,2,3-triazole-4-carboxylate |

-continued

| Intermediate | Name | Name of Starting Material 1 | Name of Starting Material 2 |
|---|---|---|---|
| 4-23 | Ethyl 1-[(6-{3-azabicyclo[3.1.0]-hexan-3-yl}-2-propylpyridin-3-yl)-methyl]-1H-imidazole-4-carboxylate | (6-{3-Azabicyclo[3.1.0]hexan-3-yl}-2-propylpyridin-3-yl)-methanol | Ethyl 1H-imidazole-4-carboxylate |
| 4-24 | Ethyl 1-[(6-{3-azabicyclo[3.1.0]-hexan-3-yl}-2-chloropyridin-3-yl)-methyl]-1H-1,2,3-triazole-4-carboxylate | (6-{3-Azabicyclo[3.1.0]hexan-3-yl}-2-chloropyridin-3-yl)-methanol | Ethyl 1H-1,2,3-triazole-4-carboxylate |
| 4-25 | Ethyl 1-[(6-{6,6-difluoro-3-azabicyclo[3.1.0]hexan-3-yl}pyridin-3-yl)methyl]-1H-1,2,3-triazole-4-carboxylate | (6-{6,6-Difluoro-3-azabicyclo[3.1.0]hexan-3-yl}-pyridin-3-yl)methanol | Ethyl 1H-1,2,3-triazole-4-carboxylate |
| 4-26 | Ethyl 1-[(6-{3-azabicyclo[3.1.0]-hexan-3-yl}-2-methylpyridin-3-yl)-methyl]-1H-imidazole-4-carboxylate | (6-{3-Azabicyclo[3.1.0]hexan-3-yl}-2-methylpyridin-3-yl)-methanol | Ethyl 1H-imidazole-4-carboxylate |
| 4-27 | Ethyl 1-[(6-{6,6-difluoro-3-azabicyclo[3.1.0]hexan-3-yl}-2-methylpyridin-3-yl)methyl]-1H-imidazole-4-carboxylate | (6-{6,6-Difluoro-3-azabicyclo[3.1.0]hexan-3-yl}-2-methylpyridin-3-yl)methanol | Ethyl 1H-imidazole-4-carboxylate |
| 4-28 | Ethyl 1-[(6-{3-azabicyclo[3.1.0]-hexan-3-yl}-2-(trifluoromethoxy)-pyridin-3-yl)methyl]-1H-imidazole-4-carboxylate | 3-[5-(Methoxymethyl)-6-(trifluoromethoxy)pyridin-2-yl]-3-azabicyclo[3.1.0]hexane | Ethyl 1H-imidazole-4-carboxylate |
| 4-29 | Ethyl 1-[(6-{3-azabicyclo[3.1.0]-hexan-3-yl}-2-bromopyridin-3-yl)-methyl]-1H-imidazole-4-carboxylate | (6-{3-Azabicyclo[3.1.0]hexan-3-yl}-2-bromopyridin-3-yl)-methanol | Ethyl 1H-imidazole-4-carboxylate |
| 4-30 | Ethyl 1-[(6-{3-azabicyclo[3.1.0]-hexan-3-yl}-2-bromopyridin-3-yl)-methyl]-1H-pyrazole-4-carboxylate | (6-{3-Azabicyclo[3.1.0]hexan-3-yl}-2-bromopyridin-3-yl)-methanol | Ethyl 1H-pyrazole-4-carboxylate |
| 4-31 | Ethyl 1-[(5-{6,6-difluoro-3-azabicyclo[3.1.0]hexan-3-yl}pyridin-2-yl)methyl]-1H-pyrazole-4-carboxylate | (5-{6,6-Difluoro-3-azabicyclo[3.1.0]hexan-3-yl}-pyridin-2-yl)methanol | Ethyl 1H-pyrazole-4-carboxylate |
| 4-32 | Ethyl 1-[(2-chloro-6-{6,6-difluoro-3-azabicyclo[3.1.0]-hexan-3-yl}-pyridin-3-yl)methyl]-1H-pyrazole-4-carboxylate | (2-Chloro-6-{6,6-difluoro-3-azabicyclo[3.1.0]hexan-3-yl}-pyridin-3-yl)methanol | Ethyl 1H-pyrazole-4-carboxylate |
| 4-33 | Ethyl 1-[(6-{5-azaspiro[2.3]hexan-5-yl}-2-chloropyridin-3-yl)methyl]-1H-pyrazole-4-carboxylate | (6-{5-Azaspiro[2.3]hexan-5-yl}-2-chloropyridin-3-yl)methanol | Ethyl 1H-pyrazole-4-carboxylate |
| 4-34 | Ethyl 1-[(5-{6,6-difluoro-3-azabicyclo[3.1.0]hexan-3-yl}pyridin-2-yl)methyl]-1H-imidazole-4-carboxylate | (5-{6,6-Difluoro-3-azabicyclo[3.1.0]hexan-3-yl}-pyridin-2-yl)methanol | Ethyl 1H-imidazole-4-carboxylate |
| 4-35 | Ethyl 1-[(2-chloro-6-{6,6-difluoro-3-azabicyclo[3.1.0]-hexan-3-yl}-pyridin-3-yl)methyl]-1H-imidazole-4-carboxylate | (2-Chloro-6-{6,6-difluoro-3-azabicyclo[3.1.0]hexan-3-yl}-pyridin-3-yl)methanol | Ethyl 1H-imidazole-4-carboxylate |
| 4-36 | Ethyl 1-[(6-{3-azabicyclo[3.1.0]-hexan-3-yl}-2-(trifluoro-methoxy)pyridin-3-yl)methyl]-1H-pyrazole-4-carboxylate | 3-[5-(Methoxymethyl)-6-(trifluoromethoxy)pyridin-2-yl]-3-azabicyclo[3.1.0]hexane | Ethyl 1H-pyrazole-4-carboxylate |
| 4-37 | Ethyl 1-[(6-{6,6-difluoro-3-azabicyclo[3.1.0]hexan-3-yl}pyridin-3-yl)methyl]-1H-imidazole-4-carboxylate | (6-{6,6-Difluoro-3-azabicyclo[3.1.0]hexan-3-yl}pyridin-3-yl)methanol | Ethyl 1H-imidazole-4-carboxylate |
| 4-38 | Ethyl 1-[(6-{3-azabicyclo[3.1.0]hexan-3-yl}-2-chloropyridin-3-yl)methyl]-1H-imidazole-4-carboxylate | (6-{3-Azabicyclo[3.1.0]hexan-3-yl}-2-chloropyridin-3-yl)methanol | Ethyl 1H-imidazole-4-carboxylate |
| 4-39 | Ethyl 1-[(6-{3-azabicyclo[3.1.0]-hexan-3-yl}pyridin-3-yl)methyl]-1H-imidazole-4-carboxylate | (6-{3-Azabicyclo[3.1.0]hexan-3-yl}pyridin-3-yl)methanol | Ethyl 1H-imidazole-4-carboxylate |
| 4-40 | Methyl 1-[(6-{3-azabicyclo-[3.1.0]hexan-3-yl}-2-methyl-pyridin-3-yl)methyl]-3-cyano-1H-pyrazole-4-carboxylate | (6-{3-Azabicyclo[3.1.0]hexan-3-yl}-2-methylpyridin-3-yl)methanol | Methyl 3-cyano-1H-pyrazole-4-carboxylate |
| 4-41 | Ethyl 1-[(6-{3-azabicyclo[3.1.0]hexan-3-yl}-4-chloropyridin-3-yl)methyl]-1H-pyrazole-4-carboxylate | (6-{3-Azabicyclo[3.1.0]hexan-3-yl}-4-chloropyridin-3-yl)methanol | Ethyl 1H-pyrazole-4-carboxylate |
| 4-42 | Ethyl 1-[(5-cyano-6-{6,6-difluoro-3-azabicyclo[3.1.0]hexan-3-yl}-4-methylpyridin-3-yl)methyl]-1H-pyrazole-4-carboxylate | 2-{6,6-Difluoro-3-azabicyclo[3.1.0]hexan-3-yl}-5-(hydroxymethyl)-4-methylpyridine-3-carbonitrile | Ethyl 1H-pyrazole-4-carboxylate |
| 4-43 | Ethyl 1-[(5-cyano-6-{6,6-difluoro-3-azabicyclo[3.1.0]hexan-3-yl}-4- | 2-{6,6-Difluoro-3-azabicyclo[3.1.0]hexan-3-yl}-5- | Ethyl 1H-imidazole-4-carboxylate |

-continued

| Intermediate | Name | Name of Starting Material 1 | Name of Starting Material 2 |
|---|---|---|---|
| | methylpyridin-3-yl)methyl]-1H-imidazole-4-carboxylate | (hydroxymethyl)-4-methylpyridine-3-carbonitrile | |
| 4-44 | Ethyl 1-[(6-{3-azabicyclo[3.1.0]-hexan-3-yl}-2-fluoropyridin-3-yl)-methyl]-1H-pyrazole-4-carboxylate | 3-[6-Fluoro-5-(methoxymethyl)pyridin-2-yl]-3-azabicyclo[3.1.0]hexane | Ethyl 1H-pyrazole-4-carboxylate |
| 4-45 | Ethyl 1-[(6-{3-azabicyclo[3.1.0]-hexan-3-yl}-4-methylpyridin-3-yl)-methyl]-1H-imidazole-4-carboxylate | (6-{3-Azabicyclo[3.1.0]hexan-3-yl}-4-methylpyridin-3-yl)-methanol | Ethyl 1H-imidazole-4-carboxylate |
| 4-46 | Ethyl 1-[(6-{6,6-difluoro-3-azabicyclo[3.1.0]hexan-3-yl}-2,4-dimethylpyridin-3-yl)methyl]-1H-imidazole-4-carboxylate | (6-{6,6-Difluoro-3-azabicyclo[3.1.0]hexan-3-yl}-2,4-dimethylpyridin-3-yl)-methanol | Ethyl 1H-imidazole-4-carboxylate |
| 4-47 | Ethyl 1-[(6-{6,6-difluoro-3-azabicyclo[3.1.0]hexan-3-yl}-2,4-dimethylpyridin-3-yl)methyl]-1H-pyrazole-4-carboxylate | (6-{6,6-Difluoro-3-azabicyclo[3.1.0]hexan-3-yl}-2,4-dimethylpyridin-3-yl)-methanol | Ethyl 1H-pyrazole-4-carboxylate |
| 4-48 | Ethyl 1-({2-chloro-6-[(1R,5S,6R)-6-methyl-3-azabicyclo[3.1.0]hexan-3-yl]pyridin-3-yl}methyl)-1H-imidazole-4-carboxylate | {2-Chloro-6-[(1R,5S,6R)-6-methyl-3-azabicyclo[3.1.0]-hexan-3-yl]pyridin-3-yl}-methanol | Ethyl 1H-imidazole-4-carboxylat |
| 4-49 | Ethyl 1-[(6-{3-azabicyclo[3.1.0]-hexan-3-yl}-5-cyanopyridin-3-yl)-methyl]-1H-pyrazole-4-carboxylate | 2-{3-Azabicyclo[3.1.0]hexan-3-yl}-5-(hydroxymethyl)pyridine-3-carbonitrile | Ethyl 1H-pyrazole-4-carboxylate |
| 4-50 | Ethyl 2-chloro-1-[(6-{6,6-difluoro-3-azabicyclo[3.1.0]hexan-3-yl}pyridin-3-yl)methyl]-1H-imidazole-4-carboxylate | (6-{6,6-difluoro-3-azabicyclo[3.1.0]hexan-3-yl}pyridin-3-yl)methanol | Ethyl 2-chloro-1H-imidazole-4-carboxylate |
| 4-51 | Ethyl 1-[(6-{3-azabicyclo[3.1.0]-hexan-3-yl}-5-cyano-4-methylpyridin-3-yl)methyl]-1H-pyrazole-4-carboxylate | 2-{3-Azabicyclo[3.1.0]hexan-3-yl}-5-(hydroxymethyl)-4-methylpyridine-3-carbonitrile | Ethyl 1H-pyrazole-4-carboxylate |
| 4-52 | Ethyl 1-[(6-{3-azabicyclo[3.1.0]-hexan-3-yl}-5-cyano-4-methylpyridin-3-yl)methyl]-1H-imidazole-4-carboxylate | 2-{3-Azabicyclo[3.1.0]hexan-3-yl}-5-(hydroxymethyl)-4-methylpyridine-3-carbonitrile | Ethyl 1H-imidazole-4-carboxylate |
| 4-53 | Ethyl 1-[(6-{3-azabicyclo[3.1.0]-hexan-3-yl}-4-chloropyridin-3-yl)-methyl]-1H-imidazole-4-carboxylate | (6-{3-Azabicyclo[3.1.0]hexan-3-yl}-4-chloropyridin-3-yl)methanol | Ethyl 1H-imidazole-4-carboxylate |
| 4-54 | Ethyl 1-[(6-{3-azabicyclo[3.1.0]-hexan-3-yl}-4-(trifluoromethyl)-pyridin-3-yl)methyl]-1H-imidazole-4-carboxylate | (6-{3-Azabicyclo[3.1.0]hexan-3-yl}-4-(trifluoromethyl)pyridin-3-yl)methanol | Ethyl 1H-imidazole-4-carboxylate |
| 4-55 | Ethyl 1-[(6-{3-azabicyclo[3.1.0]-hexan-3-yl}-5-bromo-2-methylpyridin-3-yl)methyl]-1H-imidazole-4-carboxylate | (6-{3-Azabicyclo[3.1.0]hexan-3-yl}-5-bromo-2-methylpyridin-3-yl)methanol | Ethyl 1H-imidazole-4-carboxylate |
| 4-56 | Ethyl 1-[(6-{3-azabicyclo[3.1.0]-hexan-3-yl}-5-bromo-2-methylpyridin-3-yl)methyl]-1H-pyrazole-4-carboxylate | (6-{3-Azabicyclo[3.1.0]hexan-3-yl}-5-bromo-2-methylpyridin-3-yl)methanol | Ethyl 1H-pyrazole-4-carboxylate |
| 4-57 | Ethyl 1-[(2-{6,6-difluoro-3-azabicyclo[3.1.0]hexan-3-yl}-4-methylpyrimidin-5-yl)methyl]-1H-imidazole-4-carboxylate | (2-{6,6-Difluoro-3-azabicyclo[3.1.0]hexan-3-yl}-4-methylpyrimidin-5-yl)methanol | Ethyl 1H-imidazole-4-carboxylat |
| 4-58 | Ethyl 1-[(5-{6,6-difluoro-3-azabicyclo[3.1.0]hexan-3-yl}pyridin-2-yl)methyl]-1H-1,2,3-triazole-4-carboxylate | (5-{6,6-Difluoro-3-azabicyclo[3.1.0]hexan-3-yl}-pyridin-2-yl)methanol | Ethyl 1H-1,2,3-triazole-4-carboxylate |
| 4-59 | Ethyl 1-[(6-{5-azaspiro[2.3]hexan-5-yl}-2-methylpyrimidin-3-yl)-methyl]-1H-imidazole-4-carboxylate | (2-{5-Azaspiro[2.3]hexan-5-yl}-4-methylpyrimidin-5-yl)-methanol | Ethyl 1H-imidazole-4-carboxylat |
| 4-60 | Ethyl 1-[(6-{5-azaspiro[2.3]hexan-5-yl}-2-methylpyridin-3-yl)methyl]-1H-imidazole-4-carboxylate | (2-{5-Azaspiro[2.3]hexan-5-yl}-4-methylpyridin-5-yl)methanol | Ethyl 1H-imidazole-4-carboxylate |
| 4-61 | Ethyl 1-[(6-{3-azabicyclo[3.1.0]-hexan-3-yl}-2-methylpyrimidin-3-yl)methyl]-1H-imidazole-4-carboxylate | (6-{3-Azabicyclo[3.1.0]-hexan-3-yl}-2-methyl-pyrimidin-3-yl)-methanol | Ethyl 1H-imidazole-4-carboxylate |

Intermediate 5

1-[(5-{3-Azabicyclo[3.1.0]hexan-3-yl}pyridin-2-yl) methyl]-1H-imidazole-4-carboxylic acid

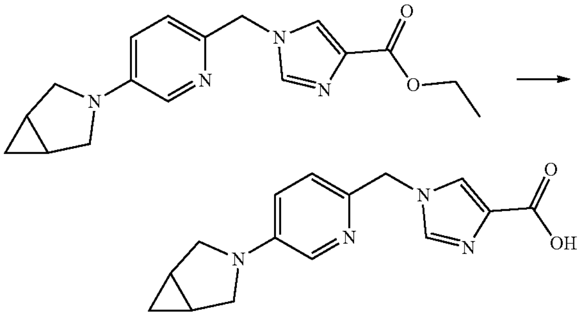

A mixture of ethyl 1-[(5-{3-azabicyclo[3.1.0]hexan-3-yl}pyridin-2-yl)methyl]-1H-imidazole-4-carboxylate (162 mg), MeOH (1 mL), THF (1 mL) and KOH (4 M aqueous solution, 648 μL) is stirred for 3 h at 50° C. After cooling to rt aqueous HCl (4 M, 648 μL) is added and the solvents are evaporated to give the crude product, which is directly used in the next step. LC (Method 2): $t_R$=0.58 min; Mass spectrum (ESI+): m/z=285 $[M+H]^+$.

Intermediates 5-1 to 5-170 are prepared in analogy to Intermediate 5:

| Intermediate | Structure | $t_R$ | Mass spectrum (ESI+): m/z $[M + H]^+$ | LC Method |
|---|---|---|---|---|
| 5-1 | 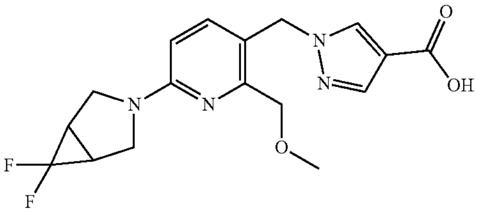 [SMILES: COCc1nc(N2CC3C(C2)C3(F)F)ccc1Cn1cc(C(=O)O)cn1] | 0.67 | 365 | Method 2 |
| 5-2 | 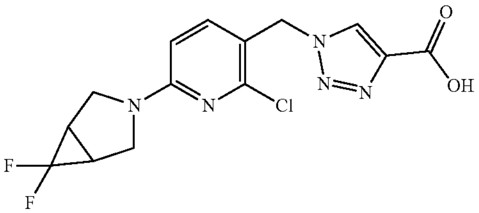 [SMILES: O=C(O)c1cn(Cc2ccc(N3CC4C(C3)C4(F)F)nc2Cl)nn1] | 0.90 | 356 | Method 2 |
| 5-3 | 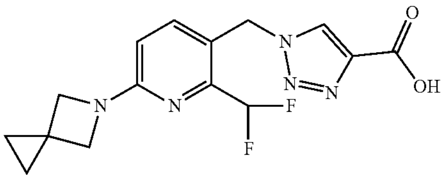 [SMILES: O=C(O)c1cn(Cc2ccc(N3CC4(CC4)C3)nc2C(F)F)nn1] | 0.91 | 336 | Method 2 |
| 5-4 | 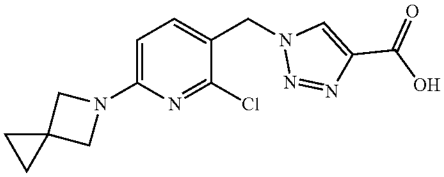 | 0.89 | 320 | Method 2 |
| 5-5 | 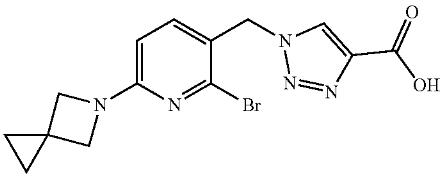 | 0.93 | 364 | Method 2 |

-continued
| Intermediate | Structure | $t_R$ | Mass spectrum (ESI+): m/z $[M + H]^+$ | LC Method |
|---|---|---|---|---|
| 5-6 | 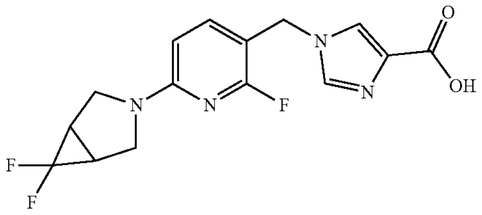 [SMILES: O=C(O)c1cn(Cc2ccc(N3CC4C(C3)C4(F)F)nc2F)cn1] | 0.73 | | Method 2 |
| 5-7 | 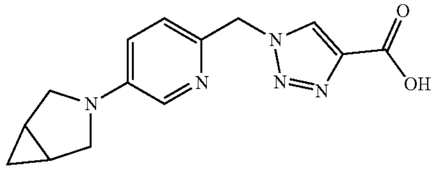 [SMILES: O=C(O)c1cn(Cc2ccc(N3CC4CC4C3)cn2)nn1] | 0.62 | 286 | Method 2 |
| 5-8 | 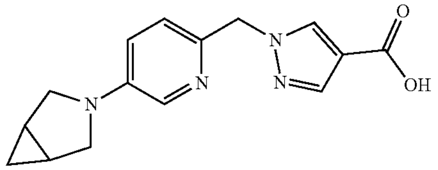 [SMILES: O=C(O)c1cnn(Cc2ccc(N3CC4CC4C3)cn2)c1] | 0.64 | 285 | Method 2 |
| 5-9 | 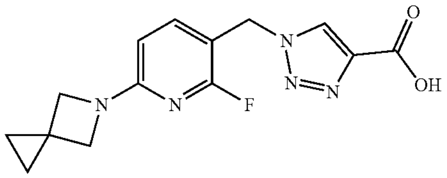 | 0.86 | 304 | Method 2 |
| 5-10 | 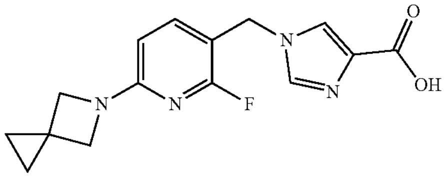 | 0.73 | | Method 2 |
| 5-11 | 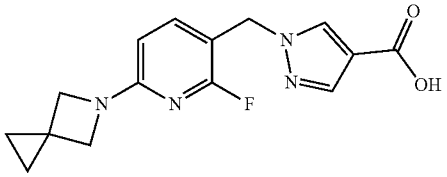 [SMILES: O=C(O)c1cnn(Cc2ccc(N3CC4(CC4)C3)nc2F)c1] | 0.90 | 303 | Method 2 |
| 5-12 | 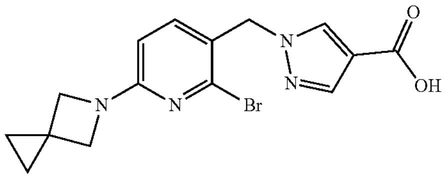 | 0.94 | 363 | Method 2 |
| 5-13 | 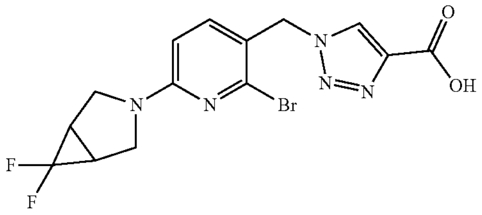 [SMILES: O=C(O)c1cn(Cc2ccc(N3CC4C(C3)C4(F)F)nc2Br)nn1] | 0.91 | 400 | Method 2 |

-continued
| Intermediate | Structure | $t_R$ | Mass spectrum (ESI+): m/z $[M + H]^+$ | LC Method |
| --- | --- | --- | --- | --- |
| 5-14 | 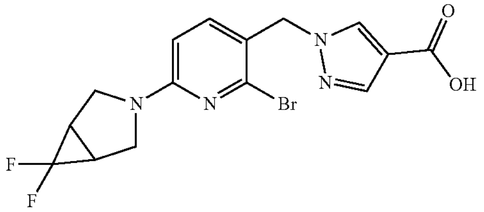 [SMILES: O=C(O)c1cnn(Cc2ccc(N3CC4C(C3)C4(F)F)nc2Br)c1] | 0.94 | 399 | Method 1 |
| 5-15 | 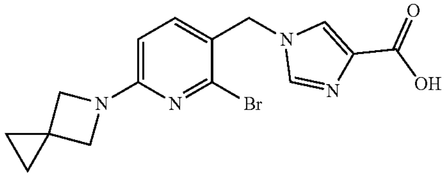 [SMILES: O=C(O)c1cn(Cc2ccc(N3CC4(CC4)C3)nc2Br)cn1] | 0.77 | | Method 2 |
| 5-16 | 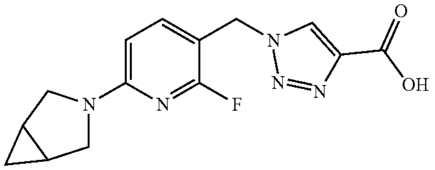 [SMILES: O=C(O)c1cn(Cc2ccc(N3CC4CC4C3)nc2F)nn1] | 0.88 | 304 | Method 2 |
| 5-17 | 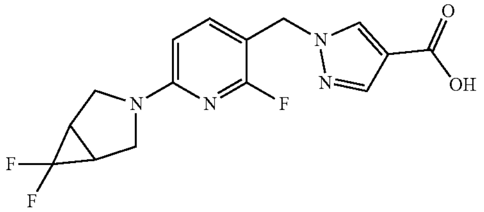 [SMILES: O=C(O)c1cnn(Cc2ccc(N3CC4C(C3)C4(F)F)nc2F)c1] | 0.89 | 339 | Method 2 |
| 5-18 | 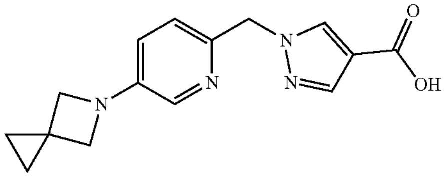 [SMILES: O=C(O)c1cnn(Cc2ccc(N3CC4(CC4)C3)cn2)c1] | 0.66 | 285 | Method 2 |
| 5-19 | 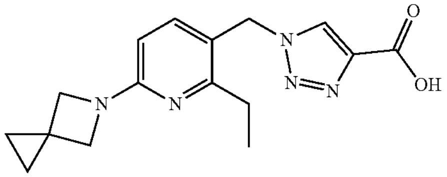 [SMILES: CCc1nc(N2CC3(CC3)C2)ccc1Cn1cc(C(=O)O)nn1] | 0.62 | 314 | Method 2 |
| 5-20 | 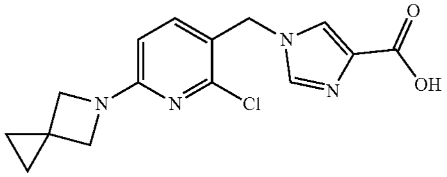 | 0.62 | | Method 1 |
| 5-21 | 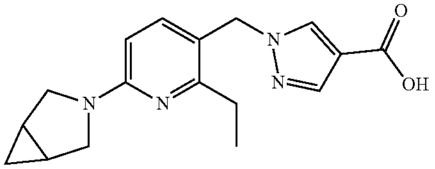 [SMILES: CCc1nc(N2CC3CC3C2)ccc1Cn1cc(C(=O)O)cn1] | 0.63 | 313 | Method 2 |

-continued
| Intermediate | Structure | $t_R$ | Mass spectrum (ESI+): m/z $[M + H]^+$ | LC Method |
|---|---|---|---|---|
| 5-22 | 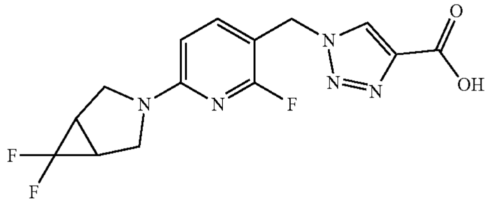 [SMILES: O=C(O)c1cn(Cc2ccc(N3CC4C(C3)C4(F)F)nc2F)nn1] | 0.86 | 362 $[M + Na]^+$ | Method 2 |
| 5-23 | 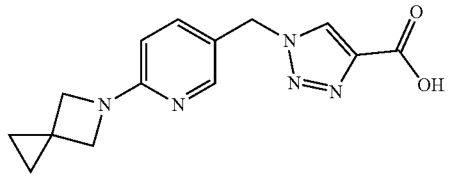 [SMILES: O=C(O)c1cn(Cc2ccc(N3CC4(CC4)C3)nc2)nn1] | 0.57 | 286 | Method 2 |
| 5-24 | 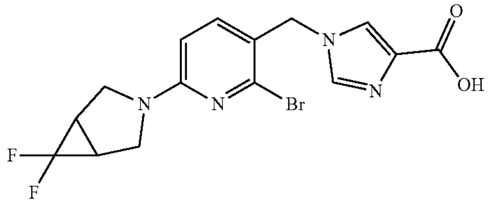 [SMILES: O=C(O)c1cn(Cc2ccc(N3CC4C(C3)C4(F)F)nc2Br)cn1] | 0.64 | | Method 1 |
| 5-25 | 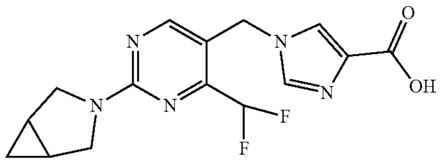 [SMILES: O=C(O)c1cn(Cc2cnc(N3CC4CC4C3)nc2C(F)F)cn1] | 0.67 | 336 | Method 2 |
| 5-26 | 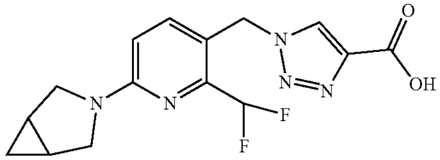 [SMILES: O=C(O)c1cn(Cc2ccc(N3CC4CC4C3)nc2C(F)F)nn1] | 0.95 | 336 | Method 2 |
| 5-27 | 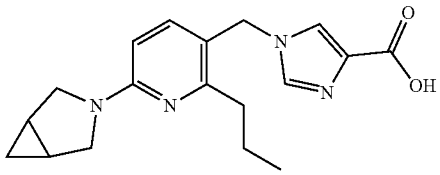 | 0.71 | 328 | Method 1 |
| 5-28 | 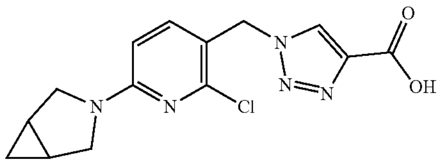 | 0.92 | 320 | Method 2 |
| 5-29 | 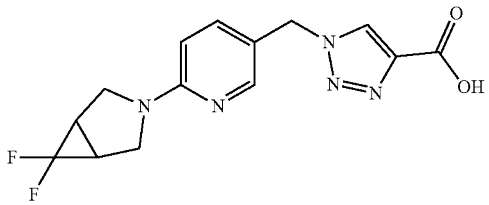 [SMILES: O=C(O)c1cn(Cc2ccc(N3CC4C(C3)C4(F)F)nc2)nn1] | 0.54 | 322 | Method 2 |

-continued
| Intermediate | Structure | $t_R$ | Mass spectrum (ESI+): m/z $[M + H]^+$ | LC Method |
|---|---|---|---|---|
| 5-30 | 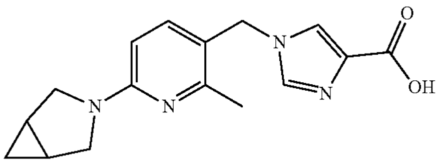 [SMILES: Cc1nc(N2CC3CC3C2)ccc1Cn1cnc(C(=O)O)c1] | 0.62 | 299 | Method 1 |
| 5-31 | 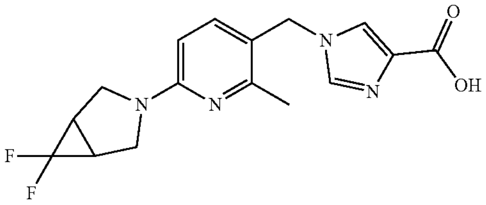 | 0.62 | 335 | Method 1 |
| 5-32 | 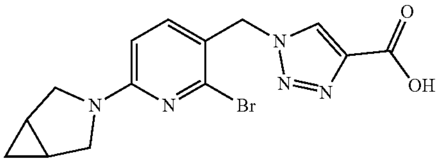 [SMILES: O=C(O)c1cn(Cc2ccc(N3CC4CC4C3)nc2Br)nn1] | 0.84 | 364 | Method 2 |
| 5-33 | 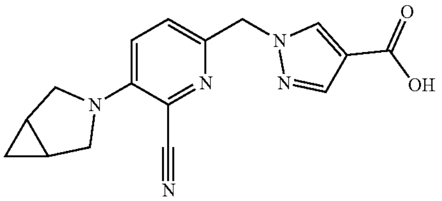 [SMILES: N#Cc1nc(Cn2cc(C(=O)O)cn2)ccc1N1CC2CC2C1] | 0.88 | 310 | Method 2 |
| 5-34 | 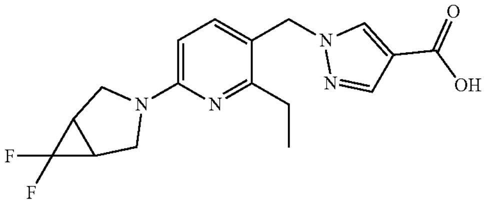 [SMILES: CCc1nc(N2CC3C(C2)C3(F)F)ccc1Cn1cc(C(=O)O)cn1] | | 349 | |
| 5-35 | 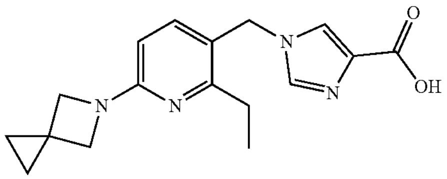 | Crude product is directly used in the next step | | |
| 5-36 | 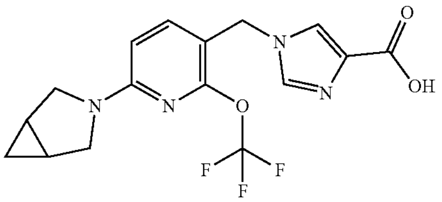 [SMILES: O=C(O)c1cn(Cc2ccc(N3CC4CC4C3)nc2OC(F)(F)F)cn1] | 0.88 | | Method 2 |
| 5-37 | 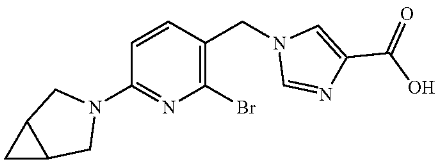 [SMILES: O=C(O)c1cn(Cc2ccc(N3CC4CC4C3)nc2Br)cn1] | 0.79 | | Method 2 |

-continued
| Intermediate | Structure | $t_R$ | Mass spectrum (ESI+): m/z $[M + H]^+$ | LC Method |
| --- | --- | --- | --- | --- |
| 5-38 | 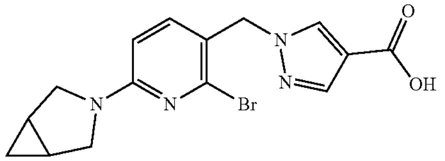 | 0.97 | 363 | Method 2 |
| 5-39 | 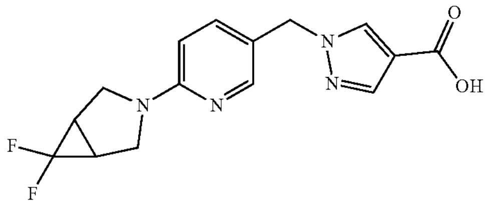 [SMILES: O=C(O)c1cnn(Cc2ccc(N3CC4C(C3)C4(F)F)nc2)c1] | 0.66 | 321 | Method 2 |
| 5-40 | 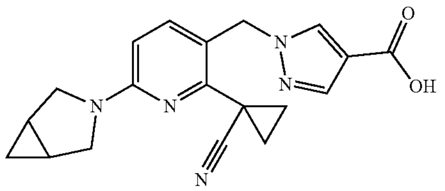 [SMILES: N#CC1(c2nc(N3CC4CC4C3)ccc2Cn2cc(C(=O)O)cn2)CC1] | 0.87 | 350 | Method 2 |
| 5-41 | 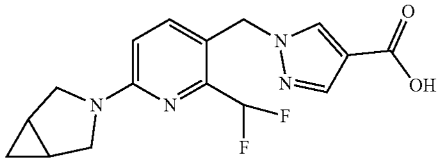 [SMILES: O=C(O)c1cnn(Cc2ccc(N3CC4CC4C3)nc2C(F)F)c1] | 0.66 | 335 | Method 1 |
| 5-42 | 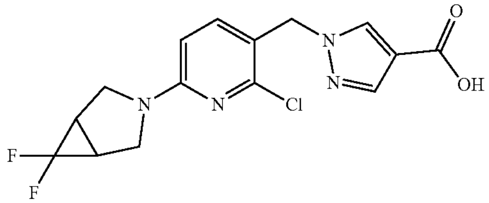 [SMILES: O=C(O)c1cnn(Cc2ccc(N3CC4C(C3)C4(F)F)nc2Cl)c1] | 0.96 | 355 | Method 2 |
| 5-43 | 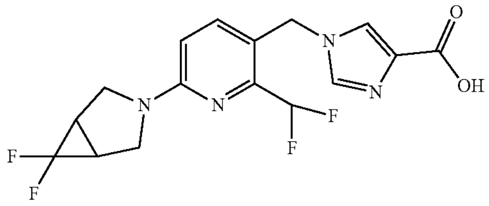 [SMILES: O=C(O)c1cn(Cc2ccc(N3CC4C(C3)C4(F)F)nc2C(F)F)cn1] | 0.65 | 371 | Method 1 |
| 5-44 | 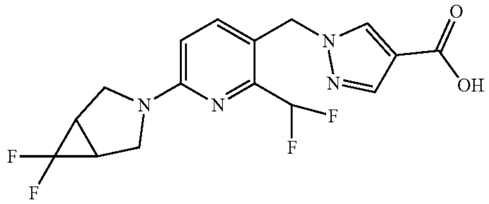 [SMILES: O=C(O)c1cnn(Cc2ccc(N3CC4C(C3)C4(F)F)nc2C(F)F)c1] | 0.65 | 371 | Method 1 |
| 5-45 | 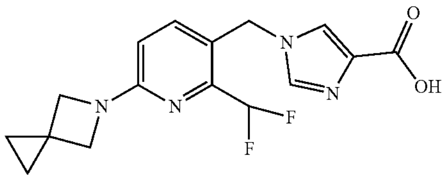 [SMILES: O=C(O)c1cn(Cc2ccc(N3CC4(CC4)C3)nc2C(F)F)cn1] | 0.64 | | Method 1 |

-continued
| Intermediate | Structure | $t_R$ | Mass spectrum (ESI+): m/z $[M + H]^+$ | LC Method |
|---|---|---|---|---|
| 5-46 | 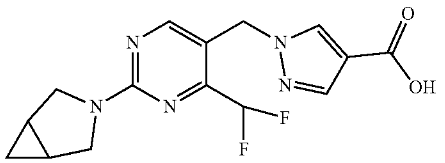 | 0.62 | 336 | Method 1 |
| 5-47 | 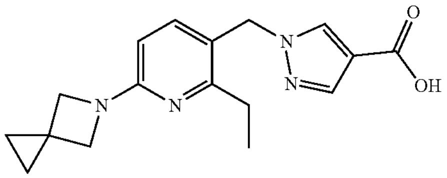 | 0.67 | 313 | Method 1 |
| 5-48 | 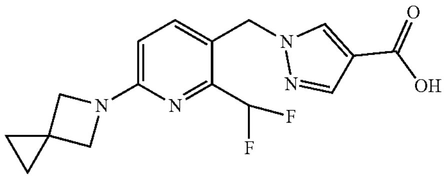 [SMILES: O=C(O)c1cnn(Cc2ccc(N3CC4(CC4)C3)nc2C(F)F)c1] | 0.64 | 335 | Method 1 |
| 5-49 | 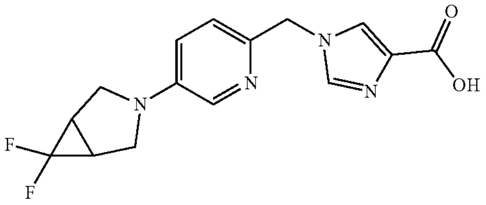 [SMILES: O=C(O)c1cn(Cc2ccc(N3CC4C(C3)C4(F)F)cn2)cn1] | 0.58 | 321 | Method 2 |
| 5-50 | 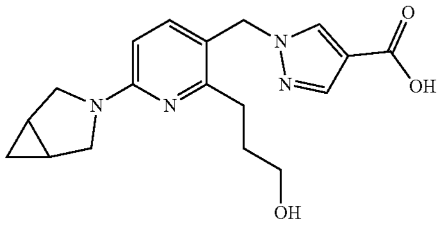 [SMILES: O=C(O)c1cnn(Cc2ccc(N3CC4CC4C3)nc2CCCO)c1] | 0.62 | 343 | Method 2 |
| 5-51 | 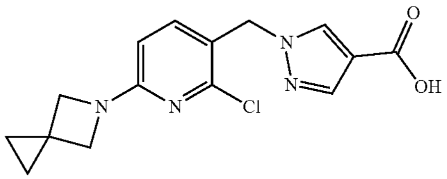 [SMILES: O=C(O)c1cnn(Cc2ccc(N3CC4(CC4)C3)nc2Cl)c1] | 0.62 | 319 | Method 1 |
| 5-52 | 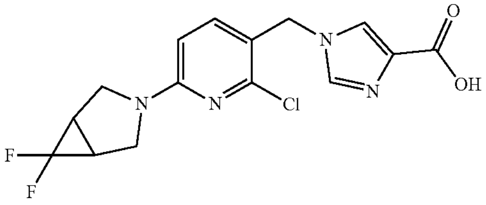 | 0.63 | 377 $[M + Na]^+$ | Method 1 |

-continued
| Intermediate | Structure | $t_R$ | Mass spectrum (ESI+): m/z $[M + H]^+$ | LC Method |
|---|---|---|---|---|
| 5-53 | 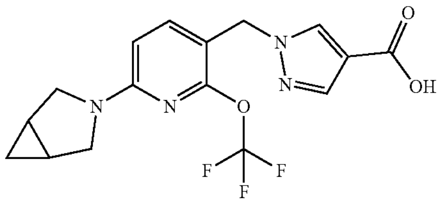 [SMILES: O=C(O)c1cnn(Cc2ccc(N3CC4CC4C3)nc2OC(F)(F)F)c1] | 1.06 | 369 | Method 2 |
| 5-54 | 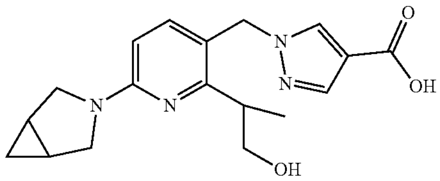 [SMILES: CC(CO)c1nc(N2CC3CC3C2)ccc1Cn1cc(C(=O)O)cn1] | 0.65 | 343 | Method 2 |
| 5-55 | 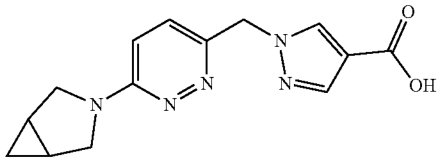 [SMILES: O=C(O)c1cnn(Cc2ccc(N3CC4CC4C3)nn2)c1] | 0.51 | 286 | Method 2 |
| 5-56 | 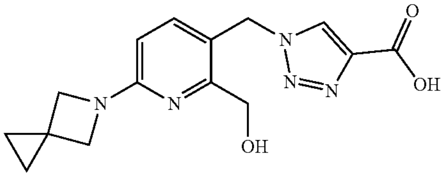 [SMILES: O=C(O)c1cn(Cc2ccc(N3CC4(CC4)C3)nc2CO)nn1] | 0.56 | 316 | Method 2 |
| 5-57 | 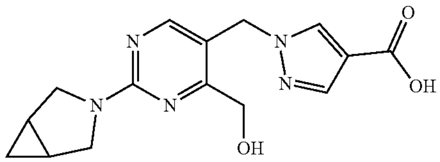 [SMILES: O=C(O)c1cnn(Cc2cnc(N3CC4CC4C3)nc2CO)c1] | 0.66 | 316 | Method 2 |
| 5-58 | 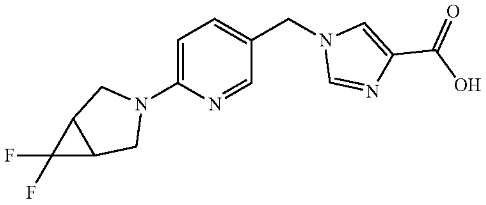 [SMILES: O=C(O)c1cn(Cc2ccc(N3CC4C(C3)C4(F)F)nc2)cn1] | 0.55 | 321 | Method 1 |
| 5-59 | 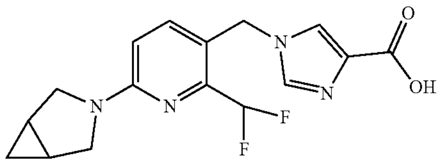 [SMILES: O=C(O)c1cn(Cc2ccc(N3CC4CC4C3)nc2C(F)F)cn1] | 0.66 | 335 | Method 1 |
| 5-60 | 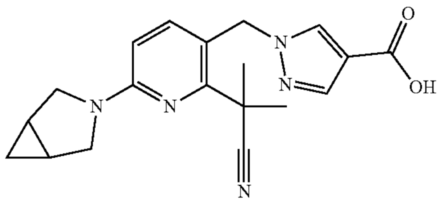 [SMILES: CC(C)(C#N)c1nc(N2CC3CC3C2)ccc1Cn1cc(C(=O)O)cn1] | 1.04 | 352 | Method 2 |

-continued
| Intermediate | Structure | $t_R$ | Mass spectrum (ESI+): m/z $[M + H]^+$ | LC Method |
| --- | --- | --- | --- | --- |
| 5-61 | 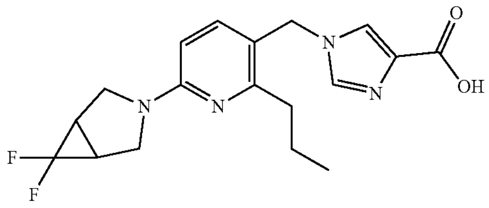 [SMILES: CCCc1nc(N2CC3C(C2)C3(F)F)ccc1Cn1cnc(C(=O)O)c1] | 0.60 | 363 | Method 2 |
| 5-62 | 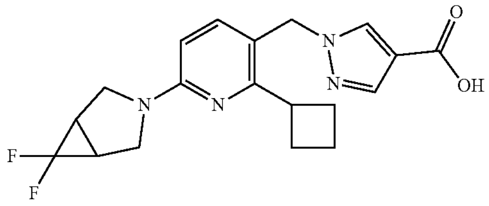 [SMILES: O=C(O)c1cnn(Cc2ccc(N3CC4C(C3)C4(F)F)nc2C2CCC2)c1] | 0.73 | 375 | Method 1 |
| 5-63 | 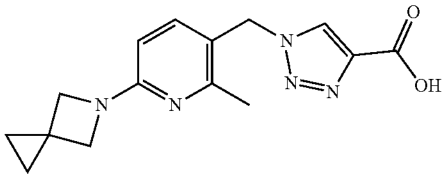 [SMILES: Cc1nc(N2CC3(CC3)C2)ccc1Cn1cc(C(=O)O)nn1] | 0.59 | 300 | Method 2 |
| 5-64 | 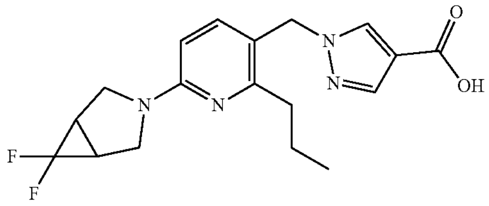 [SMILES: CCCc1nc(N2CC3C(C2)C3(F)F)ccc1Cn1cc(C(=O)O)cn1] | 0.70 | 363 | Method 1 |
| 5-65 | 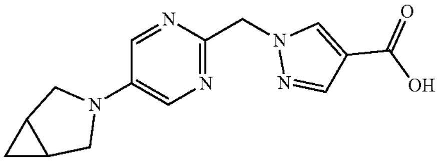 [SMILES: O=C(O)c1cnn(Cc2ncc(N3CC4CC4C3)cn2)c1] | 0.41 | 286 | Method 1 |
| 5-66 | 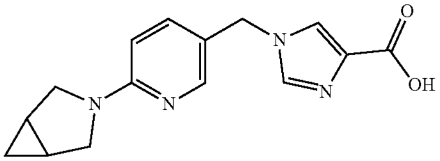 [SMILES: O=C(O)c1cn(Cc2ccc(N3CC4CC4C3)nc2)cn1] | 0.28 | 285 | Method 2 |
| 5-67 | 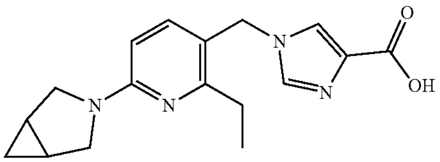 [SMILES: CCc1nc(N2CC3CC3C2)ccc1Cn1cnc(C(=O)O)c1] | 0.40 | 313 | Method 2 |
| 5-68 | 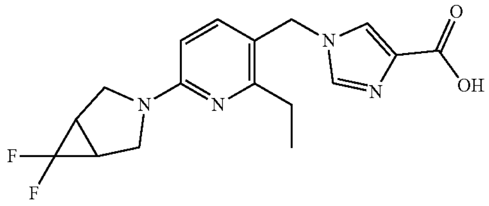 [SMILES: CCc1nc(N2CC3C(C2)C3(F)F)ccc1Cn1cnc(C(=O)O)c1] | 0.73 | 349 | Method 1 |

-continued
| Intermediate | Structure | $t_R$ | Mass spectrum (ESI+): m/z $[M + H]^+$ | LC Method |
|---|---|---|---|---|
| 5-69 | 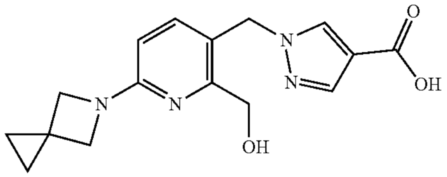 [SMILES: O=C(O)c1cnn(Cc2ccc(N3CC4(CC4)C3)nc2CO)c1] | 0.60 | 315 | Method 1 |
| 5-70 | 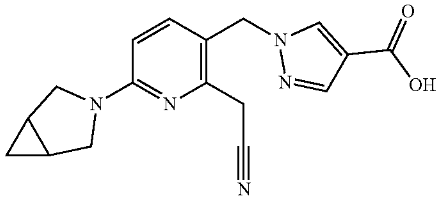 [SMILES: N#CCc1nc(N2CC3CC3C2)ccc1Cn1cc(C(=O)O)cn1] | 0.76 | 324 | Method 2 |
| 5-71 | 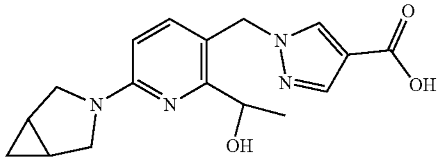 [SMILES: CC(O)c1nc(N2CC3CC3C2)ccc1Cn1cc(C(=O)O)cn1] | 0.61 | 329 | Method 2 |
| 5-72 | 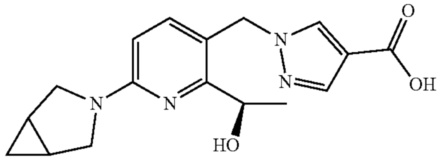 [SMILES: C[C@@H](O)c1nc(N2CC3CC3C2)ccc1Cn1cc(C(=O)O)cn1] | 0.60 | 329 | Method 2 |
| 5-73 | 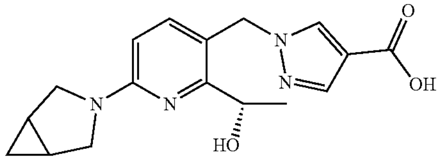 [SMILES: C[C@H](O)c1nc(N2CC3CC3C2)ccc1Cn1cc(C(=O)O)cn1] | 0.60 | 329 | Method 2 |
| 5-74 | 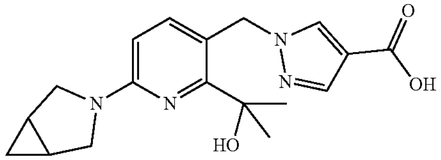 [SMILES: CC(C)(O)c1nc(N2CC3CC3C2)ccc1Cn1cc(C(=O)O)cn1] | 0.63 | 343 | Method 2 |
| 5-75 | 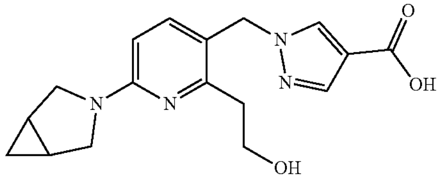 [SMILES: O=C(O)c1cnn(Cc2ccc(N3CC4CC4C3)nc2CCO)c1] | 0.58 | 329 | Method 2 |
| 5-76 | 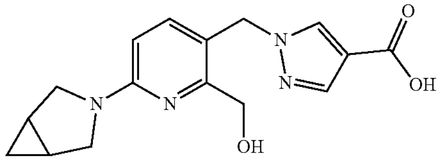 [SMILES: O=C(O)c1cnn(Cc2ccc(N3CC4CC4C3)nc2CO)c1] | 0.71 | 343 | Method 2 |

-continued
| Intermediate | Structure | $t_R$ | Mass spectrum (ESI+): m/z $[M + H]^+$ | LC Method |
|---|---|---|---|---|
| 5-77 | 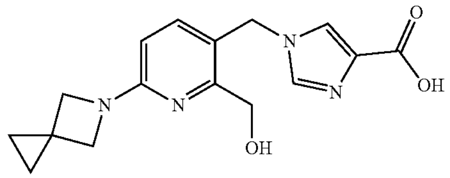 [SMILES: O=C(O)c1cn(Cc2ccc(N3CC4(CC4)C3)nc2CO)cn1] | 0.59 | 315 | Method 1 |
| 5-78 | 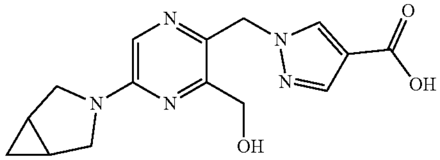 [SMILES: O=C(O)c1cnn(Cc2ncc(N3CC4CC4C3)nc2CO)c1] | 0.77 | 316 | Method 2 |
| 5-79 | 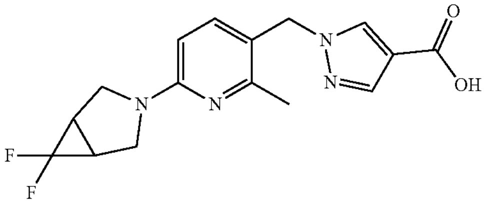 [SMILES: Cc1nc(N2CC3C(C2)C3(F)F)ccc1Cn1cc(C(=O)O)cn1] | 0.62 | 335 | Method 2 |
| 5-80 | 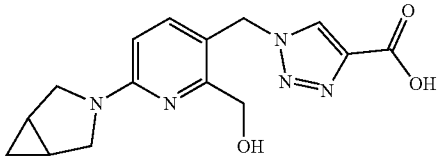 [SMILES: O=C(O)c1cn(Cc2ccc(N3CC4CC4C3)nc2CO)nn1] | 0.33 | 316 | Method 2 |
| 5-81 | 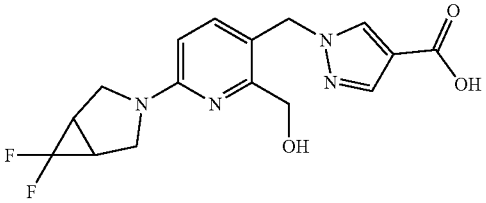 | Crude product is directly used in the next step | | |
| 5-82 | 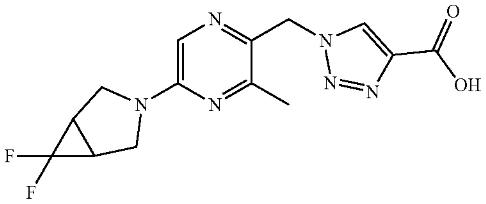 [SMILES: Cc1nc(N2CC3C(C2)C3(F)F)cnc1Cn1cc(C(=O)O)nn1] | 0.83 | 337 | Method 2 |
| 5-83 | 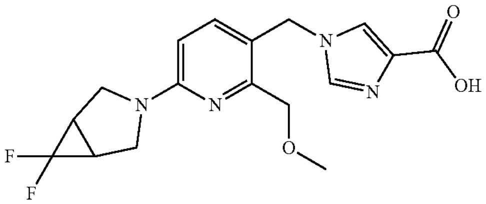 [SMILES: COCc1nc(N2CC3C(C2)C3(F)F)ccc1Cn1cnc(C(=O)O)c1] | 0.59 | 365 | Method 2 |

-continued
| Intermediate | Structure | $t_R$ | Mass spectrum (ESI+): m/z $[M + H]^+$ | LC Method |
|---|---|---|---|---|
| 5-84 | 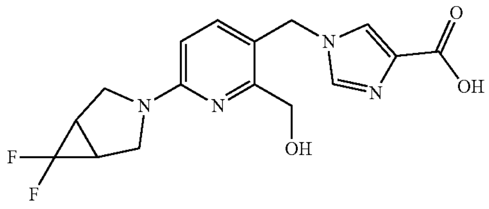 [SMILES: O=C(O)c1cn(Cc2ccc(N3CC4C(C3)C4(F)F)nc2CO)cn1] | 0.24 | 351 | Method 2 |
| 5-85 | 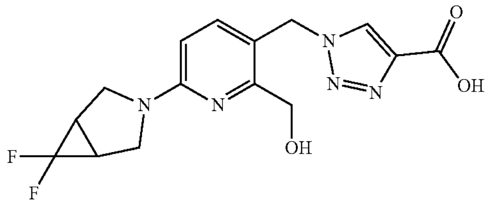 [SMILES: O=C(O)c1cn(Cc2ccc(N3CC4C(C3)C4(F)F)nc2CO)nn1] | 0.44 | 352 | Method 2 |
| 5-86 | 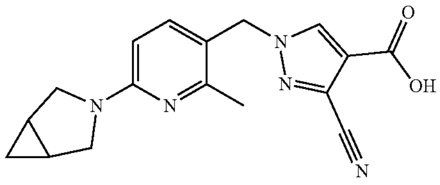 [SMILES: Cc1nc(N2CC3CC3C2)ccc1Cn1cc(C(=O)O)c(C#N)n1] | 0.69 | 324 | Method 1 |
| 5-87 | 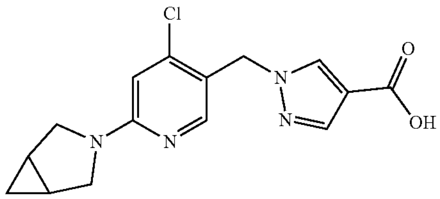 [SMILES: O=C(O)c1cnn(Cc2cnc(N3CC4CC4C3)cc2Cl)c1] | 0.66 | 319 | Method 2 |
| 5-88 | 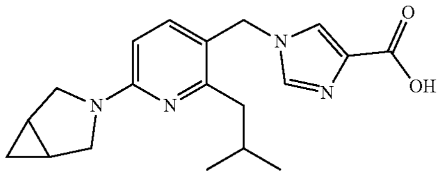 | 0.62 | 341 | Method 2 |
| 5-89 | 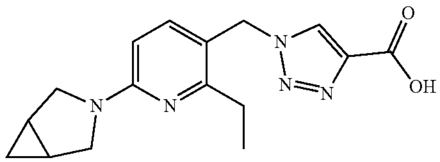 [SMILES: CCc1nc(N2CC3CC3C2)ccc1Cn1cc(C(=O)O)nn1] | 0.60 | 314 | Method 2 |
| 5-90 | 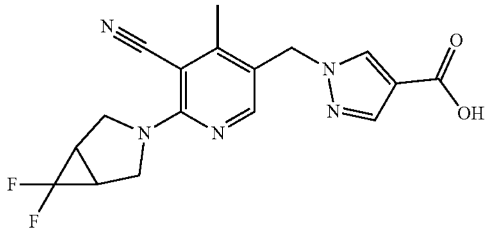 [SMILES: Cc1c(Cn2cc(C(=O)O)cn2)cnc(N2CC3C(C2)C3(F)F)c1C#N] | 0.90 | 360 | Method 2 |

-continued
| Intermediate | Structure | $t_R$ | Mass spectrum (ESI+): m/z $[M + H]^+$ | LC Method |
|---|---|---|---|---|
| 5-91 | 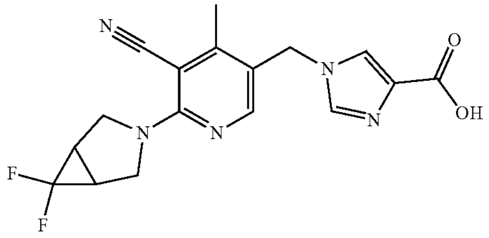 [SMILES: Cc1c(Cn2cnc(C(=O)O)c2)cnc(N2CC3C(C2)C3(F)F)c1C#N] | 0.75 | 382 $[M + Na]^+$ | Method 2 |
| 5-92 | 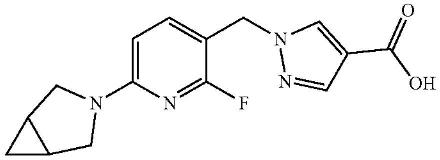 | 0.92 | 303 | Method 2 |
| 5-93 | 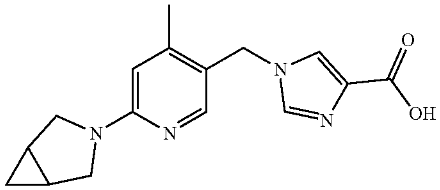 [SMILES: Cc1cc(N2CC3CC3C2)ncc1Cn1cnc(C(=O)O)c1] | 0.65 | 299 | Method 1 |
| 5-94 | 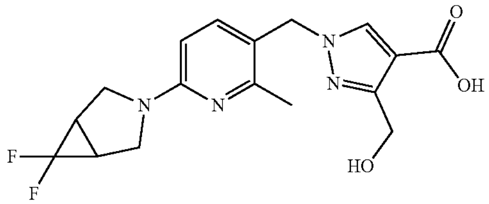 [SMILES: Cc1nc(N2CC3C(C2)C3(F)F)ccc1Cn1cc(C(=O)O)c(CO)n1] | 0.59 | 365 | Method 2 |
| 5-95 | 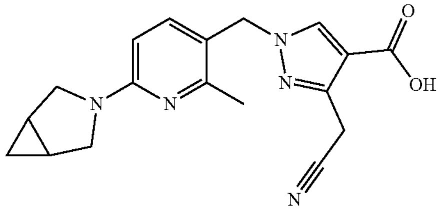 [SMILES: Cc1nc(N2CC3CC3C2)ccc1Cn1cc(C(=O)O)c(CC#N)n1] | 0.64 | 338 | Method 2 |
| 5-96 | 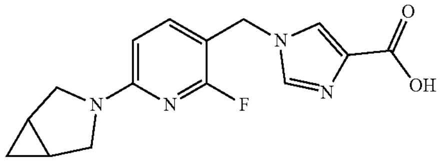 [SMILES: O=C(O)c1cn(Cc2ccc(N3CC4CC4C3)nc2F)cn1] | 0.75 | | Method 2 |
| 5-97 | 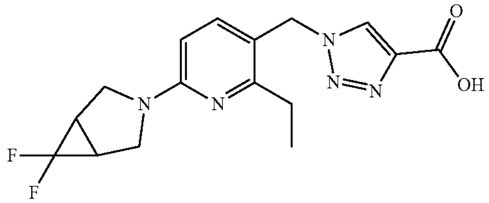 [SMILES: CCc1nc(N2CC3C(C2)C3(F)F)ccc1Cn1cc(C(=O)O)nn1] | 0.63 | 350 | Method 2 |

-continued
| Intermediate | Structure | $t_R$ | Mass spectrum (ESI+): m/z $[M + H]^+$ | LC Method |
| --- | --- | --- | --- | --- |
| 5-98 | 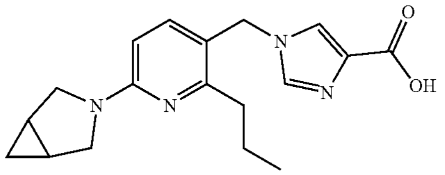 [SMILES: CCCc1nc(N2CC3CC3C2)ccc1Cn1cnc(C(=O)O)c1] | 0.57 | 327 | Method 2 |
| 5-99 | 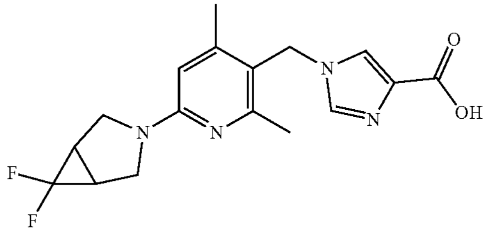 [SMILES: Cc1cc(N2CC3C(C2)C3(F)F)nc(C)c1Cn1cnc(C(=O)O)c1] | 0.64 | 349 | Method 1 |
| 5-100 | 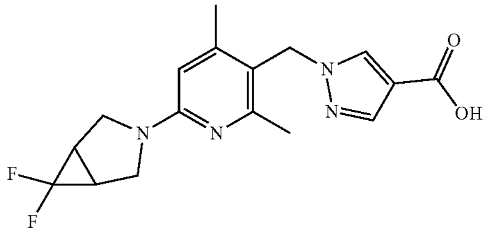 [SMILES: Cc1cc(N2CC3C(C2)C3(F)F)nc(C)c1Cn1cc(C(=O)O)cn1] | 0.67 | 349 | Method 2 |
| 5-101 | 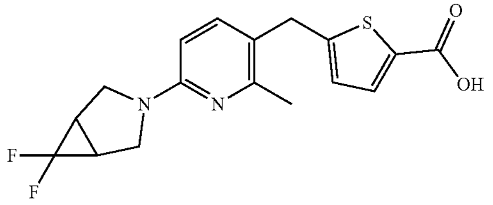 | 0.72 | 351 | Method 2 |
| 5-102 | 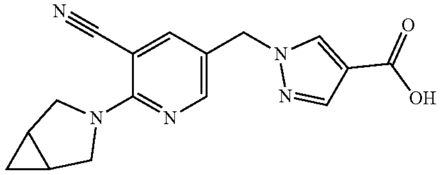 [SMILES: N#Cc1cc(Cn2cc(C(=O)O)cn2)cnc1N1CC2CC2C1] | 0.86 | 310 | Method 2 |
| 5-103 | 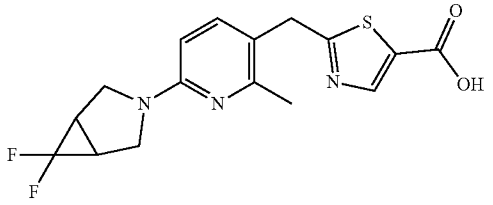 [SMILES: Cc1nc(N2CC3C(C2)C3(F)F)ccc1Cc1ncc(C(=O)O)s1] | 0.64 | 352 | Method 2 |
| 5-104 | 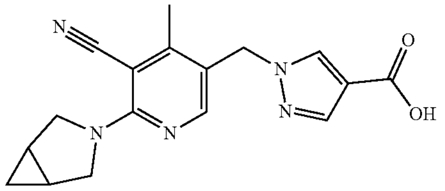 [SMILES: Cc1c(Cn2cc(C(=O)O)cn2)cnc(N2CC3CC3C2)c1C#N] | 0.87 | 324 | Method 2 |

-continued
| Intermediate | Structure | $t_R$ | Mass spectrum (ESI+): m/z $[M + H]^+$ | LC Method |
|---|---|---|---|---|
| 5-105 | 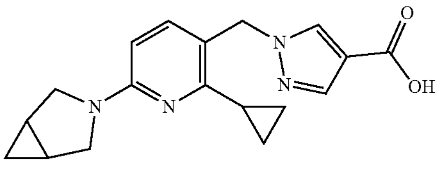 [SMILES: O=C(O)c1cnn(Cc2ccc(N3CC4CC4C3)nc2C2CC2)c1] | 0.70 | 325 | Method 2 |
| 5-106 | 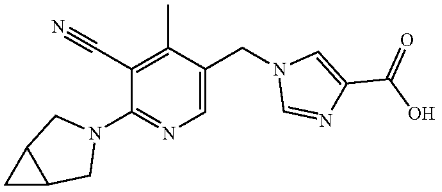 [SMILES: Cc1c(Cn2cnc(C(=O)O)c2)cnc(N2CC3CC3C2)c1C#N] | 0.73 | 322 $[M - H]^-$ | Method 2 |
| 5-107 | 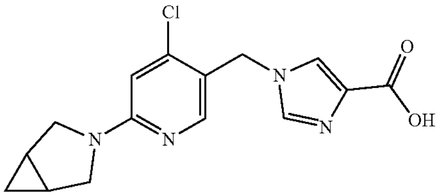 [SMILES: O=C(O)c1cn(Cc2cnc(N3CC4CC4C3)cc2Cl)cn1] | 0.56 | 319 | Method 2 |
| 5-108 | 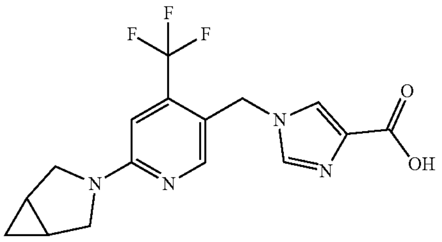 [SMILES: O=C(O)c1cn(Cc2cnc(N3CC4CC4C3)cc2C(F)(F)F)cn1] | 0.71 | 353 | Method 2 |
| 5-109 | 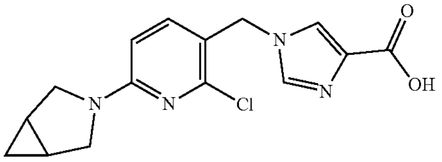 [SMILES: O=C(O)c1cn(Cc2ccc(N3CC4CC4C3)nc2Cl)cn1] | 0.78 | 319 | Method 2 |
| 5-110 | 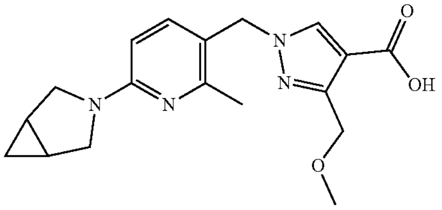 [SMILES: COCc1nn(Cc2ccc(N3CC4CC4C3)nc2C)cc1C(=O)O] | 0.63 | 343 | Method 2 |
| 5-111 | 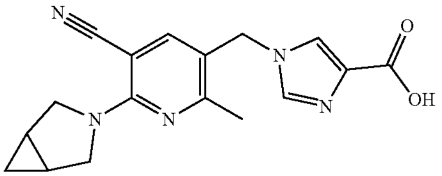 [SMILES: Cc1nc(N2CC3CC3C2)c(C#N)cc1Cn1cnc(C(=O)O)c1] | 0.78 | 324 | Method 2 |

-continued
| Intermediate | Structure | $t_R$ | Mass spectrum (ESI+): m/z $[M + H]^+$ | LC Method |
|---|---|---|---|---|
| 5-112 | 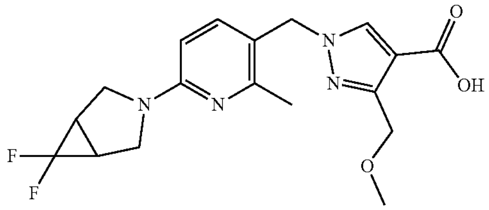 [SMILES: COCc1nn(Cc2ccc(N3CC4C(C3)C4(F)F)nc2C)cc1C(=O)O] | 0.64 | 379 | Method 2 |
| 5-113 | 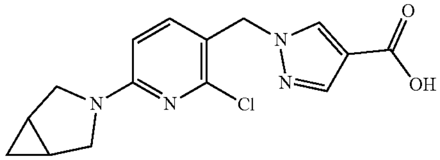 [SMILES: O=C(O)c1cnn(Cc2ccc(N3CC4CC4C3)nc2Cl)c1] | 0.97 | 319 | Method 2 |
| 5-114 | 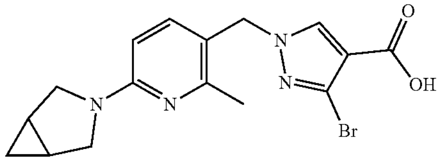 [SMILES: Cc1nc(N2CC3CC3C2)ccc1Cn1cc(C(=O)O)c(Br)n1] | 0.67 | 378 | Method 2 |
| 5-115 | 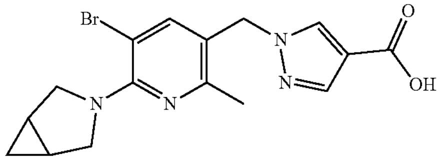 [SMILES: Cc1nc(N2CC3CC3C2)c(Br)cc1Cn1cc(C(=O)O)cn1] | 0.97 | 377 | Method 2 |
| 5-116 | 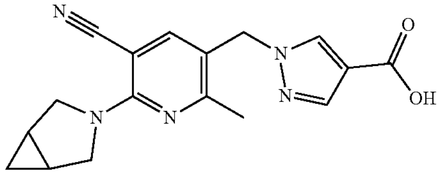 [SMILES: Cc1nc(N2CC3CC3C2)c(C#N)cc1Cn1cc(C(=O)O)cn1] | 0.95 | 324 | Method 2 |
| 5-117 | 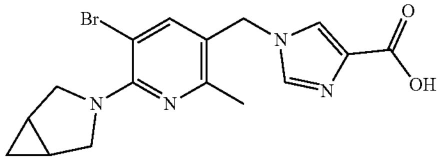 [SMILES: Cc1nc(N2CC3CC3C2)c(Br)cc1Cn1cnc(C(=O)O)c1] | 0.74 | 377 | Method 1 |
| 5-118 | 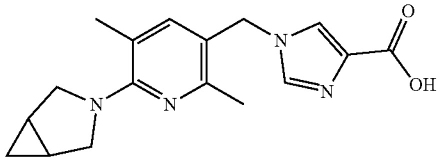 [SMILES: Cc1cc(Cn2cnc(C(=O)O)c2)c(C)nc1N1CC2CC2C1] | 0.68 | 313 | Method 2 |
| 5-119 | 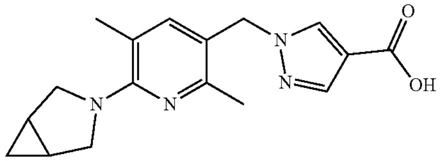 [SMILES: Cc1cc(Cn2cc(C(=O)O)cn2)c(C)nc1N1CC2CC2C1] | 0.65 | 313 | Method 2 |

-continued
| Intermediate | Structure | $t_R$ | Mass spectrum (ESI+): m/z $[M + H]^+$ | LC Method |
|---|---|---|---|---|
| 5-120 | 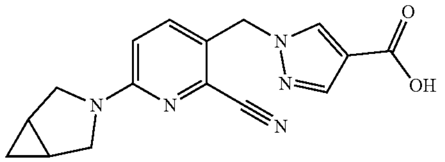 [SMILES: N#Cc1nc(N2CC3CC3C2)ccc1Cn1cc(C(=O)O)cn1] | 0.65 | 310 | Method 1 |
| 5-121 | 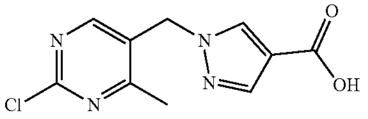 [SMILES: Cc1nc(Cl)ncc1Cn1cc(C(=O)O)cn1] | 0.68 | 253 | Method 2 |
| 5-122 | 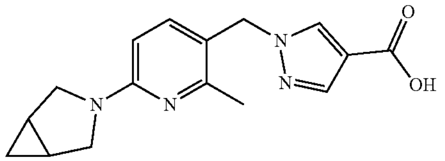 [SMILES: Cc1nc(N2CC3CC3C2)ccc1Cn1cc(C(=O)O)cn1] | 0.60 | 299 | Method 2 |
| 5-123 | 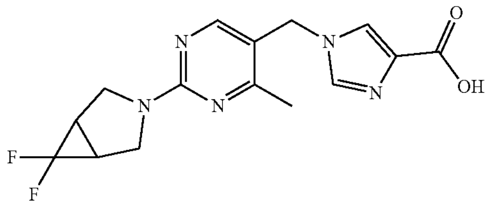 | 0.67 | 336 | Method 2 |
| 5-124 | 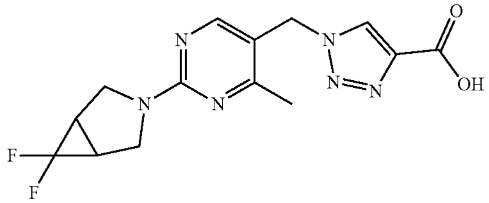 [SMILES: Cc1nc(N2CC3C(C2)C3(F)F)ncc1Cn1cnc(C(=O)O)c1] | 0.74 | 337 | Method 2 |
| 5-125 | 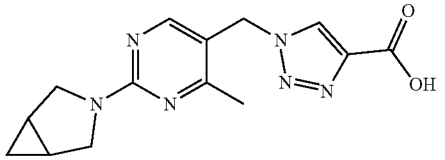 [SMILES: Cc1nc(N2CC3CC3C2)ncc1Cn1cc(C(=O)O)nn1] | 0.65 | 301 | Method 2 |
| 5-126 | 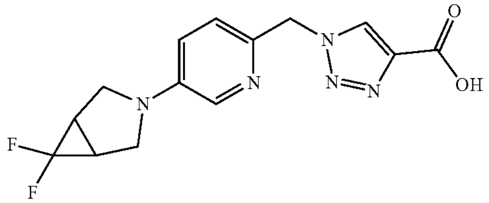 [SMILES: O=C(O)c1cn(Cc2ccc(N3CC4C(C3)C4(F)F)cn2)nn1] | 0.65 | 322 | Method 2 |
| 5-127 | 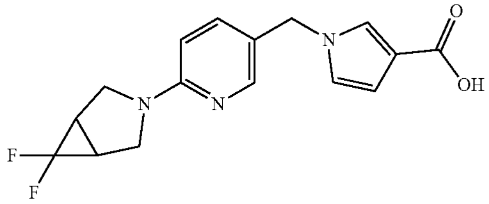 [SMILES: O=C(O)c1ccn(Cc2ccc(N3CC4C(C3)C4(F)F)nc2)c1] | 0.62 | 320 | Method 2 |

-continued
| Intermediate | Structure | $t_R$ | Mass spectrum (ESI+): m/z $[M + H]^+$ | LC Method |
|---|---|---|---|---|
| 5-128 | 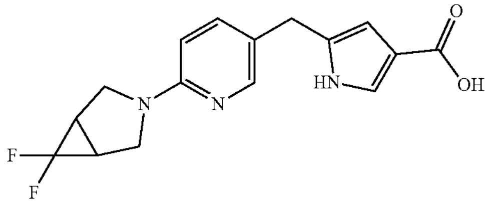 [SMILES: O=C(O)c1c[nH]c(Cc2ccc(N3CC4C(C3)C4(F)F)nc2)c1] | 0.62 | 320 | Method 2 |
| 5-129 | 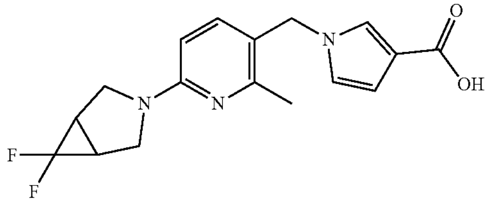 [SMILES: Cc1nc(N2CC3C(C2)C3(F)F)ccc1Cn1ccc(C(=O)O)c1] | 0.65 | 334 | Method 2 |
| 5-130 | 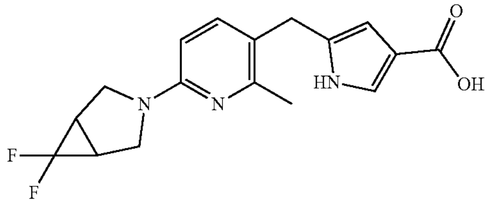 | 0.65 | 334 | Method 2 |
| 5-131 | 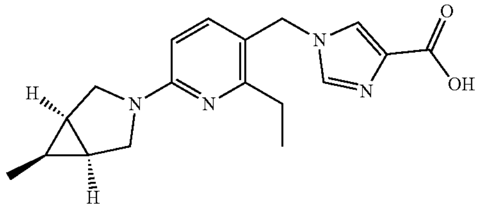 [SMILES: CCc1nc(N2C[C@@H]3[C@H](C)[C@@H]3C2)ccc1Cn1cnc(C(=O)O)c1] | 0.73 | 327 | Method 2 |
| 5-132 | 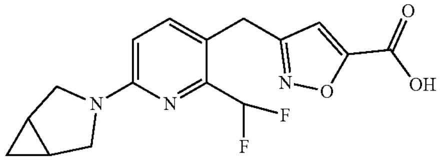 [SMILES: O=C(O)c1cc(Cc2ccc(N3CC4CC4C3)nc2C(F)F)no1] | 0.70 | 336 | Method 1 |
| 5-133 | 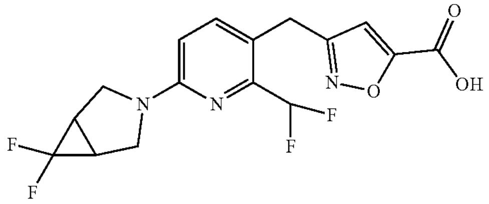 [SMILES: O=C(O)c1cc(Cc2ccc(N3CC4C(C3)C4(F)F)nc2C(F)F)no1] | 0.72 | 372 | Method 1 |
| 5-134 | 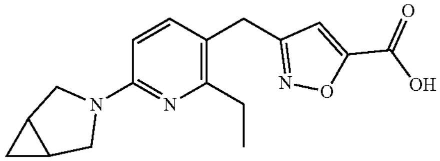 [SMILES: CCc1nc(N2CC3CC3C2)ccc1Cc1cc(C(=O)O)on1] | 0.65 | 314 | Method 2 |

-continued
| Intermediate | Structure | $t_R$ | Mass spectrum (ESI+): m/z $[M + H]^+$ | LC Method |
|---|---|---|---|---|
| 5-135 | 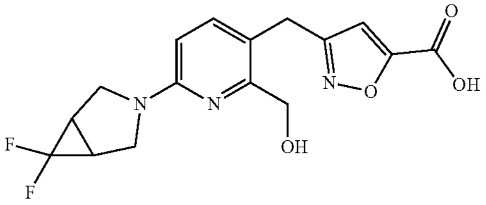 [SMILES: O=C(O)c1cc(Cc2ccc(N3CC4C(C3)C4(F)F)nc2CO)no1] | 0.64 | 352 | Method 1 |
| 5-136 | 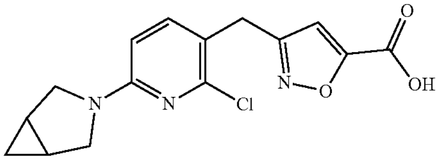 [SMILES: O=C(O)c1cc(Cc2ccc(N3CC4CC4C3)nc2Cl)no1] | 0.65 | 320 | Method 1 |
| 5-137 | 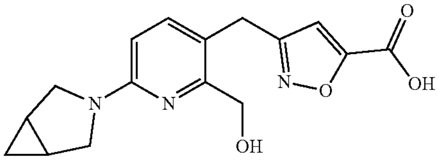 [SMILES: O=C(O)c1cc(Cc2ccc(N3CC4CC4C3)nc2CO)no1] | 0.65 | 316 | Method 1 |
| 5-138 | 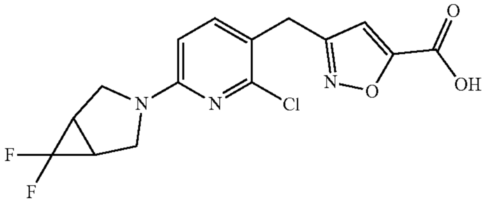 [SMILES: O=C(O)c1cc(Cc2ccc(N3CC4C(C3)C4(F)F)nc2Cl)no1] | 0.99 | 356 | Method 2 |
| 5-139 | 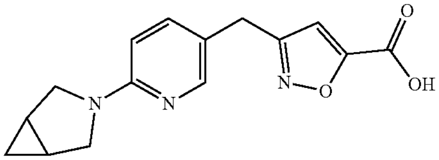 [SMILES: O=C(O)c1cc(Cc2ccc(N3CC4CC4C3)nc2)no1] | 0.61 | 286 | Method 1 |
| 5-140 | 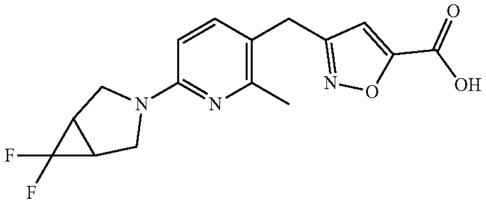 [SMILES: Cc1nc(N2CC3C(C2)C3(F)F)ccc1Cc1cc(C(=O)O)on1] | 0.64 | 336 | Method 2 |
| 5-141 | 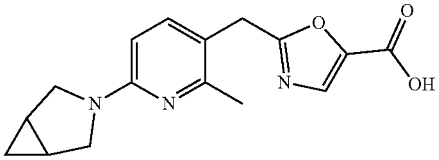 [SMILES: Cc1nc(N2CC3CC3C2)ccc1Cc1ncc(C(=O)O)o1] | 0.61 | 300 | Method 2 |
| 5-142 | 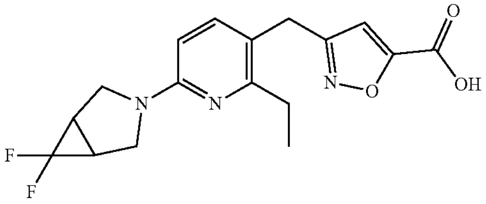 [SMILES: CCc1nc(N2CC3C(C2)C3(F)F)ccc1Cc1cc(C(=O)O)on1] | 0.68 | 350 | Method 2 |

-continued
| Intermediate | Structure | $t_R$ | Mass spectrum (ESI+): m/z $[M + H]^+$ | LC Method |
|---|---|---|---|---|
| 5-143 | 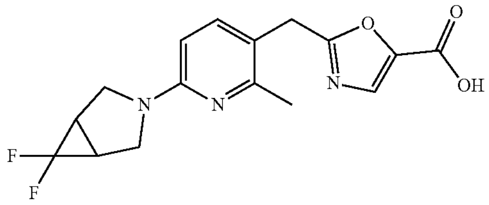 [SMILES: Cc1nc(N2CC3C(C2)C3(F)F)ccc1Cc1ncc(C(=O)O)o1] | 0.62 | 336 | Method 2 |
| 5-144 | 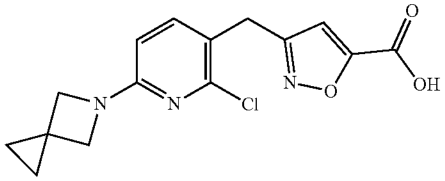 [SMILES: O=C(O)c1cc(Cc2ccc(N3CC4(CC4)C3)nc2Cl)no1] | 0.98 | 320 | Method 2 |
| 5-145 | 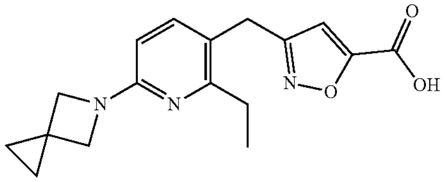 [SMILES: CCc1nc(N2CC3(CC3)C2)ccc1Cc1cc(C(=O)O)on1] | 0.67 | 314 | Method 2 |
| 5-146 | 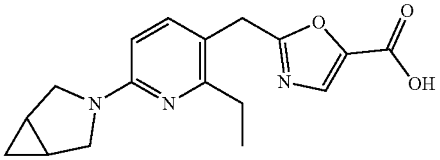 [SMILES: CCc1nc(N2CC3CC3C2)ccc1Cc1ncc(C(=O)O)o1] | 0.64 | 314 | Method 2 |
| 5-147 | 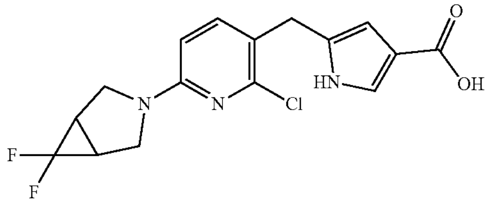 [SMILES: O=C(O)c1c[nH]c(Cc2ccc(N3CC4C(C3)C4(F)F)nc2Cl)c1] | 0.94 | 354 | Method 2 |
| 5-148 | 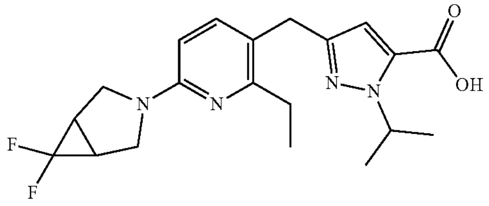 [SMILES: CCc1nc(N2CC3C(C2)C3(F)F)ccc1Cc1cc(C(=O)O)n(C(C)C)n1] | 0.78 | 391 | Method 2 |
| 5-149 | 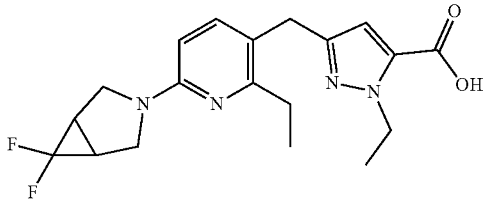 [SMILES: CCc1nc(N2CC3C(C2)C3(F)F)ccc1Cc1cc(C(=O)O)n(CC)n1] | 0.74 | 377 | Method 2 |

-continued
| Intermediate | Structure | $t_R$ | Mass spectrum (ESI+): m/z $[M + H]^+$ | LC Method |
|---|---|---|---|---|
| 5-150 | 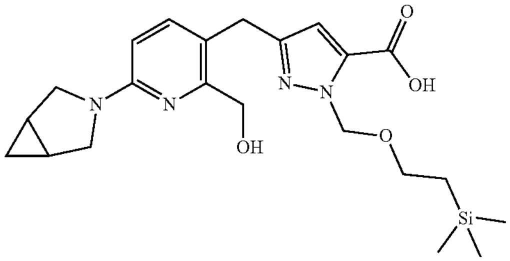 [SMILES: C[Si](C)(C)CCOCn1nc(Cc2ccc(N3CC4CC4C3)nc2CO)cc1C(=O)O] 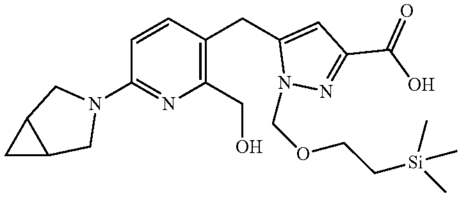 [SMILES: C[Si](C)(C)CCOCn1nc(C(=O)O)cc1Cc1ccc(N2CC3CC3C2)nc1CO] (mixture of isomers) | 0.82 and 0.84 | 445 | Method 2 |
| 5-151 | 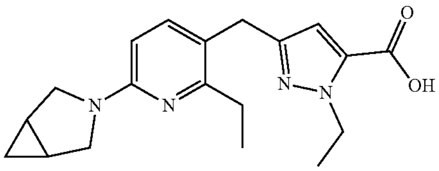 [SMILES: CCc1nc(N2CC3CC3C2)ccc1Cc1cc(C(=O)O)n(CC)n1] | 0.73 | 341 | Method 2 |
| 5-152 | 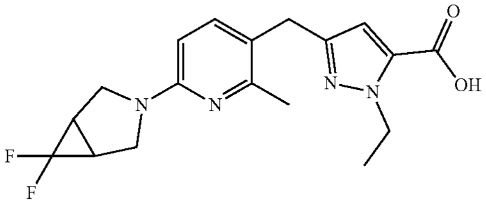 [SMILES: CCn1nc(Cc2ccc(N3CC4C(C3)C4(F)F)nc2C)cc1C(=O)O] | 0.71 | 363 | Method 2 |
| 5-153 | 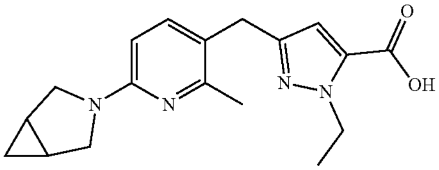 [SMILES: CCn1nc(Cc2ccc(N3CC4CC4C3)nc2C)cc1C(=O)O] | 0.70 | 327 | Method 2 |
| 5-154 | 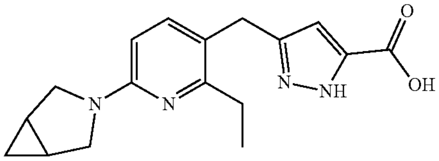 [SMILES: CCc1nc(N2CC3CC3C2)ccc1Cc1cc(C(=O)O)[nH]n1] | 0.65 | 313 | Method 2 |
| 5-155 | 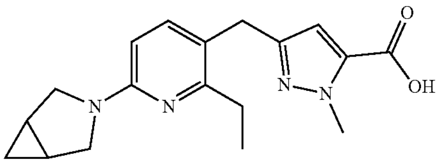 [SMILES: CCc1nc(N2CC3CC3C2)ccc1Cc1cc(C(=O)O)n(C)n1] | 0.71 | 327 | Method 2 |

-continued
| Intermediate | Structure | $t_R$ | Mass spectrum (ESI+): m/z $[M + H]^+$ | LC Method |
|---|---|---|---|---|
| 5-156 | 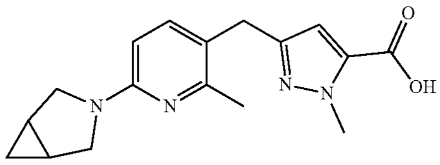 [SMILES: Cc1nc(N2CC3CC3C2)ccc1Cc1cc(C(=O)O)n(C)n1] | 0.67 | 313 | Method 2 |
| 5-157 | 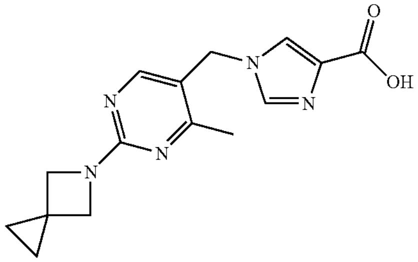 | 0.58 | 300 | Method 2 |
| 5-158 | 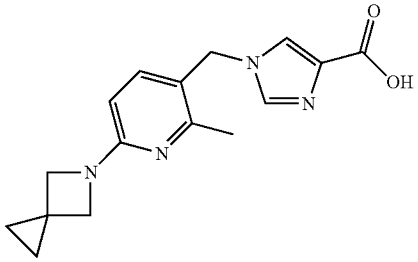 [SMILES: Cc1nc(N2CC3(CC3)C2)ccc1Cn1cnc(C(=O)O)c1] | 0.63 | 299 | Method 2 |
| 5-159 | 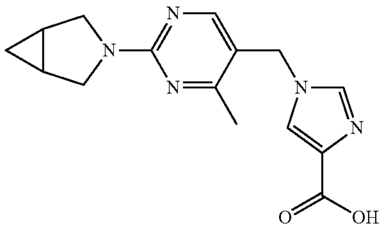 [SMILES: Cc1nc(N2CC3CC3C2)ncc1Cn1cnc(C(=O)O)c1] | 0.60 | 300 | Method 2 |
| 5-160 | 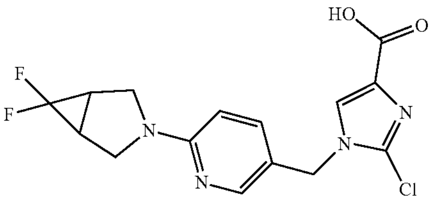 [SMILES: O=C(O)c1cn(Cc2ccc(N3CC4C(C3)C4(F)F)nc2)c(Cl)n1] | 0.65 | 355 | Method 1 |
| 5-161 | 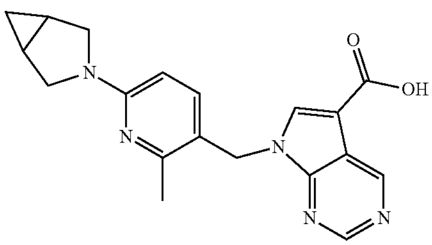 [SMILES: Cc1nc(N2CC3CC3C2)ccc1Cn1cc(C(=O)O)c2cncnc21] | 0.63 | 350 | Method 1 |

-continued
| Intermediate | Structure | $t_R$ | Mass spectrum (ESI+): m/z $[M + H]^+$ | LC Method |
|---|---|---|---|---|
| 5-162 | 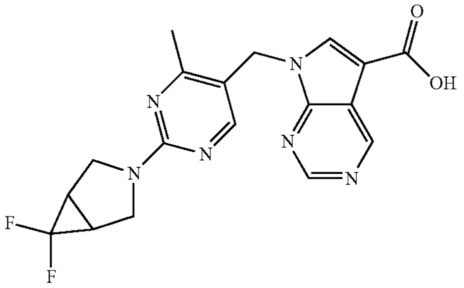 [SMILES: Cc1nc(N2CC3C(C2)C3(F)F)ncc1Cn1cc(C(=O)O)c2cncnc21] | 0.77 | 387 | Method 1 |
| 5-163 | 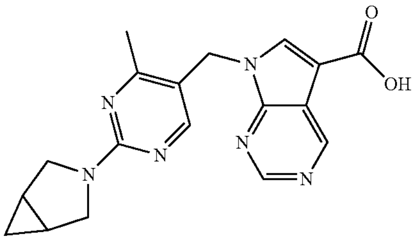 [SMILES: Cc1nc(N2CC3CC3C2)ncc1Cn1cc(C(=O)O)c2cncnc21] | 0.68 | 351 | Method 1 |
| 5-164 | 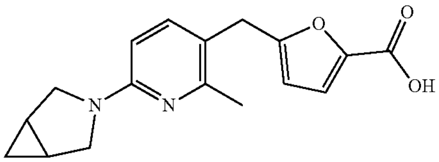 [SMILES: Cc1nc(N2CC3CC3C2)ccc1Cc1ccc(C(=O)O)o1] | 0.67 | 299 | Method 2 |
| 5-165 | 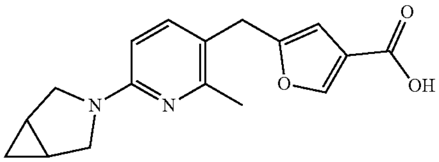 [SMILES: Cc1nc(N2CC3CC3C2)ccc1Cc1cc(C(=O)O)co1] | 0.68 | 299 | Method 2 |
| 5-166 | 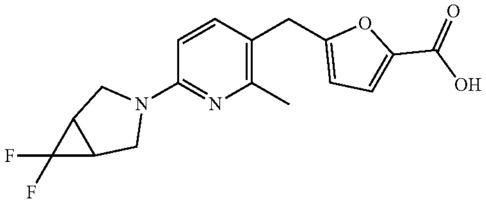 [SMILES: CCc1nc(N2CC3C(C2)C3(F)F)ccc1Cc1ccc(C(=O)O)o1] | 0.69 | 335 | Method 2 |
| 5-167 | 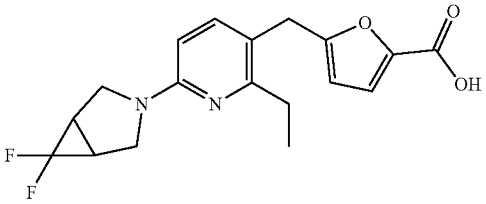 | 0.72 | 349 | Method 2 |
| 5-168 | 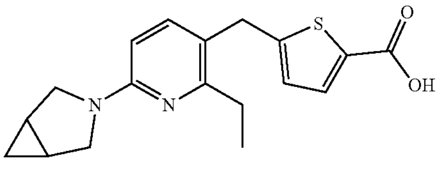 [SMILES: CCc1nc(N2CC3CC3C2)ccc1Cc1ccc(C(=O)O)s1] | 0.72 | 329 | Method 2 |

-continued

| Intermediate | Structure | $t_R$ | Mass spectrum (ESI+): m/z $[M + H]^+$ | LC Method |
|---|---|---|---|---|
| 5-169 | 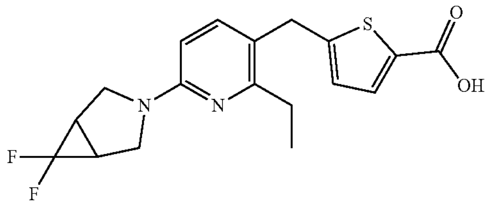 [SMILES: CCc1nc(N2CC3C(C2)C3(F)F)ccc1Cc1ccc(C(=O)O)s1] | 0.75 | 365 | Method 2 |
| 5-170 | 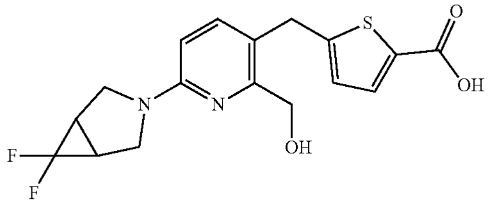 [SMILES: O=C(O)c1ccc(Cc2ccc(N3CC4C(C3)C4(F)F)nc2CO)s1] | 0.69 | 367 | Method 2 |

| Intermediate | Reaction comment |
|---|---|
| 5-1 | The reaction is conducted in EtOH for 3 h at rt. |
| 5-2 | NaOH is used instead of KOH. The reaction is conducted for 1.5 h at 70° C. |
| 5-3 | NaOH is used instead of KOH. The reaction is conducted in EtOH for 48 h at rt. The product is purified by HPLC on reversed phase (ACN, water). |
| 5-4 | NaOH is used instead of KOH. The reaction is conducted at 70° C. for 2 h. |
| 5-5 | NaOH is used instead of KOH. The reaction is conducted at 70° C. for 1 h. |
| 5-6 | NaOH is used instead of KOH. The reaction is conducted at 70° C. for 1.5 h. |
| 5-7 | NaOH is used instead of KOH. The reaction is conducted at 70° C. for 1.5 h. |
| 5-9 | NaOH is used instead of KOH. The reaction is conducted at 70° C. for 1.5 h. |
| 5-10 | NaOH is used instead of KOH. The reaction is conducted at 70° C. for 1.5 h. |
| 5-11 | NaOH is used instead of KOH. The reaction is conducted at 70° C. for 1.5 h. |
| 5-12 | NaOH is used instead of KOH. The reaction is conducted at 70° C. for 2 h. |
| 5-13 | NaOH is used instead of KOH. The reaction is conducted at 70° C. for 1 h. |
| 5-14 | NaOH is used instead of KOH. The reaction is conducted in THF/EtOH for 45 minutes at 70° C. |
| 5-15 | NaOH is used instead of KOH. The reaction is conducted at 70° C. for 1.5 h. |
| 5-16 | NaOH is used instead of KOH. The reaction is conducted at 70° C. for 1 h. |
| 5-17 | NaOH is used instead of KOH. The reaction is conducted at 70° C. for 1.5 h. |
| 5-19 | NaOH is used instead of KOH. The reaction is conducted in THF/EtOH for 2 h at 50° C. |
| 5-20 | NaOH is used instead of KOH. The reaction is conducted in THF/EtOH for 20 minutes at 70° C. |
| 5-21 | NaOH is used instead of KOH. The reaction is conducted in MeOH for 12 h at rt. |
| 5-22 | NaOH is used instead of KOH. The reaction is conducted at 70° C. for 1 h. |
| 5-23 | NaOH is used instead of KOH. The reaction is conducted at 70° C. for 0.1 h. |
| 5-24 | NaOH is used instead of KOH. The reaction is conducted in THF/EtOH for 45 minutes at 70° C. |
| 5-25 | NaOH is used instead of KOH. The reaction is conducted in THF/EtOH for 4 h at 50° C. |
| 5-26 | NaOH is used instead of KOH. The reaction is conducted at 70° C. for 1 h. |
| 5-27 | NaOH is used instead of KOH. The reaction is conducted in THF/EtOH for 2 h at 70° C. |
| 5-28 | NaOH is used instead of KOH. The reaction is conducted at 70° C. for 1 h. |
| 5-29 | The reaction is conducted at 70° C. for 1 h. |
| 5-30 | NaOH is used instead of KOH. The reaction is conducted in EtOH for 3 h at rt. |
| 5-31 | NaOH is used instead of KOH. The reaction is conducted for 1.5 h at 50° C. |
| 5-32 | NaOH is used instead of KOH. The reaction is conducted at 70° C. for 1 h. |
| 5-33 | NaOH is used instead of KOH. The reaction is conducted at 50° C. for 1 h. |
| 5-34 | NaOH is used instead of KOH. The reaction is conducted at 50° C. for 1.5 h. |
| 5-35 | NaOH is used instead of KOH. The reaction is conducted in THF/EtOH for 5 h at 50° C. |
| 5-36 | NaOH is used instead of KOH. The reaction is conducted at 70° C. for 1 h. |
| 5-37 | NaOH is used instead of KOH. The reaction is conducted at 70° C. for 1 h. |
| 5-38 | NaOH is used instead of KOH. The reaction is conducted at 70° C. for 3 h. |
| 5-40 | NaOH is used instead of KOH. The reaction is conducted at 50° C. for 1 h. |
| 5-41 | NaOH is used instead of KOH. The reaction is conducted at 70° C. for 8 h. |
| 5-42 | NaOH is used instead of KOH. The reaction is conducted at 40° C. for 4 h. |
| 5-43 | NaOH is used instead of KOH. The reaction is conducted in THF/EtOH for 45 minutes at 70° C. |
| 5-44 | NaOH is used instead of KOH. The reaction is conducted in THF/EtOH for 2 h at 70° C. |
| 5-45 | NaOH is used instead of KOH. The reaction is conducted in THF/EtOH for 45 minutes at 70° C. |
| 5-46 | The reaction is conducted in EtOH for 48 h at 50° C. |
| 5-47 | The reaction is conducted in EtOH for 4 h at 50° C. |
| 5-48 | NaOH is used instead of KOH. The reaction is conducted in THF/EtOH for 2 h at 70° C. |
| 5-49 | The reaction is conducted for 2 h at 50° C. |
| 5-50 | NaOH is used instead of KOH. The reaction is conducted in EtOH for 12 h at 40° C. |
| 5-51 | NaOH is used instead of KOH. The reaction is conducted in THF/EtOH for 1 h at 70° C. |
| 5-52 | NaOH is used instead of KOH. The reaction is conducted in THF/EtOH for 40 minutes at 70° C. |

-continued

| Intermediate | Reaction comment |
|---|---|
| 5-53 | NaOH is used instead of KOH. The reaction is conducted at 70° C. for 2 h. |
| 5-54 | NaOH is used instead of KOH. The reaction is conducted in EtOH for 12 h at rt. |
| 5-55 | NaOH is used instead of KOH. The reaction is conducted at 70° C. for 5 h. |
| 5-56 | NaOH is used instead of KOH. The reaction is conducted at 50° C. for 2 h. |
| 5-57 | NaOH is used instead of KOH. The reaction is conducted in THF for 4 h at 80° C. |
| 5-58 | NaOH is used instead of KOH. The reaction is conducted in 1,4-dioxane for 3 h at 50° C. |
| 5-59 | NaOH is used instead of KOH. The reaction is conducted in THF/EtOH for 40 minutes at 70° C. |
| 5-60 | NaOH is used instead of KOH. The reaction is conducted in EtOH for 48 h at rt. |
| 5-61 | NaOH is used instead of KOH. The reaction is conducted at 70° C. for 1 h. |
| 5-62 | NaOH is used instead of KOH. The reaction is conducted in THF/EtOH for 2 h at 70° C. |
| 5-63 | NaOH is used instead of KOH. The reaction is conducted in THF/EtOH for 2 h at 50° C. |
| 5-64 | NaOH is used instead of KOH. The reaction is conducted in THF/EtOH for 2 h at 70° C. |
| 5-65 | NaOH is used instead of KOH. The reaction is conducted in THF/EtOH for 1.5 h at70° C. |
| 5-66 | NaOH is used instead of KOH. The reaction is conducted in MeOH for 3 h at rt. |
| 5-67 | NaOH is used instead of KOH. The reaction is conducted for 2 h at 60° C. |
| 5-68 | NaOH is used instead of KOH. The reaction is conducted for 12 h at 40° C. |
| 5-69 | NaOH is used instead of KOH. The reaction is conducted in MeOH for 4 h at rt. |
| 5-70 | NaOH is used instead of KOH. The reaction is conducted in MeOH for 15 h at rt. |
| 5-71 | NaOH is used instead of KOH. The reaction is conducted for 6 h at 50° C. |
| 5-72 | NaOH is used instead of KOH. The reaction is conducted in THF/EtOH for 2.5 h at 70° C. |
| 5-73 | NaOH is used instead of KOH. The reaction is conducted in THF/EtOH for 2.5 h at 70° C. |
| 5-74 | NaOH is used instead of KOH. The reaction is conducted in THF/EtOH for 2.5 h at 70° C. |
| 5-75 | NaOH is used instead of KOH. The reaction is conducted in MeOH for 12 h at 50° C. |
| 5-76 | NaOH is used instead of KOH. The reaction is conducted in THF/EtOH for 50 minutes at rt. |
| 5-77 | NaOH is used instead of KOH. The reaction is conducted in MeOH for 4 h at rt. |
| 5-78 | NaOH is used instead of KOH. The reaction is conducted for 4 h at 50° C. |
| 5-79 | The reaction is conducted in EtOH for 12 h at 50° C. |
| 5-80 | NaOH is used instead of KOH. The reaction is conducted in EtOH for 12 h at rt. |
| 5-81 | NaOH is used instead of KOH.<br>The reaction is conducted in THF for 6 h at 80° C. and for 12 h at rt. |
| 5-82 | LiOH is used instead of KOH. The reaction is conducted in THF/MeOH for 12 h at 50° C. |
| 5-83 | NaOH is used instead of KOH. The reaction is conducted for 2 h at 40° C. |
| 5-84 | The reaction is conducted for 4 h at 40° C. |
| 5-85 | NaOH is used instead of KOH. The reaction is conducted in EtOH for 12 h at rt. |
| 5-86 | NaOH is used instead of KOH. The reaction is conducted in MeOH for 6 h at rt. |
| 5-87 | NaOH is used instead of KOH. The reaction is conducted for 3 h at 70° C. |
| 5-88 | NaOH is used instead of KOH. The reaction is conducted for 2 h at 70° C. |
| 5-89 | The reaction is conducted in EtOH for 12 h at 50° C. |
| 5-90 | NaOH is used instead of KOH. The reaction is conducted for 4.5 h at 50° C. |
| 5-91 | NaOH is used instead of KOH. The reaction is conducted for 2 h at 50° C. |
| 5-92 | The reaction is conducted for 12 h at 50° C. |
| 5-93 | NaOH is used instead of KOH. The reaction is conducted in EtOH for 2.5 h at rt. |
| 5-94 | NaOH is used instead of KOH. The reaction is conducted in 1,4-dioxane for 1 h at 90° C. |
| 5-95 | NaOH is used instead of KOH. The reaction is conducted in MeOH for 12 h at rt. |
| 5-96 | NaOH is used instead of KOH. The reaction is conducted for 1 h at 70° C. |
| 5-97 | The reaction is conducted in EtOH for 12 h at 50° C. |
| 5-98 | NaOH is used instead of KOH. The reaction is conducted for 2 h at 70° C. |
| 5-99 | NaOH is used instead of KOH. The reaction is conducted for 1 h at 70° C. |
| 5-100 | NaOH is used instead of KOH. The reaction is conducted for 1 h at 70° C. |
| 5-101 | NaOH is used instead of KOH. The reaction is conducted at 70° C. for 1 h. |
| 5-102 | NaOH is used instead of KOH. The reaction is conducted for 1 h at 70° C. |
| 5-103 | NaOH is used instead of KOH. The reaction is conducted at 70° C. for 1 h. |
| 5-104 | NaOH is used instead of KOH. The reaction is conducted for 1 h at 60° C. |
| 5-105 | NaOH is used instead of KOH. The reaction is conducted in EtOH for 12 h at rt. |
| 5-106 | NaOH is used instead of KOH. The reaction is conducted for 1 h at 60° C. |
| 5-107 | NaOH is used instead of KOH. The reaction is conducted for 2.5 h at 70° C. |
| 5-108 | NaOH is used instead of KOH. The reaction is conducted for 2.5 h at 70° C. |
| 5-109 | NaOH is used instead of KOH. The reaction is conducted in EtOH for 12 h at 40° C. |
| 5-110 | NaOH is used instead of KOH. The reaction is conducted for 7 h at 60° C. |
| 5-111 | NaOH is used instead of KOH. The reaction is conducted for 1 h at 70° C. |
| 5-112 | NaOH is used instead of KOH. The reaction is conducted for 20 h at 50° C. |
| 5-113 | NaOH is used instead of KOH. The reaction is conducted in EtOH for 12 h at 40° C. |
| 5-114 | NaOH is used instead of KOH. The reaction is conducted for 2.5 h at 60° C. |
| 5-115 | NaOH is used instead of KOH. The reaction is conducted for 2 h at 50° C. |
| 5-116 | NaOH is used instead of KOH. The reaction is conducted for 1.5 h at 70° C. |
| 5-117 | NaOH is used instead of KOH. The reaction is conducted in THF/EtOH for 2 h at 70° C. |
| 5-118 | NaOH is used instead of KOH. The reaction is conducted for 1 h at 70° C. |
| 5-119 | NaOH is used instead of KOH. The reaction is conducted for 1.5 h at 70° C. |
| 5-120 | NaOH is used instead of KOH. The reaction is conducted in EtOH for 4 h at rt. |
| 5-121 | LiOH is used instead of KOH. The reaction is conducted in THF/water for 12 h at rt. |
| 5-122 | The reaction is conducted for 48 h at 50° C. |
| 5-123 | NaOH is used instead of KOH. The reaction is conducted in MeOH for 12 h at rt. |
| 5-124 | NaOH is used instead of KOH. The reaction is conducted for 1.5 h at 50° C. |
| 5-125 | NaOH is used instead of KOH. The reaction is conducted in EtOH for 12 h at 50° C. |
| 5-126 | The reaction is conducted for 2 h at 50° C. |
| 5-127 | NaOH is used instead of KOH. The reaction is conducted for 2 days at 70° C. |
| 5-128 | NaOH is used instead of KOH. The reaction is conducted for 5 days at 70° C. |

-continued

| Intermediate | Reaction comment |
|---|---|
| 5-129 | NaOH is used instead of KOH. The reaction is conducted for 35 h at 70° C. and for 3 days at rt. |
| 5-130 | NaOH is used instead of KOH. The reaction is conducted for 24 h at 70° C. and for 2 days at 50° C. |
| 5-131 | NaOH is used instead of KOH. The reaction is conducted for h at rt. |
| 5-132 | NaOH is used instead of KOH. The reaction is conducted for 45 min at rt. |
| 5-133 | NaOH is used instead of KOH. The reaction is conducted for 45 min at rt. |
| 5-134 | NaOH is used instead of KOH. The reaction is conducted for 4 h at rt. |
| 5-135 | NaOH is used instead of KOH. The reaction is conducted for 30 min at rt. |
| 5-136 | NaOH is used instead of KOH. The reaction is conducted for 1.5 h at rt. |
| 5-137 | NaOH is used instead of KOH. The reaction is conducted for 2.5 h at rt. |
| 5-138 | NaOH is used instead of KOH. The reaction is conducted for 45 min at rt. |
| 5-139 | NaOH is used instead of KOH. The reaction is conducted for 1.5 h at rt. |
| 5-140 | NaOH is used instead of KOH. The reaction is conducted for 16 h at rt. |
| 5-141 | NaOH is used instead of KOH. The reaction is conducted for 16 h at rt. |
| 5-142 | NaOH is used instead of KOH. The reaction is conducted for 72 h at rt. |
| 5-143 | NaOH is used instead of KOH. The reaction is conducted for 18 h at rt. |
| 5-144 | NaOH is used instead of KOH. The reaction is conducted for 2 h at 50° C. |
| 5-145 | NaOH is used instead of KOH. The reaction is conducted for 30 min at 50° C. |
| 5-146 | NaOH is used instead of KOH. The reaction is conducted in MeOH for 5 h at rt. |
| 5-147 | NaOH is used instead of KOH. The reaction is conducted for 12 h at 80° C. |
| 5-148 | NaOH is used instead of KOH. The reaction is conducted for 17 h at rt. |
| 5-149 | NaOH is used instead of KOH. The reaction is conducted for 17 h at rt. |
| 5-150 | NaOH is used instead of KOH. The reaction is conducted in EtOH for 12 h at rt. |
| 5-151 | NaOH is used instead of KOH. The reaction is conducted for 1.5 h at 40° C. |
| 5-152 | NaOH is used instead of KOH. The reaction is conducted for 3 h at 40° C. |
| 5-153 | NaOH is used instead of KOH. The reaction is conducted for 45 minutes at 40° C. |
| 5-154 | NaOH is used instead of KOH. The reaction is conducted in MeOH for 12 h at rt. |
| 5-155 | NaOH is used instead of KOH. The reaction is conducted in EtOH for 5 days at rt. |
| 5-156 | NaOH is used instead of KOH. The reaction is conducted in THF for 16 h at rt. |
| 5-157 | NaOH is used instead of KOH. The reaction is conducted in MeOH for 1 h at 40° C. |
| 5-158 | NaOH is used instead of KOH. The reaction is conducted in EtOH for 2 h at rt. |
| 5-159 | NaOH is used instead of KOH. The reaction is conducted in MeOH for 1 h at 40° C. |
| 5-160 | NaOH is used instead of KOH. The reaction is conducted in 1,4-dioxane/water 2:1 for 3 h at rt. |
| 5-161 | NaOH is used instead of KOH. The reaction is conducted in MeOH/dioxane for 4 h at 50° C. The product is purified by HPLC on reversed phase (ACN, water). |
| 5-162 | LiOH is used instead of KOH. The reaction is conducted in MeOH for 6 h at 75° C. |
| 5-163 | LiOH is used instead of KOH. The reaction is conducted in MeOH for 16 h at 75° C. |
| 5-164 | NaOH is used instead of KOH. The reaction is conducted at 70° C. for 1 h. |
| 5-165 | NaOH is used instead of KOH. The reaction is conducted at 70° C. for 2 h. |
| 5-166 | NaOH is used instead of KOH. The reaction is conducted at 70° C. for 1.5 h. |
| 5-167 | NaOH is used instead of KOH. The reaction is conducted at 70° C. for 1.5 h. |
| 5-168 | NaOH is used instead of KOH. The reaction is conducted in EtOH at r.t. for 3.5 h. |
| 5-169 | NaOH is used instead of KOH. The reaction is conducted at 70° C. for 1 h. |
| 5-170 | NaOH is used instead of KOH. The reaction is conducted at 50° C. for 2 h. |

| Intermediate | Name | Name of Starting Material |
|---|---|---|
| 5-1 | 1-[(6-{6,6-Difluoro-3-azabicyclo[3.1.0]hexan-3-yl}-2-(methoxymethyl)pyridin-3-yl)methyl]-1H-pyrazole-4-carboxylic acid | Ethyl 1-[(6-{6,6-difluoro-3-azabicyclo[3.1.0]-hexan-3-yl}-2-(methoxymethyl)pyridin-3-yl)methyl]-1H-pyrazole-4-carboxylate |
| 5-2 | 1-[(2-Chloro-6-{6,6-difluoro-3-azabicyclo[3.1.0]hexan-3-yl}pyridin-3-yl)methyl]-1H-1,2,3-triazole-4-carboxylic acid | Ethyl 1-[(2-chloro-6-{6,6-difluoro-3-azabicyclo[3.1.0]hexan-3-yl}pyridin-3-yl)methyl]-1H-1,2,3-triazole-4-carboxylate |
| 5-3 | 1-[(6-{5-Azaspiro[2.3]hexan-5-yl}-2-(difluoromethyl)pyridin-3-yl)methyl]-1H-1,2,3-triazole-4-carboxylic acid | Ethyl 1-[(6-{5-Azaspiro[2.3]hexan-5-yl}-2-(difluoromethyl)pyridin-3-yl)methyl]-1H-1,2,3-triazole-4-carboxylate |
| 5-4 | 1-[(6-{5-Azaspiro[2.3]hexan-5-yl}-2-chloropyridin-3-yl)methyl]-1H-1,2,3-triazole-4-carboxylic acid | Ethyl 1-[(6-{5-azaspiro[2.3]hexan-5-yl}-2-chloropyridin-3-yl)methyl]-1H-1,2,3-triazole-4-carboxylate |
| 5-5 | 1-[(6-{5-Azaspiro[2.3]hexan-5-yl}-2-bromopyridin-3-yl)methyl]-1H-1,2,3-triazole-4-carboxylic acid | Ethyl 1-[(6-{5-azaspiro[2.3]hexan-5-yl}-2-bromopyridin-3-yl)methyl]-1H-1,2,3-triazole-4-carboxylate |
| 5-6 | 1-[(6-{6,6-Difluoro-3-azabicyclo[3.1.0]hexan-3-yl}-2-fluoropyridin-3-yl)methyl]-1H-imidazole-4-carboxylic acid | Ethyl 1-[(6-{6,6-difluoro-3-azabicyclo[3.1.0]hexan-3-yl}-2-fluoropyridin-3-yl)methyl]-1H-imidazole-4-carboxylate |
| 5-7 | 1-[(5-{3-Azabicyclo[3.1.0]hexan-3-yl}pyridin-2-yl)methyl]-1H-1,2,3-triazole-4-carboxylic acid | Ethyl 1-[(5-{3-azabicyclo[3.1.0]hexan-3-yl}-pyridin-2-yl)methyl]-1H-1,2,3-triazole-4-carboxylate |
| 5-8 | 1-[(5-{3-Azabicyclo[3.1.0]hexan-3-yl}pyridin-2-yl)methyl]-1H-pyrazole-4-carboxylic acid | Ethyl 1-[(5-{3-azabicyclo[3.1.0]hexan-3-yl}-pyridin-2-yl)methyl]-1H-pyrazole-4-carboxylate |
| 5-9 | 1-[(6-{5-Azaspiro[2.3]hexan-5-yl}-2-fluoropyridin-3-yl)methyl]-1H-1,2,3-triazole-4-carboxylic acid | Ethyl 1-[(6-{5-azaspiro[2.3]hexan-5-yl}-2-fluoropyridin-3-yl)methyl]-1H-1,2,3-triazole-4-carboxylate |

-continued

| Intermediate | Name | Name of Starting Material |
|---|---|---|
| 5-10 | 1-[(6-{5-Azaspiro[2.3]hexan-5-yl}-2-fluoropyridin-3-yl)methyl]-1H-imidazole-4-carboxylic acid | Ethyl 1-[(6-{5-azaspiro[2.3]hexan-5-yl}-2-fluoropyridin-3-yl)methyl]-1H-imidazole-4-carboxylate |
| 5-11 | 1-[(6-{5-Azaspiro[2.3]hexan-5-yl}-2-fluoropyridin-3-yl)methyl]-1H-pyrazole-4-carboxylic acid | Ethyl 1-[(6-{5-azaspiro[2.3]hexan-5-yl}-2-fluoropyridin-3-yl)methyl]-1H-pyrazole-4-carboxylate |
| 5-12 | 1-[(6-{5-Azaspiro[2.3]hexan-5-yl}-2-bromopyridin-3-yl)methyl]-1H-pyrazole-4-carboxylic acid | Ethyl 1-[(6-{5-azaspiro[2.3]hexan-5-yl}-2-bromopyridin-3-yl)methyl]-1H-pyrazole-4-carboxylate |
| 5-13 | 1-[(2-Bromo-6-{6,6-difluoro-3-azabicyclo[3.1.0]hexan-3-yl}pyridin-3-yl)methyl]-1H-1,2,3-triazole-4-carboxylic acid | Ethyl 1-[(2-bromo-6-{6,6-difluoro-3-azabicyclo[3.1.0]hexan-3-yl}pyridin-3-yl)methyl]-1H-1,2,3-triazole-4-carboxylate |
| 5-14 | 1-[(2-Bromo-6-{6,6-difluoro-3-azabicyclo[3.1.0]hexan-3-yl}pyridin-3-yl)methyl]-1H-pyrazole-4-carboxylic acid | Ethyl 1-[(2-bromo-6-{6,6-difluoro-3-azabicyclo[3.1.0]hexan-3-yl}pyridin-3-yl)methyl]-1H-pyrazole-4-carboxylate |
| 5-15 | 1-[(6-{5-Azaspiro[2.3]hexan-5-yl}-2-bromopyridin-3-yl)methyl]-1H-imidazole-4-carboxylic acid | Ethyl 1-[(6-{5-azaspiro[2.3]hexan-5-yl}-2-bromopyridin-3-yl)methyl]-1H-imidazole-4-carboxylate |
| 5-16 | 1-[(6-{3-Azabicyclo[3.1.0]hexan-3-yl}-2-fluoropyridin-3-yl)methyl]-1H-1,2,3-triazole-4-carboxylic acid | Ethyl 1-[(6-{3-azabicyclo[3.1.0]hexan-3-yl}-2-fluoropyridin-3-yl)methyl]-1H-1,2,3-triazole-4-carboxylate |
| 5-17 | 1-[(6-{6,6-Difluoro-3-azabicyclo[3.1.0]hexan-3-yl}-2-fluoropyridin-3-yl)methyl]-1H-pyrazole-4-carboxylic acid | Ethyl 1-[(6-{6,6-difluoro-3-azabicyclo[3.1.0]hexan-3-yl}-2-fluoropyridin-3-yl)methyl]-1H-pyrazole-4-carboxylate |
| 5-18 | 1-[(5-{5-Azaspiro[2.3]hexan-5-yl}pyridin-2-yl)methyl]-1H-pyrazole-4-carboxylic acid | Ethyl 1-[(5-{5-azaspiro[2.3]hexan-5-yl}pyridin-2-yl)methyl]-1H-pyrazole-4-carboxylate |
| 5-19 | 1-[(6-{5-Azaspiro[2.3]hexan-5-yl}-2-ethylpyridin-3-yl)methyl]-1H-1,2,3-triazole-4-carboxylic acid | Ethyl 1-[(6-{5-azaspiro[2.3]hexan-5-yl}-2-ethylpyridin-3-yl)methyl]-1H-1,2,3-triazole-4-carboxylate |
| 5-20 | 1-[(6-{5-Azaspiro[2.3]hexan-5-yl}-2-chloropyridin-3-yl)methyl]-1H-imidazole-4-carboxylic acid | Ethyl 1-[(6-{5-azaspiro[2.3]hexan-5-yl}-2-chloropyridin-3-yl)methyl]-1H-imidazole-4-carboxylate |
| 5-21 | 1-[(6-{3-Azabicyclo[3.1.0]hexan-3-yl}-2-ethylpyridin-3-yl)methyl]-1H-pyrazole-4-carboxylic acid | Ethyl 1-[(6-{3-azabicyclo[3.1.0]hexan-3-yl}-2-ethylpyridin-3-yl)methyl]-1H-pyrazole-4-carboxylate |
| 5-22 | 1-[(6-{6,6-Difluoro-3-azabicyclo[3.1.0]hexan-3-yl}-2-fluoropyridin-3-yl)methyl]-1H-1,2,3-triazole-4-carboxylic acid | Ethyl 1-[(6-{6,6-difluoro-3-azabicyclo[3.1.0]hexan-3-yl}-2-fluoropyridin-3-yl)methyl]-1H-1,2,3-triazole-4-carboxylate |
| 5-23 | 1-[(6-{5-Azaspiro[2.3]hexan-5-yl}pyridin-3-yl)methyl]-1H-1,2,3-triazole-4-carboxylic acid | Ethyl 1-[(6-{5-azaspiro[2.3]hexan-5-yl}pyridin-3-yl)methyl]-1H-1,2,3-triazole-4-carboxylate |
| 5-24 | 1-[(2-Bromo-6-{6,6-difluoro-3-azabicyclo[3.1.0]hexan-3-yl}pyridin-3-yl)methyl]-1H-imidazole-4-carboxylic acid | Ethyl 1-[(2-bromo-6-{6,6-difluoro-3-azabicyclo[3.1.0]hexan-3-yl}pyridin-3-yl)methyl]-1H-imidazole-4-carboxylate |
| 5-25 | 1-[(2-{3-Azabicyclo[3.1.0]hexan-3-yl}-4-(difluoromethyl)pyrimidin-5-yl)methyl]-1H-imidazole-4-carboxylic acid | Ethyl 1-[(2-{3-azabicyclo[3.1.0]hexan-3-yl}-4(difluoromethyl)pyrimidin-5-yl)methyl]-1H-imidazole-4-carboxylate |
| 5-26 | 1-[(6-{3-Azabicyclo[3.1.0]hexan-3-yl}-2-(difluoromethyl)pyridin-3-yl)methyl]-1H-1,2,3-triazole-4-carboxylic acid | Ethyl 1-[(6-{3-azabicyclo[3.1.0]hexan-3-yl}-2-(difluoromethyl)pyridin-3-yl)methyl]-1H-1,2,3-triazole-4-carboxylate |
| 5-27 | 1-[(6-{3-Azabicyclo[3.1.0]hexan-3-yl}-2-propylpyridin-3-yl)methyl]-1H-imidazole-4-carboxylic acid | Ethyl 1-[(6-{3-azabicyclo[3.1.0]hexan-3-yl}-2-propylpyridin-3-yl)methyl]-1H-imidazole-4-carboxylate |
| 5-28 | 1-[(6-{3-Azabicyclo[3.1.0]hexan-3-yl}-2-chloropyridin-3-yl)methyl]-1H-1,2,3-triazole-4-carboxylic acid | Ethyl 1-[(6-{3-azabicyclo[3.1.0]hexan-3-yl}-2-chloropyridin-3-yl)methyl]-1H-1,2,3-triazole-4-carboxylate |
| 5-29 | 1-[(6-{6,6-Difluoro-3-azabicyclo[3.1.0]hexan-3-yl}pyridin-3-yl)methyl]-1H-1,2,3-triazole-4-carboxylic acid | Ethyl 1-[(6-{6,6-difluoro-3-azabicyclo[3.1.0]hexan-3-yl}pyridin-3-yl)methyl]-1H-1,2,3-triazole-4-carboxylate |
| 5-30 | 1-[(6-{3-Azabicyclo[3.1.0]hexan-3-yl}-2-methylpyridin-3-yl)methyl]-1H-imidazole-4-carboxylic acid | Ethyl 1-[(6-{3-azabicyclo[3.1.0]hexan-3-yl}-2-methylpyridin-3-yl)methyl]-1H-imidazole-4-carboxylate |
| 5-31 | 1-[(6-{6,6-Difluoro-3-azabicyclo[3.1.0]hexan-3-yl}-2-methylpyridin-3-yl)methyl]-1H-imidazole-4-carboxylic acid | Ethyl 1-[(6-{6,6-difluoro-3-azabicyclo[3.1.0]hexan-3-yl}-2-methylpyridin-3-yl)methyl]-1H-imidazole-4-carboxylate |
| 5-32 | 1-[(6-{3-Azabicyclo[3.1.0]hexan-3-yl}-2-bromopyridin-3-yl)methyl]-1H-1,2,3-triazole-4-carboxylic acid | Ethyl 1-[(6-{3-azabicyclo[3.1.0]hexan-3-yl}-2-bromopyridin-3-yl)methyl]-1H-1,2,3-triazole-4-carboxylate |
| 5-33 | 1-[(5-{3-Azabicyclo[3.1.0]hexan-3-yl}-6-cyanopyridin-2-yl)methyl]-1H-pyrazole-4-carboxylic acid | Ethyl 1-[(5-{3-azabicyclo[3.1.0]hexan-3-yl}-6-cyanopyridin-2-yl)methyl]-1H-pyrazole-4-carboxylate |
| 5-34 | 1-[(6-{6,6-Difluoro-3-azabicyclo[3.1.0]hexan-3-yl}-2-ethylpyridin-3-yl)methyl]-1H-pyrazole-4-carboxylic acid | Ethyl 1-[(6-{6,6-difluoro-3-azabicyclo[3.1.0]hexan-3-yl}-2-ethylpyridin-3-yl)methyl]-1H-pyrazole-4-carboxylate |
| 5-35 | 1-[(6-{5-Azaspiro[2.3]hexan-5-yl}-2-ethylpyridin-3-yl)methyl]-1H-imidazole-4-carboxylic acid | Ethyl 1-[(6-{5-azaspiro[2.3]hexan-5-yl}-2-ethylpyridin-3-yl)methyl]-1H-imidazole-4-carboxylate |

-continued

| Intermediate | Name | Name of Starting Material |
|---|---|---|
| 5-36 | 1-[(6-{3-Azabicyclo[3.1.0]hexan-3-yl}-2-(trifluoromethoxy)pyridin-3-yl)methyl]-1H-imidazole-4-carboxylic acid | Ethyl 1-[(6-{3-azabicyclo[3.1.0]hexan-3-yl}-2-(trifluoromethoxy)pyridin-3-yl)methyl]-1H-imidazole-4-carboxylate |
| 5-37 | 1-[(6-{3-Azabicyclo[3.1.0]hexan-3-yl}-2-bromopyridin-3-yl)methyl]-1H-imidazole-4-carboxylic acid | Ethyl 1-[(6-{3-azabicyclo[3.1.0]hexan-3-yl}-2-bromopyridin-3-yl)methyl]-1H-imidazole-4-carboxylate |
| 5-38 | 1-[(6-{3-Azabicyclo[3.1.0]hexan-3-yl}-2-bromopyridin-3-yl)methyl]-1H-pyrazole-4-carboxylic acid | Ethyl 1-[(6-{3-azabicyclo[3.1.0]hexan-3-yl}-2-bromopyridin-3-yl)methyl]-1H-pyrazole-4-carboxylate |
| 5-39 | 1-[(5-{6,6-Difluoro-3-azabicyclo[3.1.0]hexan-3-yl}pyridin-2-yl)methyl]-1H-pyrazole-4-carboxylic acid | Ethyl 1-[(5-{6,6-difluoro-3-azabicyclo[3.1.0]hexan-3-yl}pyridin-2-yl)methyl]-1H-pyrazole-4-carboxylate |
| 5-40 | 1-[(6-{3-Azabicyclo[3.1.0]hexan-3-yl}-2-(1-cyanocyclopropyl)pyridin-3-yl)methyl]-1H-pyrazole-4-carboxylic acid | Ethyl 1-[(6-{3-azabicyclo[3.1.0]hexan-3-yl}-2-(1-cyanocyclopropyl)pyridin-3-yl)methyl]-1H-pyrazole-4-carboxylate |
| 5-41 | 1-[(6-{3-Azabicyclo[3.1.0]hexan-3-yl}-2-(difluoromethyl)pyridin-3-yl)methyl]-1H-pyrazole-4-carboxylic acid | Ethyl 1-[(6-{3-azabicyclo[3.1.0]hexan-3-yl}-2-(difluoromethyl)pyridin-3-yl)methyl]-1H-pyrazole-4-carboxylate |
| 5-42 | 1-[(2-Chloro-6-{6,6-difluoro-3-azabicyclo[3.1.0]hexan-3-yl}pyridin-3-yl)methyl]-1H-pyrazole-4-carboxylic acid | Ethyl 1-[(2-chloro-6-{6,6-difluoro-3-azabicyclo[3.1.0]hexan-3-yl}pyridin-3-yl)methyl]-1H-pyrazole-4-carboxylate |
| 5-43 | 1-[(6-{6,6-Difluoro-3-azabicyclo[3.1.0]hexan-3-yl}-2-(difluoromethyl)pyridin-3-yl)methyl]-1H-imidazole-4-carboxylic acid | Ethyl 1-[(6-{6,6-difluoro-3-azabicyclo[3.1.0]-hexan-3-yl}-2-(difluoromethyl)pyridin-3-yl)methyl]-1H-imidazole-4-carboxylate |
| 5-44 | 1-[(6-{6,6-Difluoro-3-azabicyclo[3.1.0]hexan-3-yl}-2-(difluoromethyl)pyridin-3-yl)methyl]-1H-pyrazole-4-carboxylic acid | Ethyl 1-[(6-{6,6-difluoro-3-azabicyclo[3.1.0]-hexan-3-yl}-2-(difluoromethyl)pyridin-3-yl)methyl]-1H-pyrazole-4-carboxylate |
| 5-45 | 1-[(6-{5-Azaspiro[2.3]hexan-5-yl}-2-(difluoromethyl)pyridin-3-yl)methyl]-1H-imidazole-4-carboxylic acid | Ethyl 1-[(6-{5-azaspiro[2.3]hexan-5-yl}-2-(difluoromethyl)pyridin-3-yl)methyl]-1H-imidazole-4-carboxylate |
| 5-46 | 1-[(2-{3-Azabicyclo[3.1.0]hexan-3-yl}-4-(difluoromethyl)pyrimidin-5-yl)methyl]-1H-pyrazole-4-carboxylic acid | Ethyl 1-[(2-{3-azabicyclo[3.1.0]hexan-3-yl}-4-(difluoromethyl)pyrimidin-5-yl)methyl]-1H-pyrazole-4-carboxylate |
| 5-47 | 1-[(6-{5-Azaspiro[2.3]hexan-5-yl}-2-ethylpyridin-3-yl)methyl]-1H-pyrazole-4-carboxylic acid | Ethyl 1-[(6-{5-azaspiro[2.3]hexan-5-yl}-2-ethylpyridin-3-yl)methyl]-1H-pyrazole-4-carboxylate |
| 5-48 | 1-[(6-{5-Azaspiro[2.3]hexan-5-yl}-2-(difluoromethyl)pyridin-3-yl)methyl]-1H-pyrazole-4-carboxylic acid | Ethyl 1-[(6-{5-azaspiro[2.3]hexan-5-yl}-2-(difluoromethyl)pyridin-3-yl)methyl]-1H-pyrazole-4-carboxylate |
| 5-49 | 1-[(5-{6,6-Difluoro-3-azabicyclo[3.1.0]hexan-3-yl}pyridin-2-yl)methyl]-1H-imidazole-4-carboxylic acid | Ethyl 1-[(5-{6,6-difluoro-3-azabicyclo[3.1.0]hexan-3-yl}pyridin-2-yl)methyl]-1H-imidazole-4-carboxylate |
| 5-50 | 1-[(6-{3-Azabicyclo[3.1.0]hexan-3-yl}-2-(3-hydroxypropyl)pyridin-3-yl)methyl]-1H-pyrazole-4-carboxylic acid | Ethyl 1-[(6-{3-azabicyclo[3.1.0]hexan-3-yl}-2-(3-hydroxypropyl)pyridin-3-yl)methyl]-1H-pyrazole-4-carboxylate |
| 5-51 | 1-[(6-{5-Azaspiro[2.3]hexan-5-yl}-2-chloropyridin-3-yl)methyl]-1H-pyrazole-4-carboxylic acid | Ethyl 1-[(6-{5-azaspiro[2.3]hexan-5-yl}-2-chloropyridin-3-yl)methyl]-1H-pyrazole-4-carboxylate |
| 5-52 | 1-[(2-Chloro-6-{6,6-difluoro-3-azabicyclo[3.1.0]hexan-3-yl}pyridin-3-yl)methyl]-1H-imidazole-4-carboxylic acid | Ethyl 1-[(2-chloro-6-{6,6-difluoro-3-azabicyclo[3.1.0]hexan-3-yl}pyridin-3-yl)methyl]-1H-imidazole-4-carboxylate |
| 5-53 | 1-[(6-{3-Azabicyclo[3.1.0]hexan-3-yl}-2-(trifluoromethoxy)pyridin-3-yl)methyl]-1H-pyrazole-4-carboxylic acid | Ethyl 1-[(6-{3-azabicyclo[3.1.0]hexan-3-yl}-2-(trifluoromethoxy)pyridin-3-yl)methyl]-1H-pyrazole-4-carboxylate |
| 5-54 | 1-[(6-{3-Azabicyclo[3.1.0]hexan-3-yl}-2-(1-hydroxypropan-2-yl)pyridin-3-yl)methyl]-1H-pyrazole-4-carboxylic acid | Ethyl 1-[(6-{3-azabicyclo[3.1.0]hexan-3-yl}-2-(1-hydroxypropan-2-yl)pyridin-3-yl)methyl]-1H-pyrazole-4-carboxylate |
| 5-55 | 1-[(6-{3-Azabicyclo[3.1.0]hexan-3-yl}pyridazin-3-yl)methyl]-1H-pyrazole-4-carboxylic acid | Ethyl 1-[(6-{3-azabicyclo[3.1.0]hexan-3-yl}-pyridazin-3-yl)methyl]-1H-pyrazole-4-carboxylate |
| 5-56 | 1-[(6-{5-Azaspiro[2.3]hexan-5-yl}-2-(hydroxymethyl)pyridin-3-yl)methyl]-1H-1,2,3-triazole-4-carboxylic acid | Ethyl 1-[(6-{5-azaspiro[2.3]hexan-5-yl}-2-(hydroxymethyl)pyridin-3-yl)methyl]-1H-1,2,3-triazole-4-carboxylate |
| 5-57 | 1-[(2-{3-Azabicyclo[3.1.0]hexan-3-yl}-4-(hydroxymethyl)pyrimidin-5-yl)methyl]-1H-pyrazole-4-carboxylic acid | Ethyl 1-[(2-{3-azabicyclo[3.1.0]hexan-3-yl}-4-(hydroxymethyl)pyrimidin-5-yl)methyl]-1H-pyrazole-4-carboxylate |
| 5-58 | 1-[(6-{6,6-Difluoro-3-azabicyclo[3.1.0]hexan-3-yl}pyridin-3-yl)methyl]-1H-imidazole-4-carboxylic acid | Ethyl 1-[(6-{6,6-difluoro-3-azabicyclo[3.1.0]hexan-3-yl}pyridin-3-yl)methyl]-1H-imidazole-4-carboxylate |
| 5-59 | 1-[(6-{3-Azabicyclo[3.1.0]hexan-3-yl}-2-(difluoromethyl)pyridin-3-yl)methyl]-1H-imidazole-4-carboxylic acid | Ethyl 1-[(6-{3-azabicyclo[3.1.0]hexan-3-yl}-2-(difluoromethyl)pyridin-3-yl)methyl]-1H-imidazole-4-carboxylate |
| 5-60 | 1-[(6-{3-Azabicyclo[3.1.0]hexan-3-yl}-2-(1-cyano-1-methylethyl)pyridin-3-yl)methyl]-1H-pyrazole-4-carboxylic acid | Ethyl 1-[(6-{3-azabicyclo[3.1.0]hexan-3-yl}-2-(1-cyano-1-methylethyl)pyridin-3-yl)methyl]-1H-pyrazole-4-carboxylate |

-continued

| Intermediate | Name | Name of Starting Material |
|---|---|---|
| 5-61 | 1-[(6-{6,6-Difluoro-3-azabicyclo[3.1.0]hexan-3-yl}-2-propylpyridin-3-yl)methyl]-1H-imidazole-4-carboxylic acid | Ethyl 1-[(6-{6,6-difluoro-3-azabicyclo[3.1.0]hexan-3-yl}-2-propylpyridin-3-yl)methyl]-1H-imidazole-4-carboxylate |
| 5-62 | 1-[(2-Cyclobutyl-6-{6,6-difluoro-3-azabicyclo[3.1.0]hexan-3-yl}pyridin-3-yl)methyl]-1H-pyrazole-4-carboxylic acid | Ethyl 1-[(2-cyclobutyl-6-{6,6-difluoro-3-azabicyclo[3.1.0]hexan-3-yl}pyridin-3-yl)methyl]-1H-pyrazole-4-carboxylate |
| 5-63 | 1-[(6-{5-Azaspiro[2.3]hexan-5-yl}-2-methylpyridin-3-yl)methyl]-1H-1,2,3-triazole-4-carboxylic acid | Ethyl 1-[(6-{5-azaspiro[2.3]hexan-5-yl}-2-methylpyridin-3-yl)methyl]-1H-1,2,3-triazole-4-carboxylate |
| 5-64 | 1-[(6-{6,6-Difluoro-3-azabicyclo[3.1.0]hexan-3-yl}-2-propylpyridin-3-yl)methyl]-1H-pyrazole-4-carboxylic acid | Ethyl 1-[(6-{6,6-difluoro-3-azabicyclo[3.1.0]hexan-3-yl}-2-propylpyridin-3-yl)methyl]-1H-pyrazole-4-carboxylate |
| 5-65 | 1-[(5-{3-Azabicyclo[3.1.0]hexan-3-yl}pyrimidin-2-yl)methyl]-1H-pyrazole-4-carboxylic acid | Ethyl 1-[(5-{3-azabicyclo[3.1.0]hexan-3-yl}-pyrimidin-2-yl)methyl]-1H-pyrazole-4-carboxylate |
| 5-66 | 1-[(6-{3-Azabicyclo[3.1.0]hexan-3-yl}pyridin-3-yl)methyl]-1H-imidazole-4-carboxylic acid | Ethyl 1-[(6-{3-azabicyclo[3.1.0]hexan-3-yl}-pyridin-3-yl)methyl]-1H-imidazole-4-carboxylate |
| 5-67 | 1-[(6-{3-Azabicyclo[3.1.0]hexan-3-yl}-2-ethylpyridin-3-yl)methyl]-1H-imidazole-4-carboxylic acid | Ethyl 1-[(6-{3-azabicyclo[3.1.0]hexan-3-yl}-2-ethylpyridin-3-yl)methyl]-1H-imidazole-4-carboxylate |
| 5-68 | 1-[(6-{6,6-Difluoro-3-azabicyclo[3.1.0]hexan-3-yl}-2-ethylpyridin-3-yl)methyl]-1H-imidazole-4-carboxylic acid | Ethyl 1-[(6-{6,6-difluoro-3-azabicyclo[3.1.0]hexan-3-yl}-2-ethylpyridin-3-yl)methyl]-1H-imidazole-4-carboxylate |
| 5-69 | 1-[(6-{5-Azaspiro[2.3]hexan-5-yl}-2-(hydroxymethyl)pyridin-3-yl)methyl]-1H-pyrazole-4-carboxylic acid | Ethyl 1-[(6-{5-azaspiro[2.3]hexan-5-yl}-2-(hydroxymethyl)pyridin-3-yl)methyl]-1H-pyrazole-4-carboxylatetrifluoroacetate |
| 5-70 | 1-[(6-{3-Azabicyclo[3.1.0]hexan-3-yl}-2-(cyanomethyl)pyridin-3-yl)methyl]-1H-pyrazole-4-carboxylic acid | Ethyl 1-[(6-{3-azabicyclo[3.1.0]hexan-3-yl}-2-(cyanomethyl)pyridin-3-yl)methyl]-1H-pyrazole-4-carboxylate |
| 5-71 | 1-[(6-{3-Azabicyclo[3.1.0]hexan-3-yl}-2-(1-hydroxyethyl)pyridin-3-yl)methyl]-1H-pyrazole-4-carboxylic acid | Ethyl 1-[(6-{3-azabicyclo[3.1.0]hexan-3-yl}-2-(1-hydroxyethyl)pyridin-3-yl)methyl]-1H-pyrazole-4-carboxylate |
| 5-72 | 1-[(6-{3-Azabicyclo[3.1.0]hexan-3-yl}-2-[(1R)-1-hydroxyethyl]pyridin-3-yl)methyl]-1H-pyrazole-4-carboxylic acid | Ethyl 1-[(6-{3-azabicyclo[3.1.0]hexan-3-yl}-2-[(1R)-1-hydroxyethyl]pyridin-3-yl)methyl]-1H-pyrazole-4-carboxylate |
| 5-73 | 1-[(6-{3-Azabicyclo[3.1.0]hexan-3-yl}-2-[(1S)-1-hydroxyethyl]pyridin-3-yl)methyl]-1H-pyrazole-4-carboxylic acid | Ethyl 1-[(6-{3-azabicyclo[3.1.0]hexan-3-yl}-2-[(1R)-1-hydroxyethyl]pyridin-3-yl)methyl]-1H-pyrazole-4-carboxylate |
| 5-74 | 1-[(6-{3-Azabicyclo[3.1.0]hexan-3-yl}-2-(2-hydroxypropan-2-yl)pyridin-3-yl)methyl]-1H-pyrazole-4-carboxylic acid | Ethyl 1-[(6-{3-azabicyclo[3.1.0]hexan-3-yl}-2-(2-hydroxypropan-2-yl)pyridin-3-yl)methyl]-1H-pyrazole-4-carboxylate |
| 5-75 | 1-[(6-{3-Azabicyclo[3.1.0]hexan-3-yl}-2-(2-hydroxyethyl)pyridin-3-yl)methyl]-1H-pyrazole-4-carboxylic acid | Ethyl 1-[(6-{3-azabicyclo[3.1.0]hexan-3-yl}-2-(2-hydroxyethyl)pyridin-3-yl)methyl]-1H-pyrazole-4-carboxylate |
| 5-76 | 1-[(6-{3-Azabicyclo[3.1.0]hexan-3-yl}-2-(hydroxymethyl)pyridin-3-yl)methyl]-1H-pyrazole-4-carboxylic acid | Ethyl 1-[(6-{3-azabicyclo[3.1.0]hexan-3-yl}-2-(hydroxymethyl)pyridin-3-yl)methyl]-1H-pyrazole-4-carboxylate |
| 5-77 | 1-[(6-{5-Azaspiro[2.3]hexan-5-yl}-2-(hydroxymethyl)pyridin-3-yl)methyl]-1H-imidazole-4-carboxylic acid | Ethyl 1-[(6-{5-azaspiro[2.3]hexan-5-yl}-2-(hydroxymethyl)pyridin-3-yl)methyl]-1H-imidazole-4-carboxylate |
| 5-78 | 1-[(5-{3-Azabicyclo[3.1.0]hexan-3-yl}-3-(hydroxymethyl)pyrazin-2-yl)methyl]-1H-pyrazole-4-carboxylic acid | Ethyl 1-[(5-{3-azabicyclo[3.1.0]hexan-3-yl}-3-(hydroxymethyl)pyrazin-2-yl)methyl]-1H-pyrazole-4-carboxylate |
| 5-79 | 1-[(6-{6,6-Difluoro-3-azabicyclo[3.1.0]hexan-3-yl}-2-methylpyridin-3-yl)methyl]-1H-pyrazole-4-carboxylic acid | Ethyl 1-[(6-{6,6-difluoro-3-azabicyclo[3.1.0]hexan-3-yl}-2-methylpyridin-3-yl)methyl]-1H-pyrazole-4-carboxylate |
| 5-80 | 1-[(6-{3-Azabicyclo[3.1.0]hexan-3-yl}-2-(hydroxymethyl)pyridin-3-yl)methyl]-1H-1,2,3-triazole-4-carboxylic acid | Ethyl 1-[(6-{3-azabicyclo[3.1.0]hexan-3-yl}-2-(hydroxymethyl)pyridin-3-yl)methyl]-1H-1,2,3-triazole-4-carboxylate |
| 5-81 | 1-[(6-{6,6-Difluoro-3-azabicyclo[3.1.0]hexan-3-yl}-2-(hydroxymethyl)pyridin-3-yl)methyl]-1H-pyrazole-4-carboxylic acid | Ethyl 1-[(6-{6,6-difluoro-3-azabicyclo[3.1.0]-hexan-3-yl}-2-(hydroxymethyl)pyridin-3-yl)-methyl]-1H-pyrazole-4-carboxylate |
| 5-82 | 1-[(5-{6,6-Difluoro-3-azabicyclo[3.1.0]hexan-3-yl}-3-methylpyrazin-2-yl)methyl]-1H-1,2,3-triazole-4-carboxylic acid | Ethyl 1-[(5-{6,6-difluoro-3-azabicyclo[3.1.0]hexan-3-yl}-3-methylpyrazin-2-yl)methyl]-1H-1,2,3-triazole-4-carboxylate |
| 5-83 | 1-[(6-{6,6-Difluoro-3-azabicyclo[3.1.0]hexan-3-yl}-2-(methoxymethyl)pyridin-3-yl)methyl]-1H-imidazole-4-carboxylic acid | Ethyl 1-[(6-{6,6-difluoro-3-azabicyclo[3.1.0]-hexan-3-yl}-2-(methoxymethyl)pyridin-3-yl)methyl]-1H-imidazole-4-carboxylate |
| 5-84 | 1-[(6-{6,6-Difluoro-3-azabicyclo[3.1.0]hexan-3-yl}-2-(hydroxymethyl)pyridin-3-yl)methyl]-1H-imidazole-4-carboxylic acid | Ethyl 1-[(6-{6,6-difluoro-3-azabicyclo[3.1.0]-hexan-3-yl}-2-(hydroxymethyl)pyridin-3-yl)methyl]-1H-imidazole-4-carboxylate |
| 5-85 | 1-[(6-{6,6-Difluoro-3-azabicyclo[3.1.0]hexan-3-yl}-2-(hydroxymethyl)pyridin-3-yl)methyl]-1H-1,2,3-triazole-4-carboxylic acid | Ethyl 1-[(6-{6,6-difluoro-3-azabicyclo[3.1.0]-hexan-3-yl}-2-(hydroxymethyl)pyridin-3-yl)methyl]-1H-1,2,3-triazole-4-carboxylate |

-continued

| Intermediate | Name | Name of Starting Material |
|---|---|---|
| 5-86 | 1-[(6-{3-Azabicyclo[3.1.0]hexan-3-yl}-2-methylpyridin-3-yl)methyl]-3-cyano-1H-pyrazole-4-carboxylic acid | Methyl 1-[(6-{3-azabicyclo[3.1.0]hexan-3-yl}-2-methylpyridin-3-yl)methyl]-3-cyano-1H-pyrazole-4-carboxylate |
| 5-87 | 1-[(6-{3-Azabicyclo[3.1.0]hexan-3-yl}-4-chloropyridin-3-yl)methyl]-1H-pyrazole-4-carboxylic acid | Ethyl 1-[(6-{3-azabicyclo[3.1.0]hexan-3-yl}-4-chloropyridin-3-yl)methyl]-1H-pyrazole-4-carboxylate |
| 5-88 | 1-[(6-{3-Azabicyclo[3.1.0]hexan-3-yl}-2-(2-methylpropyl)pyridin-3-yl)methyl]-1H-imidazole-4-carboxylic acid | Ethyl 1-[(6-{3-azabicyclo[3.1.0]hexan-3-yl}-2-(2-methylpropyl)pyridin-3-yl)methyl]-1H-imidazole-4-carboxylate |
| 5-89 | 1-[(6-{3-Azabicyclo[3.1.0]hexan-3-yl}-2-ethylpyridin-3-yl)methyl]-1H-1,2,3-triazole-4-carboxylic acid | Ethyl 1-[(6-{3-azabicyclo[3.1.0]hexan-3-yl}-2-ethylpyridin-3-yl)methyl]-1H-1,2,3-triazole-4-carboxylate |
| 5-90 | 1-[(5-Cyano-6-{6,6-difluoro-3-azabicyclo[3.1.0]hexan-3-yl}-4-methylpyridin-3-yl)methyl]-1H-pyrazole-4-carboxylic acid | Ethyl 1-[(5-cyano-6-{6,6-difluoro-3-azabicyclo[3.1.0]hexan-3-yl}-4-methylpyridin-3-yl)methyl]-1H-pyrazole-4-carboxylate |
| 5-91 | 1-[(5-Cyano-6-{6,6-difluoro-3-azabicyclo[3.1.0]hexan-3-yl}-4-methylpyridin-3-yl)methyl]-1H-imidazole-4-carboxylic acid | Ethyl 1-[(5-cyano-6-{6,6-difluoro-3-azabicyclo[3.1.0]hexan-3-yl}-4-methylpyridin-3-yl)methyl]-1H-imidazole-4-carboxylate |
| 5-92 | 1-[(6-{3-Azabicyclo[3.1.0]hexan-3-yl}-2-fluoropyridin-3-yl)methyl]-1H-pyrazole-4-carboxylic acid | Ethyl 1-[(6-{3-azabicyclo[3.1.0]hexan-3-yl}-2-fluoropyridin-3-yl)methyl]-1H-pyrazole-4-carboxylate |
| 5-93 | 1-[(6-{3-Azabicyclo[3.1.0]hexan-3-yl}-4-methylpyridin-3-yl)methyl]-1H-imidazole-4-carboxylic acid | Ethyl 1-[(6-{3-azabicyclo[3.1.0]hexan-3-yl}-4-methylpyridin-3-yl)methyl]-1H-imidazole-4-carboxylate |
| 5-94 | 1-[(6-{6,6-Difluoro-3-azabicyclo[3.1.0]hexan-3-yl}-2-methylpyridin-3-yl)methyl]-3-(hydroxymethyl)-1H-pyrazole-4-carboxylic acid | Ethyl 3-(chloromethyl)-1-[(6-{6,6-difluoro-3-azabicyclo[3.1.0]hexan-3-yl}-2-methylpyridin-3-yl)methyl]-1H-pyrazole-4-carboxylate |
| 5-95 | 1-[(6-{3-Azabicyclo[3.1.0]hexan-3-yl}-2-methylpyridin-3-yl)methyl]-3-(cyanomethyl)-1H-pyrazole-4-carboxylic acid | Ethyl 1-[(6-{3-azabicyclo[3.1.0]hexan-3-yl}-2-methylpyridin-3-yl)methyl]-3-(cyanomethyl)-1H-pyrazole-4-carboxylate |
| 5-96 | 1-[(6-{3-Azabicyclo[3.1.0]hexan-3-yl}-2-fluoropyridin-3-yl)methyl]-1H-imidazole-4-carboxylic acid | Ethyl 1-[(6-{3-azabicyclo[3.1.0]hexan-3-yl}-2-fluoropyridin-3-yl)methyl]-1H-imidazole-4-carboxylate |
| 5-97 | 1-[(6-{6,6-Difluoro-3-azabicyclo[3.1.0]hexan-3-yl}-2-ethylpyridin-3-yl)methyl]-1H-1,2,3-triazole-4-carboxylic acid | Ethyl 1-[(6-{6,6-difluoro-3-azabicyclo[3.1.0]hexan-3-yl}-2-ethylpyridin-3-yl)methyl]-1H-1,2,3-triazole-4-carboxylate |
| 5-98 | 1-[(6-{3-Azabicyclo[3.1.0]hexan-3-yl}-2-propylpyridin-3-yl)methyl]-1H-imidazole-4-carboxylic acid | Ethyl 1-[(6-{3-azabicyclo[3.1.0]hexan-3-yl}-2-propylpyridin-3-yl)methyl]-1H-imidazole-4-carboxylate |
| 5-99 | 1-[(6-{6,6-Difluoro-3-azabicyclo[3.1.0]hexan-3-yl}-2,4-dimethylpyridin-3-yl)methyl]-1H-imidazole-4-carboxylic acid | Ethyl 1-[(6-{6,6-difluoro-3-azabicyclo[3.1.0]-hexan-3-yl}-2,4-dimethylpyridin-3-yl)methyl]-1H-imidazole-4-carboxylate |
| 5-100 | 1-[(6-{6,6-Difluoro-3-azabicyclo[3.1.0]hexan-3-yl}-2,4-dimethylpyridin-3-yl)methyl]-1H-pyrazole-4-carboxylic acid | Ethyl 1-[(6-{6,6-difluoro-3-azabicyclo[3.1.0]-hexan-3-yl}-2,4-dimethylpyridin-3-yl)methyl]-1H-pyrazole-4-carboxylate |
| 5-101 | 5-[(6-{6,6-Difluoro-3-azabicyclo[3.1.0]hexan-3-yl}-2-methylpyridin-3-yl)methyl]thiophene-2-carboxylic acid | Ethyl 5-[(6-{6,6-difluoro-3-azabicyclo[3.1.0]-hexan-3-yl}-2-methylpyridin-3-yl)-methyl]thiophene-2-carboxylate |
| 5-102 | 1-[(6-{3-Azabicyclo[3.1.0]hexan-3-yl}-5-cyanopyridin-3-yl)methyl]-1H-pyrazole-4-carboxylic acid | Ethyl 1-[(6-{3-azabicyclo[3.1.0]hexan-3-yl}-5-cyanopyridin-3-yl)methyl]-1H-pyrazole-4-carboxylate |
| 5-103 | 2-[(6-{6,6-Difluoro-3-azabicyclo[3.1.0]hexan-3-yl}-2-methylpyridin-3-yl)methyl]-1,3-thiazole-5-carboxylic acid | Methyl 2-[(6-{6,6-difluoro-3-azabicyclo[3.1.0]-hexan-3-yl}-2-methylpyridin-3-yl)methyl]-1,3-thiazole-5-carboxylate |
| 5-104 | 1-[(6-{3-Azabicyclo[3.1.0]hexan-3-yl}-5-cyano-4-methylpyridin-3-yl)methyl]-1H-pyrazole-4-carboxylic acid | Ethyl 1-[(6-{3-azabicyclo[3.1.0]hexan-3-yl}-5-cyano-4-methylpyridin-3-yl)methyl]-1H-pyrazole-4-carboxylate |
| 5-105 | 1-[(6-{3-Azabicyclo[3.1.0]hexan-3-yl}-2-cyclopropylpyridin-3-yl)methyl]-1H-pyrazole-4-carboxylic acid | Ethyl 1-[(6-{3-azabicyclo[3.1.0]hexan-3-yl}-2-cyclopropylpyridin-3-yl)methyl]-1H-pyrazole-4-carboxylate |
| 5-106 | 1-[(6-{3-Azabicyclo[3.1.0]hexan-3-yl}-5-cyano-4-methylpyridin-3-yl)methyl]-1H-imidazole-4-carboxylic acid | Ethyl 1-[(6-{3-azabicyclo[3.1.0]hexan-3-yl}-5-cyano-4-methylpyridin-3-yl)methyl]-1H-imidazole-4-carboxylate |
| 5-107 | 1-[(6-{3-Azabicyclo[3.1.0]hexan-3-yl}-4-chloropyridin-3-yl)methyl]-1H-imidazole-4-carboxylic acid | Ethyl 1-[(6-{3-azabicyclo[3.1.0]hexan-3-yl}-4-chloropyridin-3-yl)methyl]-1H-imidazole-4-carboxylate |
| 5-108 | 1-[(6-{3-Azabicyclo[3.1.0]hexan-3-yl}-4-(trifluoromethyl)pyridin-3-yl)methyl]-1H-imidazole-4-carboxylic acid | Ethyl 1-[(6-{3-azabicyclo[3.1.0]hexan-3-yl}-4-(trifluoromethyl)pyridin-3-yl)methyl]-1H-imidazole-4-carboxylate |
| 5-109 | 1-[(6-{3-Azabicyclo[3.1.0]hexan-3-yl}-2-chloropyridin-3-yl)methyl]-1H-imidazole-4-carboxylic acid | Ethyl 1-[(6-{3-azabicyclo[3.1.0]hexan-3-yl}-2-chloropyridin-3-yl)methyl]-1H-imidazole-4-carboxylate |
| 5-110 | 1-[(6-{3-Azabicyclo[3.1.0]hexan-3-yl}-2-methylpyridin-3-yl)methyl]-3-(methoxymethyl)-1H-pyrazole-4-carboxylic acid | Ethyl 1-[(6-{3-azabicyclo[3.1.0]hexan-3-yl}-2-methylpyridin-3-yl)methyl]-3-(methoxymethyl)-1H-pyrazole-4-carboxylate |

-continued

| Intermediate | Name | Name of Starting Material |
|---|---|---|
| 5-111 | 1-[(6-{3-Azabicyclo[3.1.0]hexan-3-yl}-5-cyano-2-methylpyridin-3-yl)methyl]-1H-imidazole-4-carboxylic acid | Ethyl 1-[(6-{3-azabicyclo[3.1.0]hexan-3-yl}-5-cyano-2-methylpyridin-3-yl)methyl]-1H-imidazole-4-carboxylate |
| 5-112 | 1-[(6-{6,6-Difluoro-3-azabicyclo[3.1.0]hexan-3-yl}-2-methylpyridin-3-yl)methyl]-3-(methoxymethyl)-1H-pyrazole-4-carboxylic acid | Ethyl 1-[(6-{6,6-difluoro-3-azabicyclo[3.1.0]-hexan-3-yl}-2-methylpyridin-3-yl)methyl]-3-(methoxymethyl)-1H-pyrazole-4-carboxylate |
| 5-113 | 1-[(6-{3-Azabicyclo[3.1.0]hexan-3-yl}-2-chloropyridin-3-yl)methyl]-1H-pyrazole-4-carboxylic acid | Ethyl 1-[(6-{3-azabicyclo[3.1.0]hexan-3-yl}-2-chloropyridin-3-yl)methyl]-1H-pyrazole-4-carboxylate |
| 5-114 | 1-[(6-{3-Azabicyclo[3.1.0]hexan-3-yl}-2-methylpyridin-3-yl)methyl]-3-bromo-1H-pyrazole-4-carboxylic acid | Ethyl 1-[(6-{3-azabicyclo[3.1.0]hexan-3-yl}-2-methylpyridin-3-yl)methyl]-3-bromo-1H-pyrazole-4-carboxylate |
| 5-115 | 1-[(6-{3-Azabicyclo[3.1.0]hexan-3-yl}-5-bromo-2-methylpyridin-3-yl)methyl]-1H-pyrazole-4-carboxylic acid | Ethyl 1-[(6-{3-azabicyclo[3.1.0]hexan-3-yl}-5-bromo-2-methylpyridin-3-yl)methyl]-1H-pyrazole-4-carboxylate |
| 5-116 | 1-[(6-{3-Azabicyclo[3.1.0]hexan-3-yl}-5-cyano-2-methylpyridin-3-yl)methyl]-1H-pyrazole-4-carboxylic acid | Methyl 1-[(6-{3-azabicyclo[3.1.0]hexan-3-yl}-5-cyano-2-methylpyridin-3-yl)methyl]-1H-pyrazole-4-carboxylate |
| 5-117 | 1-[(6-{3-Azabicyclo[3.1.0]hexan-3-yl}-5-bromo-2-methylpyridin-3-yl)methyl]-1H-imidazole-4-carboxylic acid | Ethyl 1-[(6-{3-azabicyclo[3.1.0]hexan-3-yl}-5-bromo-2-methylpyridin-3-yl)methyl]-1H-imidazole-4-carboxylate |
| 5-118 | 1-[(6-{3-Azabicyclo[3.1.0]hexan-3-yl}-2,5-dimethylpyridin-3-yl)methyl]-1H-imidazole-4-carboxylic acid | Methyl 1-[(6-{3-azabicyclo[3.1.0]hexan-3-yl}-2,5-dimethylpyridin-3-yl)methyl]-1H-imidazole-4-carboxylate |
| 5-119 | 1-[(6-{3-Azabicyclo[3.1.0]hexan-3-yl}-2,5-dimethylpyridin-3-yl)methyl]-1H-pyrazole-4-carboxylic acid | Methyl 1-[(6-{3-azabicyclo[3.1.0]hexan-3-yl}-2,5-dimethylpyridin-3-yl)methyl]-1H-pyrazole-4-carboxylate |
| 5-120 | 1-[(6-{3-Azabicyclo[3.1.0]hexan-3-yl}-2-cyanopyridin-3-yl)methyl]-1H-pyrazole-4-carboxylic acid | Ethyl 1-[(6-{3-azabicyclo[3.1.0]hexan-3-yl}-2-cyanopyridin-3-yl)methyl]-1H-pyrazole-4-carboxylate |
| 5-121 | 1-[(2-Chloro-4-methylpyrimidin-5-yl)methyl]-1H-pyrazole-4-carboxylic acid | Ethyl 1-[(2-chloro-4-methylpyrimidin-5-yl)-methyl]-1H-pyrazole-4-carboxylate |
| 5-122 | 1-[(6-{3-Azabicyclo[3.1.0]hexan-3-yl}-2-methylpyridin-3-yl)methyl]-1H-pyrazole-4-carboxylic acid | Ethyl 1-[(6-{3-azabicyclo[3.1.0]hexan-3-yl}-2-methylpyridin-3-yl)methyl]-1H-pyrazole-4-carboxylate |
| 5-123 | 1-[(2-{6,6-Difluoro-3-azabicyclo[3.1.0]hexan-3-yl}-4-methylpyrimidin-5-yl)methyl]-1H-imidazole-4-carboxylic acid | Ethyl 1-[(2-{6,6-difluoro-3-azabicyclo[3.1.0]-hexan-3-yl}-4-methylpyrimidin-5-yl)methyl]-1H-imidazole-4-carboxylate |
| 5-124 | 1-[(2-{6,6-Difluoro-3-azabicyclo[3.1.0]hexan-3-yl}-4-methylpyrimidin-5-yl)methyl]-1H-1,2,3-triazole-4-carboxylic acid | Ethyl 1-[(2-{6,6-difluoro-3-azabicyclo[3.1.0]-hexan-3-yl}-4-methylpyrimidin-5-yl)methyl]-1H-1,2,3-triazole-4-carboxylate |
| 5-125 | 1-[(2-{3-Azabicyclo[3.1.0]hexan-3-yl}-4-methylpyrimidin-5-yl)methyl]-1H-1,2,3-triazole-4-carboxylic acid | Ethyl 1-[(2-{3-azabicyclo[3.1.0]hexan-3-yl}-4-methylpyrimidin-5-yl)methyl]-1H-1,2,3-triazole-4-carboxylate |
| 5-126 | 1-[(5-{6,6-Difluoro-3-azabicyclo[3.1.0]hexan-3-yl}pyridin-2-yl)methyl]-1H-1,2,3-triazole-4-carboxylic acid | Ethyl 1-[(5-{6,6-difluoro-3-azabicyclo[3.1.0]-hexan-3-yl}pyridin-2-yl)methyl]-1H-1,2,3-triazole-4-carboxylate |
| 5-127 | 1-[(6-{6,6-Difluoro-3-azabicyclo[3.1.0]hexan-3-yl}pyridin-3-yl)methyl]-1H-pyrrole-3-carboxylic acid | Methyl 1-[(6-{6,6-difluoro-3-azabicyclo[3.1.0]-hexan-3-yl}pyridin-3-yl)methyl]-1H-pyrrole-3-carboxylate |
| 5-128 | 5-[(6-{6,6-Difluoro-3-azabicyclo[3.1.0]hexan-3-yl}pyridin-3-yl)methyl]-1H-pyrrole-3-carboxylic acid | Methyl 5-[(6-{6,6-difluoro-3-azabicyclo[3.1.0]-hexan-3-yl}pyridin-3-yl)methyl]-1H-pyrrole-3-carboxylate |
| 5-129 | 1-[(6-{6,6-Difluoro-3-azabicyclo[3.1.0]hexan-3-yl}-2-methylpyridin-3-yl)methyl]-1H-pyrrole-3-carboxylic acid | Methyl 1-[(6-{6,6-difluoro-3-azabicyclo[3.1.0]-hexan-3-yl}-2-methylpyridin-3-yl)methyl]-1H-pyrrole-3-carboxylate |
| 5-130 | 5-[(6-{6,6-Difluoro-3-azabicyclo[3.1.0]hexan-3-yl}-2-methylpyridin-3-yl)methyl]-1H-pyrrole-3-carboxylic acid | Methyl 5-[(6-{6,6-difluoro-3-azabicyclo[3.1.0]-hexan-3-yl}-2-methylpyridin-3-yl)methyl]-1H-pyrrole-3-carboxylate |
| 5-131 | 1-({2-Ethyl-6-[(1R,5S,6R)-6-methyl-3-azabicyclo[3.1.0]hexan-3-yl]pyridin-3-yl}methyl)-1H-imidazole-4-carboxylic acid | Ethyl 1-({2-ethyl-6-[(1R,5S,6R)-6-methyl-3-azabicyclo[3.1.0]hexan-3-yl]pyridin-3-yl}methyl)-1H-imidazole-4-carboxylate |
| 5-132 | 3-[(6-{3-Azabicyclo[3.1.0]hexan-3-yl}-2-(difluoromethyl)pyridin-3-yl)methyl]-1,2-oxazole-5-carboxylic acid | Ethyl 3-[(6-{3-azabicyclo[3.1.0]hexan-3-yl}-2-(difluoromethyl)pyridin-3-yl)methyl]-1,2-oxazole-5-carboxylate |
| 5-133 | 3-[(6-{6,6-Difluoro-3-azabicyclo[3.1.0]hexan-3-yl}-2-(difluoromethyl)pyridin-3-yl)methyl]-1,2-oxazole-5-carboxylic acid | Ethyl 3-[(6-{6,6-difluoro-3-azabicyclo[3.1.0]-hexan-3-yl}-2-(difluoromethyl)pyridin-3-yl)methyl]-1,2-oxazole-5-carboxylate |
| 5-134 | 3-[(6-{3-Azabicyclo[3.1.0]hexan-3-yl}-2-ethylpyridin-3-yl)methyl]-1,2-oxazole-5-carboxylic acid | Ethyl 3-[(6-{3-azabicyclo[3.1.0]hexan-3-yl}-2-ethylpyridin-3-yl)methyl]-1,2-oxazole-5-carboxylate |
| 5-135 | 3-[(6-{6,6-Difluoro-3-azabicyclo[3.1.0]hexan-3-yl}-2-(hydroxymethyl)pyridin-3-yl)methyl]-1,2-oxazole-5-carboxylic acid | Ethyl 3-[(6-{6,6-difluoro-3-azabicyclo[3.1.0]-hexan-3-yl}-2-(hydroxymethyl)pyridin-3-yl)methyl]-1,2-oxazole-5-carboxylate |
| 5-136 | 3-[(6-{3-Azabicyclo[3.1.0]hexan-3-yl}-2-chloropyridin-3-yl)methyl]-1,2-oxazole-5-carboxylic acid | Ethyl 3-[(6-{3-azabicyclo[3.1.0]hexan-3-yl}-2-chloropyridin-3-yl)methyl]-1,2-oxazole-5-carboxylate |

-continued

| Intermediate | Name | Name of Starting Material |
|---|---|---|
| 5-137 | 3-[(6-{3-Azabicyclo[3.1.0]hexan-3-yl}-2-(hydroxymethyl)pyridin-3-yl)methyl]-1,2-oxazole-5-carboxylic acid | Ethyl 3-[(6-{3-azabicyclo[3.1.0]hexan-3-yl}-2-(hydroxymethyl)pyridin-3-yl)methyl]-1,2-oxazole-5-carboxylate |
| 5-138 | 3-[(2-Chloro-6-{6,6-difluoro-3-azabicyclo[3.1.0]hexan-3-yl}pyridin-3-yl)methyl]-1,2-oxazole-5-carboxylic acid | Ethyl 3-[(2-chloro-6-{6,6-difluoro-3-azabicyclo[3.1.0]hexan-3-yl}pyridin-3-yl)methyl]-1,2-oxazole-5-carboxylate |
| 5-139 | 3-[(6-{3-Azabicyclo[3.1.0]hexan-3-yl}pyridin-3-yl)methyl]-1,2-oxazole-5-carboxylic acid | Ethyl 3-[(6-{3-azabicyclo[3.1.0]hexan-3-yl}-pyridin-3-yl)methyl]-1,2-oxazole-5-carboxylate |
| 5-140 | 3-[(6-{6,6-Difluoro-3-azabicyclo[3.1.0]hexan-3-yl}-2-methylpyridin-3-yl)methyl]-1,2-oxazole-5-carboxylic acid | Ethyl 3-[(6-{6,6-difluoro-3-azabicyclo[3.1.0]-hexan-3-yl}-2-methylpyridin-3-yl)methyl]-1,2-oxazole-5-carboxylate |
| 5-141 | 2-[(6-{3-Azabicyclo[3.1.0]hexan-3-yl}-2-methylpyridin-3-yl)methyl]-1,3-oxazole-5-carboxylic acid | Methyl 2-[1-(6-{3-azabicyclo[3.1.0]hexan-3-yl}-2-methylpyridin-3-yl)-2-methoxy-2-oxoethyl]-1,3-oxazole-5-carboxylate |
| 5-142 | 3-[(6-{6,6-Difluoro-3-azabicyclo[3.1.0]hexan-3-yl}-2-ethylpyridin-3-yl)methyl]-1,2-oxazole-5-carboxylic acid | Ethyl 3-[(6-{6,6-difluoro-3-azabicyclo[3.1.0]-hexan-3-yl}-2-ethylpyridin-3-yl)methyl]-1,2-oxazole-5-carboxylate |
| 5-143 | 2-[(6-{6,6-Difluoro-3-azabicyclo[3.1.0]hexan-3-yl}-2-methylpyridin-3-yl)methyl]-1,3-oxazole-5-carboxylic acid | Ethyl 2-[(6-{6,6-difluoro-3-azabicyclo[3.1.0]-hexan-3-yl}-2-methylpyridin-3-yl)methyl]-1,3-oxazole-5-carboxylate |
| 5-144 | 3-[(6-{5-Azaspiro[2.3]hexan-5-yl}-2-chloropyridin-3-yl)methyl]-1,2-oxazole-5-carboxylic acid | Ethyl 3-[(6-{5-azaspiro[2.3]hexan-5-yl}-2-chloropyridin-3-yl)methyl]-1,2-oxazole-5-carboxylate |
| 5-145 | 3-[(6-{5-Azaspiro[2.3]hexan-5-yl}-2-ethylpyridin-3-yl)methyl]-1,2-oxazole-5-carboxylic acid | Ethyl 3-[(6-{5-azaspiro[2.3]hexan-5-yl}-2-ethylpyridin-3-yl)methyl]-1,2-oxazole-5-carboxylate |
| 5-146 | 2-[(6-{3-Azabicyclo[3.1.0]hexan-3-yl}-2-ethylpyridin-3-yl)methyl]-1,3-oxazole-5-carboxylic acid | Methyl 2-[1-(6-{3-azabicyclo[3.1.0]hexan-3-yl}-2-ethylpyridin-3-yl)-2-methoxy-2-oxoethyl]-1,3-oxazole-5-carboxylate |
| 5-147 | 5-[(2-Chloro-6-{6,6-difluoro-3-azabicyclo[3.1.0]hexan-3-yl}pyridin-3-yl)methyl]-1H-pyrrole-3-carboxylic acid | Methyl 5-[(2-chloro-6-{6,6-difluoro-3-azabicyclo[3.1.0]hexan-3-yl}pyridin-3-yl)methyl]-1H-pyrrole-3-carboxylate |
| 5-148 | 3-[(6-{6,6-Difluoro-3-azabicyclo[3.1.0]hexan-3-yl}-2-ethylpyridin-3-yl)methyl]-1-(propan-2-yl)-1H-pyrazole-5-carboxylic acid | Ethyl 3-[(6-{6,6-difluoro-3-azabicyclo[3.1.0]-hexan-3-yl}-2-ethylpyridin-3-yl)methyl]-1-(propan-2-yl)-1H-pyrazole-5-carboxylate |
| 5-149 | 3-[(6-{6,6-Difluoro-3-azabicyclo[3.1.0]hexan-3-yl}-2-ethylpyridin-3-yl)methyl]-1-ethyl-1H-pyrazole-5-carboxylic acid | Ethyl 3-[(6-{6,6-difluoro-3-azabicyclo[3.1.0]-hexan-3-yl}-2-ethylpyridin-3-yl)methyl]-1-ethyl-1H-pyrazole-5-carboxylate |
| 5-150 | 3-[(6-{3-Azabicyclo[3.1.0]hexan-3-yl}-2-(hydroxymethyl)pyridin-3-yl)methyl]-1-{[2-(trimethylsilyl)ethoxy]methyl}-1H-pyrazole-5-carboxylic acid and 5-[(6-{3-Azabicyclo[3.1.0]hexan-3-yl}-2-(hydroxymethyl)pyridin-3-yl)methyl]-1-{[2-(trimethylsilyl)ethoxy]methyl}-1H-pyrazole-3-carboxylic acid (mixture of isomers) | Ethyl 3-[(6-{3-azabicyclo[3.1.0]hexan-3-yl}-2-(hydroxymethyl)pyridin-3-yl)methyl]-1-{[2-(trimethylsilyl)ethoxy]methyl}-1H-pyrazole-5-carboxylate and Ethyl 5-[(6-{3-azabicyclo[3.1.0]hexan-3-yl}-2-(hydroxymethyl)pyridin-3-yl)methyl]-1-{[2-(trimethylsilyl)ethoxy]methyl}-1H-pyrazole-3-carboxylate (mixture of isomers) |
| 5-151 | 3-[(6-{3-Azabicyclo[3.1.0]hexan-3-yl}-2-ethylpyridin-3-yl)methyl]-1-ethyl-1H-pyrazole-5-carboxylic acid | Ethyl 3-[(6-{3-azabicyclo[3.1.0]hexan-3-yl}-2-ethylpyridin-3-yl)methyl]-1-ethyl-1H-pyrazole-5-carboxylate |
| 5-152 | 3-[(6-{6,6-Difluoro-3-azabicyclo[3.1.0]hexan-3-yl}-2-methylpyridin-3-yl)methyl]-1-ethyl-1H-pyrazole-5-carboxylic acid | Ethyl 3-[(6-{6,6-difluoro-3-azabicyclo[3.1.0]-hexan-3-yl}-2-methylpyridin-3-yl)methyl]-1-ethyl-1H-pyrazole-5-carboxylate |
| 5-153 | 3-[(6-{3-Azabicyclo[3.1.0]hexan-3-yl}-2-methylpyridin-3-yl)methyl]-1-ethyl-1H-pyrazole-5-carboxylic acid | Ethyl 3-[(6-{3-azabicyclo[3.1.0]hexan-3-yl}-2-methylpyridin-3-yl)methyl]-1-ethyl-1H-pyrazole-5-carboxylate |
| 5-154 | 3-[(6-{3-Azabicyclo[3.1.0]hexan-3-yl}-2-ethylpyridin-3-yl)methyl]-1H-pyrazole-5-carboxylic acid | Ethyl 3-[(6-{3-azabicyclo[3.1.0]hexan-3-yl}-2-ethylpyridin-3-yl)methyl]-1H-pyrazole-5-carboxylate |
| 5-155 | 3-[(6-{3-Azabicyclo[3.1.0]hexan-3-yl}-2-ethylpyridin-3-yl)methyl]-1-methyl-1H-pyrazole-5-carboxylic acid | Ethyl 3-[(6-{3-azabicyclo[3.1.0]hexan-3-yl}-2-ethylpyridin-3-yl)methyl]-1-methyl-1H-pyrazole-5-carboxylate |
| 5-156 | 3-[(6-{3-Azabicyclo[3.1.0]hexan-3-yl}-2-methylpyridin-3-yl)methyl]-1-methyl-1H-pyrazole-5-carboxylic acid | Ethyl 3-[(6-{3-azabicyclo[3.1.0]hexan-3-yl}-2-methylpyridin-3-yl)methyl]-1-methyl-1H-pyrazole-5-carboxylate |
| 5-157 | 1-[(6-{5-Azaspiro[2.3]hexan-5-yl}-2-methylpyrimidin-3-yl)methyl]-1H-imidazole-4-carboxylic acid | Ethyl 1-[(6-{5-azaspiro[2.3]hexan-5-yl}-2-methylpyrimidin-3-yl)methyl]-1H-imidazole-4-carboxylate |
| 5-158 | 1-[(6-{5-Azaspiro[2.3]hexan-5-yl}-2-methylpyridin-3-yl)methyl]-1H-imidazole-4-carboxylic acid | Ethyl 1-[(6-{5-azaspiro[2.3]hexan-5-yl}-2-methylpyridin-3-yl)methyl]-1H-imidazole-4-carboxylate |
| 5-159 | 1-[(6-{3-Azabicyclo[3.1.0]hexan-3-yl}-2-methylpyrimidin-3-yl)methyl]-1H-imidazole-4-carboxylic acid | Ethyl 1-[(6-{3-azabicyclo[3.1.0]hexan-3-yl}-2-methylpyrimidin-3-yl)methyl]-1H-imidazole-4-carboxylate |

-continued

| Intermediate | Name | Name of Starting Material |
|---|---|---|
| 5-160 | 2-chloro-1-[(6-{6,6-difluoro-3-azabicyclo[3.1.0]hexan-3-yl}pyridin-3-yl)methyl]-1H-imidazole-4-carboxylic acid | Ethyl 2-chloro-1-[(6-{6,6-difluoro-3-azabicyclo[3.1.0]hexan-3-yl}pyridin-3-yl)methyl]-1H-imidazole-4-carboxylate |
| 5-161 | 7-[(6-{3-Azabicyclo[3.1.0]hexan-3-yl}-2-methylpyridin-3-yl)methyl]-7H-pyrrolo[2,3-d]pyrimidine-5-carboxylic acid | Methyl 7-[(6-{3-azabicyclo[3.1.0]hexan-3-yl}-2-methylpyridin-3-yl)methyl]-7H-pyrrolo[2,3-d]pyrimidine-5-carboxylate |
| 5-162 | 7-[(2-{6,6-Difluoro-3-azabicyclo[3.1.0]hexan-3-yl}-4-methylpyrimidin-5-yl)methyl]-7H-pyrrolo[2,3-d]pyrimidine-5-carboxylic acid | Methyl 7-[(2-{6,6-difluoro-3-azabicyclo[3.1.0]-hexan-3-yl}-4-methylpyrimidin-5-yl)methyl]-7H-pyrrolo[2,3-d]pyrimidine-5-carboxylate |
| 5-163 | 7-[(2-{3-Azabicyclo[3.1.0]hexan-3-yl}-4-methylpyrimidin-5-yl)methyl]-7H-pyrrolo[2,3-d]pyrimidine-5-carboxylic acid | Methyl 7-[(2-{3-azabicyclo[3.1.0]hexan-3-yl}-4-methylpyrimidin-5-yl)methyl]-7H-pyrrolo[2,3-d]pyrimidine-5-carboxylate |
| 5-164 | 5-[(6-{3-Azabicyclo[3.1.0]hexan-3-yl}-2-methylpyridin-3-yl)methyl]furan-2-carboxylic acid | Methyl 5-[(6-{3-azabicyclo[3.1.0]hexan-3-yl}-2-methylpyridin-3-yl)methyl]furan-2-carboxylate |
| 5-165 | 5-[(6-{3-Azabicyclo[3.1.0]hexan-3-yl}-2-methylpyridin-3-yl)methyl]furan-3-carboxylic acid | Ethyl 5-[(6-{3-azabicyclo[3.1.0]hexan-3-yl}-2-methylpyridin-3-yl)methyl]furan-3-carboxylate |
| 5-166 | 5-[(6-{6,6-Difluoro-3-azabicyclo[3.1.0]hexan-3-yl}-2-methylpyridin-3-yl)methyl]furan-2-carboxylic acid | Methyl 5-[(6-{6,6-difluoro-3-azabicyclo[3.1.0]-hexan-3-yl}-2-methylpyridin-3-yl)methyl]furan-2-carboxylate |
| 5-167 | 5-[(6-{6,6-Difluoro-3-azabicyclo[3.1.0]hexan-3-yl}-2-ethylpyridin-3-yl)methyl]furan-2-carboxylic acid | Methyl 5-[(6-{6,6-difluoro-3-azabicyclo[3.1.0]-hexan-3-yl}-2-ethylpyridin-3-yl)methyl]furan-2-carboxylate |
| 5-168 | 5-[(6-{3-Azabicyclo[3.1.0]hexan-3-yl}-2-ethyl-pyridin-3-yl)methyl]thiophene-2-carboxylic acid | Ethyl 5-[(6-{3-azabicyclo[3.1.0]hexan-3-yl}-2-ethylpyridin-3-yl)methyl]thiophene-2-carboxylate |
| 5-169 | 5-[(6-{6,6-Difluoro-3-azabicyclo[3.1.0]hexan-3-yl}-2-ethylpyridin-3-yl)methyl]thiophene-2-carboxylic acid | Ethyl 5-[(6-{6,6-difluoro-3-azabicyclo[3.1.0]-hexan-3-yl}-2-ethylpyridin-3-yl)methyl]thiophene-2-carboxylate |
| 5-170 | 5-[(6-{6,6-Difluoro-3-azabicyclo[3.1.0]hexan-3-yl}-2-(hydroxymethyl)pyridin-3-yl)methyl]thiophene-2-carboxylic acid | Ethyl 5-[(6-{6,6-difluoro-3-azabicyclo[3.1.0]-hexan-3-yl}-2-(hydroxymethyl)-pyridin-3-yl)methyl]thiophene-2-carboxylate |

Intermediate 6

2-Bromo-6-{6,6-difluoro-3-azabicyclo[3.1.0]hexan-3-yl}pyridine-3-carbaldehyde

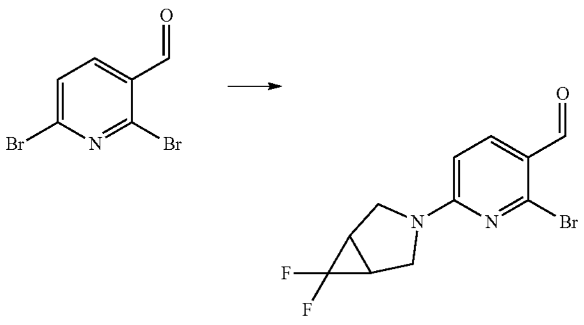

Under argon atmosphere a mixture of 2,6-dibromopyridine-3-carbaldehyde (5.0 g), 6,6-difluoro-3-azabicyclo[3.1.0]hexane hydrochloride (3.0 g) and DIPEA (8 mL) in DMF (50 mL) is stirred at 50° C. for 12 h. The mixture is cooled to rt, concentrated in vacuo, partitioned between water and EtOAc and the phases are separated. The organic phase is washed with brine, dried ($MgSO_4$), concentrated and the residue is chromatographed on silica gel (petroleum ether/EtOAc 85:15→70:30) to give the title compound.

LC (Method 2): $t_R$=1.03 min; Mass spectrum (ESI+): m/z=303 $[M+H]^+$.

Intermediates 6-1 to 6-19 are prepared in analogy to Intermediate 6:

| Intermediate | Structure | $t_R$ | Mass spectrum (ESI+): m/z $[M + H]^+$ | LC Method |
|---|---|---|---|---|
| 6-1 | 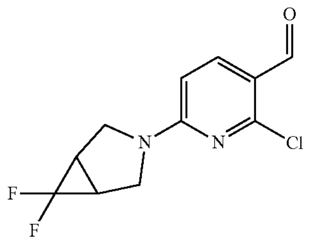 [SMILES: O=Cc1ccc(N2CC3C(C2)C3(F)F)nc1Cl] | 1.02 | 259 | Method 2 |

-continued
| Intermediate | Structure | $t_R$ | Mass spectrum (ESI+): m/z $[M + H]^+$ | LC Method |
|---|---|---|---|---|
| 6-2 | 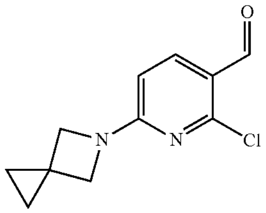 [SMILES: O=Cc1ccc(N2CC3(CC3)C2)nc1Cl] | 1.03 | 223 | Method 2 |
| 6-3 | 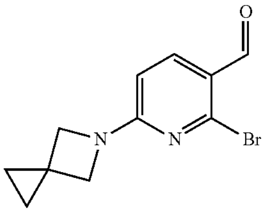 [SMILES: O=Cc1ccc(N2CC3(CC3)C2)nc1Br] | 1.05 | 267 | Method 2 |
| 6-4 | 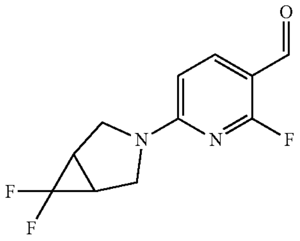 [SMILES: O=Cc1ccc(N2CC3C(C2)C3(F)F)nc1F] | 0.94 | 243 | Method 2 |
| 6-5 | 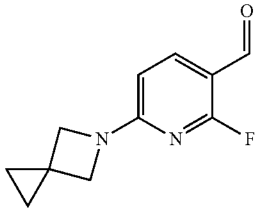 [SMILES: O=Cc1ccc(N2CC3(CC3)C2)nc1F] | 0.95 | 207 | Method 2 |
| 6-6 | 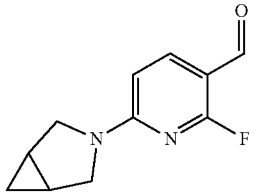 [SMILES: O=Cc1ccc(N2CC3CC3C2)nc1F] | 0.95 | 207 | Method 2 |
| 6-7 | 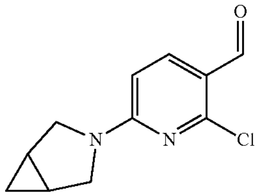 [SMILES: O=Cc1ccc(N2CC3CC3C2)nc1Cl] | 0.99 | 223 | Method 2 |
| 6-8 | 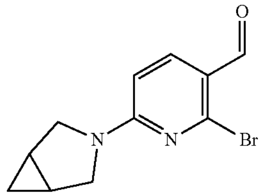 [SMILES: O=Cc1ccc(N2CC3CC3C2)nc1Br] | 1.04 | 267 | Method 2 |

-continued
| Intermediate | Structure | $t_R$ | Mass spectrum (ESI+): m/z $[M + H]^+$ | LC Method |
|---|---|---|---|---|
| 6-9 | 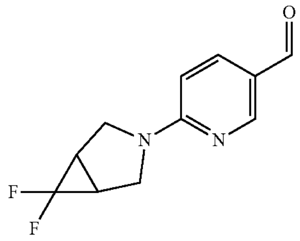 [SMILES: O=Cc1ccc(N2CC3C(C2)C3(F)F)nc1] | 0.65 | 225 | Method 2 |
| 6-10 | 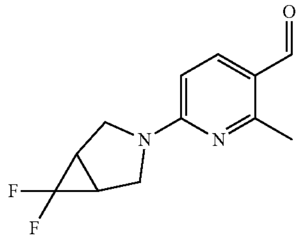 | 0.70 | 239 | Method 2 |
| 6-11 | 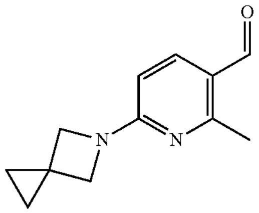 | 0.91 | 203 | Method 1 |
| 6-12 | 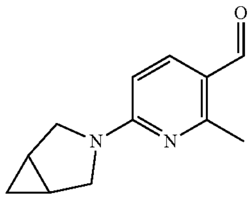 | 0.59 | 203 | Method 2 |
| 6-13 | 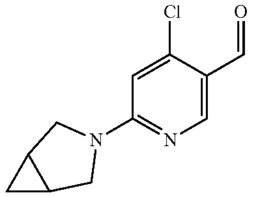 [SMILES: O=Cc1cnc(N2CC3CC3C2)cc1Cl] | 0.87 | 223 | Method 1 |
| 6-14 | 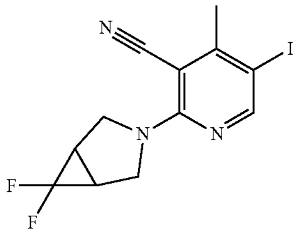 [SMILES: Cc1c(I)cnc(N2CC3C(C2)C3(F)F)c1C#N] | 1.16 | 362 | Method 1 |
| 6-15 | 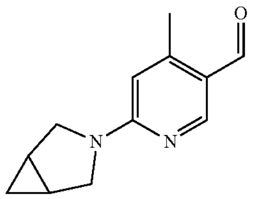 | 0.91 | 203 | Method 1 |

-continued

| Intermediate | Structure | $t_R$ | Mass spectrum (ESI+): m/z $[M + H]^+$ | LC Method |
|---|---|---|---|---|
| 6-16 | 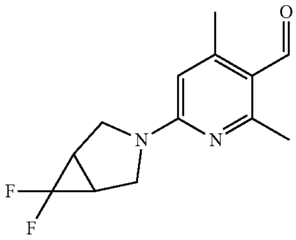 [SMILES: Cc1cc(N2CC3C(C2)C3(F)F)nc(C)c1C=O] | 0.98 | 253 | Method 1 |
| 6-17 | 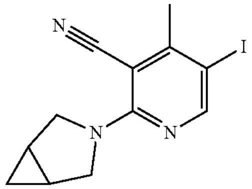 [SMILES: Cc1c(I)cnc(N2CC3CC3C2)c1C#N] | 1.17 | 326 | Method 1 |
| 6-18 | 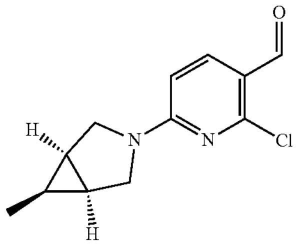 [SMILES: C[C@H]1[C@H]2CN(c3ccc(C=O)c(Cl)n3)C[C@@H]12] | 1.10 | 237 | Method 2 |
| 6-19 | 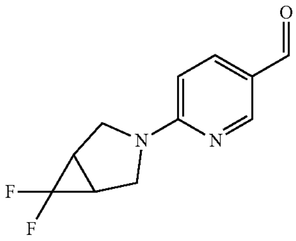 [SMILES: O=Cc1ccc(N2CC3C(C2)C3(F)F)nc1] | 0.86 | 225 | Method 2 |

| Intermediate | Reaction comment |
|---|---|
| 6-4 | $K_2CO_3$ is used as base instead of DIPEA. The reaction is conducted for 2 h at rt. |
| 6-5 | $K_2CO_3$ is used as base instead of DIPEA. The reaction is conducted for 2 h at rt. |
| 6-6 | $K_2CO_3$ is used as base instead of DIPEA. The reaction is conducted for 2 h at rt. |
| 6-7 | The reaction is conducted for 6 h at 90° C. |
| 6-8 | The reaction is conducted for 12 h at rt. |
| 6-9 | $K_2CO_3$ is used as base instead of DIPEA. The reaction is conducted for 12 h at 80° C. |
| 6-10 | $KHCO_3$ is used as base instead of DIPEA. The reaction is conducted in DMSO for 12 h at 80° C. |
| 6-11 | $KHCO_3$ is used as base instead of DIPEA. The reaction is conducted in DMSO for 12 h at 80° C. |

-continued

| Intermediate | Reaction comment |
|---|---|
| 6-12 | $KHCO_3$ is used as base instead of DIPEA. The reaction is conducted in DMSO for 48 h at 45° C. |
| 6-13 | $KHCO_3$ is used as base instead of DIPEA. The reaction is conducted in DMSO for 4 h at 45° C. |
| 6-14 | The reaction is conducted in DMSO for 12 h at 60° C. |
| 6-15 | $KHCO_3$ is used as base instead of DIPEA. The reaction is conducted in DMSO for 12 h at 60° C. |
| 6-16 | The reaction is conducted for 24 h at 70° C. |
| 6-17 | The reaction is conducted for 18 h at 50° C. |
| 6-18 | The reaction is conducted for 2 h at 50° C. |

| Intermediate | Name | Name of Starting Material 1 | Name of Starting Material 2 |
|---|---|---|---|
| 6-1 | 2-Chloro-6-{6,6-difluoro-3-azabicyclo-[3.1.0]hexan-3-yl}-pyridine-3-carbaldehyde | 2,6-Dichloropyridine-3-carbaldehyde | 6,6-Difluoro-3-azabicyclo-[3.1.0]hexane hydrochloride |

-continued

| Intermediate | Name | Name of Starting Material 1 | Name of Starting Material 2 |
|---|---|---|---|
| 6-2 | 6-{5-Azaspiro[2.3]hexan-5-yl}-2-chloropyridine-3-carbaldehyde | 2,6-Dichloropyridine-3-carbaldehyde | 5-Azaspiro[2.3]hexane trifluoroacetate |
| 6-3 | 6-{5-Azaspiro[2.3]hexan-5-yl}-2-bromopyridine-3-carbaldehyde | 2,6-Dibromopyridine-3-carbaldehyde | 5-Azaspiro[2.3]hexane trifluoroacetate |
| 6-4 | 6-{6,6-Difluoro-3-azabicyclo[3.1.0]hexan-3-yl}-2-fluoropyridine-3-carbaldehyde | 2,6-Difluoropyridine-3-carbaldehyde | 6,6-Difluoro-3-azabicyclo-[3.1.0]hexane hydrochloride |
| 6-5 | 6-{5-Azaspiro[2.3]hexan-5-yl}-2-fluoropyridine-3-carbaldehyde | 2,6-Difluoropyridine-3-carbaldehyde | 5-Azaspiro[2.3]hexane hemioxalate |
| 6-6 | 6-{3-Azabicyclo[3.1.0]hexan-3-yl}-2-fluoropyridine-3-carbaldehyde | 2,6-Difluoropyridine-3-carbaldehyde | 3-Azabicyclo[3.1.0]hexane hydrochloride |
| 6-7 | 6-{3-Azabicyclo[3.1.0]hexan-3-yl}-2-chloropyridine-3-carbaldehyde | 2,6-Dichloropyridine-3-carbaldehyde | 3-Azabicyclo[3.1.0]hexane hydrochloride |
| 6-8 | 6-{3-Azabicyclo[3.1.0]hexan-3-yl}-2-bromopyridine-3-carbaldehyde | 2,6-Dibromopyridine-3-carbaldehyde | 3-Azabicyclo[3.1.0]hexane hydrochloride |
| 6-9 | 6-{6,6-Difluoro-3-azabicyclo[3.1.0]hexan-3-yl}pyridine-3-carbaldehyde | 6-Chloropyridine-3-carbaldehyde | 6,6-Difluoro-3-azabicyclo-[3.1.0]hexane hydrochloride |
| 6-10 | 6-{6,6-Difluoro-3-azabicyclo[3.1.0]hexan-3-yl}-2-methylpyridine-3-carbaldehyde | 6-Chloro-2-methyl-pyridine-3-carbaldehyde | 6,6-Difluoro-3-azabicyclo-[3.1.0]hexane hydrochloride |
| 6-11 | 6-{5-Azaspiro[2.3]hexan-5-yl}-2-methylpyridine-3-carbaldehyde | 6-Chloro-2-methyl-pyridine-3-carbaldehyde | 5-Azaspiro[2.3]hexane trifluoroacetate |
| 6-12 | 6-{3-Azabicyclo[3.1.0]hexan-3-yl}-2-methylpyridine-3-carbaldehyde | 6-Chloro-2-methyl-pyridine-3-carbaldehyde | 3-Azabicyclo[3.1.0]hexane hydrochloride |
| 6-13 | 6-{3-Azabicyclo[3.1.0]hexan-3-yl}-4-chloropyridine-3-carbaldehyde | 4,6-Dichloropyridine-3-carbaldehyde | 3-Azabicyclo[3.1.0]hexane hydrochloride |
| 6-14 | 2-{6,6-Difluoro-3-azabicyclo-[3.1.0]hexan-3-yl}-5-iodo-4-methylpyridine-3-carbonitrile | 2-Chloro-5-iodo-4-methylpyridine-3-carbonitrile | 6,6-Difluoro-3-azabicyclo-[3.1.0]hexane hydrochloride |
| 6-15 | 6-{3-Azabicyclo[3.1.0]hexan-3-yl}-4-methylpyridine-3-carbaldehyde | 6-Chloro-4-methyl-pyridine-3-carbaldehyde | 3-Azabicyclo[3.1.0]hexane hydrochloride |
| 6-16 | 6-{6,6-Difluoro-3-azabicyclo[3.1.0]hexan-3-yl}-2,4-dimethylpyridine-3-carbaldehyde | 6-Chloro-2,4-dimethyl-pyridine-3-carbaldehyde | 6,6-Difluoro-3-azabicyclo-[3.1.0]hexane hydrochloride |
| 6-17 | 2-{3-Azabicyclo[3.1.0]hexan-3-yl}-5-iodo-4-methylpyridine-3-carbonitrile | 2-Chloro-5-iodo-4-methylpyridine-3-carbonitrile | 3-Azabicyclo[3.1.0]hexane hydrochloride |
| 6-18 | 2-Chloro-6-[(1R,5S,6R)-6-methyl-3-azabicyclo[3.1.0]hexan-3-yl]pyridine-3-carbaldehyde | 2,6-Dichloropyridine-3-carbaldehyde | (1R,5S,6R)-6-Methyl-3-azabicyclo[3.1.0]hexane hydrochloride (Obtained by separation of the diastereomers of tert-butyl 6-methyl-3-azabicyclo[3.1.0]hexane-3-carboxylate by standard RP chromatography and cleavage of the protecting group with HCl in EtOAc) |
| 6-19 | 6-{6,6-Difluoro-3-azabicyclo[3.1.0]hexan-3-yl}pyridine-3-carbaldehyde | 6-Fluoropyridine-3-carbaldehyde | 6,6-Difluoro-3-azabicyclo-[3.1.0]hexane hydrochloride |

Intermediate 7

(6-{6,6-Difluoro-3-azabicyclo[3.1.0]hexan-3-yl}-2-ethenylpyridin-3-yl)methanol

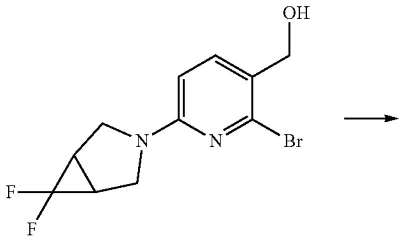

-continued

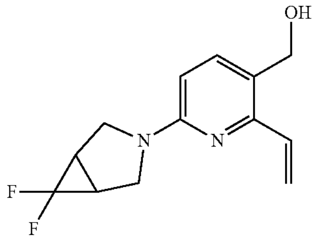

In a microwave vial a mixture of (2-bromo-6-{6,6-difluoro-3-azabicyclo[3.1.0]hexan-3-yl}pyridin-3-yl)methanol (100 mg), potassium vinyltrifluoroborate (60 mg), $K_2CO_3$ (125 mg) and THF (5 mL) is purged for 10 minutes with argon. 1,1'-Bis(diphenylphosphino)ferrocenepalladium(II) dichloride (Pd(dppf)$Cl_2$, 15 mg) is added, the vial is sealed and the mixture is stirred at 60° C. for 12 h. After cooling to rt them mixture is diluted with MeOH and purified by HPLC on reversed phase (ACN, water) to give the title compound. LC (Method 2): $t_R$=0.61 min; Mass spectrum (ESI+): m/z=253 $[M+H]^+$.

Intermediates 7-1 to 7-9 are prepared in analogy to Intermediate 7:
| Intermediate | Structure | $t_R$ | Mass spectrum (ESI+): m/z $[M + H]^+$ | LC Method |
|---|---|---|---|---|
| 7-1 | 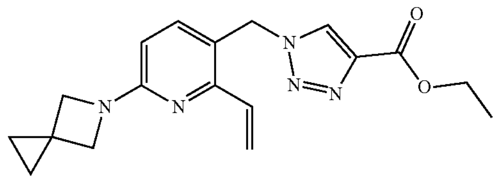 [SMILES: C=Cc1nc(N2CC3(CC3)C2)ccc1Cn1cc(C(=O)OCC)nn1] | 0.74 | 340 | Method 2 |
| 7-2 | 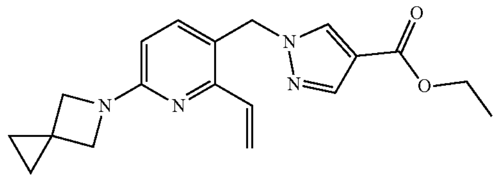 [SMILES: C=Cc1nc(N2CC3(CC3)C2)ccc1Cn1cc(C(=O)OCC)cn1] | 0.76 | 339 | Method 2 |
| 7-3 | 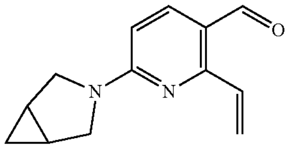 [SMILES: C=Cc1nc(N2CC3CC3C2)ccc1C=O] | 1.02 | 215 | Method 1 |
| 7-4 | 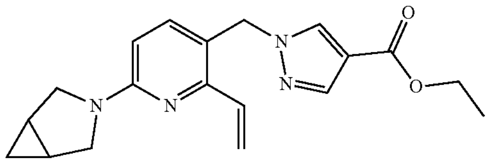 | 0.77 | 339 | Method 2 |
| 7-5 | 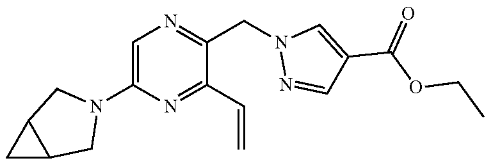 [SMILES: C=Cc1nc(N2CC3CC3C2)cnc1Cn1cc(C(=O)OCC)cn1] | 1.07 | 340 | Method 2 |
| 7-6 | 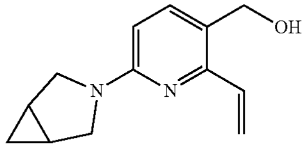 [SMILES: C=Cc1nc(N2CC3CC3C2)ccc1CO] | 0.27 | 217 | Method 2 |
| 7-7 | 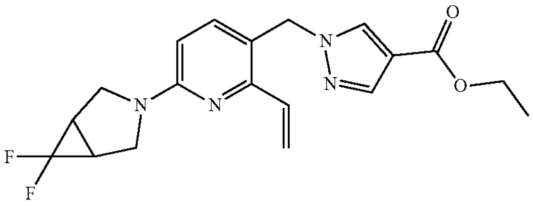 [SMILES: C=Cc1nc(N2CC3C(C2)C3(F)F)ccc1Cn1cc(C(=O)OCC)cn1] | 0.92 | 375 | Method 2 |
| 7-8 | 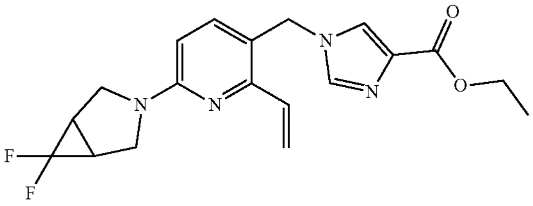 [SMILES: C=Cc1nc(N2CC3C(C2)C3(F)F)ccc1Cn1cnc(C(=O)OCC)c1] | 0.81 | 375 | Method 2 |

-continued

| Intermediate | Structure | $t_R$ | Mass spectrum (ESI+): m/z $[M + H]^+$ | LC Method |
|---|---|---|---|---|
| 7-9 | 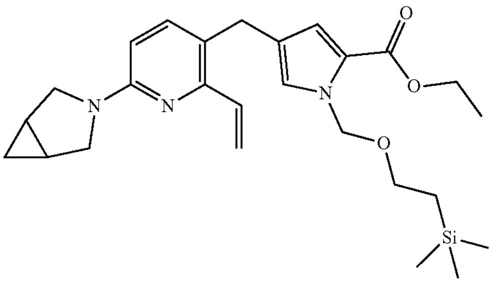 [SMILES: C=Cc1nc(N2CC3CC3C2)ccc1Cc1cc(C(=O)OCC)n(COCC[Si](C)(C)C)c1] 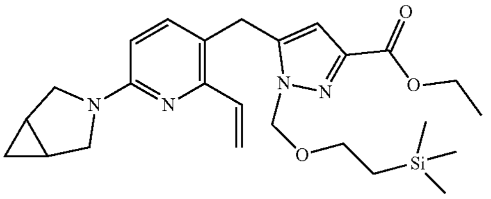 [SMILES: C=Cc1nc(N2CC3CC3C2)ccc1Cc1cc(C(=O)OCC)nn1COCC[Si](C)(C)C] (mixture of isomers) | 0.96 and 0.98 | 469 | Method 2 |

| Intermediate | Reaction comment |
|---|---|
| 7-1 | The reaction is conducted at 80° C. |
| 7-2 | The reaction is conducted at 80° C. |
| 7-4 | The reaction is conducted at 90° C. |
| 7-5 | The reaction is conducted at 100° C. for 14 h. |
| 7-6 | The reaction is conducted at 80° C. |
| 7-7 | $Na_2CO_3$ is used instead of $K_2CO_3$, vinylboronic acid pinacolester instead of potassium vinyltrifluoroborate and 1,4-dioxane instead of THF. The reaction is conducted at 100° C. for 12 h. |
| 7-8 | The reaction is conducted at 100° C. for 4 h. |
| 7-9 | The reaction is conducted at 80° C. for 3 days. The product is obtained as a mixture of isomers and used as such in the next step. |

| Intermediate | Name | Name of Starting Material |
|---|---|---|
| 7-1 | Ethyl 1-[(6-{5-azaspiro[2.3]hexan-5-yl}-2-ethenylpyridin-3-yl)methyl]-1H-1,2,3-triazole-4-carboxylate | Ethyl 1-[(6-{5-azaspiro[2.3]hexan-5-yl}-2-chloropyridin-3-yl)methyl]-1H-1,2,3-triazole-4-carboxylate |
| 7-2 | Ethyl 1-[(6-{5-azaspiro[2.3]hexan-5-yl}-2-ethenylpyridin-3-yl)methyl]-1H-pyrazole-4-carboxylate | Ethyl 1-[(6-{5-azaspiro[2.3]hexan-5-yl}-2-chloropyridin-3-yl)methyl]-1H-pyrazole-4-carboxylate |
| 7-3 | 6-{3-Azabicyclo[3.1.0]hexan-3-yl}-2-ethenylpyridine-3-carbaldehyde | 6-{3-Azabicyclo[3.1.0]hexan-3-yl}-2-chloropyridine-3-carbaldehyde |
| 7-4 | Ethyl 1-[(6-{3-azabicyclo[3.1.0]hexan-3-yl}-2-ethenylpyridin-3-yl)methyl]-1H-pyrazole-4-carboxylate | Ethyl 1-[(6-{3-azabicyclo[3.1.0]hexan-3-yl}-2-chloropyridin-3-yl)methyl]-1H-pyrazole-4-carboxylate |
| 7-5 | Ethyl 1-[(5-{3-azabicyclo[3.1.0]hexan-3-yl}-3-ethenylpyrazin-2-yl)methyl]-1H-pyrazole-4-carboxylate | Ethyl 1-[(5-{3-azabicyclo[3.1.0]hexan-3-yl}-3-chloropyrazin-2-yl)methyl]-1H-pyrazole-4-carboxylate |
| 7-6 | (6-{3-Azabicyclo[3.1.0]hexan-3-yl}-2-ethenylpyridin-3-yl)methanol | (6-{3-Azabicyclo[3.1.0]hexan-3-yl}-2-bromopyridin-3-yl)methanol |
| 7-7 | Ethyl 1-[(6-{6,6-difluoro-3-azabicyclo[3.1.0]hexan-3-yl}-2-ethenylpyridin-3-yl)methyl]-1H-pyrazole-4-carboxylate | Ethyl 1-[(2-chloro-6-{6,6-difluoro-3-azabicyclo[3.1.0]hexan-3-yl}pyridin-3-yl)methyl]-1H-pyrazole-4-carboxylate |
| 7-8 | Ethyl 1-[(6-{6,6-difluoro-3-azabicyclo[3.1.0]hexan-3-yl}-2-ethenylpyridin-3-yl)methyl]-1H-imidazole-4-carboxylate | Ethyl 1-[(2-chloro-6-{6,6-difluoro-3-azabicyclo[3.1.0]hexan-3-yl}pyridin-3-yl)methyl]-1H-imidazole-4-carboxylate |
| 7-9 | Ethyl 3-[(6-{3-azabicyclo[3.1.0]hexan-3-yl}-2-ethenylpyridin-3-yl)methyl]-1-{[2-(trimethylsilyl)ethoxy]methyl}-1H-pyrazole-5-carboxylate and Ethyl 5-[(6-{3-azabicyclo[3.1.0]hexan-3-yl}-2-ethenylpyridin-3-yl)methyl]-1-{[2-(trimethylsilyl)ethoxy]methyl}-1H-pyrazole-3-carboxylate (mixture of isomers) | Ethyl 3-[(6-{3-azabicyclo[3.1.0]hexan-3-yl}-2-chloropyridin-3-yl)methyl]-1-{[2-(trimethylsilyl)ethoxy]methyl}-1H-pyrazole-5-carboxylate and Ethyl 5-[(6-{3-azabicyclo[3.1.0]hexan-3-yl}-2-chloropyridin-3-yl)methyl]-1-{[2-(trimethylsilyl)ethoxy]methyl}-1H-pyrazole-3-carboxylate (mixture of isomers) |

Intermediate 8

Ethyl 1-[(6-{6,6-difluoro-3-azabicyclo[3.1.0]hexan-3-yl}-2-ethenylpyridin-3-yl)methyl]-1H-pyrazole-4-carboxylate

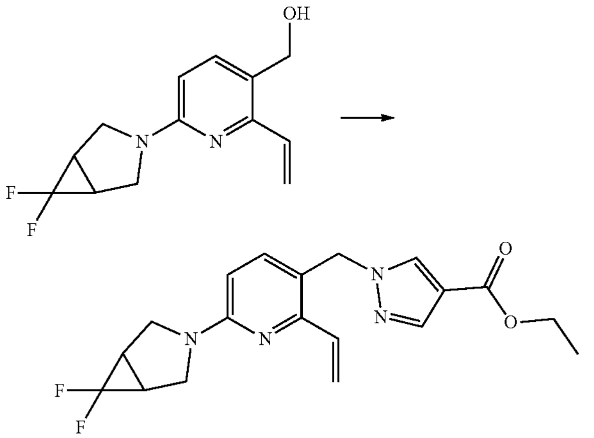

Under argon atmosphere (6-{6,6-difluoro-3-azabicyclo[3.1.0]hexan-3-yl}-2-ethenylpyridin-3-yl)methanol (877 mg) and DIPEA (1.6 mL) are dissolved in DCM (25 mL). The mixture is cooled to 0° C. and treated dropwise with methanesulfonylchloride ($CH_3$—$SO_2Cl$, 318 μL). After stirring for 15 minutes ethyl 1H-pyrazole-4-carboxylate (555 mg) is added and the mixture is stirred for 3 h at rt. Then the mixture is partitioned between water and DCM. The organic phase is dried ($MgSO_4$), concentrated and the residue is chromatographed on silica gel (petroleum ether/EtOAc 100:0→70:30) to give the title compound. LC (Method 2): $t_R$=0.93 min; Mass spectrum (ESI+): m/z=375 $[M+H]^+$.

Intermediate 9

Ethyl 1-[(6-{6,6-difluoro-3-azabicyclo[3.1.0]hexan-3-yl}-2-formylpyridin-3-yl)methyl]-1H-pyrazole-4-carboxylate

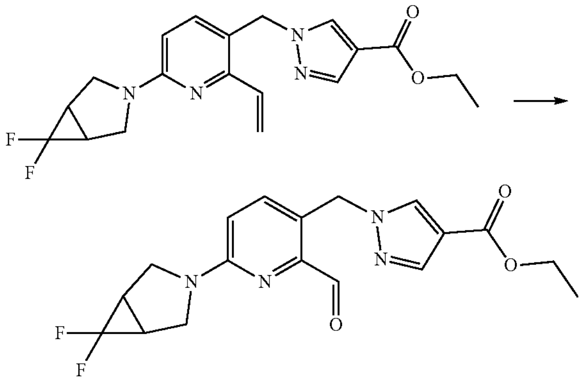

$OsO_4$ (4% in water, 283 μL) is added to a mixture of ethyl 1-[(6-{6,6-difluoro-3-azabicyclo[3.1.0]hexan-3-yl}-2-ethenylpyridin-3-yl)methyl]-1H-pyrazole-4-carboxylate (700 mg) in 1,4-dioxane (3.4 mL) and water (3.4 mL). The mixture is stirred for 30 minutes, treated with $NaIO_4$ (1.2 g) and stirred for 3 h at rt. The mixture is partitioned between water and EtOAc/MeOH (9:1). After separation of the phases, the organic phase is dried ($MgSO_4$) and concentrated to give the title compound. LC (Method 2): $t_R$=1.06 min; Mass spectrum (ESI+): m/z=377 $[M+H]^+$.

Intermediates 9-1 to 9-18 are prepared in analogy to Intermediate 9:

| Intermediate | Structure | $t_R$ | Mass spectrum (ESI+): m/z $[M + H]^+$ | LC Method |
|---|---|---|---|---|
| 9-1 | 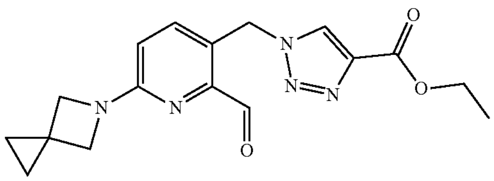 [SMILES: CCOC(=O)c1cn(Cc2ccc(N3CC4(CC4)C3)nc2C=O)nn1] | 0.90 | 342 | Method 2 |
| 9-2 | 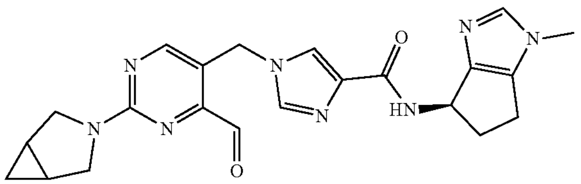 [SMILES: Cn1cnc2c1CC[C@H]2NC(=O)c1cn(Cc2cnc(N3CC4CC4C3)nc2C=O)cn1] | 0.81 | | Method 1 |
| 9-3 | 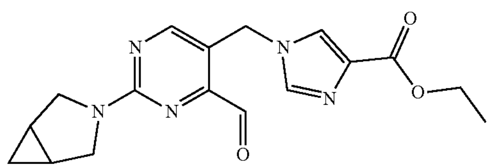 [SMILES: CCOC(=O)c1cn(Cc2cnc(N3CC4CC4C3)nc2C=O)cn1] | 0.87 | 342 | Method 1 |

-continued
| Intermediate | Structure | $t_R$ | Mass spectrum (ESI+): m/z $[M + H]^+$ | LC Method |
|---|---|---|---|---|
| 9-4 | 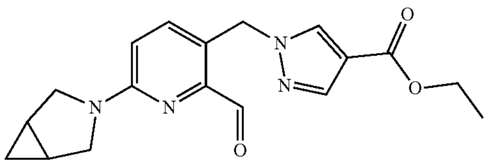 [SMILES: CCOC(=O)c1cnn(Cc2ccc(N3CC4CC4C3)nc2C=O)c1] | 1.08 | 341 | Method 1 |
| 9-5 | 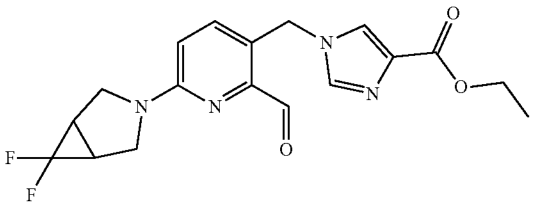 [SMILES: CCOC(=O)c1cn(Cc2ccc(N3CC4C(C3)C4(F)F)nc2C=O)cn1] | 0.95 | 377 | Method 1 |
| 9-6 | 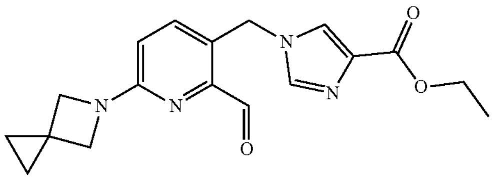 [SMILES: CCOC(=O)c1cn(Cc2ccc(N3CC4(CC4)C3)nc2C=O)cn1] | 0.95 | 341 | Method 1 |
| 9-7 | 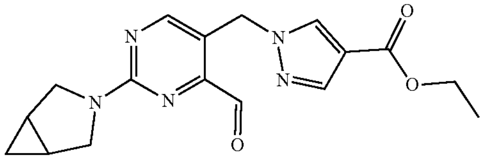 [SMILES: CCOC(=O)c1cnn(Cc2cnc(N3CC4CC4C3)nc2C=O)c1] | | 342 | |
| 9-8 | 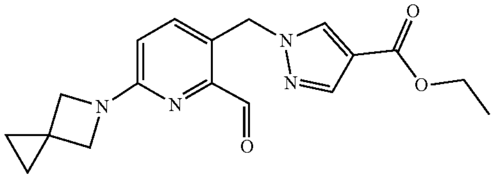 | 0.87 | 341 | Method 2 |
| 9-9 | 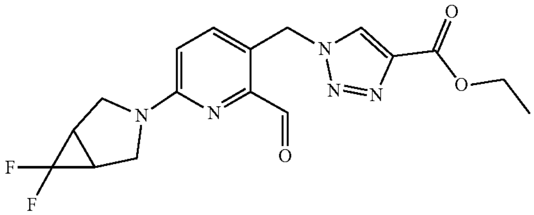 [SMILES: CCOC(=O)c1cn(Cc2ccc(N3CC4C(C3)C4(F)F)nc2C=O)nn1] | 1.00 | 378 | Method 2 |
| 9-10 | 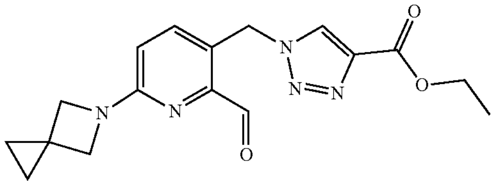 [SMILES: CCOC(=O)c1cn(Cc2ccc(N3CC4(CC4)C3)nc2C=O)nn1] | 0.99 | 340 $[M - H]^-$ | Method 1 |
| 9-11 | 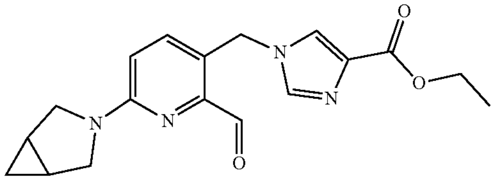 [SMILES: CCOC(=O)c1cn(Cc2ccc(N3CC4CC4C3)nc2C=O)cn1] | 0.98 | 341 | Method 1 |

-continued
| Intermediate | Structure | $t_R$ | Mass spectrum (ESI+): m/z $[M + H]^+$ | LC Method |
| --- | --- | --- | --- | --- |
| 9-12 | 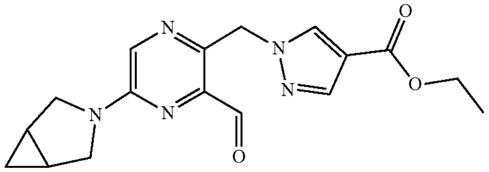 [SMILES: CCOC(=O)c1cnn(Cc2ncc(N3CC4CC4C3)nc2C=O)c1] | 0.98 | 342 | Method 1 |
| 9-13 | 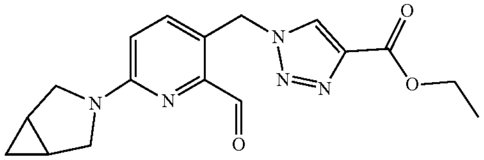 [SMILES: CCOC(=O)c1cn(Cc2ccc(N3CC4CC4C3)nc2C=O)nn1] | 0.88 | 342 | Method 2 |
| 9-14 | 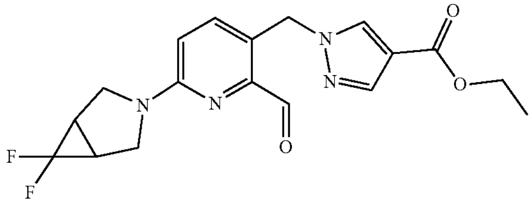 [SMILES: CCOC(=O)c1cnn(Cc2ccc(N3CC4C(C3)C4(F)F)nc2C=O)c1] | 1.05 | 377 | Method 2 |
| 9-15 | 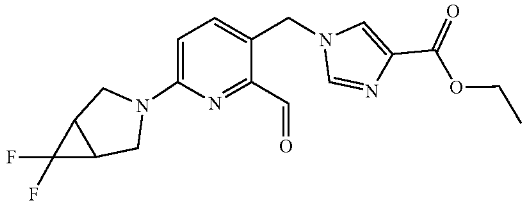 [SMILES: CCOC(=O)c1cn(Cc2ccc(N3CC4C(C3)C4(F)F)nc2C=O)cn1] | 0.87 | 377 | Method 2 |
| 9-16 | 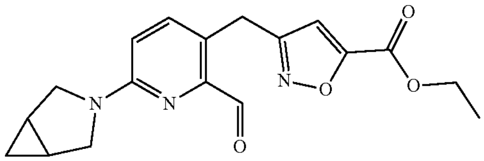 [SMILES: CCOC(=O)c1cc(Cc2ccc(N3CC4CC4C3)nc2C=O)no1] | 1.12 | 342 | Method 1 |
| 9-17 | 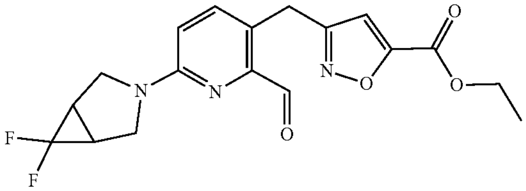 [SMILES: CCOC(=O)c1cc(Cc2ccc(N3CC4C(C3)C4(F)F)nc2C=O)no1] | 1.08 | 378 | Method 1 |
| 9-18 | 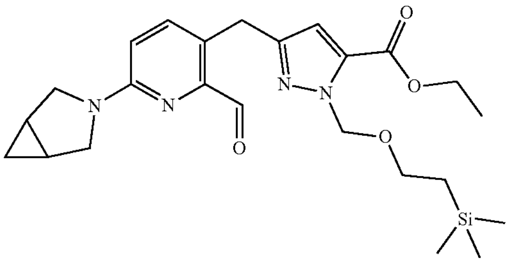 [SMILES: CCOC(=O)c1cc(Cc2ccc(N3CC4CC4C3)nc2C=O)nn1COCC[Si](C)(C)C] | 1.08 and 1.15 | 471 | Method 2 |

-continued

| Intermediate | Structure | $t_R$ | Mass spectrum (ESI+): m/z $[M + H]^+$ | LC Method |
|---|---|---|---|---|
| | 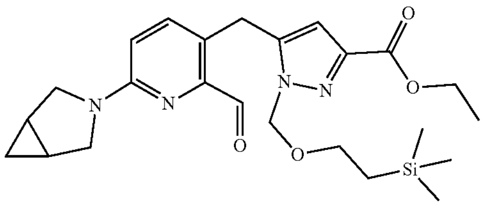 [SMILES: CCOC(=O)c1cc(Cc2ccc(N3CC4CC4C3)nc2C=O)n(COCC[Si](C)(C)C)n1] (mixture of isomers) | | | |

| Intermediate | Reaction comment |
|---|---|
| 9-3 | The mixture is stirred for 12 h after addition of $NaIO_4$. |
| 9-9 | The mixture is stirred for 12 h after addition of $NaIO_4$. |
| 9-10 | The mixture is stirred for 12 h after addition of $NaIO_4$. |
| 9-13 | The mixture is stirred for 12 h after addition of $NaIO_4$. |
| 9-16 | The mixture is stirred for 16 h after addition of $NaIO_4$. |

-continued

| Intermediate | Reaction comment |
|---|---|
| 9-18 | The mixture is stirred for 12 h after addition of $NaIO_4$. The product is obtained as a mixture of isomers. |

| Intermediate | Name | Name of Starting Material |
|---|---|---|
| 9-1 | Ethyl 1-[(6-{5-azaspiro[2.3]hexan-5-yl}-2-formylpyridin-3-yl)methyl]-1H-1,2,3-triazole-4-carboxylate | Ethyl 1-[(6-{5-azaspiro[2.3]hexan-5-yl}-2-ethenylpyridin-3-yl)methyl]-1H-1,2,3-triazole-4-carboxylate |
| 9-2 | 1-[(2-{3-Azabicyclo[3.1.0]hexan-3-yl}-4-formylpyrimidin-5-yl)methyl]-N-[(4R)-1-methyl-1H,4H,5H,6H-cyclopenta[d]imidazol-4-yl]-1H-imidazole-4-carboxamide | 1-[(2-{3-Azabicyclo[3.1.0]hexan-3-yl}-4-[(1E)-2-phenylethenyl]pyrimidin-5-yl)methyl]-N-[(4R)-1-methyl-1H,4H,5H,6H-cyclopenta-[d]imidazol-4-yl]-1H-imidazole-4-carboxamide |
| 9-3 | Ethyl 1-[(2-{3-azabicyclo[3.1.0]hexan-3-yl}-4-formylpyrimidin-5-yl)methyl]-1H-imidazole-4-carboxylate | Ethyl 1-[(2-{3-azabicyclo[3.1.0]hexan-3-yl}-4-[(1E)-2-phenylethenyl]pyrimidin-5-yl)methyl]-1H-imidazole-4-carboxylate |
| 9-4 | Ethyl 1-[(6-{3-azabicyclo[3.1.0]hexan-3-yl}-2-formylpyridin-3-yl)methyl]-1H-pyrazole-4-carboxylate | Ethyl 1-[(6-{3-azabicyclo[3.1.0]hexan-3-yl}-2-ethenylpyridin-3-yl)methyl]-1H-pyrazole-4-carboxylate |
| 9-5 | Ethyl 1-[(6-{6,6-difluoro-3-azabicyclo[3.1.0]hexan-3-yl}-2-formylpyridin-3-yl)methyl]-1H-imidazole-4-carboxylate | Ethyl 1-[(6-{6,6-difluoro-3-azabicyclo[3.1.0]hexan-3-yl}-2-ethenylpyridin-3-yl)methyl]-1H-imidazole-4-carboxylate |
| 9-6 | Ethyl 1-[(6-{5-azaspiro[2.3]hexan-5-yl}-2-formylpyridin-3-yl)methyl]-1H-imidazole-4-carboxylate | Ethyl 1-[(6-{5-azaspiro[2.3]hexan-5-yl}-2-ethenylpyridin-3-yl)methyl]-1H-imidazole-4-carboxylate |
| 9-7 | Ethyl 1-[(2-{3-azabicyclo[3.1.0]hexan-3-yl}-4-formylpyrimidin-5-yl)methyl]-1H-pyrazole-4-carboxylate | Ethyl 1-[(2-{3-azabicyclo[3.1.0]hexan-3-yl}-4-[(1E)-2-phenylethenyl]pyrimidin-5-yl)methyl]-1H-pyrazole-4-carboxylate |
| 9-8 | Ethyl 1-[(6-{5-azaspiro[2.3]hexan-5-yl}-2-formylpyridin-3-yl)methyl]-1H-pyrazole-4-carboxylate | Ethyl 1-[(6-{5-azaspiro[2.3]hexan-5-yl}-2-ethenylpyridin-3-yl)methyl]-1H-pyrazole-4-carboxylate |
| 9-9 | Ethyl 1-[(6-{6,6-difluoro-3-azabicyclo[3.1.0]hexan-3-yl}-2-formylpyridin-3-yl)methyl]-1H-1,2,3-triazole-4-carboxylate | Ethyl 1-[(6-{6,6-difluoro-3-azabicyclo[3.1.0]hexan-3-yl}-2-ethenylpyridin-3-yl)methyl]-1H-1,2,3-triazole-4-carboxylate |
| 9-10 | Ethyl 1-[(6-{5-azaspiro[2.3]hexan-5-yl}-2-formylpyridin-3-yl)methyl]-1H-1,2,3-triazole-4-carboxylate | Ethyl 1-[(6-{5-azaspiro[2.3]hexan-5-yl}-2-ethenylpyridin-3-yl)methyl]-1H-1,2,3-triazole-4-carboxylate |
| 9-11 | Ethyl 1-[(6-{3-azabicyclo[3.1.0]hexan-3-yl}-2-formylpyridin-3-yl)methyl]-1H-imidazole-4-carboxylate | Ethyl 1-[(6-{3-azabicyclo[3.1.0]hexan-3-yl}-2-ethenylpyridin-3-yl)methyl]-1H-imidazole-4-carboxylate |
| 9-12 | Ethyl 1-[(5-{3-azabicyclo[3.1.0]hexan-3-yl}-3-formylpyrazin-2-yl)methyl]-1H-pyrazole-4-carboxylate | Ethyl 1-[(5-{3-azabicyclo[3.1.0]hexan-3-yl}-3-ethenylpyrazin-2-yl)methyl]-1H-pyrazole-4-carboxylate |
| 9-13 | Ethyl 1-[(6-{3-azabicyclo[3.1.0]hexan-3-yl}-2-formylpyridin-3-yl)methyl]-1H-1,2,3-triazole-4-carboxylate | Ethyl 1-[(6-{3-azabicyclo[3.1.0]hexan-3-yl}-2-ethenylpyridin-3-yl)methyl]-1H-1,2,3-triazole-4-carboxylate |
| 9-14 | Ethyl 1-[(6-{6,6-difluoro-3-azabicyclo[3.1.0]-hexan-3-yl}-2-formylpyridin-3-yl)methyl]-1H-pyrazole-4-carboxylate | Ethyl 1-[(6-{6,6-difluoro-3-azabicyclo[3.1.0]hexan-3-yl}-2-ethenylpyridin-3-yl)methyl]-1H-pyrazole-4-carboxylate |
| 9-15 | Ethyl 1-[(6-{6,6-difluoro-3-azabicyclo[3.1.0]-hexan-3-yl}-2-formylpyridin-3-yl)methyl]-1H-imidazole-4-carboxylate | Ethyl 1-[(6-{6,6-difluoro-3-azabicyclo[3.1.0]hexan-3-yl}-2-ethenylpyridin-3-yl)methyl]-1H-imidazole-4-carboxylate |

-continued

| Intermediate | Name | Name of Starting Material |
|---|---|---|
| 9-16 | Ethyl 3-[(6-{3-azabicyclo[3.1.0]hexan-3-yl}-2-formylpyridin-3-yl)methyl]-1,2-oxazole-5-carboxylate | Ethyl 3-[(6-{3-azabicyclo[3.1.0]hexan-3-yl}-2-[(1E)-2-phenylethenyl]pyridin-3-yl)methyl]-1,2-oxazole-5-carboxylate |
| 9-17 | Ethyl 3-[(6-{6,6-difluoro-3-azabicyclo[3.1.0]hexan-3-yl}-2-formylpyridin-3-yl)methyl]-1,2-oxazole-5-carboxylate | Ethyl 3-[(6-{6,6-difluoro-3-azabicyclo[3.1.0]-hexan-3-yl}-2-[(1E)-2-phenylethenyl]pyridin-3-yl)methyl]-1,2-oxazole-5-carboxylate |
| 9-18 | Ethyl 3-[(6-{3-azabicyclo[3.1.0]hexan-3-yl}-2-formylpyridin-3-yl)methyl]-1-{[2-(trimethyl-silyl)ethoxy]methyl}-1H-pyrazole-5-carboxylate and Ethyl 5-[(6-{3-azabicyclo[3.1.0]hexan-3-yl}-2-formylpyridin-3-yl)methyl]-1-{[2-(trimethylsilyl)-ethoxy]methyl}-1H-pyrazole-3-carboxylate (mixture of isomers) | Ethyl 3-[(6-{3-azabicyclo[3.1.0]hexan-3-yl}-2-ethenylpyridin-3-yl)methyl]-1-{[2-(trimethyl-silyl)ethoxy]methyl}-1H-pyrazole-5-carboxylate and Ethyl 5-[(6-{3-azabicyclo[3.1.0]hexan-3-yl}-2-ethenylpyridin-3-yl)methyl]-1-{[2-(trimethyl-silyl)ethoxy]methyl}-1H-pyrazole-3-carboxylate (mixture of isomers) |

Intermediate 10

Ethyl 1-[(6-{6,6-difluoro-3-azabicyclo[3.1.0]hexan-3-yl}-2-(hydroxymethyl)pyridin-3-yl)methyl]-1H-pyrazole-4-carboxylate

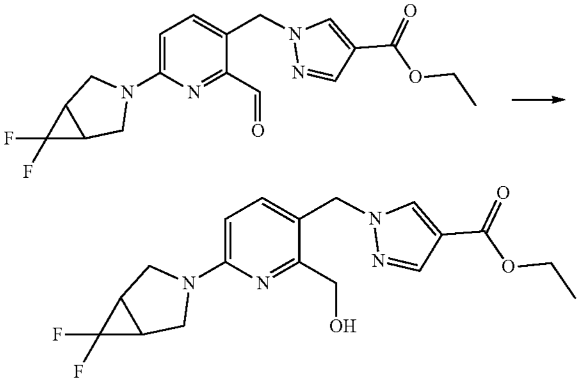

$NaBH_4$ (40 mg) is added portionwise to a ice-cooled mixture of ethyl 1-[(6-{6,6-difluoro-3-azabicyclo[3.1.0]hexan-3-yl}-2-formylpyridin-3-yl)methyl]-1H-pyrazole-4-carboxylate (200 mg) in EtOH (5 mL). The mixture is stirred for 2 h at rt, cooled to 0° C., treated with 4 M aqueous HCl (599 μL) and stirred for 5 minutes. 4 M aqueous NaOH (599 μL) is added and the mixture is diluted with EtOAc. After drying ($MgSO_4$) the mixture is filtered and concentrated. The residue is partitioned between EtOAc and saturated aqueous $NaHCO_3$. The organic phase is dried ($MgSO_4$) and concentrated to give the title compound. LC (Method 2): $t_R$=0.75 min; Mass spectrum (ESI+): m/z=379 $[M+H]^+$.

Intermediates 10-1 to 10-11 are prepared in analogy to Intermediate 10:

| Intermediate | Structure | $t_R$ | Mass spectrum (ESI+): m/z $[M + H]^+$ | LC Method |
|---|---|---|---|---|
| 10-1 | 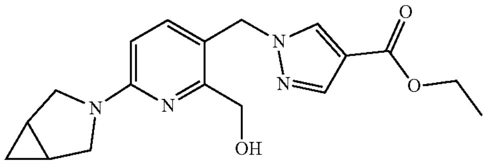 [SMILES: CCOC(=O)c1cnn(Cc2ccc(N3CC4CC4C3)nc2CO)c1] | 0.99 | 343 | Method 1 |
| 10-2 | 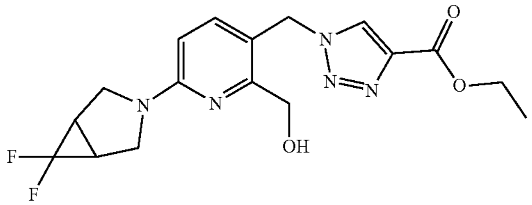 | 0.71 | 380 | Method 2 |

-continued
| Intermediate | Structure | $t_R$ | Mass spectrum (ESI+): m/z $[M + H]^+$ | LC Method |
|---|---|---|---|---|
| 10-3 | 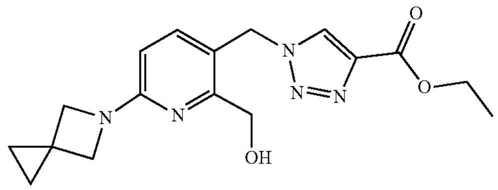 [SMILES: CCOC(=O)c1cn(Cc2ccc(N3CC4(CC4)C3)nc2CO)nn1] | 0.68 | 344 | Method 2 |
| 10-4 | 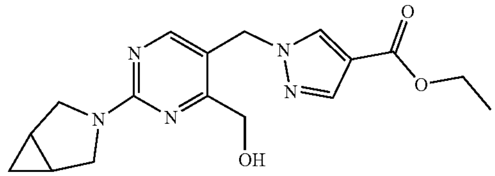 [SMILES: CCOC(=O)c1cnn(Cc2cnc(N3CC4CC4C3)nc2CO)c1] | 0.82 | 344 | Method 2 |
| 10-5 | 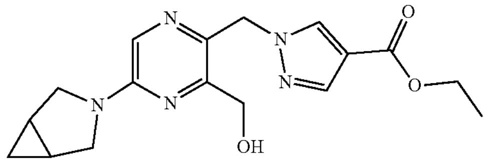 [SMILES: CCOC(=O)c1cnn(Cc2ncc(N3CC4CC4C3)nc2CO)c1] | 0.91 | 344 | Method 1 |
| 10-6 | 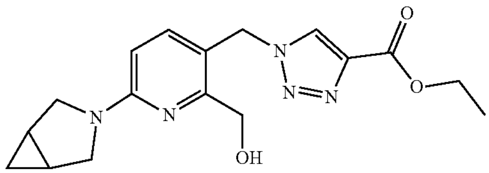 [SMILES: CCOC(=O)c1cn(Cc2ccc(N3CC4CC4C3)nc2CO)nn1] | 0.66 | 344 | Method 2 |
| 10-7 | 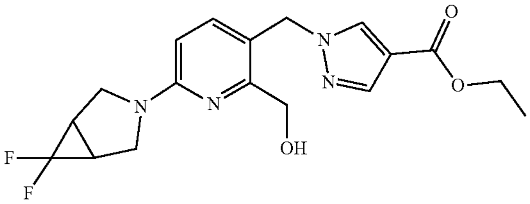 [SMILES: CCOC(=O)c1cnn(Cc2ccc(N3CC4C(C3)C4(F)F)nc2CO)c1] | 0.75 | 379 | Method 2 |
| 10-8 | 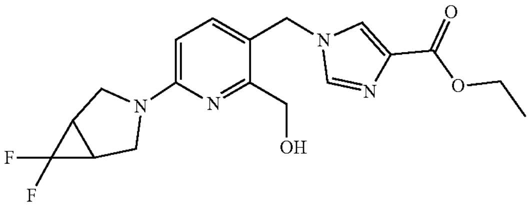 [SMILES: CCOC(=O)c1cn(Cc2ccc(N3CC4C(C3)C4(F)F)nc2CO)cn1] | 0.67 | 379 | Method 2 |
| 10-9 | 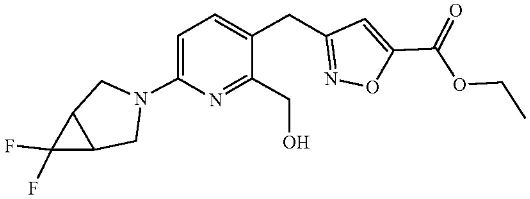 [SMILES: CCOC(=O)c1cc(Cc2ccc(N3CC4C(C3)C4(F)F)nc2CO)no1] | 1.01 | 380 | Method 1 |
| 10-10 | 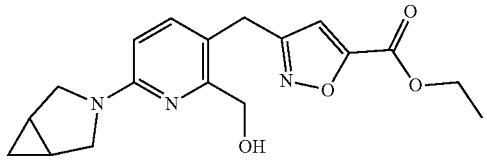 [SMILES: CCOC(=O)c1cc(Cc2ccc(N3CC4CC4C3)nc2CO)no1] | 1.05 | 344 | Method 1 |

-continued

| Intermediate | Structure | $t_R$ | Mass spectrum (ESI+): m/z $[M + H]^+$ | LC Method |
|---|---|---|---|---|
| 10-11 | 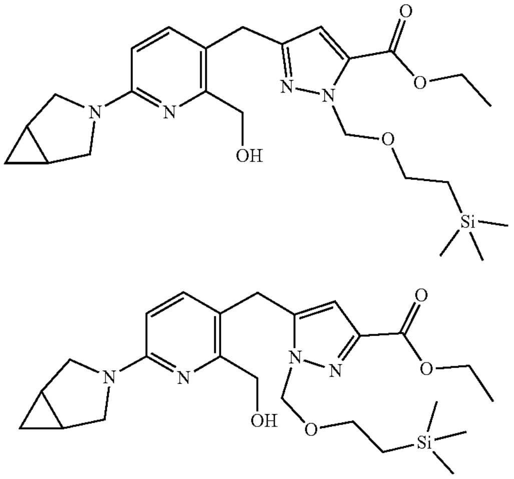 (mixture of isomers) | 0.89 and 0.93 | 473 | Method 2 |

| Intermediate | Reaction comment |
|---|---|
| 10-3 | The reaction is conducted in THF/MeOH 2:1. |
| 10-3 | The reaction is conducted in THF for 12 h at rt. |
| 10-5 | The reaction is conducted in THF/EtOH for 30 minutes at rt. |
| 10-7 | The reaction is conducted in THF/MeOH for 1 h at rt. |
| 10-8 | The reaction is conducted in THF/water 10:1 for 12 h at rt. |

-continued

| Intermediate | Reaction comment |
|---|---|
| 10-9 | The reaction is conducted for 15 minutes at rt. The reaction is quenched with saturated aqueous $NaHCO_3$ instead of HCl. |
| 10-10 | The reaction is conducted for 45 minutes at rt. The reaction is quenched with saturated aqueous $NaHCO_3$ instead of HCl. |
| 10-11 | The product is obtained as a mixture of isomers. |

| Intermediate | Name | Name of Starting Material |
|---|---|---|
| 10-1 | Ethyl 1-[(6-{3-azabicyclo[3.1.0]hexan-3-yl}-2-(hydroxymethyl)pyridin-3-yl)methyl]-1H-pyrazole-4-carboxylate | Ethyl 1-[(6-{3-azabicyclo[3.1.0]hexan-3-yl}-2-formylpyridin-3-yl)methyl]-1H-pyrazole-4-carboxylate |
| 10-2 | Ethyl 1-[(6-{6,6-difluoro-3-azabicyclo[3.1.0]-hexan-3-yl}-2-(hydroxymethyl)pyridin-3-yl)methyl]-1H-1,2,3-triazole-4-carboxylate | Ethyl 1-[(6-{6,6-difluoro-3-azabicyclo[3.1.0]-hexan-3-yl}-2-formylpyridin-3-yl)methyl]-1H-1,2,3-triazole-4-carboxylate |
| 10-3 | Ethyl 1-[(6-{5-azaspiro[2.3]hexan-5-yl}-2-(hydroxymethyl)pyridin-3-yl)methyl]-1H-1,2,3-triazole-4-carboxylate | Ethyl 1-[(6-{5-azaspiro[2.3]hexan-5-yl}-2-formylpyridin-3-yl)methyl]-1H-1,2,3-triazole-4-carboxylate |
| 10-4 | Ethyl 1-[(2-{3-azabicyclo[3.1.0]hexan-3-yl}-4-(hydroxymethyl)pyrimidin-5-yl)methyl]-1H-pyrazole-4-carboxylate | Ethyl 1-[(2-{3-azabicyclo[3.1.0]hexan-3-yl}-4-formylpyrimidin-5-yl)methyl]-1H-pyrazole-4-carboxylate |
| 10-5 | Ethyl 1-[(5-{3-azabicyclo[3.1.0]hexan-3-yl}-3-(hydroxymethyl)pyrazin-2-yl)methyl]-1H-pyrazole-4-carboxylate | Ethyl 1-[(5-{3-azabicyclo[3.1.0]hexan-3-yl}-3-formylpyrazin-2-yl)methyl]-1H-pyrazole-4-carboxylate |
| 10-6 | Ethyl 1-[(6-{3-azabicyclo[3.1.0]hexan-3-yl}-2-(hydroxymethyl)pyridin-3-yl)methyl]-1H-1,2,3-triazole-4-carboxylate | Ethyl 1-[(6-{3-azabicyclo[3.1.0]hexan-3-yl}-2-formylpyridin-3-yl)methyl]-1H-1,2,3-triazole-4-carboxylate |
| 10-7 | Ethyl 1-[(6-{6,6-difluoro-3-azabicyclo[3.1.0]-hexan-3-yl}-2-(hydroxymethyl)pyridin-3-yl)methyl]-1H-pyrazole-4-carboxylate | Ethyl 1-[(6-{6,6-difluoro-3-azabicyclo[3.1.0]-hexan-3-yl}-2-formylpyridin-3-yl)methyl]-1H-pyrazole-4-carboxylate |
| 10-8 | Ethyl 1-[(6-{6,6-difluoro-3-azabicyclo[3.1.0]-hexan-3-yl}-2-(hydroxymethyl)pyridin-3-yl)methyl]-1H-imidazole-4-carboxylate | Ethyl 1-[(6-{6,6-difluoro-3-azabicyclo[3.1.0]-hexan-3-yl}-2-formylpyridin-3-yl)methyl]-1H-imidazole-4-carboxylate |
| 10-9 | Ethyl 3-[(6-{6,6-difluoro-3-azabicyclo[3.1.0]-hexan-3-yl}-2-(hydroxymethyl)pyridin-3-yl)methyl]-1,2-oxazole-5-carboxylate | Ethyl 3-[(6-{6,6-difluoro-3-azabicyclo[3.1.0]-hexan-3-yl}-2-formylpyridin-3-yl)methyl]-1,2-oxazole-5-carboxylate |
| 10-10 | Ethyl 3-[(6-{3-azabicyclo[3.1.0]hexan-3-yl}-2-(hydroxymethyl)pyridin-3-yl)methyl]-1,2-oxazole-5-carboxylate | Ethyl 3-[(6-{3-azabicyclo[3.1.0]hexan-3-yl}-2-formylpyridin-3-yl)methyl]-1,2-oxazole-5-carboxylate |

-continued

| Intermediate | Name | Name of Starting Material |
|---|---|---|
| 10-11 | Ethyl 3-[(6-{3-azabicyclo[3.1.0]hexan-3-yl}-2-(hydroxymethyl)pyridin-3-yl)methyl]-1-{[2-(trimethylsilyl)ethoxy]methyl}-1H-pyrazole-5-carboxylate and Ethyl 5-[(6-{3-azabicyclo[3.1.0]hexan-3-yl}-2-(hydroxymethyl)pyridin-3-yl)methyl]-1-{[2-(trimethylsilyl)ethoxy]methyl}-1H-pyrazole-3-carboxylate (mixture of isomers) | Ethyl 3-[(6-{3-azabicyclo[3.1.0]hexan-3-yl}-2-formylpyridin-3-yl)methyl]-1-{[2-(trimethylsilyl)-ethoxy]methyl}-1H-pyrazole-5-carboxylate and Ethyl 5-[(6-{3-azabicyclo[3.1.0]hexan-3-yl}-2-formylpyridin-3-yl)methyl]-1-{[2-(trimethylsilyl)-ethoxy]methyl}-1H-pyrazole-3-carboxylate (mixture of isomers) |

Intermediate 11

Ethyl 1-[(6-{6,6-difluoro-3-azabicyclo[3.1.0]hexan-3-yl}-2-(methoxymethyl)pyridin-3-yl)methyl]-1H-pyrazole-4-carboxylate

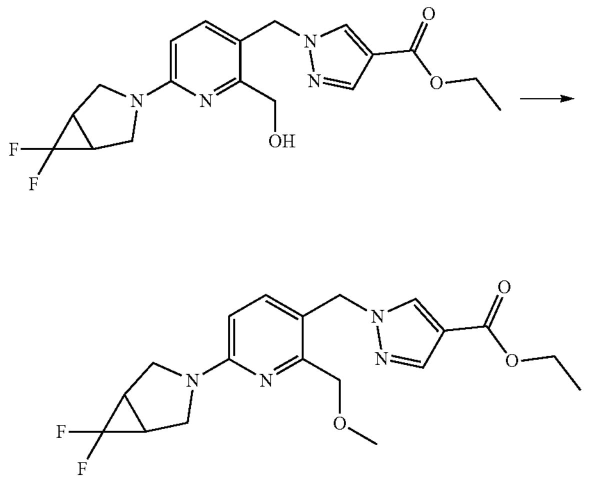

To a solution of ethyl 1-[(6-{6,6-difluoro-3-azabicyclo[3.1.0]hexan-3-yl}-2-(hydroxymethyl)pyridin-3-yl)methyl]-1H-pyrazole-4-carboxylate (89 mg) in DMF (250 μL) is added at 0° C. NaH (60% in mineral oil, 23 mg). The mixture is stirred for 15 minutes, treated with $CH_3I$ (17 μL) and stirred for 12 h at rt. The solvents are evaporated in vacuo to give the crude product, which is directly used in the next step.

LC (Method 2): $t_R$=0.83 min; Mass spectrum (ESI+): m/z=393 $[M+H]^+$.

Intermediate 11-1 is prepared in analogy to Intermediate 11:

| Intermediate | Structure | $t_R$ | Mass spectrum (ESI+): m/z $[M + H]^+$ | LC Method |
|---|---|---|---|---|
| 11-1 | 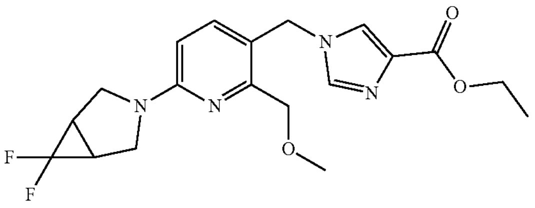 [SMILES: CCOC(=O)c1cn(Cc2ccc(N3CC4C(C3)C4(F)F)nc2COC)cn1] | 0.75 | 393 | Method 2 |

| Intermediate | Reaction comment |
|---|---|
| 11-1 | The reaction is stirred for 1 h at rt after addition of $CH_3I$. |

| Intermediate | Name | Name of Starting Material |
|---|---|---|
| 11-1 | Ethyl 1-[(6-{6,6-difluoro-3-azabicyclo[3.1.0]-hexan-3-yl}-2-(methoxymethyl) pyridin-3-yl)methyl]-1H-imidazole-4-carboxylate | Ethyl 1-[(6-{6,6-difluoro-3-azabicyclo[3.1.0]-hexan-3-yl}-2-(hydroxymethyl) pyridin-3-yl)methyl]-1H-imidazole-4-carboxylate |

Intermediate 12

Ethyl 1-[(6-{5-azaspiro[2.3]hexan-5-yl}-2-(difluoromethyl)pyridin-3-yl)methyl]-1H-1,2,3-triazole-4-carboxylate

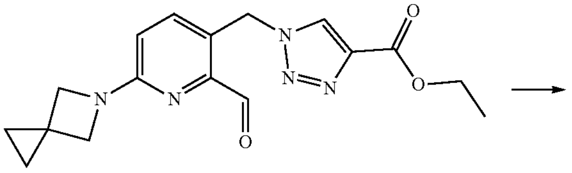

-continued

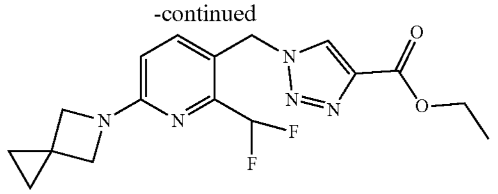

In a microwave vial ethyl 1-[(6-{5-azaspiro[2.3]hexan-5-yl}-2-formylpyridin-3-yl)methyl]-1H-1,2,3-triazole-4-carboxylate (763 mg) is dissolved in DCM (10 mL). Diethylaminosulfurtrifluoride (DAST, 1 mL) is added, the vial is sealed and the mixture is heated to 50° C. for 12 h. After cooling to rt the mixture is carefully treated with 1 N aqueous $NaHCO_3$ until gas evolution has stopped. Then the mixture is partitioned between saturated aqueous $NaHCO_3$ and DCM. The phases are separated and the aqueous phase is extracted with DCM. The combined organic phases are washed with brine, dried ($MgSO_4$) and concentrated. The residue is chromatographed on silica gel (petroleum ether/EtOAc 70:30→30:70) to give the title compound.

LC (Method 2): $t_R$=1.05 min; Mass spectrum (ESI+): m/z=364 $[M+H]^+$.

Intermediates 12-1 to 12-10 are prepared in analogy to Intermediate 12:

| Intermediate | Structure | $t_R$ | Mass spectrum (ESI+): m/z $[M + H]^+$ | LC Method |
|---|---|---|---|---|
| 12-1 | 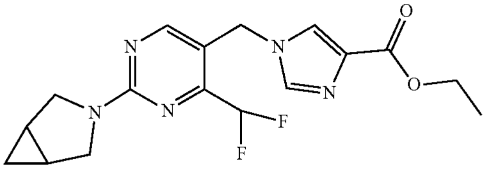 [SMILES: CCOC(=O)c1cn(Cc2cnc(N3CC4CC4C3)nc2C(F)F)cn1] | 0.88 | 364 | Method 2 |
| 12-2 | 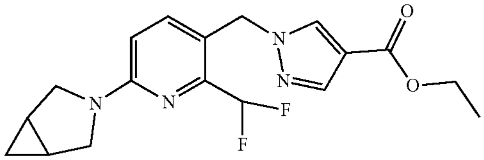 [SMILES: CCOC(=O)c1cnn(Cc2ccc(N3CC4CC4C3)nc2C(F)F)c1] | 1.08 | 363 | Method 2 |
| 12-3 | 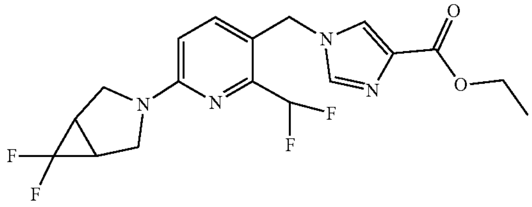 [SMILES: CCOC(=O)c1cnn(Cc2ccc(N3CC4C(C3)C4(F)F)nc2C(F)F)c1] | 0.99 | 399 | Method 1 |
| 12-4 | 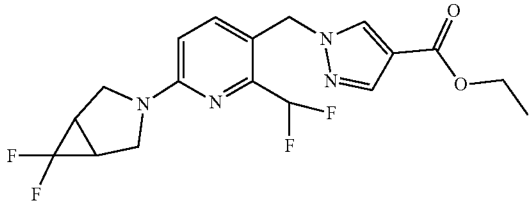 | 1.07 | 399 | Method 1 |
| 12-5 | 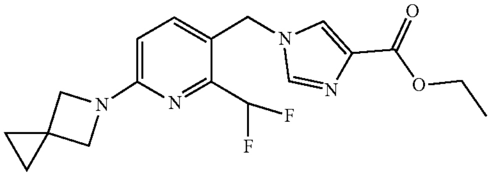 [SMILES: CCOC(=O)c1cn(Cc2ccc(N3CC4(CC4)C3)nc2C(F)F)cn1] | 1.00 | 363 | Method 1 |
| 12-6 | 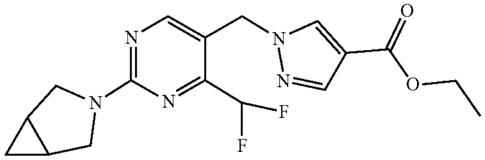 [SMILES: CCOC(=O)c1cnn(Cc2cnc(N3CC4CC4C3)nc2C(F)F)c1] | 1.10 | 364 | Method 2 |

-continued

| Intermediate | Structure | $t_R$ | Mass spectrum (ESI+): m/z $[M + H]^+$ | LC Method |
|---|---|---|---|---|
| 12-7 | 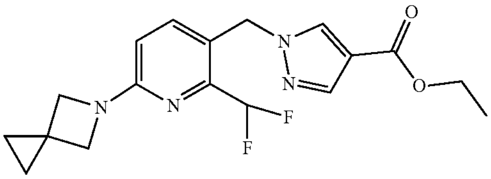 [SMILES: CCOC(=O)c1cnn(Cc2ccc(N3CC4(CC4)C3)nc2C(F)F)c1] | 1.09 | 363 | Method 1 |
| 12-8 | 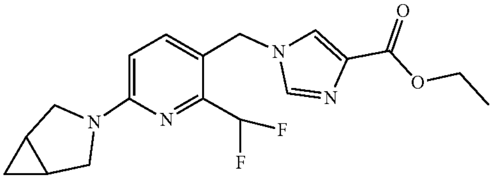 [SMILES: CCOC(=O)c1cn(Cc2ccc(N3CC4CC4C3)nc2C(F)F)cn1] | 1.03 | 363 | Method 1 |
| 12-9 | 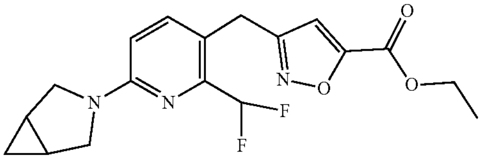 [SMILES: CCOC(=O)c1cc(Cc2ccc(N3CC4CC4C3)nc2C(F)F)no1] | 1.17 | 364 | Method 1 |
| 12-10 | 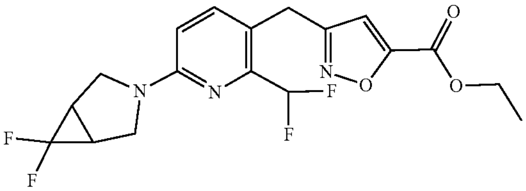 [SMILES: CCOC(=O)c1cc(Cc2ccc(N3CC4C(C3)C4(F)F)nc2C(F)F)no1] | 1.12 | 400 | Method 1 |

| Intermediate | Reaction comment |
|---|---|
| 12-9 | The reaction is conducted at 0° C. and is stirred for 1 h. |

-continued

| Intermediate | Reaction comment |
|---|---|
| 12-10 | The reaction is conducted at 0° C. and is stirred for 30 minutes. |

| Intermediate | Name | Name of Starting Material |
|---|---|---|
| 12-1 | Ethyl 1-[(2-{3-azabicyclo[3.1.0]hexan-3-yl}-4-(difluoromethyl)pyrimidin-5-yl)methyl]-1H-imidazole-4-carboxylate | Ethyl 1-[(2-{3-azabicyclo[3.1.0]hexan-3-yl}-4-formylpyrimidin-5-yl)methyl]-1H-imidazole-4-carboxylate |
| 12-2 | Ethyl 1-[(6-{3-azabicyclo[3.1.0]hexan-3-yl}-2-(difluoromethyl)pyridin-3-yl)methyl]-1H-pyrazole-4-carboxylate | Ethyl 1-[(6-{3-azabicyclo[3.1.0]hexan-3-yl}-2-formylpyridin-3-yl)methyl]-1H-pyrazole-4-carboxylate |
| 12-3 | Ethyl 1-[(6-{6,6-difluoro-3-azabicyclo[3.1.0]-hexan-3-yl}-2-(difluoromethyl)pyridin-3-yl)methyl]-1H-imidazole-4-carboxylate | Ethyl 1-[(6-{6,6-difluoro-3-azabicyclo[3.1.0]-hexan-3-yl}-2-formylpyridin-3-yl)methyl]-1H-imidazole-4-carboxylate |
| 12-4 | Ethyl 1-[(6-{6,6-difluoro-3-azabicyclo[3.1.0]-hexan-3-yl}-2-(difluoromethyl)pyridin-3-yl)methyl]-1H-pyrazole-4-carboxylate | Ethyl 1-[(6-{6,6-difluoro-3-azabicyclo[3.1.0]-hexan-3-yl}-2-formylpyridin-3-yl)methyl]-1H-pyrazole-4-carboxylate |
| 12-5 | Ethyl 1-[(6-{5-azaspiro[2.3]hexan-5-yl}-2-(difluoromethyl)pyridin-3-yl)methyl]-1H-imidazole-4-carboxylate | Ethyl 1-[(6-{5-azaspiro[2.3]hexan-5-yl}-2-formylpyridin-3-yl)methyl]-1H-imidazole-4-carboxylate |
| 12-6 | Ethyl 1-[(2-{3-azabicyclo[3.1.0]hexan-3-yl}-4-(difluoromethyl)pyrimidin-5-yl)methyl]-1H-pyrazole-4-carboxylate | Ethyl 1-[(2-{3-azabicyclo[3.1.0]hexan-3-yl}-4-formylpyrimidin-5-yl)methyl]-1H-pyrazole-4-carboxylate |
| 12-7 | Ethyl 1-[(6-{5-azaspiro[2.3]hexan-5-yl}-2-(difluoromethyl)pyridin-3-yl)methyl]-1H-pyrazole-4-carboxylate | Ethyl 1-[(6-{5-azaspiro[2.3]hexan-5-yl}-2-formylpyridin-3-yl)methyl]-1H-pyrazole-4-carboxylate |
| 12-8 | Ethyl 1-[(6-{3-azabicyclo[3.1.0]hexan-3-yl}-2-(difluoromethyl)pyridin-3-yl)methyl]-1H-imidazole-4-carboxylate | Ethyl 1-[(6-{3-azabicyclo[3.1.0]hexan-3-yl}-2-formylpyridin-3-yl)methyl]-1H-imidazole-4-carboxylate |

-continued

| Intermediate | Name | Name of Starting Material |
|---|---|---|
| 12-9 | Ethyl 3-[(6-{3-azabicyclo[3.1.0]hexan-3-yl}-2-(difluoromethyl)pyridin-3-yl)methyl]-1,2-oxazole-5-carboxylate | Ethyl 3-[(6-{3-azabicyclo[3.1.0]hexan-3-yl}-2-formylpyridin-3-yl)methyl]-1,2-oxazole-5-carboxylate |
| 12-10 | Ethyl 3-[(6-{6,6-difluoro-3-azabicyclo[3.1.0]-hexan-3-yl}-2-(difluoromethyl)pyridin-3-yl)-methyl]-1,2-oxazole-5-carboxylate | Ethyl 3-[(6-{6,6-difluoro-3-azabicyclo[3.1.0]-hexan-3-yl}-2-formylpyridin-3-yl)methyl]-1,2-oxazole-5-carboxylate |

Intermediate 13

Ethyl 2-chloro-4-[(1E)-2-phenylethenyl]pyrimidine-5-carboxylate

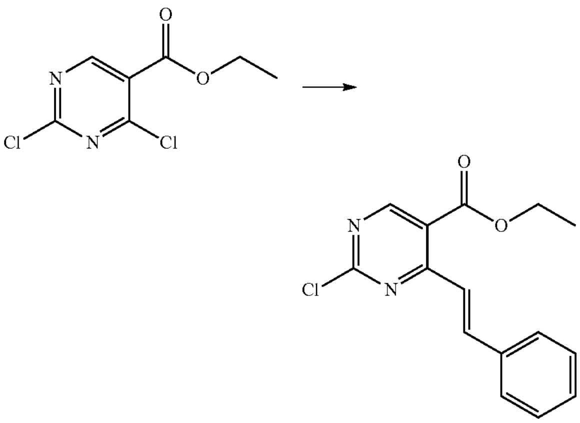

In a microwave vial a mixture of ethyl 2,4-dichloropyrimidine-5-carboxylate (2.5 g), potassium trans-beta-styryltrifluoroborate (2.5 g), $Na_2CO_3$ (2 M aqueous solution, 12.5 mL) and 1,4-dioxane (50 mL) is purged for 10 minutes with argon. Bis(di-tert-butyl(4-dimethylaminophenyl)phosphine) dichloropalladium(II) ($Pd(amphos)_2Cl_2$, 300 mg) is added, the vial is sealed and the mixture is heated to 50° C. for 2 h. After cooling to rt the mixture is partitioned between EtOAc and water. The organic phase is washed with brine, dried ($MgSO_4$) and concentrated. The residue is chromatographed on silica gel (petroleum ether/EtOAc 80:20→60:40) to give the title compound.

LC (Method 2): $t_R$=1.21 min; Mass spectrum (ESI+): m/z=289 $[M+H]^+$.

Intermediates 13-1 to 13-2 are prepared in analogy to Intermediate 13:

| Intermediate | Structure | $t_R$ | Mass spectrum (ESI+): m/z $[M + H]^+$ | LC Method |
|---|---|---|---|---|
| 13-1 | 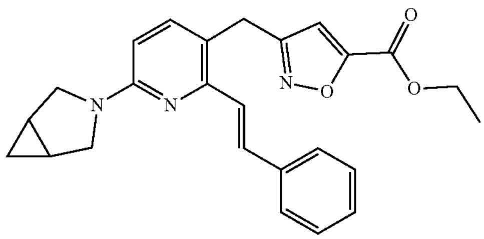 [SMILES: CCOC(=O)c1cc(Cc2ccc(N3CC4CC4C3)nc2/C=C/c2ccccc2)no1] | 1.27 | 416 | Method 1 |
| 13-2 | 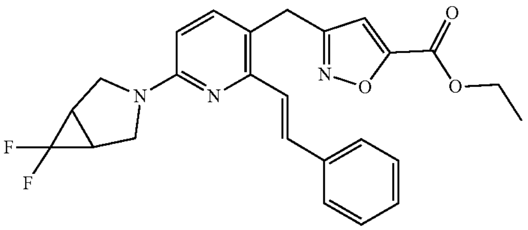 [SMILES: CCOC(=O)c1cc(Cc2ccc(N3CC4C(C3)C4(F)F)nc2/C=C/c2ccccc2)no1] | 1.20 | 452 | Method 1 |

| Intermediate | Reaction comment |
|---|---|
| 13-1 | The reaction is conducted for 15 h at 75° C. |
| 13-2 | The reaction is conducted for 18 h at 80° C. |

| Intermediate | Name | Name of Starting Material |
|---|---|---|
| 13-1 | Ethyl 3-[(6-{3-azabicyclo[3.1.0]hexan-3-yl}-2-[(1E)-2-phenylethenyl]pyridin-3-yl)methyl]-1,2-oxazole-5-carboxylate | Ethyl 3-[(6-{3-azabicyclo[3.1.0]hexan-3-yl}-2-chloropyridin-3-yl)methyl]-1,2-oxazole-5-carboxylate |
| 13-2 | Ethyl 3-[(6-{6,6-difluoro-3-azabicyclo[3.1.0]-hexan-3-yl}-2-[(1E)-2-phenylethenyl]pyridin-3-yl)methyl]-1,2-oxazole-5-carboxylate | Ethyl 3-[(2-chloro-6-{6,6-difluoro-3-azabicyclo[3.1.0]hexan-3-yl}pyridin-3-yl)methyl]-1,2-oxazole-5-carboxylate |

Intermediate 14

Ethyl 2-{3-azabicyclo[3.1.0]hexan-3-yl}-4-[(1E)-2-phenylethenyl]pyrimidine-5-carboxylate

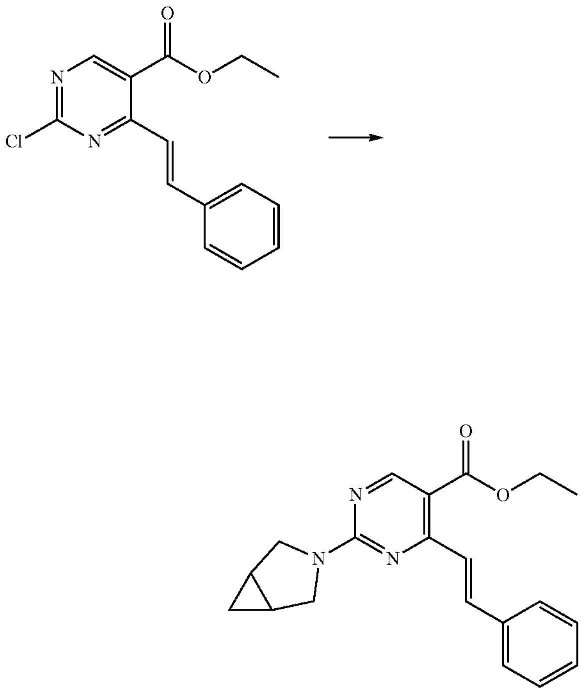

Under argon atmosphere a mixture of ethyl 2-chloro-4-[(1E)-2-phenylethenyl]pyrimidine-5-carboxylate (2.56 g), 3-azabicyclo[3.1.0]hexane hydrochloride (1.3 g) and $KHCO_3$ (2.3 g) in THF (30 mL) is stirred for 12 h at rt. The mixture is partitioned between saturated aqueous $NH_4Cl$ and EtOAc and the phases are separated. The organic phase is washed with brine, dried ($MgSO_4$), concentrated and the residue is chromatographed on silica gel (petroleum ether/EtOAc 80:20→60:40) to give the title compound.

LC (Method 2): $t_R$=1.27 min; Mass spectrum (ESI+): m/z=336 $[M+H]^+$.

Intermediate 15

(2-{3-Azabicyclo[3.1.0]hexan-3-yl}-4-[(1E)-2-phenylethenyl]pyrimidin-5-yl)methanol

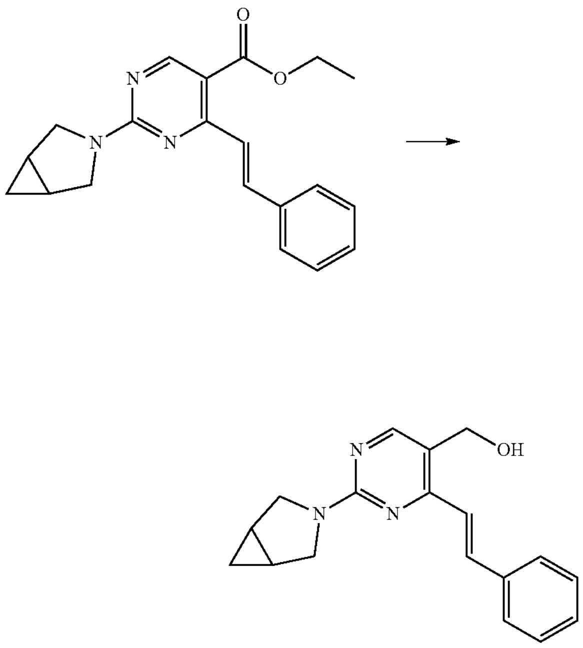

Under argon atmosphere a mixture of ethyl 2-{3-azabicyclo[3.1.0]hexan-3-yl}-4-[(1E)-2-phenylethenyl]pyrimidine-5-carboxylate (1.96 g) in THF (40 mL) is treated dropwise with diisobutylaluminiumhydride (DIBAH, 1 M in THF, 25 mL). The mixture is stirred for 2 h at rt, cooled to 0° C. and treated dropwise with 4 M aqueous HCl (15 mL). Then the mixture is stirred for 5 minutes and 4 M aqueous NaOH (15 mL) is added. The mixture is partitioned between brine and DCM and the phases are separated. The organic phase is dried ($MgSO_4$), concentrated and the residue is chromatographed on silica gel (DCM/MeOH 98:2→90:10) to give the title compound.

LC (Method 2): $t_R$=0.84 min; Mass spectrum (ESI+): m/z=294 $[M+H]^+$.

Intermediates 15-1 to 15-2 are prepared in analogy to Intermediate 15:

| Intermediate | Structure | $t_R$ | Mass spectrum (ESI+): m/z $[M + H]^+$ | LC Method |
|---|---|---|---|---|
| 15-1 | 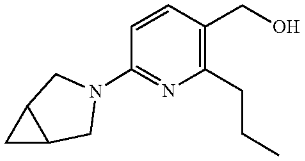 [SMILES: CCCc1nc(N2CC3CC3C2)ccc1CO] | 0.72 | 234 | Method 2 |
| 15-2 | 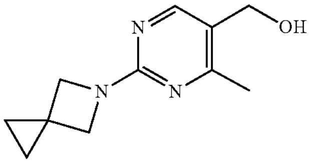 | 0.60 | 206 | Method 1 |

| Intermediate | Name | Name of Starting Material |
|---|---|---|
| 15-1 | (6-{3-Azabicyclo[3.1.0]hexan-3-yl}-2-propylpyridin-3-yl)methanol | Ethyl 6-{3-azabicyclo[3.1.0]hexan-3-yl}-2-propylpyridine-3-carboxylate |
| 15-2 | (2-{5-Azaspiro[2.3]hexan-5-yl}-4-methylpyrimidin-5-yl)methanol | Ethyl 2-{5-azaspiro[2.3]hexan-5-yl}-4-methylpyrimidine-5-carboxylate |

Intermediate 16

1-[(2-{3-Azabicyclo[3.1.0]hexan-3-yl}-4-[(1E)-2-phenylethenyl]pyrimidin-5-yl)methyl]-N-[(4R)-1-methyl-1H,4H,5H,6H-cyclopenta[d]imidazol-4-yl]-1H-imidazole-4-carboxamide

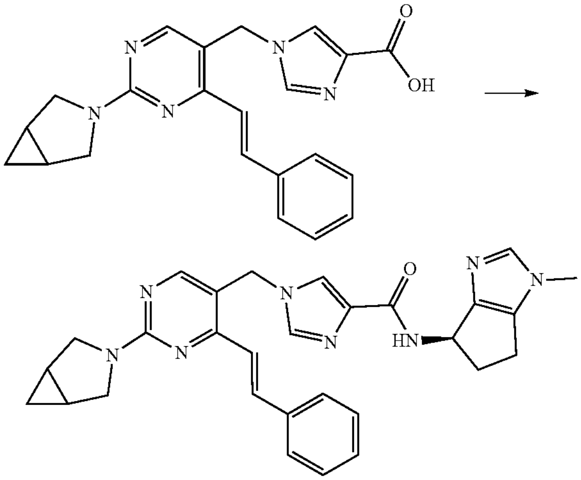

Under argon atmosphere a mixture of 1-[(2-{3-azabicyclo[3.1.0]hexan-3-yl}-4-[(1E)-2-phenylethenyl]pyrimidin-5-yl)-methyl]-1H-imidazole-4-carboxylic acid (240 mg) and DIPEA (380 μL) in DMF (3 mL) is treated with O-(7-azabenzotriazol-1-yl)-N,N,N',N'-tetramethyluronium-hexafluorophosphat (HATU, 280 mg). The mixture is stirred for 5 minutes and then treated with (4R)-1-methyl-1H,4H,5H,6H-cyclopenta[d]imidazol-4-amine dihydrochloride (145 mg). After stirring for 1 h the mixture is partitioned between water and DCM. The organic phase is washed with brine, dried ($MgSO_4$), concentrated and the residue is chromatographed on silica gel (DCM/MeOH 98:2→70:30) to give the title compound. LC (Method 1): $t_R$=1.02 min; Mass spectrum (ESI+): m/z=507 $[M+H]^+$.

Intermediate 17

Ethyl 1-[(5-{5-azaspiro[2.3]hexan-5-yl}pyridin-2-yl)methyl]-1H-pyrazole-4-carboxylate

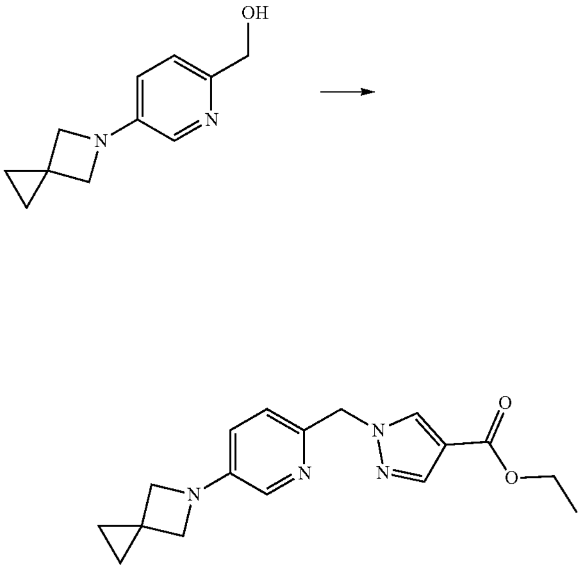

To a solution of (5-{5-azaspiro[2.3]hexan-5-yl}pyridin-2-yl)methanol (110 mg), ethyl 1H-pyrazole-4-carboxylate (122 mg) and triphenylphosphine (296 mg) in THF (2 mL) is added dropwise at 0° C. DIAD (222 μL). The mixture is stirred for 1 h while warming to rt. Then the mixture is diluted with MeOH and purified by HPLC on reversed phase (ACN, water) to give the title compound. LC (Method 2): $t_R$=0.79 min; Mass spectrum (ESI+): m/z=313 $[M+H]^+$.

Intermediate 17-1 is prepared in analogy to Intermediate 17:

| Intermediate | Structure | $t_R$ | Mass spectrum (ESI+): m/z $[M + H]^+$ | LC Method |
|---|---|---|---|---|
| 17-1 | 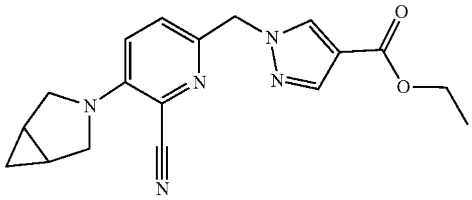 [SMILES: CCOC(=O)c1cnn(Cc2ccc(N3CC4CC4C3)c(C#N)n2)c1] | 0.99 | 338 | Method 1 |

| Intermediate | Name | Name of Starting Material 1 | Name of Starting Material 2 |
|---|---|---|---|
| 17-1 | Ethyl 1-[(5-{3-azabicyclo[3.1.0]hexan-3-yl}-6-cyanopyridin-2-yl)methyl]-1H-pyrazole-4-carboxylate | 3-{3-Azabicyclo[3.1.0]hexan-3-yl}-6-(hydroxymethyl)pyridine-2-carbonitrile | Ethyl 1H-pyrazole-4-carboxylate |

Intermediate 18

Ethyl 1-[(6-{5-azaspiro[2.3]hexan-5-yl}-2-ethylpyridin-3-yl)methyl]-1H-1,2,3-triazole-4-carboxylate

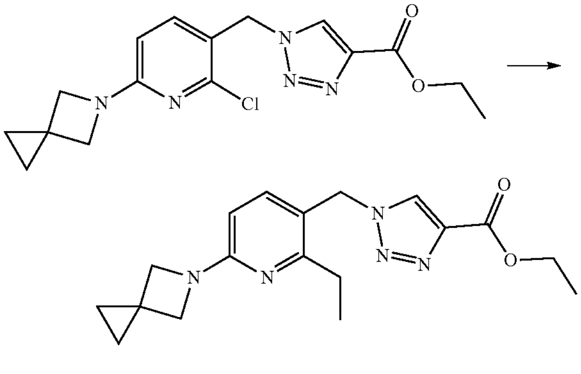

In a microwave vial a mixture of ethyl 1-[(6-{5-azaspiro[2.3]hexan-5-yl}-2-chloropyridin-3-yl)methyl]-1H-1,2,3-triazole-4-carboxylate (85 mg), ethylboronic acid (55 mg), $K_2CO_3$ (170 mg) and 1,4-dioxane (3 mL) is purged for 10 minutes with argon. 1,1'-Bis(diphenylphosphino)ferrocenepalladium(II) dichloride (Pd(dppf)$Cl_2$, 14 mg) is added, the vial is sealed and the mixture is heated to 80° C. for 12 h. Ethylboronic acid (65 mg), $K_2CO_3$ (100 mg) and 1,1'-Bis(diphenylphosphino)ferrocenepalladium(II) dichloride (Pd(dppf)$Cl_2$, 16 mg) are added and the mixture is heated for 5 h to 90° C. After cooling to rt the mixture is partitioned between water and EtOAc. The organic phase is washed with brine, dried ($MgSO_4$), concentrated and the residue is chromatographed on silica gel (petroleum ether/EtOAc 85:15→60:40) to give the title compound. LC (Method 2): $t_R$=0.72 min; Mass spectrum (ESI+): m/z=342 [M+H]+.

Intermediates 18-1 to 18-4 are prepared in analogy to Intermediate 18:

| Intermediate | Structure | $t_R$ | Mass spectrum (ESI+): m/z $[M + H]^+$ | LC Method |
|---|---|---|---|---|
| 18-1 | 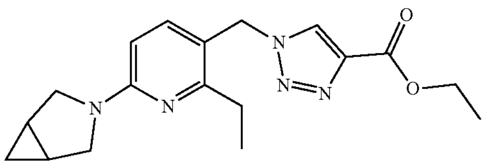 [SMILES: CCOC(=O)c1cn(Cc2ccc(N3CC4CC4C3)nc2CC)nn1] | 0.72 | 342 | Method 2 |
| 18-2 | 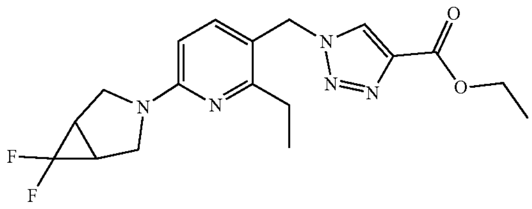 [SMILES: CCOC(=O)c1cn(Cc2ccc(N3CC4C(C3)C4(F)F)nc2CC)nn1] | 0.76 | 378 | Method 2 |

-continued

| Intermediate | Structure | $t_R$ | Mass spectrum (ESI+): m/z $[M + H]^+$ | LC Method |
|---|---|---|---|---|
| 18-3 | 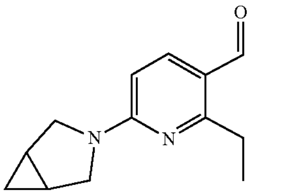 [SMILES: CCc1nc(N2CC3CC3C2)ccc1C=O] | 0.66 | 217 | Method 2 |
| 18-4 | 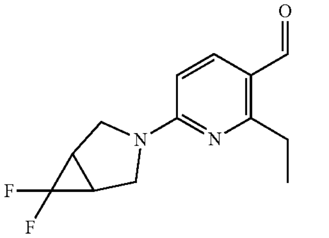 [SMILES: CCc1nc(N2CC3C(C2)C3(F)F)ccc1C=O] | 0.86 | 253 | Method 2 |

| Intermediate | Reaction comment |
|---|---|
| 18-1 | The reaction is conducted for 12 h at 80° C. |
| 18-2 | The reaction is conducted for 12 h at 80° C. |
| 18-3 | The reaction is conducted for 5 h at 70° C. |
| 18-4 | The reaction is conducted for 16 h at 80° C. |

| Intermediate | Name | Name of Starting Material |
|---|---|---|
| 18-1 | Ethyl 1-[(6-{3-azabicyclo[3.1.0]hexan-3-yl}-2-ethylpyridin-3-yl)methyl]-1H-1,2,3-triazole-4-carboxylate | Ethyl 1-[(6-{3-azabicyclo[3.1.0]hexan-3-yl}-2-bromopyridin-3-yl)methyl]-1H-1,2,3-triazole-4-carboxylate |
| 18-2 | Ethyl 1-[(6-{6,6-difluoro-3-azabicyclo[3.1.0]-hexan-3-yl}-2-ethylpyridin-3-yl)methyl]-1H-1,2,3-triazole-4-carboxylate | Ethyl 1-[(2-bromo-6-{6,6-difluoro-3-azabicyclo[3.1.0]hexan-3-yl}pyridin-3-yl)methyl]-1H-1,2,3-triazole-4-carboxylate |
| 18-3 | 6-{3-Azabicyclo[3.1.0]hexan-3-yl}-2-ethylpyridine-3-carbaldehyde | 6-{3-Azabicyclo[3.1.0]hexan-3-yl}-2-chloropyridine-3-carbaldehyde |
| 18-4 | 6-{6,6-Difluoro-3-azabicyclo[3.1.0]hexan-3-yl}-2-ethylpyridine-3-carbaldehyde | 2-Bromo-6-{6,6-difluoro-3-azabicyclo[3.1.0]-hexan-3-yl}pyridine-3-carbaldehyde |

Intermediate 19

Ethyl 1-[(6-{3-azabicyclo[3.1.0]hexan-3-yl}-2-ethylpyridin-3-yl)methyl]-1H-pyrazole-4-carboxylate

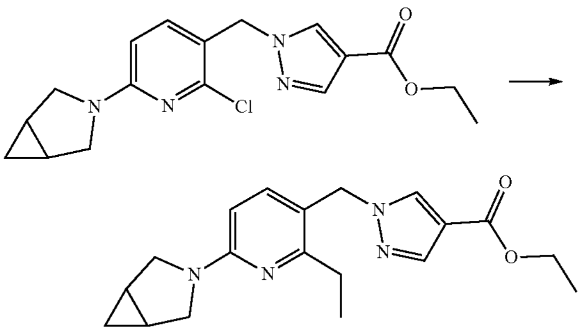

In a microwave vial a mixture of ethyl 1-[(6-{3-azabicyclo[3.1.0]hexan-3-yl}-2-chloropyridin-3-yl)methyl]-1H-pyrazole-4-carboxylate (1.43 g), diethylzinc (1 M solution in n-hexane, 6.18 mL) and 1,4-dioxane (60 mL) is purged for 10 minutes with argon. 1,1'-Bis(diphenylphosphino)ferrocenepalladium(II) dichloride (Pd(dppf)$Cl_2$, 150 mg) is added, the vial is sealed and the mixture is heated to 70° C. for 1 h. After cooling to rt the mixture is carefully treated with saturated aqueous $NH_4Cl$. The mixture is partitioned between saturated aqueous $NH_4Cl$ and EtOAc. The aqueous phase is extracted twice with EtOAc. The combined organic phases are washed with brine, dried ($MgSO_4$), concentrated and the residue is chromatographed on silica gel (petroleum ether/EtOAc 95:5→0:100) to give the title compound. LC (Method 2): $t_R$=0.75 min; Mass spectrum (ESI+): m/z=341 $[M+H]^+$.

Intermediates 19-1 to 19-15 are prepared in analogy to Intermediate 19:

| Intermediate | Structure | $t_R$ | Mass spectrum (ESI+): m/z $[M + H]^+$ | LC Method |
|---|---|---|---|---|
| 19-1 | 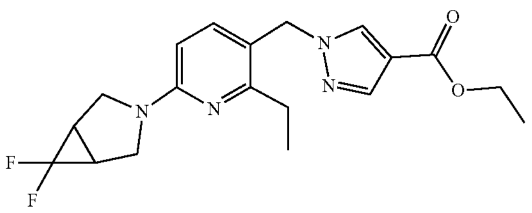 [SMILES: CCOC(=O)c1cnn(Cc2ccc(N3CC4C(C3)C4(F)F)nc2CC)c1] | | 377 | |
| 19-2 | 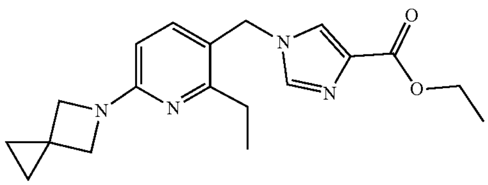 [SMILES: CCOC(=O)c1cn(Cc2ccc(N3CC4(CC4)C3)nc2CC)cn1] | 0.67 | 341 | Method 2 |
| 19-3 | 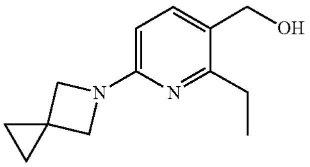 [SMILES: CCc1nc(N2CC3(CC3)C2)ccc1CO] | 0.59 | 219 | Method 2 |
| 19-4 | 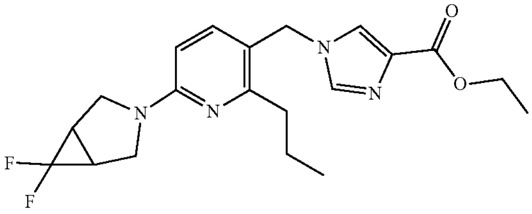 [SMILES: CCCc1nc(N2CC3C(C2)C3(F)F)ccc1Cn1cnc(C(=O)OCC)c1] | 1.06 | | Method 1 |
| 19-5 | 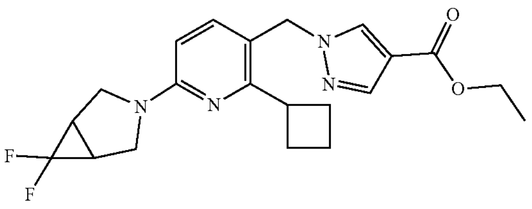 [SMILES: CCOC(=O)c1cnn(Cc2ccc(N3CC4C(C3)C4(F)F)nc2C2CCC2)c1] | 1.18 | 403 | Method 1 |
| 19-6 | 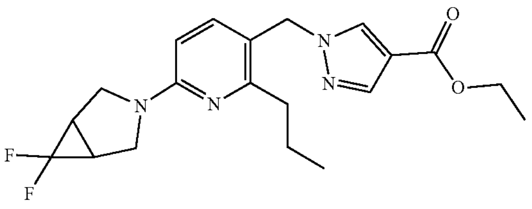 [SMILES: CCCc1nc(N2CC3C(C2)C3(F)F)ccc1Cn1cc(C(=O)OCC)cn1] | 1.14 | 391 | Method 1 |

-continued
| Intermediate | Structure | $t_R$ | Mass spectrum (ESI+): m/z $[M + H]^+$ | LC Method |
| --- | --- | --- | --- | --- |
| 19-7 | 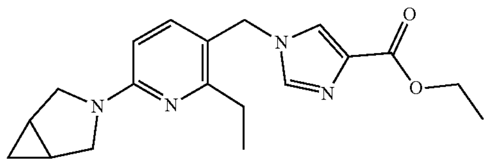 [SMILES: CCOC(=O)c1cn(Cc2ccc(N3CC4CC4C3)nc2CC)cn1] | 0.66 | 341 | Method 2 |
| 19-8 | 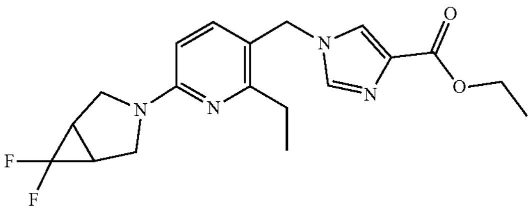 [SMILES: CCOC(=O)c1cn(Cc2ccc(N3CC4C(C3)C4(F)F)nc2CC)cn1] | 0.68 | | Method 2 |
| 19-9 | 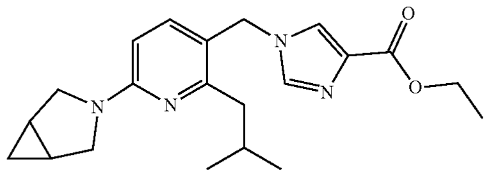 [SMILES: CCOC(=O)c1cn(Cc2ccc(N3CC4CC4C3)nc2CC(C)C)cn1] | 0.70 | | Method 2 |
| 19-10 | 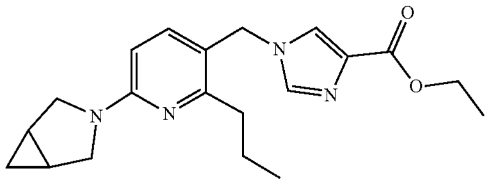 [SMILES: CCCc1nc(N2CC3CC3C2)ccc1Cn1cnc(C(=O)OCC)c1] | 0.66 | | Method 2 |
| 19-11 | 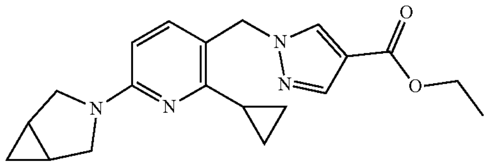 [SMILES: CCOC(=O)c1cnn(Cc2ccc(N3CC4CC4C3)nc2C2CC2)c1] | 0.85 | 353 | Method 2 |
| 19-12 | 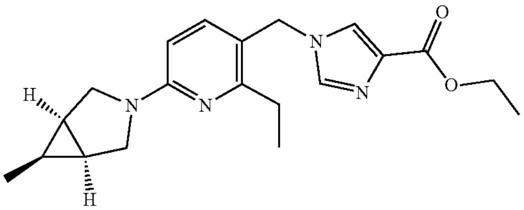 [SMILES: CCOC(=O)c1cn(Cc2ccc(N3C[C@@H]4[C@H](C)[C@@H]4C3)nc2CC)cn1] | 1.10 | 355 | Method 1 |
| 19-13 | 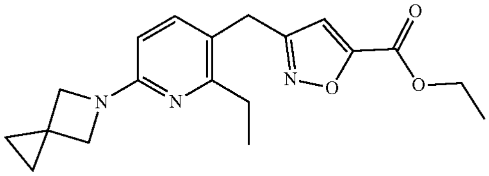 [SMILES: CCOC(=O)c1cc(Cc2ccc(N3CC4(CC4)C3)nc2CC)no1] | 0.80 | 342 | Method 2 |
| 19-14 | 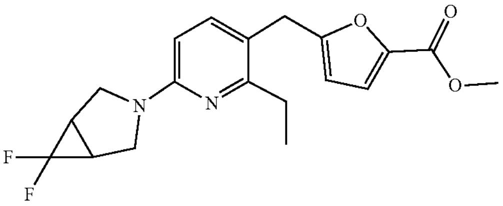 [SMILES: CCc1nc(N2CC3C(C2)C3(F)F)ccc1Cc1ccc(C(=O)OC)o1] | 0.80 | 363 | Method 2 |

-continued

| Intermediate | Structure | $t_R$ | Mass spectrum (ESI+): m/z $[M + H]^+$ | LC Method |
|---|---|---|---|---|
| 19-15 | 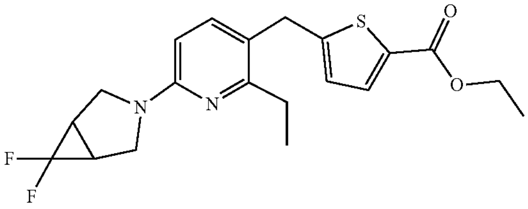 [SMILES: CCOC(=O)c1ccc(Cc2ccc(N3CC4C(C3)C4(F)F)nc2CC)s1] | 0.87 | 393 | Method 2 |

| Intermediate | Reaction comment |
|---|---|
| 19-4 | n-Propylzinc bromide is used instead of diethylzinc. |
| 19-5 | Cyclobutylzinc bromide is used instead of diethylzinc. |
| 19-6 | n-Propylzinc bromide is used instead of diethylzinc. |
| 19-7 | The reaction is conducted in the presence of LiCL in the same molar amount as diethylzinc. The reaction is heated for 2 h to 60° C. |
| 19-9 | 2-Methylpropylzinc bromide is used instead of diethylzinc and dichloro[1,3-bis(2,6-Di-3-pentylphenyl)imidazol-2-ylidene](3-chloropyridyl)palladium(II) (Pd-PEPPSI-IPent) is used instead of 1,1'-bis(diphenylphosphino)ferrocenepalladium(II) dichloride (Pd(dppf)$Cl_2$). The reaction is conducted in the presence of LiCL in the same molar amount as diethylzinc. The reaction is heated for 2 h to 60° C. |
| 19-10 | n-Propylzinc bromide is used instead of diethylzinc and dichloro[1,3-bis(2,6-Di-3-pentylphenyl)imidazol-2-ylidene](3-chloropyridyl)palladium(II) (Pd-PEPPSI-IPent) is used instead of 1,1'-bis(diphenylphosphino)ferrocenepalladium(II) dichloride (Pd(dppf)$Cl_2$). The reaction is conducted in the presence of LiCL in the same molar amount as diethylzinc. The reaction is heated for 2 h to 60° C. |
| 19-11 | Cyclopropylzinc bromide is used instead of diethylzinc. |
| 19-12 | Dichloro[1,3-bis(2,6-Di-3-pentylphenyl)imidazol-2-ylidene](3-chloropyridyl)palladium(II) (Pd-PEPPSI-IPent) is used instead of 1,1'-bis(diphenylphosphino)ferrocenepalladium(II) dichloride (Pd(dppf)$Cl_2$). The reaction is conducted in the presence of LiCL in the same molar amount as diethylzinc. The reaction is heated for 1 h to 60° C. |
| 19-13 | The reaction is conducted for 2.5 h at 80° C. |

| Intermediate | Name | Name of Starting Material |
|---|---|---|
| 19-1 | Ethyl 1-[(6-{6,6-difluoro-3-azabicyclo[3.1.0]hexan-3-yl}-2-ethylpyridin-3-yl)methyl]-1H-pyrazole-4-carboxylate | Ethyl 1-[(2-bromo-6-{6,6-difluoro-3-azabicyclo[3.1.0]hexan-3-yl}pyridin-3-yl)methyl]-1H-pyrazole-4-carboxylate |
| 19-2 | Ethyl 1-[(6-{5-azaspiro[2.3]hexan-5-yl}-2-ethylpyridin-3-yl)methyl]-1H-imidazole-4-carboxylate | Ethyl 1-[(6-{5-azaspiro[2.3]hexan-5-yl}-2-chloropyridin-3-yl)methyl]-1H-imidazole-4-carboxylate |
| 19-3 | (6-{5-Azaspiro[2.3]hexan-5-yl}-2-ethylpyridin-3-yl)methanol | (6-{5-Azaspiro[2.3]hexan-5-yl}-2-chloropyridin-3-yl)methanol |
| 19-4 | Ethyl 1-[(6-{6,6-difluoro-3-azabicyclo[3.1.0]hexan-3-yl}-2-propylpyridin-3-yl)methyl]-1H-imidazole-4-carboxylate | Ethyl 1-[(2-bromo-6-{6,6-difluoro-3-azabicyclo[3.1.0]hexan-3-yl}pyridin-3-yl)methyl]-1H-imidazole-4-carboxylate |
| 19-5 | Ethyl 1-[(2-cyclobutyl-6-{6,6-difluoro-3-azabicyclo[3.1.0]hexan-3-yl}pyridin-3-yl)methyl]-1H-pyrazole-4-carboxylate | Ethyl 1-[(2-bromo-6-{6,6-difluoro-3-azabicyclo[3.1.0]hexan-3-yl}pyridin-3-yl)methyl]-1H-pyrazole-4-carboxylate |
| 19-6 | Ethyl 1-[(6-{6,6-difluoro-3-azabicyclo[3.1.0]hexan-3-yl}-2-propylpyridin-3-yl)methyl]-1H-pyrazole-4-carboxylate | Ethyl 1-[(2-bromo-6-{6,6-difluoro-3-azabicyclo[3.1.0]hexan-3-yl}pyridin-3-yl)methyl]-1H-pyrazole-4-carboxylate |
| 19-7 | Ethyl 1-[(6-{3-azabicyclo[3.1.0]hexan-3-yl}-2-ethylpyridin-3-yl)methyl]-1H-imidazole-4-carboxylate | Ethyl 1-[(6-{3-azabicyclo[3.1.0]hexan-3-yl}-2-bromopyridin-3-yl)methyl]-1H-imidazole-4-carboxylate |
| 19-8 | Ethyl 1-[(6-{6,6-difluoro-3-azabicyclo[3.1.0]-hexan-3-yl}-2-ethylpyridin-3-yl)methyl]-1H-imidazole-4-carboxylate | Ethyl 1-[(2-bromo-6-{6,6-difluoro-3-azabicyclo[3.1.0]hexan-3-yl}pyridin-3-yl)-methyl]-1H-imidazole-4-carboxylate |
| 19-9 | Ethyl 1-[(6-{3-azabicyclo[3.1.0]hexan-3-yl}-2-(2-methylpropyl)pyridin-3-yl)methyl]-1H-imidazole-4-carboxylate | Ethyl 1-[(6-{3-azabicyclo[3.1.0]hexan-3-yl}-2-bromopyridin-3-yl)methyl]-1H-imidazole-4-carboxylate |

-continued

| Intermediate | Name | Name of Starting Material |
|---|---|---|
| 19-10 | Ethyl 1-[(6-{3-azabicyclo[3.1.0]hexan-3-yl}-2-propylpyridin-3-yl)methyl]-1H-imidazole-4-carboxylate | Ethyl 1-[(6-{3-azabicyclo[3.1.0]hexan-3-yl}-2-bromopyridin-3-yl)methyl]-1H-imidazole-4-carboxylate |
| 19-11 | Ethyl 1-[(6-{3-azabicyclo[3.1 0]hexan-3-yl}-2-cyclopropylpyridin-3-yl)methyl]-1H-pyrazole-4-carboxylate | Ethyl 1-[(6-{3-azabicyclo[3.1.0]hexan-3-yl}-2-bromopyridin-3-yl)methyl]-1H-pyrazole-4-carboxylate |
| 19-12 | Ethyl 1-({2-ethyl-6-[(1R,5S,6R)-6-methyl-3-azabicyclo[3.1.0]hexan-3-yl]pyridin-3-yl}methyl)-1H-imidazole-4-carboxylate | Ethyl 1-({2-chloro-6-[(1R,5S,6R)-6-methyl-3-azabicyclo[3.1.0]hexan-3-yl]pyridin-3-yl}methyl)-1H-imidazole-4-carboxylate |
| 19-13 | Ethyl 3-[(6-{5-azaspiro[2.3]hexan-5-yl}-2-ethylpyridin-3-yl)methyl]-1,2-oxazole-5-carboxylate | Ethyl 3-[(6-{5-azaspiro[2.3]hexan-5-yl}-2-chloropyridin-3-yl)methyl]-1,2-oxazole-5-carboxylate |
| 19-14 | Methyl 5-[(6-{6,6-difluoro-3-azabicyclo[3.1.0]-hexan-3-yl}-2-ethylpyridin-3-yl)methyl]furan-2-carboxylate | Methyl 5-[(2-bromo-6-{6,6-difluoro-3-azabicyclo[3.1.0]hexan-3-yl}pyridin-3-yl)methyl]furan-2-carboxylate |
| 19-15 | Ethyl 5-[(6-{6,6-difluoro-3-azabicyclo[3.1.0]hexan-3-yl}-2-ethylpyridin-3-yl)methyl]thiophene-2-carboxylate | Ethyl 5-[(2-bromo-6-{6,6-difluoro-3-azabicyclo[3.1.0]hexan-3-yl}pyridin-3-yl)methyl]thiophene-2-carboxylate |

Intermediate 20

Ethyl 1-[(6-{5-azaspiro[2.3]hexan-5-yl}pyridin-3-yl)methyl]-1H-1,2,3-triazole-4-carboxylate

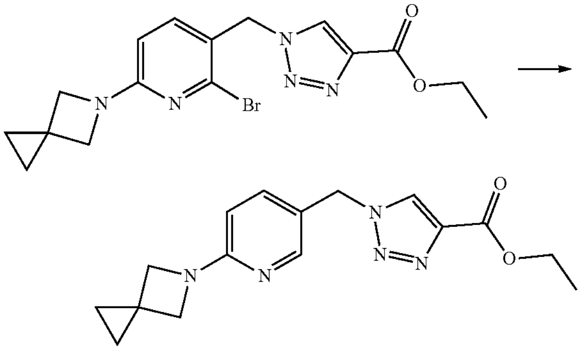

A mixture of ethyl 1-[(6-{5-azaspiro[2.3]hexan-5-yl}-2-bromopyridin-3-yl)methyl]-1H-1,2,3-triazole-4-carboxylate (150 mg), 10% palladium on carbon (20 mg) in EtOH (4 mL) and THF (4 mL) is shaken under hydrogen atmosphere (3 bar) at rt for 3.5 h. The mixture is filtered, the filtrate is concentrated and the residue is purified by HPLC on reversed phase (ACN, water) to give the title compound. LC (Method 2): $t_R$=0.68 min; Mass spectrum (ESI+): m/z=314 $[M+H]^+$.

Intermediate 21

Ethyl 1-[(6-{3-azabicyclo[3.1.0]hexan-3-yl}-2-(difluoromethyl)pyridin-3-yl)methyl]-1H-1,2,3-triazole-4-carboxylate

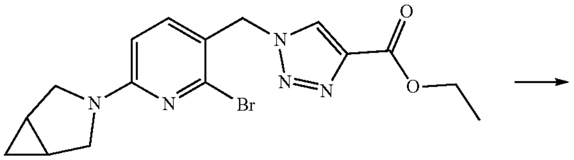

-continued

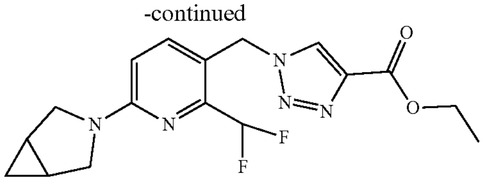

In a microwave vial a mixture of ethyl 1-[(6-{3-azabicyclo[3.1.0]hexan-3-yl}-2-bromopyridin-3-yl)methyl]-1H-1,2,3-triazole-4-carboxylate (250 mg), CsF (290 mg) and CuF (121 mg) in NMP (4 mL) is treated with difluoromethyltrimethylsilane (435 μL). The vial is sealed and the mixture is heated to 120° C. for 1.5 h. The mixture is partitioned between half-saturated aqueous $NaHCO_3$ and EtOAc. Then the mixture is filtered over celite and the filter cake is washed with EtOAc. The phases are separated and the aqueous phase is extracted twice with EtOAc. The combined organic phases are dried ($MgSO_4$), concentrated and the residue is purified by HPLC on reversed phase (ACN, water) to give the title compound. LC (Method 2): $t_R$=1.10 min; Mass spectrum (ESI+): m/z=364 $[M+H]^+$.

Intermediate 22

Ethyl 2-chloro-4-propylpyrimidine-5-carboxylate

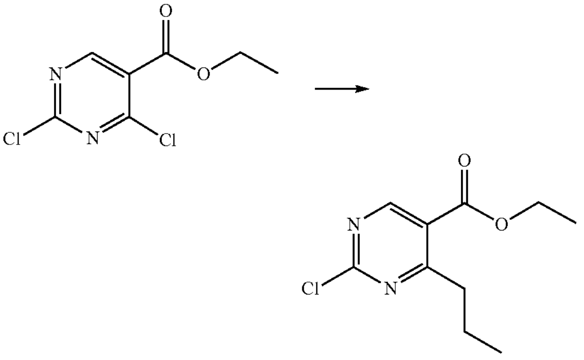

In a microwave vial a mixture of ethyl 2,4-dichloropyrimidine-5-carboxylate (1 g), n-propylzinc bromide (0.5 M in THF, 9.5 mL) and 1,1'-bis(diphenylphosphino)ferrocenepalladium(II) dichloride (Pd(dppf)$Cl_2$, 66 mg) in 1,4-dioxane (25 mL) is purged for 10 minutes with argon. The vial is sealed and the mixture is heated to 70° C. for 1 h. Then n-propylzinc bromide (0.5 M in THF, 5 mL) is added and the mixture is heated for 45 minutes to 70° C. After cooling to rt the mixture is partitioned between EtOAc and saturated aqueous $NH_4Cl$. The aqueous phase is extracted twice with EtOAc. The combined organic phases are washed with brine, dried ($MgSO_4$) and concentrated. The residue is chromatographed on silica gel (petroleum ether/EtOAc 98:2→90:10) to give the title compound.

LC (Method 2): $t_R$=1.10 min; Mass spectrum (ESI+): m/z=229 $[M+H]^+$.

Intermediate 23

Ethyl 2-{3-azabicyclo[3.1.0]hexan-3-yl}-4-propylpyrimidine-5-carboxylate

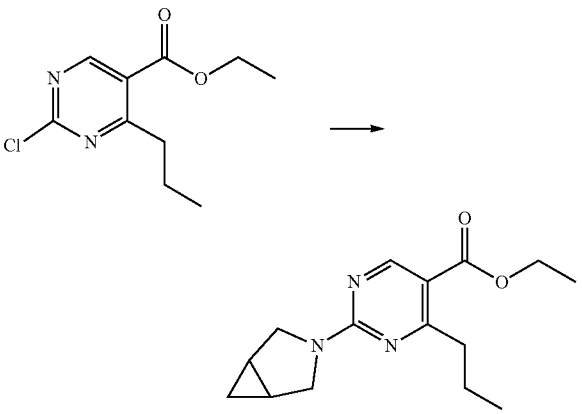

Under argon atmosphere a mixture of ethyl 2-chloro-4-propylpyrimidine-5-carboxylate (546 mg), 3-azabicyclo[3.1.0]hexane hydrochloride (328 mg) and $K_2CO_3$ (663 mg) in DMF (15 mL) is stirred for 2 h at rt. The mixture is partitioned between water and EtOAc and the phases are separated. The aqueous phase is extracted twice with EtOAc. The combined organic phases are washed with brine, dried ($MgSO_4$), concentrated and the residue is purified by HPLC on reversed phase (ACN, water) to give the title compound.

LC (Method 2): $t_R$=1.09 min; Mass spectrum (ESI+): m/z=276 $[M+H]^+$.

Intermediate 24

Methyl 5-{3-azabicyclo[3.1.0]hexan-3-yl}-6-cyanopyridine-2-carboxylate

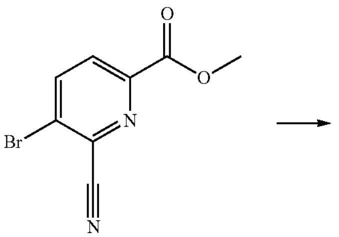

-continued

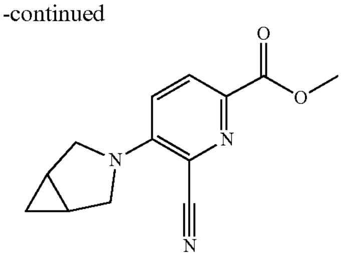

Under argon atmosphere a mixture of methyl 5-bromo-6-cyanopyridine-2-carboxylate (500 mg), 3-azabicyclo[3.1.0]hexane hydrochloride (289 mg) and $K_2CO_3$ (717 mg) in NMP (5 mL) is stirred for 12 h at 80° C. The mixture is poured into water. The precipitate is collected by filtration, washed with water and dried in vacuo to give the title compound. LC (Method 2): $t_R$=0.92 min; Mass spectrum (ESI+): m/z=244 $[M+H]^+$.

Intermediate 25

3-{3-Azabicyclo[3.1.0]hexan-3-yl}-6-(hydroxymethyl)pyridine-2-carbonitrile

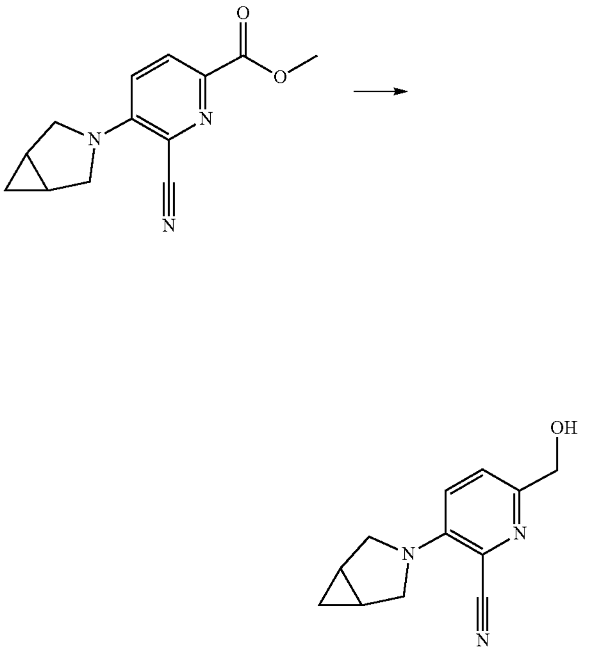

$NaBH_4$ (131 mg) is added portionwise to a mixture of methyl 5-{3-azabicyclo[3.1.0]hexan-3-yl}-6-cyanopyridine-2-carboxylate (280 mg) and $CaCl_2$ (507 mg) in THF (8 mL) and EtOH (8 mL). The mixture is stirred for 2 h at rt and for 1 h at 45° C. Then the mixture is partitioned between saturated aqueous $NaHCO_3$ and EtOAc. The precipitate is filtered off. The aqueous phase is extracted with EtOAc. The combined organic phases are dried ($MgSO_4$), concentrated and the residue is purified by HPLC on reversed phase (ACN, water) to give the title compound.

LC (Method 1): $t_R$=0.81 min; Mass spectrum (ESI+): m/z=216 $[M+H]^+$.

Intermediate 25-1 is prepared in analogy to Intermediate 25:

| Intermediate | Structure | $t_R$ | Mass spectrum (ESI+): m/z $[M + H]^+$ | LC Method |
|---|---|---|---|---|
| 25-1 | 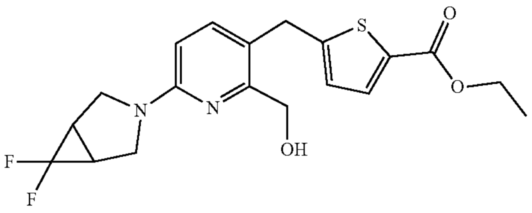 [SMILES: CCOC(=O)c1ccc(Cc2ccc(N3CC4C(C3)C4(F)F)nc2CO)s1] | 0.83 | 395 | Method 2 |

| Intermediate | Reaction comment |
|---|---|
| 25-1 | The reaction is conducted at rt for 24 h. |

| Intermediate | Name | Name of Starting Material |
|---|---|---|
| 25-1 | Ethyl 5-[(6-{6,6-difluoro-3-azabicyclo[3.1.0]-hexan-3-yl}-2-(hydroxymethyl)-pyridin-3-yl)methyl]thiophene-2-carboxylate | Ethyl 6-{6,6-difluoro-3-azabicyclo[3.1.0]hexan-3-yl}-3-{[5-(ethoxycarbonyl)thiophen-2-yl]methyl}pyridine-2-carboxylate |

Intermediate 26

Methyl 6-{3-azabicyclo[3.1.0]hexan-3-yl}-2-(trifluoromethoxy)pyridine-3-carboxylate

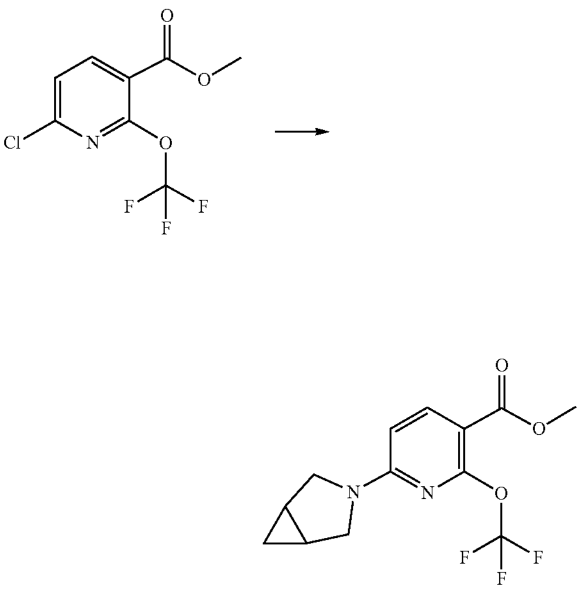

Under argon atmosphere a mixture of methyl 6-chloro-2-(trifluoromethoxy)pyridine-3-carboxylate (1 g), 3-azabicyclo[3.1.0]hexane hydrochloride (538 mg) and $K_2CO_3$ (1.1 g) in DMF (20 mL) is stirred for 4 h at rt. The mixture is partitioned between water and EtOAc. The aqueous phase is extracted twice with EtOAc. The combined organic phases are dried ($MgSO_4$), concentrated and the residue is purified by HPLC on reversed phase (ACN, water) to give the title compound. LC (Method 2): $t_R$=1.18 min; Mass spectrum (ESI+): m/z=303 $[M+H]^+$.

Intermediate 27

3-[5-(Methoxymethyl)-6-(trifluoromethoxy)pyridin-2-yl]-3-azabicyclo[3.1.0]hexane

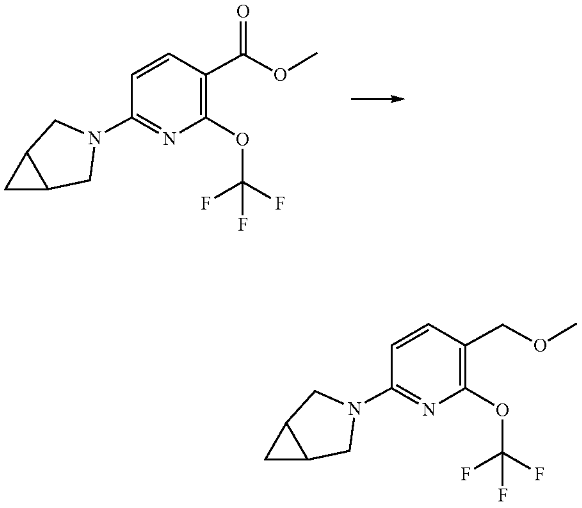

$LiBH_4$ (250 mg) is added portionwise to a mixture of methyl 6-{3-azabicyclo[3.1.0]hexan-3-yl}-2-(trifluoromethoxy)pyridine-3-carboxylate (384 mg) in THF (5 mL). The mixture is stirred for 12 h at rt. Then the mixture is poured into 1 N aqueous HCl and stirred vigorously for 20 minutes. Thereafter the mixture is partitioned between saturated aqueous $NaHCO_3$ and EtOAc. The aqueous phase is extracted twice with EtOAc. The combined organic phases are dried ($MgSO_4$), concentrated and the residue is purified by HPLC on reversed phase (ACN, water) to give the title compound. LC (Method 2): $t_R$=1.22 min; Mass spectrum (ESI+): m/z=289 $[M+H]^+$.

Intermediate 28

Ethyl 1-[(6-{3-azabicyclo[3.1.0]hexan-3-yl}-2-ethenylpyridin-3-yl)methyl]-1H-pyrazole-4-carboxylate

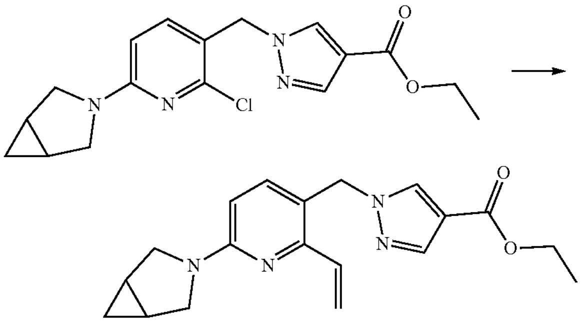

In a microwave vial a mixture of ethyl 1-[(6-{3-azabicyclo[3.1.0]hexan-3-yl}-2-chloropyridin-3-yl)methyl]-1H-pyrazole-4-carboxylate (5.62 g), vinylboronic acid pinacolester (2.9 mL), $Na_2CO_3$ (1 M aqueous solution, 40.5 mL) and 1,4-dioxane (75 mL) is purged for 10 minutes with argon. 1,1'-Bis(diphenylphosphino)ferrocenepalladium(II) dichloride (Pd(dppf)$Cl_2$, 662 mg) is added, the vial is sealed and the mixture is heated to 100° C. for 12 h. After cooling to rt the mixture is partitioned between water and EtOAc. The aqueous phase is extracted twice with EtOAc. The combined organic phases are dried ($MgSO_4$), concentrated and the residue is chromatographed on silica gel (petroleum ether/EtOAc 100:0→50:50) to give the title compound.

LC (Method 2): $t_R$=0.78 min; Mass spectrum (ESI+): m/z=339 $[M+H]^+$.

Intermediates 28-1 to 28-5 are prepared in analogy to Intermediate 28:

| Intermediate | Structure | $t_R$ | Mass spectrum (ESI+): m/z $[M + H]^+$ | LC Method |
|---|---|---|---|---|
| 28-1 | 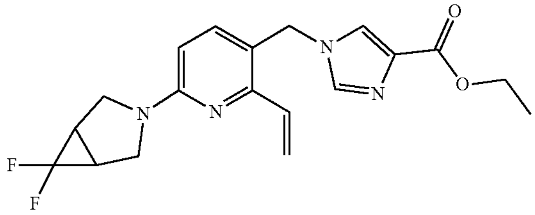 [SMILES: C=Cc1nc(N2CC3C(C2)C3(F)F)ccc1Cn1cnc(C(=O)OCC)c1] | 0.99 | | Method 1 |
| 28-2 | 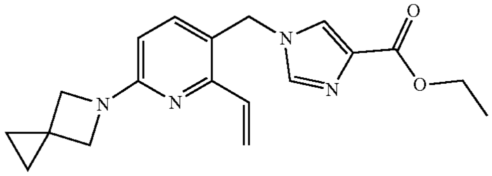 [SMILES: C=Cc1nc(N2CC3(CC3)C2)ccc1Cn1cnc(C(=O)OCC)c1] | 1.01 | 339 | Method 1 |
| 28-3 | 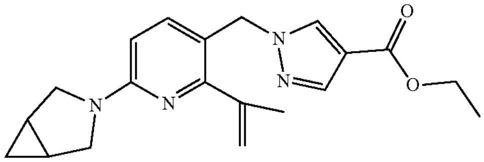 [SMILES: C=C(C)c1nc(N2CC3CC3C2)ccc1Cn1cc(C(=O)OCC)cn1] | 0.79 | 353 | Method 2 |
| 28-4 | 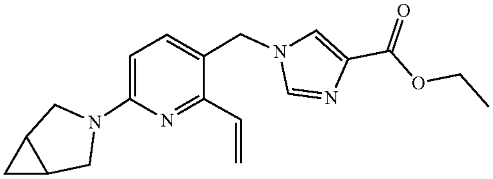 [SMILES: C=Cc1nc(N2CC3CC3C2)ccc1Cn1cnc(C(=O)OCC)c1] | 1.04 | 339 | Method 1 |
| 28-5 | 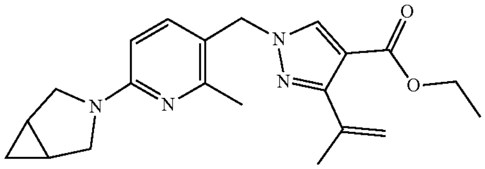 [SMILES: C=C(C)c1nn(Cc2ccc(N3CC4CC4C3)nc2C)cc1C(=O)OCC] | 0.82 | 367 | Method 2 |

| Intermediate | Reaction comment |
|---|---|
| 28-3 | Isopropenylboronic acid pinacolester is used instead of vinylboronic acid pinacolester. |
| 28-5 | Isopropenylboronic acid pinacolester is used instead of vinylboronic acid pinacolester. The reaction is conducted for 18 h at 80° C. |

| Intermediate | Name | Name of Starting Material |
|---|---|---|
| 28-1 | Ethyl 1-[(6-{6,6-difluoro-3-azabicyclo[3.1.0]hexan-3-yl}-2-ethenylpyridin-3-yl)methyl]-1H-imidazole-4-carboxylate | Ethyl 1-[(2-bromo-6-{6,6-difluoro-3-azabicyclo[3.1.0]hexan-3-yl}pyridin-3-yl)methyl]-1H-imidazole-4-carboxylate |
| 28-2 | Ethyl 1-[(6-{5-azaspiro[2.3]hexan-5-yl}-2-ethenylpyridin-3-yl)methyl]-1H-imidazole-4-carboxylate | Ethyl 1-[(6-{5-azaspiro[2.3]hexan-5-yl}-2-chloropyridin-3-yl)methyl]-1H-imidazole-4-carboxylate |
| 28-3 | Ethyl 1-[(6-{3-azabicyclo[3.1.0]hexan-3-yl}-2-(prop-1-en-2-yl)pyridin-3-yl)methyl]-1H-pyrazole-4-carboxylate | Ethyl 1-[(6-{3-azabicyclo[3.1.0]hexan-3-yl}-2-chloropyridin-3-yl)methyl]-1H-pyrazole-4-carboxylate |
| 28-4 | Ethyl 1-[(6-{3-azabicyclo[3.1.0]hexan-3-yl}-2-ethenylpyridin-3-yl)methyl]-1H-imidazole-4-carboxylate | Ethyl 1-[(6-{3-azabicyclo[3.1.0]hexan-3-yl}-2-chloropyridin-3-yl)methyl]-1H-imidazole-4-carboxylate |
| 28-5 | Ethyl 1-[(6-{3-azabicyclo[3.1.0]hexan-3-yl}-2-methylpyridin-3-yl)methyl]-3-(prop-1-en-2-yl)-1H-pyrazole-4-carboxylate | Ethyl 1-[(6-{3-azabicyclo[3.1.0]hexan-3-yl}-2-methylpyridin-3-yl)methyl]-3-bromo-1H-pyrazole-4-carboxylate |

Intermediate 29

Ethyl 1-[(6-{3-azabicyclo[3.1.0]hexan-3-yl}-2-(cyanomethyl)pyridin-3-yl)methyl]-1H-pyrazole-4-carboxylate

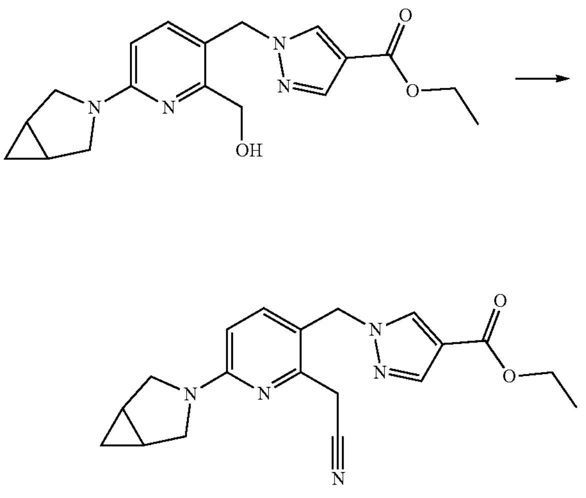

To a solution of ethyl 1-[(6-{3-azabicyclo[3.1.0]hexan-3-yl}-2-(hydroxymethyl)pyridin-3-yl)methyl]-1H-pyrazole-4-carboxylate (400 mg), 2-hydroxy-2-methylpropanenitrile (140 μL) and triphenylphosphine (460 mg) in THF (6 mL) is added dropwise DBAD (360 μL). The mixture is stirred for 45 minutes. 2-Hydroxy-2-methylpropanenitrile (140 μL), triphenylphosphine (460 mg) and DBAD (360 μL) are added successively and the mixture is stirred again for 45 minutes. Then the mixture is diluted with THF and purified by HPLC on reversed phase (ACN, water) to give the title compound. LC (Method 2): $t_R$=0.97 min; Mass spectrum (ESI+): m/z=352 $[M+H]^+$.

Intermediate 30

Ethyl 1-[(6-{3-azabicyclo[3.1.0]hexan-3-yl}-2-(1-cyanocyclopropyl)pyridin-3-yl)methyl]-1H-pyrazole-4-carboxylate

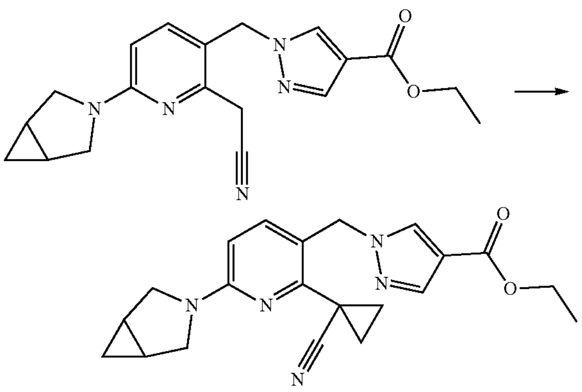

A mixture of ethyl 1-[(6-{3-azabicyclo[3.1.0]hexan-3-yl}-2-(cyanomethyl)pyridin-3-yl)methyl]-1H-pyrazole-4-carboxylate (212 mg) in DMSO (7 mL) is cooled to 10° C. and treated portionwise with NaH (60% in mineral oil, 60 mg). The mixture is stirred for 15 minutes at rt, cooled to 0° C. and treated with 1,2-dibromoethane (80 μL). Then the mixture is stirred for 1 h at rt. After cooling to 0° C. the mixture is treated with saturated aqueous $NH_4Cl$. The mixture is then extracted twice with EtOAc. The combined organic phases are washed with water, dried ($MgSO_4$), concentrated and the residue is chromatographed on silica gel (petroleum ether/EtOAc 90:10→60:40) to give the title compound.

LC (Method 2): $t_R$=1.06 min; Mass spectrum (ESI+): m/z=378 $[M+H]^+$.

Intermediate 30-1 is prepared in analogy to Intermediate 30:

| Intermediate | Structure | $t_R$ | Mass spectrum (ESI+): m/z $[M + H]^+$ | LC Method |
|---|---|---|---|---|
| 30-1 | 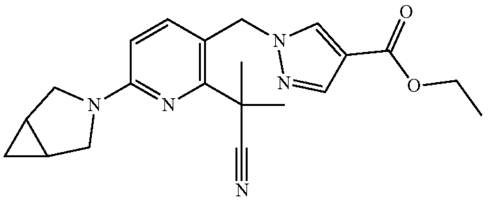 [SMILES: CCOC(=O)c1cnn(Cc2ccc(N3CC4CC4C3)nc2C(C)(C)C#N)c1] | 1.16 | 380 | Method 1 |

| Intermediate | Reaction comment |
|---|---|
| 30-1 | The reaction is conducted in DMF. $CH_3I$ is used instead of 1,2-dibromoethane. |

| Intermediate | Name | Name of Starting Material |
|---|---|---|
| 30-1 | Ethyl 1-[(6-{3-azabicyclo [3.1.0]hexan-3-yl}-2-(1-cyano-1-methylethyl) pyridin-3-yl)methyl]-1H-pyrazole-4-carboxylate | Ethyl 1-[(6-{3-azabicyclo [3.1.0]hexan-3-yl}-2-(cyanomethyl)pyridin-3-yl)methyl]-1H-pyrazole-4-carboxylate |

Intermediate 31

Ethyl 1-[(2-{3-azabicyclo[3.1.0]hexan-3-yl}-4-[(1E)-2-phenylethenyl]pyrimidin-5-yl)methyl]-1H-pyrazole-4-carboxylate

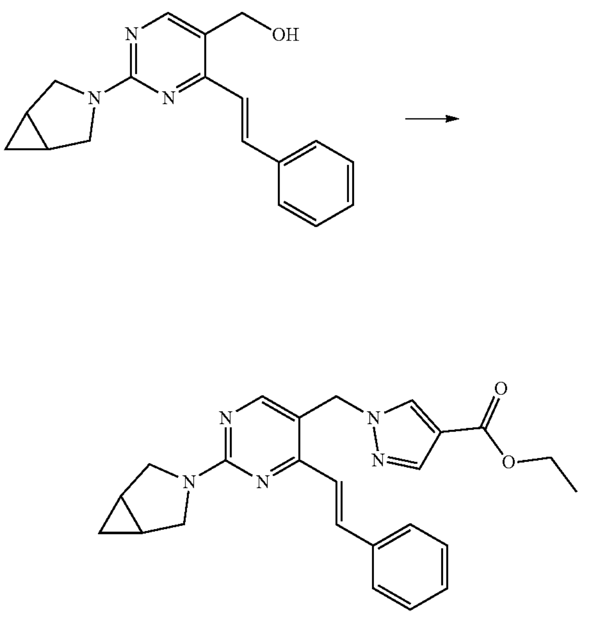

$SOCl_2$ (5 mL) is added under argon atmosphere to a mixture of (2-{3-azabicyclo[3.1.0]hexan-3-yl}-4-[(1E)-2-phenylethenyl]pyrimidin-5-yl)methanol (1.89 g) in toluene (20 mL). The mixture is heated to 60° C. for 3 h, cooled to rt and concentrated in vacuo. The residue is taken up in DCM (20 mL) and added dropwise to a mixture of ethyl 1H-pyrazole-4-carboxylate (950 mg) and DIPEA (2.2 mL) in DCM (20 mL). After stirring for 12 h at rt the mixture is partitioned between water and DCM. The organic phase is washed with brine, dried ($MgSO_4$), concentrated and the residue is chromatographed on silica gel (petroleum ether/EtOAc 50:50→0:100) to give the title compound.

LC (Method 2): $t_R$=1.06 min; Mass spectrum (ESI+): m/z=416 $[M+H]^+$.

Intermediate 32

1-[(6-{3-Azabicyclo[3.1.0]hexan-3-yl}-2-(methoxymethyl)pyridin-3-yl)methyl]-1H-pyrazole-4-carboxylic acid

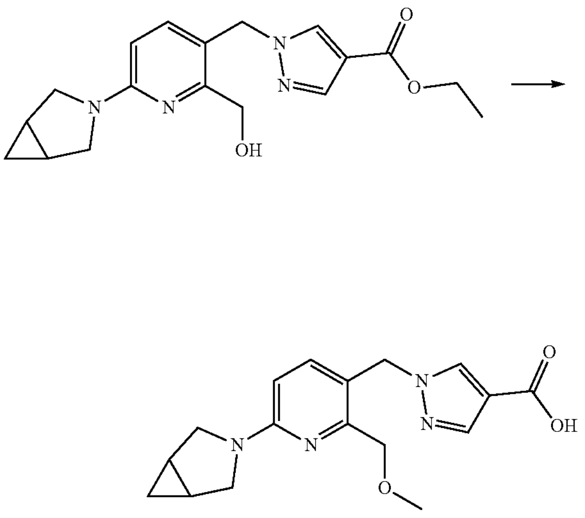

To a solution of ethyl 1-[(6-{3-azabicyclo[3.1.0]hexan-3-yl}-2-(hydroxymethyl)pyridin-3-yl)methyl]-1H-pyrazole-4-carboxylate (900 mg) in DMF (10 mL) is added at 0° C. NaH (60% in mineral oil, 263 mg). The mixture is stirred for 30 minutes, treated with $CH_3I$ (222 μL) and stirred for 1.5 h at 0° C. EtOH (4 mL) and aqueous NaOH (4 M, 4.2 mL) are added and the mixture is stirred for 12 h at 70° C. After cooling to rt aqueous HCl (4 M, 3 mL) is added and the mixture is partitioned between water and EtOAc. The aqueous phase is extracted with EtOAc. The combined organic phases are washed with brine, dried ($MgSO_4$), concentrated and the residue is purified by HPLC on reversed phase (ACN, water) to give the title compound. LC (Method 2): $t_R$=0.62 min; Mass spectrum (ESI+): m/z=329 $[M+H]^+$.

Intermediates 32-1 to 32-3 are prepared in analogy to Intermediate 32:

| Intermediate | Structure | $t_R$ | Mass spectrum (ESI+): m/z $[M + H]^+$ | LC Method |
|---|---|---|---|---|
| 32-1 | 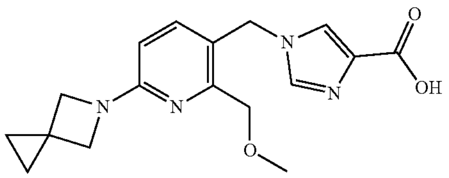 [SMILES: COCc1nc(N2CC3(CC3)C2)ccc1Cn1cnc(C(=O)O)c1] | 0.63 | 329 | Method 1 |
| 32-2 | 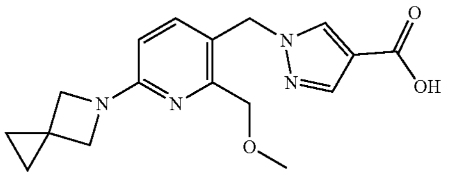 [SMILES: COCc1nc(N2CC3(CC3)C2)ccc1Cn1cc(C(=O)O)cn1] | 0.63 | 329 | Method 1 |
| 32-3 | 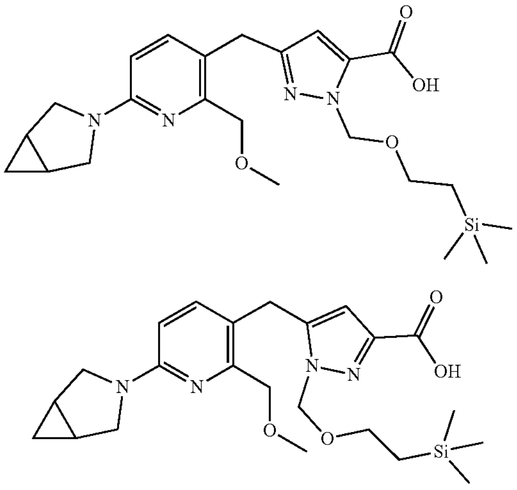 (mixture of isomers) | 0.85 and 0.86 | 459 | Method 2 |

| Intermediate | Reaction comment |
|---|---|
| 32-3 | After addition of $CH_3I$ the mixture is stirred for 12 h at rt. Then water is added and the mixture is purified by HPLC on reversed phase (ACN, water) to give the title compounds as a mixture of isomers. |

-continued

| Intermediate | Name | Name of Starting Material |
|---|---|---|
| 32-1 | 1-[(6-{5-Azaspiro[2.3]hexan-5-yl}-2-(methoxymethyl)pyridin-3-yl)methyl]-1H-imidazole-4-carboxylic acid | Ethyl 1-[(6-{5-azaspiro[2.3]hexan-5-yl}-2-(hydroxymethyl)pyridin-3-yl)methyl]-1H-imidazole-4-carboxylate |
| 32-2 | 1-[(6-{5-Azaspiro[2.3]hexan-5-yl}-2-(methoxymethyl)pyridin-3-yl)methyl]-1H-pyrazole-4-carboxylic acid | Ethyl 1-[(6-{5-azaspiro[2.3]hexan-5-yl}-2-(hydroxymethyl)pyridin-3-yl)methyl]-1H-pyrazole-4-carboxylate trifluoroacetate |
| 32-3 | 3-[(6-{3-Azabicyclo[3.1.0]hexan-3-yl}-2-(methoxymethyl)pyridin-3-yl)methyl]-1-{[2-(trimethylsilyl)ethoxy]methyl}-1H-pyrazole-5-carboxylic acid and 5-[(6-{3-Azabicyclo[3.1.0]hexan-3-yl}-2-(methoxymethyl)pyridin-3-yl)methyl]-1-{[2-(trimethylsilyl)ethoxy]methyl}-1H-pyrazole-3-carboxylic acid (mixture of isomers) | Ethyl 3-[(6-{3-azabicyclo[3.1.0]hexan-3-yl}-2-(hydroxymethyl)pyridin-3-yl)methyl]-1-{[2-(trimethylsilyl)ethoxy]methyl}-1H-pyrazole-5-carboxylate and Ethyl 5-[(6-{3-azabicyclo[3.1.0]hexan-3-yl}-2-(hydroxymethyl)pyridin-3-yl)methyl]-1-{[2-(trimethylsilyl)ethoxy]methyl}-1H-pyrazole-3-carboxylate (mixture of isomers) |

Intermediate 33

Ethyl 1-[(6-{5-azaspiro[2.3]hexan-5-yl}-2-ethylpyridin-3-yl)methyl]-1H-pyrazole-4-carboxylate

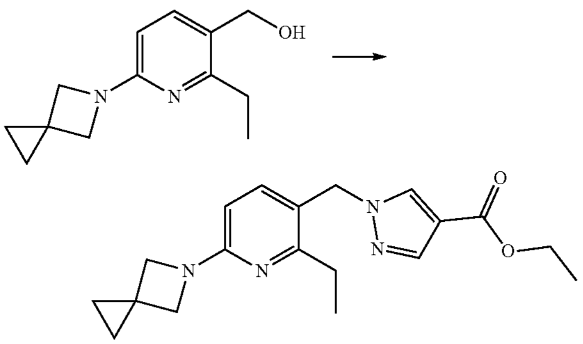

To a ice-cooled solution of (6-{5-azaspiro[2.3]hexan-5-yl}-2-ethylpyridin-3-yl)methanol (400 mg), ethyl 1H-pyrazole-4-carboxylate (800 mg) and tributylphosphine (1.6 mL) in THF (10 mL) is added dropwise DBAD (1.35 g). The mixture is stirred for 45 minutes. Saturated aqueous $NaHCO_3$ is added and the mixture is stirred vigorously for 5 minutes. Then the mixture is filtered over celite. The aqueous phase is extracted twice with EtOAc and the combined organic phases are washed with brine and dried ($MgSO_4$). The solvents are evaporated in vacuo and the residue is chromatographed on silica gel (petroleum ether/EtOAc 70:30→0:100) to give the title compound.

LC (Method 2): $t_R$=0.78 min; Mass spectrum (ESI+): m/z=341 $[M+H]^+$.

Intermediates 33-1 to 33-5 are prepared in analogy to Intermediate 33:

| Intermediate | Structure | $t_R$ | Mass spectrum (ESI+): m/z $[M + H]^+$ | LC Method |
|---|---|---|---|---|
| 33-1 | 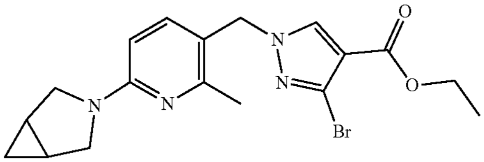 [SMILES: CCOC(=O)c1cn(Cc2ccc(N3CC4CC4C3)nc2C)nc1Br] | 1.14 | 405 | Method 1 |
| 33-2 | 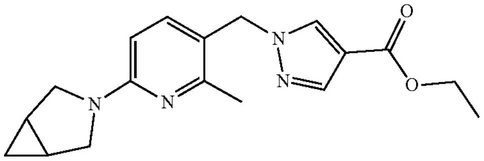 [SMILES: CCOC(=O)c1cnn(Cc2ccc(N3CC4CC4C3)nc2C)c1] | 0.73 | 327 | Method 2 |
| 33-3 | 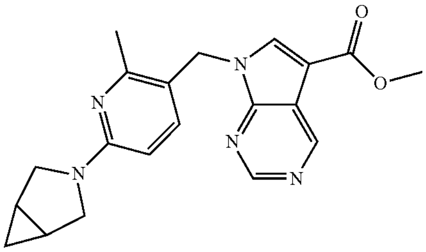 [SMILES: COC(=O)c1cn(Cc2ccc(N3CC4CC4C3)nc2C)c2ncncc12] | 0.65 | 364 | Method 1 |
| 33-4 | 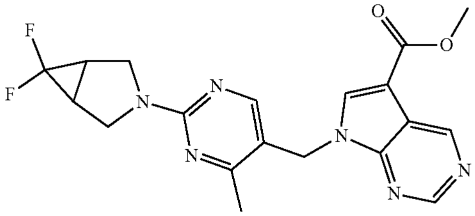 [SMILES: COC(=O)c1cn(Cc2cnc(N3CC4C(C3)C4(F)F)nc2C)c2ncncc12] | 0.84 | 401 | Method 1 |

-continued

| Intermediate | Structure | $t_R$ | Mass spectrum (ESI+): m/z $[M + H]^+$ | LC Method |
|---|---|---|---|---|
| 33-5 | 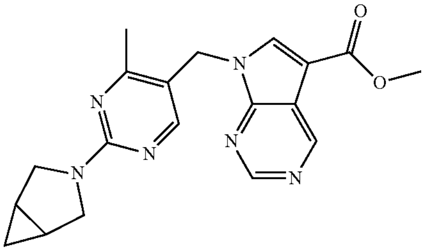 [SMILES: COC(=O)c1cn(Cc2cnc(N3CC4CC4C3)nc2C)c2ncncc12] | 0.77 | 365 | Method 1 |

| Intermediate | Reaction comment |
|---|---|
| 33-1 | DBAD is added to the reaction mixture at 0° C. The mixture is stirred for 12 h while warming to rt. |
| 33-4 | DBAD is added to the reaction mixture at 0° C. The mixture is stirred for 12 h while warming to rt. |
| 33-5 | DBAD is added to the reaction mixture at 0° C. The mixture is stirred for 12 h while warming to rt. |

| Intermediate | Name | Name of Starting Material 1 | Name of Starting Material 2 |
|---|---|---|---|
| 33-1 | Ethyl 1-[(6-{3-azabicyclo[3.1.0]-hexan-3-yl}-2-methylpyridin-3-yl)methyl]-3-bromo-1H-pyrazole-4-carboxylate | (6-{3-Azabicyclo[3.1.0]-hexan-3-yl}-2-methylpyridin-3-yl)methanol | Ethyl 3-bromo-1H-pyrazole-4-carboxylate |
| 33-2 | Ethyl 1-[(6-{3-azabicyclo[3.1.0]-hexan-3-yl}-2-methylpyridin-3-yl)methyl]-1H-pyrazole-4-carboxylate | (6-{3-Azabicyclo[3.1.0]-hexan-3-yl}-2-methylpyridin-3-yl)methanol | Ethyl 1H-pyrazole-4-carboxylate |
| 33-3 | Methyl 7-[(6-{3-azabicyclo[3.1.0]-hexan-3-yl}-2-methylpyridin-3-yl)-methyl]-7H-pyrrolo[2,3-d]pyrimidine-5-carboxylate | (6-{3-Azabicyclo[3.1.0]-hexan-3-yl}-2-methyl-pyridin-3-yl)methanol | Methyl 7H-pyrrolo[2,3-d]pyrimidine-5-carboxylate |
| 33-4 | Methyl 7-[(2-{6,6-difluoro-3-azabicyclo[3.1.0]hexan-3-yl}-4-methylpyrimidin-5-yl)methyl]-7H-pyrrolo[2,3-d]pyrimidine-5-carboxylate | (2-{6,6-Difluoro-3-azabicyclo[3.1.0]hexan-3-yl}-4-methylpyrimidin-5-yl)methanol | Methyl 7H-pyrrolo[2,3-d]pyrimidine-5-carboxylate |
| 33-5 | Methyl 7-[(2-{3-azabicyclo[3.1.0]-hexan-3-yl}-4-methylpyrimidin-5-yl)-methyl]-7H-pyrrolo[2,3-d]pyrimidine-5-carboxylate | (2-{3-Azabicyclo[3.1.0]-hexan-3-yl}-4-methyl-pyrimidin-5-yl)methanol | Methyl 7H-pyrrolo[2,3-d]pyrimidine-5-carboxylate |

Intermediate 34

Ethyl 1-[(6-{3-azabicyclo[3.1.0]hexan-3-yl}-2-[(1E)-3-(benzyloxy)prop-1-en-1-yl]pyridin-3-yl) methyl]-1H-pyrazole-4-carboxylate

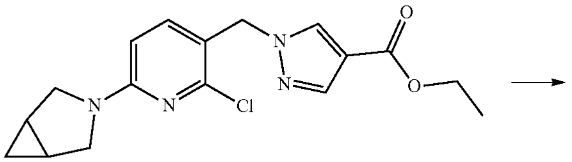

-continued

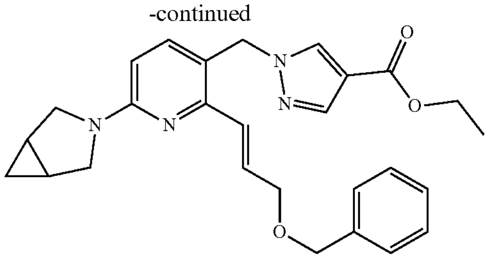

In a microwave vial a mixture of ethyl 1-[(6-{3-azabicyclo[3.1.0]hexan-3-yl}-2-chloropyridin-3-yl)methyl]-1H-pyrazole-4-carboxylate (100 mg), potassium (E)-3-(benzyloxy)prop-1-enyltrifluoroborate (88 mg), $K_2CO_3$ (100 mg) and THF (5 mL) is purged for 10 minutes with argon. 1,1'-Bis(diphenylphosphino)ferrocenepalladium(II) dichloride ($Pd(dppf)Cl_2$, 15 mg) is added, the vial is sealed and the mixture is heated to 80° C. for 15 h. After cooling to rt the mixture is partitioned between water and EtOAc. The aqueous phase is extracted with EtOAc. The combined organic phases are washed with brine, dried ($MgSO_4$), concentrated in vacuo and the residue is chromatographed on silica gel (petroleum ether/EtOAc 70:30→0:100) to give the title compound.

LC (Method 2): $t_R$=0.95 min; Mass spectrum (ESI+): m/z=459 $[M+H]^+$.

Intermediate 35

Ethyl 1-[(6-{3-azabicyclo[3.1.0]hexan-3-yl}-2-(3-hydroxypropyl)pyridin-3-yl)methyl]-1H-pyrazole-4-carboxylate

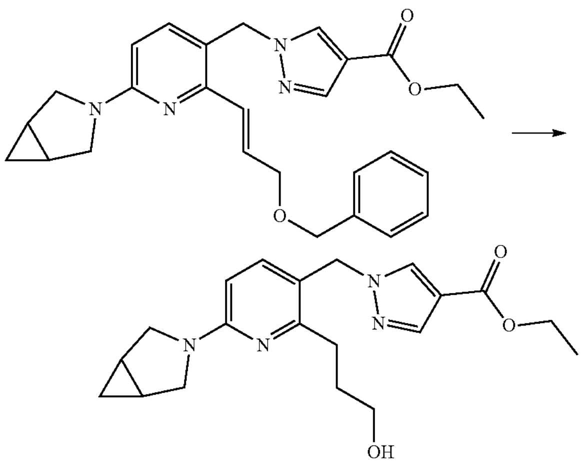

A mixture of ethyl 1-[(6-{3-azabicyclo[3.1.0]hexan-3-yl}-2-[(1E)-3-(benzyloxy)prop-1-en-1-yl]pyridin-3-yl)methyl]-1H-pyrazole-4-carboxylate (60 mg), 10% palladium on carbon (6 mg) in THF (2 mL) and acetic acid (8 μL) is shaken under hydrogen atmosphere (3 bar) at rt for 12 h. The mixture is filtered, the filtrate is concentrated and the residue is chromatographed on silica gel (petroleum ether/EtOAc 70:30→0:100) to give the title compound.

LC (Method 2): $t_R$=0.73 min; Mass spectrum (ESI+): m/z=371 $[M+H]^+$.

Intermediate 36

3-[5-(Azidomethyl)-6-ethenylpyridin-2-yl]-6,6-difluoro-3-azabicyclo[3.1.0]hexane

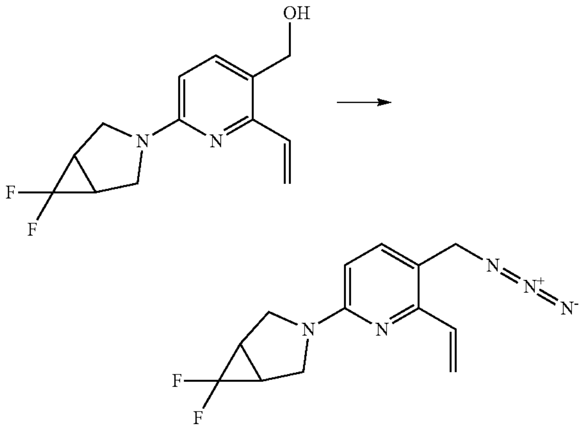

Under argon atmosphere diphenylphosphorylazide (1.4 mL) is added dropwise to an ice-cooled mixture of (6-{6,6-difluoro-3-azabicyclo[3.1.0]hexan-3-yl}-2-ethenylpyridin-3-yl)methanol (1.34 g) and DBU (1.05 mL) in toluene (10 mL) and ACN (10 mL). The mixture is stirred for 12 h while warming to rt. Then the mixture is partitioned between water and EtOAc. The aqueous phase is extracted with EtOAc. The combined organic phases are washed with brine, dried ($MgSO_4$), concentrated in vacuo and the residue is chromatographed on silica gel (petroleum ether/EtOAc 99:1→50:50) to give the title compound. LC (Method 2): $t_R$=0.88 min; Mass spectrum (ESI+): m/z=278 $[M+H]^+$.

Intermediates 36-1 to 36-5 are prepared in analogy to Intermediate 36:

| Intermediate | Structure | $t_R$ | Mass spectrum (ESI+): m/z $[M + H]^+$ | LC Method |
|---|---|---|---|---|
| 36-1 | 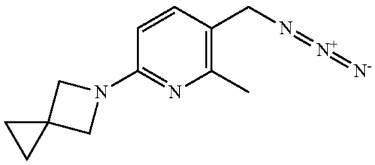 [SMILES: Cc1nc(N2CC3(CC3)C2)ccc1CN=[N+]=[N-]] | 0.69 | 230 | Method 2 |
| 36-2 | 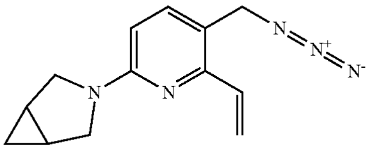 [SMILES: C=Cc1nc(N2CC3CC3C2)ccc1CN=[N+]=[N-]] | 0.72 | 242 | Method 2 |
| 36-3 | 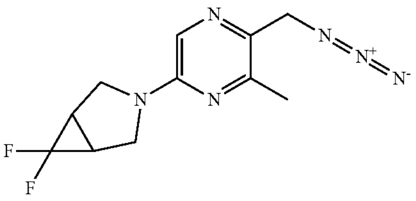 [SMILES: Cc1nc(N2CC3C(C2)C3(F)F)cnc1CN=[N+]=[N-]] | 1.00 | 267 | Method 2 |

-continued

| Intermediate | Structure | $t_R$ | Mass spectrum (ESI+): m/z $[M + H]^+$ | LC Method |
|---|---|---|---|---|
| 36-4 | 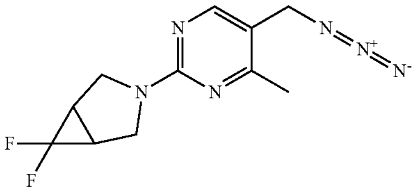 [SMILES: Cc1nc(N2CC3C(C2)C3(F)F)ncc1CN=[N+]=[N-]] | 0.97 | 267 | Method 2 |
| 36-5 | 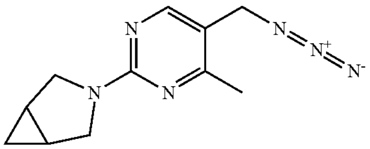 [SMILES: Cc1nc(N2CC3CC3C2)ncc1CN=[N+]=[N-]] | 0.75 | 231 | Method 2 |

| Intermediate | Reaction comment |
|---|---|
| 36-3 | The reaction is conducted in toluene/ACN 1:1. |
| 36-4 | The reaction is conducted in toluene/ACN 1:1. |
| 36-5 | The reaction is conducted in toluene/ACN 1:1. |

| Intermediate | Name | Name of Starting Material |
|---|---|---|
| 36-1 | 5-[5-(Azidomethyl)-6-methylpyridin-2-yl]-5-azaspiro[2.3]hexane | (6-{5-Azaspiro[2.3]hexan-5-yl}-2-methylpyridin-3-yl)methanol |
| 36-2 | 3-[5-(Azidomethyl)-6-ethenylpyridin-2-yl]-3-azabicyclo[3.1.0]hexane | (6-{3-Azabicyclo[3.1.0]hexan-3-yl}-2-ethenylpyridin-3-yl)methanol |
| 36-3 | 3-[5-(Azidomethyl)-6-methylpyrazin-2-yl]-6,6-difluoro-3-azabicyclo[3.1.0]hexane | (5-{6,6-Difluoro-3-azabicyclo[3.1.0]hexan-3-yl}-3-methylpyrazin-2-yl)methanol |
| 36-4 | 3-[5-(Azidomethyl)-4-methylpyrimidin-2-yl]-6,6-difluoro-3-azabicyclo[3.1.0]hexane | (2-{6,6-Difluoro-3-azabicyclo[3.1.0]hexan-3-yl}-4-methylpyrimidin-5-yl)methanol |
| 36-5 | 3-[5-(Azidomethyl)-4-methylpyrimidin-2-yl]-3-azabicyclo[3.1.0]hexane | (2-{3-Azabicyclo[3.1.0]hexan-3-yl}-4-methylpyrimidin-5-yl)methanol |

Intermediate 37

Ethyl 1-[(6-{6,6-difluoro-3-azabicyclo[3.1.0]hexan-3-yl}-2-ethenylpyridin-3-yl)methyl]-1H-1,2,3-triazole-4-carboxylate

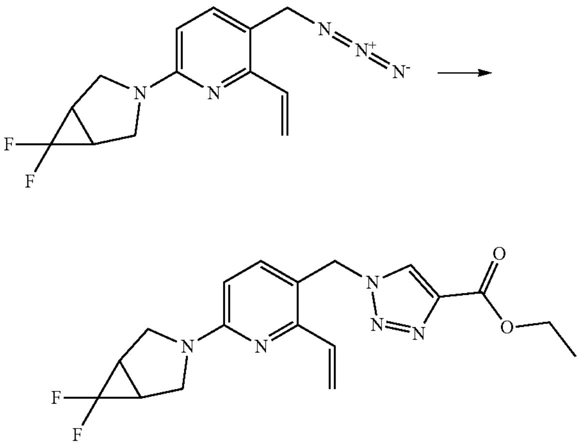

A mixture of 3-[5-(azidomethyl)-6-ethenylpyridin-2-yl]-6,6-difluoro-3-azabicyclo[3.1.0]hexane (794 mg), propiolic acid ethylester (320 μL), $CuSO_4$ (92 mg) and sodium (L)-ascorbate (568 mg) in tert.-butanol (8 mL) and water (8 mL) is stirred at rt for 48 h. The mixture is partitioned between water and EtOAc. The aqueous phase is extracted with EtOAc.

The combined organic phases are washed with brine, dried ($MgSO_4$), concentrated in vacuo and the residue is chromatographed on silica gel (petroleum ether/EtOAc 99:1→50:50) to give the title compound.

LC (Method 2): $t_R$=0.89 min; Mass spectrum (ESI+): m/z=376 $[M+H]^+$.

Intermediates 37-1 to 37-5 are prepared in analogy to Intermediate 37:

| Intermediate | Structure | $t_R$ | Mass spectrum (ESI+): m/z $[M + H]^+$ | LC Method |
|---|---|---|---|---|
| 37-1 | 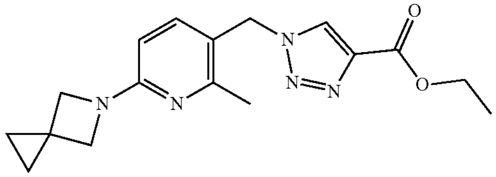 [SMILES: CCOC(=O)c1cn(Cc2ccc(N3CC4(CC4)C3)nc2C)nn1] | 0.69 | 328 | Method 2 |
| 37-2 | 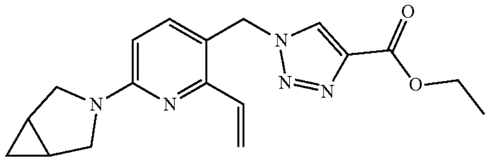 [SMILES: C=Cc1nc(N2CC3CC3C2)ccc1Cn1cc(C(=O)OCC)nn1] | 0.74 | 340 | Method 2 |
| 37-3 | 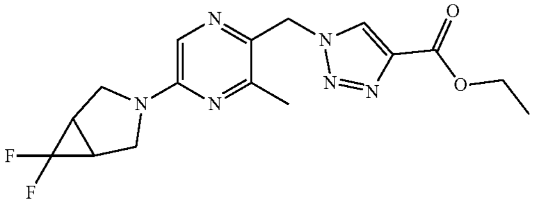 [SMILES: CCOC(=O)c1cn(Cc2ncc(N3CC4C(C3)C4(F)F)nc2C)nn1] | 0.95 | 365 | Method 2 |
| 37-4 | 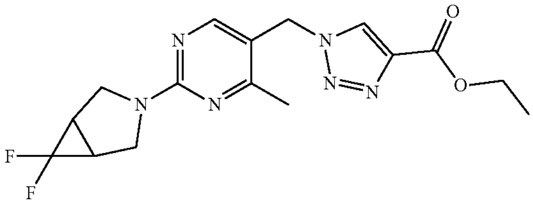 [SMILES: CCOC(=O)c1cn(Cc2cnc(N3CC4C(C3)C4(F)F)nc2C)nn1] | 0.87 | 365 | Method 2 |
| 37-5 | 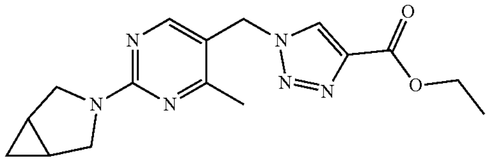 [SMILES: CCOC(=O)c1cn(Cc2cnc(N3CC4CC4C3)nc2C)nn1] | 0.79 | 329 | Method 2 |

| Intermediate | Reaction comment |
|---|---|
| 37-3 | The reaction is conducted for 12 h. |
| 37-5 | The reaction is conducted for 5 days. |

| Intermediate | Name | Name of Starting Material |
|---|---|---|
| 37-1 | Ethyl 1-[(6-{5-azaspiro[2.3]hexan-5-yl}-2-methyl-pyridin-3-yl)methyl]-1H-1,2,3-triazole-4-carboxylate | 5-[5-(Azidomethyl)-6-methylpyridin-2-yl]-5-azaspiro[2.3]hexane |
| 37-2 | Ethyl 1-[(6-{3-azabicyclo[3.1.0]hexan-3-yl}-2-ethenylpyridin-3-yl)methyl]-1H-1,2,3-triazole-4-carboxylate | 3-[5-(Azidomethyl)-6-ethenylpyridin-2-yl]-3-azabicyclo[3.1.0]hexane |
| 37-3 | Ethyl 1-[(5-{6,6-difluoro-3-azabicyclo[3.1.0]hexan-3-yl}-3-methylpyrazin-2-yl)methyl]-1H-1,2,3-triazole-4-carboxylate | 3-[5-(Azidomethyl)-6-methylpyrazin-2-yl]-6,6-difluoro-3-azabicyclo[3.1.0]hexane |
| 37-4 | Ethyl 1- [(2-{6,6-difluoro-3-azabicyclo[3.1.0]-hexan-3-yl}-4-methylpyrimidin-5-yl)methyl]-1H-1,2,3-triazole-4-carboxylate | 3-[5-(Azidomethyl)-4-methylpyrimidin-2-yl]-6,6-difluoro-3-azabicyclo[3.1.0]hexane |
| 37-5 | Ethyl 1-[(2-{3-azabicyclo[3.1.0]hexan-3-yl}-4-methylpyrimidin-5-yl)methyl]-1H-1,2,3-triazole-4-carboxylate | 3-[5-(Azidomethyl)-4-methylpyrimidin-2-yl]-3-azabicyclo[3.1.0]hexane |

Intermediate 38

1-[(6-{6,6-Difluoro-3-azabicyclo[3.1.0]hexan-3-yl}-2-(methoxymethyl)pyridin-3-yl)methyl]-1H-1,2,3-triazole-4-carboxylic acid

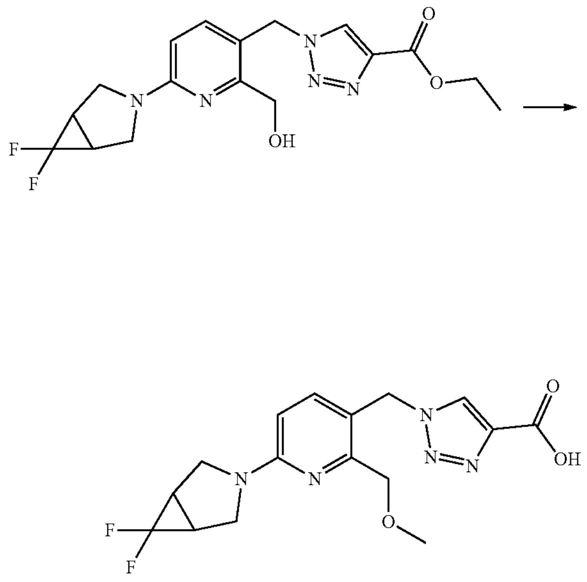

To a solution of ethyl 1-[(6-{6,6-difluoro-3-azabicyclo[3.1.0]hexan-3-yl}-2-(hydroxymethyl)pyridin-3-yl)methyl]-1H-1,2,3-triazole-4-carboxylate (175 mg) in DMF (2 mL) is added at 0° C. NaH (60% in mineral oil, 45 mg). The mixture is stirred for 30 minutes at rt, treated with $CH_3I$ (30 μL) and stirred for 12 h at rt. Water is added and the mixture is concentrated in vacuo. The residue is taken up in DCM/isopropanol 1:1 and filtered. The filtrate is dried ($MgSO_4$) and concentrated in vacuo to give the title compound.

LC (Method 2): $t_R$=0.65 min; Mass spectrum (ESI+): m/z=366 [M+H].

Intermediate 39

Ethyl 1-[(6-{3-azabicyclo[3.1.0]hexan-3-yl}-2-(1-hydroxypropan-2-yl)pyridin-3-yl)methyl]-1H-pyrazole-4-carboxylate

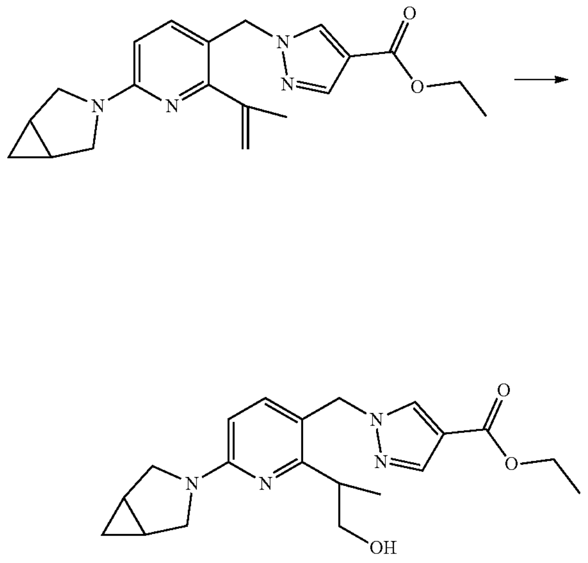

A mixture of ethyl 1-[(6-{3-azabicyclo[3.1.0]hexan-3-yl}-2-(prop-1-en-2-yl)pyridin-3-yl)methyl]-1H-pyrazole-4-carboxylate (270 mg) and 9-borabicyclo(3.3.1)nonane (3.1 mL) is stirred for 48 h at rt. 9-Borabicyclo(3.3.1)nonane (6 mL) is added and stirring is continued for 12 h. The mixture is cooled to 0° C. and treated dropwise with water (3 mL) and $H_2O_2$ (35% in water, 3.35 mL). Then the mixture is stirred for 30 minutes at rt. Aqueous NaOH (2 M, 340 NL) is added, the mixture is stirred for 20 minutes and then cooled to 0° C. Saturated aqueous $Na_2S_2O_3$ is slowly added and the aqueous phase is extracted twice with EtOAc. The combined organic phases are washed with brine, dried ($MgSO_4$), concentrated in vacuo and the residue is chromatographed on silica gel (petroleum ether/EtOAc 80:20→0:100) to give the title compound. LC (Method 2): $t_R$=0.76 min; Mass spectrum (ESI+): m/z=371 $[M+H]^+$.

Intermediate 39-1 is prepared in analogy to Intermediate 39:

| Intermediate | Structure | $t_R$ | Mass spectrum (ESI+): m/z $[M + H]^+$ | LC Method |
|---|---|---|---|---|
| 39-1 | 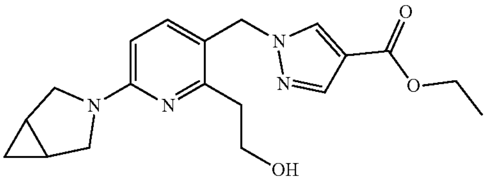 [SMILES: CCOC(=O)c1cnn(Cc2ccc(N3CC4CC4C3)nc2CCO)c1] | 0.98 | 357 | Method 1 |

| Intermediate | Reaction comment |
|---|---|
| 39-1 | The hydroboration is conducted for 3 h at rt. |

| Intermediate | Name | Name of Starting Material |
|---|---|---|
| 39-1 | Ethyl 1-[(6-{3-azabicyclo[3.1.0]hexan-3-yl}-2-(2-hydroxyethyl)pyridin-3-yl)methyl]-1H-pyrazole-4-carboxylate | Ethyl 1-[(6-{3-azabicyclo[3.1.0]hexan-3-yl}-2-ethenylpyridin-3-yl)methyl]-1H-pyrazole-4-carboxylate |

Intermediate 40

Methyl 6-{3-azabicyclo[3.1.0]hexan-3-yl}pyridazine-3-carboxylate

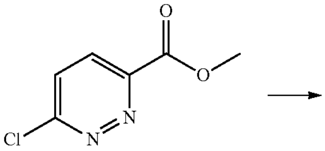

-continued

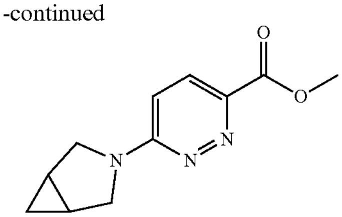

Under argon atmosphere a mixture of methyl 6-chloropyridazine-3-carboxylate (2.5 g), 3-azabicyclo[3.1.0]hexane hydrochloride (1.99 g) and $K_2CO_3$ (4.02 g) in DMF (50 mL) is stirred for 12 h at rt. The mixture is partitioned between water and EtOAc and stirred for 20 minutes. The precipitate is collected by filtration and dried in vacuo to give the title compound. LC (Method 2): $t_R$=0.60 min; Mass spectrum (ESI+): m/z=220 $[M+H]^+$.

Intermediates 40-1 to 40-8 are prepared in analog to Intermediate 40:

| Intermediate | Structure | $t_R$ | Mass spectrum (ESI+): m/z $[M + H]^+$ | LC Method |
|---|---|---|---|---|
| 40-1 | 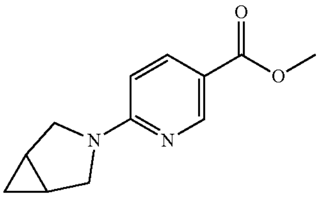 [SMILES: COC(=O)c1ccc(N2CC3CC3C2)nc1] | 0.68 | 219 | Method 2 |

-continued
| Intermediate | Structure | $t_R$ | Mass spectrum (ESI+): m/z $[M + H]^+$ | LC Method |
|---|---|---|---|---|
| 40-2 | 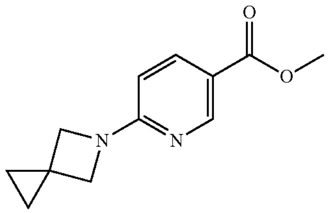 [SMILES: COC(=O)c1ccc(N2CC3(CC3)C2)nc1] | 0.96 | 219 | Method 1 |
| 40-3 | 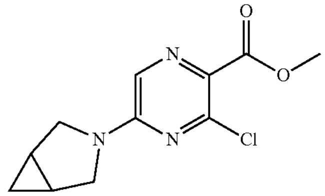 [SMILES: COC(=O)c1ncc(N2CC3CC3C2)nc1Cl] | 0.93 | 254 | Method 2 |
| 40-4 | 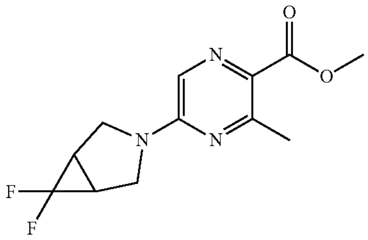 [SMILES: COC(=O)c1ncc(N2CC3C(C2)C3(F)F)nc1C] | 0.93 | 270 | Method 2 |
| 40-5 | 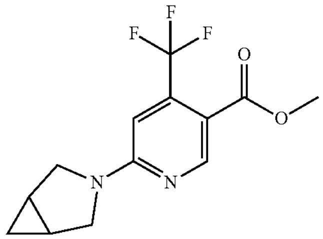 [SMILES: COC(=O)c1cnc(N2CC3CC3C2)cc1C(F)(F)F] | 1.07 | 287 | Method 1 |
| 40-6 | 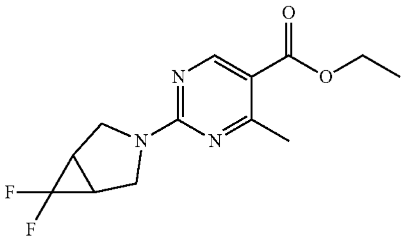 [SMILES: CCOC(=O)c1cnc(N2CC3C(C2)C3(F)F)nc1C] | 1.02 | 284 | Method 2 |
| 40-7 | 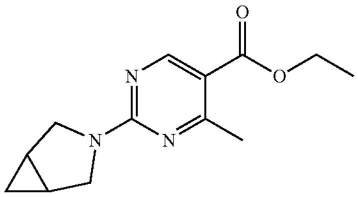 [SMILES: CCOC(=O)c1cnc(N2CC3CC3C2)nc1C] | 1.02 | 248 | Method 2 |

-continued

| Intermediate | Structure | $t_R$ | Mass spectrum (ESI+): m/z $[M + H]^+$ | LC Method |
|---|---|---|---|---|
| 40-8 | 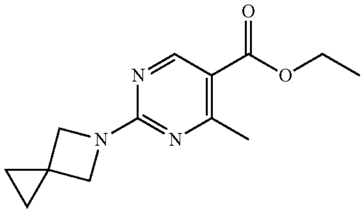 [SMILES: CCOC(=O)c1cnc(N2CC3(CC3)C2)nc1C] | 1.00 | 248 | Method 1 |

| Intermediate | Reaction comment |
|---|---|
| 40-1 | The reaction is conducted at 90° C. for 12 h. |
| 40-3 | The reaction is conducted for 48 h at rt. |
| 40-4 | The reaction is conducted at 90° C. for 12 h. |
| 40-5 | $KHCO_3$ is used instead of $K_2CO_3$ and DMSO instead of DMF. The reaction is conducted at 45° C. for 4 h. |
| 40-6 | The reaction is conducted at 90° C. for 1 h. |
| 40-7 | The reaction is conducted at 90° C. for 1 h. |

| Intermediate | Name | Name of Starting Material 1 | Name of Starting Material 2 |
|---|---|---|---|
| 40-1 | Methyl 6-{3-azabicyclo[3.1.0]-hexan-3-yl}pyridine-3-carboxylate | Methyl 6-chloropyridine-3-carboxylate | 3-Azabicyclo[3.1.0]hexane hydrochloride |
| 40-2 | Methyl 6-{5-azaspiro[2.3]hexan-5-yl}pyridine-3-carboxylate | Methyl 6-fluororopyridine-3-carboxylate | 5-Azaspiro[2.3]hexane trifluoroacetate |
| 40-3 | Methyl 5-{3-azabicyclo[3.1.0]-hexan-3-yl}-3-chloropyrazine-2-carboxylate | Methyl 3,5-dichloropyrazine-2-carboxylate | 3-Azabicyclo[3.1.0]hexane hydrochloride |
| 40-4 | Methyl 5-{6,6-difluoro-3-azabicyclo[3.1.0]hexan-3-yl}-3-methylpyrazine-2-carboxylate | Methyl 5-chloro-3-methylpyrazine-2-carboxylate | 6,6-Difluoro-3-azabicyclo[3.1.0]hexane hydrochloride |
| 40-5 | Methyl 6-{3-azabicyclo[3.1.0]-hexan-3-yl}-4-(trifluoromethyl)-pyridine-3-carboxylate | Methyl 6-chloro-4-(trifluoromethyl)pyridine-3-carboxylate | 3-Azabicyclo[3.1.0]hexane hydrochloride |
| 40-6 | Ethyl 2-{6,6-difluoro-3-azabicyclo[3.1.0]hexan-3-yl}-4-methylpyrimidine-5-carboxylate | Ethyl 2-chloro-4-methylpyrimidine-5-carboxylate | 6,6-Difluoro-3-azabicyclo[3.1.0]hexane hydrochloride |
| 40-7 | Ethyl 2-{3-azabicyclo[3.1.0]hexan-3-yl}-4-methylpyrimidine-5-carboxylate | Ethyl 2-chloro-4-methylpyrimidine-5-carboxylate | 3-Azabicyclo[3.1.0]hexane hydrochloride |
| 40-8 | Ethyl 2-{5-azaspiro[2.3]hexan-5-yl}-4-methylpyrimidine-5-carboxylate | Ethyl 2-chloro-4-methylpyrimidine-5-carboxylate | 5-azaspiro[2.3]hexane trifluoroacetate |

Intermediate 41

(6-{3-Azabicyclo[3.1.0]hexan-3-yl}pyridazin-3-yl) methanol

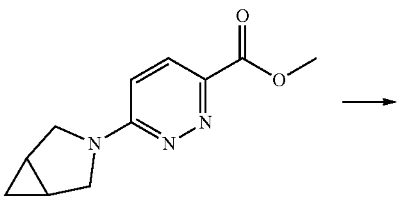

-continued

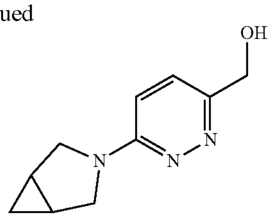

$NaBH_4$ (76 mg) is added portionwise to a mixture of methyl 6-{3-azabicyclo[3.1.0]hexan-3-yl}pyridazine-3-carboxylate (200 mg) and $CaCl_2$ (54 mg) in MeOH (4 mL). The mixture is stirred for 24 h at 70° C. After cooling to rt 1 M aqueous HCl is added until a pH-value of 2 is reached. The mixture is stirred for 15 minutes and then partitioned between saturated aqueous $NaHCO_3$ and EtOAc. The aqueous phase is extracted twice with EtOAc and twice with EtOAc/isopropanol 1:1. The combined organic phases are dried ($MgSO_4$), concentrated in vacuo and the residue is purified by HPLC on reversed phase (ACN, water) to give the title compound.

LC (Method 1): $t_R$=0.67 min; Mass spectrum (ESI+): m/z=192 $[M+H]^+$.

Intermediate 41-1 is prepared in analogy to Intermediate 41:

| Intermediate | Structure | $t_R$ | Mass spectrum (ESI+): m/z $[M + H]^+$ | LC Method |
|---|---|---|---|---|
| 41-1 | 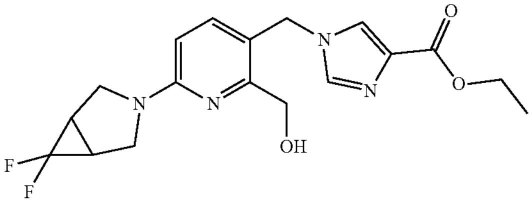 [SMILES: CCOC(=O)c1cn(Cc2ccc(N3CC4C(C3)C4(F)F)nc2CO)cn1] | 0.67 | 379 | Method 2 |

| Intermediate | Reaction comment |
|---|---|
| 41-1 | The reaction is conducted in THF/EtOH 1:1 for 8 h at rt. |

| Intermediate | Name | Name of Starting Material |
|---|---|---|
| 41-1 | Ethyl 1-[(6-{6,6-difluoro-3-azabicyclo[3.1.0]-hexan-3-yl}-2-(hydroxymethyl)pyridin-3-yl)methyl]-1H-imidazole-4-carboxylate | Ethyl 6-{6,6-difluoro-3-azabicyclo[3.1.0]hexan-3-yl}-3-{[4-(ethoxycarbonyl)-1H-imidazol-1-yl]methyl}pyridine-2-carboxylate |

Intermediate 42

Ethyl 1-[(6-{3-azabicyclo[3.1.0]hexan-3-yl}pyridazin-3-yl)methyl]-1H-pyrazole-4-carboxylate

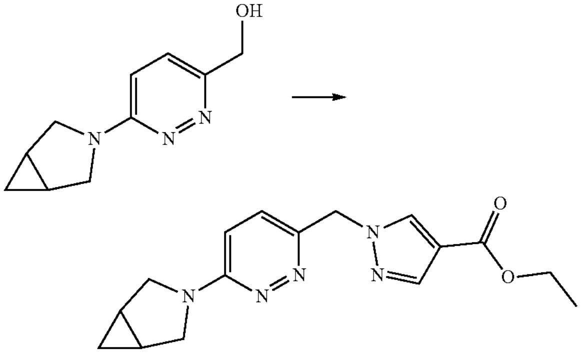

To a solution of (6-{3-azabicyclo[3.1.0]hexan-3-yl}pyridazin-3-yl)methanol (105 mg), ethyl 1H-pyrazole-4-carboxylate (81 mg) and triphenylphosphine (166 mg) in THF (2 ml) is added DBAD (139 mg). The mixture is stirred for 1.5 h diluted with DMF and purified by HPLC on reversed phase (ACN, water) to give the title compound.

LC (Method 2): $t_R$=0.68 min; Mass spectrum (ESI+): m/z=314 $[M+H]^+$.

Intermediates 42-1 to 42-2 are prepared in analogy to Intermediate 42:

| Intermediate | Structure | $t_R$ | Mass spectrum (ESI+): m/z $[M + H]^+$ | LC Method |
|---|---|---|---|---|
| 42-1 | 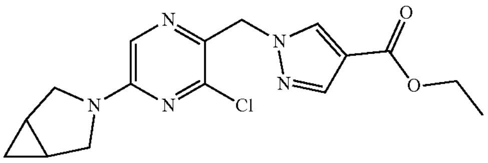 [SMILES: CCOC(=O)c1cnn(Cc2ncc(N3CC4CC4C3)nc2Cl)c1] | 1.04 | 348 | Method 2 |
| 42-2 | 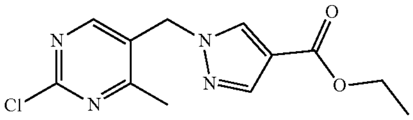 [SMILES: CCOC(=O)c1cnn(Cc2cnc(Cl)nc2C)c1] | 0.89 | 281 | Method 2 |

| Intermediate | Reaction comment |
|---|---|
| 42-1 | The reaction mixture is chromatographed on silica gel (petroleum ether/EtOAc 95:5 → 45:55) to give the title compound. |
| 42-2 | The reaction mixture is stirred for 12 h at rt. The crude product is chromatographed on silica gel (cyclohexane/EtOAc 50:50 → 0:100) to give the title compound. |

| Intermediate | Name | Name of Starting Material 1 | Name of Starting Material 2 |
|---|---|---|---|
| 42-1 | Ethyl 1-[(5-{3-azabicyclo[3.1.0]-hexan-3-yl}-3-chloropyrazin-2-yl)methyl]-1H-pyrazole-4-carboxylate | (5-{3-Azabicyclo[3.1.0]-hexan-3-yl}-3-chloropyrazin-2-yl)methanol | Ethyl 1H-pyrazole-4-carboxylate |
| 42-2 | Ethyl 1-[(2-chloro-4-methyl-pyrimidin-5-yl)methyl]-1H-pyrazole-4-carboxylate | (2-Chloro-4-methyl-pyrimidin-5-yl)methanol | Ethyl 1H-pyrazole-4-carboxylate |

Intermediate 43

Ethyl 1-[(5-bromopyrimidin-2-yl)methyl]-1H-pyrazole-4-carboxylate

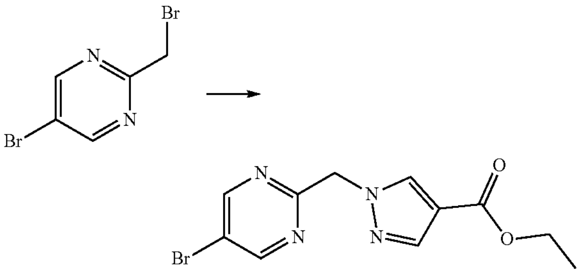

A mixture of 5-bromo-2-(bromomethyl)pyrimidine (1.5 g), $K_2CO_3$ (2.4 g) and ethyl 1H-pyrazole-4-carboxylate (814 mg) in DMF (20 mL) is stirred for 1.5 h at rt. The mixture is diluted with THF and filtered over celite. The filter cake is washed twice with THF. The combined filtrates are concentrated and the residue is chromatographed on silica gel (petroleum ether/EtOAc 80:20→0:100) to give the title compound.

LC (Method 1): $t_R$=0.85 min; Mass spectrum (ESI+): m/z=311 $[M+H]^+$.

Intermediate 44

Ethyl 1-[(5-{3-azabicyclo[3.1.0]hexan-3-yl}pyrimidin-2-yl)methyl]-1H-pyrazole-4-carboxylate

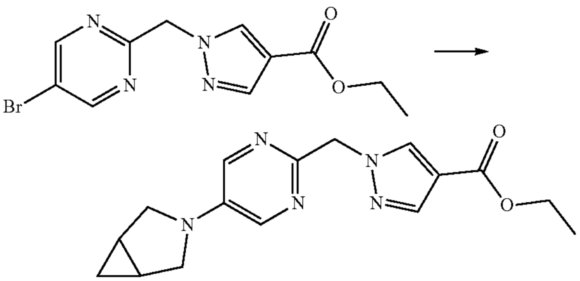

In a microwave vial a mixture of ethyl 1-[(5-bromopyrimidin-2-yl)methyl]-1H-pyrazole-4-carboxylate (500 mg), 3-azabicyclo[3.1.0]hexane hydrochloride (384 mg), $Cs_2CO_3$ (1.6 g), tris(dibenzylideneacetone)dipalladium(0) ($Pd_2dba_3$, 74 mg) and 4,5-bis(diphenylphosphino)-9,9-dimethylxanthene (Xantphos, 93 mg) in DMF (1.3 mL) and toluene (3.8 mL) is purged for 10 minutes with argon. The vial is sealed and the mixture is heated to 90° C. for 2 h. Then the mixture is partitioned between water and EtOAc. The aqueous phase is extracted with EtOAc. The combined organic phases are dried ($MgSO_4$), concentrated in vacuo and the residue is chromatographed on silica gel (petroleum ether/EtOAc 90:10→20:80) to give the title compound. LC (Method 1): $t_R$=0.91 min; Mass spectrum (ESI+): m/z=314 [M+H]$^+$.

Intermediate 45

(6-{3-Azabicyclo[3.1.0]hexan-3-yl}pyridin-3-yl) methanol

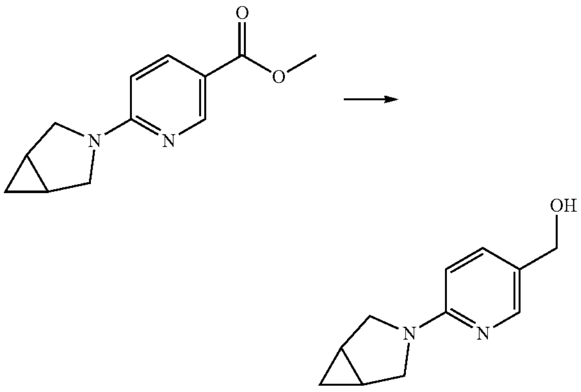

A mixture of methyl 6-{3-azabicyclo[3.1.0]hexan-3-yl}pyridine-3-carboxylate (8 g) and $LiBH_4$ (2 M solution in THF, 20 mL) in THF (60 mL) and MeOH (3 mL) is stirred for 12 h at 60° C. $LiBH_4$ (2 M solution in THF, 5 mL) is added and the mixture is stirred for 2 h at 60° C. Then the mixture is cooled to 0° C. and carefully treated with water. The mixture is concentrated and the residue is partitioned between water and EtOAc. The organic phase is dried ($MgSO_4$), concentrated in vacuo and the residue is chromatographed on silica gel (DCM/MeOH 0:100→90:10) to give the title compound. LC (Method 1): $t_R$=0.79 min; Mass spectrum (ESI+): m/z=191 [M+H]$^+$.

Intermediates 45-1 to 45-3 are prepared in analogy to Intermediate 45:

| Intermediate | Structure | $t_R$ | Mass spectrum (ESI+): m/z [M + H]$^+$ | LC Method |
|---|---|---|---|---|
| 45-1 | 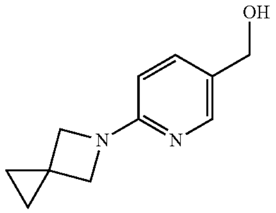 [SMILES: OCc1ccc(N2CC3(CC3)C2)nc1] | 0.80 | 191 | Method 1 |
| 45-2 | 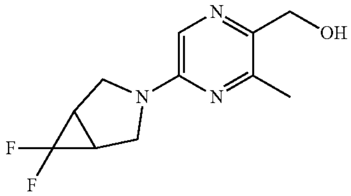 [SMILES: Cc1nc(N2CC3C(C2)C3(F)F)cnc1CO] | 0.71 | 242 | Method 2 |
| 45-3 | 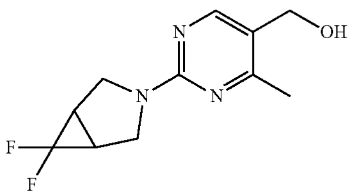 [SMILES: Cc1nc(N2CC3C(C2)C3(F)F)ncc1CO] | 0.62 | 242 | Method 2 |

| Intermediate | Reaction comment |
|---|---|
| 45-2 | The reaction is conducted in 1,4-dioxane/MeOH 15:1 for 3 h at rt. |
| 45-3 | The reaction is conducted for 12 h at 50° C. |

| Intermediate | Name | Name of Starting Material |
|---|---|---|
| 45-1 | (6-{5-Azaspiro[2.3]hexan-5-yl}pyridin-3-yl)-methanol | Methyl 6-{5-azaspiro[2.3]hexan-5-yl}pyridine-3-carboxylate |
| 45-2 | (5-{6,6-Difluoro-3-azabicyclo[3.1.0]hexan-3-yl}-3-methylpyrazin-2-yl)methanol | Methyl 5-{6,6-difluoro-3-azabicyclo[3.1.0]-hexan-3-yl}-3-methylpyrazine-2-carboxylate |
| 45-3 | (2-{6,6-Difluoro-3-azabicyclo[3.1.0]hexan-3-yl}-4-methylpyrimidin-5-yl)methanol | Ethyl 2-{6,6-difluoro-3-azabicyclo[3.1.0]-hexan-3-yl}-4-methylpyrimidine-5-carboxylate |

Intermediate 46

1-[(6-{5-Azaspiro[2.3]hexan-5-yl}pyridin-3-yl)methyl]-1H-pyrazole-4-carboxylic acid trifluoroacetate

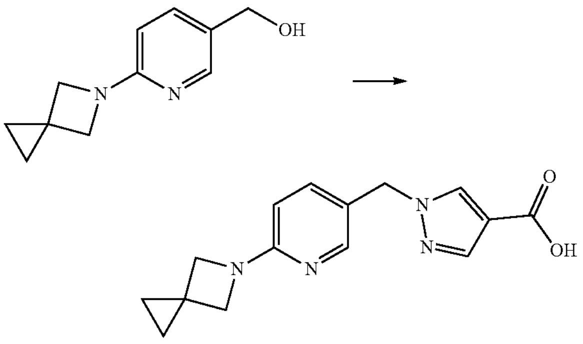

To an ice-cooled solution of (6-{5-azaspiro[2.3]hexan-5-yl}pyridin-3-yl)methanol (170 mg), ethyl 1H-pyrazole-4-carboxylate (130 mg) and tributylphosphine (450 μL) in THF (5 mL) is added dropwise DBAD (338 mg). The mixture is stirred for 48 h. Then the mixture is concentrated in vacuo. The residue is taken up in MeOH (10 mL) and aqueous NaOH (1 M, 5 mL) and stirred for 2 h at rt. After neutralization with trifluoroacetic acid the crude product is purified by HPLC on reversed phase (ACN, water) to give the title compound.

LC (Method 1): $t_R$=0.65 min; Mass spectrum (ESI+): m/z=285 $[M+H]^+$.

Intermediate 47

1-[(6-{5-Azaspiro[2.3]hexan-5-yl}pyridin-3-yl)methyl]-1H-imidazole-4-carboxylic acid trifluoroacetate

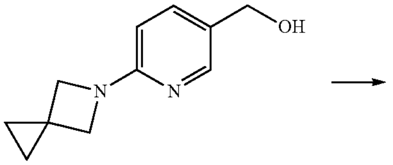

-continued

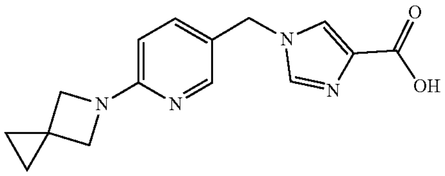

In a microwave vial a mixture of (6-{5-azaspiro[2.3]hexan-5-yl}pyridin-3-yl)methanol (85 mg), ethyl 1H-imidazole-4-carboxylate (76 mg) and p-toluenesulfonic acid (90 mg) in ACN (4 mL) is heated for 48 h to 75° C., for 3 h to 90° C., for 3 h to 100° C. and for 12 h to 80° C. After cooling to rt the mixture is diluted with ACN and purified by HPLC on reversed phase (ACN, water). The product thus obtained is dissolved in MeOH (2 mL) and aqueous NaOH (1 M, 500 μL). After stirring for 2 h at rt the mixture is neutralized with trifluoroacetic and purified by HPLC on reversed phase (ACN, water) to give the title compound. LC (Method 2): $t_R$=0.40 min; Mass spectrum (ESI+): m/z=285 $[M+H]^+$.

Intermediate 48

1-[(6-{6,6-Difluoro-3-azabicyclo[3.1.0]hexan-3-yl}-2-formylpyridin-3-yl)methyl]-N-[(4R)-1-methyl-1H,4H,5H,6H-cyclopenta[d]imidazol-4-yl]-1H-1,2,3-triazole-4-carboxamide

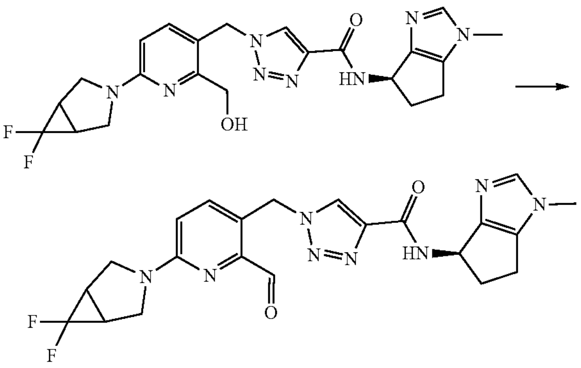

A mixture of 1-[(6-{6,6-difluoro-3-azabicyclo[3.1.0]hexan-3-yl}-2-(hydroxymethyl)pyridin-3-yl)methyl]-N-[(4R)-1-methyl-1H,4H,5H,6H-cyclopenta[d]imidazol-4-yl]-1H-1,2,3-triazole-4-carboxamide (19 mg) and 1,1,1-tris (acetyloxy)-1,1-dihydro-1,2-benziodoxol-3-(1H)-one (Dess-Martin periodinane, 26 mg) in DCM (2 mL) is stirred for 3 h at rt. The mixture is partitioned between saturated aqueous $NaHCO_3$ and DCM. The aqueous phase is extracted with DCM for three times. The combined organic phases are dried ($Na_2SO_4$) and concentrated in vacuo to give the title compound. LC (Method 1): $t_R$=0.89 min; Mass spectrum (ESI+): m/z=469 $[M+H]^+$.

Intermediate 48-1 is prepared in analogy to Intermediate 48:

| Intermediate | Structure | $t_R$ | Mass spectrum (ESI+): m/z $[M + H]^+$ | LC Method |
|---|---|---|---|---|
| 48-1 | 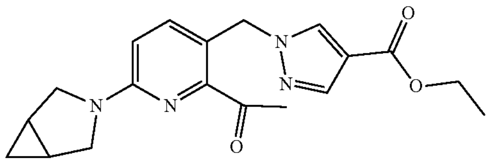 [SMILES: CCOC(=O)c1cnn(Cc2ccc(N3CC4CC4C3)nc2C(C)=O)c1] | 1.10 | 355 | Method 2 |

| Intermediate | Reaction comment |
|---|---|
| 48-1 | The crude product is chromatographed on silica gel (petroleum ether/EtOAc 95:5 → 70:30) to give the title compound. |

| Intermediate | Name | Name of Starting Material |
|---|---|---|
| 48-1 | Ethyl 1-[(2-acetyl-6-{3-azabicyclo[3.1.0]hexan-3-yl}pyridin-3-yl)methyl]-1H-pyrazole-4-carboxylate | Ethyl 1-[(6-{3-azabicyclo[3.1.0]hexan-3-yl}-2-(1-hydroxyethyl)pyridin-3-yl)methyl]-1H-pyrazole-4-carboxylate |

Intermediate 49

Ethyl 6-{5-azaspiro[2.3]hexan-5-yl}-3-{[4-(ethoxy-carbonyl)-1H-imidazol-1-yl]methyl}pyridine-2-carboxylate

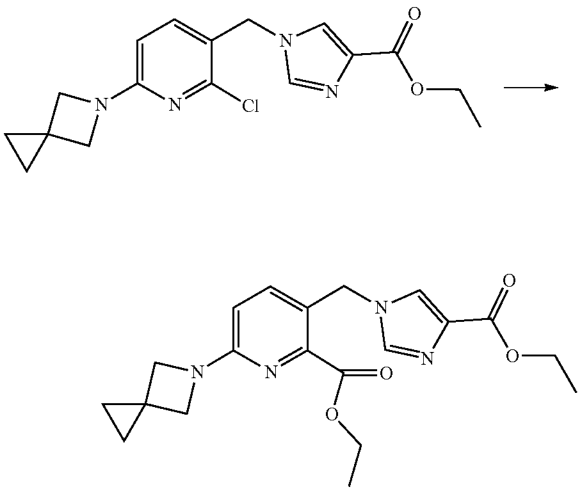

A mixture of ethyl 1-[(6-{5-azaspiro[2.3]hexan-5-yl}-2-chloropyridin-3-yl)methyl]-1H-imidazole-4-carboxylate (860 mg), bis(triphenylphosphine)palladium(II) dichloride ($Pd(PPh_3)_2Cl_2$, 200 mg) and triethylamine (1.1 mL) in EtOH (60 mL) is heated under a carbonmonoxide atmosphere of 10 bar to 130° C. for 5 h. The solvents are evaporated in vacuo and the residue is purified by HPLC on reversed phase (ACN, water) to give the title compound.

LC (Method 2): $t_R$=0.89 min; Mass spectrum (ESI+): m/z=385 $[M+H]^+$.

Intermediates 49-1 to 49-4 are prepared in analogy to Intermediate 49:

| Intermediate | Structure | $t_R$ | Mass spectrum (ESI+): m/z $[M + H]^+$ | LC Method |
|---|---|---|---|---|
| 49-1 | 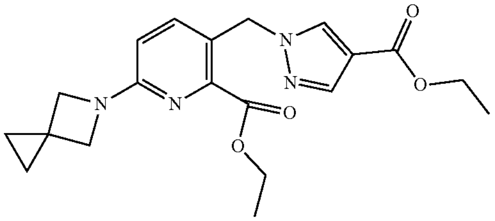 [SMILES: CCOC(=O)c1cnn(Cc2ccc(N3CC4(CC4)C3)nc2C(=O)OCC)c1] | 1.03 | 385 | Method 2 |
| 49-2 | 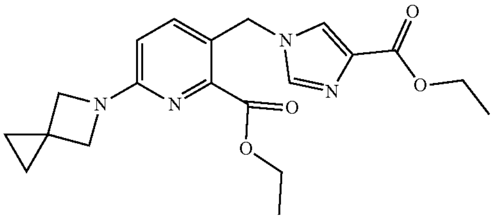 [SMILES: CCOC(=O)c1cn(Cc2ccc(N3CC4(CC4)C3)nc2C(=O)OCC)cn1] | 0.89 | 385 | Method 2 |
| 49-3 | 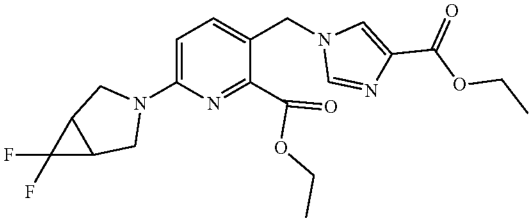 [SMILES: CCOC(=O)c1cn(Cc2ccc(N3CC4C(C3)C4(F)F)nc2C(=O)OCC)cn1] | 0.89 | 421 | Method 2 |
| 49-4 | 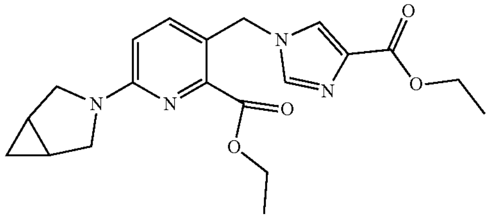 [SMILES: CCOC(=O)c1cn(Cc2ccc(N3CC4CC4C3)nc2C(=O)OCC)cn1] | 0.91 | 385 | Method 2 |

| Intermediate | Reaction comment |
|---|---|
| 49-3 | The reaction is conducted under a carbonmonoxide atmosphere of 5 bar at 90° C. |
| 49-4 | The reaction is conducted under a carbonmonoxide atmosphere of 4 bar at 100° C. for 14 h. |

| Intermediate | Name | Name of Starting Material |
|---|---|---|
| 49-1 | Ethyl 6-{5-azaspiro[2.3]hexan-5-yl}-3-{[4-(ethoxycarbonyl)-1H-pyrazol-1-yl]methyl}pyridine-2-carboxylate | Ethyl 1-[(6-{5-azaspiro[2.3]hexan-5-yl}-2-chloropyridin-3-yl)methyl]-1H-pyrazole-4-carboxylate |
| 49-2 | Ethyl 6-{5-azaspiro[2.3]hexan-5-yl}-3-{[4-(ethoxycarbonyl)-1H-imidazol-1-yl]methyl}pyridine-2-carboxylate | Ethyl 1-[(6-{5-azaspiro[2.3]hexan-5-yl}-2-chloropyridin-3-yl)methyl]-1H-imidazole-4-carboxylate |
| 49-3 | Ethyl 6-{6,6-difluoro-3-azabicyclo[3.1.0]hexan-3-yl}-3-{[4-(ethoxycarbonyl)-1H-imidazol-1-yl]methyl}pyridine-2-carboxylate | Ethyl 1-[(2-bromo-6-{6,6-difluoro-3-azabicyclo[3.1.0]hexan-3-yl}pyridin-3-yl)methyl]-1H-imidazole-4-carboxylate |
| 49-4 | Ethyl 6-{3-azabicyclo[3.1.0]hexan-3-yl}-3-{[4-(ethoxycarbonyl)-1H-imidazol-1-yl]methyl}pyridine-2-carboxylate | Ethyl 1-[(6-{3-azabicyclo[3.1.0]hexan-3-yl}-2-bromopyridin-3-yl)methyl]-1H-imidazole-4-carboxylate |

Intermediate 50

Ethyl 1-[(6-{5-azaspiro[2.3]hexan-5-yl}-2-(hydroxymethyl)pyridin-3-yl)methyl]-1H-imidazole-4-carboxylate bistrifluoroacetate

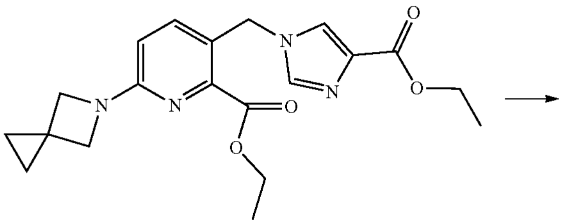

-continued

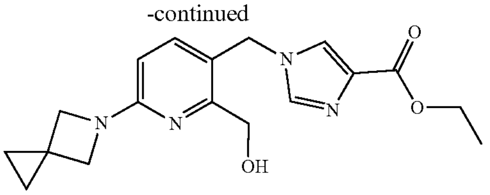

$LiBH_4$ (150 mg) is added portionwise to a mixture of ethyl 6-{5-azaspiro[2.3]hexan-5-yl}-3-{[4-(ethoxycarbonyl)-1H-imidazol-1-yl]methyl}pyridine-2-carboxylate (705 mg) in THF (15 mL). The mixture is stirred for 2 h at rt, cooled to 0° C., treated with aqueous HCl (4 M, 2 mL) and purified by HPLC on reversed phase (ACN, water) to give the title compound. LC (Method 1): $t_R$=0.91 min; Mass spectrum (ESI+): m/z=343 $[M+H]^+$.

Intermediates 50-1 to 50-2 are prepared in analogy to Intermediate 50:

| Intermediate | Structure | $t_R$ | Mass spectrum (ESI+): m/z $[M+H]^+$ | LC Method |
|---|---|---|---|---|
| 50-1 | 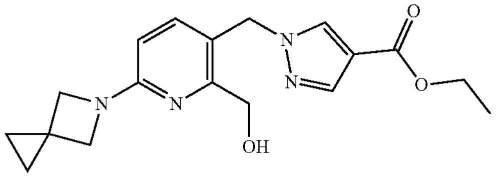 [SMILES: CCOC(=O)c1cnn(Cc2ccc(N3CC4(CC4)C3)nc2CO)c1] | 1.00 | 343 | Method 1 |
| 50-2 | 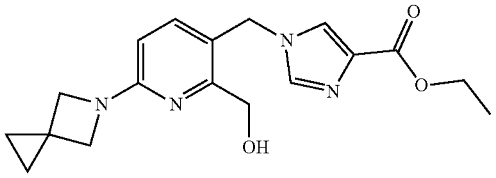 [SMILES: CCOC(=O)c1cn(Cc2ccc(N3CC4(CC4)C3)nc2CO)cn1] | 0.91 | 343 | Method 1 |

| Intermediate | Name | Name of Starting Material |
|---|---|---|
| 50-1 | Ethyl 1-[(6-{5-azaspiro[2.3]hexan-5-yl}-2-(hydroxymethyl)pyridin-3-yl)methyl]-1H-pyrazole-4-carboxylate trifluoroacetate | Ethyl 6-{5-azaspiro[2.3]hexan-5-yl}-3-{[4-(ethoxycarbonyl)-1H-pyrazol-1-yl]methyl}pyridine-2-carboxylate |
| 50-2 | Ethyl 1-[(6-{5-azaspiro[2.3]hexan-5-yl}-2-(hydroxymethyl)pyridin-3-yl)methyl]-1H-imidazole-4-carboxylate | Ethyl 6-{5-azaspiro[2.3]hexan-5-yl}-3-{[4-(ethoxycarbonyl)-1H-imidazol-1-yl]methyl}pyridine-2-carboxylate |

Intermediate 51

1-[(6-{6,6-Difluoro-3-azabicyclo[3.1.0]hexan-3-yl}pyridin-3-yl)methyl]-1H-pyrazole-4-carboxylic acid trifluoroacetate

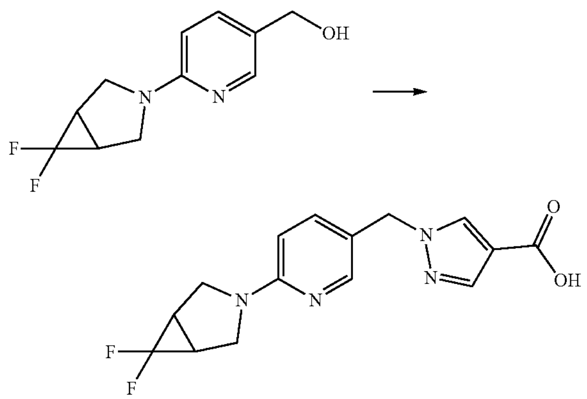

To an ice-cooled solution of (6-{6,6-difluoro-3-azabicyclo[3.1.0]hexan-3-yl}pyridin-3-yl)methanol (158 mg), ethyl 1H-pyrazole-4-carboxylate (100 mg) and tributylphosphine (210 μL) in THF (2 mL) is added dropwise DBAD (190 mg). The mixture is stirred for 30 minutes and is then treated with aqueous NaOH (4 M, 750 μL). After stirring for 12 h at rt, aqueous HCl (4 M, 750 μL) is added and the mixture is purified by HPLC on reversed phase (ACN, water) to give the title compound. LC (Method 2): $t_R$=0.63 min; Mass spectrum (ESI+): m/z=321 $[M+H]^+$.

Intermediate 52

Ethyl 1-[(6-{3-azabicyclo[3.1.0]hexan-3-yl}-2-(1-hydroxyethyl)pyridin-3-yl)methyl]-1H-pyrazole-4-carboxylate

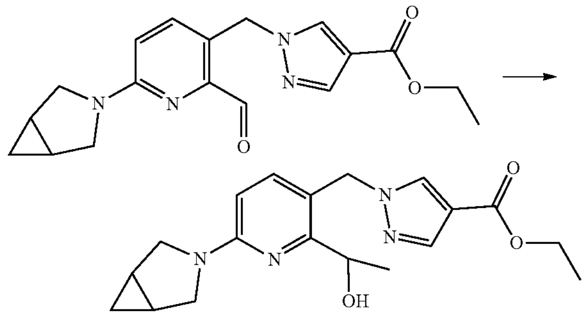

$CH_3MgBr$ (3 M in diethylether, 1.22 mL) is added dropwise at −40° C. to a mixture of ethyl 1-[(6-{3-azabicyclo[3.1.0]-hexan-3-yl}-2-formylpyridin-3-yl)methyl]-1H-pyrazole-4-carboxylate (1 g) in THF (20 mL). The mixture is stirred for minutes while warming to −25° C. Aqueous HCl (1 M, 4 mL) is added. After stirring for 5 minutes the mixture is partitioned between saturated aqueous $NaHCO_3$ and EtOAc. The aqueous phase is extracted with EtOAc. The combined organic phases are washed with brine, dried ($MgSO_4$) and concentrated in vacuo to give the title compound.

LC (Method 2): $t_R$=0.73 min; Mass spectrum (ESI+): m/z=357 $[M+H]^+$.

Intermediate 52-1 is prepared in analogy to Intermediate 52:

| Intermediate | Structure | $t_R$ | Mass spectrum (ESI+): m/z $[M + H]^+$ | LC Method |
|---|---|---|---|---|
| 52-1 | 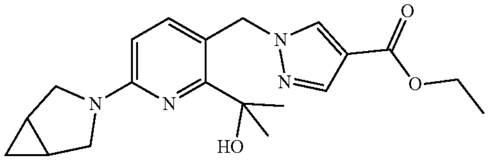 [SMILES: CCOC(=O)c1cnn(Cc2ccc(N3CC4CC4C3)nc2C(C)(C)O)c1] | 1.10 | 371 | Method 1 |

| Intermediate | Reaction comment |
|---|---|
| 52-1 | The reaction is conducted at −10° C. |

| Intermediate | Name | Name of Starting Material |
|---|---|---|
| 52-1 | Ethyl 1-[(6-{3-azabicyclo[3.1.0]hexan-3-yl}-2-(2-hydroxypropan-2-yl)pyridin-3-yl)methyl]-1H-pyrazole-4-carboxylate | Ethyl 1-[(2-acetyl-6-{3-azabicyclo[3.1.0]hexan-3-yl}pyridin-3-yl)methyl]-1H-pyrazole-4-carboxylate |

Intermediate 53

Ethyl 1-[(6-{3-azabicyclo[3.1.0]hexan-3-yl}-2-[(1R)-1-hydroxyethyl]pyridin-3-yl)methyl]-1H-pyrazole-4-carboxylate

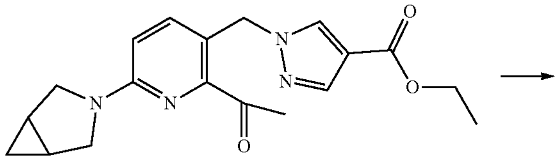

-continued

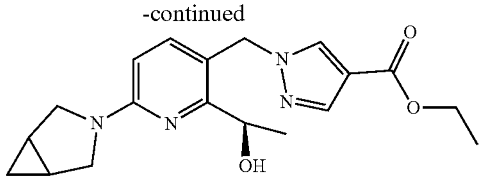

Triethylamine (246 μL) is dissolved in DCM (3 mL), cooled to 0° C. and treated successively with formic acid (75 μL), ethyl 1-[(2-acetyl-6-{3-azabicyclo[3.1.0]hexan-3-yl}pyridin-3-yl)methyl]-1H-pyrazole-4-carboxylate (200 mg) and chloro{[(1R,2R)-(−)-2-amino-1,2-diphenylethyl](4-toluenesulfonyl)amido}(mesitylene)ruthenium(II) (RuCl[(R,R)-Tsdpen(mesitylene), 23 mg]. The mixture is stirred for 24 h while warming to rt. The mixture is concentrated, taken up in THF (5 mL), treated with a solution of $NH_3$ in MeOH (7 M, 1 mL), and water (1 mL). Then the mixture is purified by HPLC on reversed phase (ACN, water) to give the title compound.

LC (Method 1): $t_R$=1.03 min; Mass spectrum (ESI+): m/z=357 [M+H]$^+$.

Intermediate 53-1 is prepared in analogy to Intermediate 53:

-continued

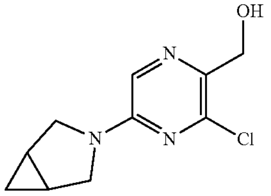

$LiBH_4$ (744 mg) is added portionwise to an ice-cooled mixture of methyl 5-{3-azabicyclo[3.1.0]hexan-3-yl}-3-chloropyrazine-2-carboxylate (4.33 g) in THF (80 mL). The mixture is stirred for 2 h at rt. After cooling to 0° C. aqueous HCl (4 M, 10 mL) is added and the mixture is stirred for 10 minutes. Then the mixture is partitioned between saturated aqueous $NaHCO_3$ and EtOAc. The aqueous phase is extracted twice with EtOAc. The combined organic phases are dried ($MgSO_4$), concentrated in vacuo and the residue is chromatographed on silica gel (petroleum ether/EtOAc 80:20→50:50) to give the title compound. LC (Method 2): $t_R$=0.85 min; Mass spectrum (ESI+): m/z=226 [M+H]$^+$.

| Intermediate | Structure | $t_R$ | Mass spectrum (ESI+): m/z [M + H]$^+$ | LC Method |
|---|---|---|---|---|
| 53-1 | 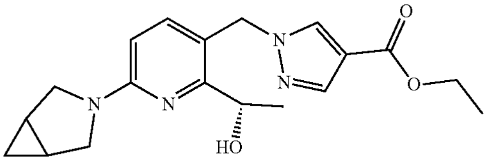 [SMILES: CCOC(=O)c1cnn(Cc2ccc(N3CC4CC4C3)nc2[C@H](C)O)c1] | 1.03 | 357 | Method 1 |

| Intermediate | Reaction comment |
|---|---|
| 53-1 | RuCl[(S,S)-Tsdpen(mesitylene) is used instead of RuCl[(R,R)-Tsdpen(mesitylene). |

| Intermediate | Name | Name of Starting Material |
|---|---|---|
| 53-1 | Ethyl 1-[(6-{3-azabicyclo[3.1.0]hexan-3-yl}-2-[(1S)-1-hydroxyethyl]pyridin-3-yl)methyl]-1H-pyrazole-4-carboxylate | Ethyl 1-[(2-acetyl-6-{3-azabicyclo[3.1.0]hexan-3-yl}pyridin-3-yl)methyl]-1H-pyrazole-4-carboxylate |

Intermediate 54

(5-{3-Azabicyclo[3.1.0]hexan-3-yl}-3-chloropyrazin-2-yl)methanol

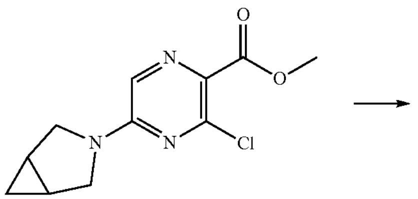

Intermediate 55

Ethyl 1-[(6-{6,6-difluoro-3-azabicyclo[3.1.0]hexan-3-yl}-2-methylpyridin-3-yl)methyl]-1H-pyrazole-4-carboxylate

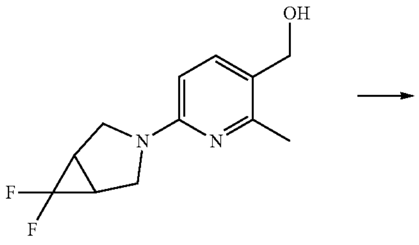

-continued

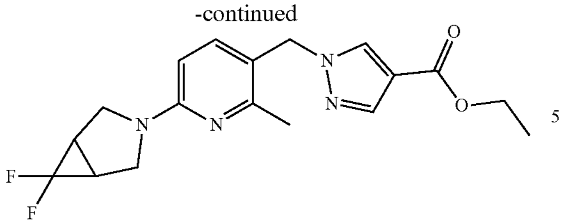

Under argon atmosphere an ice-cooled mixture of (6-{6,6-difluoro-3-azabicyclo[3.1.0]hexan-3-yl}-2-methylpyridin-3-yl)methanol (20 g) and DIPEA (32 mL) in DCM (400 mL) is treated dropwise with $CH_3SO_2Cl$ (7.2 mL). The mixture is stirred for 15 minutes and then treated with ethyl 1H-pyrazole-4-carboxylate (12 g). After stirring for 4 h at rt the mixture is partitioned between water and DCM. The organic phase is dried ($MgSO_4$) and concentrated in vacuo to give the crude product which is directly used in the next step.

LC (Method 2): $t_R$=0.76 min; Mass spectrum (ESI+): m/z=363 $[M+H]^+$.

Intermediate 55-1 is prepared in analogy to Intermediate 55:

-continued

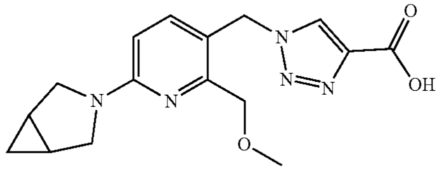

| Intermediate | Structure | $t_R$ | Mass spectrum (ESI+): m/z $[M + H]^+$ | LC Method |
|---|---|---|---|---|
| 55-1 | 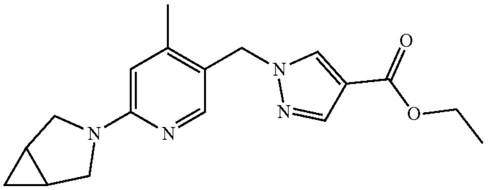 [SMILES: CCOC(=O)c1cnn(Cc2cnc(N3CC4CC4C3)cc2C)c1] | 1.02 | 327 | Method 1 |

| Intermediate | Reaction comment |
|---|---|
| 55-1 | After the addition of ethyl 1H-pyrazole-4-carboxylate the reaction mixture is stirred for 12 h at rt. |

| Intermediate | Name | Name of Starting Material 1 | Name of Starting Material 2 |
|---|---|---|---|
| 55-1 | Ethyl 1-[(6-{3-azabicyclo[3.1.0]-hexan-3-yl}-4-methylpyridin-3-yl)-methyl]-1H-pyrazole-4-carboxylate | (6-{3-Azabicyclo[3.1.0]hexan-3-yl}-4-methylpyridin-3-yl)-methanol | Ethyl 1H-pyrazole-4-carboxylate |

Intermediate 56

1-[(6-{3-Azabicyclo[3.1.0]hexan-3-yl}-2-(methoxymethyl)pyridin-3-yl)methyl]-1H-1,2,3-triazole-4-carboxylic acid

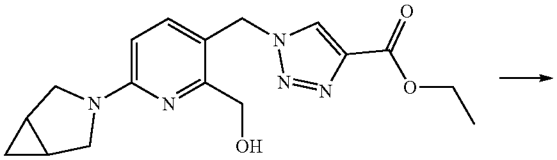

To a solution of ethyl 1-[6-{3-azabicyclo[3.1.0]hexan-3-yl}-2-(hydroxymethyl)pyridin-3-yl)methyl]-1H-1,2,3-triazole-4-carboxylate (86 mg) in DMF (2 mL) is added at 0° C. NaH (60% in mineral oil, 25 mg). The mixture is stirred for 30 minutes at rt, treated with $CH_3I$ (16 μL) and stirred for 12 h. Water is carefully added. The mixture is concentrated in vacuo and the residue is taken up in DCM/isopropanol 1:1. Then the mixture is filtered and the filtrate is concentrated in vacuo to give the crude product which is directly used in the next step.

LC (Method 2): $t_R$=0.58 min; Mass spectrum (ESI+): m/z=330 $[M+H]^+$.

Intermediates 56-1 to 56-2 are prepared in analogy to Intermediate 56:

| Intermediate | Structure | $t_R$ | Mass spectrum (ESI+): m/z $[M + H]^+$ | LC Method |
|---|---|---|---|---|
| 56-1 | 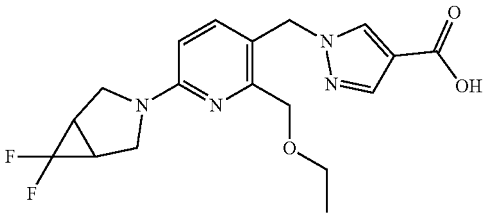 [SMILES: CCOCc1nc(N2CC3C(C2)C3(F)F)ccc1Cn1cc(C(=O)O)cn1] | 0.71 | 379 | Method 2 |
| 56-2 | 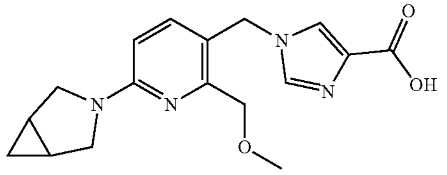 [SMILES: COCc1nc(N2CC3CC3C2)ccc1Cn1cnc(C(=O)O)c1] | 0.53 | 329 | Method 2 |

| Intermediate | Reaction comment |
|---|---|
| 56-1 | Iodoethane is used instead of $CH_3I$. |
| 56-2 | After addition of $CH_3I$ the mixture is stirred for 4 h. Then aqueous NaOH (4M) is added until pH of 12 is reached and the mixture is stirred for 1 h at 50° C. The mixture is neutralized by addition of acetic acid and purified by HPLC on reversed phase (ACN, water). |

| Intermediate | Name | Name of Starting Material |
|---|---|---|
| 56-1 | 1-[(6-{6,6-Difluoro-3-azabicyclo[3.1.0]hexan-3-yl}-2-(ethoxymethyl)pyridin-3-yl)methyl]-1H-pyrazole-4-carboxylic acid | Ethyl 1-[(6-{6,6-difluoro-3-azabicyclo[3.1.0]-hexan-3-yl}-2-(hydroxymethyl)pyridin-3-yl)methyl]-1H-pyrazole-4-carboxylate |
| 56-2 | 1-[(6-{3-Azabicyclo[3.1.0]hexan-3-yl}-2-(methoxymethyl)pyridin-3-yl)methyl]-1H-imidazole-4-carboxylic acid | Ethyl 1-[(6-{3-azabicyclo[3.1.0]hexan-3-yl}-2-(hydroxymethyl)pyridin-3-yl)methyl]-1H-imidazole-4-carboxylate |

Intermediate 57

1-[(6-{6,6-Difluoro-3-azabicyclo[3.1.0]hexan-3-yl}-2-methoxypyridin-3-yl)methyl]-1H-imidazole-4-carboxylic acid

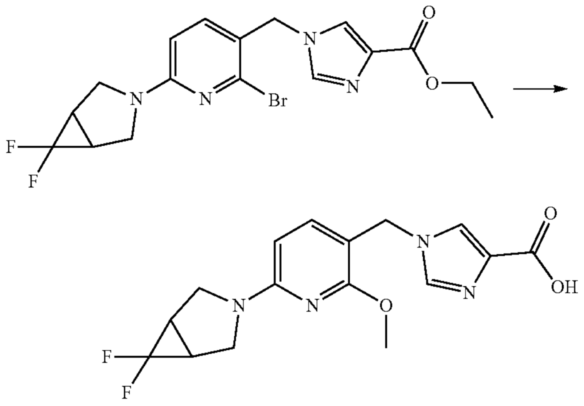

A mixture of ethyl 1-[(2-bromo-6-{6,6-difluoro-3-azabicyclo[3.1.0]hexan-3-yl}pyridin-3-yl)methyl]-1H-imidazole-4-carboxylate (190 mg) and $NaOCH_3$ (1 M in MeOH, 4.5 mL) is heated for 2.5 h to 155° C. and for 3 h to 165° C. Purification by HPLC on reversed phase (ACN, water) gives the title compound. LC (Method 2): $t_R$=0.84 min.

Intermediate 57-1 is prepared in analogy to Intermediate 57:

| Intermediate | Structure | $t_R$ | Mass spectrum (ESI+): m/z $[M + H]^+$ | LC Method |
|---|---|---|---|---|
| 57-1 | 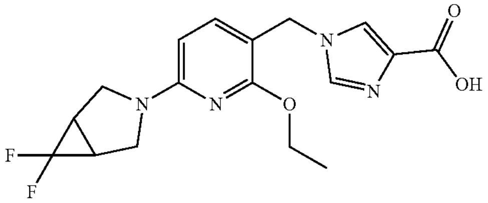 [SMILES: CCOc1nc(N2CC3C(C2)C3(F)F)ccc1Cn1cnc(C(=O)O)c1] | 0.85 | | Method 2 |

| Intermediate | Reaction comment |
|---|---|
| 57-1 | $NaOCH_2CH_3$ in EtOH is used instead of $NaOCH_3$ in MeOH. The reaction is conducted for 12 h at 150° C. |

| Intermediate | Name | Name of Starting Material |
|---|---|---|
| 57-1 | 1-[(6-{6,6-Difluoro-3-azabicyclo[3.1.0]hexan-3-yl}-2-ethoxypyridin-3-yl)methyl]-1H-imidazole-4-carboxylic acid | Ethyl 1-[(2-chloro-6-{6,6-difluoro-3-azabicyclo[3.1.0]hexan-3-yl}pyridin-3-yl)methyl]-1H-imidazole-4-carboxylate |

Intermediate 58

1-[(6-{3-Azabicyclo[3.1.0]hexan-3-yl}-2-(hydroxymethyl)pyridin-3-yl)methyl]-1H-imidazole-4-carboxylic acid Intermediate 58-1

Ethyl 1-[(6-{3-azabicyclo[3.1.0]hexan-3-yl}-2-(hydroxymethyl)pyridin-3-yl)methyl]-1H-imidazole-4-carboxylate

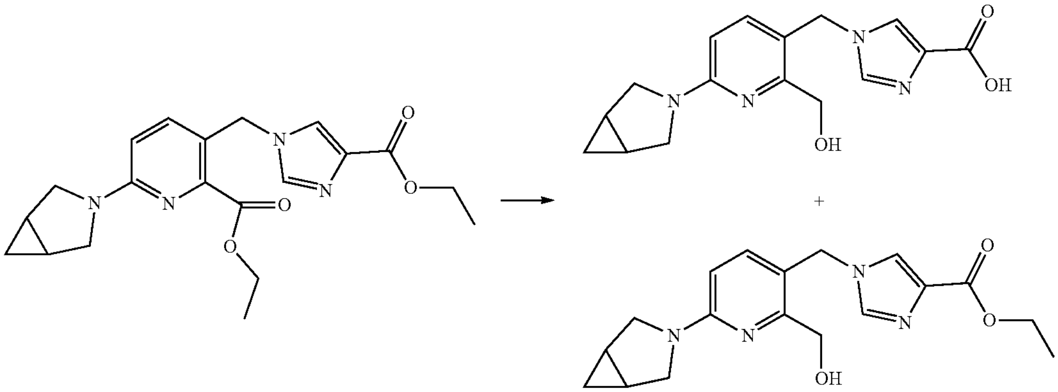 [SMILES: CCOC(=O)c1cn(Cc2ccc(N3CC4CC4C3)nc2C(=O)OCC)cn1 ; CCOC(=O)c1cn(Cc2ccc(N3CC4CC4C3)nc2CO)cn1 ; O=C(O)c1cn(Cc2ccc(N3CC4CC4C3)nc2CO)cn1]

$LiBH_4$ (356 mg) is added portionwise to a mixture of ethyl 6-{3-azabicyclo[3.1.0]hexan-3-yl}-3-{[4-(ethoxycarbonyl)-1H-imidazol-1-yl]methyl}pyridine-2-carboxylate (1.65 g) in THF (25 mL). The mixture is stirred for 14 h at rt, cooled to 0° C. and treated with aqueous HCl (1 M, 5 mL). Then the mixture is neutralized by addition of NaOH (4 M) and purified by HPLC on reversed phase (ACN, water) to give the title compounds.

1-[(6-{3-Azabicyclo[3.1.0]hexan-3-yl}-2-(hydroxymethyl)pyridin-3-yl)methyl]-1H-imidazole-4-carboxylic acid LC (Method 1): $t_R$=0.64 min; Mass spectrum (ESI+): m/z=315 $[M+H]^+$.

Ethyl 1-[(6-{3-azabicyclo[3.1.0]hexan-3-yl}-2-(hydroxymethyl)pyridin-3-yl)methyl]-1H-imidazole-4-carboxylate LC (Method 1): $t_R$=0.94 min; Mass spectrum (ESI+): m/z=343 $[M+H]^+$.

Intermediate 59

2-Hydroxy-5-iodo-4-methylpyridine-3-carbonitrile

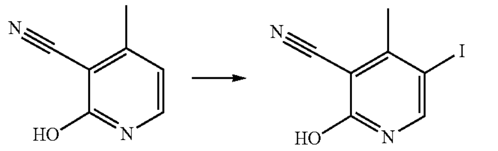

Under argon atmosphere an ice-cooled mixture of 2-hydroxy-4-methylpyridine-3-carbonitrile (3 g) in DCM (100 mL) is treated with trifluoroacetic acid (5 mL). Then N-iodosuccinimide (7.55 g) is added portionwise. The mixture is stirred for 3 h while warming to rt. The mixture is concentrated in vacuo, half-saturated aqueous $Na_2S_2O_3$ is added and the mixture is stirred for 10 minutes. The precipitate is collected by filtration, washed with water and diethylether and dried in vacuo to give the title compound. LC (Method 2): $t_R$=0.72 min; Mass spectrum (ESI+): m/z=261 $[M+H]^+$.

Intermediate 60

2-Chloro-5-iodo-4-methylpyridine-3-carbonitrile

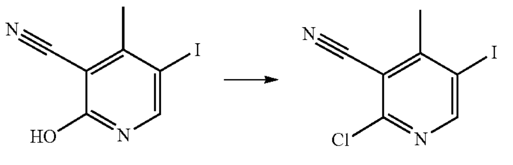

A mixture of 2-hydroxy-5-iodo-4-methylpyridine-3-carbonitrile (6.27 g) in $POCl_3$ is stirred for 5 h at 100° C. The mixture is concentrated in vacuo. The residue is taken up in DCM (200 mL) and treated with water. Then the mixture is neutralized by careful addition of saturated aqueous $NaHCO_3$. The phases are separated and the aqueous phase is extracted twice with DCM. The combined organic phases are washed with saturated aqueous $NaHCO_3$, dried ($MgSO_4$) and concentrated in vacuo to give the crude product which is directly used in the next step.

LC (Method 1): $t_R$=1.02 min; Mass spectrum (ESI+): m/z=278 $[M+H]^+$.

Intermediate 61

2-{6,6-Difluoro-3-azabicyclo[3.1.0]hexan-3-yl}-5-formyl-4-methylpyridine-3-carbonitrile

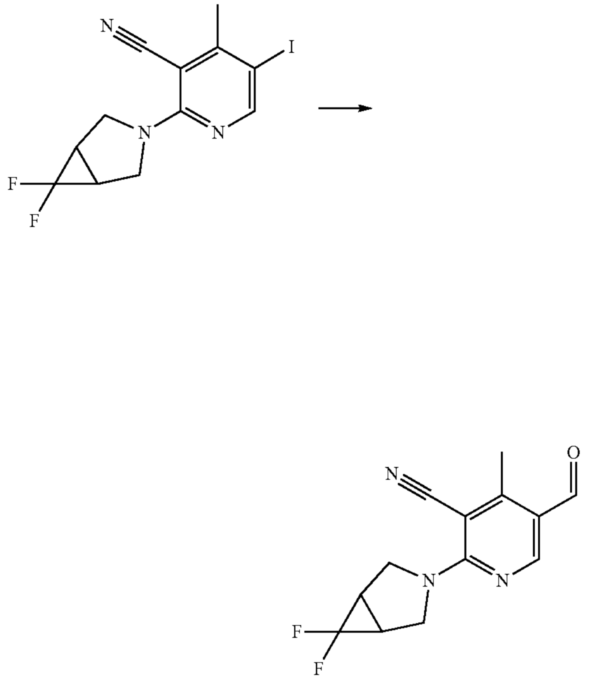

A mixture of 2-{6,6-difluoro-3-azabicyclo[3.1.0]hexan-3-yl}-5-iodo-4-methylpyridine-3-carbonitrile (2.3 g) in THF (30 mL) is cooled to −78° C., treated dropwise with isopropylmagnesium chloride (iPrMgCl, 2 M solution in THF, 3.82 mL) and stirred for 30 minutes. Then the mixture is warmed to 0° C., treated dropwise with DMF (2.47 mL) and stirred for 40 minutes. Water is carefully added and the mixture is partitioned between half-saturated aqueous $NH_4Cl$ and EtOAc. The aqueous phase is extracted with EtOAc and the combined organic phases are concentrated in vacuo to give the crude product which is directly used in the next step.

LC (Method 2): $t_R$=0.96 min; Mass spectrum (ESI+): m/z=264 $[M+H]^+$.

Intermediate 61-1 is prepared in analogy to Intermediate 61:

| Intermediate | Structure | $t_R$ | Mass spectrum (ESI+): m/z $[M + H]^+$ | LC Method |
|---|---|---|---|---|
| 61-1 | 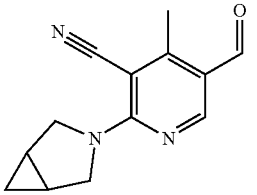 [SMILES: Cc1c(C=O)cnc(N2CC3CC3C2)c1C#N] | 0.98 | 228 | Method 2 |

| Intermediate | Name | Name of Starting Material |
|---|---|---|
| 61-1 | 2-{3-Azabicyclo[3.1.0]hexan-3-yl}-5-formyl-4-methylpyridine-3-carbonitrile | 2-{3-Azabicyclo[3.1.0]hexan-3-yl}-5-iodo-4-methylpyridine-3-carbonitrile |

Intermediate 62

N'-[(E)-(6-{6,6-Difluoro-3-azabicyclo[3.1.0]hexan-3-yl}-2-methylpyridin-3-yl)methylidene]acetohydrazide

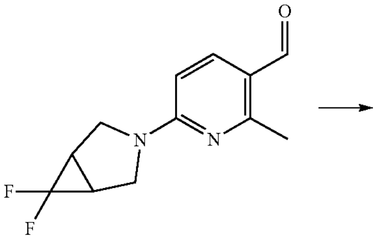

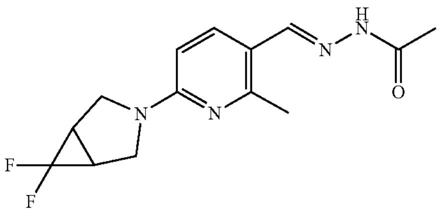

A mixture of 6-{6,6-difluoro-3-azabicyclo[3.1.0]hexan-3-yl}-2-methylpyridine-3-carbaldehyde (5.8 g) and acetohydrazide (2.36 g) in MeOH (100 mL) is refluxed for 12 h. The mixture is concentrated in vacuo, taken up in toluene, treated with p-toluenesulfonic acid (100 mg) and refluxed in a Dean-Stark apparatus for 16 h. After cooling to rt the precipitate is collected by filtration, washed with tert.-butyl-methyl-ether and dried in vacuo to give the title compound. LC (Method 2): $t_R$=0.64 min; Mass spectrum (ESI+): m/z=295 $[M+H]^+$.

Intermediate 62-1 is prepared in analogy to Intermediate 62:

| Intermediate | Structure | $t_R$ | Mass spectrum (ESI+): m/z $[M + H]^+$ | LC Method |
|---|---|---|---|---|
| 62-1 | 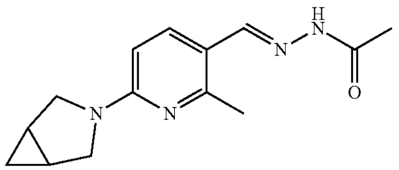 [SMILES: CC(=O)N/N=C/c1ccc(N2CC3CC3C2)nc1C] | 0.61 | 259 | Method 2 |

| Intermediate | Name | Name of Starting Material |
|---|---|---|
| 62-1 | N'-[(E)-(6-{3-Azabicyclo[3.1.0]hexan-3-yl}-2-methylpyridin-3-yl)methylidene]acetohydrazide | 6-{3-Azabicyclo[3.1.0]hexan-3-yl}-2-methylpyridine-3-carbaldehyde |

Intermediate 63

N'-[(6-{6,6-Difluoro-3-azabicyclo[3.1.0]hexan-3-yl}-2-methylpyridin-3-yl)methyl]acetohydrazide

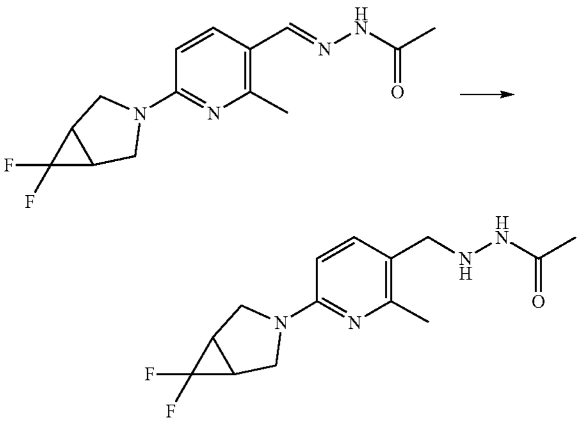

A mixture of N'-[(E)-(6-{6,6-difluoro-3-azabicyclo[3.1.0]hexan-3-yl}-2-methylpyridin-3-yl)methylidene]acetohydrazide (5.6 g) and 10% palladium on carbon (300 mg) in MeOH (80 mL) and THF (20 mL) is shaken under hydrogen atmosphere (3 bar) at rt for 3.5 h. The mixture is filtered, the filtrate is concentrated and the residue is taken up in tert.-butyl-methyl-ether (100 mL) and EtOAc (10 mL). After stirring for 3 h the precipitate is collected by filtration, washed with tert.-butyl-methyl-ether and dried in vacuo to give the title compound.

LC (Method 2): $t_R$=0.58 min; Mass spectrum (ESI+): m/z=297 $[M+H]^+$.

Intermediate 63-1 is prepared in analogy to Intermediate 63:

| Intermediate | Structure | $t_R$ | Mass spectrum (ESI+): m/z $[M + H]^+$ | LC Method |
|---|---|---|---|---|
| 63-1 | 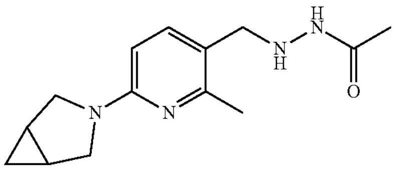 [SMILES: CC(=O)NNCc1ccc(N2CC3CC3C2)nc1C] | 0.57 | 261 | Method 2 |

| Intermediate | Name | Name of Starting Material |
|---|---|---|
| 63-1 | N'-[(6-{3-Azabicyclo[3.1.0]hexan-3-yl}-2-methylpyridin-3-yl)methyl]acetohydrazide | N'-[(E)-(6-{3-Azabicyclo[3.1.0]hexan-3-yl}-2-methylpyridin-3-yl)methylidene]acetohydrazide |

Intermediate 64

Ethyl 3-(chloromethyl)-1-[(6-{6,6-difluoro-3-azabicyclo[3.1.0]hexan-3-yl}-2-methylpyridin-3-yl)methyl]-1H-pyrazole-4-carboxylate

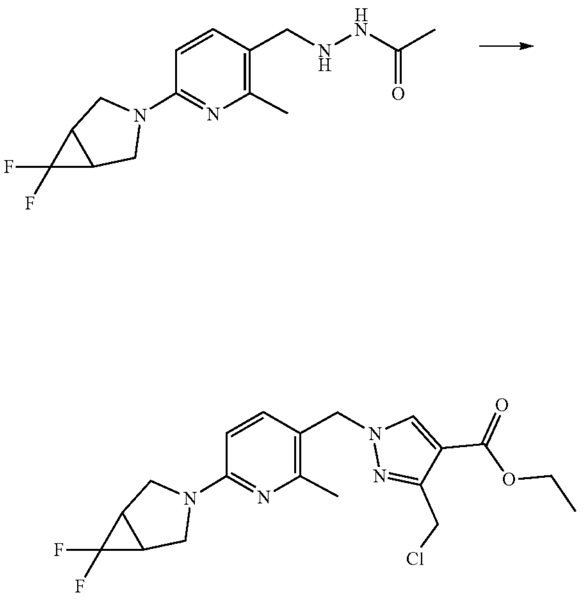

A mixture of N'-[(6-{6,6-difluoro-3-azabicyclo[3.1.0]hexan-3-yl}-2-methylpyridin-3-yl)methyl]acetohydrazide (1.9 g) and ethyl 4-chloro-2-(ethoxymethylidene)-3-oxobutanoate (1.68 g) in EtOH (30 mL) is stirred for 12 h at rt. The mixture is concentrated and then partitioned between DCM and saturated aqueous $Na_2CO_3$. The aqueous phase is extracted with DCM. The combined organic phases are washed with brine, dried ($MgSO_4$) and concentrated in vacuo to give the title compound. LC (Method 2): $t_R$=0.82 min; Mass spectrum (ESI+): m/z=411 $[M+H]^+$.

Intermediate 64-1 is prepared in analogy to Intermediate 64:

| Intermediate | Structure | $t_R$ | Mass spectrum (ESI+): m/z $[M + H]^+$ | LC Method |
|---|---|---|---|---|
| 64-1 | 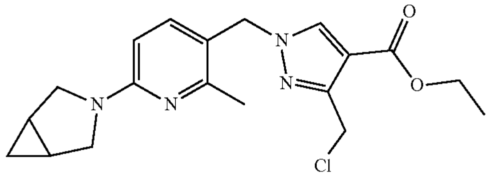 [SMILES: CCOC(=O)c1cn(Cc2ccc(N3CC4CC4C3)nc2C)nc1CCl] | 0.81 | 375 | Method 2 |

| Intermediate | Name | Name of Starting Material |
|---|---|---|
| 64-1 | Ethyl 1-[(6-{3-azabicyclo[3.1.0]hexan-3-yl}-2-methylpyridin-3-yl)methyl]-3-(chloromethyl)-1H-pyrazole-4-carboxylate | N'-[(6-{3-Azabicyclo[3.1.0]hexan-3-yl}-2-methylpyridin-3-yl)methyl]acetohydrazide |

Intermediate 65

Ethyl 1-[(6-{3-azabicyclo[3.1.0]hexan-3-yl}-2-methylpyridin-3-yl)methyl]-3-(cyanomethyl)-1H-pyrazole-4-carboxylate

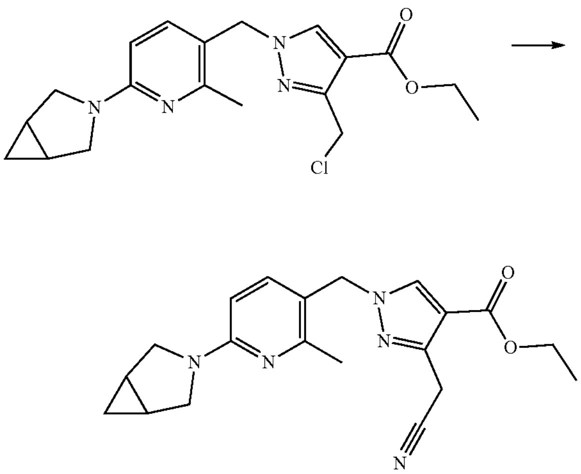

A mixture of ethyl 1-[(6-{3-azabicyclo[3.1.0]hexan-3-yl}-2-methylpyridin-3-yl)methyl]-3-(chloromethyl)-1H-pyrazole-4-carboxylate (700 mg) and KCN (250 mg) in DMSO (5 mL) and water (2 mL) is heated to 85° C. for 2 h. The mixture is partitioned between water and EtOAc. The aqueous phase is extracted 4 times with EtOAc. The combined organic phases are washed with brine, dried ($MgSO_4$) and concentrated in vacuo to give the title compound.

LC (Method 2): $t_R$=0.74 min; Mass spectrum (ESI+): m/z=366 $[M+H]^+$.

Intermediate 66

1-[(6-{3-Azabicyclo[3.1.0]hexan-3-yl}-2-methylpyridin-3-yl)methyl]-3-(cyanomethyl)-N-[(4R)-1-methyl-1H,4H,5H,6H-cyclopenta[d]imidazol-4-yl]-1H-pyrazole-4-carboxamide

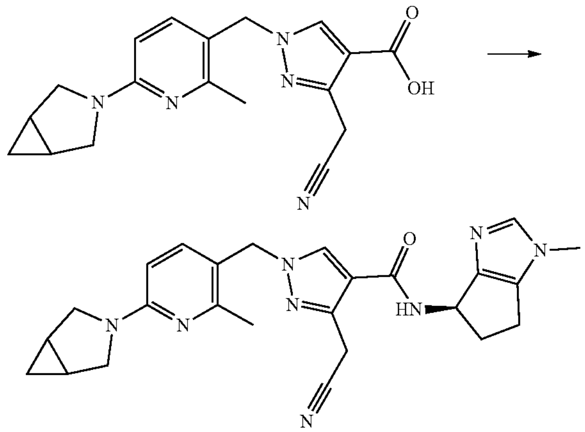

A mixture of 1-[(6-{3-azabicyclo[3.1.0]hexan-3-yl}-2-methylpyridin-3-yl)methyl]-3-(cyanomethyl)-1H-pyrazole-4-carboxylic acid (230 mg), DIPEA (466 μL) and O-(7-azabenzotriazol-1-yl)-N,N,N',N'-tetramethyluronium-hexafluorophosphat (HATU, 272 mg) in DMF (4 mL) is stirred for 5 min. (4R)-1-Methyl-1H,4H,5H,6H-cyclopenta[d]imidazol-4-amine dihydrochloride (143 mg) is added and the mixture is stirred for 2 h. The mixture is partitioned between water and EtOAc. The aqueous phase is extracted three times with EtOAc. The combined organic phases are washed with brine, dried ($MgSO_4$), Concentrated in vacuo and chromatographed on silica gel (DCM/(DCM/MeOH/7 N $NH_3$ in MeOH 50:48:2) 90:10→60:40) to give the title compound.

LC (Method 2): $t_R$=0.63 min; Mass spectrum ($ESI^+$): m/z=457 $[M+H]^+$.

Intermediates 66-1 to 66-4 are prepared in analogy to Intermediate 66:

| Intermediate | Structure | $t_R$ | Mass spectrum (ESI+): m/z $[M + H]^+$ | LC Method |
|---|---|---|---|---|
| 66-1 | 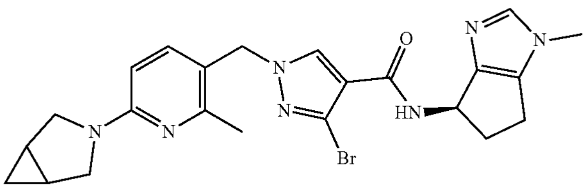 [SMILES: Cc1nc(N2CC3CC3C2)ccc1Cn1cc(C(=O)N[C@@H]2CCc3c2ncn3C)c(Br)n1] | 0.97 | 496 | Method 1 |
| 66-2 | 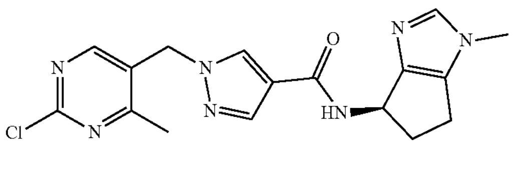 [SMILES: Cc1nc(Cl)ncc1Cn1cc(C(=O)N[C@@H]2CCc3c2ncn3C)cn1] | 0.64 | 372 | Method 2 |

-continued

| Intermediate | Structure | $t_R$ | Mass spectrum (ESI+): m/z $[M + H]^+$ | LC Method |
|---|---|---|---|---|
| 66-3 | 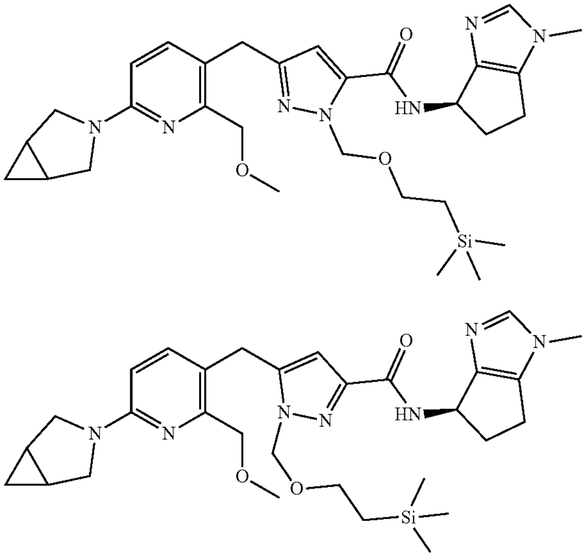 (mixture of isomers) | 0.78 | 578 | Method 2 |
| 66-4 | 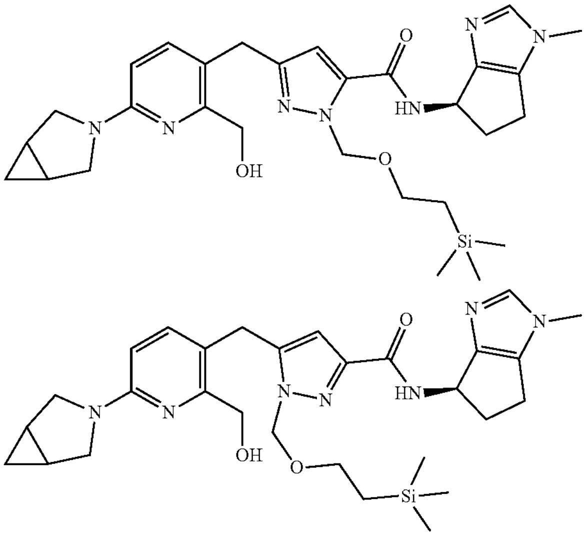 (mixture of isomers) | 0.76 | 564 | Method 2 |

| Intermediate | Reaction comment |
|---|---|
| 66-3 | The product is obtained as a mixture of isomers. |
| 66-4 | The product is obtained as a mixture of isomers. |

| Intermediate | Name | Name of Starting Material |
|---|---|---|
| 66-1 | 1-[(6-{3-Azabicyclo[3.1.0]hexan-3-yl}-2-methylpyridin-3-yl)methyl]-3-bromo-N-[(4R)-1-methyl-1H,4H,5H,6H-cyclopenta[d]imidazol-4-yl]-1H-pyrazole-4-carboxamide | 1-[(6-{3-Azabicyclo[3.1.0]hexan-3-yl}-2-methylpyridin-3-yl)methyl]-3-bromo-1H-pyrazole-4-carboxylic acid |

-continued

| Intermediate | Name | Name of Starting Material |
|---|---|---|
| 66-2 | 1-[(2-Chloro-4-methylpyrimidin-5-yl)methyl]-N-[(4R)-1-methyl-1H,4H,5H,6H-cydopenta[d]-imidazol-4-yl]-1H-pyrazole-4-carboxamide | 1-[(2-Chloro-4-methylpyrimidin-5-yl)methyl]-1H-pyrazole-4-carboxylic acid |
| 66-3 | 3-[(6-{3-Azabicyclo[3.1.0]hexan-3-yl}-2-(methoxymethyl)pyridin-3-yl)methyl]-N-[(4R)-1-methyl-1H,4H,5H,6H-cyclopenta[d]imidazol-4-yl]-1-{[2-(trimethylsilyl)ethoxy]methyl}-1H-pyrazole-5-carboxamide and 5-[(6-{3-Azabicyclo[3.1.0]hexan-3-yl}-2-(methoxymethyl)pyridin-3-yl)methyl]-N-[(4R)-1-methyl-1H,4H,5H,6H-cyclopenta[d]imidazol-4-yl]-1-{[2-(trimethylsilyl)ethoxy]methyl}-1H-pyrazole-3-carboxamide (mixture of isomers) | 3-[(6-{3-Azabicyclo[3.1.0]hexan-3-yl}-2-(methoxymethyl)pyridin-3-yl)methyl]-1-{[2-(trimethylsilyl)ethoxy]methyl}-1H-pyrazole-5-carboxylic acid and 5-[(6-{3-Azabicyclo[3.1.0]hexan-3-yl}-2-(methoxymethyl)pyridin-3-yl)methyl]-1-{[2-(trimethylsilyl)ethoxy]methyl}-1H-pyrazole-3-carboxylic acid (mixture of isomers) |
| 66-4 | 3-[(6-{3-Azabicyclo[3.1.0]hexan-3-yl}-2-(hydroxymethyl)pyridin-3-yl)methyl]-N-[(4R)-1-methyl-1H,4H,5H,6H-cyclopenta[d]imidazol-4-yl]-1-{[2-(trimethylsilyl)ethoxy]methyl}-1H-pyrazole-5-carboxamide and 5-[(6-{3-Azabicyclo[3.1.0]hexan-3-yl}-2-(hydroxymethyl)pyridin-3-yl)methyl]-N-[(4R)-1-methyl-1H,4H,5H,6H-cyclopenta[d]imidazol-4-yl]-1-{[2-(trimethylsilyl)ethoxy]methyl}-1H-pyrazole-3-carboxamide (mixture of isomers) | 3-[(6-{3-Azabicyclo[3.1.0]hexan-3-yl}-2-(hydroxymethyl)pyridin-3-yl)methyl]-1-{[2-(trimethylsilyl)ethoxy]methyl}-1H-pyrazole-5-carboxylic acid and 5-[(6-{3-Azabicyclo[3.1.0]hexan-3-yl}-2-(hydroxymethyl)pyridin-3-yl)methyl]-1-{[2-(trimethylsilyl)ethoxy]methyl}-1H-pyrazole-3-carboxylic acid (mixture of isomers) |

Intermediate 67

Methyl 2-{1-[(6-{3-azabicyclo[3.1.0]hexan-3-yl}-2-methylpyridin-3-yl)methyl]-4-{[(4R)-1-methyl-1H, 4H,5H,6H- cyclopenta[d]imidazol-4-yl]carbamoyl}-1H-pyrazol-3-yl}acetate

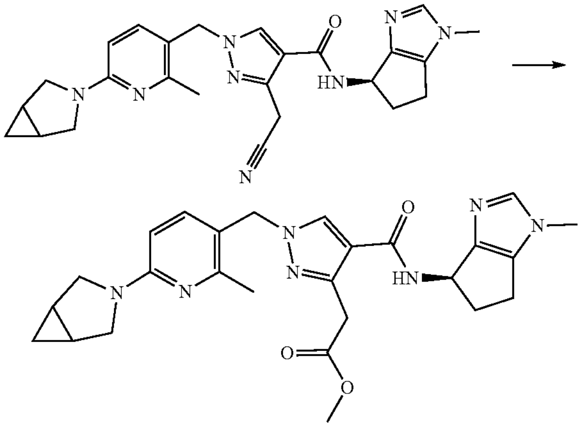

A mixture of 1-[(6-{3-azabicyclo[3.1.0]hexan-3-yl}-2-methylpyridin-3-yl)methyl]-3-(cyanomethyl)-N-[(4R)-1-methyl-1H,4H,5H,6H-cyclopenta[d]imidazol-4-yl]-1H-pyrazole-4-carboxamide (330 mg) in $CH_3COOH$ (2 mL) and concentrated aqueous HCl (2 mL) is heated for 1 h to 110° C. The mixture is cooled to rt treated with aqueous NaOH (4 M, 15 mL) and stirred for 10 minutes. Then aqueous HCl (4 M, 15 mL) is added and the mixture is washed twice with EtOAc. The aqueous phase is concentrated in vacuo and the residue is added to a mixture of acetyl chloride (50 μL) in MeOH (10 mL). The mixture is heated to 90° C. for 90 minutes. After cooling to rt the mixture is neutralized with aqueous NaOH (1 M), concentrated in vacuo and the residue is chromatographed on silica gel (cyclohexane/EtOAc 90:10→70:30) to give the title compound.

LC (Method 2): $t_R$=0.63 min; Mass spectrum ($ESI^+$): m/z=490 $[M+H]^+$.

Intermediate 68

Ethyl 1-[(6-{3-azabicyclo[3.1.0]hexan-3-yl}-2-fluoropyridin-3-yl)methyl]-1H-imidazole-4-carboxylate

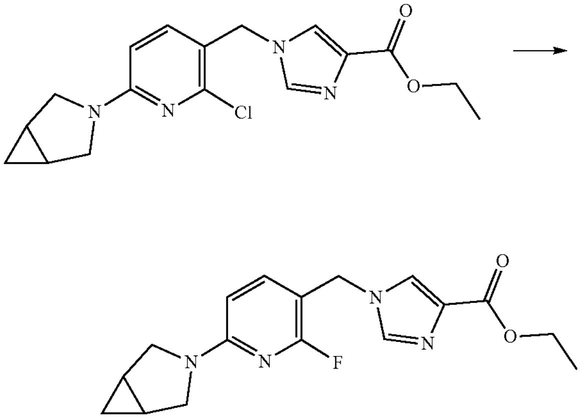 [SMILES: CCOC(=O)c1cn(Cc2ccc(N3CC4CC4C3)nc2Cl)cn1 ; CCOC(=O)c1cn(Cc2ccc(N3CC4CC4C3)nc2F)cn1]

A mixture of ethyl 1-[(6-{3-azabicyclo[3.1.0]hexan-3-yl}-2-chloropyridin-3-yl)methyl]-1H-imidazole-4-carboxylate (200 mg) and tetrabutylammonium fluoride trihydrate (269 mg) in DMF (2 mL) is heated to 80° C. for 12 h. After cooling to rt the mixture is partitioned between saturated aqueous $NaHCO_3$ and EtOAc. The aqueous phase is extracted for 4 times with EtOAc. The combined organic phases are concentrated in vacuo and purified by HPLC on reversed phase (ACN, water) to give the title compound. LC (Method 1): $t_R$=0.96 min.

Intermediate 69

2-{3-Azabicyclo[3.1.0]hexan-3-yl}-5-bromopyridine-3-carbonitrile

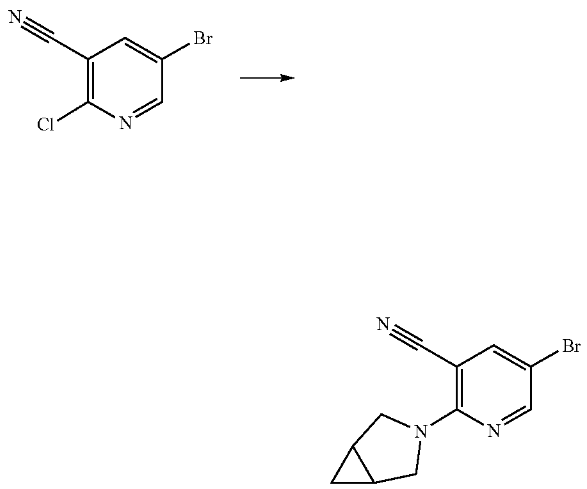

Under argon atmosphere a mixture of 5-bromo-2-chloropyridine-3-carbonitrile (1.0 g), 3-azabicyclo[3.1.0]hexane hydrochloride (605 mg) and DIPEA (2 mL) in DMF (10 mL) is heated to 80° C. for 2 h. The mixture is cooled, concentrated, partitioned between water and EtOAc and the phases are separated. The aqueous is extracted twice with EtOAc. The combined organic phases are washed with brine, dried ($MgSO_4$), concentrated and the residue is chromatographed on silica gel (petroleum ether/EtOAc 98:2→95:5) to give the title compound.

LC (Method 2): $t_R$=1.13 min; Mass spectrum (ESI+): m/z=264 $[M+H]^+$.

Intermediate 69-1 is prepared in analogy to Intermediate 69:

| Intermediate | Structure | $t_R$ | Mass spectrum (ESI+): m/z $[M + H]^+$ | LC Method |
|---|---|---|---|---|
| 69-1 | 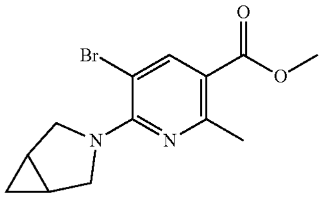 [SMILES: COC(=O)c1cc(Br)c(N2CC3CC3C2)nc1C] | 1.25 | 311 | Method 1 |

| Intermediate | Reaction comment |
|---|---|
| 69-1 | The reaction is conducted for 12 h at 80° C. |

| Intermediate | Name | Name of Starting Material 1 | Name of Starting Material 2 |
|---|---|---|---|
| 69-1 | Methyl 6-{3-azabicyclo[3.1.0]-hexan-3-yl}-5-bromo-2-methylpyridine-3-carboxylate | Methyl 5-bromo-6-chloro-2-methylpyridine-3-carboxylate | 3-azabicyclo[3.1.0]hexane hydrochloride |

Intermediate 70

Methyl 6-{3-azabicyclo[3.1.0]hexan-3-yl}-5-cyano-pyridine-3-carboxylate

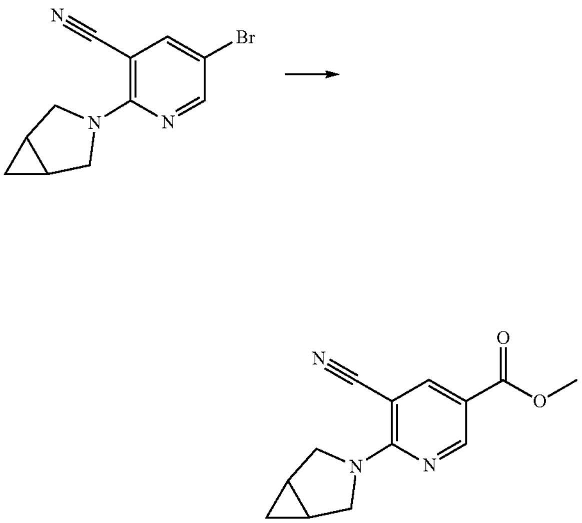

Under argon atmosphere a mixture of 2-{3-azabicyclo[3.1.0]hexan-3-yl}-5-bromopyridine-3-carbonitrile (773 mg) and triethylamine (489 NL) and (1,1'-bis(diphenylphosphino)ferrocene)palladium(II) dichloride (119 mg) in DMF (15 mL) and MeOH (15 mL) is heated to 80° C. for 22 h under a CO atmosphere of 10 bar. The mixture is cooled, concentrated in vacuo and the residue is purified by HPLC on reversed phase (ACN, water) to give the title compound.

LC (Method 1): $t_R$=0.99 min; Mass spectrum (ESI+): m/z=244 $[M+H]^+$.

Intermediates 70-1 to 70-3 are prepared in analog to Intermediate 70:

| Intermediate | Structure | $t_R$ | Mass spectrum (ESI+): m/z $[M + H]^+$ | LC Method |
|---|---|---|---|---|
| 70-1 | 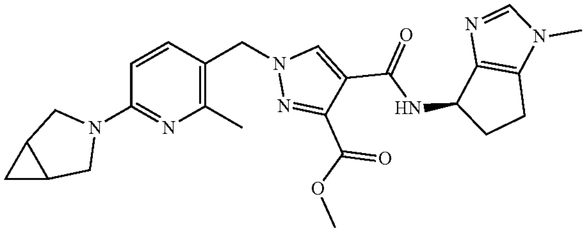 [SMILES: COC(=O)c1nn(Cc2ccc(N3CC4CC4C3)nc2C)cc1C(=O)N[C@@H]1CCc2c1ncn2C] | 0.64 | 476 | Method 2 |
| 70-2 | 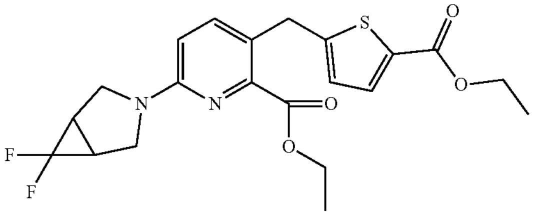 [SMILES: CCOC(=O)c1ccc(Cc2ccc(N3CC4C(C3)C4(F)F)nc2C(=O)OCC)s1] | 1.14 | 437 | Method 2 |
| 70-3 | 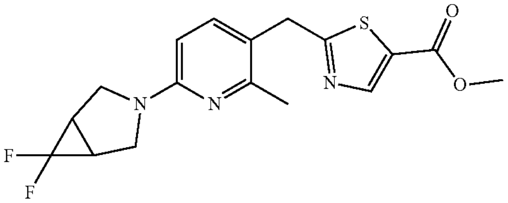 | 0.72 | 366 | Method 2 |

| Intermediate | Reaction comment |
|---|---|
| 70-1 | MeOH is used instead of a DMF/MeOH mixture. The reaction is conducted at 100° C. for 2 h under a CO atmosphere of 12 bar |
| 70-2 | EtOH is used instead of MeOH. Bis(triphenylphosphine)palladium(II) dichloride is used instead of (1,1'-bis(diphenylphosphino)ferrocene)palladium(II) dichloride. The reaction is conducted at 90° C. for 17 h under a CO atmosphere of 5 bar. |
| 70-3 | The reaction is conducted at 90° C. for 6 h. |

| Intermediate | Name | Name of Starting Material |
|---|---|---|
| 70-1 | Methyl 1-[(6-{3-azabicyclo[3.1.0]hexan-3-yl}-2-methylpyridin-3-yl)methyl]-4-{[(4R)-1-methyl-1H,4H,5H,6H-cyclopenta[d]imidazol-4-yl]carbamoyl}-1H-pyrazole-3-carboxylate | 1-[(6-{3-Azabicyclo[3.1.0]hexan-3-yl}-2-methylpyridin-3-yl)methyl]-3-bromo-N-[(4R)-1-methyl-1H,4H,5H,6H-cyclopenta[d]imidazol-4-yl]-1H-pyrazole-4-carboxamide |
| 70-2 | Ethyl 6-{6,6-difluoro-3-azabicyclo[3.1.0]hexan-3-yl}-3-{[5-(ethoxycarbonyl)thiophen-2-yl]methyl}pyridine-2-carboxylate | Ethyl 5-[(2-bromo-6-{6,6-difluoro-3-azabicyclo[3.1.0]hexan-3-yl}pyridin-3-yl)methyl]thiophene-2-carboxylate |
| 70-3 | Methyl 2-[(6-{6,6-difluoro-3-azabicyclo[3.1.0]-hexan-3-yl}-2-methylpyridin-3-yl)methyl]-1,3-thiazole-5-carboxylate | 3-{5-[(5-Bromo-1,3-thiazol-2-yl)methyl]-6-methylpyridin-2-yl}-6,6-difluoro-3-azabicyclo[3.1.0]hexane |

Intermediate 71

2-{3-Azabicyclo[3.1.0]hexan-3-yl}-5-(hydroxymethyl)pyridine-3-carbonitrile

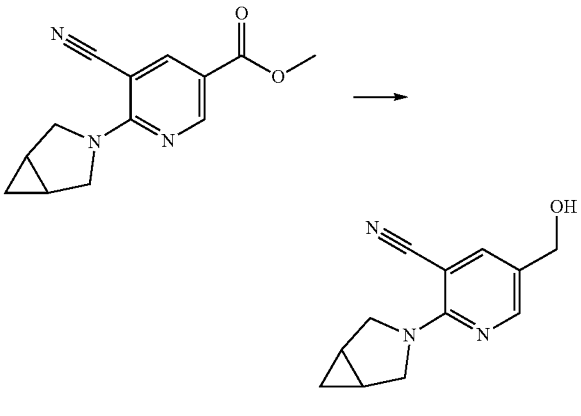

A mixture of methyl 6-{3-azabicyclo[3.1.0]hexan-3-yl}-5-cyanopyridine-3-carboxylate (300 mg) in THF (5 mL) is cooled to −50° C. and treated dropwise with $LiAlH_4$ (1 M solution in THF, 1.4 mL). The mixture is stirred for 3 h at −20° C. and then carefully treated with water (1 mL). After dilution with DCM the mixture is stirred for 30 minutes. The precipitate is filtered off and the filter cake is washed with DM. The combined filtrates are diluted with water. The phases are separated. The aqueous phase is extracted twice with DEM. The combined organic phases are dried ($MgSO_4$), concentrated and purified by HPLC on reversed phase (ACN, water) to give the title compound.

LC (Method 1): $t_R$=0.81 min; Mass spectrum (ESI+): m/z=216 $[M+H]^+$.

Intermediates 71-1 to 71-2 are prepared in analogy to Intermediate 71:

| Intermediate | Structure | $t_R$ | Mass spectrum (ESI+): m/z $[M + H]^+$ | LC Method |
|---|---|---|---|---|
| 71-1 | 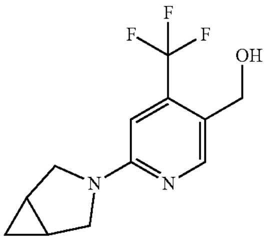 [SMILES: OCc1cnc(N2CC3CC3C2)cc1C(F)(F)F] | 0.93 | 259 | Method 1 |
| 71-2 | 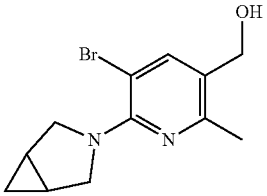 [SMILES: Cc1nc(N2CC3CC3C2)c(Br)cc1CO] | 0.77 | 283 | Method 2 |

| Intermediate | Reaction comment |
|---|---|
| 71-1 | The reaction is conducted for 3 h at −25° C. Then 10% $NH_4Cl$ in water is carefully added. The mixture is partitioned between water and EtOAc and filtered over celite. The phases are separated and the aqueous phase is extracted with EtOAc. The combined organic phases are dried ($MgSO_4$) and concentrated in vacuo to give the crude product, which is used directly in the next step. |

| Intermediate | Name | Name of Starting Material |
|---|---|---|
| 71-1 | (6-{3-Azabicyclo[3.1.0]hexan-3-yl}-4-(trifluoromethyl)pyridin-3-yl)methanol | Methyl 6-{3-azabicyclo[3.1.0]hexan-3-yl}-4-(trifluoromethyl)pyridine-3-carboxylate |
| 71-2 | (6-{3-Azabicyclo[3.1.0]hexan-3-yl}-5-bromo-2-methylpyridin-3-yl)methanol | Methyl 6-{3-azabicyclo[3.1.0]hexan-3-yl}-5-bromo-2-methylpyridine-3-carboxylate |

Intermediate 72

Ethyl 1-[(6-{3-azabicyclo[3.1.0]hexan-3-yl}-2-methylpyridin-3-yl)methyl]-3-(methoxymethyl)-1H-pyrazole-4-carboxylate

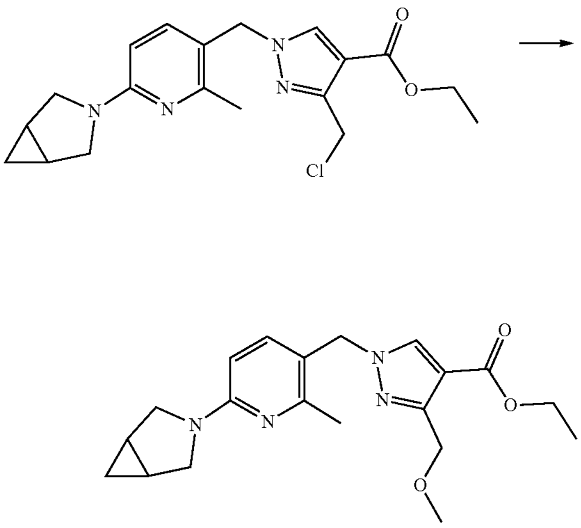

A mixture of ethyl 1-[(6-{3-azabicyclo[3.1.0]hexan-3-yl}-2-methylpyridin-3-yl)methyl]-3-(chloromethyl)-1H-pyrazole-4-carboxylate (100 mg) and NaI (10 mg) in MeOH (4 mL) is heated under argon atmosphere in a microwave vial at 90° C. for 12 h. The mixture is diluted with MeOH and water and purified by HPLC on reversed phase (ACN, water) to give the title compound. LC (Method 1): $t_R$=1.07 min; Mass spectrum (ESI+): m/z=371 $[M+H]^+$.

Intermediate 72-1 is prepared in analogy to Intermediate 72:

| Intermediate | Structure | $t_R$ | Mass spectrum (ESI+): m/z $[M + H]^+$ | LC Method |
|---|---|---|---|---|
| 72-1 | 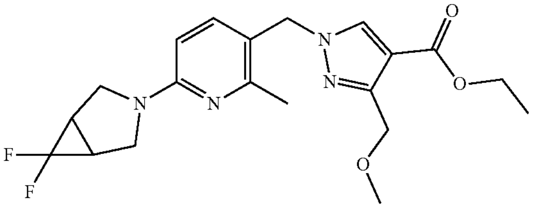 [SMILES: CCOC(=O)c1cn(Cc2ccc(N3CC4C(C3)C4(F)F)nc2C)nc1COC] | 1.04 | 407 | Method 1 |

| Intermediate | Reaction comment |
|---|---|
| 72-1 | The reaction is conducted at 100° C. |

| Intermediate | Name | Name of Starting Material |
|---|---|---|
| 72-1 | Ethyl 1-[(6-{6,6-difluoro-3-azabicyclo[3.1.0]-hexan-3-yl}-2-methylpyridin-3-yl)methyl]-3-(methoxymethyl)-1H-pyrazole-4-carboxylate | Ethyl 3-(chloromethyl)-1-[(6-{6,6-difluoro-3-azabicyclo[3.1.0]hexan-3-yl}-2-methylpyridin-3-yl)methyl]-1H-pyrazole-4-carboxylate |

Intermediate 73

Ethyl 1-[(6-{3-azabicyclo[3.1.0]hexan-3-yl}-5-cyano-2-methylpyridin-3-yl)methyl]-1H-imidazole-4-carboxylate

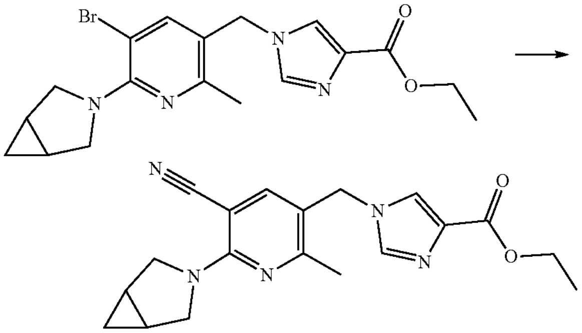

In a microwave vial N,N,N',N'-tetramethylethylenediamine (196 μL) is added to a mixture of ethyl 1-[(6-{3-azabicyclo[3.1.0]hexan-3-yl}-5-bromo-2-methylpyridin-3-yl)methyl]-1H-imidazole-4-carboxylate (530 mg), NaCN (77 mg), CuCN (25 mg) and KI (43 mg) in toluene (15 mL). The vial is sealed and the mixture is heated to 130° C. for 18 h. After cooling to rt the mixture is partitioned between water and EtOAc. The aqueous phase is extracted with EtOAc. The combined organic phases are dried ($MgSO_4$), concentrated and the residue is purified by HPLC on reversed phase (ACN, water) to give the title compound.

LC (Method 1): $t_R$=0.99 min; Mass spectrum (ESI+): m/z=352 $[M+H]^+$.

Intermediate 73-1 is prepared in analogy to Intermediate 73:

| Intermediate | Structure | $t_R$ | Mass spectrum (ESI+): m/z $[M + H]^+$ | LC Method |
|---|---|---|---|---|
| 73-1 | 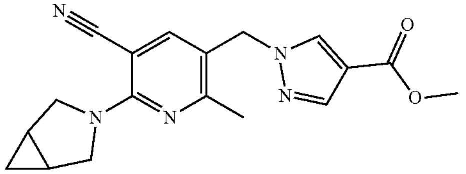 [SMILES: COC(=O)c1cnn(Cc2cc(C#N)c(N3CC4CC4C3)nc2C)c1] | 1.04 | 338 | Method 1 |

| Intermediate | Name | Name of Starting Material |
|---|---|---|
| 73-1 | Methyl 1-[(6-{3-azabicyclo[3.1.0]hexan-3-yl}-5-cyano-2-methylpyridin-3-yl)methyl]-1H-pyrazole-4-carboxylate | Methyl 1-[(6-{3-azabicyclo[3.1.0]hexan-3-yl}-5-bromo-2-methylpyridin-3-yl)methyl]-1H-pyrazole-4-carboxylate |

Intermediate 74

1-[(6-{3-Azabicyclo[3.1.0]hexan-3-yl}-2-methylpyridin-3-yl)methyl]-3-(2-hydroxypropan-2-yl)-1H-pyrazole-4-carboxylic acid hydrochloride

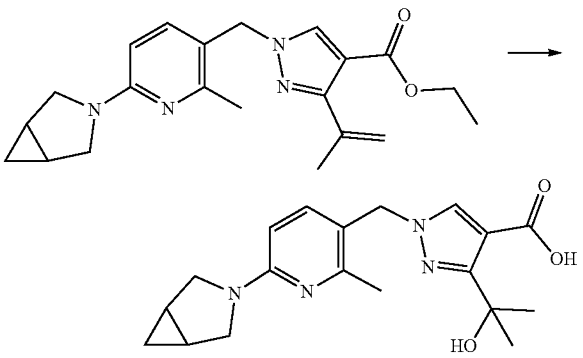

A mixture of ethyl 1-[(6-{3-azabicyclo[3.1.0]hexan-3-yl}-2-methylpyridin-3-yl)methyl]-3-(prop-1-en-2-yl)-1H-pyrazole-4-carboxylate (66 mg) in aqueous HCl (4 M, 5 mL) is heated to 60° C. for 12 h. The mixture is concentrated in vacuo to give the crude product, which is directly used in the next step.

LC (Method 2): $t_R$=0.67 min; Mass spectrum (ESI+): m/z=357 $[M+H]^+$.

Intermediate 75

Methyl 1-[(6-{3-azabicyclo[3.1.0]hexan-3-yl}-5-bromo-2-methylpyridin-3-yl)methyl]-1H-pyrazole-4-carboxylate

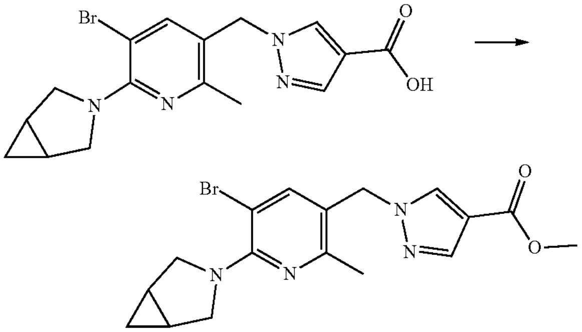

A mixture of 1-[(6-{3-azabicyclo[3.1.0]hexan-3-yl}-5-bromo-2-methylpyridin-3-yl)methyl]-1H-pyrazole-4-carboxylic acid (920 mg) and concentrated aqueous $H_2SO_4$ (182 µL) in MeOH (10 mL) is heated to 40° C. for 12 h. After cooling to rt the mixture is partitioned between EtOAc and saturated aqueous $NaHCO_3$. The aqueous phase is extracted with EtOAc. The combined organic phases are dried ($MgSO_4$), concentrated and the residue is purified by HPLC on reversed phase (ACN, water) to give the title compound.

LC (Method 1): $t_R$=1.17 min; Mass spectrum (ESI+): m/z=391 $[M+H]^+$.

Intermediate 75-1 is prepared in analogy to Intermediate 75:

| Intermediate | Structure | $t_R$ | Mass spectrum (ESI+): m/z $[M + H]^+$ | LC Method |
|---|---|---|---|---|
| 75-1 | 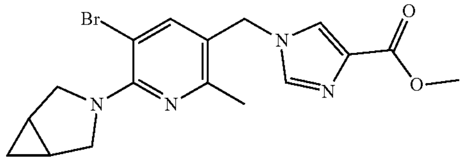 [SMILES: COC(=O)c1cn(Cc2cc(Br)c(N3CC4CC4C3)nc2C)cn1] | 1.07 | | Method 1 |

| Intermediate | Reaction comment |
|---|---|
| 75-1 | The reaction is conducted for 12 h at 70° C. |

| Intermediate | Name | Name of Starting Material |
|---|---|---|
| 75-1 | Methyl 1-[(6-{3-azabicyclo[3.1.0]hexan-3-yl}-5-bromo-2-methylpyridin-3-yl)methyl]-1H-imidazole-4-carboxylate | 1-[(6-{3-Azabicyclo[3.1.0]hexan-3-yl}-5-bromo-2-methylpyridin-3-yl)methyl]-1H-imidazole-4-carboxylic acid |

Intermediate 76

Methyl 1-[(6-{3-azabicyclo[3.1.0]hexan-3-yl}-2,5-dimethylpyridin-3-yl)methyl]-1H-imidazole-4-carboxylate

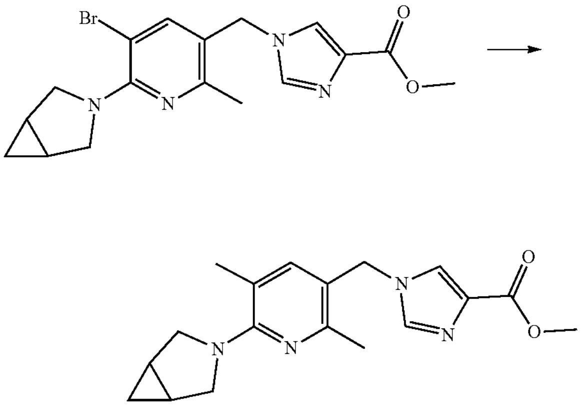

In a microwave vial a mixture of methyl 1-[(6-{3-azabicyclo[3.1.0]hexan-3-yl}-5-bromo-2-methylpyridin-3-yl)methyl]-1H-imidazole-4-carboxylate (120 mg), trimethylboroxine (77 mg) and $K_2CO_3$ (127 mg) in DMF (4 mL) is purged for minutes with argon. Tetrakis(triphenylphosphine)palladium(0) ($Pd(PPh_3)_4$, 71 mg) is added, the vial is sealed and the mixture is heated for 12 h to 110° C. After cooling to rt the mixture is partitioned between half-saturated aqueous NaCl and EtOAc. The aqueous phase is extracted with EtOAc. The combined organic phases are dried ($MgSO_4$), concentrated and the residue is purified by HPLC on reversed phase (ACN, water) to give the title compound.

LC (Method 2): $t_R$=0.63 min; Mass spectrum (ESI+): m/z=327 $[M+H]^+$.

Intermediate 76-1 is prepared in analogy to Intermediate 76:

| Intermediate | Structure | $t_R$ | Mass spectrum (ESI+): m/z $[M + H]^+$ | LC Method |
|---|---|---|---|---|
| 76-1 | 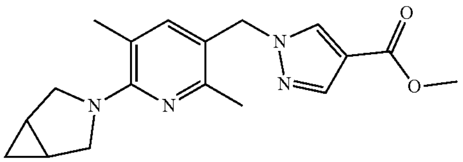 [SMILES: COC(=O)c1cnn(Cc2cc(C)c(N3CC4CC4C3)nc2C)c1] | 1.10 | 327 | Method 1 |

| Intermediate | Name | Name of Starting Material |
|---|---|---|
| 76-1 | Methyl 1-[(6-{3-azabicyclo[3.1.0]hexan-3-yl}-2,5-dimethylpyridin-3-yl)methyl]-1H-pyrazole-4-carboxylate | Methyl 1-[(6-{3-azabicyclo[3.1.0]hexan-3-yl}-5-bromo-2-methylpyridin-3-yl)methyl]-1H-pyrazole-4-carboxylate |

Intermediate 77

Ethyl 1-[(6-chloro-2-cyanopyridin-3-yl)methyl]-1H-pyrazole-4-carboxylate

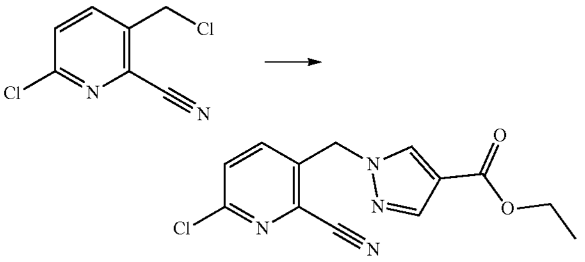

A mixture of 6-chloro-3-(chloromethyl)pyridine-2-carbonitrile (37 mg), ethyl 1H-pyrazole-4-carboxylate (30 mg) and $Cs_2CO_3$ (100 mg) in THF (2 mL) is stirred for 8 h at rt. Then the mixture is neutralized by addition of trifluoroacetic acid and purified by HPLC on reversed phase (ACN, water) to give the title compound.

LC (Method 1): $t_R$=0.94 min; Mass spectrum (ESI+): m/z=291 $[M+H]^+$.

Intermediate 78

Ethyl 1-[(6-{3-azabicyclo[3.1.0]hexan-3-yl}-2-cyanopyridin-3-yl)methyl]-1H-pyrazole-4-carboxylate

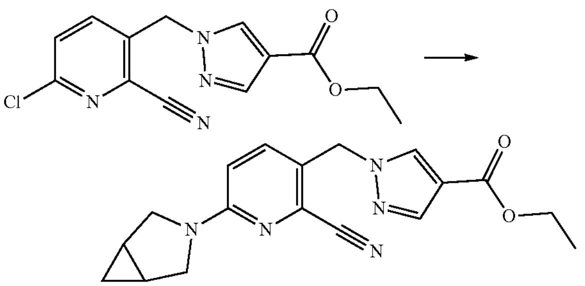

A mixture of ethyl 1-[(6-chloro-2-cyanopyridin-3-yl)methyl]-1H-pyrazole-4-carboxylate (1 g), 3-azabicyclo[3.1.0]-hexane hydrochloride (411 mg) and DIPEA (1.8 mL) in NMP (20 mL) is stirred for 12 h at 140° C. After cooling to rt the mixture is partitioned between water and EtOAc. The aqueous phase is extracted with EtOAc. The combined organic phases are washed with water, dried ($MgSO_4$), concentrated and the residue is purified by HPLC on reversed phase (ACN, water) to give the title compound. LC (Method 1): $t_R$=1.04 min; Mass spectrum (ESI+): m/z=338 $[M+H]^+$.

Intermediate 79

2-Chloro-4-methylpyrimidine-5-carboxylic acid

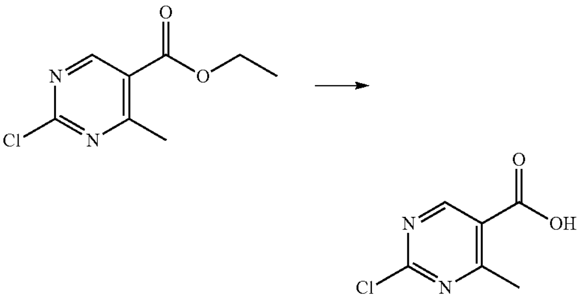

A mixture of ethyl 2-chloro-4-methylpyrimidine-5-carboxylate (25 g) and NaOH (6.5 g) in water (200 mL) is stirred at 40° C. for 3 h. After cooling to rt the mixture is treated with aqueous HCl (4 M) until a pH-value of 2 is reached. The precipitate is collected by filtration, washed with water and dried in vacuo to give the title compound.

LC (Method 2): $t_R$=0.68 min; Mass spectrum (ESI+): m/z=173 $[M+H]^+$.

Intermediate 80

(2-Chloro-4-methylpyrimidin-5-yl)methanol

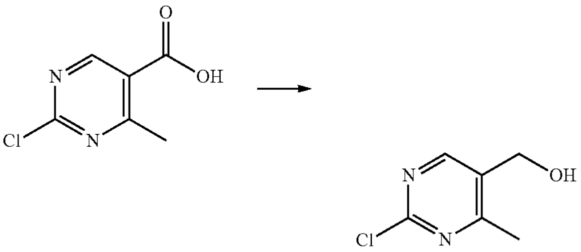

A mixture of 2-chloro-4-methylpyrimidine-5-carboxylic acid (8.5 g) and N-methylmorpholine (5.14 mL) in 1,2-dimethoxyethane (200 mL) is cooled to −10° C. and treated dropwise with isobutylchloroformate (6.2 mL). The mixture is stirred for 30 minutes and then treated dropwise with a solution of $NaBH_4$ (1.81 g) in water (20 mL). The mixture is stirred for 30 minutes while warming to rt and then partitioned between water and EtOAc. The aqueous phase is extracted with EtOAc for 3 times. The combined organic phases are washed with brine, dried ($MgSO_4$), concentrated and the residue is chromatographed on silica gel (petroleum ether/(EtOAc/MeOH 8:2) 70:30) to give the title compound. LC (Method 2): $t_R$=0.51 min; Mass spectrum (ESI+): m/z=159 $[M+H]^+$.

Intermediate 81

(2-{3-Azabicyclo[3.1.0]hexan-3-yl}-4-methylpyrimidin-5-yl)methanol

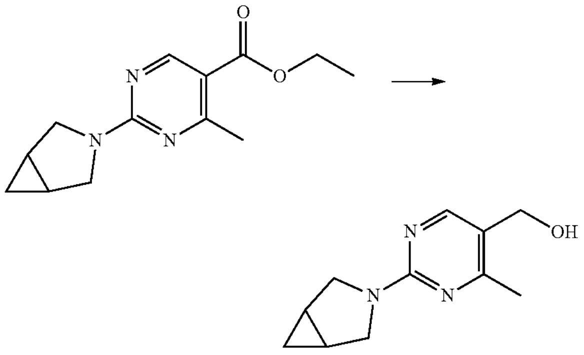

Diisobutylaluminiumhydride (1 M in THF, 80 mL) is added dropwise at −10° C. to a mixture of ethyl 2-{3-azabicyclo[3.1.0]hexan-3-yl}-4-methylpyrimidine-5-carboxylate (8.7 g) in THF (70 mL). The mixture is stirred for 1 h while warming to 0° C. This mixture is then added dropwise under ice-cooling to a mixture of aqueous NaOH (4 M, 6 mL) in water (150 mL). After stirring for 1 h the mixture is filtered over celite. The filter cake is washed with EtOAc/MeOH 9:1. The combined filtrates are dried ($MgSO_4$), concentrated and the residue is chromatographed on silica gel (EtOAc/MeOH 95:5→95:5) to give the title compound.

LC (Method 2): $t_R$=0.59 min; Mass spectrum (ESI+): m/z=206 $[M+H]^+$.

Intermediate 82

Methyl 1-[(6-{6,6-difluoro-3-azabicyclo[3.1.0]hexan-3-yl}pyridin-3-yl)methyl]-1H-pyrrole-3-carboxylate and Intermediate 83

Methyl 5-[(6-{6,6-difluoro-3-azabicyclo[3.1.0]hexan-3-yl}pyridin-3-yl)methyl]-1H-pyrrole-3-carboxylate

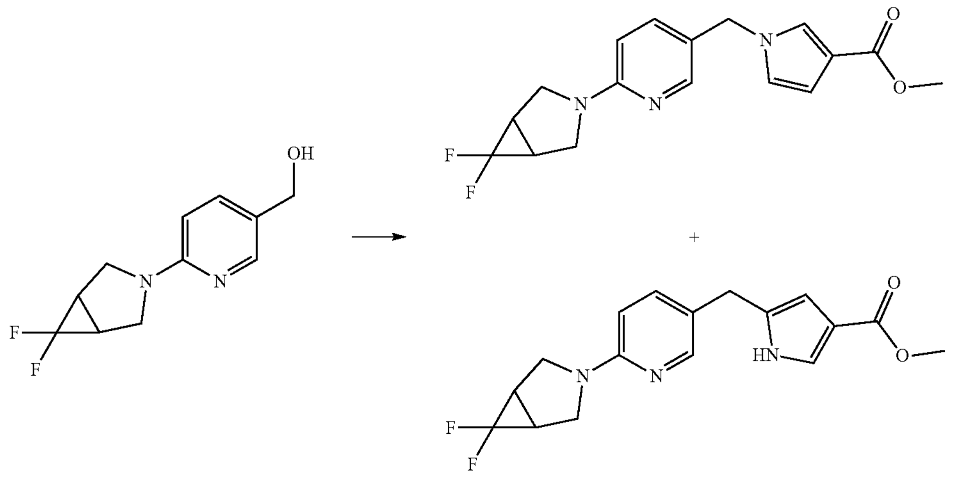 [SMILES: OCc1ccc(N2CC3C(C2)C3(F)F)nc1 ; COC(=O)c1ccn(Cc2ccc(N3CC4C(C3)C4(F)F)nc2)c1 ; COC(=O)c1c[nH]c(Cc2ccc(N3CC4C(C3)C4(F)F)nc2)c1]

Under argon atmosphere a mixture of (6-{6,6-difluoro-3-azabicyclo[3.1.0]hexan-3-yl}pyridin-3-yl)methanol (1.2 g), DIPEA (1.8 mL) in DCM (5 mL) is treated dropwise with $CH_3SO_2Cl$ (513 NL). The mixture is stirred for 15 minutes and then added dropwise to a mixture obtained by treatment of a solution of methyl 1H-pyrrole-3-carboxylate (863 mg) in DMF (15 mL) with KOtBu (893 mg). The mixture thus obtained is stirred for 5 days at rt. Then the mixture is partitioned between saturated aqueous $NaHCO_3$ and EtOAc. The aqueous phase is extracted twice with EtOAc. The combined organic phases are dried ($MgSO_4$), concentrated in vacuo and purified by HPLC on reversed phase (ACN, water) to give the title compounds.

Methyl 1-[(6-{6,6-difluoro-3-azabicyclo[3.1.0]hexan-3-yl}pyridin-3-yl)methyl]-1H-pyrrole-3-carboxylate (Intermediate 82): LC (Method 2): $t_R$=0.71 min; Mass spectrum (ESI+): m/z=334 $[M+H]^+$.

Methyl 5-[(6-{6,6-difluoro-3-azabicyclo[3.1.0]hexan-3-yl}pyridin-3-yl)methyl]-1H-pyrrole-3-carboxylate (Intermediate 83): LC (Method 2): $t_R$=0.70 min; Mass spectrum (ESI+): m/z=334 $[M+H]^+$.

Intermediate 84

Methyl 1-[(6-{6,6-difluoro-3-azabicyclo[3.1.0]hexan-3-yl}-2-methylpyridin-3-yl)methyl]-1H-pyrrole-3-carboxylate and Intermediate 85

Methyl 5-[(6-{6,6-difluoro-3-azabicyclo[3.1.0]hexan-3-yl}-2-methylpyridin-3-yl)methyl]-1H-pyrrole-3-carboxylate

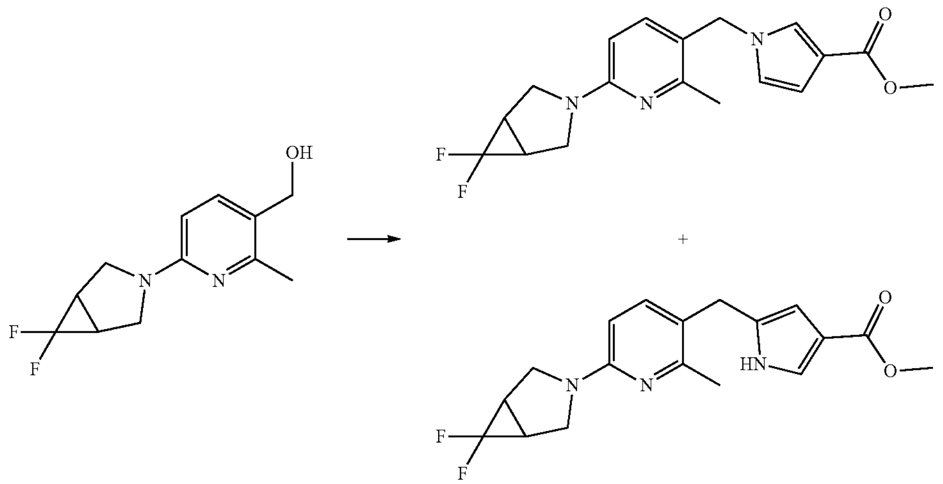 [SMILES: Cc1nc(N2CC3C(C2)C3(F)F)ccc1CO ; COC(=O)c1c[nH]c(Cc2ccc(N3CC4C(C3)C4(F)F)nc2C)c1 ; COC(=O)c1ccn(Cc2ccc(N3CC4C(C3)C4(F)F)nc2C)c1]

Under argon atmosphere a mixture of (6-{6,6-difluoro-3-azabicyclo[3.1.0]hexan-3-yl}-2-methylpyridin-3-yl)methanol (1.1 g), DIPEA (1.2 mL) in DCM (15 mL) is treated dropwise with $CH_3SO_2Cl$ (656 μL). The mixture is stirred for 15 minutes and then added dropwise to a mixture obtained by treatment of a solution of methyl 1H-pyrrole-3-carboxylate (745 mg) in DMF (30 mL) with KOtBu (771 mg). The mixture thus obtained is stirred for 1 h at rt. Then the mixture is partitioned between saturated aqueous $NaHCO_3$ and DCM. The aqueous phase is extracted twice with DCM. The combined organic phases are dried ($MgSO_4$), concentrated in vacuo and the residue is chromatographed on silica gel (petroleum ether/EtOAc 90:10→50:50) to give the title compound.

Methyl 1-[(6-{6,6-difluoro-3-azabicyclo[3.1.0]hexan-3-yl}-2-methylpyridin-3-yl)methyl]-1H-pyrrole-3-carboxylate (Intermediate 84): LC (Method 2): $t_R$=0.74 min; Mass spectrum (ESI+): m/z=348 $[M+H]^+$.

Methyl 5-[(6-{6,6-difluoro-3-azabicyclo[3.1.0]hexan-3-yl}-2-methylpyridin-3-yl)methyl]-1H-pyrrole-3-carboxylate (Intermediate 85): LC (Method 2): $t_R$=0.73 min; Mass spectrum (ESI+): m/z=348 $[M+H]^+$.

Intermediate 86

Ethyl 3-[(6-{3-azabicyclo[3.1.0]hexan-3-yl}-2-chloropyridin-3-yl)methyl]-1,2-oxazole-5-carboxylate

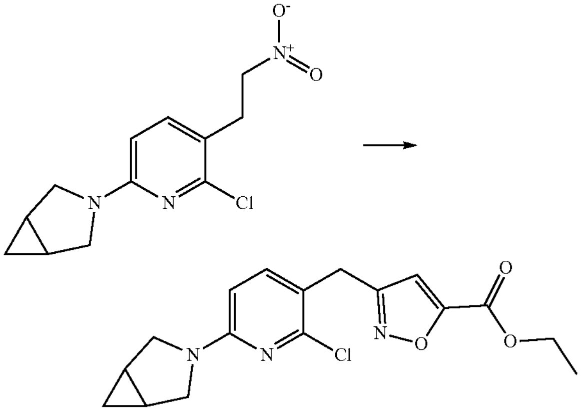

A mixture of 3-[6-chloro-5-(2-nitroethyl)pyridin-2-yl]-3-azabicyclo[3.1.0]hexane (2.58 g), $Boc_2O$ (4.42 g), ethyl propiolate (3.03 mL), DMAP (176 mg), and ACN (60 mL) is stirred for 18 h at 23° C. Purification by HPLC on reversed phase (ACN, water) gives the title compound. LC (Method 1): $t_R$=1.15 min; Mass spectrum (ESI+): m/z=348 $[M+H]^+$.

Intermediates 86-1 to 86-2 are prepared in analogy to Intermediate 86:

| Intermediate | Structure | $t_R$ | Mass spectrum (ESI+): m/z $[M + H]^+$ | LC Method |
|---|---|---|---|---|
| 86-1 | 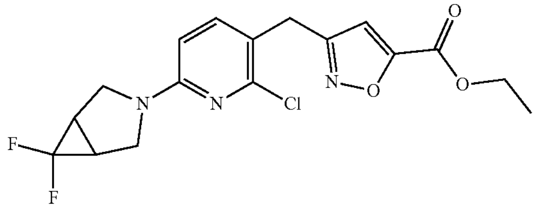 [SMILES: CCOC(=O)c1cc(Cc2ccc(N3CC4C(C3)C4(F)F)nc2Cl)no1] | 1.11 | 384 | Method 1 |
| 86-2 | 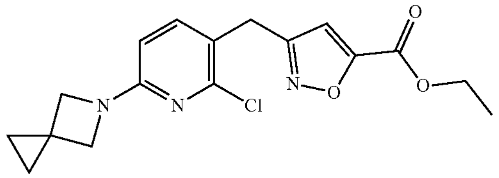 [SMILES: CCOC(=O)c1cc(Cc2ccc(N3CC4(CC4)C3)nc2Cl)no1] | 1.14 | 348 | Method 2 |

| Intermediate | Name | Name of Starting Material |
|---|---|---|
| 86-1 | Ethyl 3-[(2-chloro-6-{6,6-difluoro-3-azabicyclo[3.1.0]-hexan-3-yl}pyridin-3-yl)-methyl]-1,2-oxazole-5-carboxylate | 3-[6-Chloro-5-(2-nitroethyl)pyridin-2-yl]-6,6-difluoro-3-azabicyclo[3.1.0]hexane |
| 86-2 | Ethyl 3-[(6-{5-azaspiro[2.3]hexan-5-yl}-2-chloropyridin-3-yl)methyl]-1,2-oxazole-5-carboxylate | 5-[6-Chloro-5-(2-nitroethyl)pyridin-2-yl]-5-azaspiro[2.3]hexane |

Intermediate 87

3-[6-Chloro-5-(2-nitroethyl)pyridin-2-yl]-3-azabicyclo[3.1.0]hexane

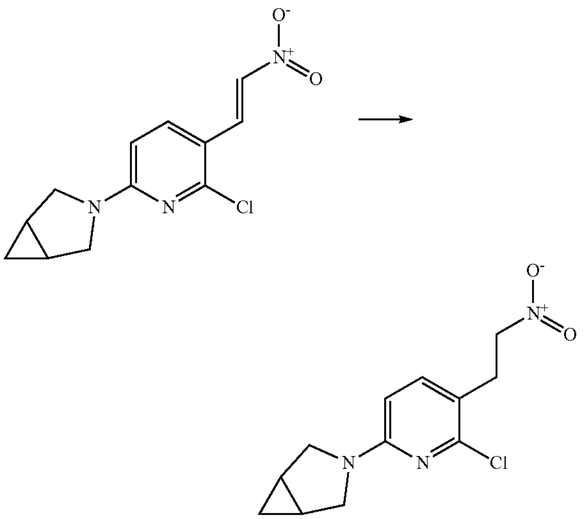

A mixture of 3-{6-chloro-5-[(1E)-2-nitroethenyl]pyridin-2-yl}-3-azabicyclo[3.1.0]hexane (4.0 g), $NaBH_4$ (726 mg), acetic acid (5 mL), and DMSO (30 mL) is stirred for 30 min at 0° C., and for 1 h at rt. The mixture is diluted with water and EtOAc and the phases are separated. The aqueous phase is extracted three times with EtOAc. The combined organic phases are washed with brine, dried ($MgSO_4$), concentrated and the residue is chromatographed on silica gel (cyclohexane/EtOAc 100:0→30:70) to give the title compound.

LC (Method 2): $t_R$=1.10 min. Mass spectrum (ESI+): m/z=268 $[M+H]^+$.

Intermediates 87-1 to 87-2 are prepared in analogy to Intermediate 87:

| Intermediate | Structure | $t_R$ | Mass spectrum (ESI+): m/z $[M + H]^+$ | LC Method |
|---|---|---|---|---|
| 87-1 | 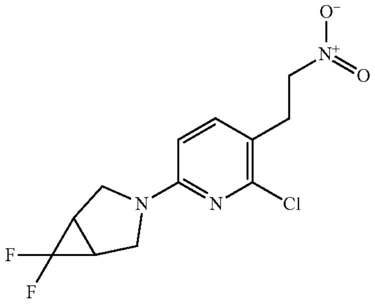 [SMILES: O=[N+]([O-])CCc1ccc(N2CC3C(C2)C3(F)F)nc1Cl] | 1.07 | 304 | Method 2 |
| 87-2 | 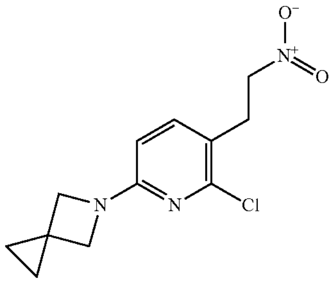 [SMILES: O=[N+]([O-])CCc1ccc(N2CC3(CC3)C2)nc1Cl] | 1.07 | 268 | Method 2 |

| Intermediate | Name | Name of Starting Material |
|---|---|---|
| 87-1 | 3-[6-Chloro-5-(2-nitroethyl)pyridin-2-yl]-6,6-difluoro-3-azabicyclo[3.1.0]hexane | 3-{6-Chloro-5-[(1E)-2-nitroethenyl]pyridin-2-yl}-6,6-difluoro-3-azabicyclo[3.1.0]hexane |
| 87-2 | 5-[6-Chloro-5-(2-nitroethyl)pyridin-2-yl]-5-azaspiro[2.3]hexane | 5-{6-Chloro-5-[(1E)-2-nitroethenyl]pyridin-2-yl}-5-azaspiro[2.3]hexane |

Intermediate 88

3-{6-Chloro-5-[(1E)-2-nitroethenyl]pyridin-2-yl}-3-azabicyclo[3.1.0]hexane

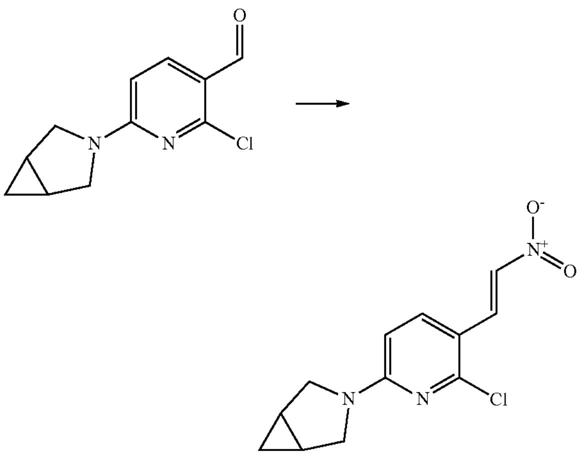

A mixture of 6-{3-azabicyclo[3.1.0]hexan-3-yl}-2-chloropyridine-3-carbaldehyde (500 mg), nitromethane (1.6 mL), ammonium acetate (346 mg), and acetic acid (10 mL) is stirred for 18 h at 100° C. The mixture is cooled to rt and added dropwise to a cold mixture of EtOAc, water, and saturated aqueous $NaHCO_3$. The phases are separated, and the aqueous phase is extracted three times with EtOAc. The combined organic phases are washed with brine, dried ($MgSO_4$) and concentrated to give the crude title compound.

LC (Method 2): $t_R$=1.14 min. Mass spectrum (ESI+): m/z=266 $[M+H]^+$.

Intermediates 88-1 to 88-2 are prepared in analog to Intermediate 88:

-continued

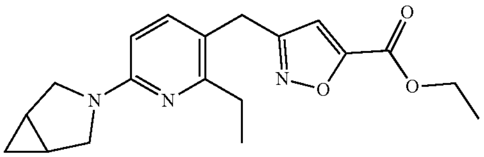

| Intermediate | Structure | $t_R$ | Mass spectrum (ESI+): m/z $[M + H]^+$ | LC Method |
|---|---|---|---|---|
| 88-1 | 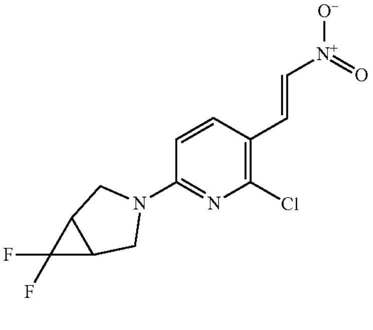 [SMILES: O=[N+]([O-])/C=C/c1ccc(N2CC3C(C2)C3(F)F)nc1Cl] | 1.10 | 302 | Method 2 |
| 88-2 | 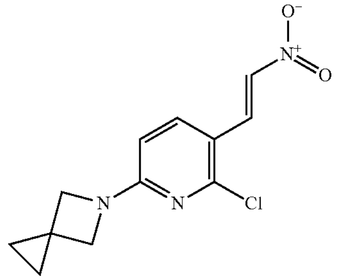 [SMILES: O=[N+]([O-])/C=C/c1ccc(N2CC3(CC3)C2)nc1Cl] | 1.11 | 266 | Method 2 |

| Intermediate | Name | Name of Starting Material |
|---|---|---|
| 88-1 | 3-{6-Chloro-5-[(1E)-2-nitroethenyl]pyridin-2-yl}-6,6-difluoro-3-azabicyclo[3.1.0]hexane | 2-Chloro-6-{6,6-difluoro-3-azabicyclo[3.1.0]-hexan-3-yl}pyridine-3-carbaldehyde |
| 88-2 | 5-{6-Chloro-5-[(1E)-2-nitroethenyl]pyridin-2-yl}-5-azaspiro[2.3]hexane | 6-{5-Azaspiro[2.3]hexan-5-yl}-2-chloropyridine-3-carbaldehyde |

Intermediate 89

Ethyl 3-[(6-{3-azabicyclo[3.1.0]hexan-3-yl}-2-ethylpyridin-3-yl)methyl]-1,2-oxazole-5-carboxylate

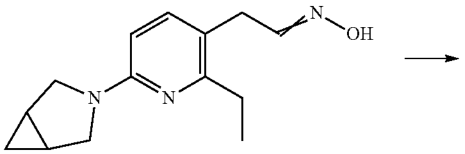

A mixture of (E,Z)—N-[2-(6-{3-azabicyclo[3.1.0]hexan-3-yl}-2-ethylpyridin-3-yl)ethylidene]hydroxylamine (2.45 g), ethyl prop-2-ynoate (2.0 mL), aqueous NaOCl 15% (34 mL), and THF (20 mL) is stirred for 3 h at rt. The mixture is diluted with EtOAc and water, and the aqueous phase is extracted three times with EtOAc. The combined organic phases are washed with brine, dried ($MgSO_4$), concentrated and the residue is chromatographed on silica gel (petroleum ether/EtOAc 99:1→70:30) to give the title compound.

LC (Method 2): $t_R$=0.79 min. Mass spectrum (ESI+): m/z=342 $[M+H]^+$.

Intermediates 89-1 to 89-2 are prepared in analogy to Intermediate 89:

| Intermediate | Structure | $t_R$ | Mass spectrum (ESI+): m/z [M + H]$^+$ | LC Method |
|---|---|---|---|---|
| 89-1 | 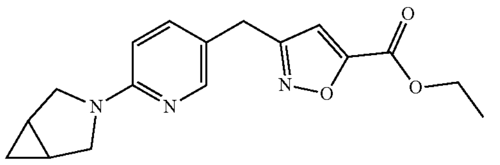 [SMILES: CCOC(=O)c1cc(Cc2ccc(N3CC4CC4C3)nc2)no1] | 1.04 | 314 | Method 1 |
| 89-2 | 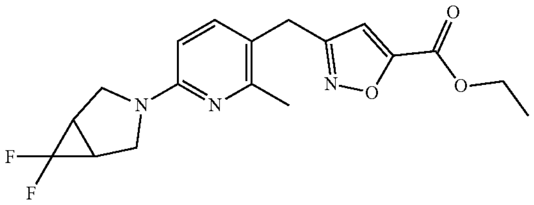 [SMILES: CCOC(=O)c1cc(Cc2ccc(N3CC4C(C3)C4(F)F)nc2C)no1] | 0.76 | 364 | Method 2 |

| Intermediate | Reaction comment |
|---|---|
| 89-1 | The reaction is conducted in DCM instead of THF. |

| Intermediate | Name | Name of Starting Material |
|---|---|---|
| 89-1 | Ethyl 3-[(6-{3-azabicyclo[3.1.0]hexan-3-yl}-pyridin-3-yl)methyl]-1,2-oxazole-5-carboxylate | (E,Z)-N-[2-(6-{3-Azabicyclo[3.1.0]hexan-3-yl}pyridin-3-yl)ethylidene]hydroxylamine |
| 89-2 | Ethyl 3-[(6-{6,6-difluoro-3-azabicyclo[3.1.0]-hexan-3-yl}-2-methylpyridin-3-yl)methyl]-1,2-oxazole-5-carboxylate | (E,Z)-N-[2-(6-{6,6-Difluoro-3-azabicyclo[3.1.0]-hexan-3-yl}-2-methylpyridin-3-yl)-ethylidene]hydroxylamine |

Intermediate 90

(E,Z)—N-[2-(6-{3-Azabicyclo[3.1.0]hexan-3-yl}-2-ethylpyridin-3-yl)ethylidene]hydroxylamine

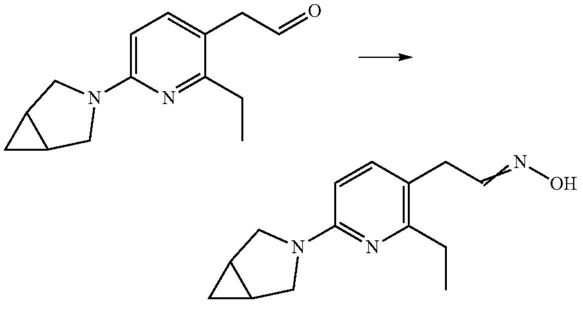

A mixture of 2-(6-{3-azabicyclo[3.1.0]hexan-3-yl}-2-ethylpyridin-3-yl)acetaldehyde (2.22 g), hydroxylamine hydrochloride (1.35 g), $Na_2CO_3$ (1.23 g) water (8.0 mL), and MeOH (40 mL) is stirred for 2 h at rt. The mixture is concentrated, and the residue is treated with water, stirred for 15 minutes, and filtered. The precipitate is washed with water and dried in a desiccator, to give the title compound as a mixture of isomers.

LC (Method 2): $t_R$=0.62 and 0.64 min. Mass spectrum (ESI+): m/z=246 [M+H]$^+$.

Intermediates 90-1 to 90-3 are prepared in analogy to Intermediate 90:

| Intermediate | Structure | $t_R$ | Mass spectrum (ESI+): m/z [M + H]$^+$ | LC Method |
|---|---|---|---|---|
| 90-1 | 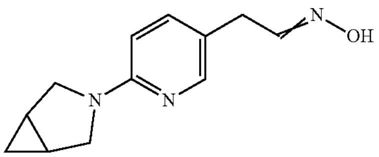 [SMILES: ON=CCc1ccc(N2CC3CC3C2)nc1] | 0.82 and 0.84 | 218 | Method 1 |

-continued

| Intermediate | Structure | $t_R$ | Mass spectrum (ESI+): m/z [M + H]$^+$ | LC Method |
|---|---|---|---|---|
| 90-2 | 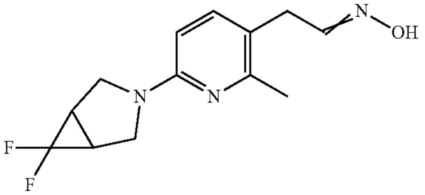 [SMILES: Cc1nc(N2CC3C(C2)C3(F)F)ccc1CC=NO] | 0.61 and 0.63 | 268 | Method 2 |
| 90-3 | 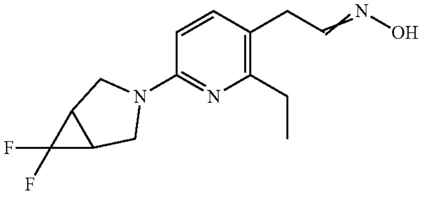 [SMILES: CCc1nc(N2CC3C(C2)C3(F)F)ccc1CC=NO] | 0.65 | 282 | Method 2 |

| Intermediate | Name | Name of Starting Material |
|---|---|---|
| 90-1 | (E,Z)-N-[2-(6-{3-Azabicyclo[3.1.0]hexan-3-yl}pyridin-3-yl)ethylidene]hydroxylamine | 2-(6-{3-Azabicyclo[3.1.0]hexan-3-yl}-pyridin-3-yl)acetaldehyde |
| 90-2 | (E,Z)-N-[2-(6-{6,6-Difluoro-3-azabicyclo[3.1.0]hexan-3-yl}-2-methylpyridin-3-yl)ethylidene]hydroxylamine | 2-(6-{6,6-Difluoro-3-azabicyclo[3.1.0]hexan-3-yl}-2-methylpyridin-3-yl)acetaldehyde |
| 90-3 | (E,Z)-N-[2-(6-{6,6-Difluoro-3-azabicyclo[3.1.0]hexan-3-yl}-2-ethylpyridin-3-yl)ethylidene]hydroxylamine | 2-(6-{6,6-Difluoro-3-azabicyclo[3.1.0]hexan-3-yl}-2-ethylpyridin-3-yl)acetaldehyde |

Intermediate 91

2-(6-{3-Azabicyclo[3.1.0]hexan-3-yl}-2-ethylpyridin-3-yl)acetaldehyde

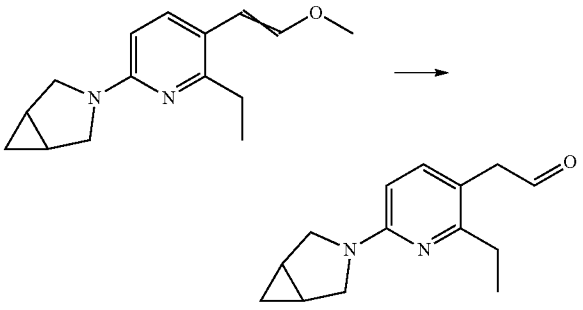

A mixture of 3-[6-ethyl-5-(2-methoxyethenyl)pyridin-2-yl]-3-azabicyclo[3.1.0]hexane (2.36 g), concentrated HCl (4.0 mL), and 1,4-dioxane (24 mL) is stirred for 1 h at rt. The mixture is carefully neutralized with a saturated aqueous solution of $NaHCO_3$, and the aqueous phase is extracted twice with EtOAc. The combined organic phases are washed with brine, dried ($MgSO_4$) and concentrated, to give the title compound.

LC (Method 2): $t_R$=0.58 min. Mass spectrum (ESI+): m/z=231 [M+H]$^+$.

Intermediates 91-1 to 91-3 are prepared in analogy to Intermediate 91:

| Intermediate | Structure | $t_R$ | Mass spectrum (ESI+): m/z [M + H]$^+$ | LC Method |
|---|---|---|---|---|
| 91-1 | 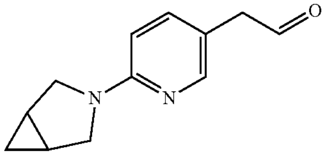 [SMILES: O=CCc1ccc(N2CC3CC3C2)nc1] | 0.83 | 203 | Method 1 |

-continued

| Intermediate | Structure | $t_R$ | Mass spectrum (ESI+): m/z $[M + H]^+$ | LC Method |
|---|---|---|---|---|
| 91-2 | 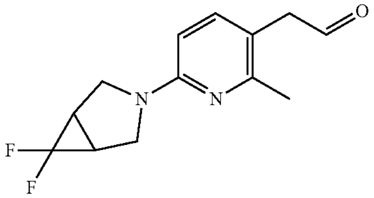 [SMILES: Cc1nc(N2CC3C(C2)C3(F)F)ccc1CC=O] | 0.60 | 253 | Method 2 |
| 91-3 | 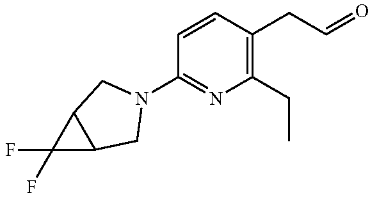 [SMILES: CCc1nc(N2CC3C(C2)C3(F)F)ccc1CC=O] | 0.62 | 267 | Method 2 |

| Intermediate | Name | Name of Starting Material |
|---|---|---|
| 91-1 | 2-(6-{3-Azabicyclo[3.1.0]hexan-3-yl}pyridin-3-yl)acetaldehyde | 3-[5-(2-Methoxyethenyl)pyridin-2-yl]-3-azabicyclo[3.1.0]hexane |
| 91-2 | 2-(6-{6,6-Difluoro-3-azabicyclo[3.1.0]hexan-3-yl}-2-methylpyridin-3-yl)acetaldehyde | 6,6-Difluoro-3-[5-(2-methoxyethenyl)-6-methylpyridin-2-yl]-3-azabicyclo[3.1.0]hexane |
| 91-3 | 2-(6-{6,6-Difluoro-3-azabicyclo[3.1.0]hexan-3-yl}-2-ethylpyridin-3-yl)acetaldehyde | 3-[6-Ethyl-5-(2-methoxyethenyl)pyridin-2-yl]-6,6-difluoro-3-azabicyclo[3.1.0]hexane |

Intermediate 92

3-[6-Ethyl-5-(2-methoxyethenyl)pyridin-2-yl]-3-azabicyclo[3.1.0]hexane

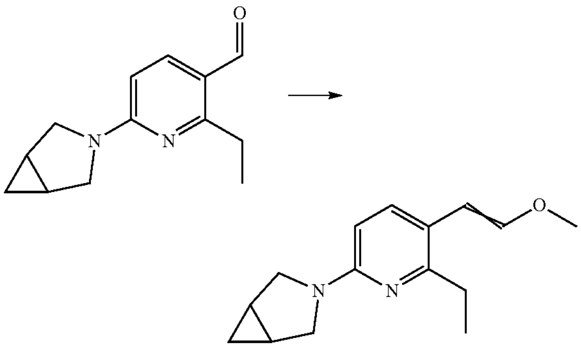

A mixture of (methoxymethyl)triphenylphosphonium chloride (10.0 g) in THF (80 mL) is treated dropwise with NaHMDS (2 M in THF, 14.6 mL), at −40° C. under argon atmosphere, and stirred for 15 minutes at this temperature. This mixture is treated dropwise with a mixture of 6-{3-azabicyclo[3.1.0]hexan-3-yl}-2-ethylpyridine-3-carbaldehyde (2.09 g) in THF (20 mL) at −40° C. Then the mixture is warmed over 4 h to rt. The mixture is diluted with EtOAc, and the organic layer is washed with water and brine, dried ($MgSO_4$), and concentrated. The residue is stirred in diisopropylether and the precipitate is filtered off. The filtrate is concentrate, and the residue is chromatographed on silica gel (petroleum ether/EtOAc 99:1→70:30) to give the title compound as a mixture of isomers.

LC (Method 2): $t_R$=0.74 and 0.76 min (mixture of isomers). Mass spectrum (ESI+): m/z=245 $[M+H]^+$.

Intermediates 92-1 to 92-3 are prepared in analogy to Intermediate 92:

| Intermediate | Structure | $t_R$ | Mass spectrum (ESI+): m/z $[M + H]^+$ | LC Method |
|---|---|---|---|---|
| 92-1 | 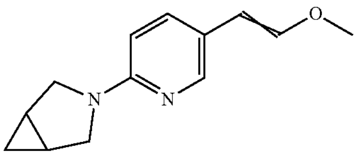 [SMILES: COC=Cc1ccc(N2CC3CC3C2)nc1] | 0.99 and 1.01 | 217 | Method 1 |

-continued

| Intermediate | Structure | $t_R$ | Mass spectrum (ESI+): m/z $[M + H]^+$ | LC Method |
|---|---|---|---|---|
| 92-2 | 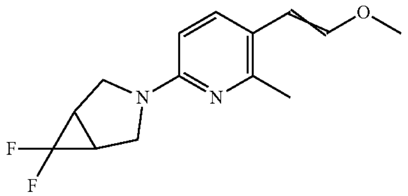 [SMILES: COC=Cc1ccc(N2CC3C(C2)C3(F)F)nc1C] | 0.73 and 0.74 | 267 | Method 2 |
| 92-3 | 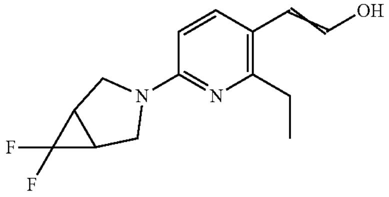 [SMILES: CCc1nc(N2CC3C(C2)C3(F)F)ccc1C=CO] | 0.75 | 281 | Method 2 |

| Intermediate | Name | Name of Starting Material |
|---|---|---|
| 92-1 | 3-[5-(2-Methoxyethenyl)pyridin-2-yl]-3-azabicyclo[3.1.0]hexane | 6-{3-Azabicyclo[3.1.0]hexan-3-yl}pyridine-3-carbaldehyde |
| 92-2 | 6,6-Difluoro-3-[5-(2-methoxyethenyl)-6-methylpyridin-2-yl]-3-azabicyclo[3.1.0]hexane | 6-{6,6-Difluoro-3-azabicyclo[3.1.0]hexan-3-yl}-2-methylpyridine-3-carbaldehyde |
| 92-3 | 3-[6-Ethyl-5-(2-methoxyethenyl)pyridin-2-yl]-6,6-difluoro-3-azabicyclo[3.1.0]hexane | 6-{6,6-Difluoro-3-azabicyclo[3.1.0]hexan-3-yl}-2-ethylpyridine-3-carbaldehyde |

Intermediate 93

Methyl 2-[1-(6-{3-azabicyclo[3.1.0]hexan-3-yl}-2-methylpyridin-3-yl)-2-methoxy-2-oxoethyl]-1,3-oxazole-5-carboxylate

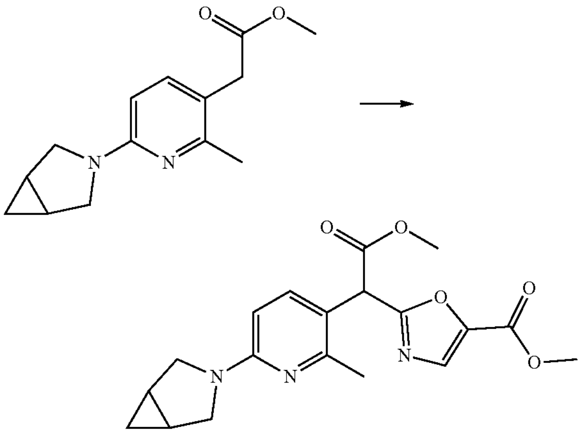

A mixture of methyl 2-(6-{3-azabicyclo[3.1.0]hexan-3-yl}-2-methylpyridin-3-yl)acetate (460 mg) in THF (5 mL) is treated dropwise with NaHMDS (2M in THF, 1.1 mL), at −78° C. under argon atmosphere and is stirred for 15 minutes at this temperature. This mixture is treated dropwise with a mixture of methyl 2-chloro-1,3-oxazole-5-carboxylate (305 mg) in THF (3 mL) at −78° C. and is then warmed over 18 h to rt. The mixture is quenched with saturated aqueous $NH_4Cl$ and the aqueous phase is extracted twice with EtOAc. The combined organic phases are dried ($MgSO_4$), concentrated and the residue is chromatographed on silica gel (petroleum ether/EtOAc 80:20→20:80) to give the title compound. LC (Method 2): $t_R$=0.72 min. Mass spectrum (ESI+): m/z=372 $[M+H]^+$.

Intermediates 93-1 to 93-2 are prepared in analogy to Intermediate 93:

| Intermediate | Structure | $t_R$ | Mass spectrum (ESI+): m/z $[M + H]^+$ | LC Method |
|---|---|---|---|---|
| 93-1 | 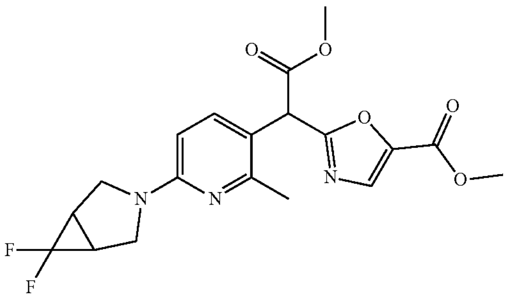 [SMILES: COC(=O)c1cnc(C(C(=O)OC)c2ccc(N3CC4C(C3)C4(F)F)nc2C)o1] | 0.75 | 408 | Method 2 |
| 93-2 | 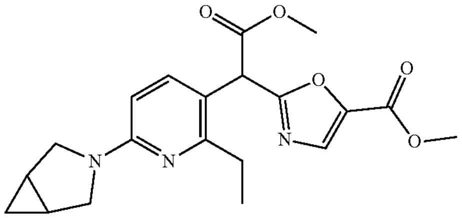 [SMILES: CCc1nc(N2CC3CC3C2)ccc1C(C(=O)OC)c1ncc(C(=O)OC)o1] | 0.77 | 386 | Method 2 |

| Intermediate | Name | Name of Starting Material |
|---|---|---|
| 93-1 | Methyl 2-[1-(6-{6,6-difluoro-3-azabicyclo[3.1.0]-hexan-3-yl}-2-methylpyridin-3-yl)-2-methoxy-2-oxoethyl]-1,3-oxazole-5-carboxylate | Methyl 2-(6-{6,6-difluoro-3-azabicyclo[3.1.0]-hexan-3-yl}-2-methylpyridin-3-yl)acetate |
| 93-2 | Methyl 2-[1-(6-{3-azabicyclo[3.1.0]hexan-3-yl}-2-ethylpyridin-3-yl)-2-methoxy-2-oxoethyl]-1,3-oxazole-5-carboxylate | Methyl 2-(6-{3-azabicyclo[3.1.0]hexan-3-yl}-2-ethylpyridin-3-yl)acetate |

Intermediate 94

Methyl 2-(6-{3-azabicyclo[3.1.0]hexan-3-yl}-2-methylpyridin-3-yl)acetate

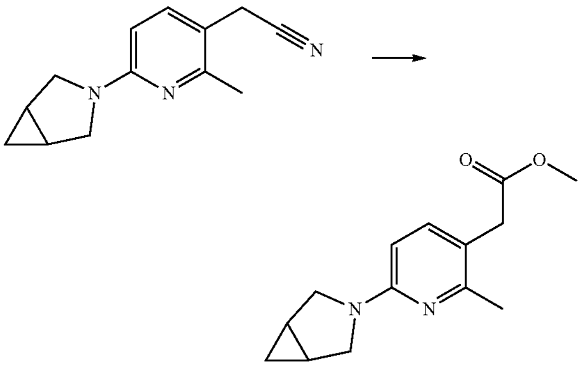

A mixture of 2-(6-{3-azabicyclo[3.1.0]hexan-3-yl}-2-methylpyridin-3-yl)acetonitrile (473 mg) in MeOH (5 mL) is treated with $SOCl_2$ (575 μL) at rt, and the mixture is stirred for 6 h, before being treated with saturated aqueous $NaHCO_3$. The aqueous phase is extracted twice with DCM, and the combined organic layers are washed with brine, dried ($MgSO_4$) and concentrated to give the title compound. LC (Method 2): $t_R$=0.64 min. Mass spectrum (ESI+): m/z=247 $[M+H]^+$.

Intermediates 94-1 to 94-2 are prepared in analogy to Intermediate 94:

| Intermediate | Structure | $t_R$ | Mass spectrum (ESI+): m/z $[M + H]^+$ | LC Method |
|---|---|---|---|---|
| 94-1 | 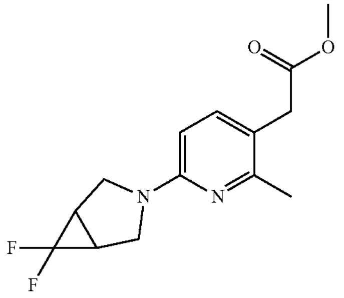 [SMILES: COC(=O)Cc1ccc(N2CC3C(C2)C3(F)F)nc1C] | 0.66 | 283 | Method 2 |
| 94-2 | 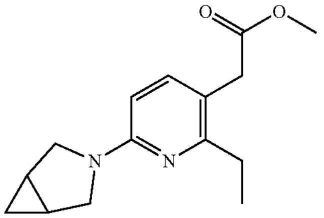 [SMILES: CCc1nc(N2CC3CC3C2)ccc1CC(=O)OC] | 0.69 | 261 | Method 2 |

| Intermediate | Reaction comment |
|---|---|
| 94-1 | The reaction is conducted for 18 h at 50° C. |
| 94-2 | The reaction is conducted for 24 h. |

| Intermediate | Name | Name of Starting Material |
|---|---|---|
| 94-1 | Methyl 2-(6-{6,6-difluoro-3-azabicyclo[3.1.0]-hexan-3-yl}-2-methylpyridin-3-yl)acetate | 2-(6-{6,6-Difluoro-3-azabicyclo[3.1.0]hexan-3-yl}-2-methylpyridin-3-yl)acetonitrile |
| 94-2 | Methyl 2-(6-{3-azabicyclo[3.1.0]hexan-3-yl}-2-ethylpyridin-3-yl)acetate | 2-(6-{3-Azabicyclo[3.1.0]hexan-3-yl}-2-ethylpyridin-3-yl)acetonitrile |

Intermediate 95

2-(6-{3-Azabicyclo[3.1.0]hexan-3-yl}-2-methylpyridin-3-yl)acetonitrile

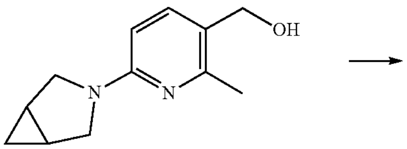

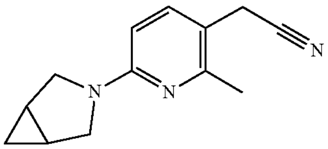

A mixture of (6-{3-azabicyclo[3.1.0]hexan-3-yl}-2-methylpyridin-3-yl)methanol (1.96 g) in THF (15 mL) is treated with 2-hydroxy-2-methylpropionitrile (895 mg), triphenylphosphine ($PPh_3$, 3.80 g), and DIAD (2.36 g), at 0° C. The mixture is stirred for 66 h at rt and quenched with a saturated aqueous solution of $NaHCO_3$. The aqueous phase is extracted with EtOAc. The organic phase is washed with brine, dried ($MgSO_4$), concentrated and the residue is chromatographed on silica gel (petroleum ether/EtOAc 90:10→80:20) to give the title compound.

LC (Method 1: $t_R$=0.97 min. Mass spectrum (ESI+): m/z=214 $[M+H]^+$.

Intermediates 95-1 to 95-2 are prepared in analog to Intermediate 95:

| Intermediate | Structure | $t_R$ | Mass spectrum (ESI+): m/z $[M + H]^+$ | LC Method |
|---|---|---|---|---|
| 95-1 | 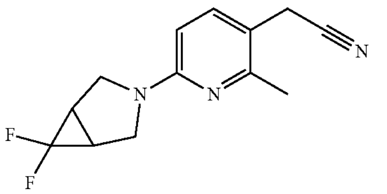 [SMILES: Cc1nc(N2CC3C(C2)C3(F)F)ccc1CC#N] | 0.95 | 250 | Method 1 |
| 95-2 | 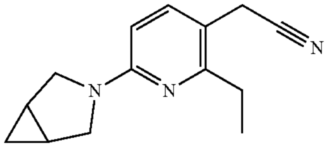 [SMILES: CCc1nc(N2CC3CC3C2)ccc1CC#N] | 0.63 | 228 | Method 2 |

| Intermediate | Reaction comment |
|---|---|
| 95-1 | The reaction is conducted for 18 h at rt. |
| 95-2 | The reaction is conducted for 12 h at rt. |

| Intermediate | Name | Name of Starting Material |
|---|---|---|
| 95-1 | 2-(6-{6,6-Difluoro-3-azabicyclo[3.1.0]hexan-3-yl}-2-methylpyridin-3-yl)acetonitrile | (6-{6,6-Difluoro-3-azabicyclo[3.1.0]hexan-3-yl}-2-methylpyridin-3-yl)methanol |
| 95-2 | 2-(6-{3-Azabicyclo[3.1.0]hexan-3-yl}-2-ethylpyridin-3-yl)acetonitrile | (6-{3-Azabicyclo[3.1.0]hexan-3-yl}-2-ethylpyridin-3-yl)methanol |

Intermediate 96

Ethyl 3-[(6-{6,6-difluoro-3-azabicyclo[3.1.0]hexan-3-yl}-2-ethylpyridin-3-yl)methyl]-1,2-oxazole-5-carboxylate

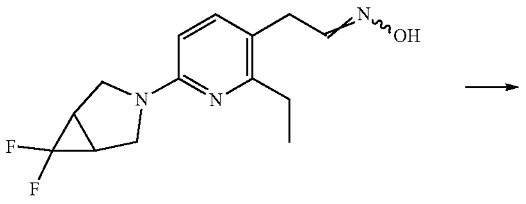

-continued

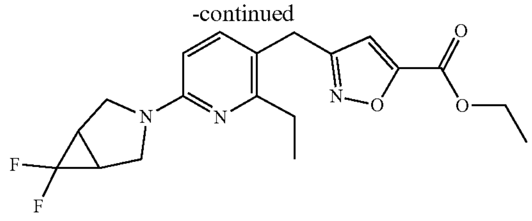

A mixture of N-[2-(6-{6,6-difluoro-3-azabicyclo[3.1.0]hexan-3-yl}-2-ethylpyridin-3-yl)ethylidene]hydroxylamine (100 mg), ethyl prop-2-ynoate (47 NL), oxone (328 mg), $Na_2CO_3$ (57 mg), NaCl (23 mg), MeOH (2 mL) and water (100 NL) is stirred for 5 h at rt, and concentrated. The residue is partitioned between water and EtOAc. The organic phase is washed with brine, dried ($MgSO_4$), concentrated and the residue is chromatographed on silica gel (petroleum ether/EtOAc 99:01→50:50) to give the title compound.

LC (Method 2): $t_R$=0.81 min. Mass spectrum (ESI+): m/z=378 $[M+H]^+$.

Intermediate 97

Methyl 5-[(2-chloro-6-{6,6-difluoro-3-azabicyclo[3.1.0]hexan-3-yl}pyridin-3-yl)methyl]-1H-pyrrole-3-carboxylate

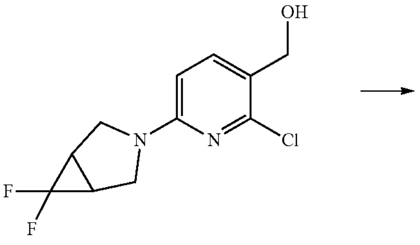

-continued

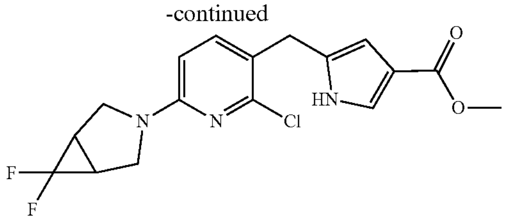

Under argon atmosphere a mixture of (2-chloro-6-{6,6-difluoro-3-azabicyclo[3.1.0]hexan-3-yl}pyridin-3-yl)methanol (300 mg), DIPEA (782 μL) in DCM (1.5 mL) is treated dropwise with $CH_3SO_2Cl$ (222 μL). The mixture is stirred for 15 minutes and then added dropwise to a mixture obtained by treatment of a solution of methyl 1H-pyrrole-3-carboxylate (187 mg) in DMF (4 mL) with KOtBu (194 mg). The mixture thus obtained is stirred for 12 h at 40° C. Then the mixture is partitioned between saturated aqueous $NaHCO_3$ and EtOAc. The aqueous phase is extracted twice with EtOAc. The combined organic phases are dried ($MgSO_4$), concentrated in vacuo and the residue is purified by HPLC on reversed phase (ACN, water) to give the title compound.

LC (Method 2): $t_R$=1.05 min; Mass spectrum (ESI+): m/z=368 $[M+H]^+$.

Intermediate 98

Ethyl 5-iodo-1H-pyrazole-3-carboxylate

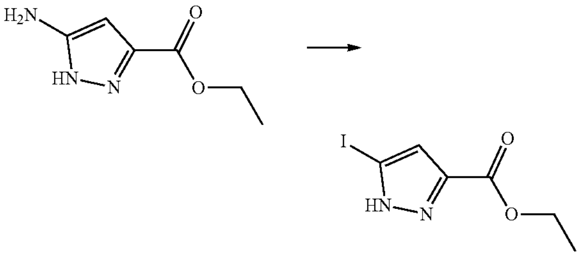

Ethyl 5-amino-1H-pyrazole-3-carboxylate (10 g) is added portionwise at 0° C. to a mixture of water (240 mL) and concentrated aqueous $H_2SO_4$ (120 mL). To this mixture is added dropwise a solution of $NaNO_2$ (4.65 g) in water (10 mL). The mixture is stirred for 2 h and is then treated dropwise with a solution of KI (12.0 g) in water (10 mL). The mixture is stirred for 3 h while warming to rt. Then the mixture is cooled to 0° C. and neutralized by careful addition of saturated aqueous $K_2CO_3$. The mixture is extracted twice with EtOAc. The combined organic phases are washed with 20% $Na_2S_2O_3$ in water, dried ($MgSO_4$), concentrated and the residue is chromatographed on silica gel (petroleum ether/EtOAc 95:5→70:30) to give the title compound.

LC (Method 2): $t_R$=0.86 min. Mass spectrum (ESI+): m/z=267 $[M+H]^+$.

Intermediate 98-1 is prepared in analogy to Intermediate 98:

| Intermediate | Structure | $t_R$ | Mass spectrum (ESI+): m/z $[M + H]^+$ | LC Method |
|---|---|---|---|---|
| 98-1 | 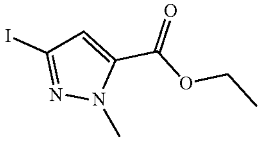 | 1.02 | 281 | Method 2 |

| Intermediate | Name | Name of Starting Material |
|---|---|---|
| 98-1 | Ethyl 3-iodo-1-methyl-1H-pyrazole-5-carboxylate | Ethyl 3-amino-1-methyl-1H-pyrazole-5-carboxylate hydrochloride |

Intermediate 99

Ethyl 3-iodo-1-(propan-2-yl)-1H-pyrazole-5-carboxylate

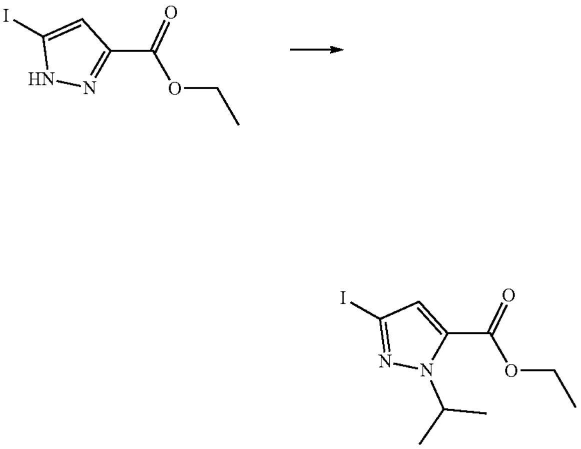

NaH (60% in mineral oil, 180 mg) is added portionwise at 0° C. to a mixture of ethyl 5-iodo-1H-pyrazole-3-carboxylate (1.0 g) in DMF (15 mL). The mixture is stirred for 30 minutes and then treated with 2-iodopropane (451 μL). The mixture is stirred for 4 h while warming to rt. Then the mixture is partitioned between saturated aqueous $NH_4Cl$ and EtOAc. The aqueous phase is extracted twice with EtOAc. The combined organic phases are dried ($MgSO_4$), concentrated in vacuo and the residue is purified by HPLC on reversed phase (ACN, water) to give the title compound.

LC (Method 2): $t_R$=1.08 min. Mass spectrum (ESI+): m/z=309 $[M+H]^+$.

Intermediates 99-1 to 99-2 are prepared in analogy to Intermediate 99:

| Intermediate | Structure | $t_R$ | Mass spectrum (ESI+): m/z $[M + H]^+$ | LC Method |
|---|---|---|---|---|
| 99-1 | 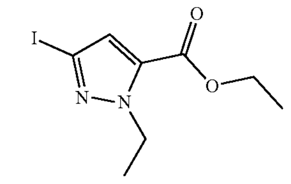 | 1.02 | 295 | Method 2 |
| 99-2 | 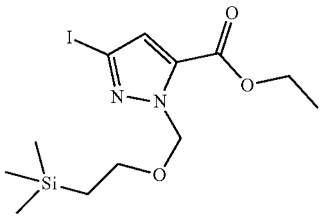 [SMILES: CCOC(=O)c1cc(I)nn1COCC[Si](C)(C)C] | 1.24 | 397 | Method 2 |

| Intermediate | Reaction comment |
|---|---|
| 99-1 | Iodoethane is used instead of 2-iodopropane. |
| 99-2 | (2-Chloromethoxy-ethyl)-trimethyl-silane (SEM-Cl) is used instead of 2-iodopropane. |

| Intermediate | Name | Name of Starting Material |
|---|---|---|
| 99-1 | Ethyl 1-ethyl-3-iodo-1H-pyrazole-5-carboxylate | Ethyl 5-iodo-1H-pyrazole-3-carboxylate |
| 99-2 | Ethyl 3-iodo-1-{[2-(trimethylsilyl)ethoxy]methyl}-1H-pyrazole-5-carboxylate | Ethyl 5-iodo-1H-pyrazole-3-carboxylate |

Intermediate 100

Ethyl 3-[(6-{6,6-difluoro-3-azabicyclo[3.1.0]hexan-3-yl}-2-ethylpyridin-3-yl)(hydroxy)methyl]-1-(propan-2-yl)-1H-pyrazole-5-carboxylate

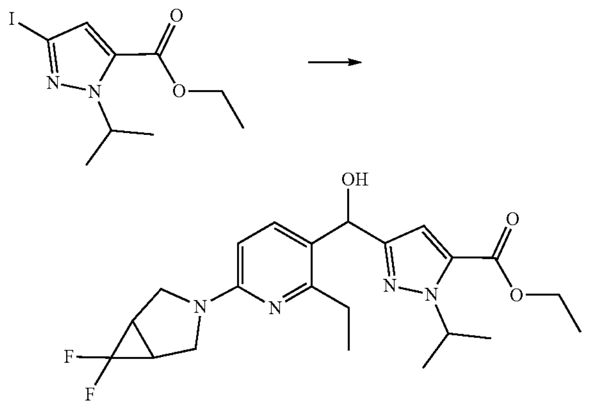

A mixture of ethyl 3-iodo-1-(propan-2-yl)-1H-pyrazole-5-carboxylate (100 mg) in THF (2 mL) is treated dropwise at −40° C. under argon atmosphere with iPrMgClxLiCl (1.3 M in THF, 300 μL). The mixture is stirred for 30 minutes and then treated dropwise with a mixture of 6-{6,6-difluoro-3-azabicyclo[3.1.0]hexan-3-yl}-2-ethylpyridine-3-carbaldehyde (90 mg) in THF (2 mL). After stirring for 3 h at −40° C. the mixture is partitioned between saturated aqueous $NH_4Cl$ and EtOAc. The aqueous phase is extracted with EtOAc. The combined organic phases are dried ($MgSO_4$) and concentrated in vacuo to give the crude product, which is directly used in the next step.

LC (Method 2): $t_R$=0.85 min. Mass spectrum (ESI+): m/z=435 $[M+H]^+$.

Intermediates 100-1 to 100-8 are prepared in analogy to Intermediate 100:

| Intermediate | Structure | $t_R$ | Mass spectrum (ESI+): m/z $[M + H]^+$ | LC Method |
|---|---|---|---|---|
| 100-1 | 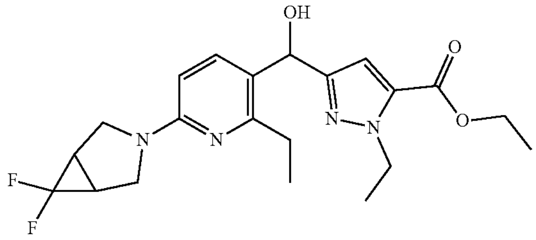 [SMILES: CCOC(=O)c1cc(C(O)c2ccc(N3CC4C(C3)C4(F)F)nc2CC)nn1CC] | 0.81 | 421 | Method 2 |
| 100-2 | 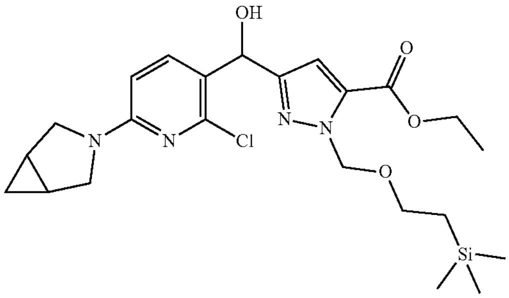 [SMILES: CCOC(=O)c1cc(C(O)c2ccc(N3CC4CC4C3)nc2Cl)nn1COCC[Si](C)(C)C] | 1.20 | 493 | Method 2 |
| 100-3 | 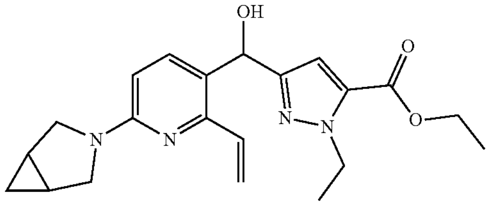 [SMILES: C=Cc1nc(N2CC3CC3C2)ccc1C(O)c1cc(C(=O)OCC)n(CC)n1] | 0.78 | 383 | Method 2 |
| 100-4 | 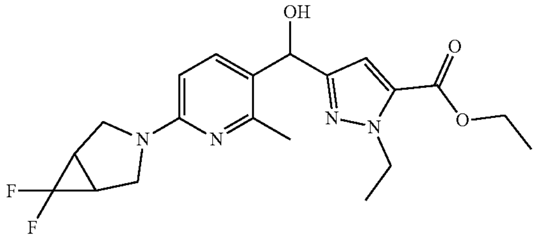 [SMILES: CCOC(=O)c1cc(C(O)c2ccc(N3CC4C(C3)C4(F)F)nc2C)nn1CC] | 0.77 | 407 | Method 2 |
| 100-5 | 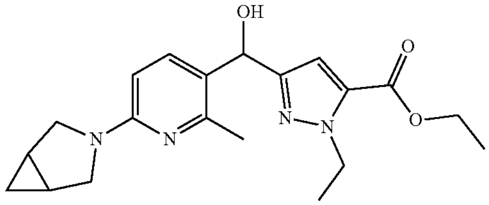 [SMILES: CCOC(=O)c1cc(C(O)c2ccc(N3CC4CC4C3)nc2C)nn1CC] | 0.71 | 371 | Method 2 |
| 100-6 | 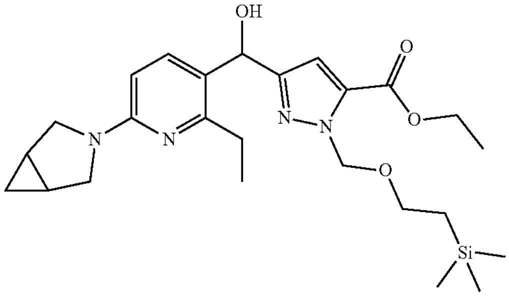 [SMILES: CCOC(=O)c1cc(C(O)c2ccc(N3CC4CC4C3)nc2CC)nn1COCC[Si](C)(C)C] | 0.94 | 487 | Method 2 |

-continued

| Intermediate | Structure | $t_R$ | Mass spectrum (ESI+): m/z $[M + H]^+$ | LC Method |
|---|---|---|---|---|
| 100-7 | 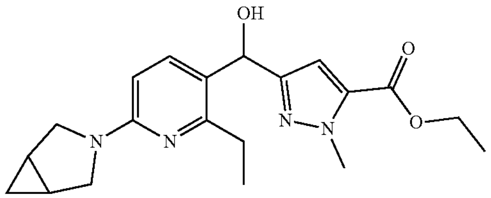 [SMILES: CCOC(=O)c1cc(C(O)c2ccc(N3CC4CC4C3)nc2CC)nn1C] | 0.77 | 371 | Method 2 |
| 100-8 | 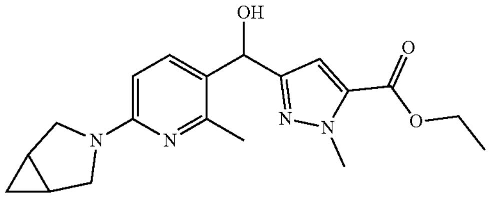 [SMILES: CCOC(=O)c1cc(C(O)c2ccc(N3CC4CC4C3)nc2C)nn1C] | | 357 | |

| Intermediate | Reaction comment |
|---|---|
| 100-2 | The aldehyde is added to the reaction mixture at −78° C., then the mixture is stirred for 1 h while warming to rt. The crude reaction product is purified by chromatography on silica gel (petroleum ether/EtOAc 99:1 → 50:50). |
| 100-3 | The reaction is conducted for 30 minutes at −40° C. and for 30 minutes at rt. |
| 100-4 | The reaction is conducted for 30 minutes at −40° C. and for 30 minutes at rt. |
| 100-5 | The reaction is conducted for 30 minutes at −40° C. and for 30 minutes at rt. |
| 100-6 | The aldehyde is added to the reaction mixture at −78° C., then the mixture is stirred for 1 h while warming to rt. The crude reaction product is purified by chromatography on silica gel (petroleum ether/EtOAc 90:10 → 70:30). |
| 100-7 | The aldehyde is added to the reaction mixture at −78° C., then the mixture is stirred for 1 h while warming to rt. The crude reaction product is purified by chromatography on silica gel (petroleum ether/EtOAc 60:40 → 0:100). |
| 100-8 | The aldehyde is added to the reaction mixture at −78° C., then the mixture is stirred for 2 h while warming to rt. The crude reaction product is purified by chromatography on silica gel (cyclohexane/EtOAc 90:10 → 50:50). |

| Intermediate | Name | Name of Starting Material 1 | Name of Starting Material 2 |
|---|---|---|---|
| 100-1 | Ethyl 3-[(6-{6,6-difluoro-3-azabicyclo[3.1.0]-hexan-3-yl}-2-ethylpyridin-3-yl)(hydroxy)-methyl]-1-ethyl-1H-pyrazole-5-carboxylate | Ethyl 1-ethyl-3-iodo-1H-pyrazole-5-carboxylate | 6-{6,6-Difluoro-3-azabicyclo-[3.1.0]hexan-3-yl}-2-ethyl-pyridine-3-carbaldehyde |
| 100-2 | Ethyl 3-[(6-{3-azabicyclo[3.1.0]hexan-3-yl}-2-chloropyridin-3-yl)(hydroxy)-methyl]-1-{[2-(trimethylsilyl)ethoxy]-methyl}-1H-pyrazole-5-carboxylate | Ethyl 3-iodo-1-{[2-(trimethylsilyl)ethoxy] methyl}-1H-pyrazole-5-carboxylate | 6-{3-Azabicyclo[3.1.0]hexan-3-yl}-2-chloropyridine-3-carbaldehyde |
| 100-3 | Ethyl 3-[(6-{3-azabicyclo[3.1.0]hexan-3-yl}-2-ethenylpyridin-3-yl)(hydroxy)-methyl]-1-ethyl-1H-pyrazole-5-carboxylate | Ethyl 1-ethyl-3-iodo-1H-pyrazole-5-carboxylate | 6-{3-Azabicyclo[3.1.0]hexan-3-yl}-2-ethenylpyridine-3-carbaldehyde |
| 100-4 | Ethyl 3-[(6-{6,6-difluoro-3-azabicyclo[3.1.0]-hexan-3-yl}-2-methylpyridin-3-yl)(hydroxy)-methyl]-1-ethyl-1H-pyrazole-5-carboxylate | Ethyl 1-ethyl-3-iodo-1H-pyrazole-5-carboxylate | 6-{6,6-Difluoro-3-azabicyclo-[3.1.0]hexan-3-yl}-2-methyl-pyridine-3-carbaldehyde |
| 100-5 | Ethyl 3-[(6-{3-azabicyclo[3.1.0]hexan-3-yl}-2-methylpyridin-3-yl)(hydroxy)-methyl]-1-ethyl-1H-pyrazole-5-carboxylate | Ethyl 1-ethyl-3-iodo-1H-pyrazole-5-carboxylate | 6-{3-Azabicyclo[3.1.0]hexan-3-yl}-2-methylpyridine-3-carbaldehyde |
| 100-6 | Ethyl 3-[(6-{3-azabicyclo[3.1.0]hexan-3-yl}-2-ethylpyridin-3-yl)(hydroxy)methyl]-1-{[2-(trimethylsilyl)ethoxy]methyl}-1H-pyrazole-5-carboxylate | Ethyl 3-iodo-1-{[2-(trimethylsilyl)ethoxy] methyl}-1H-pyrazole-5-carboxylate | 6-{3-Azabicyclo[3.1.0]hexan-3-yl}-2-ethylpyridine-3-carbaldehyde |

-continued

| Intermediate | Name | Name of Starting Material 1 | Name of Starting Material 2 |
| --- | --- | --- | --- |
| 100-7 | Ethyl 3-[(6-{3-azabicyclo[3.1.0]hexan-3-yl}-2-ethylpyridin-3-yl)(hydroxy)methyl]-1-methyl-1H-pyrazole-5-carboxylate | Ethyl 3-iodo-1-methyl-1H-pyrazole-5-carboxylate | 6-{3-Azabicyclo[3.1.0]-hexan-3-yl}-2-ethylpyridine-3-carbaldehyde |
| 100-8 | Ethyl 3-[(6-{3-azabicyclo[3.1.0]hexan-3-yl}-2-methylpyridin-3-yl)(hydroxy)-methyl]-1-methyl-1H-pyrazole-5-carboxylate | Ethyl 3-iodo-1-methyl-1H-pyrazole-5-carboxylate | 6-{3-Azabicyclo[3.1.0]-hexan-3-yl}-2-methyl-pyridine-3-carbaldehyde |

Intermediate 101

Ethyl 3-[(6-{6,6-difluoro-3-azabicyclo[3.1.0]hexan-3-yl}-2-ethylpyridin-3-yl)methyl]-1-(propan-2-yl)-1H-pyrazole-5-carboxylate

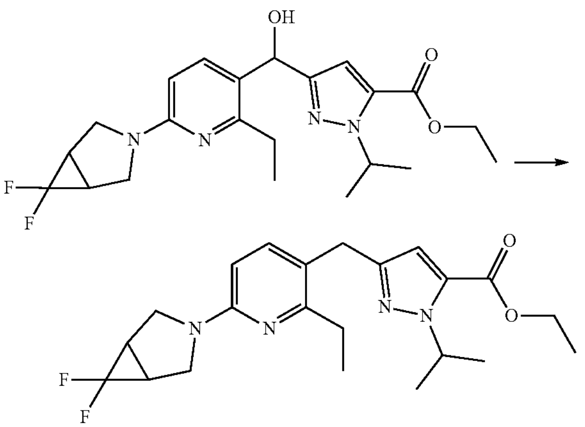

A mixture of ethyl 3-[(6-{6,6-difluoro-3-azabicyclo[3.1.0]hexan-3-yl}-2-ethylpyridin-3-yl)(hydroxy)methyl]-1-(propan-2-yl)-1H-pyrazole-5-carboxylate (141 mg), triethylsilane (492 NL) and trifluoroacetic acid (594 NL) in 1,2-dichloroethane (1.18 mL) is stirred under argon atmosphere for 30 minutes at rt. The mixture is concentrated in vacuo to give the crude product, which is directly used in the next step.

LC (Method 2): $t_R$=0.90 min. Mass spectrum (ESI+): m/z=419 $[M+H]^+$.

Intermediates 101-1 to 101-12 are prepared in analogy to Intermediate 101:

| Intermediate | Structure | $t_R$ | Mass spectrum (ESI+): m/z $[M + H]^+$ | LC Method |
| --- | --- | --- | --- | --- |
| 101-1 | 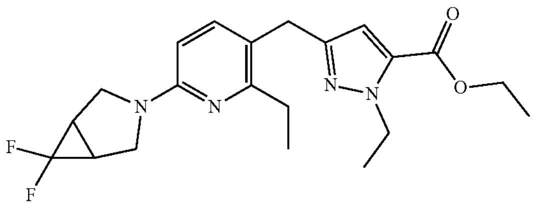 [SMILES: CCOC(=O)c1cc(Cc2ccc(N3CC4C(C3)C4(F)F)nc2CC)nn1CC] | 0.86 | 405 | Method 2 |
| 101-2 | 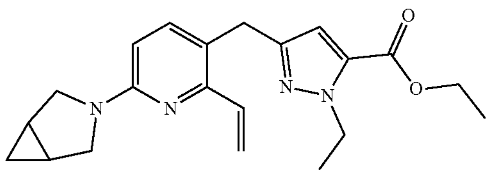 [SMILES: C=Cc1nc(N2CC3CC3C2)ccc1Cc1cc(C(=O)OCC)n(CC)n1] | 0.84 | 367 | Method 2 |
| 101-3 | 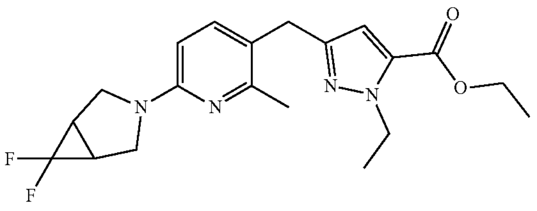 [SMILES: CCOC(=O)c1cc(Cc2ccc(N3CC4C(C3)C4(F)F)nc2C)nn1CC] | 0.82 | 391 | Method 2 |

-continued
| Intermediate | Structure | $t_R$ | Mass spectrum (ESI+): m/z $[M + H]^+$ | LC Method |
| --- | --- | --- | --- | --- |
| 101-4 | 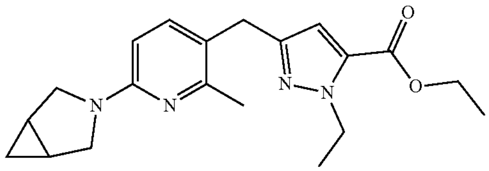 [SMILES: CCOC(=O)c1cc(Cc2ccc(N3CC4CC4C3)nc2C)nn1CC] | 0.82 | 355 | Method 2 |
| 101-5 | 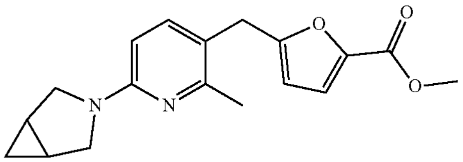 [SMILES: COC(=O)c1ccc(Cc2ccc(N3CC4CC4C3)nc2C)o1] | 0.74 | 313 | Method 2 |
| 101-6 | 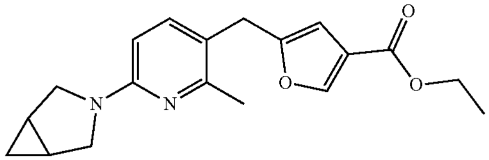 [SMILES: CCOC(=O)c1coc(Cc2ccc(N3CC4CC4C3)nc2C)c1] | 1.19 | 327 | Method 1 |
| 101-7 | 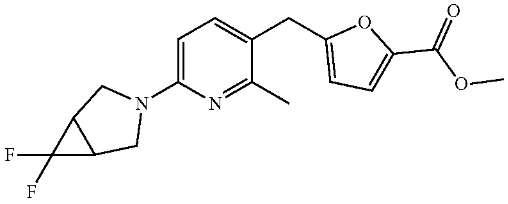 [SMILES: COC(=O)c1ccc(Cc2ccc(N3CC4C(C3)C4(F)F)nc2C)o1] | 0.77 | 349 | Method 2 |
| 101-8 | 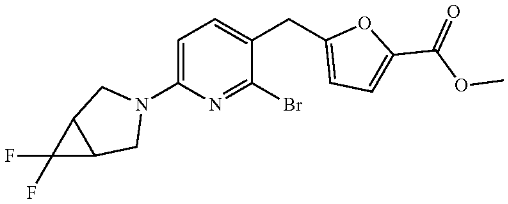 [SMILES: COC(=O)c1ccc(Cc2ccc(N3CC4C(C3)C4(F)F)nc2Br)o1] | 1.12 | 413 | Method 1 |
| 101-9 | 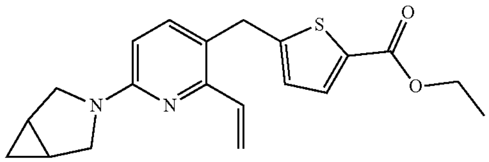 [SMILES: C=Cc1nc(N2CC3CC3C2)ccc1Cc1ccc(C(=O)OCC)s1] | 0.85 | 355 | Method 2 |
| 101-10 | 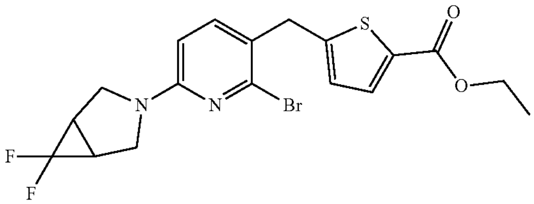 [SMILES: CCOC(=O)c1ccc(Cc2ccc(N3CC4C(C3)C4(F)F)nc2Br)s1] | 1.22 | 443 | Method 2 |
| 101-11 | 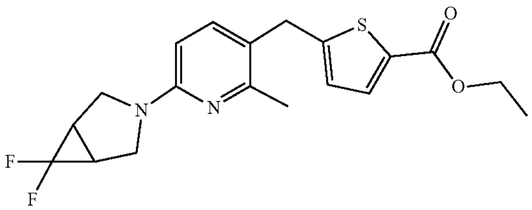 [SMILES: CCOC(=O)c1ccc(Cc2ccc(N3CC4C(C3)C4(F)F)nc2C)s1] | 0.84 | 379 | Method 2 |

-continued

| Intermediate | Structure | $t_R$ | Mass spectrum (ESI+): m/z $[M + H]^+$ | LC Method |
|---|---|---|---|---|
| 101-12 | 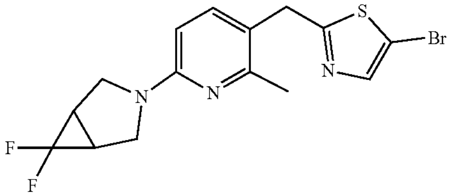 [SMILES: Cc1nc(N2CC3C(C2)C3(F)F)ccc1Cc1ncc(Br)s1] | 0.78 | 386 | Method 2 |

| Intermediate | Reaction comment |
|---|---|
| 101-1 | The reaction is conducted for 2 h at rt. |
| 101-2 | The reaction is conducted for 4 h at 30° C. |
| 101-3 | The reaction is conducted for 45 minutes at 30° C. |
| 101-4 | The reaction is conducted for 30 minutes at 30° C. |
| 100-5 | The reaction is conducted at 40° C. for 20 h. The product is purified by HPLC on reversed phase (ACN, water). |
| 101-6 | The reaction is conducted at 50° C. for 2 h. |

-continued

| Intermediate | Reaction comment |
|---|---|
| 101-7 | The reaction is conducted at 50° C. for 30 minutes. |
| 101-8 | The reaction is conducted at 50° C. for 30 minutes. |
| 101-9 | The reaction is conducted at rt for 1.5 h. |
| 101-10 | The reaction is conducted at 30° C. for 2 h. |
| 101-11 | The reaction is conducted at 50° C. for 30 minutes. |
| 101-12 | The reaction is conducted at 70° C. for 2 h. |

| Intermediate | Name | Name of Starting Material |
|---|---|---|
| 101-1 | Ethyl 3-[(6-{6,6-difluoro-3-azabicyclo[3.1.0]hexan-3-yl}-2-ethylpyridin-3-yl)methyl]-1-ethyl-1H-pyrazole-5-carboxylate | Ethyl 3-[(6-{6,6-difluoro-3-azabicyclo[3.1.0]-hexan-3-yl}-2-ethylpyridin-3-yl)(hydroxy)-methyl]-1-ethyl-1H-pyrazole-5-carboxylate |
| 101-2 | Ethyl 3-[(6-{3-azabicyclo[3.1.0]hexan-3-yl}-2-ethenylpyridin-3-yl)methyl]-1-ethyl-1H-pyrazole-5-carboxylate | Ethyl 3-[(6-{3-azabicydo[3.1.0]hexan-3-yl}-2-ethenylpyridin-3-yl)(hydroxy)methyl]-1-ethyl-1H-pyrazole-5-carboxylate |
| 101-3 | Ethyl 3-[(6-{6,6-difluoro-3-azabicyclo[3.1.0]hexan-3-yl}-2-methylpyridin-3-yl)methyl]-1-ethyl-1H-pyrazole-5-carboxylate | Ethyl 3-[(6-{6,6-difluoro-3-azabicyclo[3.1.0]-hexan-3-yl}-2-methylpyridin-3-yl)(hydroxy)-methyl]-1-ethyl-1H-pyrazole-5-carboxylate |
| 101-4 | Ethyl 3-[(6-{3-azabicyclo[3.1.0]hexan-3-yl}-2-methylpyridin-3-yl)methyl]-1-ethyl-1H-pyrazole-5-carboxylate | Ethyl 3-[(6-{3-azabicydo[3.1.0]hexan-3-yl}-2-methylpyridin-3-yl)(hydroxy)methyl]-1-ethyl-1H-pyrazole-5-carboxylate |
| 101-5 | Methyl 5-[(6-{3-azabicyclo[3.1.0]hexan-3-yl}-2-methylpyridin-3-yl)methyl]furan-2-carboxylate | Methyl 5-[(6-{3-azabicyclo[3.1.0]hexan-3-yl}-2-methylpyridin-3-yl)(hydroxy)methyl]furan-2-carboxylate |
| 101-6 | Ethyl 5-[(6-{3-azabicyclo[3.1.0]hexan-3-yl}-2-methylpyridin-3-yl)methyl]furan-3-carboxylate | Ethyl 5-[(6-{3-azabicydo[3.1.0]hexan-3-yl}-2-methylpyridin-3-yl)(hydroxy)methyl]furan-3-carboxylate |
| 101-7 | Methyl 5-[(6-{6,6-difluoro-3-azabicyclo[3.1.0]hexan-3-yl}-2-methylpyridin-3-yl)methyl]furan-2-carboxylate | Methyl 5-[(6-{6,6-difluoro-3-azabicyclo[3.1.0]hexan-3-yl}-2-methylpyridin-3-yl)(hydroxy)methyl]furan-2-carboxylate |
| 101-8 | Methyl 5-[(2-bromo-6-{6,6-difluoro-3-azabicyclo[3.1.0]hexan-3-yl}pyridin-3-yl)methyl]furan-2-carboxylate | Methyl 5-[(2-bromo-6-{6,6-difluoro-3-azabicyclo[3.1.0]hexan-3-yl}pyridin-3-yl)(hydroxy)methyl]furan-2-carboxylate |
| 101-9 | Ethyl 5-[(6-{3-azabicyclo[3.1.0]hexan-3-yl}-2-ethenylpyridin-3-yl)methyl]thiophene-2-carboxylate | Ethyl 5-[(6-{3-azabicydo[3.1.0]hexan-3-yl}-2-ethenylpyridin-3-yl)(hydroxy)methyl]thiophene-2-carboxylate |
| 101-10 | Ethyl 5-[(2-bromo-6-{6,6-difluoro-3-azabicyclo[3.1.0]hexan-3-yl}pyridin-3-yl)methyl]thiophene-2-carboxylate | Ethyl 5-[(2-bromo-6-{6,6-difluoro-3-azabicyclo[3.1.0]hexan-3-yl}pyridin-3-yl)(hydroxy)methyl]thiophene-2-carboxylate |
| 101-11 | Ethyl 5-[(6-{6,6-difluoro-3-azabicyclo[3.1.0]hexan-3-yl}-2-methylpyridin-3-yl)methyl]thiophene-2-carboxylate | Ethyl 5-[(6-{6,6-difluoro-3-azabicyclo[3.1.0]hexan-3-yl}-2-methylpyridin-3-yl)(hydroxy)methyl]thiophene-2-carboxylate |
| 101-12 | 3-{5-[(5-Bromo-1,3-thiazol-2-yl)methyl]-6-methylpyridin-2-yl}-6,6-difluoro-3-azabicyclo[3.1.0]hexane | (5-Bromo-1,3-thiazol-2-yl)(6-{6,6-difluoro-3-azabicyclo[3.1.0]hexan-3-yl}-2-methylpyridin-3-yl)methanol |

Intermediate 102

Ethyl 3-[(6-{3-azabicyclo[3.1.0]hexan-3-yl}-2-chloropyridin-3-yl)methyl]-1H-pyrazole-5-carboxylate

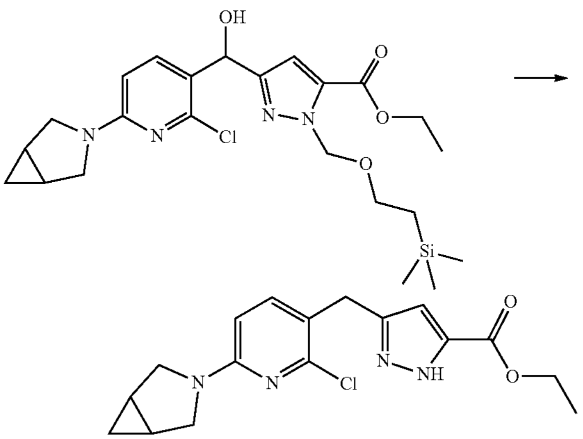

A mixture of ethyl 3-[(6-{3-azabicyclo[3.1.0]hexan-3-yl}-2-chloropyridin-3-yl)(hydroxy)methyl]-1-{[2-(trimethylsilyl)ethoxy]methyl}-1H-pyrazole-5-carboxylate (848 mg), triethylsilane (1.38 mL), trifluoroacetic acid (663 μL) and borontrifluoride-diethyletherate ($BF_3xOEt_2$, 2.3 mL) in DCM (8 mL) is stirred under argon atmosphere for 12 h at rt. The mixture is partitioned between water and DCM. The aqueous phase is extracted twice with DCM. The combined organic phases are washed with brine, dried ($MgSO_4$), concentrated in vacuo and the residue is chromatographed on silica gel (petroleum ether/EtOAc 80:20→0:100) to give the title compound.

LC (Method 2): $t_R$=1.05 min. Mass spectrum (ESI+): m/z=347 $[M+H]^+$.

Intermediates 102-1 to 102-3 are prepared in analogy to Intermediate 102:

| Intermediate | Structure | $t_R$ | Mass spectrum (ESI+): m/z $[M + H]^+$ | LC Method |
|---|---|---|---|---|
| 102-1 | 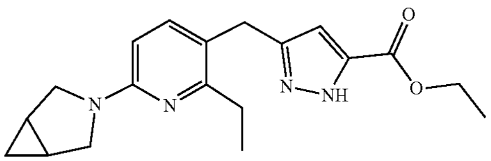 [SMILES: CCOC(=O)c1cc(Cc2ccc(N3CC4CC4C3)nc2CC)n[nH]1] | 0.75 | 341 | Method 2 |
| 102-2 | 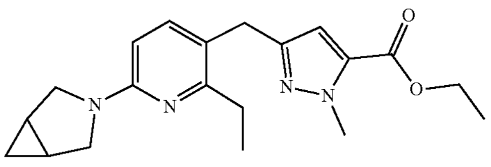 [SMILES: CCOC(=O)c1cc(Cc2ccc(N3CC4CC4C3)nc2CC)nn1C] | 0.82 | 355 | Method 2 |
| 102-3 | 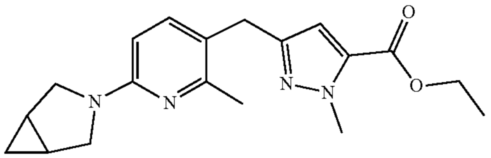 [SMILES: CCOC(=O)c1cc(Cc2ccc(N3CC4CC4C3)nc2C)nn1C] | 1.15 | 341 | Method 1 |

| Intermediate | Reaction comment |
|---|---|
| 102-3 | The reaction is conducted at 0° C. The mixture is stirred for 1.5 h while warming to rt. |

| Intermediate | Name | Name of Starting Material |
|---|---|---|
| 102-1 | Ethyl 3-[(6-{3-azabicyclo[3.1.0]hexan-3-yl}-2-ethylpyridin-3-yl)methyl]-1H-pyrazole-5-carboxylate | Ethyl 3-[(6-{3-azabicyclo[3.1.0]hexan-3-yl}-2-ethyl-pyridin-3-yl)(hydroxy)methyl]-1-{[2-(trimethylsilyl)-ethoxy]methyl}-1H-pyrazole-5-carboxylate |
| 102-2 | Ethyl 3-[(6-{3-azabicyclo[3.1.0]hexan-3-yl}-2-ethylpyridin-3-yl)methyl]-1-methyl-1H-pyrazole-5-carboxylate | Ethyl 3-[(6-{3-azabicyclo[3.1.0]hexan-3-yl}-2-ethylpyridin-3-yl)(hydroxy)methyl]-1-methyl-1H-pyrazole-5-carboxylate |
| 102-3 | Ethyl 3-[(6-{3-azabicyclo[3.1.0]hexan-3-yl}-2-methylpyridin-3-yl)methyl]-1-methyl-1H-pyrazole-5-carboxylate | Ethyl 3-[(6-{3-azabicyclo[3.1.0]hexan-3-yl}-2-methylpyridin-3-yl)(hydroxy)methyl]-1-methyl-1H-pyrazole-5-carboxylate |

Intermediate 103

Ethyl 3-[(6-{3-azabicyclo[3.1.0]hexan-3-yl}-2-chloropyridin-3-yl)methyl]-1-{[2-(trimethylsilyl)ethoxy]methyl}-1H-pyrazole-5-carboxylate and Ethyl 5-[(6-{3-azabicyclo[3.1.0]hexan-3-yl}-2-chloropyridin-3-yl)methyl]-1-({[2-(trimethylsilyl)ethyl]amino}methyl)-1-{[2-(trimethylsilyl)ethoxy]methyl}-1H-pyrazole-3-carboxylate (Mixture of Isomers)

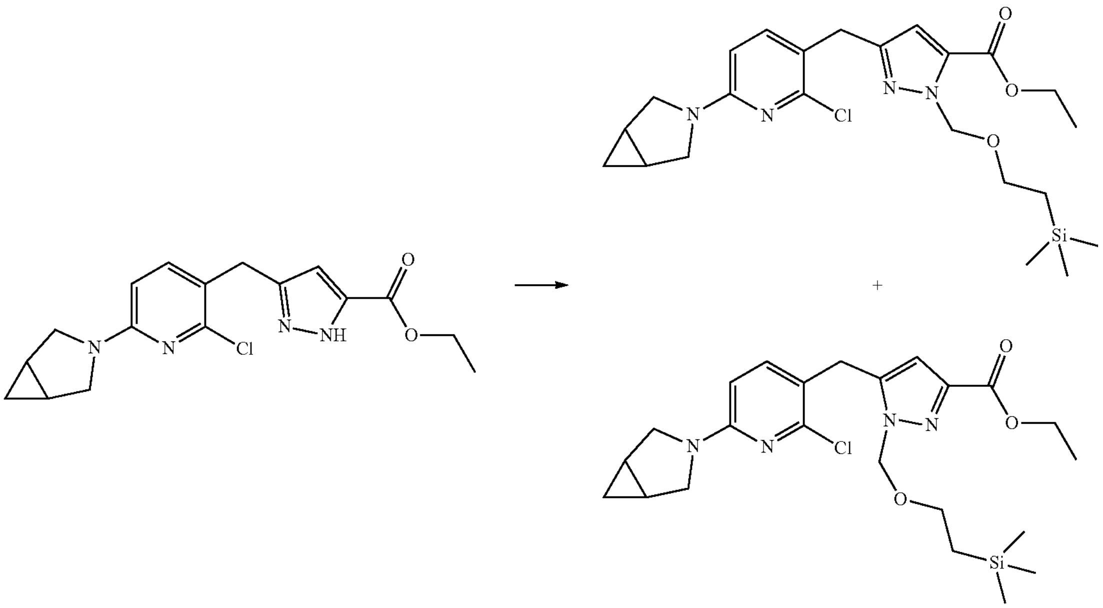 [SMILES: CCOC(=O)c1cc(Cc2ccc(N3CC4CC4C3)nc2Cl)n[nH]1 ; CCOC(=O)c1cc(Cc2ccc(N3CC4CC4C3)nc2Cl)n(COCC[Si](C)(C)C)n1 ; CCOC(=O)c1cc(Cc2ccc(N3CC4CC4C3)nc2Cl)nn1COCC[Si](C)(C)C]

NaH (60% in mineral oil, 73 mg) is added under argon atmosphere at 0° C. to a mixture of ethyl 3-[(6-{3-azabicyclo[3.1.0]hexan-3-yl}-2-chloropyridin-3-yl)methyl]-1H-pyrazole-5-carboxylate (500 mg) in DMF (3 mL). The mixture is stirred for 30 minutes and then treated dropwise with (2-chloromethoxy-ethyl)-trimethyl-silane (SEM-Cl, 313 μL). The mixture is stirred for 2 h while warming to rt. Then the mixture is partitioned between saturated aqueous $NH_4Cl$ and EtOAc. The aqueous phase is extracted with EtOAc. The combined organic phases are washed with brine, dried ($MgSO_4$), concentrated in vacuo and the residue is chromatographed on silica gel (petroleum ether/EtOAc 99:1→70:30) to give the title compounds as a mixture of isomers.

LC (Method 2): $t_R$=1.05 min. Mass spectrum (ESI+): m/z=347 $[M+H]^+$.

Intermediate 104

Ethyl 3-[(6-{3-azabicyclo[3.1.0]hexan-3-yl}-2-ethylpyridin-3-yl)methyl]-1-ethyl-1H-pyrazole-5-carboxylate

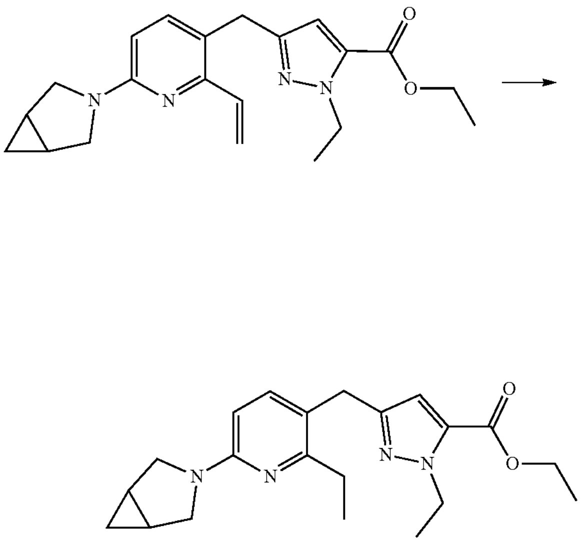

A mixture of ethyl 3-[(6-{3-azabicyclo[3.1.0]hexan-3-yl}-2-ethenylpyridin-3-yl)methyl]-1-ethyl-1H-pyrazole-5-carboxylate (40 mg), 10% palladium on carbon (5 mg) in MeOH (3 mL) is shaken under hydrogen atmosphere (3 bar) at rt for 4.5 h. The mixture is filtered and the filtrate is concentrated in vacuo to give the crude product, which is directly used in the next step. LC (Method 2): $t_R$=0.84 min; Mass spectrum (ESI+): m/z=369 $[M+H]^+$.

Intermediates 104-1 is prepared in analogy to Intermediate 104:

Intermediate 105

Ethyl 3-[(6-fluoro-2-methylpyridin-3-yl)(hydroxy)methyl]-1-methyl-1H-pyrazole-5-carboxylate

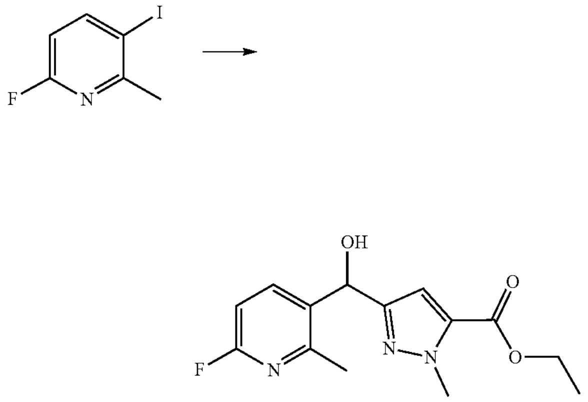

A mixture of 6-fluoro-3-iodo-2-methylpyridine (550 mg) in THF (25 mL) is treated dropwise at −50° C. under argon atmosphere with iPrMgClxLiCl (1.3 M in THF, 2.2 mL). The mixture is stirred for 1 h and then treated dropwise with a mixture of ethyl 3-formyl-1-methyl-1H-pyrazole-5-carboxylate (300 mg) in THF (1 mL). After stirring for 1 h at −50° C. the mixture is partitioned between saturated aqueous $NH_4Cl$ and EtOAc. The aqueous phase is extracted with EtOAc. The combined organic phases are dried ($MgSO_4$), concentrated in vacuo and the residue is chromatographed on silica gel (petroleum ether/EtOAc 90:10→50:50) to give the title compound.

LC (Method 2): $t_R$=0.89 min. Mass spectrum (ESI+): m/z=294 $[M+H]^+$.

| Intermediate | Structure | $t_R$ | Mass spectrum (ESI+): m/z $[M + H]^+$ | LC Method |
|---|---|---|---|---|
| 104-1 | 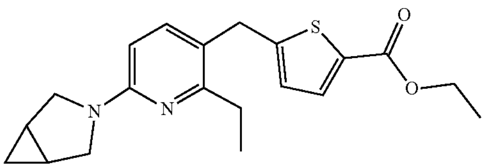 [SMILES: CCOC(=O)c1ccc(Cc2ccc(N3CC4CC4C3)nc2CC)s1] | 0.75 | 357 | Method 2 |

| Intermediate | Reaction comment |
|---|---|
| 104-1 | The reaction is conducted at rt for 4 h under 1 bar hydrogen atmosphere. The product is purified by HPLC on reversed phase (ACN, water). |

| Intermediate | Name | Name of Starting Material |
|---|---|---|
| 104-1 | Ethyl 5-[(6-{3-azabicydo[3.1.0]hexan-3-yl}-2-ethylpyridin-3-yl)methyl]thiophene-2-carboxylate | Ethyl 5-[(6-{3-azabicyclo[3.1.0]hexan-3-yl}-2-ethenylpyridin-3-yl)methyl]thiophene-2-carboxylate |

Intermediate 106

3-[(6-{6,6-Difluoro-3-azabicyclo[3.1.0]hexan-3-yl}-2-methylpyridin-3-yl)(hydroxy)methyl]-1-methyl-1H-pyrazole-5-carboxylic acid

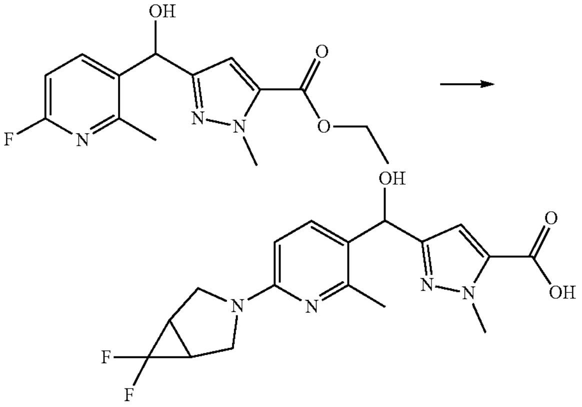

A mixture of ethyl 3-[(6-fluoro-2-methylpyridin-3-yl)(hydroxy)methyl]-1-methyl-1H-pyrazole-5-carboxylate (430 mg), 6,6-difluoro-3-azabicyclo[3.1.0]hexane hydrochloride (1.36 g) and $K_2CO_3$ (2.4 g) in DMSO (10 mL) is heated for 48 h to 150° C. After cooling to rt the mixture is diluted with ACN, filtered and purified by HPLC on reversed phase (ACN, water) to give the title compound. LC (Method 2): $t_R$=0.63 min; Mass spectrum (ESI+): m/z=365 $[M+H]^+$.

Intermediate 107

3-[(6-{6,6-Difluoro-3-azabicyclo[3.1.0]hexan-3-yl}-2-methylpyridin-3-yl)methyl]-1-methyl-1H-pyrazole-5-carboxylic acid

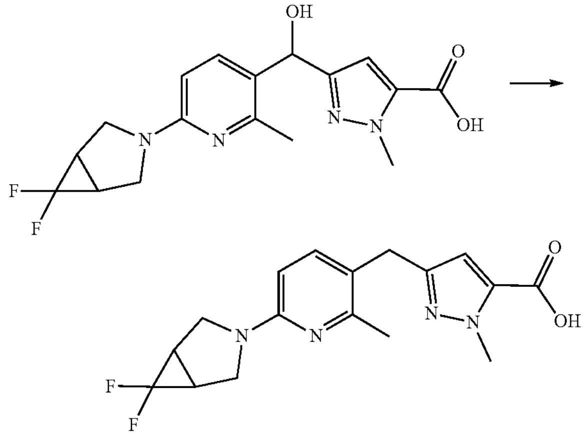

A mixture of 3-[(6-{6,6-difluoro-3-azabicyclo[3.1.0]hexan-3-yl}-2-methylpyridin-3-yl)(hydroxy)methyl]-1-methyl-1H-pyrazole-5-carboxylic acid (173 mg), triethylsilane (380 μL), trifluoroacetic acid (185 μL) and borontrifluoride-diethyletherate ($BF_3xOEt_2$, 293 μL) in DCM (3 mL) and THF (1 mL) is stirred under argon atmosphere for 12 h at rt. The mixture is diluted with water and purified by HPLC on reversed phase (ACN, water) to give the title compound.

LC (Method 2): $t_R$=0.69 min. Mass spectrum (ESI+): m/z=349 $[M+H]^+$.

Intermediate 108

1-[(6-{5-Azaspiro[2.3]hexan-5-yl}-2-methylpyridin-3-yl)methyl]-1H-pyrazole-4-carboxylic acid

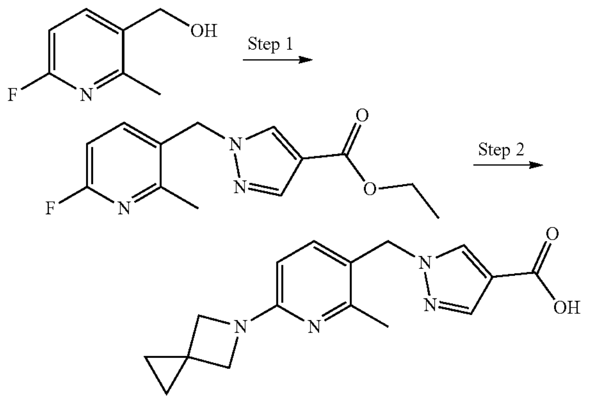

Step 1: Ethyl 1-[(6-fluoro-2-methylpyridin-3-yl)methyl]-1H-pyrazole-4-carboxylate (6-Fluoro-2-methylpyridin-3-yl)methanol (4.12 g) is dissolved in THF (50 mL) and cooled to −10° C. Ethyl 1H-pyrazole-4-carboxylate (4.43 g) and tributyl phosphine (9 mL) are added. Di-tert.-butyl-azodicarboxylate (DBAD, 7.4 g) is slowly added portionwise, the mixture is stirred at rt for 45 min and concentrated in vacuo. The residue is chromatographed on silica gel (cyclohexane/EtOAc) to give the title compound.

LC (Method 2): $t_R$=0.88 min; Mass spectrum ($ESI^+$): m/z=264 $[M+H]^+$.

Step 2: 1-[(6-{5-Azaspiro[2.3]hexan-5-yl}-2-methylpyridin-3-yl)methyl]-1H-pyrazole-4-carboxylic acid Ethyl 1-[(6-fluoro-2-methylpyridin-3-yl)methyl]-1H-pyrazole-4-carboxylate (0.5 g) is dissolved in DMSO (2 mL). 5-Azaspiro[2.3]hexane trifluoroacetate (1.2 g) and DIPEA (2 mL) are added and the mixture is stirred for 16 h at 100° C. and additional 5 h at 120° C. After cooling to rt, the N,N-diisopropyl-ethylamine phase is removed, 4 M NaOH (4 mL) is added and stirred at 60° C. for 2 h. Aqueous HCl (4 M, 4 mL) is added and the mixture is purified by HPLC on reversed phase (ACN, water) to give the title compound. LC (Method 1): $t_R$=0.68 min; Mass spectrum ($ESI^+$): m/z=299 $[M+H]^+$.

Intermediate 109

Methyl 5-[(6-{3-azabicyclo[3.1.0]hexan-3-yl}-2-methylpyridin-3-yl)(hydroxy)methyl]furan-2-carboxylate

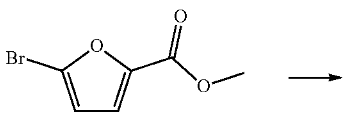

-continued

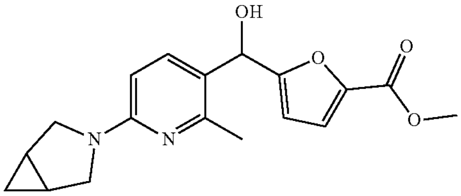

A mixture of methyl 5-bromofuran-2-carboxylate (500 mg) in THF (15 mL) is treated dropwise at −50° C. with iPrMgClxLiCl (1.3 M in THF, 1.95 mL). The mixture is stirred at for 30 minutes at −50° C. and then cooled to −78° C. 6-{3-Azabicyclo[3.1.0]hexan-3-yl}-2-methylpyridine-3-carbaldehyde (592 mg) in THF (8 mL) is added and the mixture is stirred for 1 h at −78° C. and then for 30 minutes at 0° C. The reaction is quenched with saturated aqueous $NH_4Cl$ and water. The mixture is extracted with EtOAc. The combined organic phases are dried ($MgSO_4$), concentrated in vacuo and the residue is chromatographed on silica gel (petroleum ether/EtOAc 85:15→50:50) to give the title compound.

LC (Method 2): $t_R$=0.70 min. Mass spectrum (ESI+): m/z=329 $[M+H]^+$.

Intermediates 109-1 to 109-7 are prepared in analogy to Intermediate 109:

| Intermediate | Structure | $t_R$ | Mass spectrum (ESI+): m/z $[M + H]^+$ | LC Method |
|---|---|---|---|---|
| 109-1 | 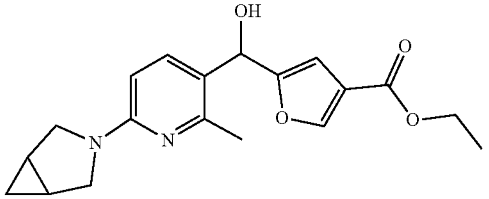 [SMILES: CCOC(=O)c1coc(C(O)c2ccc(N3CC4CC4C3)nc2C)c1] | 1.05 | 343 | Method 1 |
| 109-2 | 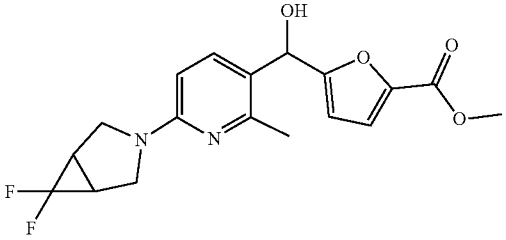 [SMILES: COC(=O)c1ccc(C(O)c2ccc(N3CC4C(C3)C4(F)F)nc2C)o1] | 0.97 | 365 | Method 1 |
| 109-3 | 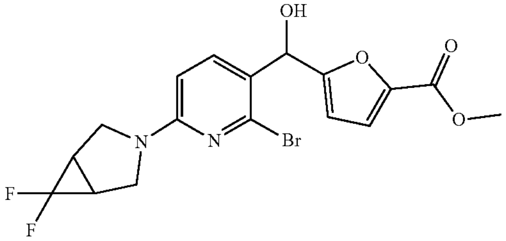 [SMILES: COC(=O)c1ccc(C(O)c2ccc(N3CC4C(C3)C4(F)F)nc2Br)o1] | 1.04 | 429 | Method 2 |
| 109-4 | 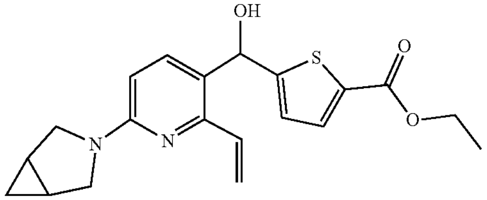 [SMILES: C=Cc1nc(N2CC3CC3C2)ccc1C(O)c1ccc(C(=O)OCC)s1] | 0.80 | 371 | Method 2 |
| 109-5 | 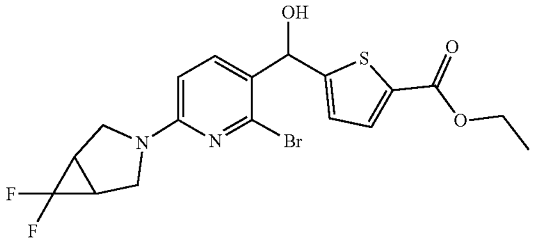 [SMILES: CCOC(=O)c1ccc(C(O)c2ccc(N3CC4C(C3)C4(F)F)nc2C)s1] | 1.12 | 459 | Method 2 |

-continued

| Intermediate | Structure | $t_R$ | Mass spectrum (ESI+): m/z $[M + H]^+$ | LC Method |
|---|---|---|---|---|
| 109-6 | 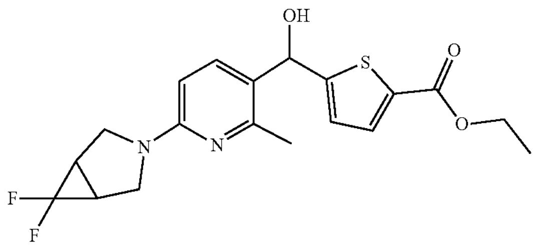 | 0.807 | 395 | Method 2 |
| 109-7 | 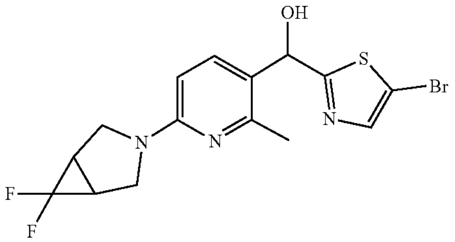 [SMILES: Cc1nc(N2CC3C(C2)C3(F)F)ccc1C(O)c1ncc(Br)s1] | 0.74 | 402 | Method 2 |

| Intermediate | Reaction comment |
|---|---|
| 109-1 | After addition of iPrMgClxLiCl the mixture is slowly warmed to −10° C. over 2 h. Then the mixture is cooled to −30° C. and the aldehyde is added, followed by stirring for 1 h while warming to −10° C. |
| 109-3 | The reaction is conducted at −78° C. The product is purified by HPLC on reversed phase (ACN, water). |
| 109-4 | The reaction is conducted at −60° C. instead of −50° C. and warmed after the addition to rt over 17 h. |

-continued

| Intermediate | Reaction comment |
|---|---|
| 109-5 | The reaction is conducted at −78° C. |
| 109-6 | The reaction is conducted at −78° C. The product is purified by HPLC on reversed phase (ACN, water). |
| 109-7 | The reaction is conducted at −78° C. The product is purified by HPLC on reversed phase (ACN, water). |

| Intermediate | Name | Name of Starting Material 1 | Name of Starting Material 2 |
|---|---|---|---|
| 109-1 | Ethyl 5-[(6-{3-azabicyclo[3.1.0]hexan-3-yl}-2-methylpyridin-3-yl)-(hydroxy)methyl]furan-3-carboxylate | 3-(5-Iodo-6-methyl-pyridin-2-yl)-3-aza-bicyclo[3.1.0]hexane | Ethyl 5-formylfuran-3-carboxylate |
| 109-2 | Methyl 5-[(6-{6,6-difluoro-3-azabicyclo-[3.1.0]hexan-3-yl}-2-methyl-pyridin-3-yl)(hydroxy)methyl]furan-2-carboxylate | Methyl 5-bromofuran-2-carboxylate | 6-{6,6-Difluoro-3-azabicyclo-[3.1.0]hexan-3-yl}-2-methyl-pyridine-3-carbaldehyde |
| 109-3 | Methyl 5-[(2-bromo-6-{6,6-difluoro-3-azabicyclo[3.1.0]hexan-3-yl}pyridin-3-yl)(hydroxy)methyl]furan-2-carboxylate | Methyl 5-bromofuran-2-carboxylate | 2-Bromo-6-{6,6-difluoro-3-azabicyclo[3.1.0]hexan-3-yl}pyridine-3-carbaldehyde |
| 109-4 | Ethyl 5-[(6-{3-azabicyclo[3.1.0]hexan-3-yl}-2-ethenylpyridin-3-yl)(hydroxy)-methyl]thiophene-2-carboxylate | Ethyl 5-bromothiophene-2-carboxylate | 6-{3-Azabicyclo[3.1.0]hexan-3-yl}-2-ethenylpyridine-3-carbaldehyde |
| 109-5 | Ethyl 5-[(2-bromo-6-{6,6-difluoro-3-azabicyclo[3.1.0]hexan-3-yl}pyridin-3-yl)(hydroxy)methyl]thiophene-2-carboxylate | Ethyl 5-bromothiophene-2-carboxylate | 2-Bromo-6-{6,6-difluoro-3-azabicyclo[3.1.0]hexan-3-yl}pyridine-3-carbaldehyde |
| 109-6 | Ethyl 5-[(6-{6,6-difluoro-3-azabicyclo-[3.1.0]hexan-3-yl}-2-methylpyridin-3-yl)(hydroxy)methyl]-thiophene-2-carboxylate | Ethyl 5-bromothiophene-2-carboxylate | 6-{6,6-Difluoro-3-azabicyclo-[3.1.0]hexan-3-yl}-2-methyl-pyridine-3-carbaldehyde |
| 109-7 | (5-Bromo-1,3-thiazol-2-yl)(6-{6,6-difluoro-3-azabicyclo[3.1.0]hexan-3-yl}-2-methylpyridin-3-yl)methanol | 2,5-Dibromo-1,3-thiazole | 6-{6,6-Difluoro-3-azabicyclo-[3.1.0]hexan-3-yl}-2-methyl-pyridine-3-carbaldehyde |

Intermediate 110

1-[(4-{3-Azabicyclo[3.1.0]hexan-3-yl}-3-cyanophenyl)methyl]-1H-pyrazole-4-carboxylic acid

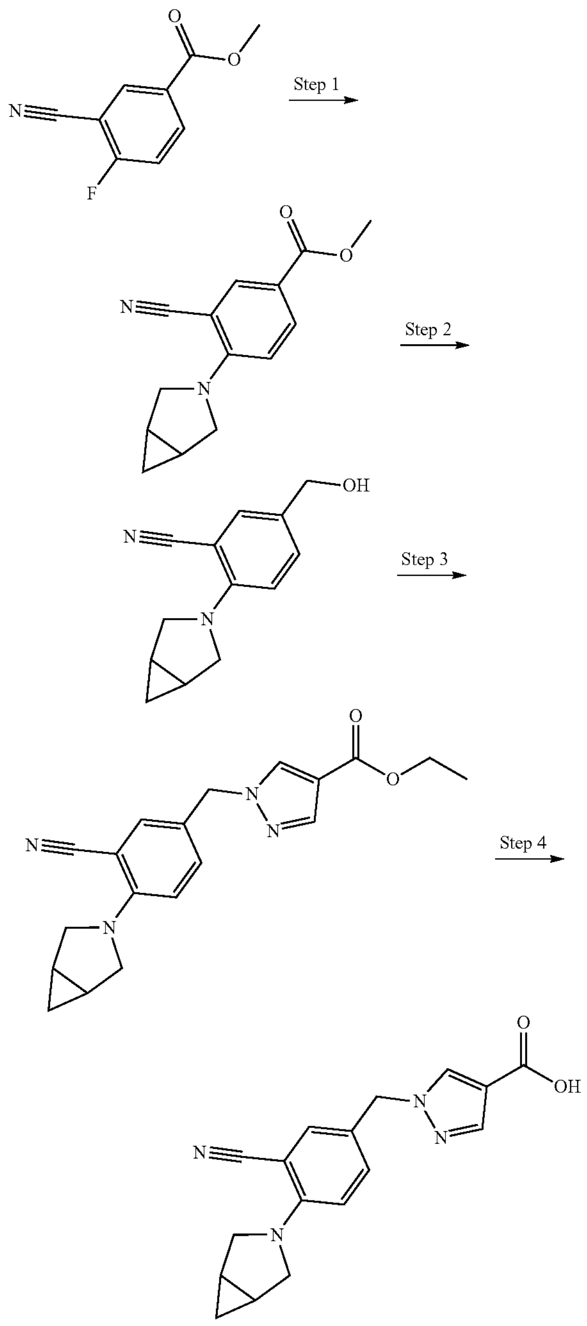

Step 1: Methyl 4-{3-azabicyclo[3.1.0]hexan-3-yl}-3-cyanobenzoate

The title compound is prepared from methyl 3-cyano-4-fluorobenzoate and 3-azabicyclo[3.1.0]hexane hydrochloride following a procedure analogous to that described in Step 1 of Intermediate 111.

Step 2: 2-{3-Azabicyclo[3.1.0]hexan-3-yl}-5-(hydroxymethyl)benzonitrile

The title compound is prepared from methyl 4-{3-azabicyclo[3.1.0]hexan-3-yl}-3-cyanobenzoate following a procedure analogous to that described in Step 4 of Intermediate 118.

LC (Method 2): $t_R$=0.92 min; Mass spectrum (ESI$^+$): m/z=215 $[M+H]^+$.

Step 3: Ethyl 1-[(4-{3-azabicyclo[3.1.0]hexan-3-yl}-3-cyanophenyl)methyl]-1H-pyrazole-4-carboxylate The title compound is prepared from 2-{3-azabicyclo[3.1.0]hexan-3-yl}-5-(hydroxymethyl)benzonitrile and ethyl 1H-pyrazole-4-carboxylate following a procedure analogous to that described in Step 3 of Intermediate 111.

Step 4: 1-[(4-{3-Azabicyclo[3.1.0]hexan-3-yl}-3-cyanophenyl)methyl]-1H-pyrazole-4-carboxylic acid The title compound is prepared from ethyl 1-[(4-{3-azabicyclo[3.1.0]hexan-3-yl}-3-cyanophenyl)methyl]-1H-pyrazole-4-carboxylate following a procedure analogous to that described in Step 4 of Intermediate 111.

Intermediate 111

1-[(4-{3-Azabicyclo[3.1.0]hexan-3-yl}-3,5-difluorophenyl)methyl]-1H-pyrazole-4-carboxylic acid

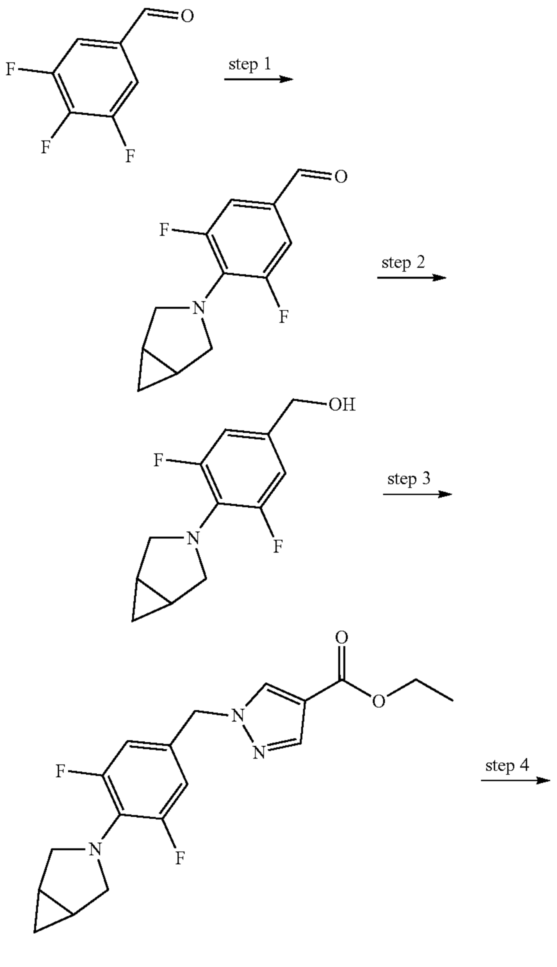

-continued

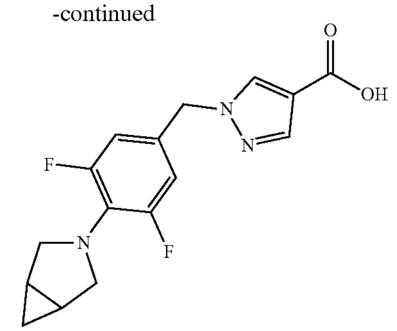

Step 1: 4-{3-Azabicyclo[3.1.0]hexan-3-yl}-3,5-difluorobenzaldehyde

A mixture of 3,4,5-trifluorobenzaldehyde (1.50 g), 3-azabicyclo[3.1.0]hexane hydrochloride (1.23 g), $^{i}Pr_2NEt$ (4 mL), and DMF (15 mL) is stirred at 70° C. overnight. After cooling to rt, water is added and the resulting mixture is extracted with ethyl acetate (3×). The combined extract is dried ($Na_2SO_4$) and concentrated. The residue is chromatographed on silica gel (petroleum ether/EtOAc 98:2→95:5) to give the title compound.

LC (Method 2): $t_R$=1.13 min; Mass spectrum ($ESI^+$): m/z=224 $[M+H]^+$.

Step 2: (4-{3-Azabicyclo[3.1.0]hexan-3-yl}-3,5-difluorophenyl)methanol $NaBH_4$ (0.18 g) is added portionwise to 4-{3-azabicyclo[3.1.0]hexan-3-yl}-3,5-difluorobenzaldehyde (0.97 g) in THF (10 mL) and methanol (10 mL) at 0° C. The mixture is stirred for 1 h in the cooling bath and another 30 min at rt before aqueous HCl solution (1 mol/L) is added. The mixture is stirred for 30 min before it is neutralized with aqueous $NaHCO_3$ solution. The mixture is extracted with ethyl acetate (2×), and the combined extract is dried ($Na_2SO_4$) and concentrated. The residue is chromatographed on silica gel (petroleum ether/EtOAc 95:5→85:15) to give the title compound.

LC (Method 2): $t_R$=1.04 min; Mass spectrum ($ESI^+$): m/z=226 $[M+H]^+$.

Step 3: Ethyl 1-[(4-{3-azabicyclo[3.1.0]hexan-3-yl}-3,5-difluorophenyl)methyl]-1H-pyrazole-4-carboxylate A mixture of (4-{3-azabicyclo[3.1.0]hexan-3-yl}-3,5-difluorophenyl)methanol (0.62 g), ethyl 1H-pyrazole-4-carboxylate (0.48 g), p-toluenesulfonic acid (0.28 g), and MeCN (5 mL) is stirred at 70° C. for 1.5 h (if the reaction is not complete and depending on the degree of conversion the temperature is increased and/or reaction time is extended). After cooling to room temperature, the mixture is concentrated, water is added, and the resulting mixture is neutralized with aqueous $NaHCO_3$ solution. The resulting mixture is extracted with ethyl acetate (3×), and the combined extract is dried ($Na_2SO_4$) and concentrated. The residue is chromatographed (HPLC; ACN/water/ammonia) to give the title compound. LC (Method 2): $t_R$=1.20 min; Mass spectrum ($ESI^+$): m/z=348 $[M+H]^+$.

Step 4: 1-[(4-{3-Azabicyclo[3.1.0]hexan-3-yl}-3,5-difluorophenyl)methyl]-1H-pyrazole-4-carboxylic acid A mixture of ethyl 1-[(4-{3-azabicyclo[3.1.0]hexan-3-yl}-3,5-difluorophenyl)methyl]-1H-pyrazole-4-carboxylate (0.10 g), aqueous NaOH (4 mol/L; 0.5 mL), THF (2 mL), and EtOH (2 mL) is stirred at 70° C. for 1.5 h. After cooling to room temperature, the mixture is concentrated. Water (2 mL) and aqueous HCl (4 mol/L; 0.5 mL) are added, and the resulting mixture is adjusted to a pH value of ca. 5 with aq. NaOH. The precipitate formed is separated and dried and used as is in the next reaction step; alternatively, if no precipitate forms, the aqueous phase is concentrated and the remainder is used as is in the next reaction step.

LC (Method 2): $t_R$=1.04 min; Mass spectrum ($ESI^+$): m/z=320 $[M+H]^+$.

Intermediate 112

2-[(4-{3-Azabicyclo[3.1.0]hexan-3-yl}-3,5-difluorophenyl)methyl]-1H-imidazole-5-carboxylic acid

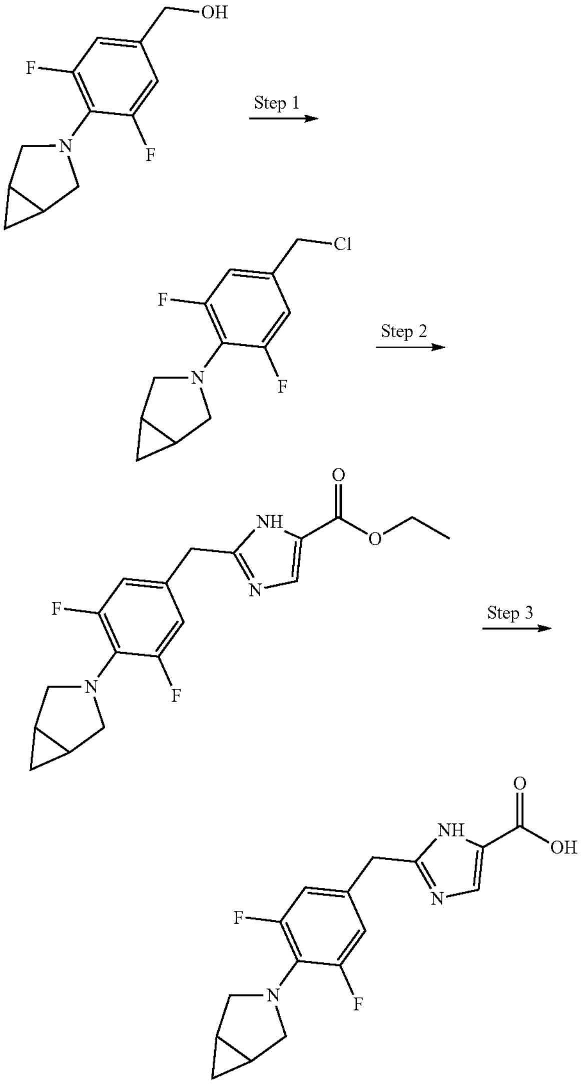

Step 1: 3-[4-(Chloromethyl)-2,6-difluorophenyl]-3-azabicyclo[3.1.0]hexane

A mixture of (4-{3-azabicyclo[3.1.0]hexan-3-yl}-3,5-difluorophenyl)methanol (60 mg), $SOCl_2$ (0.04 mL), and dichloromethane (1 mL) is stirred at room temperature for 30 min. The mixture is concentrated, taken up in toluene, concentrated again, and used as is in the next reaction step.

Step 2: Ethyl 2-[(4-{3-azabicyclo[3.1.0]hexan-3-yl}-3,5-difluorophenyl)methyl]-1H-imidazole-5-carboxylate LiO$^t$Bu (21 mg) is added to a mixture of ethyl 1H-imidazole-4-carboxylate (37 mg), $^t$BuOH (0.4 mL), and DCM (1.6 mL) chilled in an ice bath. The mixture is stirred for 5 min prior to the addition of 3-[4-(chloromethyl)-2,6-difluorophenyl]-3-azabicyclo[3.1.0]hexane (65 mg, crude product from Step 1) in DCM (0.4 mL). The cooling bath is removed, and the mixture is stirred at 40° C. overnight. After cooling to rt, water and DCM are added. The organic phase is separated, and the aqueous phase is extracted with DCM (2×). The combined organic extract is concentrated, and the residue is chromatographed (HPLC; ACN/water/ammonia) to give the title compound.

LC (Method 2): $t_R$=0.89 min; Mass spectrum (ESI$^+$): m/z=348 [M+H]$^+$.

Step 3: 2-[(4-{3-Azabicyclo[3.1.0]hexan-3-yl}-3,5-difluorophenyl)methyl]-1H-imidazole-5-carboxylic acid The title compound is prepared from ethyl 2-[(4-{3-azabicyclo[3.1.0]hexan-3-yl}-3,5-difluorophenyl)methyl]-1H-imidazole-5-carboxylate following a procedure analogous to that described in Step 4 of Intermediate 111.

LC (Method 2): $t_R$=0.82 min; Mass spectrum (ESI$^+$): m/z=320 [M+H]$^+$.

Intermediate 113

1-[(4-{3-Azabicyclo[3.1.0]hexan-3-yl}-3-cyano-2-methylphenyl)methyl]-1H-pyrazole-4-carboxylic acid

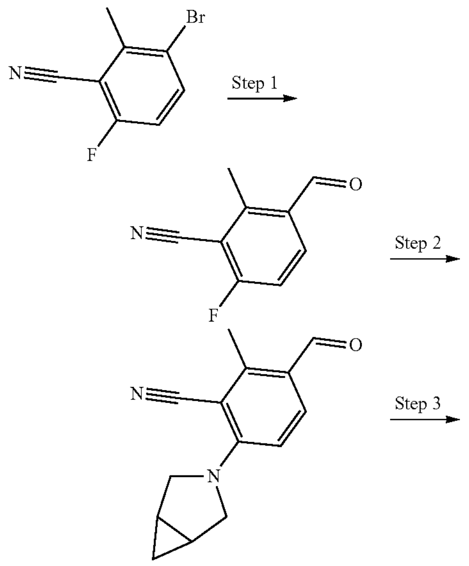

-continued

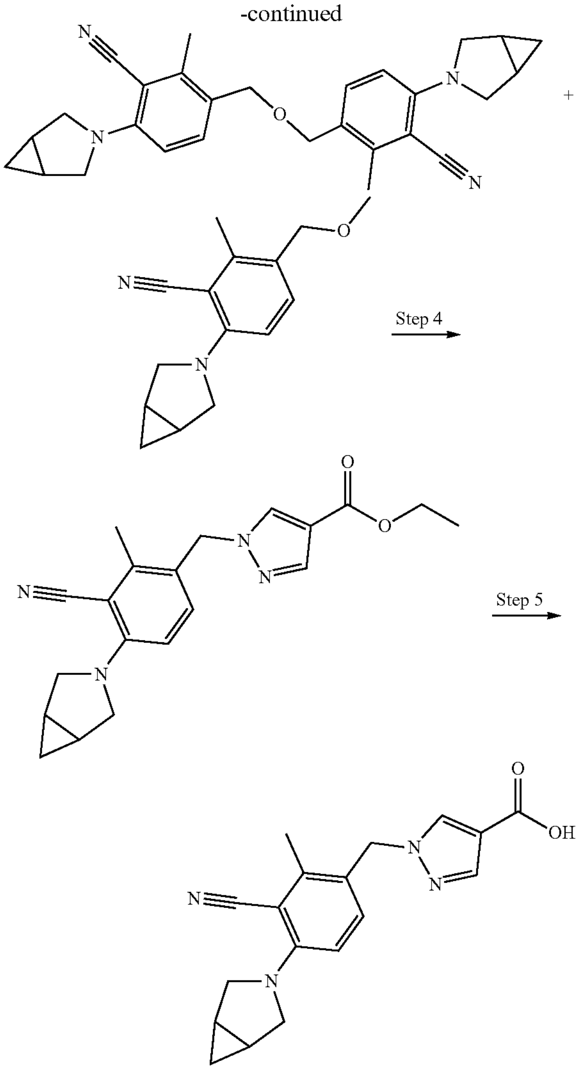

Step 1: 6-Fluoro-3-formyl-2-methylbenzonitrile $^i$PrMgCl*LiCl (Turbo Grignard; 1.3 mol/L in THF, 3.8 mL) is added dropwise to 3-bromo-6-fluoro-2-methylbenzonitrile (1.0 g) in THF (25 mL) at −20° C. The mixture is warmed to 0° C. over a period of 1.3 h prior to the addition of another portion of iPrMgCl*LiCl (Turbo Grignard; 1.3 mol/L in THF, 1.0 mL). The cooling bath is removed, and the mixture is stirred for another 45 min. The mixture is cooled to −20° C., and DMF (0.8 mL) is added. After stirring for 50 min, the cooling bath is removed, and the reaction is quenched by adding aqueous $NH_4Cl$ solution at rt. The mixture is extracted with EtOAc (3×), and the combined extract is dried ($Na_2SO_4$) and concentrated. The residue is chromatographed on silica gel (cyclohexane/EtOAc 24:1→3:1) to give the title compound. LC (Method 2): $t_R$=0.87 min.

Step 2: 6-{3-Azabicyclo[3.1.0]hexan-3-yl}-3-formyl-2-methylbenzonitrile

A mixture of 6-fluoro-3-formyl-2-methylbenzonitrile (515 mg), $KHCO_3$ (0.79 g), 3-azabicyclo[3.1.0]hexane hydrochloride (453 mg), and DMSO (10 mL) is stirred at 70° C. for 1.3 h. After cooling to rt, water is added, and the mixture is stirred for 30 min. The precipitate is separated by filtration, washed with water (2×), and dried at 65° C. to give the title compound. LC (Method 1): $t_R$=0.97 min; Mass spectrum ($ESI^+$): m/z=227 $[M+H]^+$.

Step 3: 6-{3-Azabicyclo[3.1.0]hexan-3-yl}-3-{[(4-{3-azabicyclo[3.1.0]hexan-3-yl}-3-cyano-2-methylphenyl)methoxy]methyl}-2-methylbenzonitrile $NaBH_4$ (0.21 g) is added portionwise to 6-{3-azabicyclo[3.1.0]hexan-3-yl}-3-formyl-2-methylbenzonitrile (0.63 g) in THF (10 mL) and MeOH (5 mL) at rt. The mixture is stirred for 1 h before aqueous HCl solution (1 mol/L) is added. The mixture is stirred for 1 h before it is neutralized with aqueous $NaHCO_3$ solution. The mixture is extracted with EtOAc (2×), and the combined extract is dried ($Na_2SO_4$) and concentrated to afford a mixture of the title compound and 6-{3-azabicyclo[3.1.0]hexan-3-yl}-3-(methoxymethyl)-2-methylbenzonitrile that is used as is in the next reaction step (both components are competent starting materials for the next step).

LC (Method 1): $t_R$=1.27 min; Mass spectrum ($ESI^+$): m/z=439 $[M+H]^+$.

Step 4: Ethyl 1-[(4-{3-azabicyclo[3.1.0]hexan-3-yl}-3-cyano-2-methylphenyl)methyl]-1H-pyrazole-4-carboxylate The title compound is prepared from the mixture obtained in Step 3 of Intermediate 113, 6-{3-azabicyclo[3.1.0]hexan-3-yl}-3-{[(4-{3-azabicyclo[3.1.0]hexan-3-yl}-3-cyano-2-methylphenyl)methoxy]methyl}-2-methylbenzonitrile and 6-{3-azabicyclo[3.1.0]hexan-3-yl}-3-(methoxymethyl)-2-methylbenzonitrile, and ethyl 1H-pyrazole-4-carboxylate following a procedure analogous to that described in Step 3 of Intermediate 111.

LC (Method 1): $t_R$=1.08 min; Mass spectrum ($ESI^+$): m/z=351 $[M+H]^+$.

Step 5: 1-[(4-{3-Azabicyclo[3.1.0]hexan-3-yl}-3-cyano-2-methylphenyl)methyl]-1H-pyrazole-4-carboxylic acid The title compound is prepared from ethyl 1-[(4-{3-azabicyclo[3.1.0]hexan-3-yl}-3-cyano-2-methylphenyl)methyl]-1H-pyrazole-4-carboxylate following a procedure analogous to that described in Step 4 of Intermediate 111.

LC (Method 2): $t_R$=0.96 min; Mass spectrum ($ESI^+$): m/z=323 $[M+H]^+$.

Intermediate 114

1-[(4-{3-Azabicyclo[3.1.0]hexan-3-yl}-3-cyano-2-methylphenyl)methyl]-1H-imidazole-4-carboxylic acid

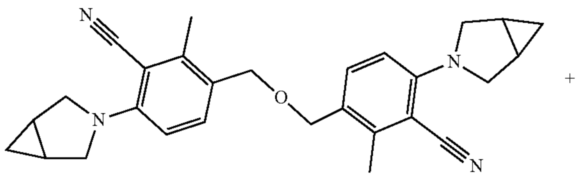

-continued

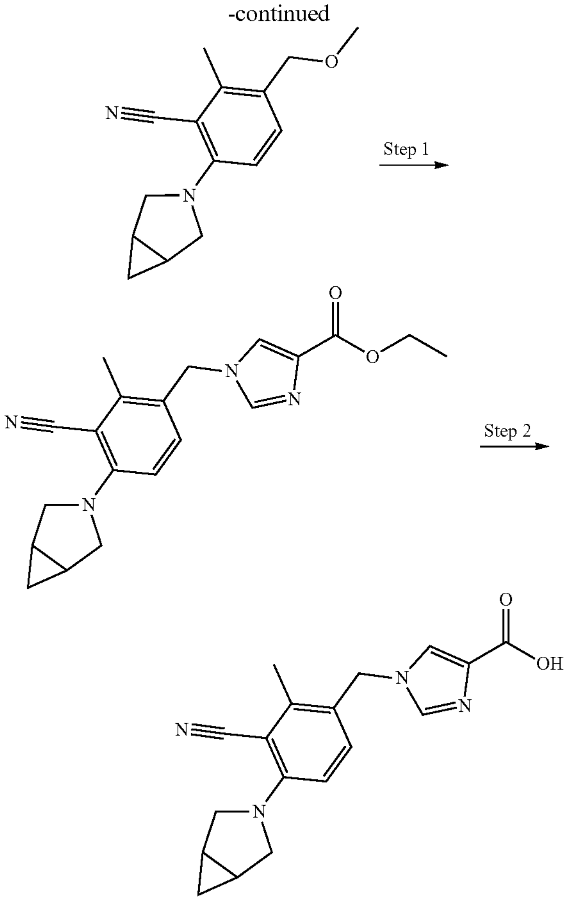

Step 1: Ethyl 1-[(4-{3-azabicyclo[3.1.0]hexan-3-yl}-3-cyano-2-methylphenyl)methyl]-1H-imidazole-4-carboxylate The title compound is prepared from the mixture obtained in Step 3 of Intermediate 113, 6-{3-azabicyclo[3.1.0]hexan-3-yl}-3-{[(4-{3-azabicyclo[3.1.0]hexan-3-yl}-3-cyano-2-methylphenyl)methoxy]methyl}-2-methylbenzonitrile and 6-{3-azabicyclo[3.1.0]hexan-3-yl}-3-(methoxymethyl)-2-methylbenzonitrile, and ethyl 1H-imidazole-4-carboxylate following a procedure analogous to that described in Step 3 of Intermediate 111.

LC (Method 1): $t_R$=0.99 min; Mass spectrum ($ESI^+$): m/z=351 $[M+H]^+$.

Step 2: 1-[(4-{3-Azabicyclo[3.1.0]hexan-3-yl}-3-cyano-2-methylphenyl)methyl]-1H-imidazole-4-carboxylic acid The title compound is prepared from ethyl 1-[(4-{3-azabicyclo[3.1.0]hexan-3-yl}-3-cyano-2-methylphenyl)methyl]-1H-imidazole-4-carboxylate following a procedure analogous to that described in Step 4 of Intermediate 111.

LC (Method 2): $t_R$=0.80 min; Mass spectrum ($ESI^+$): m/z=323 $[M+H]^+$.

Intermediate 115

1-[(4-{3-Azabicyclo[3.1.0]hexan-3-yl}-3-cyano-5-fluorophenyl)methyl]-1H-pyrazole-4-carboxylic acid

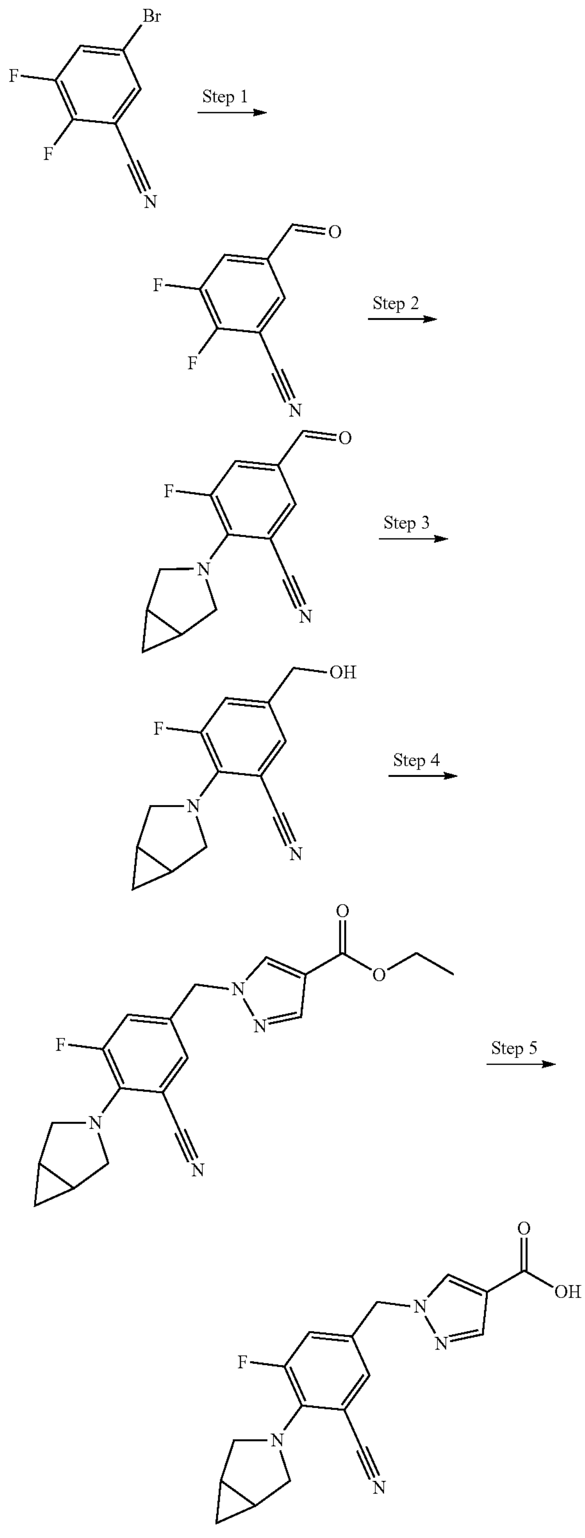

Step 1: 2,3-Difluoro-5-formylbenzonitrile

The title compound is prepared from 5-bromo-2,3-difluorobenzonitrile following a procedure analogous to that described in Step 1 of Intermediate 113. LC (Method 2): $t_R$=0.84 min.

Step 2: 2-{3-Azabicyclo[3.1.0]hexan-3-yl}-3-fluoro-5-formylbenzonitrile

The title compound is prepared from 2,3-difluoro-5-formylbenzonitrile and 3-azabicyclo[3.1.0]hexane hydrochloride following a procedure analogous to that described in Step 1 of Intermediate 111.

LC (Method 2): $t_R$=1.03 min; Mass spectrum (ESI$^+$): m/z=231 [M+H]$^+$.

Step 3: 2-{3-Azabicyclo[3.1.0]hexan-3-yl}-3-fluoro-5-(hydroxymethyl)benzonitrile The title compound is prepared from 2-{3-azabicyclo[3.1.0]hexan-3-yl}-3-fluoro-5-formylbenzonitrile following a procedure analogous to that described in Step 2 of Intermediate 111.

LC (Method 2): $t_R$=0.99 min; Mass spectrum (ESI$^+$): m/z=233 [M+H]$^+$.

Step 4: Ethyl 1-[(4-{3-azabicyclo[3.1.0]hexan-3-yl}-3-cyano-5-fluorophenyl)methyl]-1H-pyrazole-4-carboxylate The title compound is prepared from 2-{3-azabicyclo[3.1.0]hexan-3-yl}-3-fluoro-5-(hydroxymethyl)benzonitrile and ethyl 1H-pyrazole-4-carboxylate following a procedure analogous to that described in Step 3 of Intermediate 111.

LC (Method 2): $t_R$=1.10 min; Mass spectrum (ESI$^+$): m/z=355 [M+H]$^+$.

Step 5: 1-[(4-{3-Azabicyclo[3.1.0]hexan-3-yl}-3-cyano-5-fluorophenyl)methyl]-1H-pyrazole-4-carboxylic acid The title compound is prepared from ethyl 1-[(4-{3-azabicyclo[3.1.0]hexan-3-yl}-3-cyano-5-fluorophenyl)methyl]-1H-pyrazole-4-carboxylate following a procedure analogous to that described in Step 4 of Intermediate 111.

LC (Method 2): $t_R$=0.99 min; Mass spectrum (ESI$^+$): m/z=327 [M+H]$^+$.

Intermediate 116

1-[(4-{3-Azabicyclo[3.1.0]hexan-3-yl}-3-cyanophenyl)methyl]-1H-imidazole-4-carboxylic acid

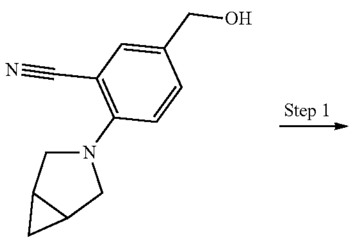

-continued

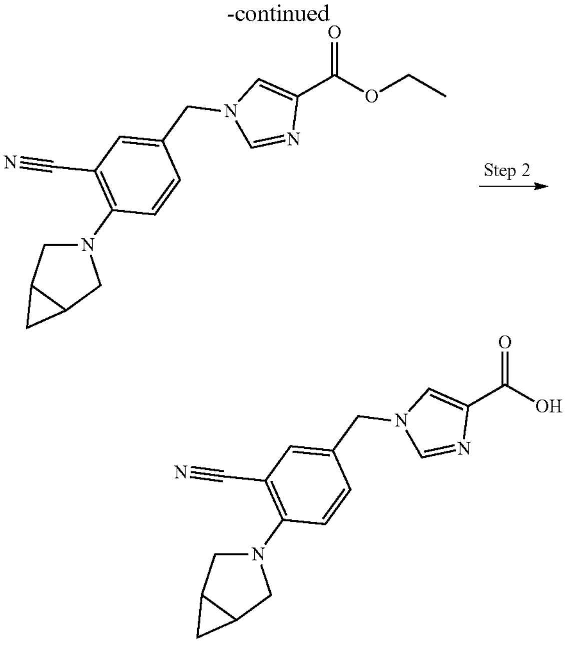

Step 1: Ethyl 1-[(4-{3-azabicyclo[3.1.0]hexan-3-yl}-3-cyanophenyl)methyl]-1H-imidazole-4-carboxylate The title compound is prepared from 2-{3-azabicyclo[3.1.0]hexan-3-yl}-5-(hydroxymethyl)benzonitrile and ethyl 1H-imidazole-4-carboxylate following a procedure analogous to that described in Step 3 of Intermediate 111.

Step 2: 1-[(4-{3-Azabicyclo[3.1.0]hexan-3-yl}-3-cyanophenyl)methyl]-1H-imidazole-4-carboxylic acid The title compound is prepared from ethyl 1-[(4-{3-azabicyclo[3.1.0]hexan-3-yl}-3-cyanophenyl)methyl]-1H-imidazole-4-carboxylate following a procedure analogous to that described in Step 4 of Intermediate 111.

Intermediate 117

1-[(4-{3-Azabicyclo[3.1.0]hexan-3-yl}-3,5-dicyanophenyl)methyl]-1H-pyrazole-4-carboxylic acid

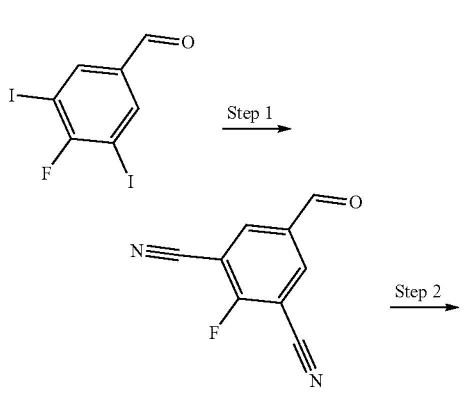

-continued

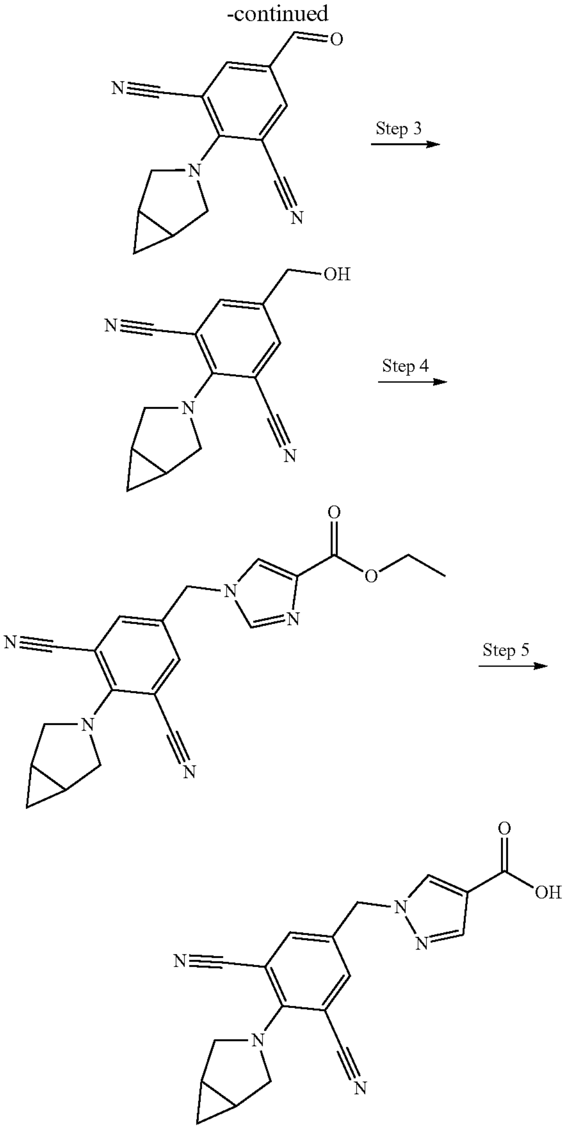

Step 1: 2-Fluoro-5-formylbenzene-1,3-dicarbonitrile

A mixture of 4-fluoro-3,5-diiodobenzaldehyde (2.00 g), copper(I) cyanide (1.05 g), and DMF (25 mL) is stirred at 120° C. for 24 h. After cooling to rt, water is added, and the resulting mixture is extracted with ethyl acetate (3×). The combined extract is dried ($Na_2SO_4$) and concentrated. The residue is chromatographed on silica gel (petroleum ether/EtOAc 95:51→70:30) to give the title compound.

Step 2: 2-{3-Azabicyclo[3.1.0]hexan-3-yl}-5-formylbenzene-1,3-dicarbonitrile The title compound is prepared from 2-fluoro-5-formylbenzene-1,3-dicarbonitrile and 3-azabicyclo[3.1.0]hexane hydrochloride following a procedure analogous to that described in Step 1 of Intermediate 111.

LC (Method 2): $t_R$=0.95 min; Mass spectrum ($ESI^+$): m/z=238 $[M+H]^+$.

Step 3: 2-{3-azabicyclo[3.1.0]hexan-3-yl}-5-(hydroxymethyl)benzene-1,3-dicarbonitrile The title compound is prepared from 2-{3-azabicyclo[3.1.0]hexan-3-yl}-5-formylbenzene-1,3-dicarbonitrile following a procedure analogous to that described in Step 2 of Intermediate 111.

LC (Method 2): $t_R$=0.92 min; Mass spectrum (ESI$^+$): m/z=240 [M+H]$^+$.

Step 4: Ethyl 1-[(4-{3-azabicyclo[3.1.0]hexan-3-yl}-3,5-dicyanophenyl)methyl]-1H-pyrazole-4-carboxylate The title compound is prepared from 2-{3-azabicyclo[3.1.0]hexan-3-yl}-5-(hydroxymethyl)benzene-1,3-dicarbonitrile and ethyl 1H-pyrazole-4-carboxylate following a procedure analogous to that described in Step 3 of Intermediate 111.

LC (Method 2): $t_R$=1.07 min; Mass spectrum (ESI$^+$): m/z=362 [M+H]$^+$.

Step 5: 1-[(4-{3-Azabicyclo[3.1.0]hexan-3-yl}-3,5-dicyanophenyl)methyl]-1H-pyrazole-4-carboxylic acid The title compound is prepared from ethyl 1-[(4-{3-azabicyclo[3.1.0]hexan-3-yl}-3,5-dicyanophenyl)methyl]-1H-pyrazole-4-carboxylate following a procedure analogous to that described in Step 4 of Intermediate 111.

LC (Method 2): $t_R$=0.92 min; Mass spectrum (ESI$^+$): m/z=334 [M+H]$^+$.

Intermediate 118

1-[(4-{3-Azabicyclo[3.1.0]hexan-3-yl}-3-cyano-2-fluorophenyl)methyl]-1H-pyrazole-4-carboxylic acid

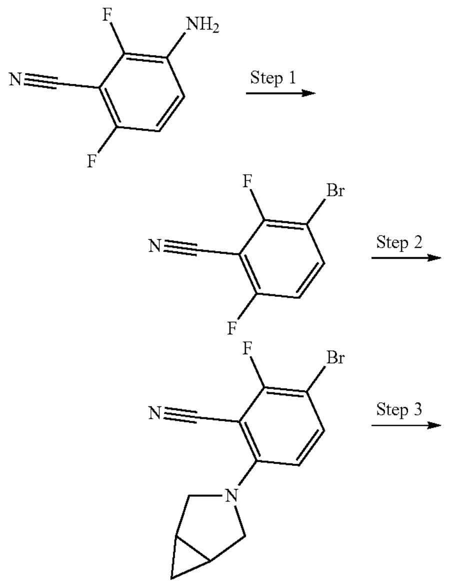

-continued

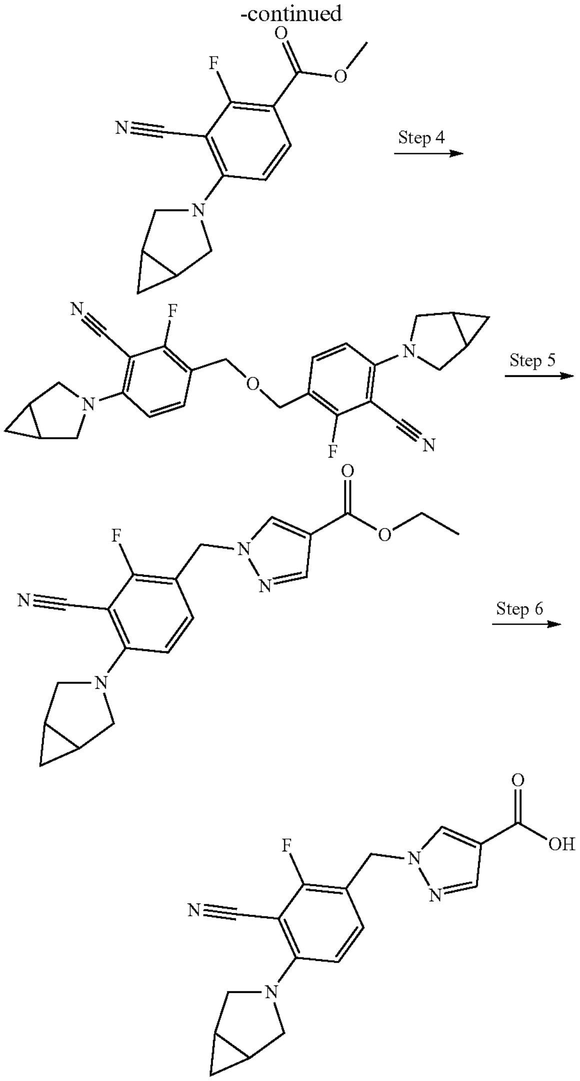

Step 1: 3-Bromo-2,6-difluorobenzonitrile

3-Amino-2,6-difluorobenzonitrile (2.50 g) dissolved in ACN (45 mL) is added dropwise to a mixture of copper(II) bromide (4.49 g), tert-butyl nitrite (3.8 mL), and ACN (45 mL) stirred at 65° C. The mixture is stirred at 65° C. for 1 h and then cooled to rt. 20% Aqueous HCl solution is added, and the resulting mixture is extracted with diethyl ether. The combined extract is dried ($Na_2SO_4$) and concentrated. The residue is chromatographed on silica gel (cyclohexane/EtOAc 7:3) to give the title compound. LC (Method 2): $t_R$=1.01 min.

Step 2: 6-{3-Azabicyclo[3.1.0]hexan-3-yl}-3-bromo-2-fluorobenzonitrile

The title compound is prepared from 3-bromo-2,6-difluorobenzonitrile and 3-azabicyclo[3.1.0]hexane hydrochloride following a procedure analogous to that described in Step 1 of Intermediate 111.

LC (Method 2): $t_R$=1.17 min; Mass spectrum (ESI$^+$): m/z=281/283 (Br) [M+H]$^+$.

Step 3: Methyl 4-{3-azabicyclo[3.1.0]hexan-3-yl}-3-cyano-2-fluorobenzoate

A mixture of 6-{3-azabicyclo[3.1.0]hexan-3-yl}-3-bromo-2-fluorobenzonitrile (500 mg), $PdCl_2$(dppf) (72 mg), $NEt_3$ (0.3 mL), and MeOH (6 mL) is stirred under an atmosphere of carbon monoxide (10 bar) at 80° C. overnight. After cooling to rt, the mixture is filtered, and the filtrate is concentrated. The residue is chromatographed on silica gel (cyclohexane/EtOAc 6:4) to give the title compound.

LC (Method 2): $t_R$=1.05 min; Mass spectrum ($ESI^+$): m/z=261 $[M+H]^+$.

Step 4: 6-{3-Azabicyclo[3.1.0]hexan-3-yl}-3-{[(4-{3-azabicyclo[3.1.0]hexan-3-yl}-3-cyano-2-fluorophenyl)methoxy]-methyl}-2-fluorobenzonitrile Methyl 4-{3-azabicyclo[3.1.0]hexan-3-yl}-3-cyano-2-fluorobenzoate (0.42 g) dissolved in THF (5 mL) is added dropwise to $LiAlH_4$ in THF (2.3 mol/L; 0.70 mL) at −50° C. The mixture is stirred while warming to −20° C. for 1.5 h and then quenched by the addition of aqueous HCl solution (1 mol/L). The resulting mixture is extracted with EtOAc (3×), and the combined extract is dried ($Na_2SO_4$) and concentrated. The residue is chromatographed on silica gel (cyclohexane/EtOAc 1:0→1:1) to give the title compound. Depending on the workup procedure, 6-{3-azabicyclo[3.1.0]hexan-3-yl}-2-fluoro-3-(hydroxymethyl)benzonitrile is also or exclusively obtained; the latter can be analogously used in the next reaction step. Mass spectrum ($ESI^+$): m/z=447 $[M+H]^+$.

Step 5: Ethyl 1-[(4-{3-azabicyclo[3.1.0]hexan-3-yl}-3-cyano-2-fluorophenyl)methyl]-1H-pyrazole-4-carboxylate The title compound is prepared from 6-{3-azabicyclo[3.1.0]hexan-3-yl}-3-{[(4-{3-azabicyclo[3.1.0]hexan-3-yl}-3-cyano-2-fluorophenyl)methoxy]methyl}-2-fluorobenzonitrile and ethyl 1H-pyrazole-4-carboxylate following a procedure analogous to that described in Step 3 of Intermediate 111.

LC (Method 1): $t_R$=1.06 min; Mass spectrum ($ESI^+$): m/z=355 $[M+H]^+$.

Step 6: 1-[(4-{3-Azabicyclo[3.1.0]hexan-3-yl}-3-cyano-2-fluorophenyl)methyl]-1H-pyrazole-4-carboxylic acid The title compound is prepared from ethyl 1-[(4-{3-azabicyclo[3.1.0]hexan-3-yl}-3-cyano-2-fluorophenyl)methyl]-1H-pyrazole-4-carboxylate following a procedure analogous to that described in Step 4 of Intermediate 111.

LC (Method 2): $t_R$=0.94 min; Mass spectrum ($ESI^+$): m/z=349 $[M+Na]^+$.

Intermediate 119

1-[(4-{6,6-Difluoro-3-azabicyclo[3.1.0]hexan-3-yl}-2-methylphenyl)methyl]-1H-pyrazole-4-carboxylic acid

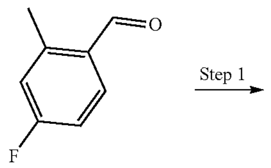

-continued

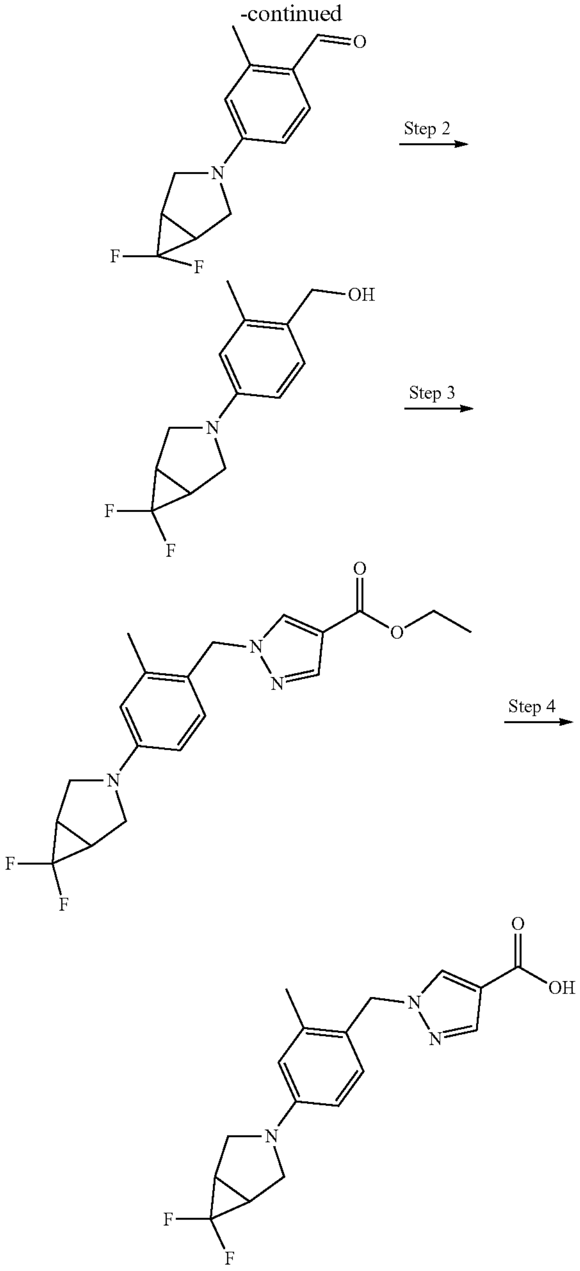

Step 1: 4-{6,6-Difluoro-3-azabicyclo[3.1.0]hexan-3-yl}-2-methylbenzaldehyde

The title compound is prepared from 4-fluoro-2-methylbenzaldehyde and 6,6-difluoro-3-azabicyclo[3.1.0]hexane following a procedure analogous to that described in Step 1 of Intermediate 111; $K_2CO_3$ instead of Hunig's base is used at 130° C. LC (Method 2): $t_R$=1.01 min; Mass spectrum ($ESI^+$): m/z=238 $[M+H]^+$.

Step 2: (4-{6,6-Difluoro-3-azabicyclo[3.1.0]hexan-3-yl}-2-methylphenyl)methanol

The title compound is prepared from 4-{6,6-difluoro-3-azabicyclo[3.1.0]hexan-3-yl}-2-methylbenzaldehyde following a procedure analogous to that described in Step 2 of Intermediate 111.

Step 3: Ethyl 1-[(4-{6,6-difluoro-3-azabicyclo[3.1.0]hexan-3-yl}-2-methylphenyl)methyl]-1H-pyrazole-4-carboxylate The title compound is prepared from (4-{6,6-difluoro-3-azabicyclo[3.1.0]hexan-3-yl}-2-methylphenyl)methanol and ethyl 1H-pyrazole-4-carboxylate following a procedure analogous to that described in Step 3 of Intermediate 111.

LC (Method 2): $t_R$=1.13 min; Mass spectrum ($ESI^+$): m/z=362 $[M+H]^+$.

Step 4: 1-[(4-{6,6-Difluoro-3-azabicyclo[3.1.0]hexan-3-yl}-2-methylphenyl)methyl]-1H-pyrazole-4-carboxylic acid The title compound is prepared from ethyl 1-[(4-{6,6-difluoro-3-azabicyclo[3.1.0]hexan-3-yl}-2-methylphenyl)methyl]-1H-pyrazole-4-carboxylate following a procedure analogous to that described in Step 4 of Intermediate 111.

LC (Method 2): $t_R$=0.98 min; Mass spectrum ($ESI^+$): m/z=334 $[M+H]^+$.

Intermediate 120

1-[(4-{3-Azabicyclo[3.1.0]hexan-3-yl}-5-cyano-2-methylphenyl)methyl]-1H-pyrazole-4-carboxylic acid

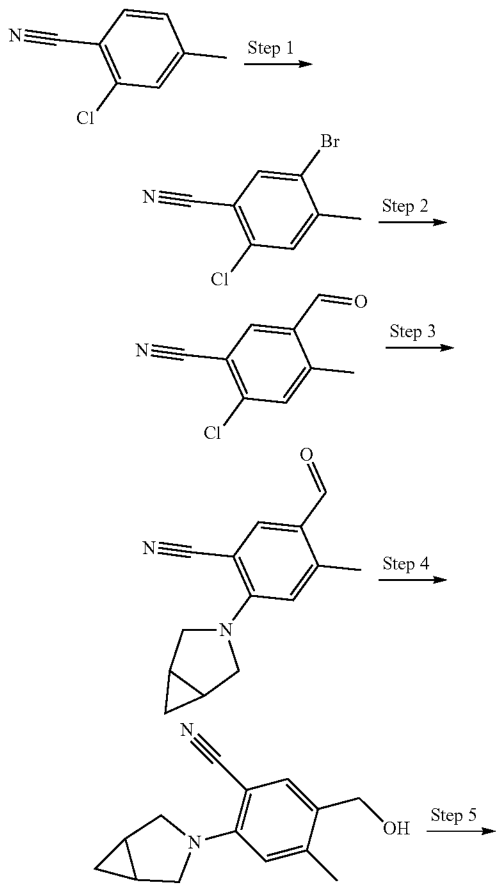

-continued

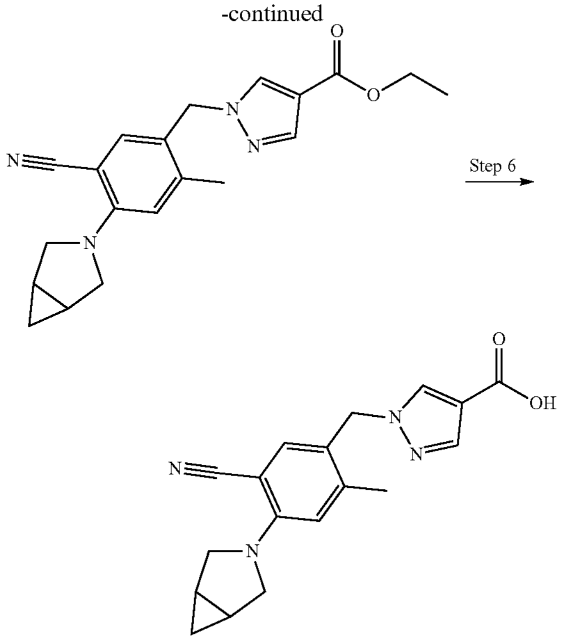

Step 1: 5-Bromo-2-chloro-4-methylbenzonitrile

N-bromosuccinimide (3.50 g) and trifluoroacetic acid (25 mL) are added to 2-chloro-4-methylbenzonitrile (2.50 g) in concentrated sulfuric acid at rt. The mixture is stirred at rt for 24 h. The mixture is cooled to 0° C. and then slowly poured into an ice-cold solution of aqueous NaOH solution (4 mol/L; 125 mL). The precipitate is separated by filtration and purified by chromatography on silica gel (cyclohexane/EtOAc) to give the title compound.

LC (Method 1): $t_R$=1.07 min.

Step 2: 2-Chloro-5-formyl-4-methylbenzonitrile

The title compound is prepared from 5-bromo-2-chloro-4-methylbenzonitrile following a procedure analogous to that described in Step 1 of Intermediate 113. LC (Method 1): $t_R$=0.90 min; Mass spectrum ($ESI^-$): m/z=178 $[M-H]^-$.

Step 3: 2-{3-Azabicyclo[3.1.0]hexan-3-yl}-5-formyl-4-methylbenzonitrile

The title compound is prepared from 2-chloro-5-formyl-4-methylbenzonitrile and 3-azabicyclo[3.1.0]hexane hydrochloride following a procedure analogous to that described in Step 1 of Intermediate 111.

LC (Method 2): $t_R$=1.02 min; Mass spectrum ($ESI^+$): m/z=227 $[M+H]^+$.

Step 4: 2-{3-Azabicyclo[3.1.0]hexan-3-yl}-5-(hydroxymethyl)-4-methylbenzonitrile The title compound is prepared from 2-{3-azabicyclo[3.1.0]hexan-3-yl}-5-formyl-4-methylbenzonitrile following a procedure analogous to that described in Step 2 of Intermediate 111.

LC (Method 2): $t_R$=0.96 min; Mass spectrum ($ESI^+$): m/z=229 $[M+H]^+$.

Step 5: Ethyl 1-[(4-{3-azabicyclo[3.1.0]hexan-3-yl}-5-cyano-2-methylphenyl)methyl]-1H-pyrazole-4-carboxylate The title compound is prepared from 2-{3-azabicyclo[3.1.0]hexan-3-yl}-5-(hydroxymethyl)-4-methylbenzonitrile and ethyl 1H-pyrazole-4-carboxylate following a procedure analogous to that described in Step 3 of Intermediate 111.

LC (Method 1): $t_R$=1.08 min; Mass spectrum ($ESI^+$): m/z=351 $[M+H]^+$.

Step 6: 1-[(4-{3-Azabicyclo[3.1.0]hexan-3-yl}-5-cyano-2-methylphenyl)methyl]-1H-pyrazole-4-carboxylic acid The title compound is prepared from ethyl 1-[(4-{3-azabicyclo[3.1.0]hexan-3-yl}-5-cyano-2-methylphenyl)methyl]-1H-pyrazole-4-carboxylate following a procedure analogous to that described in Step 4 of Intermediate 111.

LC (Method 1): $t_R$=0.68 min; Mass spectrum ($ESI^+$): m/z=323 $[M+H]^+$.

Intermediate 121

1-[(4-{3-Azabicyclo[3.1.0]hexan-3-yl}-3-cyano-2-fluorophenyl)methyl]-1H-imidazole-4-carboxylic acid

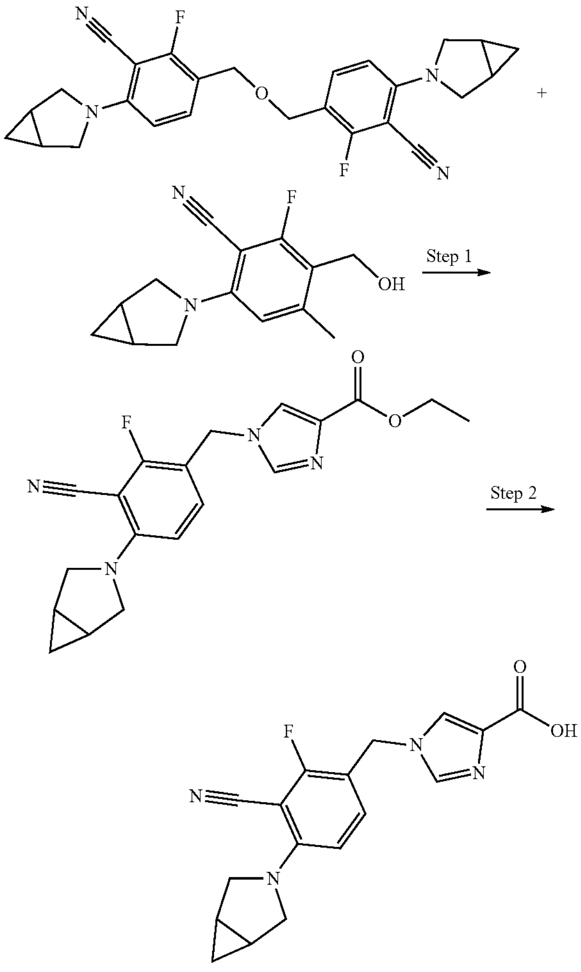

Step 1: Ethyl 1-[(4-{3-azabicyclo[3.1.0]hexan-3-yl}-3-cyano-2-fluorophenyl)methyl]-1H-imidazole-4-carboxylate The title compound is prepared from a mixture of 6-{3-azabicyclo[3.1.0]hexan-3-yl}-3-{[(4-{3-azabicyclo[3.1.0]hexan-3-yl}-3-cyano-2-fluorophenyl)methoxy]methyl}-2-fluorobenzonitrile and 6-{3-azabicyclo[3.1.0]hexan-3-yl}-2-fluoro-3-(hydroxymethyl)benzonitrile, obtained after workup in Step 4 of Intermediate 118, and ethyl 1H-imidazole-4-carboxylate following a procedure analogous to that described in Step 3 of Intermediate 111; the reaction is conducted at 140° C. in a microwave oven. LC (Method 1): $t_R$=0.90 min; Mass spectrum ($ESI^+$): m/z=355 $[M+H]^+$.

Step 2: 1-[(4-{3-Azabicyclo[3.1.0]hexan-3-yl}-3-cyano-2-fluorophenyl)methyl]-1H-imidazole-4-carboxylic acid The title compound is prepared from ethyl 1-[(4-{3-azabicyclo[3.1.0]hexan-3-yl}-3-cyano-2-fluorophenyl)methyl]-1H-imidazole-4-carboxylate following a procedure analogous to that described in Step 4 of Intermediate 111.

LC (Method 2): $t_R$=0.78 min; Mass spectrum ($ESI^+$): m/z=327 $[M+H]^+$.

Intermediate 122

1-[(4-{3-Azabicyclo[3.1.0]hexan-3-yl}-2-chloro-3-cyanophenyl)methyl]-1H-pyrazole-4-carboxylic acid

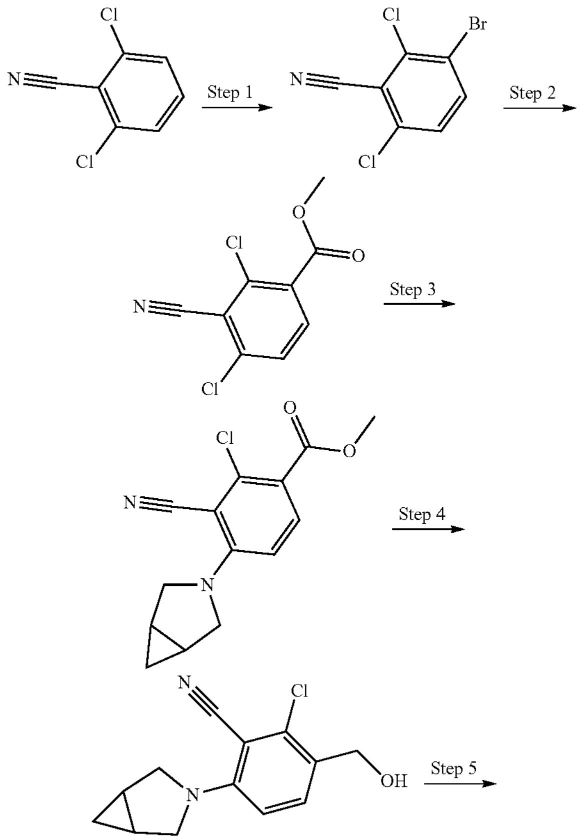

-continued

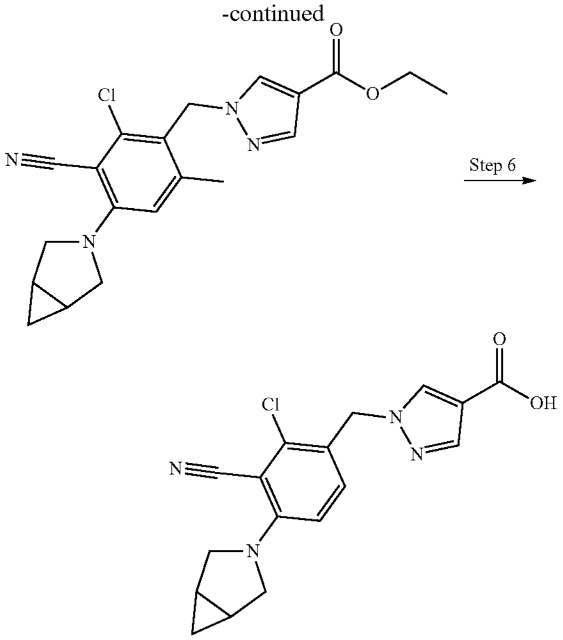

Step 1: 3-Bromo-2,6-dichlorobenzonitrile $KBrO_3$ (7.28 g) is added in portions to 2,6-dichlorobenzonitrile (2.50 g) in concentrated sulfuric acid chilled in an ice bath. The mixture is warmed in the cooling bath to rt and then stirred at this temperature overnight. The mixture is poured onto ice, and saturated aqueous $K_2CO_3$ solution is added to neutralize the solution. The resulting mixture is extracted with DCM (3×), and the combined extract is dried ($Na_2SO_4$) and concentrated. The residue is chromatographed on silica gel (cyclohexane/EtOAc 1:0→7:3) to give the title compound.

LC (Method 2): $t_R$=1.09 min.

Step 2: Methyl 2,4-dichloro-3-cyanobenzoate

The title compound is prepared from 3-bromo-2,6-dichlorobenzonitrile following a procedure analogous to that described in Step 3 of Intermediate 118; the reaction is conducted in a mixture of DMF and MeOH.

LC (Method 2): $t_R$=1.00 min.

Step 3: Methyl 4-{3-azabicyclo[3.1.0]hexan-3-yl}-2-chloro-3-cyanobenzoate

The title compound is prepared from methyl 2,4-dichloro-3-cyanobenzoate and 3-azabicyclo[3.1.0]hexane hydrochloride following a procedure analogous to that described in Step 1 of Intermediate 111.

LC (Method 2): $t_R$=1.07 min; Mass spectrum ($ESI^+$): m/z=277 $[M+H]^+$.

Step 4: 6-{3-Azabicyclo[3.1.0]hexan-3-yl}-2-chloro-3-(hydroxymethyl)benzonitrile The title compound is prepared from methyl 4-{3-azabicyclo[3.1.0]hexan-3-yl}-2-chloro-3-cyanobenzoate following a procedure analogous to that described in Step 4 of Intermediate 118.

LC (Method 2): $t_R$=0.96 min; Mass spectrum ($ESI^+$): m/z=249 $[M+H]^+$.

Step 5: Ethyl 1-[(4-{3-azabicyclo[3.1.0]hexan-3-yl}-2-chloro-3-cyano-6-methylphenyl)methyl]-1H-pyrazole-4-carboxylate The title compound is prepared from 6-{3-azabicyclo[3.1.0]hexan-3-yl}-2-chloro-3-(hydroxymethyl)benzonitrile and ethyl 1H-pyrazole-4-carboxylate following a procedure analogous to that described in Step 3 of Intermediate 111.

LC (Method 2): $t_R$=1.10 min.

Step 6: 1-[(4-{3-Azabicyclo[3.1.0]hexan-3-yl}-2-chloro-3-cyanophenyl)methyl]-1H-pyrazole-4-carboxylic acid The title compound is prepared from ethyl 1-[(4-{3-azabicyclo[3.1.0]hexan-3-yl}-2-chloro-3-cyano-6-methylphenyl)methyl]-1H-pyrazole-4-carboxylate following a procedure analogous to that described in Step 4 of Intermediate 111. LC (Method 2): $t_R$=0.96 min.

Intermediate 123

1-[(4-{3-Azabicyclo[3.1.0]hexan-3-yl}-2-chloro-3-cyanophenyl)methyl]-1H-imidazole-4-carboxylic acid

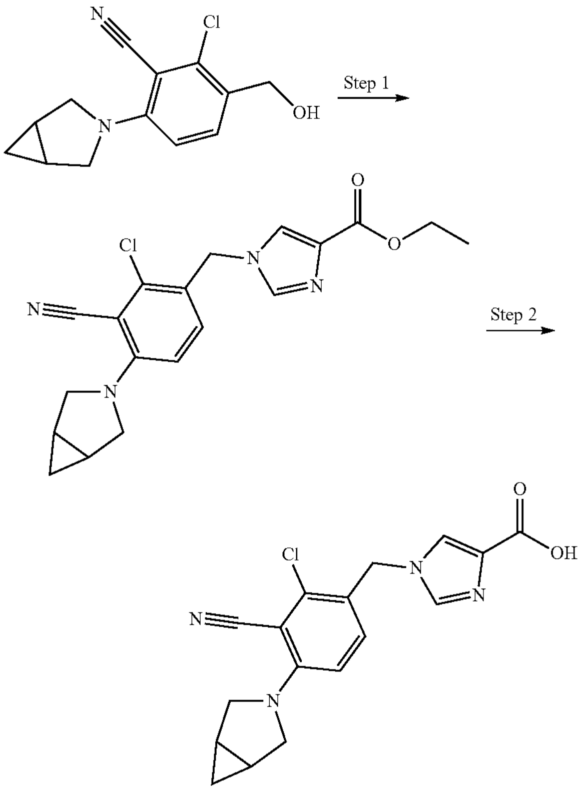

Step 1: Ethyl 1-[(4-{3-azabicyclo[3.1.0]hexan-3-yl}-2-chloro-3-cyanophenyl)methyl]-1H-imidazole-4-carboxylate The title compound is prepared from 6-{3-azabicyclo[3.1.0]hexan-3-yl}-2-chloro-3-(hydroxymethyl)benzonitrile and ethyl 1H-imidazole-4-carboxylate following a procedure analogous to that described in Step 3 of Intermediate 111; the reaction is conducted at 100° C. LC (Method 1): $t_R$=0.98 min; Mass spectrum ($ESI^+$): m/z=371 $[M+H]^+$.

Step 2: 1-[(4-{3-Azabicyclo[3.1.0]hexan-3-yl}-2-chloro-3-cyanophenyl)methyl]-1H-imidazole-4-carboxylic acid The title compound is prepared from ethyl 1-[(4-{3-azabicyclo[3.1.0]hexan-3-yl}-2-chloro-3-cyanophenyl) methyl]-1H-imidazole-4-carboxylate following a procedure analogous to that described in Step 4 of Intermediate 111.

LC (Method 2): $t_R$=0.80 min; Mass spectrum ($ESI^+$): m/z=343 $[M+H]^+$.

Intermediate 124

1-[(4-{3-Azabicyclo[3.1.0]hexan-3-yl}-2-bromophenyl)methyl]-1H-imidazole-4-carboxylic acid

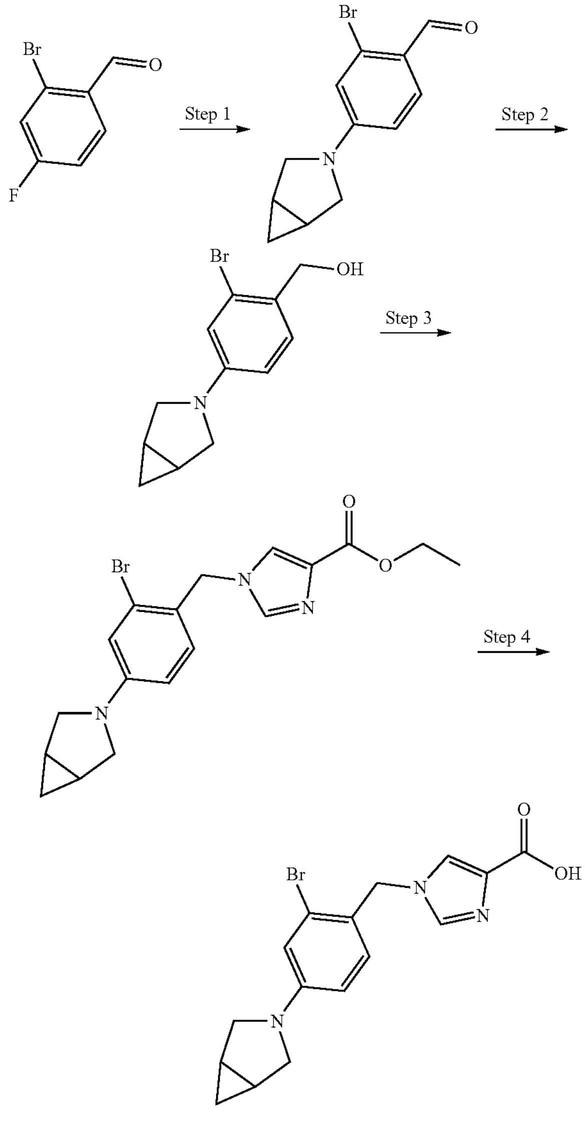

Step 1: 4-{3-Azabicyclo[3.1.0]hexan-3-yl}-2-bromobenzaldehyde

The title compound is prepared from 2-bromo-4-fluorobenzaldehyde and 3-azabicyclo[3.1.0]hexane hydrochloride following a procedure analogous to that described in Step 1 of Intermediate 111; $K_2CO_3$ instead of Hunig's base and NMP instead of DMF are used at 120° C.

LC (Method 2): $t_R$=1.08 min; Mass spectrum ($ESI^+$): m/z=266/268 (Br) $[M+H]^+$.

Step 2: (4-{3-Azabicyclo[3.1.0]hexan-3-yl}-2-bromophenyl)methanol

The title compound is prepared from 4-{3-azabicyclo[3.1.0]hexan-3-yl}-2-bromobenzaldehyde following a procedure analogous to that described in Step 2 of Intermediate 111.

LC (Method 2): $t_R$=1.01 min; Mass spectrum ($ESI^+$): m/z=268/270 (Br) $[M+H]^+$.

Step 3: Ethyl 1-[(4-{3-azabicyclo[3.1.0]hexan-3-yl}-2-bromophenyl)methyl]-1H-imidazole-4-carboxylate The title compound is prepared from (4-{3-azabicyclo[3.1.0]hexan-3-yl}-2-bromophenyl)methanol and ethyl 1H-imidazole-4-carboxylate following a procedure analogous to that described in Step 3 of Intermediate 111.

LC (Method 2): $t_R$=0.96 min; Mass spectrum ($ESI^+$): m/z=390/392 (Br) $[M+H]^+$.

Step 4: 1-[(4-{3-Azabicyclo[3.1.0]hexan-3-yl}-2-bromophenyl)methyl]-1H-imidazole-4-carboxylic acid The title compound is prepared from ethyl 1-[(4-{3-azabicyclo[3.1.0]hexan-3-yl}-2-bromophenyl)methyl]-1H-imidazole-4-carboxylate following a procedure analogous to that described in Step 4 of Intermediate 111.

LC (Method 2): $t_R$=0.85 min.

Intermediate 125

1-[(4-{3-Azabicyclo[3.1.0]hexan-3-yl}-2-methylphenyl)methyl]-1H-imidazole-4-carboxylic acid

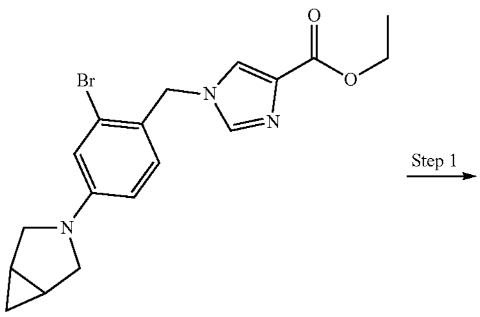

-continued

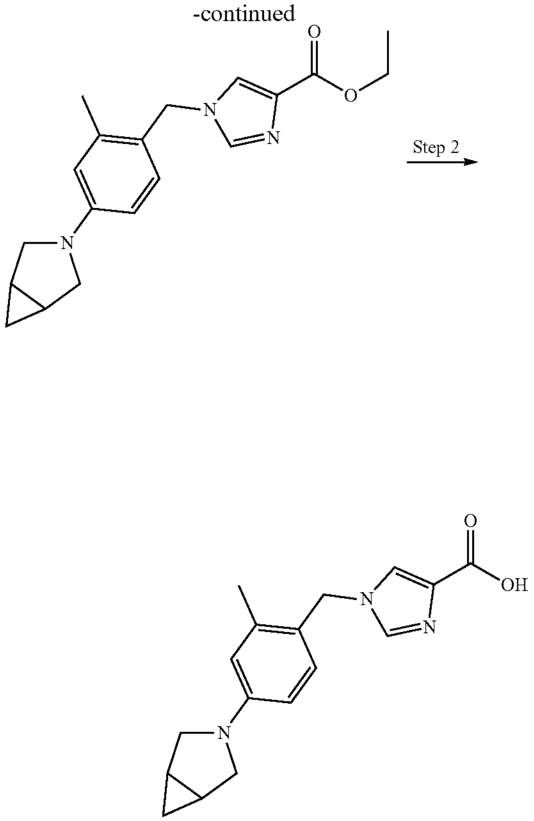

Step 1: Ethyl 1-[(4-{3-azabicyclo[3.1.0]hexan-3-yl}-2-methylphenyl)methyl]-1H-imidazole-4-carboxylate A flask charged with a stir bar, ethyl 1-[(4-{3-azabicyclo[3.1.0]hexan-3-yl}-2-bromophenyl)methyl]-1H-imidazole-4-carboxylate (100 mg), methylboronic acid (23 mg), $Cs_2CO_3$ (0.25 g), and 1,4-dioxane (1.5 mL) is flushed with Ar for 10 min. $PdCl_2$(dppf) (21 mg) is added, the flask is sealed, and the mixture is stirred at 110° C. for 1.5 h. After cooling to rt, the mixture is diluted with MeOH and chromatographed (HPLC; ACN/water/ammonia) to give the title compound.

LC (Method 2): $t_R$=0.91 min.

Step 2: 1-[(4-{3-Azabicyclo[3.1.0]hexan-3-yl}-2-methylphenyl)methyl]-1H-imidazole-4-carboxylic acid The title compound is prepared from ethyl 1-[(4-{3-azabicyclo[3.1.0]hexan-3-yl}-2-methylphenyl)methyl]-1H-imidazole-4-carboxylate following a procedure analogous to that described in Step 4 of Intermediate 111.

LC (Method 2): $t_R$=0.81 min.

Intermediate 126

1-[(4-{3-Azabicyclo[3.1.0]hexan-3-yl}-2-cyanophenyl)methyl]-1H-imidazole-4-carboxylic acid

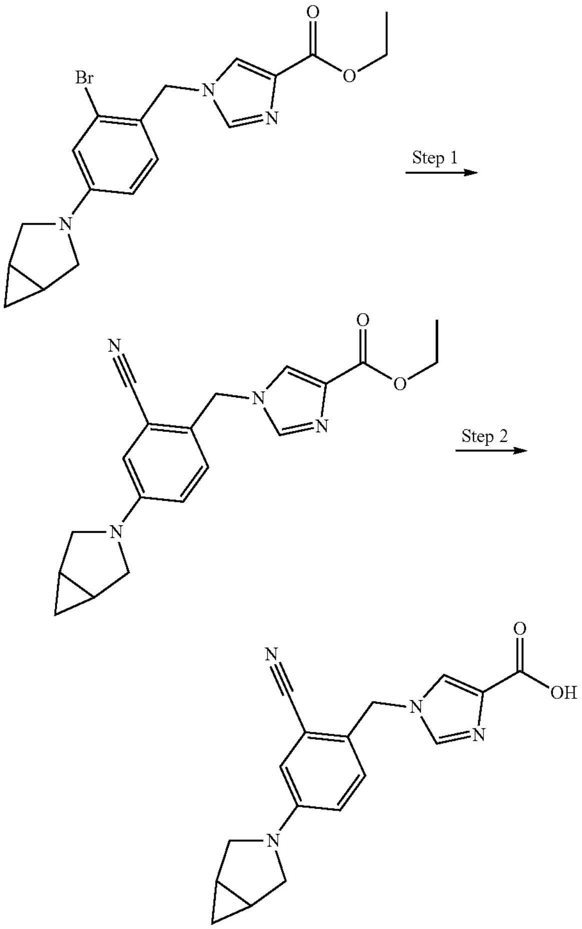

Step 1: Ethyl 1-[(4-{3-azabicyclo[3.1.0]hexan-3-yl}-2-cyanophenyl)methyl]-1H-imidazole-4-carboxylate A flask charged with a stir bar, ethyl 1-[(4-{3-azabicyclo[3.1.0]hexan-3-yl}-2-bromophenyl)methyl]-1H-imidazole-4-carboxylate (100 mg), $Zn(CN)_2$ (60 mg), zinc (8 mg), $Pd_2(dba)_3$ (23 mg), and ${}^tBu_3P*HBF_4$ (15 mg) is flushed with Ar for 10 min. NMP (1 mL) is added, the flask is sealed, and the mixture is stirred at 80° C. for 2 h. After cooling to rt, the mixture is diluted with DMF and chromatographed (HPLC; ACN/water/ammonia) to give the title compound.

LC (Method 2): $t_R$=0.90 min; Mass spectrum ($ESI^+$): m/z=337 $[M+H]^+$.

Step 2: 1-[(4-{3-Azabicyclo[3.1.0]hexan-3-yl}-2-cyanophenyl)methyl]-1H-imidazole-4-carboxylic acid The title compound is prepared from ethyl 1-[(4-{3-azabicyclo[3.1.0]hexan-3-yl}-2-cyanophenyl)methyl]-1H-imidazole-4-carboxylate following a procedure analogous to that described in Step 4 of Intermediate 111.

LC (Method 2): $t_R$=0.79 min; Mass spectrum ($ESI^+$): m/z=309 $[M+H]^+$.

Intermediate 127

1-[(4-{3-Azabicyclo[3.1.0]hexan-3-yl}-2-(hydroxymethyl)phenyl)methyl]-1H-imidazole-4-carboxylic acid

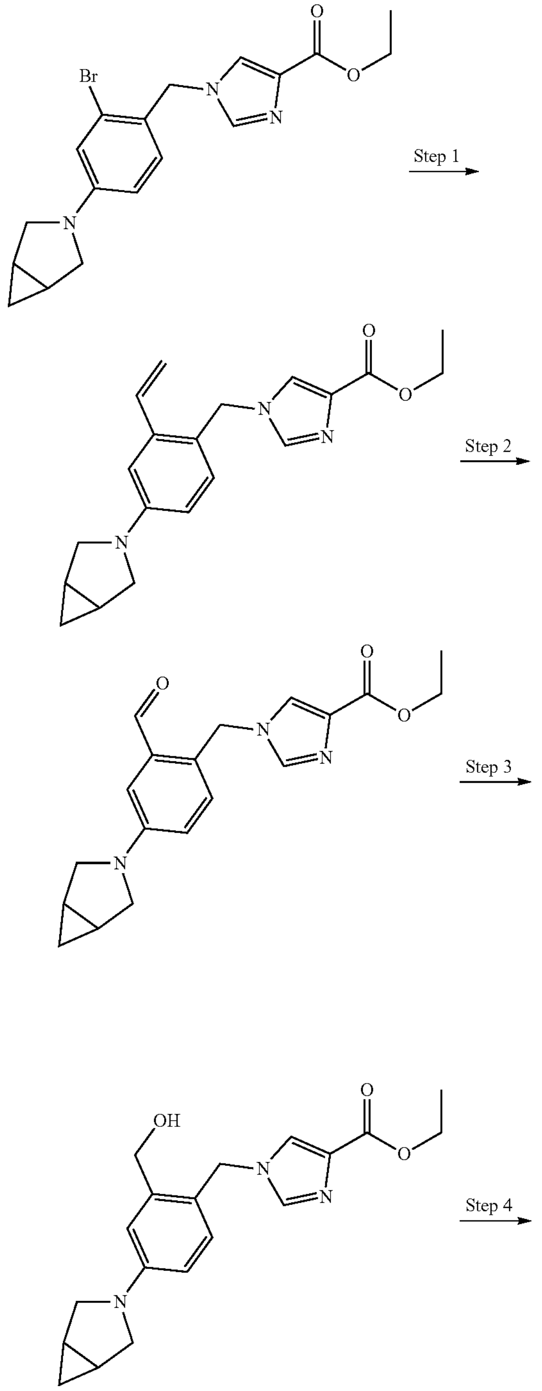

-continued

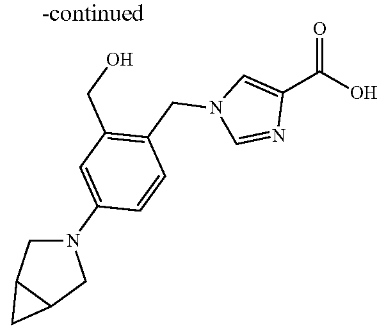

Step 1: Ethyl 1-[(4-{3-azabicyclo[3.1.0]hexan-3-yl}-2-ethenylphenyl)methyl]-1H-imidazole-4-carboxylate A flask charged with a stir bar, ethyl 1-[(4-{3-azabicyclo[3.1.0]hexan-3-yl}-2-bromophenyl)methyl]-1H-imidazole-4-carboxylate (500 mg), vinylboronic acid (0.25 mL), aq. $Na_2CO_3$ solution (1 mol/L; 3.2 mL), and 1,4-dioxane (9 mL) is flushed with Ar for 10 min. $PdCl_2$(dppf) (53 mg) is added, the flask is sealed, and the mixture is stirred at 100° C. for 2.5 h. After cooling to rt, the mixture is diluted with brine, and the resulting mixture is extracted with EtOAc (3×). The combined extract is dried ($Na_2SO_4$) and concentrated. The residue is chromatographed on silica gel (cyclohexane/EtOAc 4:1→0:1) to give the title compound. LC (Method 2): $t_R$=0.93 min.

Step 2: Ethyl 1-[(4-{3-azabicyclo[3.1.0]hexan-3-yl}-2-formylphenyl)methyl]-1H-imidazole-4-carboxylate $OsO_4$ (4% in water; 0.14 mL) is added to a mixture of ethyl 1-[(4-{3-azabicyclo[3.1.0]hexan-3-yl}-2-ethenylphenyl)methyl]-1H-imidazole-4-carboxylate (300 mg), water (4 mL), and 1,4-dioxane (4 mL) at room temperature. After stirring the mixture for 10 min, $NaIO_4$ (0.57 g) is added. The mixture is stirred for 2.5 h, and then ethyl acetate/methanol (9:1; 20 mL) and water (20 mL) are added. The mixture is extracted with ethyl acetate (3×), and the combined extract is dried ($Na_2SO_4$) and concentrated. The residue is chromatographed on silica gel (cyclohexane/ethyl acetate 70:30→0:1) to give the title compound.

LC (Method 1): $t_R$=0.99 min; Mass spectrum (ESI$^+$): m/z=340 $[M+H]^+$.

Step 3: Ethyl 1-[(4-{3-azabicyclo[3.1.0]hexan-3-yl}-2-(hydroxymethyl)phenyl)methyl]-1H-imidazole-4-carboxylate The title compound is prepared from ethyl 1-[(4-{3-azabicyclo[3.1.0]hexan-3-yl}-2-formylphenyl)methyl]-1H-imidazole-4-carboxylate following a procedure analogous to that described in Step 2 of Intermediate 111.

LC (Method 1): $t_R$=0.81 min.

Step 4: 1-[(4-{3-Azabicyclo[3.1.0]hexan-3-yl}-2-(hydroxymethyl)phenyl)methyl]-1H-imidazole-4-carboxylic acid The title compound is prepared from ethyl 1-[(4-{3-azabicyclo[3.1.0]hexan-3-yl}-2-(hydroxymethyl)phenyl)

methyl]-1H-imidazole-4-carboxylate following a procedure analogous to that described in Step 4 of Intermediate 111.

LC (Method 2): $t_R$=0.72 min.

Intermediate 128

1-[(2-Cyano-4-{6,6-difluoro-3-azabicyclo[3.1.0]hexan-3-yl}phenyl)methyl]-1H-pyrazole-4-carboxylic acid

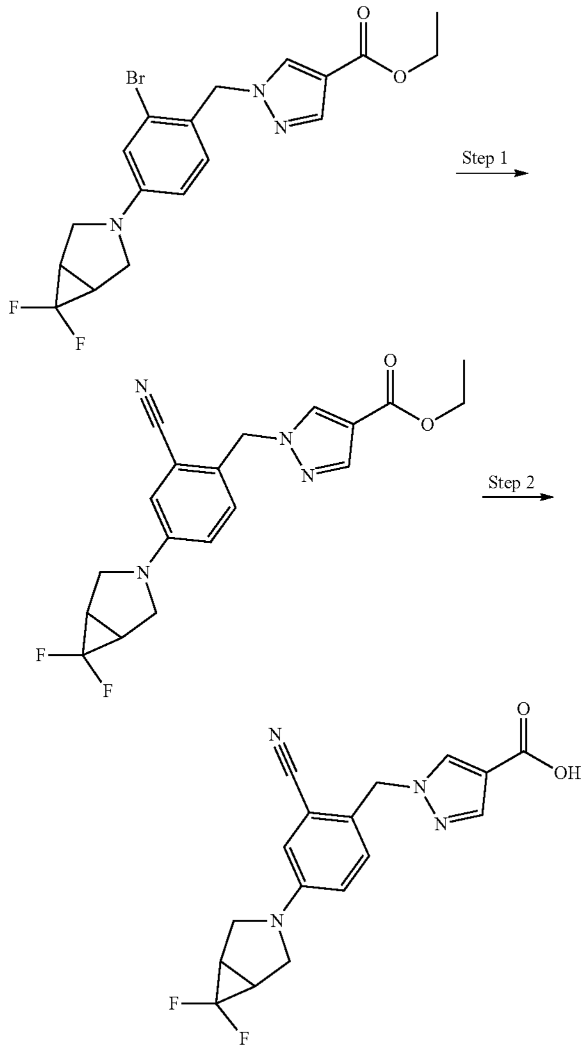

Step 1: Ethyl 1-[(2-cyano-4-{6,6-difluoro-3-azabicyclo[3.1.0]hexan-3-yl}phenyl)methyl]-1H-pyrazole-4-carboxylate The title compound is prepared from ethyl 1-[(2-bromo-4-{6,6-difluoro-3-azabicyclo[3.1.0]hexan-3-yl}phenyl)methyl]-1H-pyrazole-4-carboxylate following a procedure analogous to that described in Step 1 of Intermediate 126.

LC (Method 1): $t_R$=1.03 min.

Step 2: 1-[(2-Cyano-4-{6,6-difluoro-3-azabicyclo[3.1.0]hexan-3-yl}phenyl)methyl]-1H-pyrazole-4-carboxylic acid The title compound is prepared from ethyl 1-[(2-cyano-4-{6,6-difluoro-3-azabicyclo[3.1.0]hexan-3-yl}phenyl)

methyl]-1H-pyrazole-4-carboxylate following a procedure analogous to that described in Step 4 of Intermediate 111.

LC (Method 1): $t_R$=0.63 min.

Intermediate 129

1-[(2-Bromo-4-{6,6-difluoro-3-azabicyclo[3.1.0]hexan-3-yl}phenyl)methyl]-1H-pyrazole-4-carboxylic acid

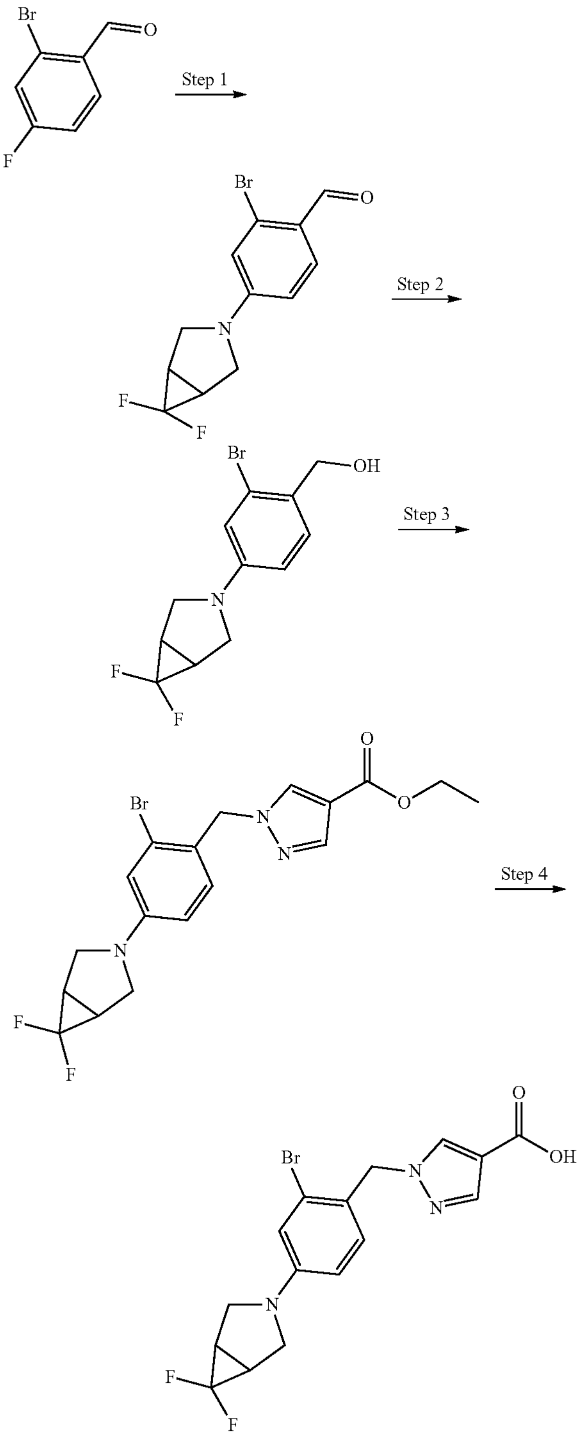

Step 1: 2-Bromo-4-{6,6-difluoro-3-azabicyclo[3.1.0]hexan-3-yl}benzaldehyde

The title compound is prepared from 2-bromo-4-fluorobenzaldehyde and 6,6-difluoro-3-azabicyclo[3.1.0]hexane hydrochloride following a procedure analogous to that described in Step 1 of Intermediate 111; $K_2CO_3$ instead of Hunig's base and NMP instead of DMF are used at 120° C.

LC (Method 2): $t_R$=1.02 min; Mass spectrum ($ESI^+$): m/z=302/304 (Br) $[M+H]^+$.

Step 2: (2-Bromo-4-{6,6-difluoro-3-azabicyclo[3.1.0]hexan-3-yl}phenyl)methanol

The title compound is prepared from 2-bromo-4-{6,6-difluoro-3-azabicyclo[3.1.0]hexan-3-yl}benzaldehyde following a procedure analogous to that described in Step 2 of Intermediate 111.

LC (Method 2): $t_R$=0.96 min; Mass spectrum ($ESI^+$): m/z=304/306 (Br) $[M+H]^+$.

Step 3: Ethyl 1-[(2-bromo-4-{6,6-difluoro-3-azabicyclo[3.1.0]hexan-3-yl}phenyl)methyl]-1H-pyrazole-4-carboxylate The title compound is prepared from (2-bromo-4-{6,6-difluoro-3-azabicyclo[3.1.0]hexan-3-yl}phenyl)methanol and ethyl 1H-pyrazole-4-carboxylate following a procedure analogous to that described in Step 3 of Intermediate 111.

LC (Method 2): $t_R$=1.09 min; Mass spectrum ($ESI^+$): m/z=426/428 (Br) $[M+H]^+$.

Step 4: 1-[(2-Bromo-4-{6,6-difluoro-3-azabicyclo[3.1.0]hexan-3-yl}phenyl)methyl]-1H-pyrazole-4-carboxylic acid The title compound is prepared from ethyl 1-[(2-bromo-4-{6,6-difluoro-3-azabicyclo[3.1.0]hexan-3-yl}phenyl)methyl]-1H-pyrazole-4-carboxylate following a procedure analogous to that described in Step 4 of Intermediate 111.

LC (Method 1): $t_R$=0.68 min.

Intermediate 130

1-[(2-Cyano-4-{6,6-difluoro-3-azabicyclo[3.1.0]hexan-3-yl}phenyl)methyl]-1H-imidazole-4-carboxylic acid

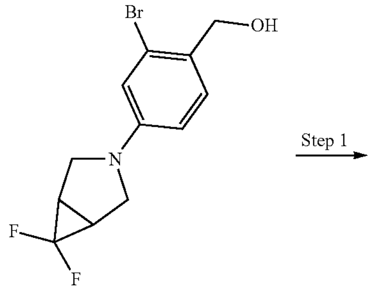

-continued

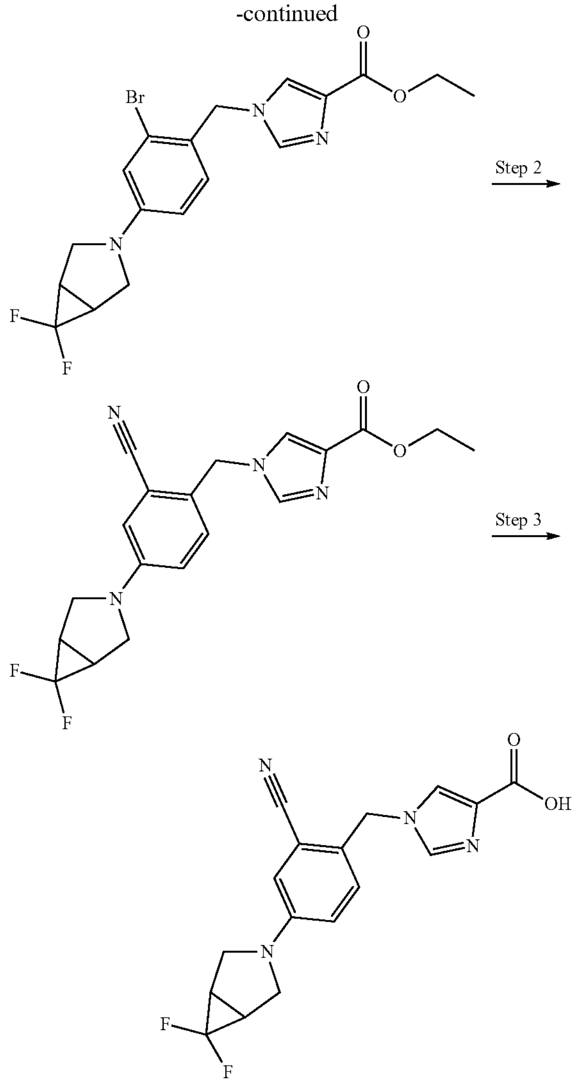

Step 1: Ethyl 1-[(2-bromo-4-{6,6-difluoro-3-azabicyclo[3.1.0]hexan-3-yl}phenyl)methyl]-1H-imidazole-4-carboxylate The title compound is prepared from (2-bromo-4-{6,6-difluoro-3-azabicyclo[3.1.0]hexan-3-yl}phenyl)methanol and ethyl 1H-imidazole-4-carboxylate following a procedure analogous to that described in Step 3 of Intermediate 111.

LC (Method 2): $t_R$=0.91 min.

Step 2: Ethyl 1-[(2-cyano-4-{6,6-difluoro-3-azabicyclo[3.1.0]hexan-3-yl}phenyl)methyl]-1H-imidazole-4-carboxylate The title compound is prepared from ethyl 1-[(2-bromo-4-{6,6-difluoro-3-azabicyclo[3.1.0]hexan-3-yl}phenyl)methyl]-1H-imidazole-4-carboxylate and zinc(II) cyanide following a procedure analogous to that described in Step 1 of Intermediate 126. LC (Method 1): $t_R$=0.95 min; Mass spectrum ($ESI^+$): m/z=373 $[M+H]^+$.

Step 3: 1-[(2-Cyano-4-{6,6-difluoro-3-azabicyclo[3.1.0]hexan-3-yl}phenyl)methyl]-1H-imidazole-4-carboxylic acid The title compound is prepared from ethyl 1-[(2-cyano-4-{6,6-difluoro-3-azabicyclo[3.1.0]hexan-3-yl}phenyl)methyl]-1H-imidazole-4-carboxylate following a procedure analogous to that described in Step 4 of Intermediate 111.

LC (Method 1): $t_R$=0.64 min; Mass spectrum ($ESI^+$): m/z=345 $[M+H]^+$.

Intermediate 131

1-[(2-Chloro-4-{6,6-difluoro-3-azabicyclo[3.1.0]hexan-3-yl}phenyl)methyl]-1H-imidazole-4-carboxylic acid

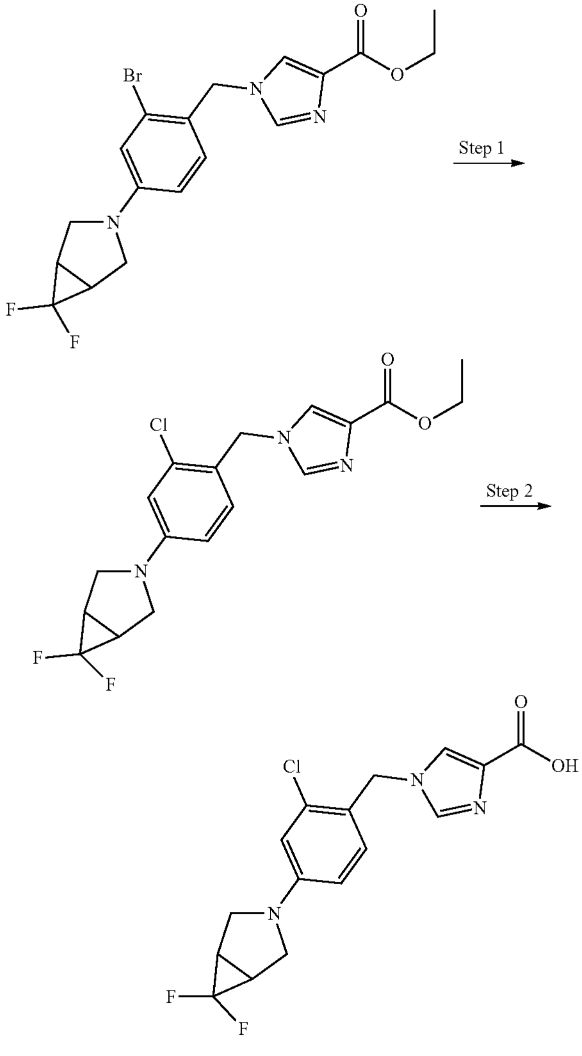

Step 1: Ethyl 1-[(2-chloro-4-{6,6-difluoro-3-azabicyclo[3.1.0]hexan-3-yl}phenyl)methyl]-1H-imidazole-4-carboxylate A mixture of ethyl 1-[(2-bromo-4-{6,6-difluoro-3-azabicyclo[3.1.0]hexan-3-yl}phenyl)methyl]-1H-imidazole-4-carboxylate (200 mg), copper(I) chloride (92 mg), and NMP is stirred at 160° C. for 2.5 h. After cooling to rt, the mixture is diluted with water and extracted with EtOAc (3×). The combined extract is dried ($Na_2SO_4$) and concentrated. The residue is chromatographed (HPLC; ACN/water/ammonia) to give the title compound.

LC (Method 2): $t_R$=0.92 min; Mass spectrum ($ESI^+$): m/z=382 $[M+H]^+$.

Step 2: 1-[(2-Chloro-4-{6,6-difluoro-3-azabicyclo[3.1.0]hexan-3-yl}phenyl)methyl]-1H-imidazole-4-carboxylic acid The title compound is prepared from ethyl 1-[(2-chloro-4-{6,6-difluoro-3-azabicyclo[3.1.0]hexan-3-yl}phenyl)methyl]-1H-imidazole-4-carboxylate following a procedure analogous to that described in Step 4 of Intermediate 111.

LC (Method 1): $t_R$=0.67 min; Mass spectrum ($ESI^-$): m/z=352 $[M-H]^-$.

Intermediate 132

1-[(4-{6,6-Difluoro-3-azabicyclo[3.1.0]hexan-3-yl}-2-fluorophenyl)methyl]-1H-imidazole-4-carboxylic acid

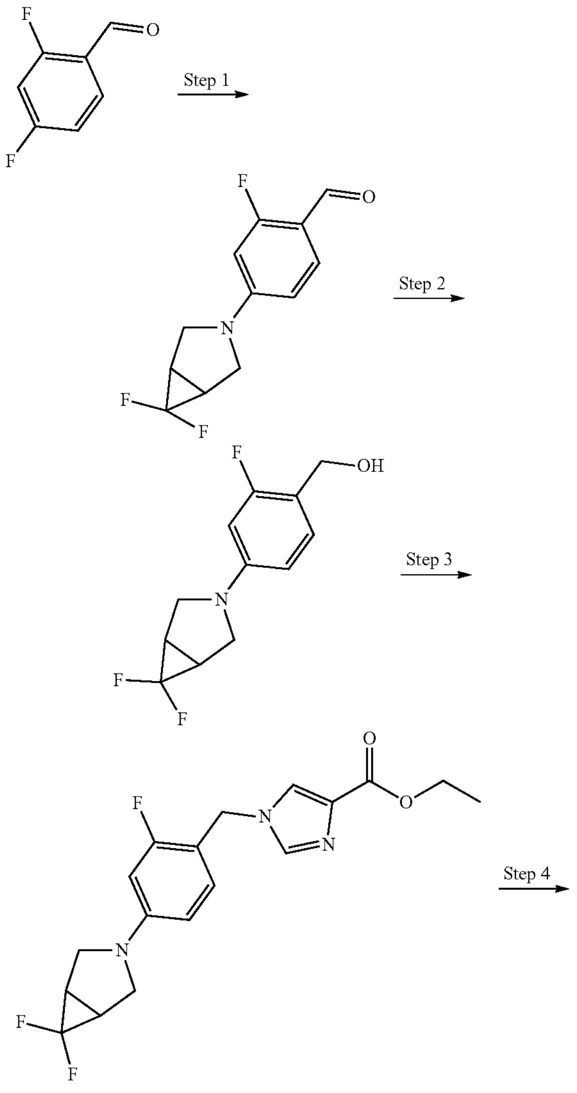

-continued

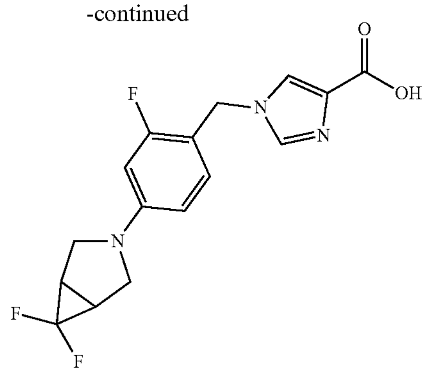

Step 1: 4-{6,6-Difluoro-3-azabicyclo[3.1.0]hexan-3-yl}-2-fluorobenzaldehyde

The title compound is prepared from 2,4-difluorobenzaldehyde and 6,6-difluoro-3-azabicyclo[3.1.0]hexane hydrochloride following a procedure analogous to that described in Step 1 of Intermediate 111; $K_2CO_3$ instead of Hunig's base and NMP instead of DMF are used. Mass spectrum ($ESI^+$): m/z=242 $[M+H]^+$.

Step 2: (4-{6,6-Difluoro-3-azabicyclo[3.1.0]hexan-3-yl}-2-fluorophenyl)methanol

The title compound is prepared from 4-{6,6-difluoro-3-azabicyclo[3.1.0]hexan-3-yl}-2-fluorobenzaldehyde following a procedure analogous to that described in Step 2 of Intermediate 111.

LC (Method 2): $t_R$=0.93 min; Mass spectrum ($ESI^+$): m/z=244 $[M+H]^+$.

Step 3: Ethyl 1-[(4-{6,6-difluoro-3-azabicyclo[3.1.0]hexan-3-yl}-2-fluorophenyl)methyl]-1H-imidazole-4-carboxylate The title compound is prepared from (4-{6,6-difluoro-3-azabicyclo[3.1.0]hexan-3-yl}-2-fluorophenyl)methanol and ethyl 1H-imidazole-4-carboxylate following a procedure analogous to that described in Step 3 of Intermediate 111.

Step 4: 1-[(4-{6,6-Difluoro-3-azabicyclo[3.1.0]hexan-3-yl}-2-fluorophenyl)methyl]-1H-imidazole-4-carboxylic acid The title compound is prepared from ethyl 1-[(4-{6,6-difluoro-3-azabicyclo[3.1.0]hexan-3-yl}-2-fluorophenyl)methyl]-1H-imidazole-4-carboxylate following a procedure analogous to that described in Step 4 of Intermediate 111.

LC (Method 2): $t_R$=0.79 min.

Intermediate 133

1-[(4-{6,6-Difluoro-3-azabicyclo[3.1.0]hexan-3-yl}-2-fluorophenyl)methyl]-1H-pyrazole-4-carboxylic acid

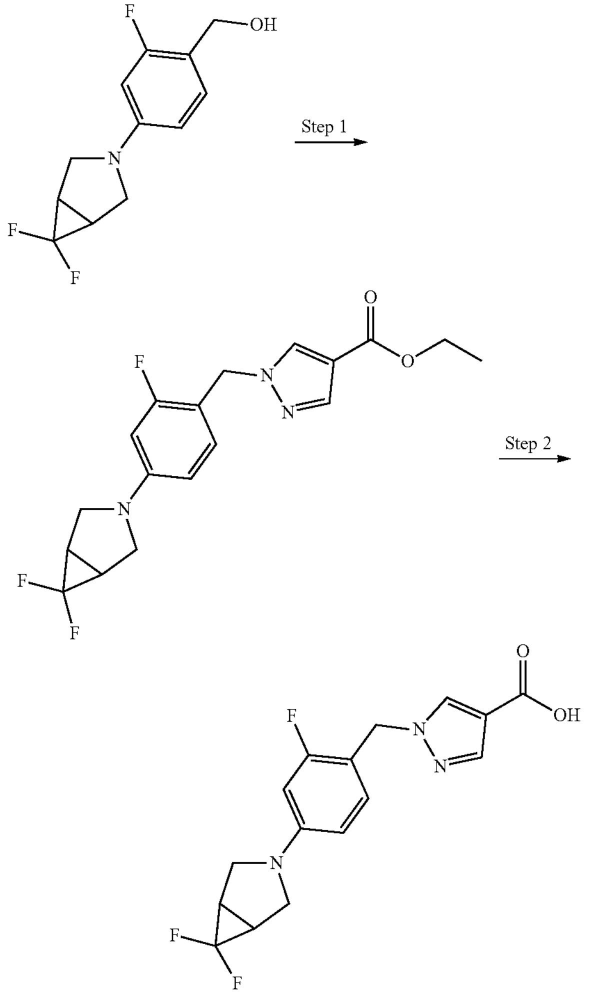

Step 1: Ethyl 1-[(4-{6,6-difluoro-3-azabicyclo[3.1.0]hexan-3-yl}-2-fluorophenyl)methyl]-1H-pyrazole-4-carboxylate The title compound is prepared from (4-{6,6-difluoro-3-azabicyclo[3.1.0]hexan-3-yl}-2-fluorophenyl)methanol and ethyl 1H-pyrazole-4-carboxylate following a procedure analogous to that described in Step 3 of Intermediate 111.

LC (Method 2): $t_R$=1.10 min; Mass spectrum ($ESI^+$): m/z=366 $[M+H]^+$.

Step 2: 1-[(4-{6,6-Difluoro-3-azabicyclo[3.1.0]hexan-3-yl}-2-fluorophenyl)methyl]-1H-pyrazole-4-carboxylic acid The title compound is prepared from ethyl 1-[(4-{6,6-difluoro-3-azabicyclo[3.1.0]hexan-3-yl}-2-fluorophenyl)methyl]-1H-pyrazole-4-carboxylate following a procedure analogous to that described in Step 4 of Intermediate 111.

Synthesis of Examples

Example 1

1-[(2-Chloro-6-{6,6-difluoro-3-azabicyclo[3.1.0]hexan-3-yl}pyridin-3-yl)methyl]-N-[(4R)-1-methyl-1H,4H,5H,6H-cyclopenta[d]imidazol-4-yl]-1H-1,2,3-triazole-4-carboxamide

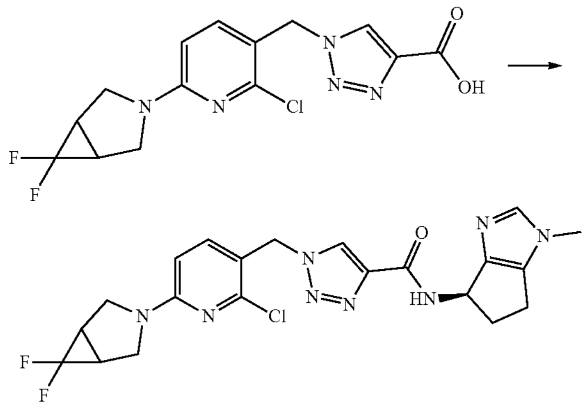

A mixture of 1-[(2-chloro-6-{6,6-difluoro-3-azabicyclo[3.1.0]hexan-3-yl}pyridin-3-yl)methyl]-1H-1,2,3-triazole-4-carboxylic acid (46 mg), DIPEA (111 μL) and O-(7-azabenzotriazol-1-yl)-N,N,N',N'-tetramethyluronium-hexafluorophosphat (HATU, 57 mg) in DMF (1 mL) is stirred for 5 min. (4R)-1-Methyl-1H,4H,5H,6H-cyclopenta[d]imidazol-4-amine dihydrochloride (33 mg) is added and the mixture is stirred for 1 h. The mixture is purified by HPLC on reversed phase (ACN, water) to give the title compound.

LC (Method 1): $t_R$=0.91 min; Mass spectrum (ESI$^+$): m/z=475 [M+H]$^+$.

Examples 2 to 213 are prepared in analogy to example 1:

| Example | Structure | $t_R$ | Mass spectrum (ESI+): m/z [M + H]$^+$ | LC Method |
|---|---|---|---|---|
| 2 | 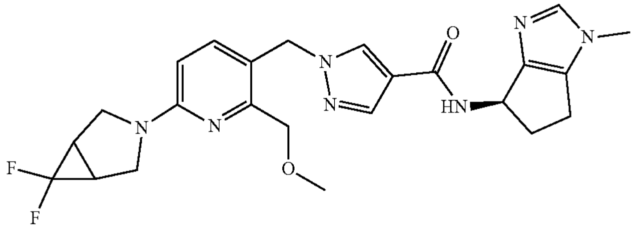 [SMILES: COCc1nc(N2CC3C(C2)C3(F)F)ccc1Cn1cc(C(=O)N[C@@H]2CCc3c2ncn3C)cn1] | 0.64 | 484 | Method 2 |
| 3 | 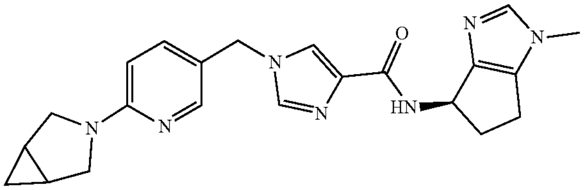 [SMILES: Cn1cnc2c1CC[C@H]2NC(=O)c1cn(Cc2ccc(N3CC4CC4C3)nc2)cn1] | 0.62 | 404 | Method 2 |
| 4 | 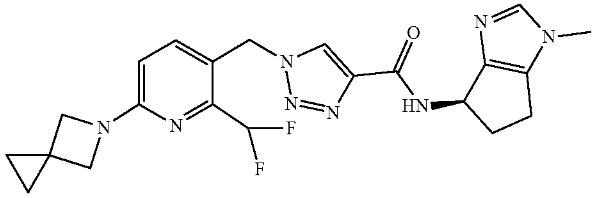 [SMILES: Cn1cnc2c1CC[C@H]2NC(=O)c1cn(Cc2ccc(N3CC4(CC4)C3)nc2C(F)F)nn1] | 0.95 | 455 | Method 1 |
| 5 | 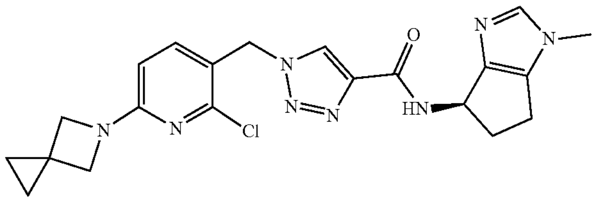 [SMILES: Cn1cnc2c1CC[C@H]2NC(=O)c1cn(Cc2ccc(N3CC4(CC4)C3)nc2Cl)nn1] | 0.78 | 439 | Method 2 |

-continued
| Example | Structure | $t_R$ | Mass spectrum (ESI+): m/z [M + H]+ | LC Method |
|---|---|---|---|---|
| 6 | 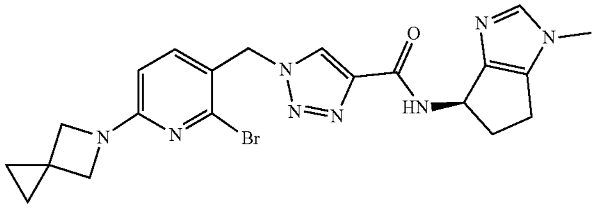 [SMILES: Cn1cnc2c1CC[C@H]2NC(=O)c1cn(Cc2ccc(N3CC4(CC4)C3)nc2Br)nn1] | 0.80 | 483 | Method 2 |
| 7 | 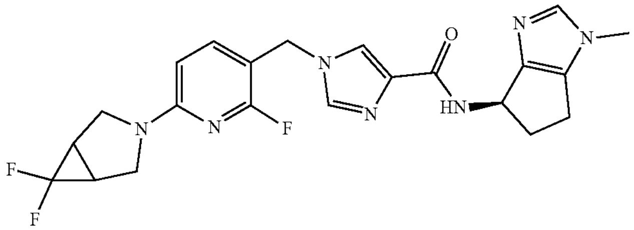 | 0.73 | 458 | Method 2 |
| 8 | 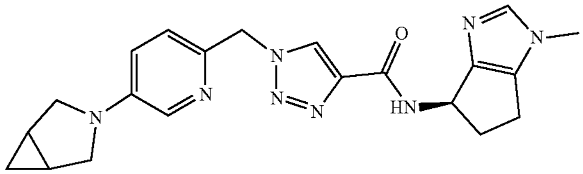 [SMILES: Cn1cnc2c1CC[C@H]2NC(=O)c1cn(Cc2ccc(N3CC4CC4C3)cn2)nn1] | 0.64 | 405 | Method 2 |
| 9 | 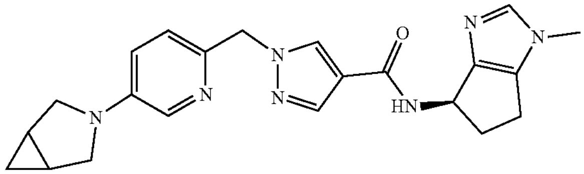 [SMILES: Cn1cnc2c1CC[C@H]2NC(=O)c1cnn(Cc2ccc(N3CC4CC4C3)cn2)c1] | 0.62 | 407 | Method 2 |
| 10 | 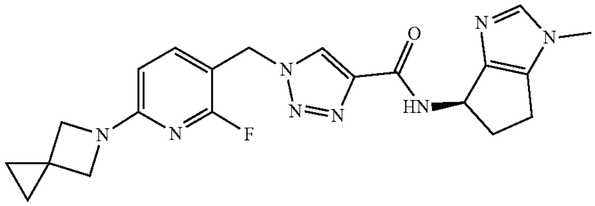 [SMILES: Cn1cnc2c1CC[C@H]2NC(=O)c1cn(Cc2ccc(N3CC4(CC4)C3)nc2F)nn1] | 0.77 | 423 | Method 2 |
| 11 | 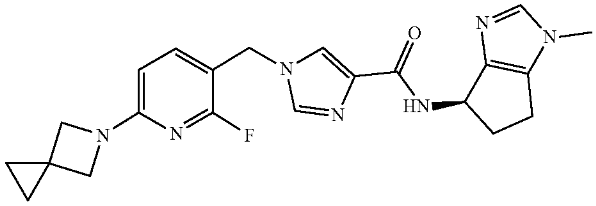 [SMILES: Cn1cnc2c1CC[C@H]2NC(=O)c1cn(Cc2ccc(N3CC4(CC4)C3)nc2F)cn1] | 0.73 | 422 | Method 2 |
| 12 | 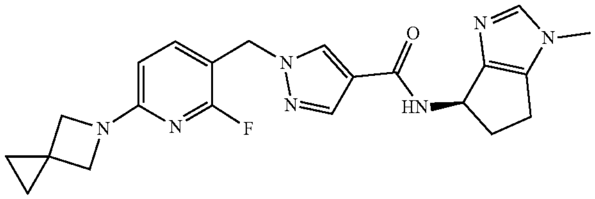 [SMILES: Cn1cnc2c1CC[C@H]2NC(=O)c1cnn(Cc2ccc(N3CC4(CC4)C3)nc2F)c1] | 0.77 | 422 | Method 2 |

-continued
| Example | Structure | $t_R$ | Mass spectrum (ESI+): m/z [M + H]+ | LC Method |
|---|---|---|---|---|
| 13 | 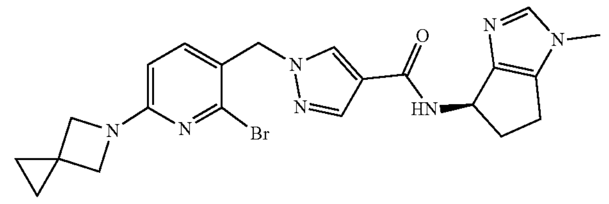 [SMILES: Cn1cnc2c1CC[C@H]2NC(=O)c1cnn(Cc2ccc(N3CC4(CC4)C3)nc2Br)c1] | 0.79 | 482 | Method 2 |
| 14 | 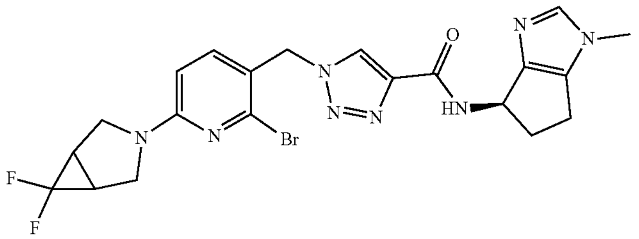 [SMILES: Cn1cnc2c1CC[C@H]2NC(=O)c1cn(Cc2ccc(N3CC4C(C3)C4(F)F)nc2Br)nn1] | 0.93 | 519 | Method 1 |
| 15 | 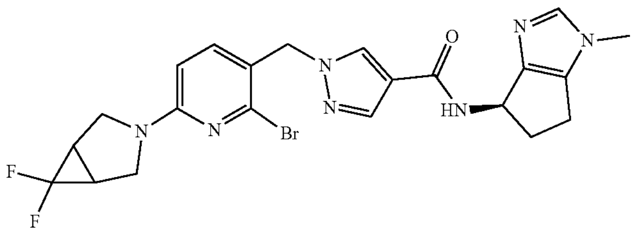 | 0.92 | 518 | Method 1 |
| 16 | 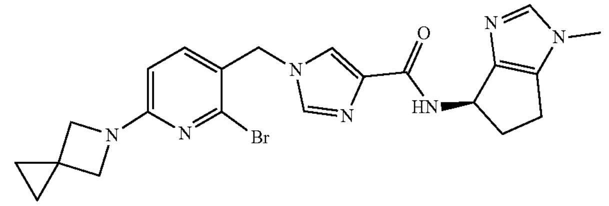 [SMILES: Cn1cnc2c1CC[C@H]2NC(=O)c1cn(Cc2ccc(N3CC4(CC4)C3)nc2Br)cn1] | 0.76 | 482 | Method 2 |
| 17 | 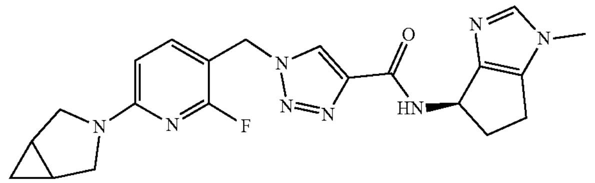 [SMILES: Cn1cnc2c1CC[C@H]2NC(=O)c1cn(Cc2ccc(N3CC4CC4C3)nc2F)nn1] | 0.78 | 423 | Method 2 |
| 18 | 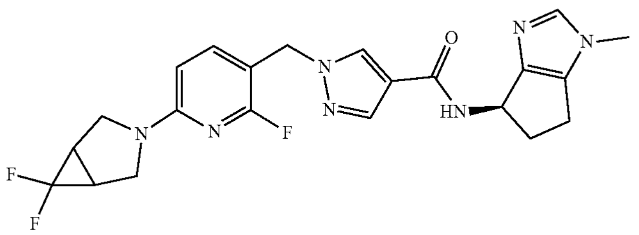 [SMILES: Cn1cnc2c1CC[C@H]2NC(=O)c1cnn(Cc2ccc(N3CC4C(C3)C4(F)F)nc2F)c1] | 0.77 | 458 | Method 2 |
| 19 | 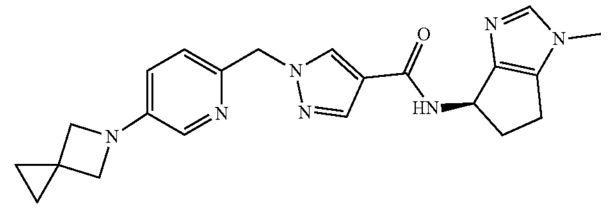 [SMILES: Cn1cnc2c1CC[C@H]2NC(=O)c1cnn(Cc2ccc(N3CC4(CC4)C3)cn2)c1] | 0.64 | 404 | Method 2 |

-continued
| Example | Structure | $t_R$ | Mass spectrum (ESI+): m/z $[M + H]^+$ | LC Method |
|---|---|---|---|---|
| 20 | 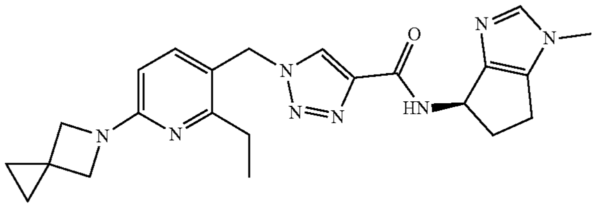 [SMILES: CCc1nc(N2CC3(CC3)C2)ccc1Cn1cc(C(=O)N[C@@H]2CCc3c2ncn3C)nn1] | 0.94 | 433 | Method 1 |
| 21 | 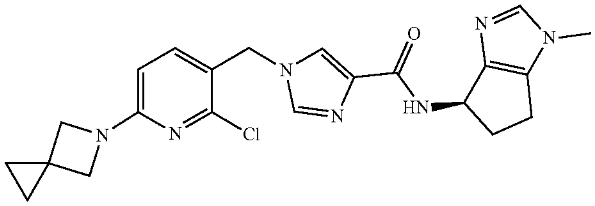 [SMILES: Cn1cnc2c1CC[C@H]2NC(=O)c1cn(Cc2ccc(N3CC4(CC4)C3)nc2Cl)cn1] | 0.91 | 438 | Method 1 |
| 22 | 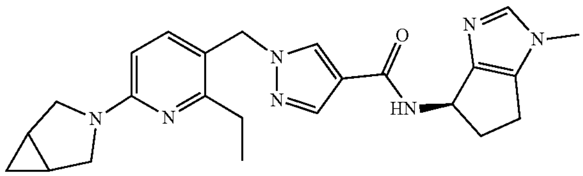 [SMILES: CCc1nc(N2CC3CC3C2)ccc1Cn1cc(C(=O)N[C@@H]2CCc3c2ncn3C)cn1] | 0.96 | 432 | Method 1 |
| 23 | 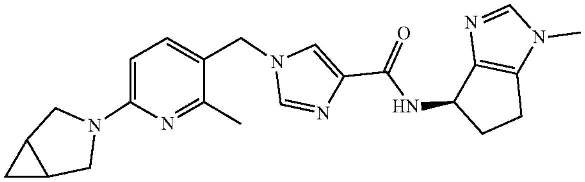 [SMILES: Cc1nc(N2CC3CC3C2)ccc1Cn1cnc(C(=O)N[C@@H]2CCc3c2ncn3C)c1] | 0.55 | 418 | Method 2 |
| 24 | 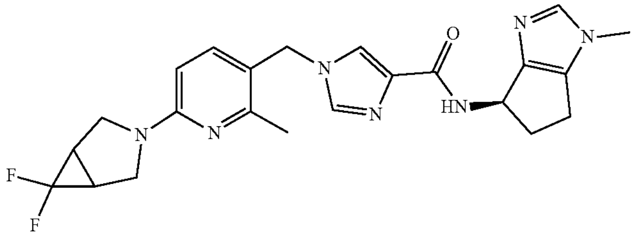 [SMILES: Cc1nc(N2CC3C(C2)C3(F)F)ccc1Cn1cnc(C(=O)N[C@@H]2CCc3c2ncn3C)c1] | 0.89 | 454 | Method 1 |
| 25 | 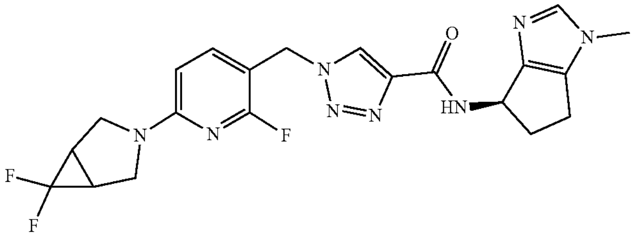 | 0.77 | 459 | Method 2 |
| 26 | 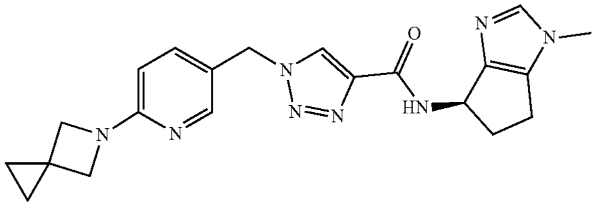 [SMILES: Cn1cnc2c1CC[C@H]2NC(=O)c1cn(Cc2ccc(N3CC4(CC4)C3)nc2)nn1] | 0.59 | 405 | Method 2 |

-continued
| Example | Structure | $t_R$ | Mass spectrum (ESI+): m/z $[M + H]^+$ | LC Method |
|---|---|---|---|---|
| 27 | 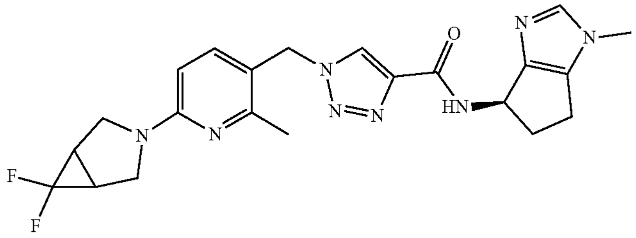 [SMILES: Cc1nc(N2CC3C(C2)C3(F)F)ccc1Cn1cc(C(=O)N[C@@H]2CCc3c2ncn3C)nn1] | 0.90 | 455 | Method 1 |
| 28 | 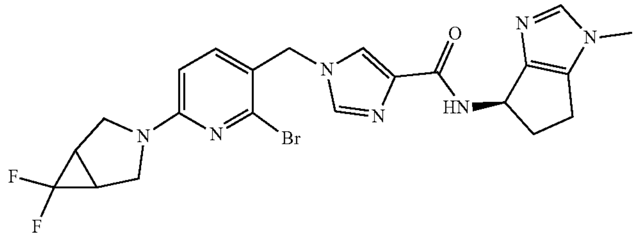 [SMILES: Cn1cnc2c1CC[C@H]2NC(=O)c1cn(Cc2ccc(N3CC4C(C3)C4(F)F)nc2Br)cn1] | 0.92 | 518 | Method 1 |
| 29 | 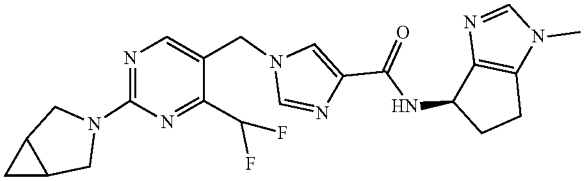 [SMILES: Cn1cnc2c1CC[C@H]2NC(=O)c1cn(Cc2cnc(N3CC4CC4C3)nc2C(F)F)cn1] | 0.74 | 455 | Method 2 |
| 30 | 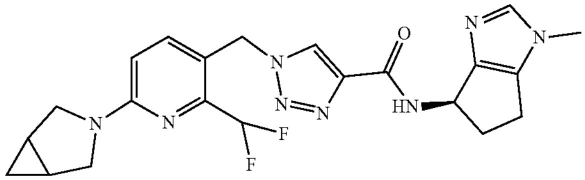 [SMILES: Cn1cnc2c1CC[C@H]2NC(=O)c1cn(Cc2ccc(N3CC4CC4C3)nc2C(F)F)nn1] | 0.82 | 455 | Method 2 |
| 31 | 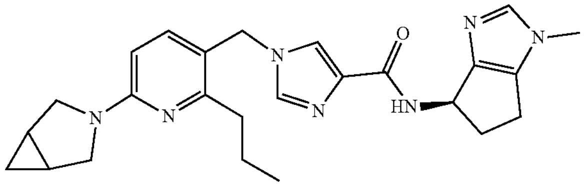 [SMILES: CCCc1nc(N2CC3CC3C2)ccc1Cn1cnc(C(=O)N[C@@H]2CCc3c2ncn3C)c1] | 0.95 | 447 | Method 1 |
| 32 | 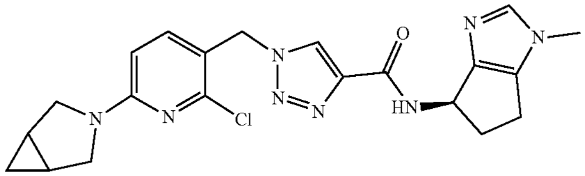 [SMILES: Cn1cnc2c1CC[C@H]2NC(=O)c1cn(Cc2ccc(N3CC4CC4C3)nc2Cl)nn1] | 0.80 | 439 | Method 2 |
| 33 | 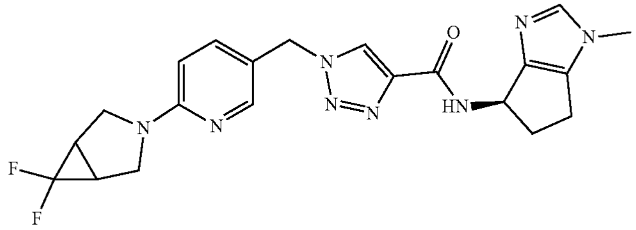 [SMILES: Cn1cnc2c1CC[C@H]2NC(=O)c1cn(Cc2ccc(N3CC4C(C3)C4(F)F)nc2)nn1] | 0.58 | 441 | Method 2 |

-continued
| Example | Structure | $t_R$ | Mass spectrum (ESI+): m/z $[M + H]^+$ | LC Method |
|---|---|---|---|---|
| 34 | 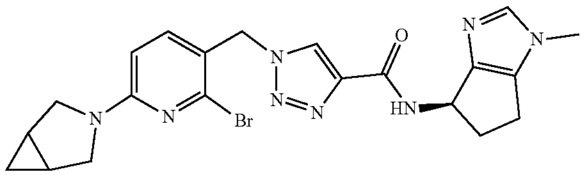 [SMILES: Cn1cnc2c1CC[C@H]2NC(=O)c1cn(Cc2ccc(N3CC4CC4C3)nc2Br)nn1] | 0.81 | 483 | Method 2 |
| 35 | 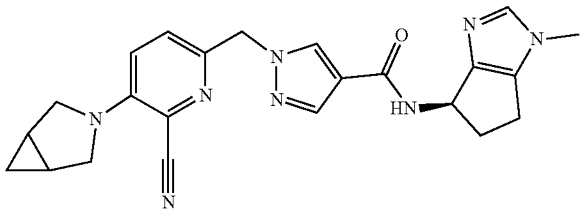 [SMILES: Cn1cnc2c1CC[C@H]2NC(=O)c1cnn(Cc2ccc(N3CC4CC4C3)c(C#N)n2)c1] | 0.75 | 429 | Method 2 |
| 36 | 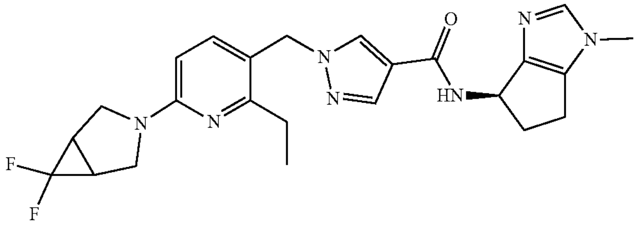 [SMILES: CCc1nc(N2CC3C(C2)C3(F)F)ccc1Cn1cc(C(=O)N[C@@H]2CCc3c2ncn3C)cn1] | 0.64 | 468 | Method 2 |
| 37 | 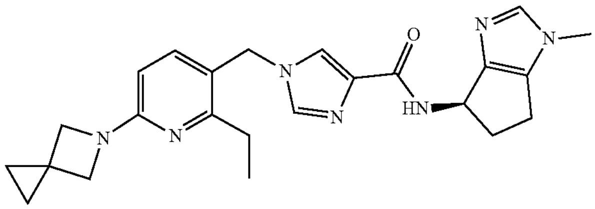 [SMILES: CCc1nc(N2CC3(CC3)C2)ccc1Cn1cnc(C(=O)N[C@@H]2CCc3c2ncn3C)c1] | 0.93 | 432 | Method 1 |
| 38 | 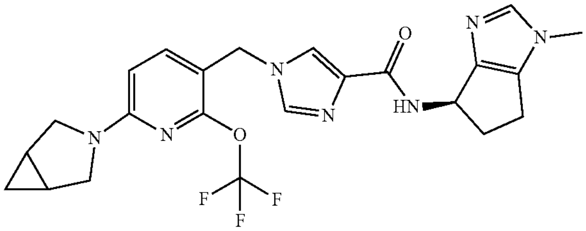 [SMILES: Cn1cnc2c1CC[C@H]2NC(=O)c1cn(Cc2ccc(N3CC4CC4C3)nc2OC(F)(F)F)cn1] | 0.84 | 488 | Method 2 |
| 39 | 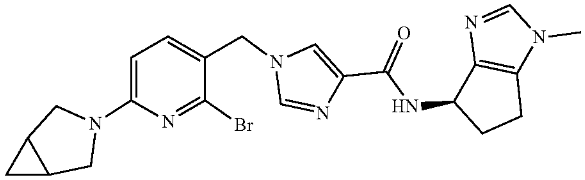 [SMILES: Cn1cnc2c1CC[C@H]2NC(=O)c1cn(Cc2ccc(N3CC4CC4C3)nc2Br)cn1] | 0.77 | 482 | Method 2 |
| 40 | 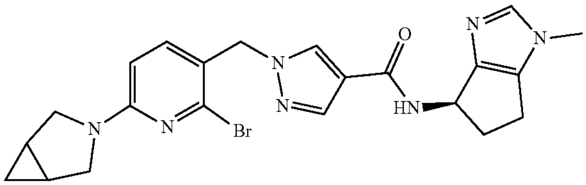 [SMILES: Cn1cnc2c1CC[C@H]2NC(=O)c1cnn(Cc2ccc(N3CC4CC4C3)nc2Br)c1] | 0.81 | 482 | Method 2 |

-continued
| Example | Structure | $t_R$ | Mass spectrum (ESI+): m/z $[M + H]^+$ | LC Method |
|---|---|---|---|---|
| 41 | 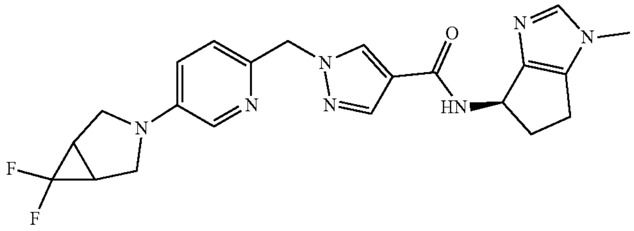 [SMILES: Cn1cnc2c1CC[C@H]2NC(=O)c1cnn(Cc2ccc(N3CC4C(C3)C4(F)F)cn2)c1] | 0.82 | 440 | Method 1 |
| 42 | 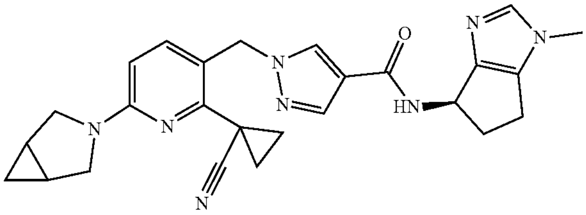 [SMILES: Cn1cnc2c1CC[C@H]2NC(=O)c1cnn(Cc2ccc(N3CC4CC4C3)nc2C2(C#N)CC2)c1] | 0.76 | 469 | Method 2 |
| 43 | 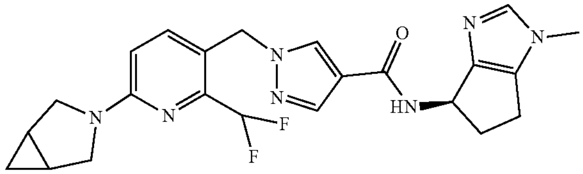 [SMILES: Cn1cnc2c1CC[C@H]2NC(=O)c1cnn(Cc2ccc(N3CC4CC4C3)nc2C(F)F)c1] | 0.95 | 454 | Method 1 |
| 44 | 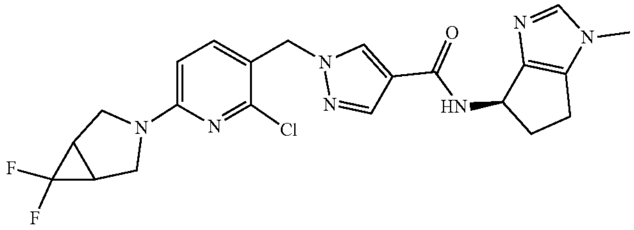 [SMILES: Cn1cnc2c1CC[C@H]2NC(=O)c1cnn(Cc2ccc(N3CC4C(C3)C4(F)F)nc2Cl)c1] | 0.79 | 474 | Method 2 |
| 45 | 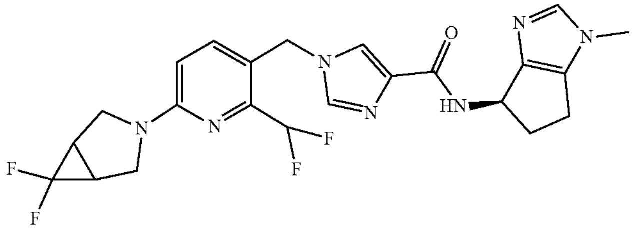 | 0.93 | 490 | Method 1 |
| 46 | 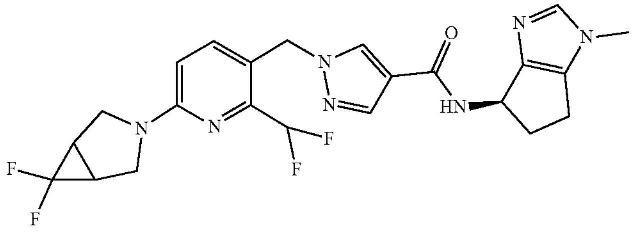 [SMILES: Cn1cnc2c1CC[C@H]2NC(=O)c1cnn(Cc2ccc(N3CC4C(C3)C4(F)F)nc2C(F)F)c1] | 0.92 | 490 | Method 1 |

-continued
| Example | Structure | $t_R$ | Mass spectrum (ESI+): m/z $[M + H]^+$ | LC Method |
|---|---|---|---|---|
| 47 | 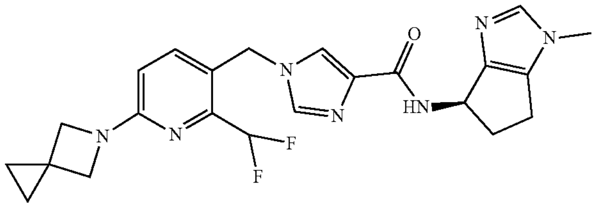 [SMILES: Cn1cnc2c1CC[C@H]2NC(=O)c1cn(Cc2ccc(N3CC4(CC4)C3)nc2C(F)F)cn1] | 0.93 | 454 | Method 1 |
| 48 | 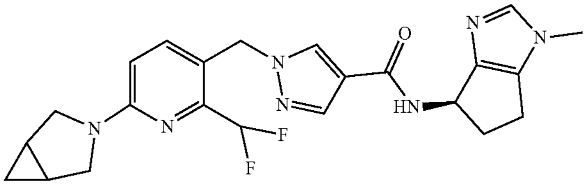 [SMILES: Cn1cnc2c1CC[C@H]2NC(=O)c1cnn(Cc2ccc(N3CC4CC4C3)nc2C(F)F)c1] | 0.79 | 455 | Method 2 |
| 49 | 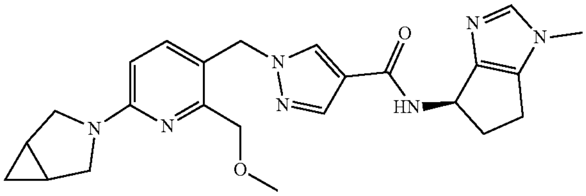 [SMILES: COCc1nc(N2CC3CC3C2)ccc1Cn1cc(C(=O)N[C@@H]2CCc3c2ncn3C)cn1] | 0.90 | 448 | Method 1 |
| 50 | 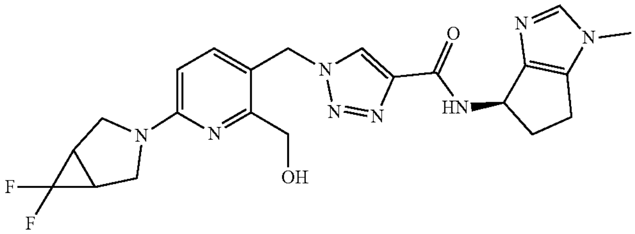 [SMILES: Cn1cnc2c1CC[C@H]2NC(=O)c1cn(Cc2ccc(N3CC4C(C3)C4(F)F)nc2CO)nn1] | 0.84 | 471 | Method 1 |
| 51 | 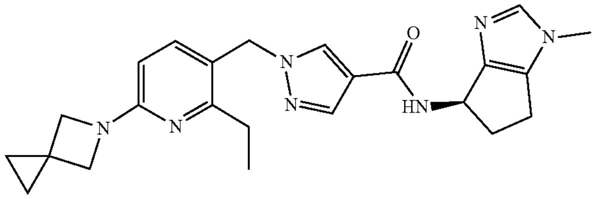 [SMILES: CCc1nc(N2CC3(CC3)C2)ccc1Cn1cc(C(=O)N[C@@H]2CCc3c2ncn3C)cn1] | 0.92 | 432 | Method 1 |
| 52 | 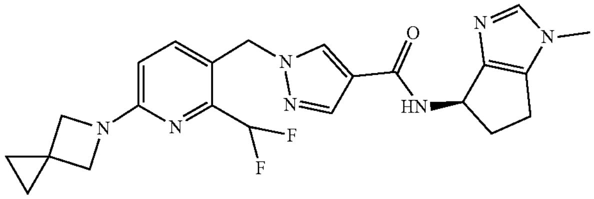 [SMILES: Cn1cnc2c1CC[C@H]2NC(=O)c1cnn(Cc2ccc(N3CC4(CC4)C3)nc2C(F)F)c1] | 0.78 | 454 | Method 2 |
| 53 | 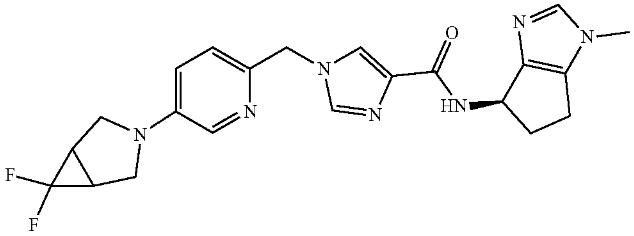 [SMILES: Cn1cnc2c1CC[C@H]2NC(=O)c1cn(Cc2ccc(N3CC4C(C3)C4(F)F)cn2)cn1] | 0.62 | 440 | Method 2 |

-continued
| Example | Structure | $t_R$ | Mass spectrum (ESI+): m/z $[M + H]^+$ | LC Method |
|---|---|---|---|---|
| 54 | 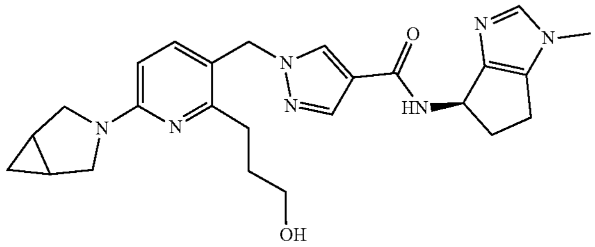 [SMILES: Cn1cnc2c1CC[C@H]2NC(=O)c1cnn(Cc2ccc(N3CC4CC4C3)nc2CCCO)c1] | 0.67 | 462 | Method 1 |
| 55 | 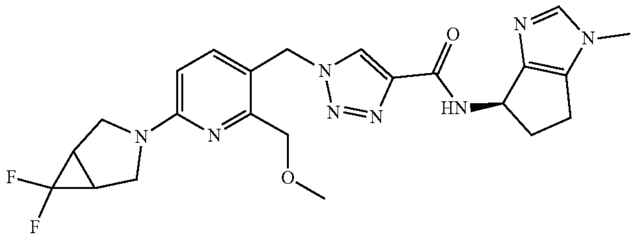 [SMILES: COCc1nc(N2CC3C(C2)C3(F)F)ccc1Cn1cc(C(=O)N[C@@H]2CCc3c2ncn3C)nn1] | 0.90 | 485 | Method 1 |
| 56 | 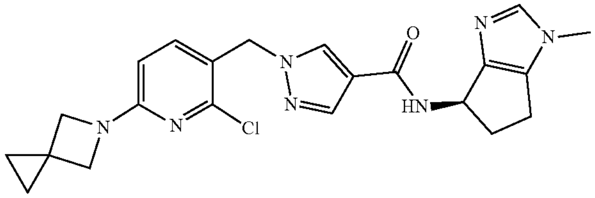 [SMILES: Cn1cnc2c1CC[C@H]2NC(=O)c1cnn(Cc2ccc(N3CC4(CC4)C3)nc2Cl)c1] | 0.78 | 438 | Method 2 |
| 57 | 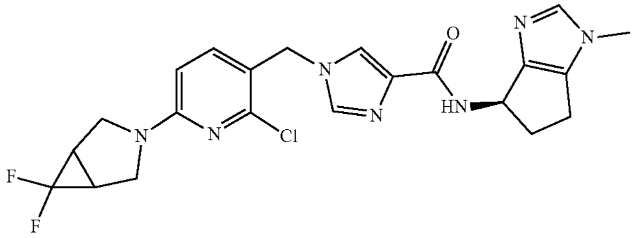 [SMILES: Cn1cnc2c1CC[C@H]2NC(=O)c1cn(Cc2ccc(N3CC4C(C3)C4(F)F)nc2Cl)cn1] | 0.91 | 474 | Method 1 |
| 58 | 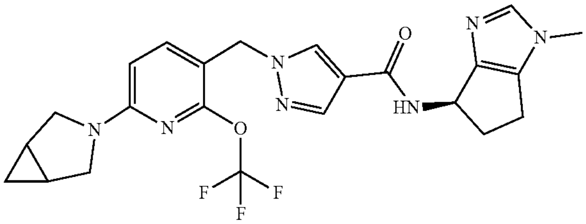 [SMILES: Cn1cnc2c1CC[C@H]2NC(=O)c1cnn(Cc2ccc(N3CC4CC4C3)nc2OC(F)(F)F)c1] | 0.88 | 488 | Method 2 |
| 59 | 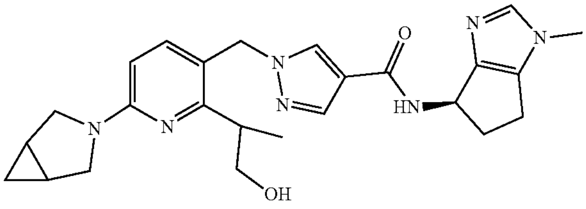 [SMILES: CC(CO)c1nc(N2CC3CC3C2)ccc1Cn1cc(C(=O)N[C@@H]2CCc3c2ncn3C)cn1] | 0.90 | 462 | Method 1 |

-continued
| Example | Structure | $t_R$ | Mass spectrum (ESI+): m/z $[M + H]^+$ | LC Method |
|---|---|---|---|---|
| 60 | 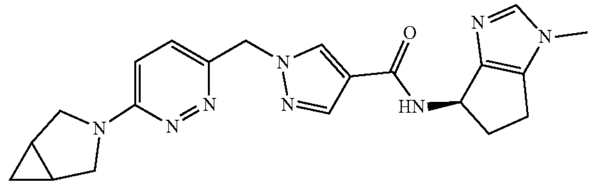 [SMILES: Cn1cnc2c1CC[C@H]2NC(=O)c1cnn(Cc2ccc(N3CC4CC4C3)nn2)c1] | 0.55 | 405 | Method 2 |
| 61 | 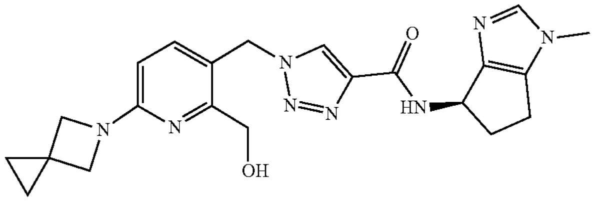 [SMILES: Cn1cnc2c1CC[C@H]2NC(=O)c1cn(Cc2ccc(N3CC4(CC4)C3)nc2CO)nn1] | 0.59 | 435 | Method 2 |
| 62 | 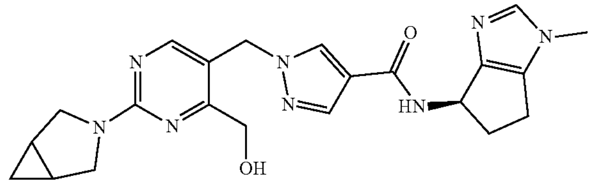 [SMILES: Cn1cnc2c1CC[C@H]2NC(=O)c1cnn(Cc2cnc(N3CC4CC4C3)nc2CO)c1] | 0.64 | 435 | Method 2 |
| 63 | 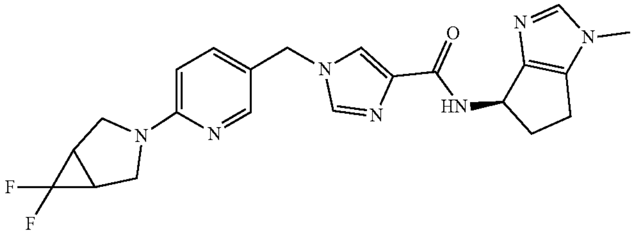 [SMILES: Cn1cnc2c1CC[C@H]2NC(=O)c1cn(Cc2ccc(N3CC4C(C3)C4(F)F)nc2)cn1] | 0.58 | 440 | Method 4 |
| 64 | 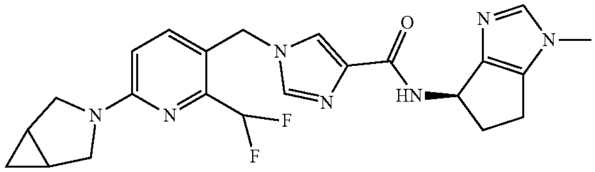 [SMILES: Cn1cnc2c1CC[C@H]2NC(=O)c1cn(Cc2ccc(N3CC4CC4C3)nc2C(F)F)cn1] | 0.95 | 454 | Method 1 |
| 65 | 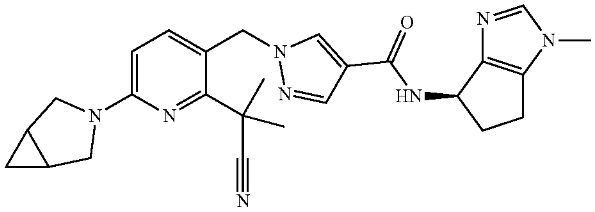 [SMILES: Cn1cnc2c1CC[C@H]2NC(=O)c1cnn(Cc2ccc(N3CC4CC4C3)nc2C(C)(C)C#N)c1] | 1.00 | 471 | Method 1 |
| 66 | 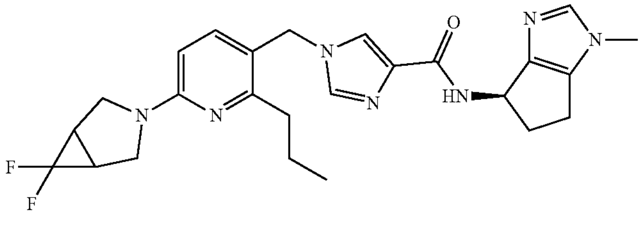 | 0.98 | 482 | Method 1 |

-continued
| Example | Structure | $t_R$ | Mass spectrum (ESI+): m/z $[M + H]^+$ | LC Method |
|---|---|---|---|---|
| 67 | 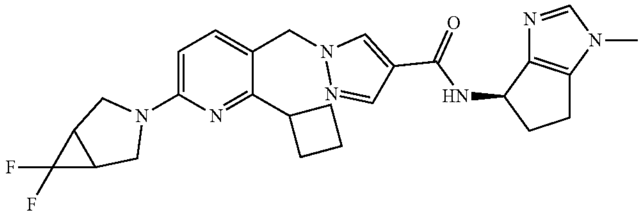 [SMILES: Cn1cnc2c1CC[C@H]2NC(=O)c1cnn(Cc2ccc(N3CC4C(C3)C4(F)F)nc2C2CCC2)c1] | 1.02 | 494 | Method 1 |
| 68 | 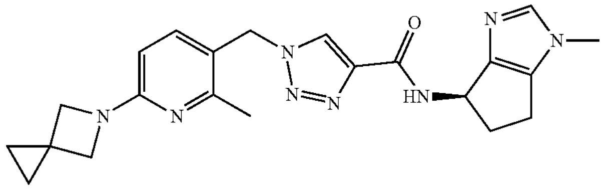 [SMILES: Cc1nc(N2CC3(CC3)C2)ccc1Cn1cc(C(=O)N[C@@H]2CCc3c2ncn3C)nn1] | 0.87 | 419 | Method 1 |
| 69 | 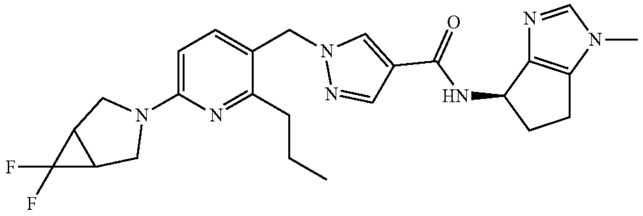 [SMILES: CCCc1nc(N2CC3C(C2)C3(F)F)ccc1Cn1cc(C(=O)N[C@@H]2CCc3c2ncn3C)cn1] | 0.98 | 482 | Method 1 |
| 70 | 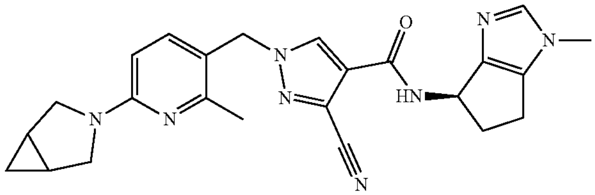 [SMILES: Cc1nc(N2CC3CC3C2)ccc1Cn1cc(C(=O)N[C@@H]2CCc3c2ncn3C)c(C#N)n1] | 0.97 | 443 | Method 1 |
| 71 | 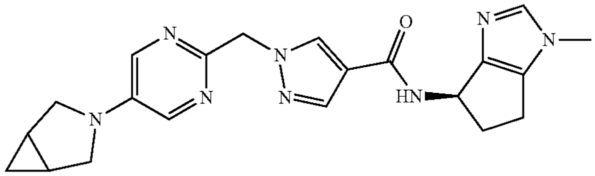 [SMILES: Cn1cnc2c1CC[C@H]2NC(=O)c1cnn(Cc2ncc(N3CC4CC4C3)cn2)c1] | 0.79 | 405 | Method 1 |
| 72 | 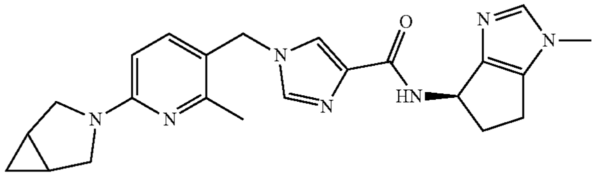 [SMILES: Cc1nc(N2CC3CC3C2)ccc1Cn1cnc(C(=O)N[C@@H]2CCc3c2ncn3C)c1] | 0.87 | 404 | Method 1 |
| 73 | 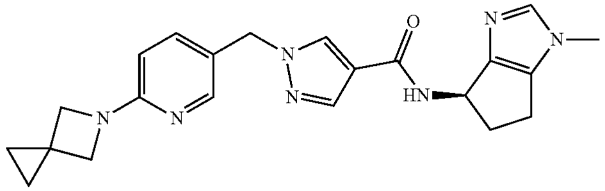 [SMILES: Cn1cnc2c1CC[C@H]2NC(=O)c1cnn(Cc2ccc(N3CC4(CC4)C3)nc2)c1] | 0.86 | 404 | Method 1 |

-continued
| Example | Structure | $t_R$ | Mass spectrum (ESI+): m/z $[M + H]^+$ | LC Method |
|---|---|---|---|---|
| 74 | 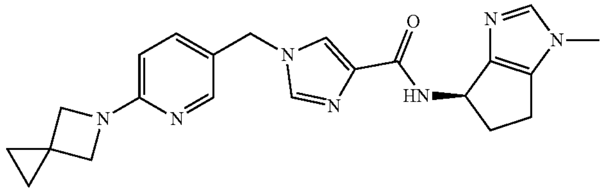 [SMILES: Cn1cnc2c1CC[C@H]2NC(=O)c1cn(Cc2ccc(N3CC4(CC4)C3)nc2)cn1] | 0.86 | 404 | Method 1 |
| 75 | 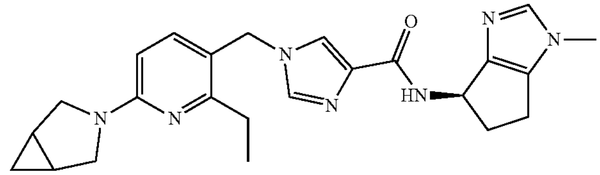 [SMILES: CCc1nc(N2CC3CC3C2)ccc1Cn1cnc(C(=O)N[C@@H]2CCc3c2ncn3C)c1] | 0.60 | 432 | Method 2 |
| 76 | 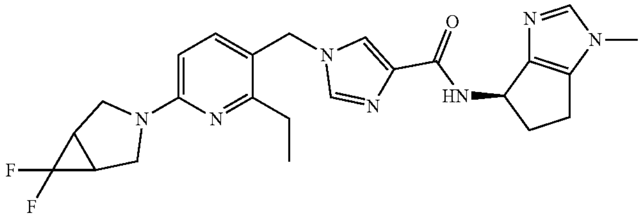 [SMILES: CCc1nc(N2CC3C(C2)C3(F)F)ccc1Cn1cnc(C(=O)N[C@@H]2CCc3c2ncn3C)c1] | 0.60 | 468 | Method 2 |
| 77 | 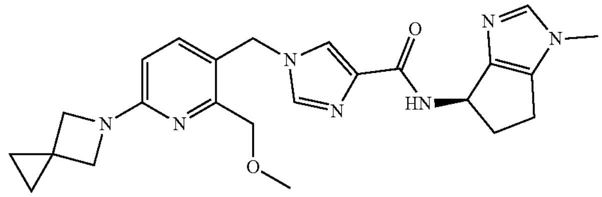 | 0.63 | 448 | Method 5 |
| 78 | 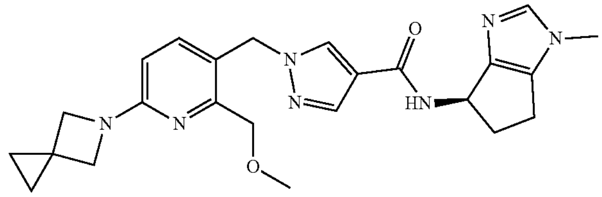 [SMILES: COCc1nc(N2CC3(CC3)C2)ccc1Cn1cc(C(=O)N[C@@H]2CCc3c2ncn3C)cn1] | 0.62 | 448 | Method 5 |
| 79 | 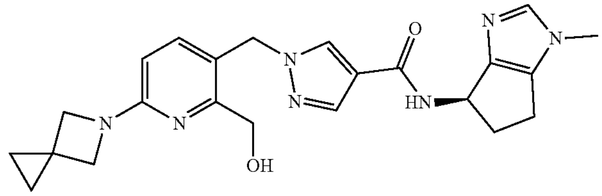 [SMILES: Cn1cnc2c1CC[C@H]2NC(=O)c1cnn(Cc2ccc(N3CC4(CC4)C3)nc2CO)c1] | 0.58 | 434 | Method 5 |
| 80 | 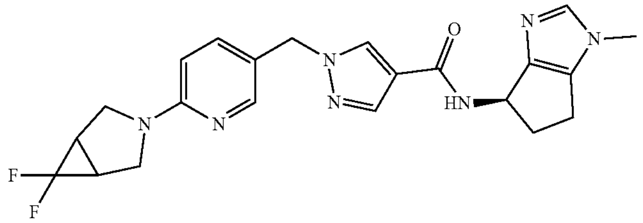 [SMILES: Cn1cnc2c1CC[C@H]2NC(=O)c1cnn(Cc2ccc(N3CC4C(C3)C4(F)F)nc2)c1] | 0.58 | 440 | Method 5 |

-continued
| Example | Structure | $t_R$ | Mass spectrum (ESI+): m/z $[M + H]^+$ | LC Method |
|---|---|---|---|---|
| 81 | 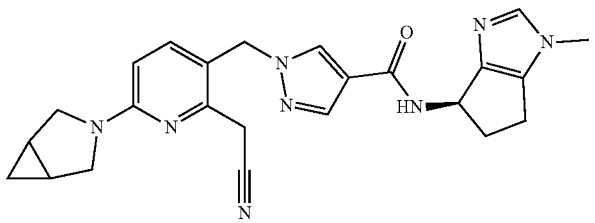 [SMILES: Cn1cnc2c1CC[C@H]2NC(=O)c1cnn(Cc2ccc(N3CC4CC4C3)nc2CC#N)c1] | 0.89 | 443 | Method 1 |
| 82 | 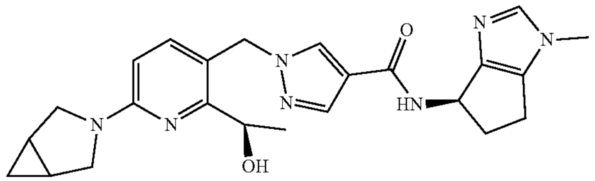 [SMILES: C[C@@H](O)c1nc(N2CC3CC3C2)ccc1Cn1cc(C(=O)N[C@@H]2CCc3c2ncn3C)cn1] | 0.89 | 448 | Method 1 |
| 83 | 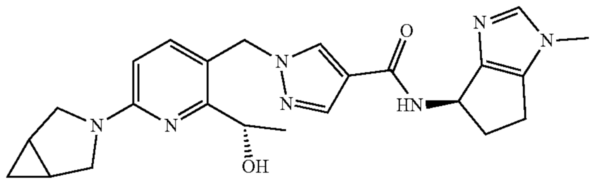 [SMILES: C[C@H](O)c1nc(N2CC3CC3C2)ccc1Cn1cc(C(=O)N[C@@H]2CCc3c2ncn3C)cn1] | 0.89 | 448 | Method 1 |
| 84 | 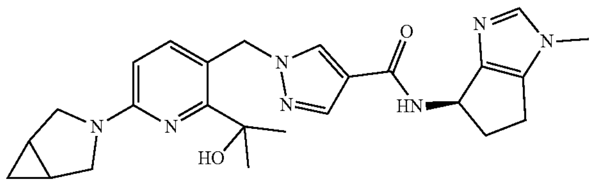 [SMILES: Cn1cnc2c1CC[C@H]2NC(=O)c1cnn(Cc2ccc(N3CC4CC4C3)nc2C(C)(C)O)c1] | 0.61 | 462 | Method 2 |
| 85 | 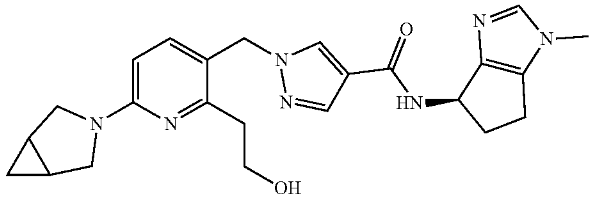 [SMILES: Cn1cnc2c1CC[C@H]2NC(=O)c1cnn(Cc2ccc(N3CC4CC4C3)nc2CCO)c1] | 0.85 | 448 | Method 1 |
| 86 | 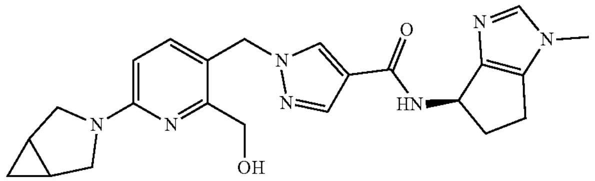 [SMILES: Cn1cnc2c1CC[C@H]2NC(=O)c1cnn(Cc2ccc(N3CC4CC4C3)nc2CO)c1] | 0.85 | 434 | Method 1 |
| 87 | 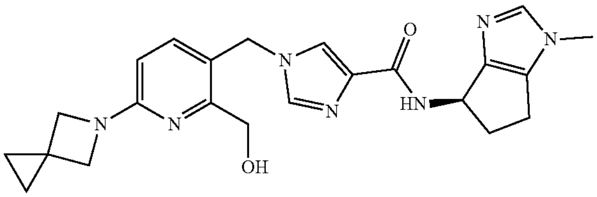 [SMILES: Cn1cnc2c1CC[C@H]2NC(=O)c1cn(Cc2ccc(N3CC4(CC4)C3)nc2CO)cn1] | 0.52 | 434 | Method 5 |

-continued
| Example | Structure | $t_R$ | Mass spectrum (ESI+): m/z $[M + H]^+$ | LC Method |
|---|---|---|---|---|
| 88 | 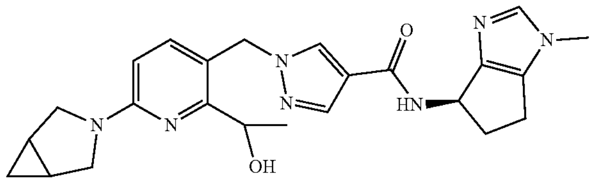 [SMILES: CC(O)c1nc(N2CC3CC3C2)ccc1Cn1cc(C(=O)N[C@@H]2CCc3c2ncn3C)cn1] | 0.89 | 448 | Method 1 |
| 89 | 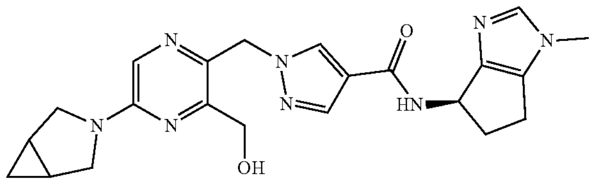 [SMILES: Cn1cnc2c1CC[C@H]2NC(=O)c1cnn(Cc2ncc(N3CC4CC4C3)nc2CO)c1] | 0.69 | 435 | Method 2 |
| 90 | 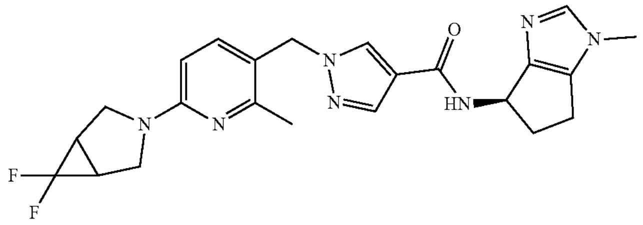 [SMILES: Cc1nc(N2CC3C(C2)C3(F)F)ccc1Cn1cc(C(=O)N[C@@H]2CCc3c2ncn3C)cn1] | 0.62 | 454 | Method 2 |
| 91 | 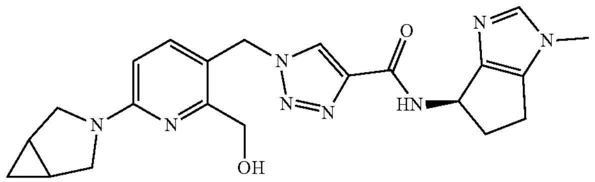 | 0.86 | 435 | Method 1 |
| 92 | 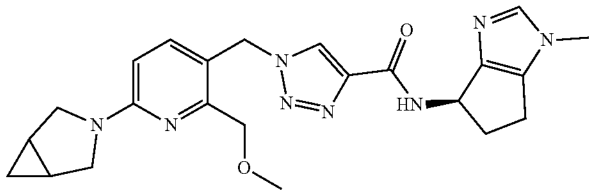 [SMILES: COCc1nc(N2CC3CC3C2)ccc1Cn1cc(C(=O)N[C@@H]2CCc3c2ncn3C)nn1] | 0.93 | 449 | Method 1 |
| 93 | 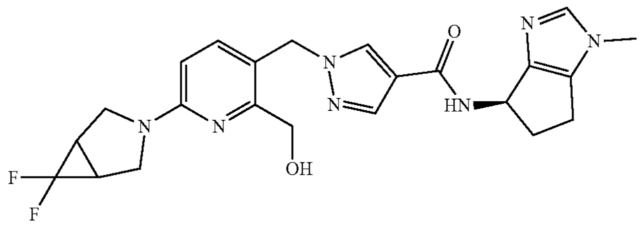 [SMILES: Cn1cnc2c1CC[C@H]2NC(=O)c1cnn(Cc2ccc(N3CC4C(C3)C4(F)F)nc2CO)c1] | 0.60 | 470 | Method 2 |
| 94 | 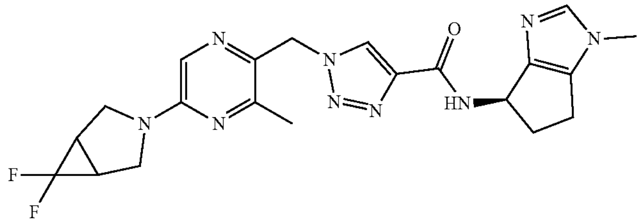 [SMILES: Cc1nc(N2CC3C(C2)C3(F)F)cnc1Cn1cc(C(=O)N[C@@H]2CCc3c2ncn3C)nn1] | 0.76 | 456 | Method 2 |

-continued
| Example | Structure | $t_R$ | Mass spectrum (ESI+): m/z $[M + H]^+$ | LC Method |
|---|---|---|---|---|
| 95 | 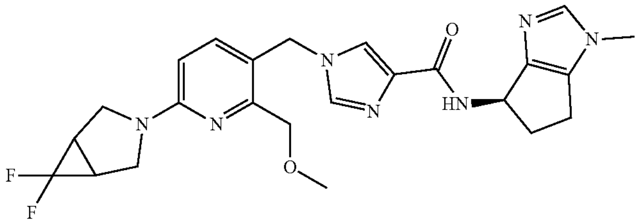 [SMILES: COCc1nc(N2CC3C(C2)C3(F)F)ccc1Cn1cnc(C(=O)N[C@@H]2CCc3c2ncn3C)c1] | 0.64 | 484 | Method 2 |
| 96 | 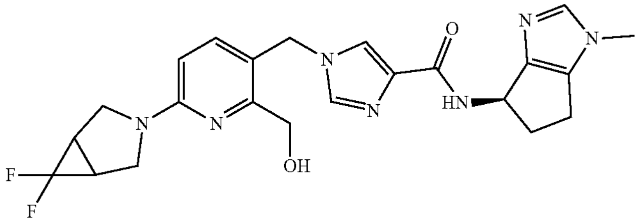 [SMILES: Cn1cnc2c1CC[C@H]2NC(=O)c1cn(Cc2ccc(N3CC4C(C3)C4(F)F)nc2CO)cn1] | 0.59 | 470 | Method 2 |
| 97 | 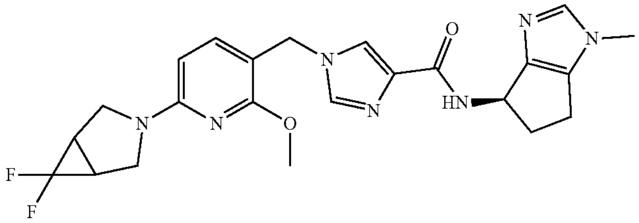 [SMILES: COc1nc(N2CC3C(C2)C3(F)F)ccc1Cn1cnc(C(=O)N[C@@H]2CCc3c2ncn3C)c1] | 0.73 | 470 | Method 5 |
| 98 | 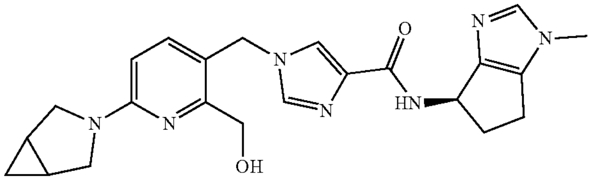 [SMILES: Cn1cnc2c1CC[C@H]2NC(=O)c1cn(Cc2ccc(N3CC4CC4C3)nc2CO)cn1] | 0.88 | 434 | Method 1 |
| 99 | 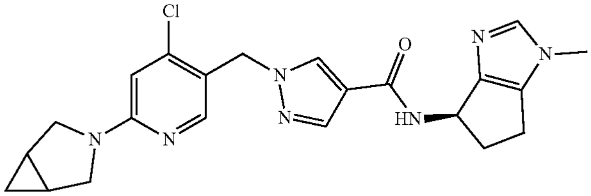 [SMILES: Cn1cnc2c1CC[C@H]2NC(=O)c1cnn(Cc2cnc(N3CC4CC4C3)cc2Cl)c1] | 0.89 | 438 | Method 1 |
| 100 | 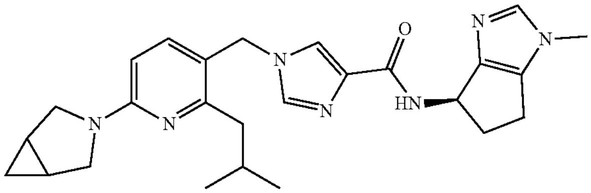 [SMILES: CC(C)Cc1nc(N2CC3CC3C2)ccc1Cn1cnc(C(=O)N[C@@H]2CCc3c2ncn3C)c1] | 0.65 | 460 | Method 2 |
| 101 | 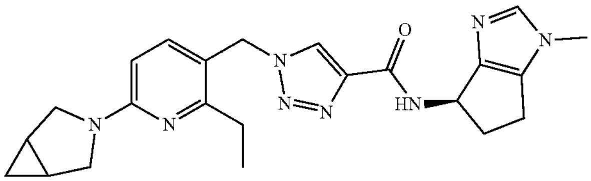 [SMILES: CCc1nc(N2CC3CC3C2)ccc1Cn1cc(C(=O)N[C@@H]2CCc3c2ncn3C)nn1] | 0.99 | 433 | Method 1 |

-continued
| Example | Structure | $t_R$ | Mass spectrum (ESI+): m/z $[M + H]^+$ | LC Method |
|---|---|---|---|---|
| 102 | 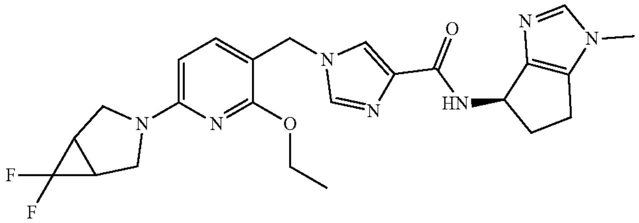 [SMILES: CCOc1nc(N2CC3C(C2)C3(F)F)ccc1Cn1cnc(C(=O)N[C@@H]2CCc3c2ncn3C)c1] | 0.83 | 484 | Method 2 |
| 103 | 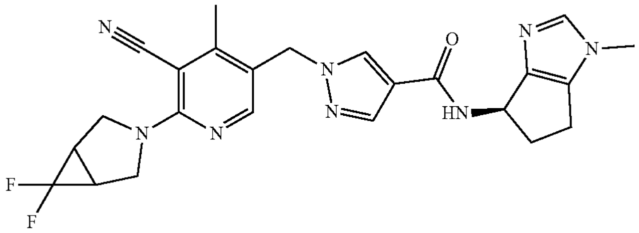 | 0.88 | 479 | Method 1 |
| 104 | 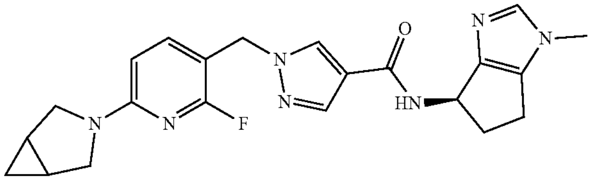 [SMILES: Cn1cnc2c1CC[C@H]2NC(=O)c1cnn(Cc2ccc(N3CC4CC4C3)nc2F)c1] | 0.78 | 422 | Method 2 |
| 105 | 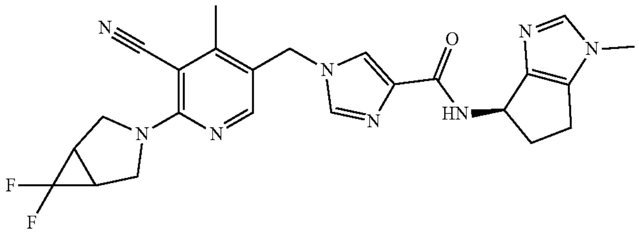 [SMILES: Cc1c(Cn2cnc(C(=O)N[C@@H]3CCc4c3ncn4C)c2)cnc(N2CC3C(C2)C3(F)F)c1C#N] | 0.87 | 479 | Method 1 |
| 106 | 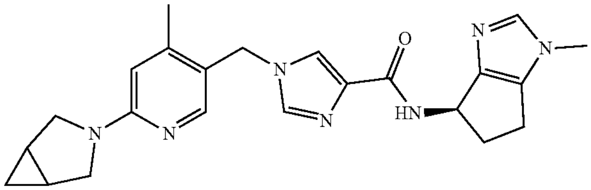 [SMILES: Cc1cc(N2CC3CC3C2)ncc1Cn1cnc(C(=O)N[C@@H]2CCc3c2ncn3C)c1] | 0.87 | 418 | Method 1 |
| 107 | 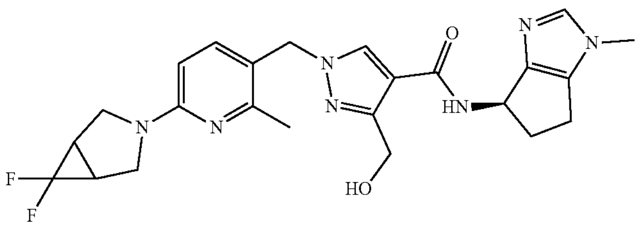 [SMILES: Cc1nc(N2CC3C(C2)C3(F)F)ccc1Cn1cc(C(=O)N[C@@H]2CCc3c2ncn3C)c(CO)n1] | 0.88 | 484 | Method 1 |
| 108 | 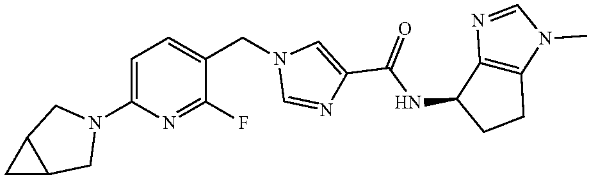 | 0.74 | 422 | Method 2 |

-continued
| Example | Structure | $t_R$ | Mass spectrum (ESI+): m/z $[M + H]^+$ | LC Method |
|---|---|---|---|---|
| 109 | 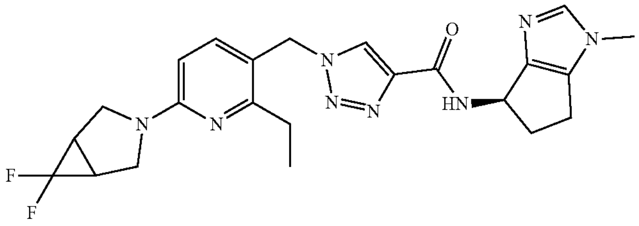 [SMILES: CCc1nc(N2CC3C(C2)C3(F)F)ccc1Cn1cc(C(=O)N[C@@H]2CCc3c2ncn3C)nn1] | 0.96 | 469 | Method 1 |
| 110 | 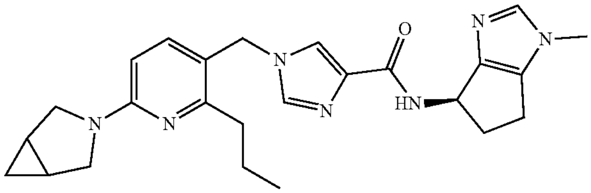 [SMILES: CCCc1nc(N2CC3CC3C2)ccc1Cn1cnc(C(=O)N[C@@H]2CCc3c2ncn3C)c1] | 0.62 | 446 | Method 2 |
| 111 | 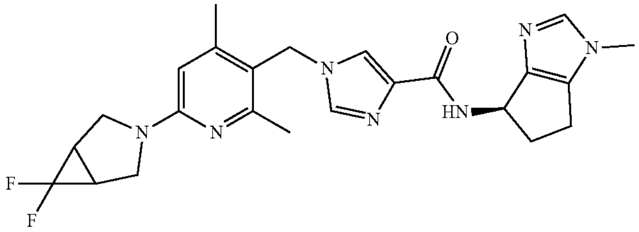 [SMILES: Cc1cc(N2CC3C(C2)C3(F)F)nc(C)c1Cn1cnc(C(=O)N[C@@H]2CCc3c2ncn3C)c1] | 0.62 | 468 | Method 2 |
| 112 | 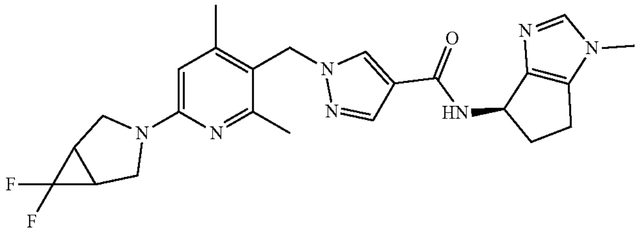 [SMILES: Cc1cc(N2CC3C(C2)C3(F)F)nc(C)c1Cn1cc(C(=O)N[C@@H]2CCc3c2ncn3C)cn1] | 0.64 | 468 | Method 2 |
| 113 | 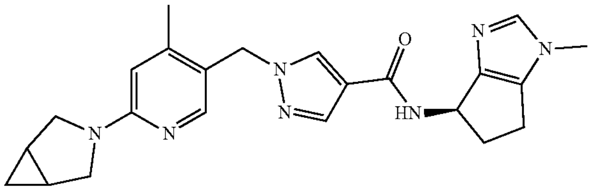 [SMILES: Cc1cc(N2CC3CC3C2)ncc1Cn1cc(C(=O)N[C@@H]2CCc3c2ncn3C)cn1] | 0.63 | 418 | Method 4 |
| 114 | 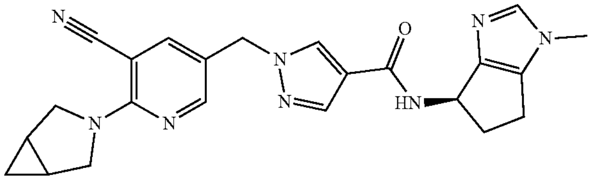 [SMILES: Cn1cnc2c1CC[C@H]2NC(=O)c1cnn(Cc2cnc(N3CC4CC4C3)c(C#N)c2)c1] | 0.75 | 429 | Method 2 |
| 115 | 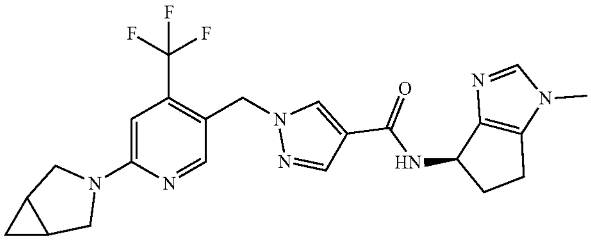 [SMILES: Cn1cnc2c1CC[C@H]2NC(=O)c1cnn(Cc2cnc(N3CC4CC4C3)cc2C(F)(F)F)c1] | 0.93 | 472 | Method 1 |

-continued
| Example | Structure | $t_R$ | Mass spectrum (ESI+): m/z $[M + H]^+$ | LC Method |
|---|---|---|---|---|
| 116 | 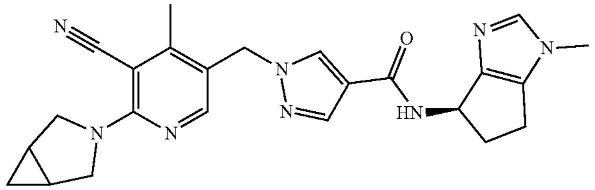 [SMILES: Cc1c(Cn2cc(C(=O)N[C@@H]3CCc4c3ncn4C)cn2)cnc(N2CC3CC3C2)c1C#N] | 0.76 | 443 | Method 2 |
| 117 | 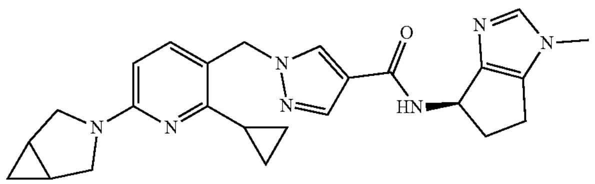 [SMILES: Cn1cnc2c1CC[C@H]2NC(=O)c1cnn(Cc2ccc(N3CC4CC4C3)nc2C2CC2)c1] | 0.66 | 444 | Method 2 |
| 118 | 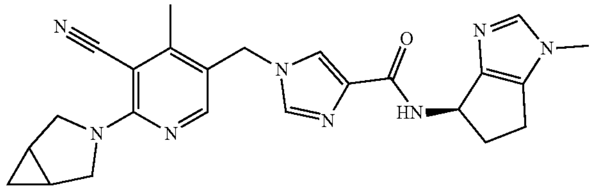 [SMILES: Cc1c(Cn2cnc(C(=O)N[C@@H]3CCc4c3ncn4C)c2)cnc(N2CC3CC3C2)c1C#N] | 0.74 | 443 | Method 2 |
| 119 | 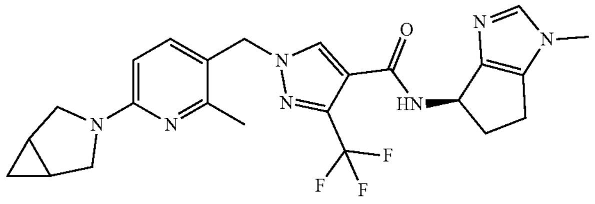 [SMILES: Cc1nc(N2CC3CC3C2)ccc1Cn1cc(C(=O)N[C@@H]2CCc3c2ncn3C)c(C(F)(F)F)n1] | 0.81 | 486 | Method 5 |
| 120 | 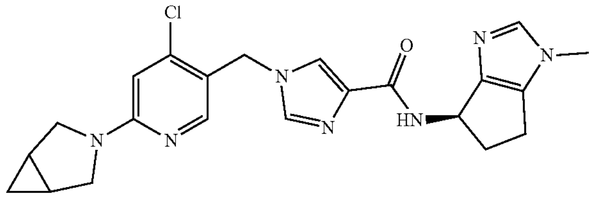 [SMILES: Cn1cnc2c1CC[C@H]2NC(=O)c1cn(Cc2cnc(N3CC4CC4C3)cc2Cl)cn1] | 0.89 | 438 | Method 1 |
| 121 | 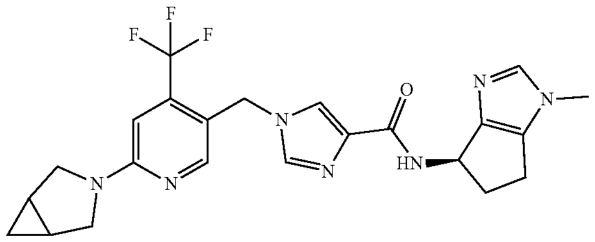 [SMILES: Cn1cnc2c1CC[C@H]2NC(=O)c1cn(Cc2cnc(N3CC4CC4C3)cc2C(F)(F)F)cn1] | 0.93 | 472 | Method 1 |
| 122 | 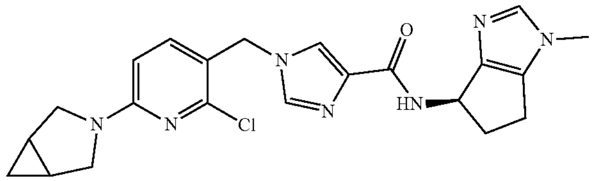 | 0.77 | 437 | Method 2 |

-continued
| Example | Structure | $t_R$ | Mass spectrum (ESI+): m/z $[M + H]^+$ | LC Method |
|---|---|---|---|---|
| 123 | 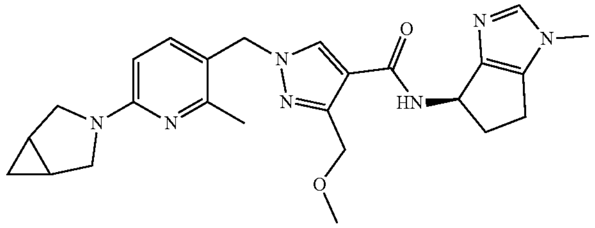 [SMILES: COCc1nn(Cc2ccc(N3CC4CC4C3)nc2C)cc1C(=O)N[C@@H]1CCc2c1ncn2C] | 0.94 | 462 | Method 1 |
| 124 | 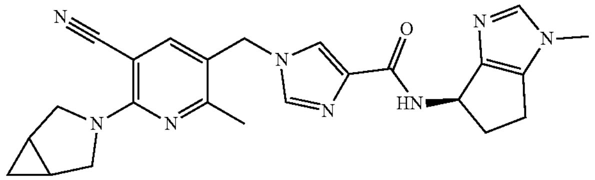 [SMILES: Cc1nc(N2CC3CC3C2)c(C#N)cc1Cn1cnc(C(=O)N[C@@H]2CCc3c2ncn3C)c1] | 0.77 | 443 | Method 2 |
| 125 | 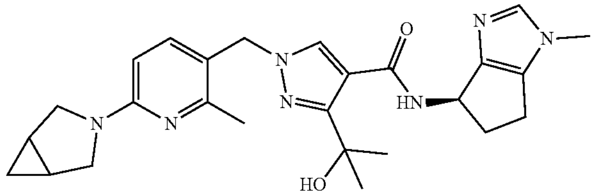 [SMILES: Cc1nc(N2CC3CC3C2)ccc1Cn1cc(C(=O)N[C@@H]2CCc3c2ncn3C)c(C(C)(C)O)n1] | 0.97 | 476 | Method 1 |
| 126 | 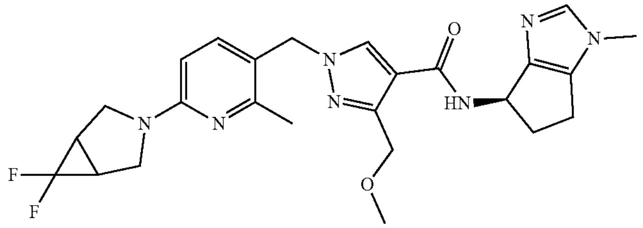 [SMILES: COCc1nn(Cc2ccc(N3CC4C(C3)C4(F)F)nc2C)cc1C(=O)N[C@@H]1CCc2c1ncn2C] | 0.93 | 498 | Method 1 |
| 127 | 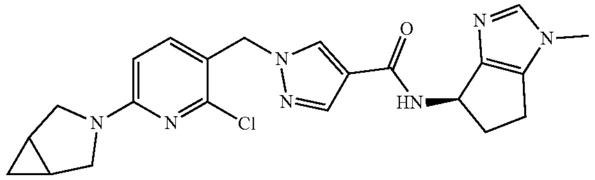 | 0.92 | 438 | Method 1 |
| 128 | 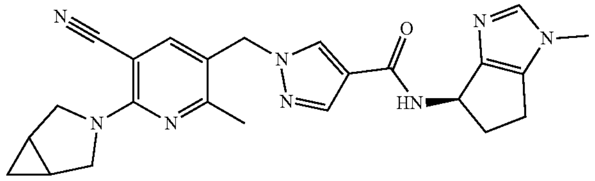 [SMILES: Cc1nc(N2CC3CC3C2)c(C#N)cc1Cn1cc(C(=O)N[C@@H]2CCc3c2ncn3C)cn1] | 0.93 | 443 | Method 1 |
| 129 | 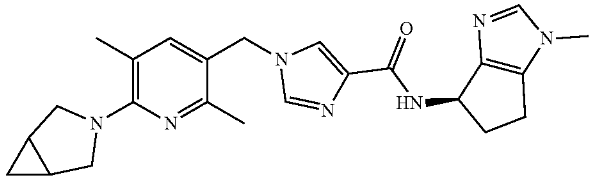 [SMILES: Cc1cc(Cn2cnc(C(=O)N[C@@H]3CCc4c3ncn4C)c2)c(C)nc1N1CC2CC2C1] | 0.97 | 432 | Method 1 |

-continued
| Example | Structure | $t_R$ | Mass spectrum (ESI+): m/z $[M + H]^+$ | LC Method |
|---|---|---|---|---|
| 130 | 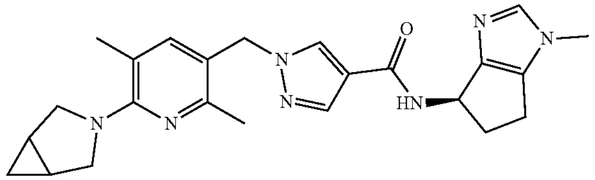 [SMILES: Cc1cc(Cn2cc(C(=O)N[C@@H]3CCc4c3ncn4C)cn2)c(C)nc1N1CC2CC2C1] | 0.97 | 432 | Method 1 |
| 131 | 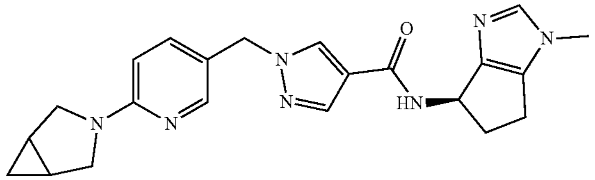 [SMILES: Cn1cnc2c1CC[C@H]2NC(=O)c1cnn(Cc2ccc(N3CC4CC4C3)nc2)c1] | 0.59 | 404 | Method 5 |
| 132 | 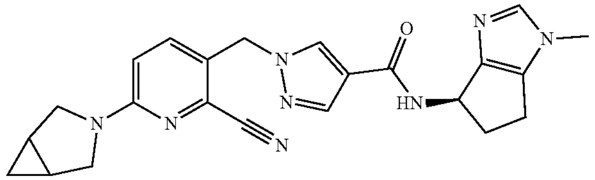 [SMILES: Cn1cnc2c1CC[C@H]2NC(=O)c1cnn(Cc2ccc(N3CC4CC4C3)nc2C#N)c1] | 0.67 | 429 | Method 5 |
| 133 | 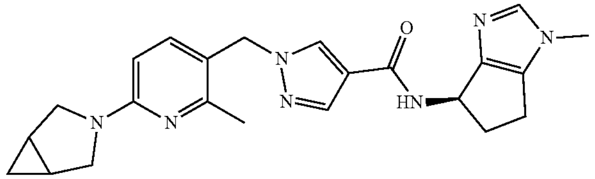 [SMILES: Cc1nc(N2CC3CC3C2)ccc1Cn1cc(C(=O)N[C@@H]2CCc3c2ncn3C)cn1] | 0.89 | 418 | Method 1 |
| 134 | 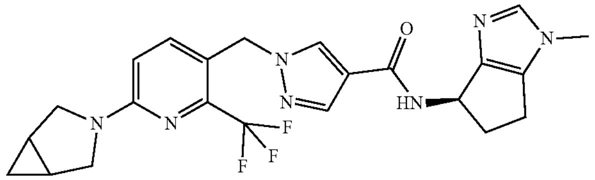 [SMILES: Cn1cnc2c1CC[C@H]2NC(=O)c1cnn(Cc2ccc(N3CC4CC4C3)nc2C(F)(F)F)c1] | 0.80 | 472 | Method 5 |
| 135 | 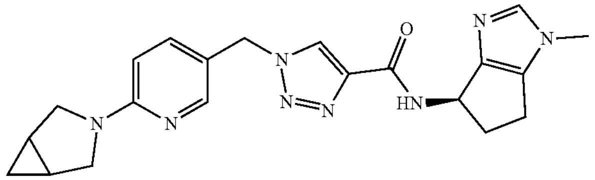 [SMILES: Cn1cnc2c1CC[C@H]2NC(=O)c1cn(Cc2ccc(N3CC4CC4C3)nc2)nn1] | 0.61 | 405 | Method 5 |
| 136 | 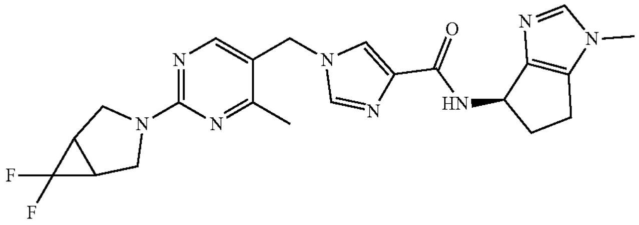 [SMILES: Cc1nc(N2CC3C(C2)C3(F)F)ncc1Cn1cnc(C(=O)N[C@@H]2CCc3c2ncn3C)c1] | 0.69 | 455 | Method 2 |

-continued
| Example | Structure | $t_R$ | Mass spectrum (ESI+): m/z $[M + H]^+$ | LC Method |
| --- | --- | --- | --- | --- |
| 137 | 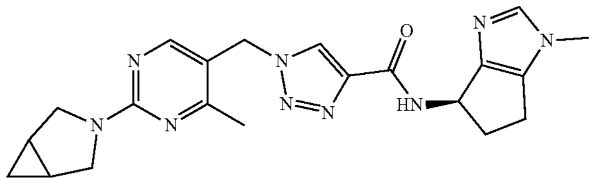 [SMILES: Cc1nc(N2CC3CC3C2)ncc1Cn1cc(C(=O)N[C@@H]2CCc3c2ncn3C)nn1] | 0.86 | 420 | Method 1 |
| 138 | 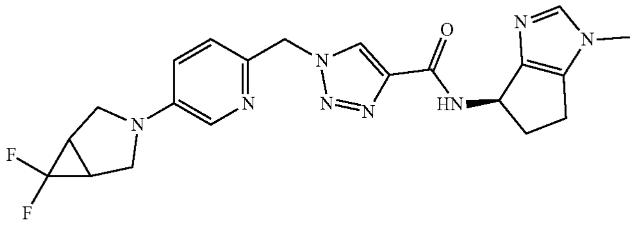 [SMILES: Cn1cnc2c1CC[C@H]2NC(=O)c1cn(Cc2ccc(N3CC4C(C3)C4(F)F)cn2)nn1] | 0.64 | 441 | Method 2 |
| 139 | 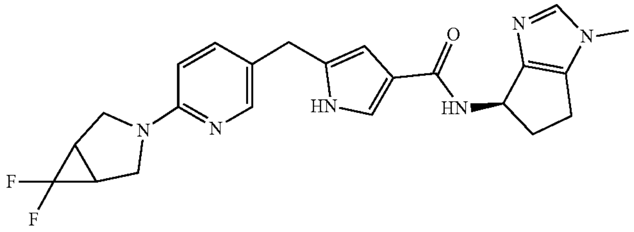 [SMILES: Cn1cnc2c1CC[C@H]2NC(=O)c1c[nH]c(Cc2ccc(N3CC4C(C3)C4(F)F)nc2)c1] | 0.60 | 439 | Method 2 |
| 140 | 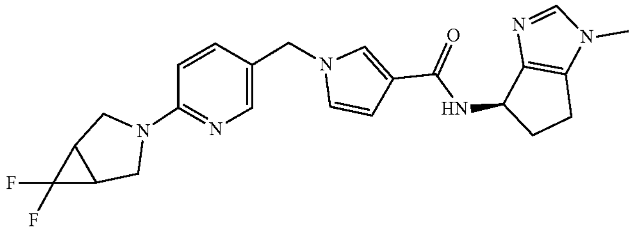 [SMILES: Cn1cnc2c1CC[C@H]2NC(=O)c1ccn(Cc2ccc(N3CC4C(C3)C4(F)F)nc2)c1] | 0.60 | 439 | Method 2 |
| 141 | 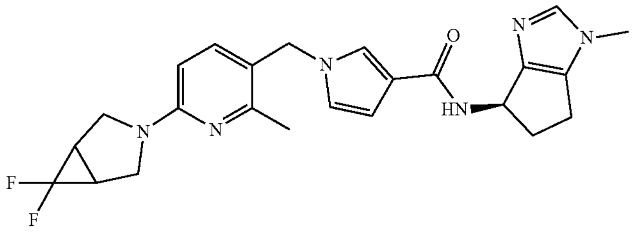 [SMILES: Cc1nc(N2CC3C(C2)C3(F)F)ccc1Cn1ccc(C(=O)N[C@@H]2CCc3c2ncn3C)c1] | 0.62 | 453 | Method 2 |
| 142 | 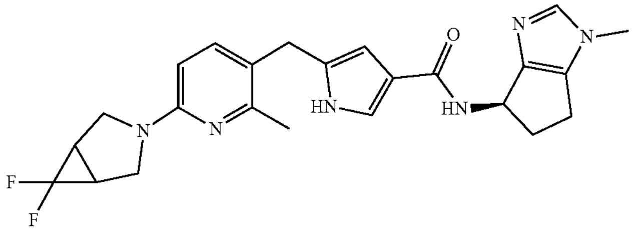 [SMILES: Cc1nc(N2CC3C(C2)C3(F)F)ccc1Cc1cc(C(=O)N[C@@H]2CCc3c2ncn3C)c[nH]1] | 0.63 | 453 | Method 2 |

-continued
| Example | Structure | $t_R$ | Mass spectrum (ESI+): m/z $[M + H]^+$ | LC Method |
|---|---|---|---|---|
| 143 | 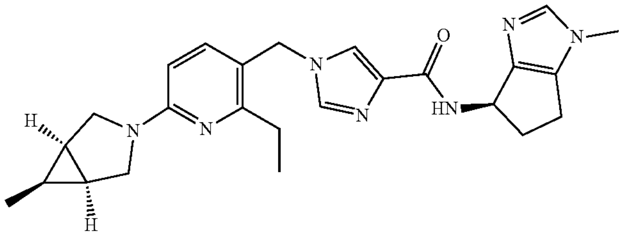 | 1.02 | 446 | Method 1 |
| 144 | 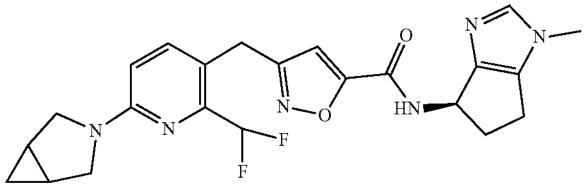 [SMILES: Cn1cnc2c1CC[C@H]2NC(=O)c1cc(Cc2ccc(N3CC4CC4C3)nc2C(F)F)no1] | 1.01 | 455 | Method 1 |
| 145 | 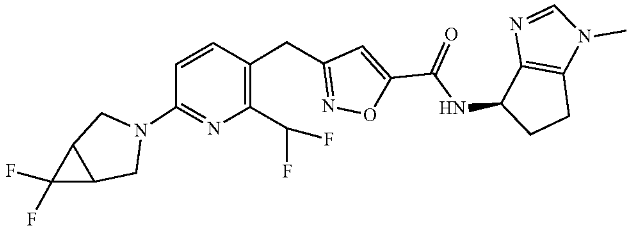 [SMILES: Cn1cnc2c1CC[C@H]2NC(=O)c1cc(Cc2ccc(N3CC4C(C3)C4(F)F)nc2C(F)F)no1] | 0.98 | 491 | Method 1 |
| 146 | 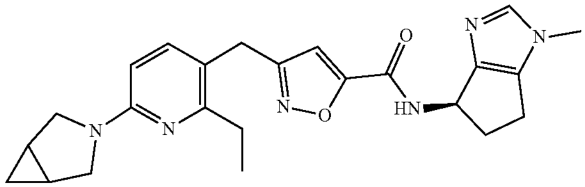 [SMILES: CCc1nc(N2CC3CC3C2)ccc1Cc1cc(C(=O)N[C@@H]2CCc3c2ncn3C)on1] | 1.03 | 433 | Method 1 |
| 147 | 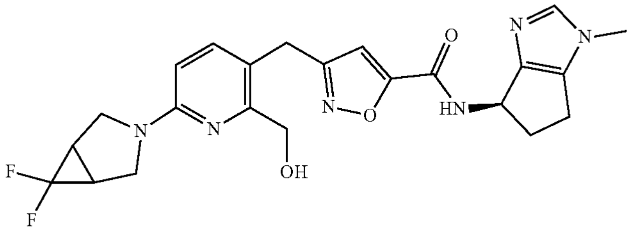 [SMILES: Cn1cnc2c1CC[C@H]2NC(=O)c1cc(Cc2ccc(N3CC4C(C3)C4(F)F)nc2CO)no1] | 0.88 | 471 | Method 1 |
| 148 | 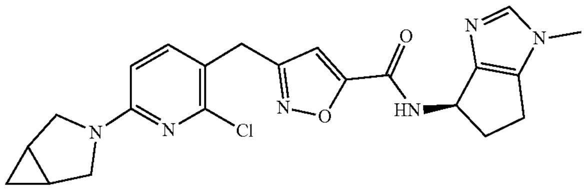 [SMILES: Cn1cnc2c1CC[C@H]2NC(=O)c1cc(Cc2ccc(N3CC4CC4C3)nc2Cl)no1] | 0.98 | 439 | Method 1 |
| 149 | 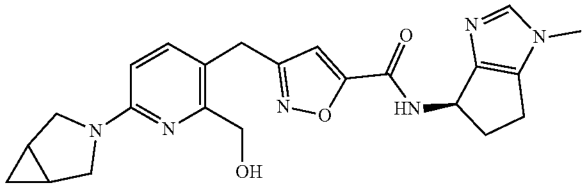 [SMILES: Cn1cnc2c1CC[C@H]2NC(=O)c1cc(Cc2ccc(N3CC4CC4C3)nc2CO)no1] | 0.91 | 435 | Method 1 |

-continued
| Example | Structure | $t_R$ | Mass spectrum (ESI+): m/z $[M + H]^+$ | LC Method |
|---|---|---|---|---|
| 150 | 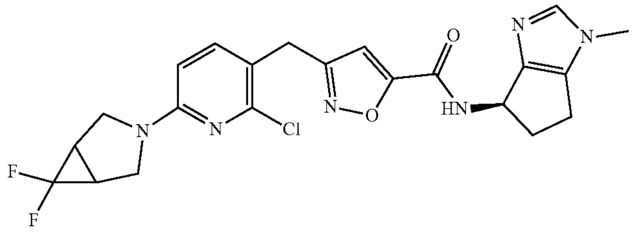 [SMILES: Cn1cnc2c1CC[C@H]2NC(=O)c1cc(Cc2ccc(N3CC4C(C3)C4(F)F)nc2Cl)no1] | 0.96 | 475 | Method 1 |
| 151 | 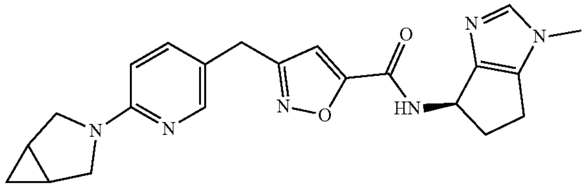 [SMILES: Cn1cnc2c1CC[C@H]2NC(=O)c1cc(Cc2ccc(N3CC4CC4C3)nc2)no1] | 0.88 | 405 | Method 1 |
| 152 | 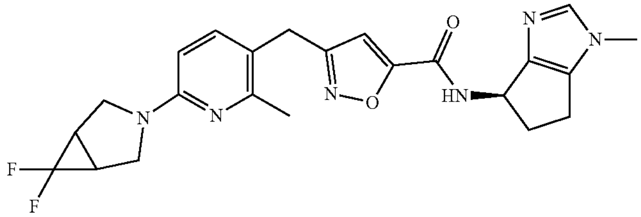 [SMILES: Cc1nc(N2CC3C(C2)C3(F)F)ccc1Cc1cc(C(=O)N[C@@H]2CCc3c2ncn3C)on1] | 0.94 | 455 | Method 1 |
| 153 | 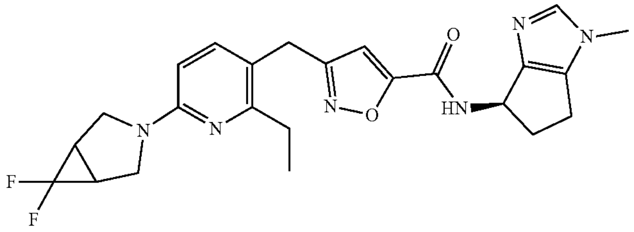 [SMILES: CCc1nc(N2CC3C(C2)C3(F)F)ccc1Cc1cc(C(=O)N[C@@H]2CCc3c2ncn3C)on1] | 1.06 | 469 | Method 1 |
| 154 | 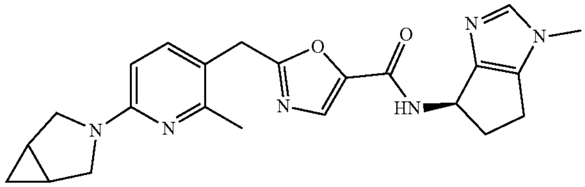 [SMILES: Cc1nc(N2CC3CC3C2)ccc1Cc1ncc(C(=O)N[C@@H]2CCc3c2ncn3C)o1] | 0.91 | 419 | Method 1 |
| 155 | 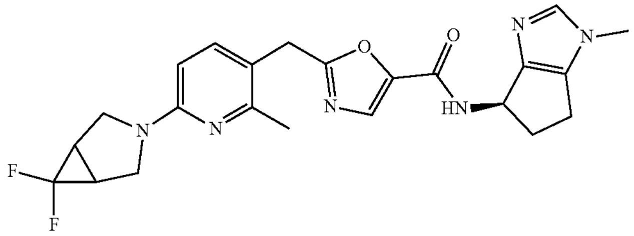 [SMILES: Cc1nc(N2CC3C(C2)C3(F)F)ccc1Cc1ncc(C(=O)N[C@@H]2CCc3c2ncn3C)o1] | 0.89 | 455 | Method 1 |
| 156 | 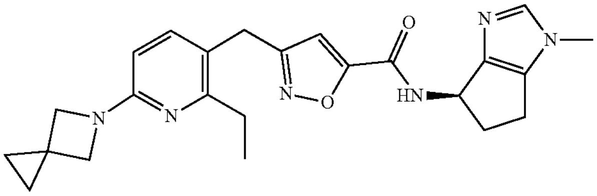 [SMILES: CCc1nc(N2CC3(CC3)C2)ccc1Cc1cc(C(=O)N[C@@H]2CCc3c2ncn3C)on1] | 0.97 | 433 | Method 1 |

-continued
| Example | Structure | $t_R$ | Mass spectrum (ESI+): m/z $[M + H]^+$ | LC Method |
|---|---|---|---|---|
| 157 | 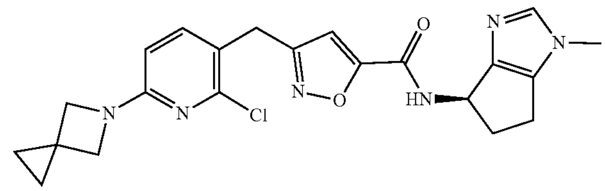 [SMILES: Cn1cnc2c1CC[C@H]2NC(=O)c1cc(Cc2ccc(N3CC4(CC4)C3)nc2Cl)no1] | 0.95 | 439 | Method 1 |
| 158 | 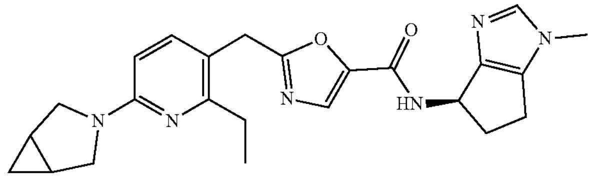 [SMILES: CCc1nc(N2CC3CC3C2)ccc1Cc1ncc(C(=O)N[C@@H]2CCc3c2ncn3C)o1] | 0.78 | 433 | Method 5 |
| 159 | 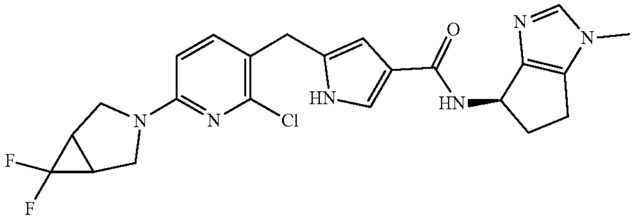 [SMILES: Cn1cnc2c1CC[C@H]2NC(=O)c1c[nH]c(Cc2ccc(N3CC4C(C3)C4(F)F)nc2Cl)c1] | 0.82 | 473 | Method 2 |
| 160 | 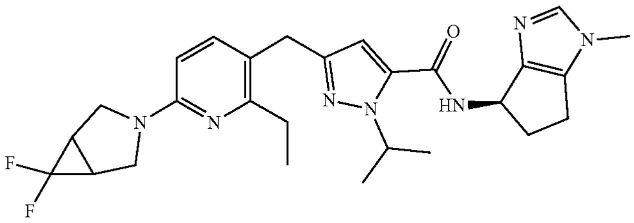 [SMILES: CCc1nc(N2CC3C(C2)C3(F)F)ccc1Cc1cc(C(=O)N[C@@H]2CCc3c2ncn3C)n(C(C)C)n1] | 1.07 | 510 | Method 1 |
| 161 | 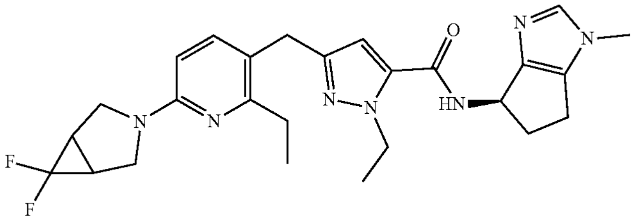 [SMILES: CCc1nc(N2CC3C(C2)C3(F)F)ccc1Cc1cc(C(=O)N[C@@H]2CCc3c2ncn3C)n(CC)n1] | 1.03 | 496 | Method 1 |
| 162 | 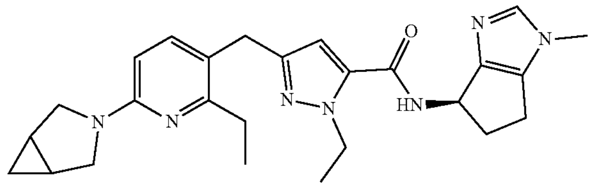 [SMILES: CCc1nc(N2CC3CC3C2)ccc1Cc1cc(C(=O)N[C@@H]2CCc3c2ncn3C)n(CC)n1] | 1.05 | 460 | Method 1 |
| 163 | 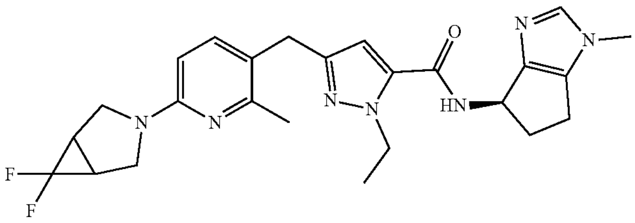 [SMILES: CCn1nc(Cc2ccc(N3CC4C(C3)C4(F)F)nc2C)cc1C(=O)N[C@@H]1CCc2c1ncn2C] | 0.97 | 482 | Method 1 |

-continued
| Example | Structure | $t_R$ | Mass spectrum (ESI+): m/z $[M + H]^+$ | LC Method |
|---|---|---|---|---|
| 164 | 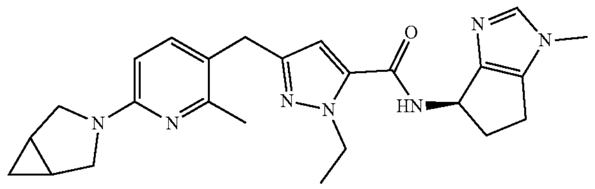 [SMILES: CCn1nc(Cc2ccc(N3CC4CC4C3)nc2C)cc1C(=O)N[C@@H]1CCc2c1ncn2C] | 0.98 | 446 | Method 1 |
| 165 | 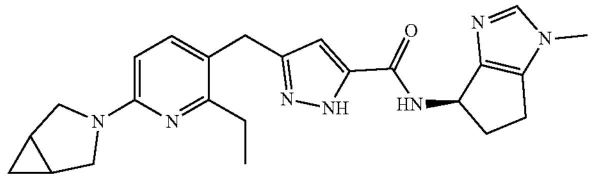 [SMILES: CCc1nc(N2CC3CC3C2)ccc1Cc1cc(C(=O)N[C@@H]2CCc3c2ncn3C)[nH]n1] | 0.96 | 432 | Method 1 |
| 166 | 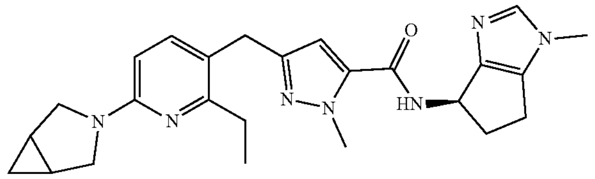 [SMILES: CCc1nc(N2CC3CC3C2)ccc1Cc1cc(C(=O)N[C@@H]2CCc3c2ncn3C)n(C)n1] | 0.66 | 446 | Method 2 |
| 167 | 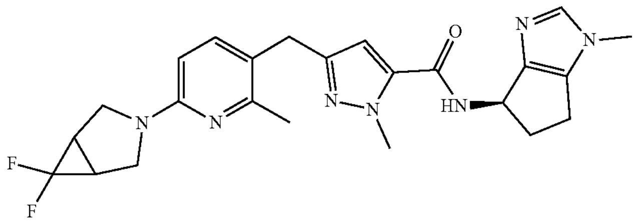 [SMILES: Cc1nc(N2CC3C(C2)C3(F)F)ccc1Cc1cc(C(=O)N[C@@H]2CCc3c2ncn3C)n(C)n1] | 0.94 | 468 | Method 1 |
| 168 | 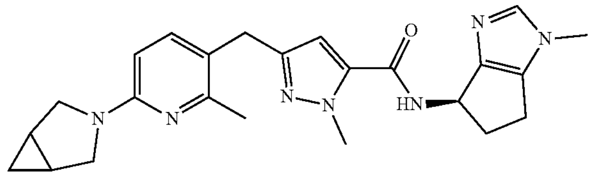 [SMILES: Cc1nc(N2CC3CC3C2)ccc1Cc1cc(C(=O)N[C@@H]2CCc3c2ncn3C)n(C)n1] | 0.96 | 432 | Method 1 |
| 169 | 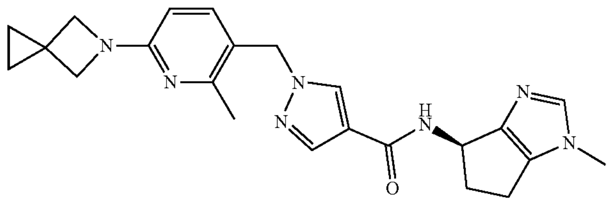 [SMILES: Cc1nc(N2CC3(CC3)C2)ccc1Cn1cc(C(=O)N[C@@H]2CCc3c2ncn3C)cn1] | 0.62 | 418 | Method 5 |
| 170 | 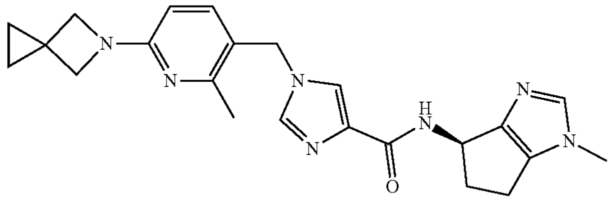 [SMILES: Cc1nc(N2CC3(CC3)C2)ccc1Cn1cnc(C(=O)N[C@@H]2CCc3c2ncn3C)c1] | 0.62 | 418 | Method 5 |

-continued
| Example | Structure | $t_R$ | Mass spectrum (ESI+): m/z $[M + H]^+$ | LC Method |
|---|---|---|---|---|
| 171 | 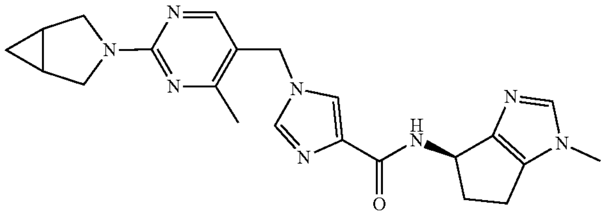 [SMILES: Cc1nc(N2CC3CC3C2)ncc1Cn1cnc(C(=O)N[C@@H]2CCc3c2ncn3C)c1] | 0.59 | 419 | Method 5 |
| 172 | 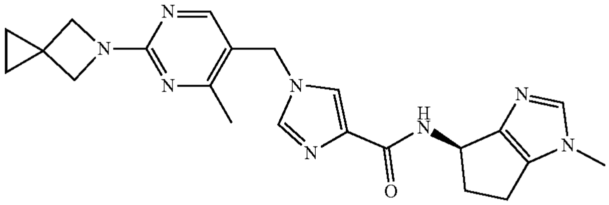 [SMILES: Cc1nc(N2CC3(CC3)C2)ncc1Cn1cnc(C(=O)N[C@@H]2CCc3c2ncn3C)c1] | 0.55 | 419 | Method 5 |
| 173 | 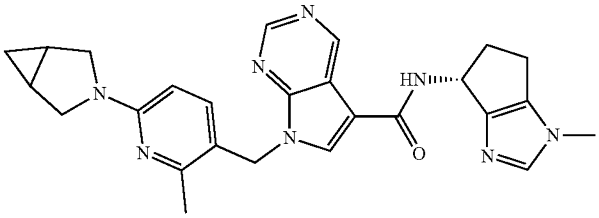 [SMILES: Cc1nc(N2CC3CC3C2)ccc1Cn1cc(C(=O)N[C@@H]2CCc3c2ncn3C)c2cncnc21] | 0.71 | 469 | Method 5 |
| 174 | 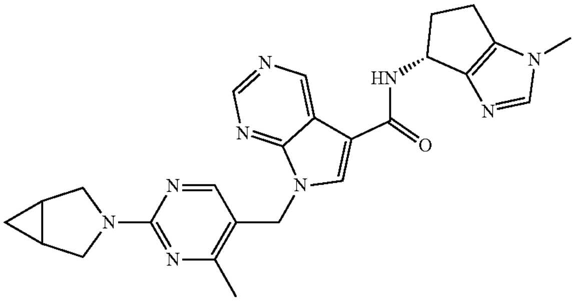 [SMILES: Cc1nc(N2CC3CC3C2)ncc1Cn1cc(C(=O)N[C@@H]2CCc3c2ncn3C)c2cncnc21] | 0.64 | 470 | Method 5 |
| 175 | 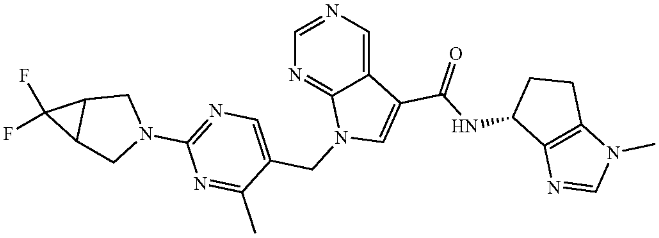 [SMILES: Cc1nc(N2CC3C(C2)C3(F)F)ncc1Cn1cc(C(=O)N[C@@H]2CCc3c2ncn3C)c2cncnc21] | 0.63 | 506 | Method 5 |
| 176 | 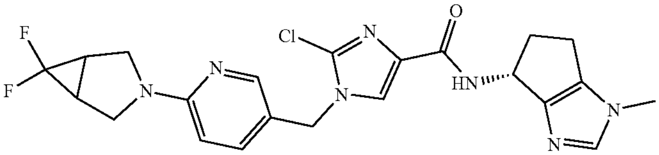 [SMILES: Cn1cnc2c1CC[C@H]2NC(=O)c1cn(Cc2ccc(N3CC4C(C3)C4(F)F)nc2)c(Cl)n1] | 0.66 | 474 | Method 5 |

-continued
| Example | Structure | $t_R$ | Mass spectrum (ESI+): m/z $[M + H]^+$ | LC Method |
|---|---|---|---|---|
| 177 | 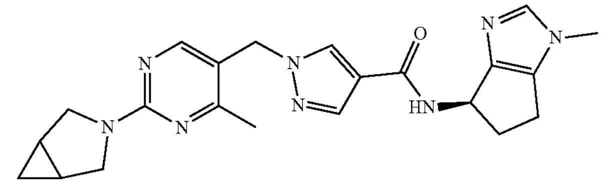 [SMILES: Cc1nc(N2CC3CC3C2)ncc1Cn1cc(C(=O)N[C@@H]2CCc3c2ncn3C)cn1] | 0.59 | 419 | Method 5 |
| 178 | 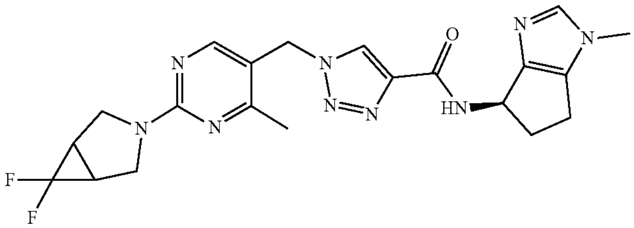 [SMILES: Cc1nc(N2CC3C(C2)C3(F)F)ncc1Cn1cc(C(=O)N[C@@H]2CCc3c2ncn3C)nn1] | 0.62 | 456 | Method 5 |
| 179 | 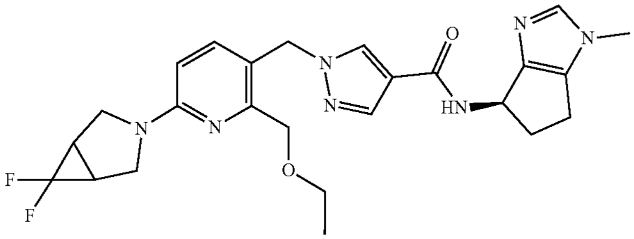 [SMILES: CCOCc1nc(N2CC3C(C2)C3(F)F)ccc1Cn1cc(C(=O)N[C@@H]2CCc3c2ncn3C)cn1] | 0.92 | 498 | Method 1 |
| 180 | 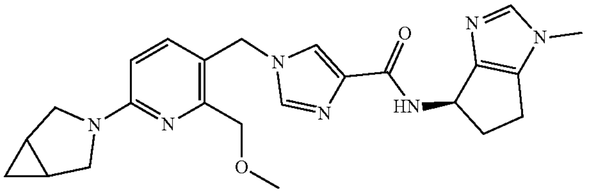 [SMILES: COCc1nc(N2CC3CC3C2)ccc1Cn1cnc(C(=O)N[C@@H]2CCc3c2ncn3C)c1] | 0.90 | 448 | Method 1 |
| 181 | 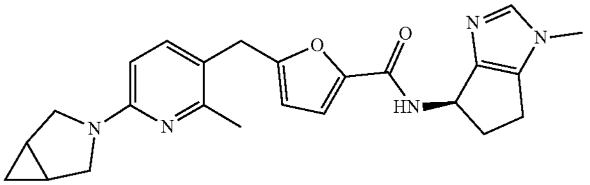 [SMILES: Cc1nc(N2CC3CC3C2)ccc1Cc1ccc(C(=O)N[C@@H]2CCc3c2ncn3C)o1] | 0.63 | 418 | Method 2 |
| 182 | 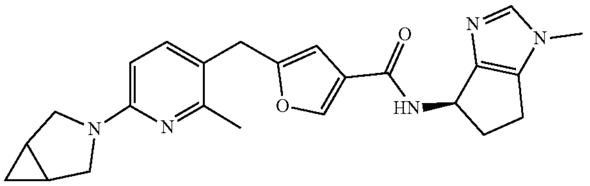 [SMILES: Cc1nc(N2CC3CC3C2)ccc1Cc1cc(C(=O)N[C@@H]2CCc3c2ncn3C)co1] | 0.63 | 418 | Method 2 |
| 183 | 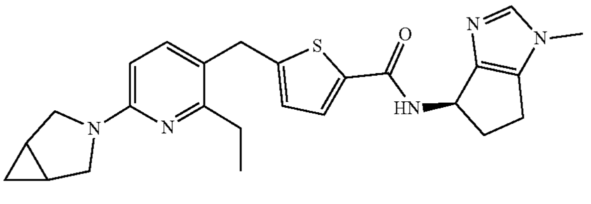 [SMILES: CCc1nc(N2CC3CC3C2)ccc1Cc1ccc(C(=O)N[C@@H]2CCc3c2ncn3C)s1] | 1.08 | 448 | Method 1 |

-continued
| Example | Structure | $t_R$ | Mass spectrum (ESI+): m/z $[M + H]^+$ | LC Method |
|---|---|---|---|---|
| 184 | 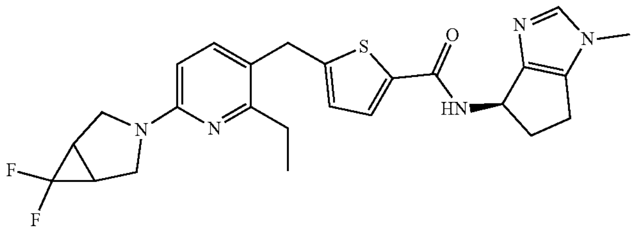 [SMILES: CCc1nc(N2CC3C(C2)C3(F)F)ccc1Cc1ccc(C(=O)N[C@@H]2CCc3c2ncn3C)s1] | 0.69 | 484 | Method 2 |
| 185 | 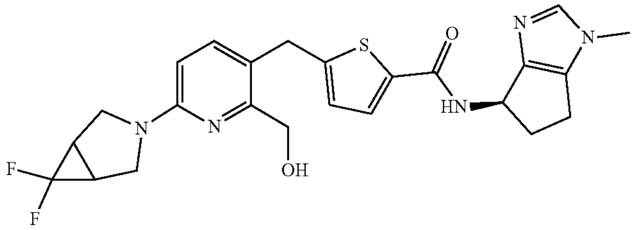 [SMILES: Cn1cnc2c1CC[C@H]2NC(=O)c1ccc(Cc2ccc(N3CC4C(C3)C4(F)F)nc2CO)s1] | 0.65 | 486 | Method 2 |
| 186 | 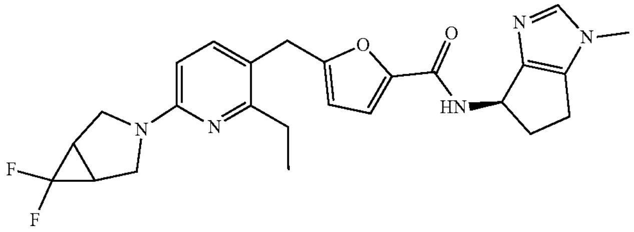 [SMILES: CCc1nc(N2CC3C(C2)C3(F)F)ccc1Cc1ccc(C(=O)N[C@@H]2CCc3c2ncn3C)o1] | 0.67 | 468 | Method 2 |
| 187 | 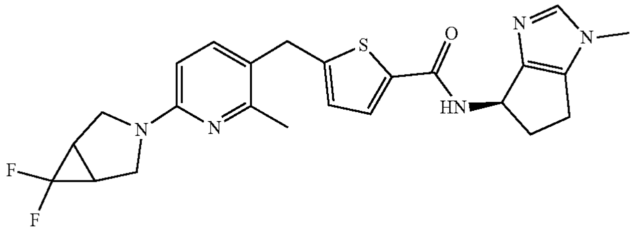 | 0.67 | 470 | Method 2 |
| 188 | 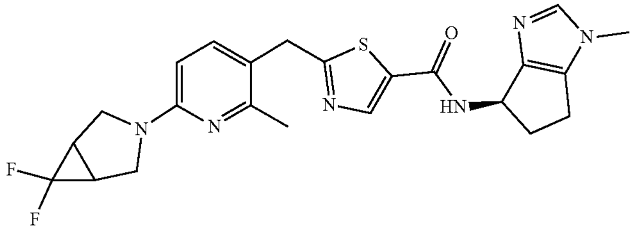 [SMILES: Cc1nc(N2CC3C(C2)C3(F)F)ccc1Cc1ccc(C(=O)N[C@@H]2CCc3c2ncn3C)o1] | 0.66 | 471 | Method 2 |
| 189 | 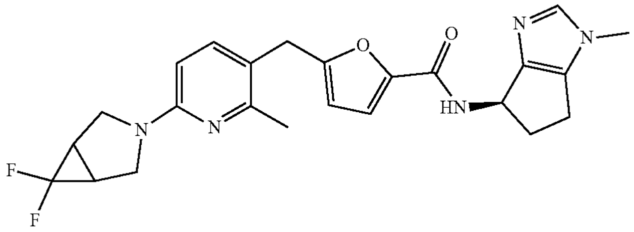 | 0.66 | 454 | Method 2 |

-continued
| Example | Structure | $t_R$ | Mass spectrum (ESI+): m/z $[M + H]^+$ | LC Method |
| --- | --- | --- | --- | --- |
| 190 | 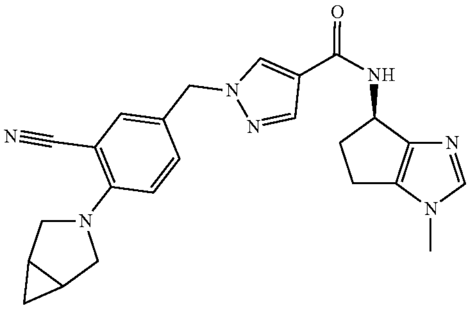 [SMILES: Cn1cnc2c1CC[C@H]2NC(=O)c1cnn(Cc2ccc(N3CC4CC4C3)c(C#N)c2)c1] | 0.80 | 428 | Method 2 |
| 191 | 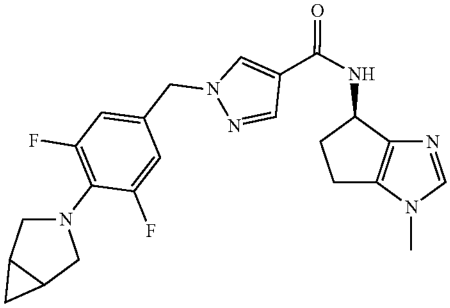 [SMILES: Cn1cnc2c1CC[C@H]2NC(=O)c1cnn(Cc2cc(F)c(N3CC4CC4C3)c(F)c2)c1] | 0.98 | 439 | Method 5 |
| 192 | 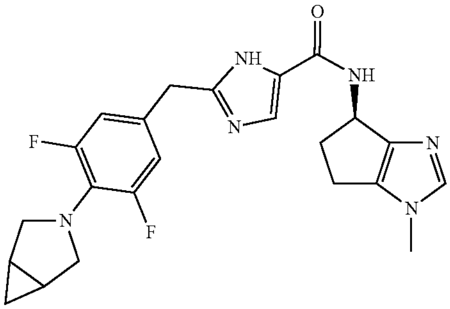 [SMILES: Cn1cnc2c1CC[C@H]2NC(=O)c1cnc(Cc2cc(F)c(N3CC4CC4C3)c(F)c2)[nH]1] | 0.98 | 439 | Method 1 |
| 193 | 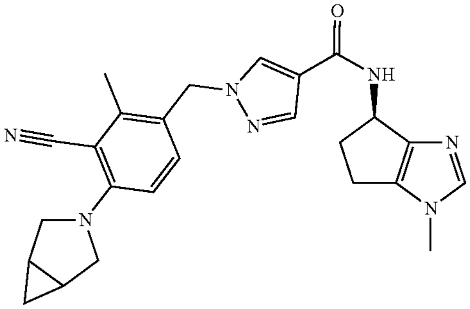 [SMILES: Cc1c(Cn2cc(C(=O)N[C@@H]3CCc4c3ncn4C)cn2)ccc(N2CC3CC3C2)c1C#N] | 0.92 | 442 | Method 1 |
| 194 | 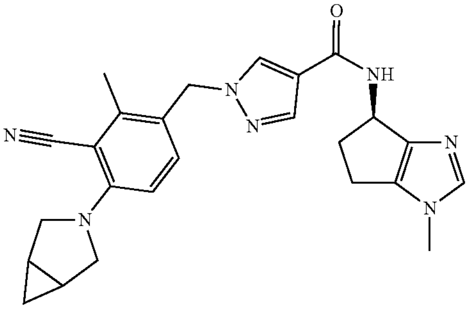 [SMILES: Cc1c(Cn2cc(C(=O)N[C@@H]3CCc4c3ncn4C)cn2)ccc(N2CC3CC3C2)c1C#N] | 0.92 | 442 | Method 1 |

-continued
| Ex-ample | Structure | $t_R$ | Mass spectrum (ESI+): m/z $[M + H]^+$ | LC Method |
|---|---|---|---|---|
| 195 | 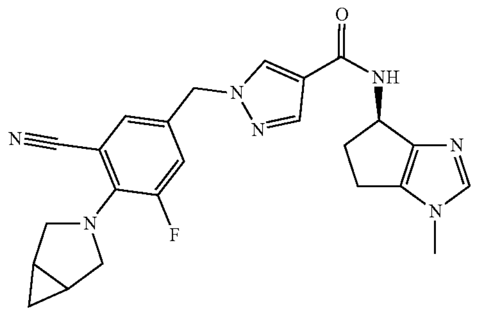 [SMILES: Cn1cnc2c1CC[C@H]2NC(=O)c1cnn(Cc2cc(F)c(N3CC4CC4C3)c(C#N)c2)c1] | 0.83 | 446 | Method 2 |
| 196 | 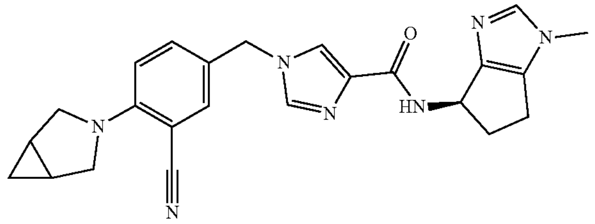 [SMILES: Cn1cnc2c1CC[C@H]2NC(=O)c1cn(Cc2ccc(N3CC4CC4C3)c(C#N)c2)cn1] | 0.78 | 428 | Method 2 |
| 197 | 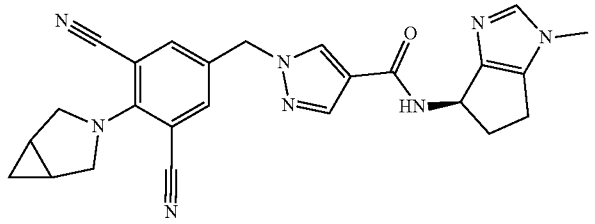 [SMILES: Cn1cnc2c1CC[C@H]2NC(=O)c1cnn(Cc2cc(C#N)c(N3CC4CC4C3)c(C#N)c2)c1] | 0.79 | 453 | Method 2 |
| 198 | 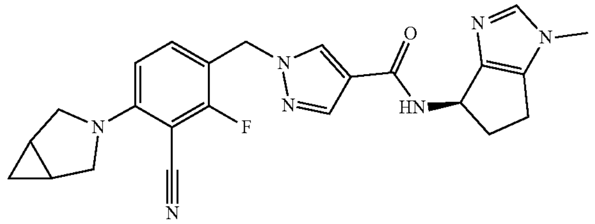 | 0.59 | 446 | Method 5 |
| 199 | 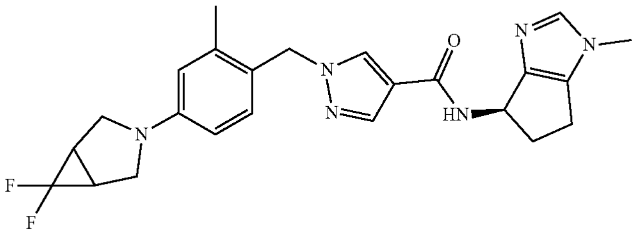 [SMILES: Cc1cc(N2CC3C(C2)C3(F)F)ccc1Cn1cc(C(=O)N[C@@H]2CCc3c2ncn3C)cn1] | 0.84 | 453 | Method 2 |
| 200 | 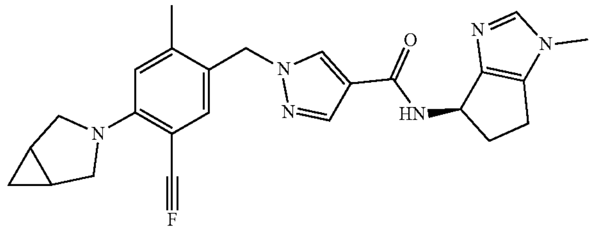 | 0.72 | 442 | Method 5 |

-continued
| Example | Structure | $t_R$ | Mass spectrum (ESI+): m/z $[M + H]^+$ | LC Method |
|---|---|---|---|---|
| 201 | 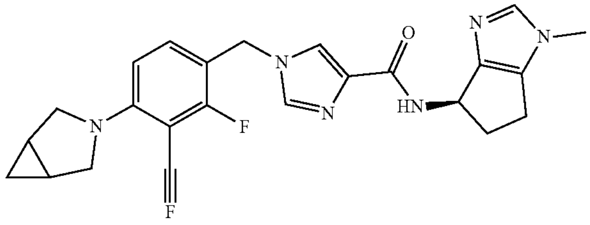 | 0.67 | 446 | Method 4 |
| 202 | 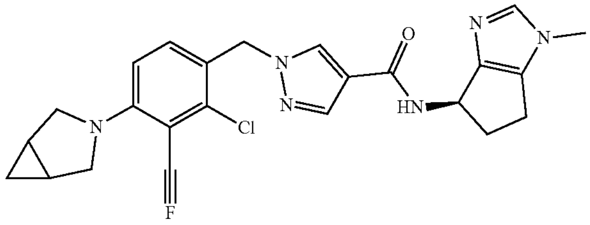 | 0.83 | 462 | Method 2 |
| 203 | 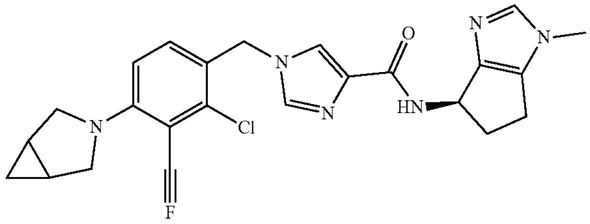 | 0.54 | 462 | Method 5 |
| 204 | 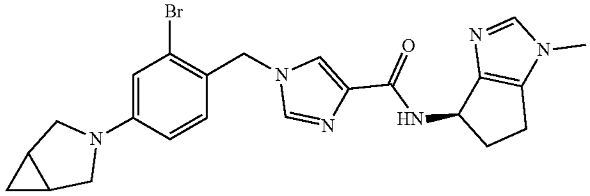 [SMILES: Cn1cnc2c1CC[C@H]2NC(=O)c1cn(Cc2ccc(N3CC4CC4C3)cc2Br)cn1] | 0.82 | 481/483 (Br) | Method 2 |
| 205 | 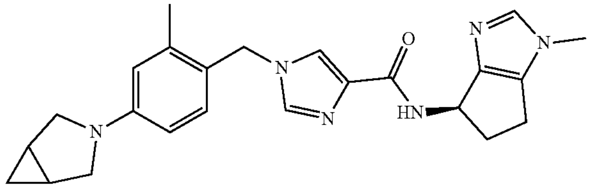 [SMILES: Cc1cc(N2CC3CC3C2)ccc1Cn1cnc(C(=O)N[C@@H]2CCc3c2ncn3C)c1] | 0.78 | 417 | Method 2 |
| 206 | 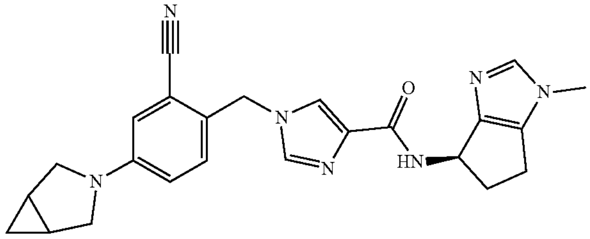 [SMILES: Cn1cnc2c1CC[C@H]2NC(=O)c1cn(Cc2ccc(N3CC4CC4C3)cc2CN)cn1] | 0.69 | 428 | Method 1 |

-continued
| Example | Structure | $t_R$ | Mass spectrum (ESI+): m/z $[M + H]^+$ | LC Method |
|---|---|---|---|---|
| 207 | 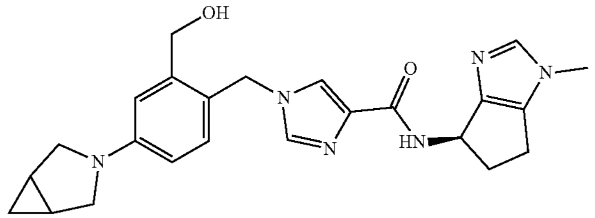 [SMILES: Cn1cnc2c1CC[C@H]2NC(=O)c1cn(Cc2ccc(N3CC4CC4C3)cc2CO)cn1] | 0.87 | 433 | Method 1 |
| 208 | 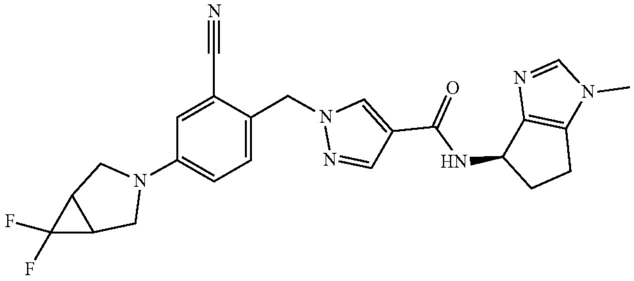 [SMILES: Cn1cnc2c1CC[C@H]2NC(=O)c1cnn(Cc2ccc(N3CC4C(C3)C4(F)F)cc2C#N)c1] | 0.90 | 464 | Method 1 |
| 209 | 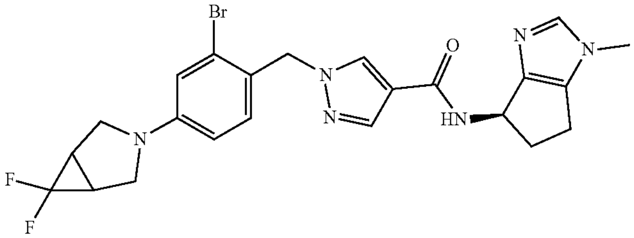 [SMILES: Cn1cnc2c1CC[C@H]2NC(=O)c1cnn(Cc2ccc(N3CC4C(C3)C4(F)F)cc2Br)c1] | 0.95 | 517/519 (Br) | Method 1 |
| 210 | 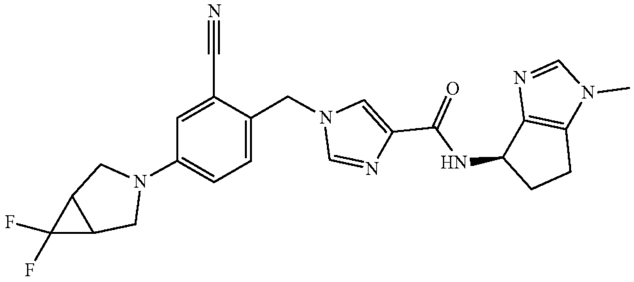 [SMILES: Cn1cnc2c1CC[C@H]2NC(=O)c1cn(Cc2ccc(N3CC4C(C3)C4(F)F)cc2C#N)cn1] | 0.65 | 464 | Method 5 |
| 211 | 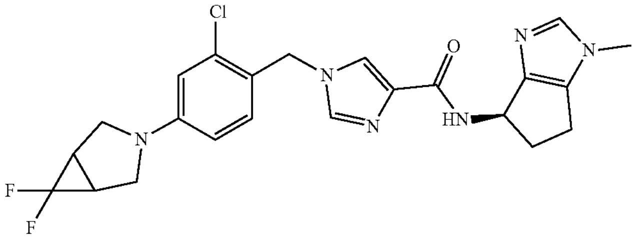 | 0.74 | 473 | Method 5 |
| 212 | 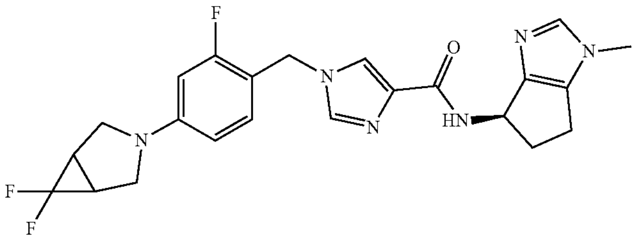 [SMILES: Cn1cnc2c1CC[C@H]2NC(=O)c1cn(Cc2ccc(N3CC4C(C3)C4(F)F)cc2F)cn1] | 0.70 | 457 | Method 4 |

-continued

| Example | Structure | $t_R$ | Mass spectrum (ESI+): m/z $[M + H]^+$ | LC Method |
|---|---|---|---|---|
| 213 | 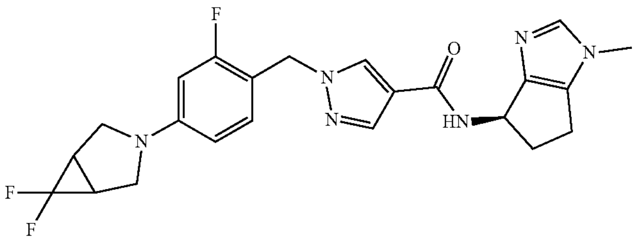 [SMILES: Cn1cnc2c1CC[C@H]2NC(=O)c1cnn(Cc2ccc(N3CC4C(C3)C4(F)F)cc2F)c1] | 0.81 | 457 | Method 2 |

| Example | Name | Name of Starting Material |
|---|---|---|
| 2 | 1-[(6-{6,6-Difluoro-3-azabicyclo[3.1.0]hexan-3-yl}-2-(methoxymethyl)pyridin-3-yl)methyl]-N-[(4R)-1-methyl-1H,4H,5H,6H-cyclopenta[d]-imidazol-4-yl]-1H-pyrazole-4-carboxamide | 1-[(6-{6,6-Difluoro-3-azabicyclo[3.1.0]hexan-3-yl}-2-(methoxymethyl)pyridin-3-yl)methyl]-1H-pyrazole-4-carboxylic acid |
| 3 | 1-[(5-{3-Azabicyclo[3.1.0]hexan-3-yl}pyridin-2-yl)methyl]-N-[(4R)-1-methyl-1H,4H,5H,6H-cyclopenta[d]imidazol-4-yl]-1H-imidazole-4-carboxamide | 1-[(5-{3-Azabicyclo[3.1.0]hexan-3-yl}pyridin-2-yl)methyl]-1H-imidazole-4-carboxylic acid |
| 4 | 1-[(6-{5-Azaspiro[2.3]hexan-5-yl}-2-(difluoromethyl)-pyridin-3-yl)methyl]-N-[(4R)-1-methyl-1H,4H,5H,6H-cyclopenta[d]imidazol-4-yl]-1H-1,2,3-triazole-4-carboxamide | 1-[(6-{5-Azaspiro[2.3]hexan-5-yl}-2-(difluoromethyl)pyridin-3-yl)methyl]-1H-1,2,3-triazole-4-carboxylic acid |
| 5 | 1-[(6-{5-Azaspiro[2.3]hexan-5-yl}-2-chloropyridin-3-yl)methyl]-N-[(4R)-1-methyl-1H,4H,5H,6H-cyclopenta[d]imidazol-4-yl]-1H-1,2,3-triazole-4-carboxamide | 1-[(6-{5-Azaspiro[2.3]hexan-5-yl}-2-chloropyridin-3-yl)methyl]-1H-1,2,3-triazole-4-carboxylic acid |
| 6 | 1-[(6-{5-Azaspiro[2.3]hexan-5-yl}-2-bromopyridin-3-yl)methyl]-N-[(4R)-1-methyl-1H,4H,5H,6H-cyclopenta[d]imidazol-4-yl]-1H-1,2,3-triazole-4-carboxamide | 1-[(6-{5-Azaspiro[2.3]hexan-5-yl}-2-bromopyridin-3-yl)methyl]-1H-1,2,3-triazole-4-carboxylic acid |
| 7 | 1-[(6-{6,6-Difluoro-3-azabicyclo[3.1.0]hexan-3-yl}-2-fluoropyridin-3-yl)methyl]-N-[(4R)-1-methyl-1H,4H,5H,6H-cyclopenta[d]imidazol-4-yl]-1H-imidazole-4-carboxamide | 1-[(6-{6,6-Difluoro-3-azabicyclo-[3.1.0]hexan-3-yl}-2-fluoropyridin-3-yl)-methyl]-1H-imidazole-4-carboxylic acid |
| 8 | 1-[(5-{3-Azabicyclo[3.1.0]hexan-3-yl}pyridin-2-yl)methyl]-N-[(4R)-1-methyl-1H,4H,5H,6H-cyclopenta[d]imidazol-4-yl]-1H-1,2,3-triazole-4-carboxamide | 1-[(5-{3-Azabicyclo[3.1.0]hexan-3-yl}pyridin-2-yl)methyl]-1H-1,2,3-triazole-4-carboxylic acid |
| 9 | 1-[(5-{3-Azabicyclo[3.1.0]hexan-3-yl}pyridin-2-yl)methyl]-N-[(4R)-1-methyl-1H,4H,5H,6H-cyclopenta[d]imidazol-4-yl]-1H-pyrazole-4-carboxamide | 1-[(5-{3-Azabicyclo[3.1.0]hexan-3-yl}pyridin-2-yl)methyl]-1H-pyrazole-4-carboxylic acid |
| 10 | 1-[(6-{5-Azaspiro[2.3]hexan-5-yl}-2-fluoropyridin-3-yl)methyl]-N-[(4R)-1-methyl-1H,4H,5H,6H-cyclopenta[d]imidazol-4-yl]-1H-1,2,3-triazole-4-carboxamide | 1-[(6-{5-Azaspiro[2.3]hexan-5-yl}-2-fluoropyridin-3-yl)methyl]-1H-1,2,3-triazole-4-carboxylic acid |
| 11 | 1-[(6-{5-Azaspiro[2.3]hexan-5-yl}-2-fluoropyridin-3-yl)methyl]-N-[(4R)-1-methyl-1H,4H,5H,6H-cyclopenta[d]imidazol-4-yl]-1H-imidazole-4-carboxamide | 1-[(6-{5-Azaspiro[2.3]hexan-5-yl}-2-fluoropyridin-3-yl)methyl]-1H-imidazole-4-carboxylic acid |
| 12 | 1-[(6-{5-Azaspiro[2.3]hexan-5-yl}-2-fluoropyridin-3-yl)methyl]-N-[(4R)-1-methyl-1H,4H,5H,6H-cyclopenta[d]imidazol-4-yl]-1H-pyrazole-4-carboxamide | 1-[(6-{5-Azaspiro[2.3]hexan-5-yl}-2-fluoropyridin-3-yl)methyl]-1H-pyrazole-4-carboxylic acid |
| 13 | 1-[(6-{5-Azaspiro[2.3]hexan-5-yl}-2-bromopyridin-3-yl)methyl]-N-[(4R)-1-methyl-1H,4H,5H,6H-cyclopenta[d]imidazol-4-yl]-1H-pyrazole-4-carboxamide | 1-[(6-{5-Azaspiro[2.3]hexan-5-yl}-2-bromopyridin-3-yl)methyl]-1H-pyrazole-4-carboxylic acid |
| 14 | 1-[(2-Bromo-6-{6,6-difluoro-3-azabicyclo-[3.1.0]hexan-3-yl}pyridin-3-yl)methyl]-N-[(4R)-1-methyl-1H,4H,5H,6H-cyclopenta[d]imidazol-4-yl]-1H-1,2,3-triazole-4-carboxamide | 1-[(2-Bromo-6-{6,6-difluoro-3-azabicyclo[3.1.0]hexan-3-yl}pyridin-3-yl)methyl]-1H-1,2,3-triazole-4-carboxylic acid |
| 15 | 1-[(2-Bromo-6-{6,6-difluoro-3-azabicyclo-[3.1.0]hexan-3-yl}pyridin-3-yl)methyl]-N-[(4R)-1-methyl-1H,4H,5H,6H-cyclopenta[d]imidazol-4-yl]-1H-pyrazole-4-carboxamide | 1-[(2-Bromo-6-{6,6-difluoro-3-aza-bicyclo[3.1.0]hexan-3-yl}pyridin-3-yl)-methyl]-1H-pyrazole-4-carboxylic acid |
| 16 | 1-[(6-{5-Azaspiro[2.3]hexan-5-yl}-2-bromopyridin-3-yl)methyl]-N-[(4R)-1-methyl-1H,4H,5H,6H-cyclopenta[d]imidazol-4-yl]-1H-imidazole-4-carboxamide | 1-[(6-{5-Azaspiro[2.3]hexan-5-yl}-2-bromopyridin-3-yl)methyl]-1H-imidazole-4-carboxylic acid |
| 17 | 1-[(6-{3-Azabicyclo[3.1.0]hexan-3-yl}-2-fluoropyridin-3-yl)methyl]-N-[(4R)-1-methyl-1H,4H,5H,6H-cyclopenta[d]imidazol-4-yl]-1H-1,2,3-triazole-4-carboxamide | 1-[(6-{3-Azabicyclo[3.1.0]hexan-3-yl}-2-fluoropyridin-3-yl)methyl]-1H-1,2,3-triazole-4-carboxylic acid |
| 18 | 1-[(6-{6,6-Difluoro-3-azabicyclo[3.1.0]hexan-3-yl}-2-fluoropyridin-3-yl)methyl]-N-[(4R)-1-methyl-1H,4H,5H,6H-cyclopenta[d]imidazol-4-yl]-1H-pyrazole-4-carboxamide | 1-[(6-{6,6-Difluoro-3-azabicyclo-[3.1.0]hexan-3-yl}-2-fluoropyridin-3-yl)-methyl]-1H-pyrazole-4-carboxylic acid |
| 19 | 1-[(5-{5-Azaspiro[2.3]hexan-5-yl}pyridin-2-yl)-methyl]-N-[(4R)-1-methyl-1H,4H,5H,6H-cyclopenta[d]imidazol-4-yl]-1H-pyrazole-4-carboxamide | 1-[(5-{5-Azaspiro[2.3]hexan-5-yl}pyridin-2-yl)methyl]-1H-pyrazole-4-carboxylic acid |

-continued

| Example | Name | Name of Starting Material |
|---|---|---|
| 20 | 1-[(6-{5-Azaspiro[2.3]hexan-5-yl}-2-ethylpyridin-3-yl)methyl]-N-[(4R)-1-methyl-1H,4H,5H,6H-cyclopenta[d]imidazol-4-yl]-1H-1,2,3-triazole-4-carboxamide | 1-[(6-{5-Azaspiro[2.3]hexan-5-yl}-2-ethylpyridin-3-yl)methyl]-1H-1,2,3-triazole-4-carboxylic acid |
| 21 | 1-[(6-{5-Azaspiro[2.3]hexan-5-yl}-2-chloropyridin-3-yl)methyl]-N-[(4R)-1-methyl-1H,4H,5H,6H-cyclopenta[d]imidazol-4-yl]-1H-imidazole-4-carboxamide | 1-[(6-{5-Azaspiro[2.3]hexan-5-yl}-2-chloropyridin-3-yl)methyl]-1H-imidazole-4-carboxylic acid |
| 22 | 1-[(6-{3-Azabicyclo[3.1.0]hexan-3-yl}-2-ethylpyridin-3-yl)methyl]-N-[(4R)-1-methyl-1H,4H,5H,6H-cyclopenta[d]imidazol-4-yl]-1H-pyrazole-4-carboxamide | 1-[(6-{3-Azabicyclo[3.1.0]hexan-3-yl}-2-ethylpyridin-3-yl)methyl]-1H-pyrazole-4-carboxylic acid |
| 23 | 1-[(6-{3-Azabicyclo[3.1.0]hexan-3-yl}-2-methylpyridin-3-yl)methyl]-N-[(4R)-1-methyl-1H,4H,5H,6H-cyclopenta[d]imidazol-4-yl]-1H-imidazole-4-carboxamide | 1-[(6-{3-Azabicyclo[3.1.0]hexan-3-yl}-2-methylpyridin-3-yl)methyl]-1H-imidazole-4-carboxylic acid |
| 24 | 1-[(6-{6,6-Difluoro-3-azabicyclo[3.1.0]hexan-3-yl}-2-methylpyridin-3-yl)methyl]-N-[(4R)-1-methyl-1H,4H,5H,6H-cyclopenta[d]imidazol-4-yl]-1H-imidazole-4-carboxamide | 1-[(6-{6,6-Difluoro-3-azabicyclo-[3.1.0]hexan-3-yl}-2-methylpyridin-3-yl)-methyl]-1H-imidazole-4-carboxylic acid |
| 25 | 1-[(6-{6,6-Difluoro-3-azabicyclo[3.1.0]hexan-3-yl}-2-fluoropyridin-3-yl)methyl]-N-[(4R)-1-methyl-1H,4H,5H,6H-cyclopenta[d]imidazol-4-yl]-1H-1,2,3-triazole-4-carboxamide | 1-[(6-{6,6-Difluoro-3-azabicyclo[3.1.0]hexan-3-yl}-2-fluoropyridin-3-yl)methyl]-1H-1,2,3-triazole-4-carboxylic acid |
| 26 | 1-[(6-{5-Azaspiro[2.3]hexan-5-yl}pyridin-3-yl)-methyl]-N-[(4R)-1-methyl-1H,4H,5H,6H-cyclopenta[d]imidazol-4-yl]-1H-1,2,3-triazole-4-carboxamide | 1-[(6-{5-Azaspiro[2.3]hexan-5-yl}pyridin-3-yl)methyl]-1H-1,2,3-triazole-4-carboxylic acid |
| 27 | 1-[(6-{6,6-Difluoro-3-azabicyclo[3.1.0]hexan-3-yl}-2-methylpyridin-3-yl)methyl]-N-[(4R)-1-methyl-1H,4H,5H,6H-cyclopenta[d]imidazol-4-yl]-1H-1,2,3-triazole-4-carboxamide | 1-[(6-{6,6-Difluoro-3-azabicyclo[3.1.0]hexan-3-yl}-2-methylpyridin-3-yl)methyl]-1H-1,2,3-triazole-4-carboxylic acid |
| 28 | 1-[(2-Bromo-6-{6,6-difluoro-3-azabicyclo-[3.1.0]hexan-3-yl}pyridin-3-yl)methyl]-N-[(4R)-1-methyl-1H,4H,5H,6H-cyclopenta[d]imidazol-4-yl]-1H-imidazole-4-carboxamide | 1-[(2-Bromo-6-{6,6-difluoro-3-aza-bicyclo[3.1.0]hexan-3-yl}pyridin-3-yl)-methyl]-1H-imidazole-4-carboxylic acid |
| 29 | 1-[(2-{3-Azabicyclo[3.1.0]hexan-3-yl}-4-(difluoromethyl)-pyrimidin-5-yl)methyl]-N-[(4R)-1-methyl-1H,4H,5H,6H-cyclopenta[d]imidazol-4-yl]-1H-imidazole-4-carboxamide | 1-[(2-{3-Azabicyclo[3.1.0]hexan-3-yl}-4-(difluoromethyl)pyrimidin-5-yl)methyl]-1H-imidazole-4-carboxylic acid |
| 30 | 1-[(6-{3-Azabicyclo[3.1.0]hexan-3-yl}-2-(difluoromethyl)-pyridin-3-yl)methyl]-N-[(4R)-1-methyl-1H,4H,5H,6H-cyclopenta[d]imidazol-4-yl]-1H-1,2,3-triazole-4-carboxamide | 1-[(6-{3-Azabicyclo[3.1.0]hexan-3-yl}-2-(difluoromethyl)pyridin-3-yl)methyl]-1H-1,2,3-triazole-4-carboxylic acid |
| 31 | 1-[(6-{3-Azabicyclo[3.1.0]hexan-3-yl}-2-propylpyridin-3-yl)methyl]-N-[(4R)-1-methyl-1H,4H,5H,6H-cyclopenta[d]imidazol-4-yl]-1H-imidazole-4-carboxamide | 1-[(6-{3-Azabicyclo[3.1.0]hexan-3-yl}-2-propylpyridin-3-yl)methyl]-1H-imidazole-4-carboxylic acid |
| 32 | 1-[(6-{3-Azabicyclo[3.1.0]hexan-3-yl}-2-chloropyridin-3-yl)methyl]-N-[(4R)-1-methyl-1H,4H,5H,6H-cyclopenta-[d]imidazol-4-yl]-1H-1,2,3-triazole-4-carboxamide | 1-[(6-{3-Azabicyclo[3.1.0]hexan-3-yl}-2-chloropyridin-3-yl)methyl]-1H-1,2,3-triazole-4-carboxylic acid |
| 33 | 1-[(6-{6,6-Difluoro-3-azabicyclo[3.1.0]hexan-3-yl}pyridin-3-yl)methyl]-N-[(4R)-1-methyl-1H,4H,5H,6H-cyclopenta[d]imidazol-4-yl]-1H-1,2,3-triazole-4-carboxamide | 1-[(6-{6,6-Difluoro-3-azabicyclo-[3.10]hexan-3-yl}pyridin-3-yl)methyl]-1H-1,2,3-triazole-4-carboxylic acid |
| 34 | 1-[(6-{3-Azabicyclo[3.1.0]hexan-3-yl}-2-bromopyridin-3-yl)methyl]-N-[(4R)-1-methyl-1H,4H,5H,6H-cyclopenta-[d]imidazol-4-yl]-1H-1,2,3-triazole-4-carboxamide | 1-[(6-{3-Azabicyclo[3.1.0]hexan-3-yl}-2-bromopyridin-3-yl)methyl]-1H-1,2,3-triazole-4-carboxylic acid |
| 35 | 1-[(5-{3-Azabicyclo[3.1.0]hexan-3-yl}-6-cyanopyridin-2-yl)methyl]-N-[(4R)-1-methyl-1H,4H,5H,6H-cyclopenta[d]imidazol-4-yl]-1H-pyrazole-4-carboxamide | 1-[(5-{3-Azabicyclo[3.1.0]hexan-3-yl}-6-cyanopyridin-2-yl)methyl]-1H-pyrazole-4-carboxylic acid |
| 36 | 1-[(6-{6,6-Difluoro-3-azabicyclo[3.1.0]hexan-3-yl}-2-ethylpyridin-3-yl)methyl]-N-[(4R)-1-methyl-1H,4H,5H,6H-cyclopenta[d]imidazol-4-yl]-1H-pyrazole-4-carboxamide | 1-[(6-{6,6-Difluoro-3-azabicyclo-[3.1.0]hexan-3-yl}-2-ethylpyridin-3-yl)-methyl]-1H-pyrazole-4-carboxylic acid |
| 37 | 1-[(6-{5-Azaspiro[2.3]hexan-5-yl}-2-ethylpyridin-3-yl)methyl]-N-[(4R)-1-methyl-1H,4H,5H,6H-cyclopenta[d]imidazol-4-yl]-1H-imidazole-4-carboxamide | 1-[(6-{5-Azaspiro[2.3]hexan-5-yl}-2-ethylpyridin-3-yl)methyl]-1H-imidazole-4-carboxylic acid |
| 38 | 1-[(6-{3-Azabicyclo[3.1.0]hexan-3-yl}-2-(trifluoromethoxy)-pyridin-3-yl)methyl]-N-[(4R)-1-methyl-1H,4H,5H,6H-cyclopenta[d]imidazol-4-yl]-1H-imidazole-4-carboxamide | 1-[(6-{3-Azabicyclo[3.1.0]hexan-3-yl}-2-(trifluoromethoxy)pyridin-3-yl)methyl]-1H-imidazole-4-carboxylic acid |
| 39 | 1-[(6-{3-Azabicyclo[3.1.0]hexan-3-yl}-2-bromopyridin-3-yl)methyl]-N-[(4R)-1-methyl-1H,4H,5H,6H-cyclopenta[d]imidazol-4-yl]-1H-imidazole-4-carboxamide | 1-[(6-{3-Azabicyclo[3.1.0]hexan-3-yl}-2-bromopyridin-3-yl)methyl]-1H-imidazole-4-carboxylic acid |
| 40 | 1-[(6-{3-Azabicyclo[3.1.0]hexan-3-yl}-2-bromopyridin-3-yl)methyl]-N-[(4R)-1-methyl-1H,4H,5H,6H-cyclopenta[d]imidazol-4-yl]-1H-pyrazole-4-carboxamide | 1-[(6-{3-Azabicyclo[3.1.0]hexan-3-yl}-2-bromopyridin-3-yl)methyl]-1H-pyrazole-4-carboxylic acid |
| 41 | 1-[(5-{6,6-Difluoro-3-azabicyclo[3.1.0]hexan-3-yl}pyridin-2-yl)methyl]-N-[(4R)-1-methyl-1H,4H,5H,6H-cyclopenta[d]imidazol-4-yl]-1H-pyrazole-4-carboxamide | 1-[(5-{6,6-Difluoro-3-azabicyclo-[3.10]hexan-3-yl}pyridin-2-yl)methyl]-1H-pyrazole-4-carboxylic acid |
| 42 | 1-[(6-{3-Azabicyclo[3.1.0]hexan-3-yl}-2-(1-cyanocyclopropyl)-pyridin-3-yl)methyl]-N-[(4R)-1-methyl-1H,4H,5H,6H-cyclopenta[d]imidazol-4-yl]-1H-pyrazole-4-carboxamide | 1-[(6-{3-Azabicyclo[3.1.0]hexan-3-yl}-2-(1-cyanocyclopropyl)pyridin-3-yl)-methyl]-1H-pyrazole-4-carboxylic acid |
| 43 | 1-[(6-{3-Azabicyclo[3.1.0]hexan-3-yl}-2-(difluoromethyl)-pyridin-3-yl)methyl]-N-[(4R)-1-methyl-1H,4H,5H,6H-cyclopenta[d]imidazol-4-yl]-1H-pyrazole-4-carboxamide | 1-[(6-{3-Azabicyclo[3.1.0]hexan-3-yl}-2-(difluoromethyl)pyridin-3-yl)methyl]-1H-pyrazole-4-carboxylic acid |
| 44 | 1-[(2-Chloro-6-{6,6-difluoro-3-azabicyclo-[3.1.0]hexan-3-yl}pyridin-3-yl)methyl]-N-[(4R)-1-methyl-1H,4H,5H,6H-cyclopenta[d]imidazol-4-yl]-1H-pyrazole-4-carboxamide | 1-[(2-Chloro-6-{6,6-difluoro-3-aza-bicyclo[3.1.0]hexan-3-yl}pyridin-3-yl)-methyl]-1H-pyrazole-4-carboxylic acid |

-continued

| Example | Name | Name of Starting Material |
|---|---|---|
| 45 | 1-[(6-{6,6-Difluoro-3-azabicyclo[3.1.0]hexan-3-yl}-2-(difluoromethyl)pyridin-3-yl)methyl]-N-[(4R)-1-methyl-1H,4H,5H,6H-cyclopenta-[d]imidazol-4-yl]-1H-imidazole-4-carboxamide | 1-[(6-{6,6-Difluoro-3-azabicyclo[3.1.0]hexan-3-yl}-2-(difluoromethyl)pyridin-3-yl)methyl]-1H-imidazole-4-carboxylic acid |
| 46 | 1-[(6-{6,6-Difluoro-3-azabicyclo[3.1.0]hexan-3-yl}-2-(difluoromethyl)pyridin-3-yl)methyl]-N-[(4R)-1-methyl-1H,4H,5H,6H-cyclopenta-[d]imidazol-4-yl]-1H-pyrazole-4-carboxamide | 1-[(6-{6,6-Difluoro-3-azabicyclo[3.1.0]hexan-3-yl}-2-(difluoromethyl)pyridin-3-yl)methyl]-1H-pyrazole-4-carboxylic acid |
| 47 | 1-[(6-{5-Azaspiro[2.3]hexan-5-yl}-2-(difluoromethyl)-pyridin-3-yl)methyl]-N-[(4R)-1-methyl-1H,4H,5H,6H-cyclopenta[d]imidazol-4-yl]-1H-imidazole-4-carboxamide | 1-[(6-{5-Azaspiro[2.3]hexan-5-yl}-2-(difluoromethyl)pyridin-3-yl)methyl]-1H-imidazole-4-carboxylic acid |
| 48 | 1-[(6-{3-Azabicyclo[3.1.0]hexan-3-yl}-2-(difluoromethyl)-pyridin-3-yl)methyl]-N-[(4R)-1-methyl-1H,4H,5H,6H-cyclopenta[d]imidazol-4-yl]-1H-pyrazole-4-carboxamide | 1-[(6-{3-Azabicyclo[3.1.0]hexan-3-yl}-2-(difluoromethyl)pyridin-3-yl)methyl]-1H-pyrazole-4-carboxylic acid |
| 49 | 1-[(6-{3-Azabicyclo[3.1.0]hexan-3-yl}-2-(methoxymethyl)-pyridin-3-yl)methyl]-N-[(4R)-1-methyl-1H,4H,5H,6H-cyclopenta[d]imidazol-4-yl]-1H-pyrazole-4-carboxamide | 1-[(6-{3-Azabicyclo[3.1.0]hexan-3-yl}-2-(methoxymethyl)pyridin-3-yl)methyl]-1H-pyrazole-4-carboxylic acid |
| 50 | 1-[(6-{6,6-Difluoro-3-azabicyclo[3.1.0]hexan-3-yl}-2-(hydroxymethyl)pyridin-3-yl)methyl]-N-[(4R)-1-methyl-1H,4H,5H,6H-cyclopenta[d]-imidazol-4-yl]-1H-1,2,3-triazole-4-carboxamide | 1-[(6-{6,6-Difluoro-3-azabicyclo[3.1.0]hexan-3-yl}-2-(hydroxymethyl)pyridin-3-yl)methyl]-1H-1,2,3-triazole-4-carboxylic acid |
| 51 | 1-[(6-{5-Azaspiro[2.3]hexan-5-yl}-2-ethylpyridin-3-yl)methyl]-N-[(4R)-1-methyl-1H,4H,5H,6H-cyclopenta[d]imidazol-4-yl]-1H-pyrazole-4-carboxamide | 1-[(6-{5-Azaspiro[2.3]hexan-5-yl}-2-ethylpyridin-3-yl)methyl]-1H-pyrazole-4-carboxylic acid |
| 52 | 1-[(6-{5-Azaspiro[2.3]hexan-5-yl}-2-(difluoromethyl)-pyridin-3-yl)methyl]-N-[(4R)-1-methyl-1H,4H,5H,6H-cyclopenta[d]imidazol-4-yl]-1H-pyrazole-4-carboxamide | 1-[(6-{5-Azaspiro[2.3]hexan-5-yl}-2-(difluoromethyl)pyridin-3-yl)methyl]-1H-pyrazole-4-carboxylic acid |
| 53 | 1-[(5-{6,6-Difluoro-3-azabicyclo[3.1.0]hexan-3-yl}pyridin-2-yl)methyl]-N-[(4R)-1-methyl-1H,4H,5H,6H-cyclopenta[d]imidazol-4-yl]-1H-imidazole-4-carboxamide | 1-[(5-{6,6-Difluoro-3-azabicyclo-[3.10]hexan-3-yl}pyridin-2-yl)methyl]-1H-imidazole-4-carboxylic acid |
| 54 | 1-[(6-{3-Azabicyclo[3.1.0]hexan-3-yl}-2-(3-hydroxypropyl)-pyridin-3-yl)methyl]-N-[(4R)-1-methyl-1H,4H,5H,6H-cyclopenta[d]imidazol-4-yl]-1H-pyrazole-4-carboxamide | 1-[(6-{3-Azabicyclo[3.1.0]hexan-3-yl}-2-(3-hydroxypropyl)pyridin-3-yl)methyl]-1H-pyrazole-4-carboxylic acid |
| 55 | 1-[(6-{6,6-Difluoro-3-azabicyclo[3.1.0]hexan-3-yl}-2-(methoxymethyl)pyridin-3-yl)methyl]-N-[(4R)-1-methyl-1H,4H,5H,6H-cyclopenta[d]-imidazol-4-yl]-1H-1,2,3-triazole-4-carboxamide | 1-[(6-{6,6-Difluoro-3-azabicyclo[3.1.0]hexan-3-yl}-2-(methoxymethyl)pyridin-3-yl)methyl]-1H-1,2,3-triazole-4-carboxylic acid |
| 56 | 1-[(6-{5-Azaspiro[2.3]hexan-5-yl}-2-chloropyridin-3-yl)methyl]-N-[(4R)-1-methyl-1H,4H,5H,6H-cyclopenta[d]imidazol-4-yl]-1H-pyrazole-4-carboxamide | 1-[(6-{5-Azaspiro[2.3]hexan-5-yl}-2-chloropyridin-3-yl)methyl]-1H-pyrazole-4-carboxylic acid |
| 57 | 1-[(2-Chloro-6-{6,6-difluoro-3-azabicyclo[3.1.0]-hexan-3-yl}pyridin-3-yl)methyl]-N-[(4R)-1-methyl-1H,4H,5H,6H-cyclopenta[d]imidazol-4-yl]-1H-imidazole-4-carboxamide | 1-[(2-Chloro-6-{6,6-difluoro-3-aza-bicyclo[3.1.0]hexan-3-yl}pyridin-3-yl)-methyl]-1H-imidazole-4-carboxylic acid |
| 58 | 1-[(6-{3-Azabicyclo[3.1.0]hexan-3-yl}-2-(trifluoromethoxy)-pyridin-3-yl)methyl]-N-[(4R)-1-methyl-1H,4H,5H,6H-cyclopenta[d]imidazol-4-yl]-1H-pyrazole-4-carboxamide | 1-[(6-{3-Azabicyclo[3.1.0]hexan-3-yl}-2-(trifluoromethoxy)pyridin-3-yl)methyl]-1H-pyrazole-4-carboxylic acid |
| 59 | 1-[(6-{3-Azabicyclo[3.1.0]hexan-3-yl}-2-(1-hydroxypropan-2-yl)pyridin-3-yl)methyl]-N-[(4R)-1-methyl-1H,4H,5H,6H-cyclopenta[d]imidazol-4-yl]-1H-pyrazole-4-carboxamide | 1-[(6-{3-Azabicyclo[3.1.0]hexan-3-yl}-2-(1-hydroxypropan-2-yl)pyridin-3-yl)-methyl]-1H-pyrazole-4-carboxylic acid |
| 60 | 1-[(6-{3-Azabicyclo[3.1.0]hexan-3-yl}pyridazin-3-yl)methyl]-N-[(4R)-1-methyl-1H,4H,5H,6H-cyclopenta[d]imidazol-4-yl]-1H-pyrazole-4-carboxamide | 1-[(6-{3-Azabicyclo[3.1.0]hexan-3-yl}pyridazin-3-yl)methyl]-1H-pyrazole-4-carboxylic acid |
| 61 | 1-[(6-{5-Azaspiro[2.3]hexan-5-yl}-2-(hydroxymethyl)-pyridin-3-yl)methyl]-N-[(4R)-1-methyl-1H,4H,5H,6H-cyclo-penta[d]imidazol-4-yl]-1H-1,2,3-triazole-4-carboxamide | 1-[(6-{5-Azaspiro[2.3]hexan-5-yl}-2-(hydroxymethyl)pyridin-3-yl)methyl]-1H-1,2,3-triazole-4-carboxylic acid |
| 62 | 1-[(2-{3-Azabicyclo[3.1.0]hexan-3-yl}-4-(hydroxymethyl)-pyrimidin-5-yl)methyl]-N-[(4R)-1-methyl-1H,4H,5H,6H-cyclopenta[d]imidazol-4-yl]-1H-pyrazole-4-carboxamide | 1-[(2-{3-Azabicyclo[3.1.0]hexan-3-yl}-4-(hydroxymethyl)pyrimidin-5-yl)methyl]-1H-pyrazole-4-carboxylic acid |
| 63 | 1-[(6-{6,6-Difluoro-3-azabicyclo[3.1.0]hexan-3-yl}pyridin-3-yl)methyl]-N-[(4R)-1-methyl-1H,4H,5H,6H-cyclopenta[d]imidazol-4-yl]-1H-imidazole-4-carboxamide | 1-[(6-{6,6-Difluoro-3-azabicyclo-[3.10]hexan-3-yl}pyridin-3-yl)methyl]-1H-imidazole-4-carboxylic acid |
| 64 | 1-[(6-{3-Azabicyclo[3.1.0]hexan-3-yl}-2-(difluoromethyl)-pyridin-3-yl)methyl]-N-[(4R)-1-methyl-1H,4H,5H,6H-cyclopenta[d]imidazol-4-yl]-1H-imidazole-4-carboxamide | 1-[(6-{3-Azabicyclo[3.1.0]hexan-3-yl}-2-(difluoromethyl)pyridin-3-yl)methyl]-1H-imidazole-4-carboxylic acid |
| 65 | 1-[(6-{3-Azabicyclo[3.1.0]hexan-3-yl}-2-(1-cyano-1-methylethyl)pyridin-3-yl)methyl]-N-[(4R)-1-methyl-1H,4H,5H,6H-cyclopenta[d]-imidazol-4-yl]-1H-pyrazole-4-carboxamide | 1-[(6-{3-Azabicyclo[3.1.0]hexan-3-yl}-2-(1-cyano-1-methylethyl)pyridin-3-yl)-methyl]-1H-pyrazole-4-carboxylic acid |
| 66 | 1-[(6-{6,6-Difluoro-3-azabicyclo[3.1.0]hexan-3-yl}-2-propylpyridin-3-yl)methyl]-N-[(4R)-1-methyl-1H,4H,5H,6H-cyclopenta[d]imidazol-4-yl]-1H-imidazole-4-carboxamide | 1-[(6-{6,6-Difluoro-3-azabicyclo-[3.1.0]hexan-3-yl}-2-propylpyridin-3-yl)-methyl]-1H-imidazole-4-carboxylic acid |
| 67 | 1-[(2-Cydobutyl-6-{6,6-difluoro-3-azabicyclo[3.1.0]hexan-3-yl}pyridin-3-yl)methyl]-N-[(4R)-1-methyl-1H,4H,5H,6H-cyclopenta[d]imidazol-4-yl]-1H-pyrazole-4-carboxamide | 1-[(2-Cyclobutyl-6-{6,6-difluoro-3-aza-bicyclo[3.1.0]hexan-3-yl}pyridin-3-yl)-methyl]-1H-pyrazole-4-carboxylic acid |
| 68 | 1-[(6-{5-Azaspiro[2.3]hexan-5-yl}-2-methylpyridin-3-yl)-methyl]-N-[(4R)-1-methyl-1H,4H,5H,6H-cyclo-penta[d]imidazol-4-yl]-1H-1,2,3-triazole-4-carboxamide | 1-[(6-{5-Azaspiro[2.3]hexan-5-yl}-2-methylpyridin-3-yl)methyl]-1H-1,2,3-triazole-4-carboxylic acid |

-continued

| Example | Name | Name of Starting Material |
|---|---|---|
| 69 | 1-[(6-{6,6-Difluoro-3-azabicyclo[3.1.0]hexan-3-yl}-2-propylpyridin-3-yl)methyl]-N-[(4R)-1-methyl-1H,4H,5H,6H-cyclopenta[d]imidazol-4-yl]-1H-pyrazole-4-carboxamide | 1-[(6-{6,6-Difluoro-3-azabicyclo[3.1.0]-hexan-3-yl}-2-propylpyridin-3-yl)-methyl]-1H-pyrazole-4-carboxylic acid |
| 70 | 1-[(6-{3-Azabicyclo[3.1.0]hexan-3-yl}-2-methylpyridin-3-yl)methyl]-3-cyano-N-[(4R)-1-methyl-1H,4H,5H,6H-cyclopenta[d]imidazol-4-yl]-1H-pyrazole-4-carboxamide | 1-[(6-{3-Azabicyclo[3.1.0]hexan-3-yl}-2-methylpyridin-3-yl)methyl]-3-cyano-1H-pyrazole-4-carboxylic acid |
| 71 | 1-[(5-{3-Azabicyclo[3.1.0]hexan-3-yl}pyrimidin-2-yl)methyl]-N-[(4R)-1-methyl-1H,4H,5H,6H-cyclopenta[d]imidazol-4-yl]-1H-pyrazole-4-carboxamide | 1-[(5-{3-Azabicyclo[3.1.0]hexan-3-yl}pyrimidin-2-yl)methyl]-1H-pyrazole-4-carboxylic acid |
| 72 | 1-[(6-{3-Azabicyclo[3.1.0]hexan-3-yl}pyridin-3-yl)methyl]-N-[(4R)-1-methyl-1H,4H,5H,6H-cyclopenta[d]imidazol-4-yl]-1H-imidazole-4-carboxamide | 1-[(6-{3-Azabicyclo[3.1.0]hexan-3-yl}pyridin-3-yl)methyl]-1H-imidazole-4-carboxylic acid |
| 73 | 1-[(6-{5-Azaspiro[2.3]hexan-5-yl}pyridin-3-yl)-methyl]-N-[(4R)-1-methyl-1H,4H,5H,6H-cyclopenta[d]imidazol-4-yl]-1H-pyrazole-4-carboxamide | 1-[(6-{5-Azaspiro[2.3]hexan-5-yl}pyridin-3-yl)methyl]-1H-pyrazole-4-carboxylic acid trifluoroacetate |
| 74 | 1-[(6-{5-Azaspiro[2.3]hexan-5-yl}pyridin-3-yl)-methyl]-N-[(4R)-1-methyl-1H,4H,5H,6H-cyclopenta[d]imidazol-4-yl]-1H-imidazole-4-carboxamide | 1-[(6-{5-Azaspiro[2.3]hexan-5-yl}pyridin-3-yl)methyl]-1H-imidazole-4-carboxylic acid trifluoroacetate |
| 75 | 1-[(6-{3-Azabicyclo[3.1.0]hexan-3-yl}-2-ethylpyridin-3-yl)methyl]-N-[(4R)-1-methyl-1H,4H,5H,6H-cyclopenta[d]imidazol-4-yl]-1H-imidazole-4-carboxamide | 1-[(6-{3-Azabicyclo[3.1.0]hexan-3-yl}-2-ethylpyridin-3-yl)methyl]-1H-imidazole-4-carboxylic acid |
| 76 | 1-[(6-{6,6-Difluoro-3-azabicyclo[3.1.0]hexan-3-yl}-2-ethylpyridin-3-yl)methyl]-N-[(4R)-1-methyl-1H,4H,5H,6H-cyclopenta[d]imidazol-4-yl]-1H-imidazole-4-carboxamide | 1-[(6-{6,6-Difluoro-3-azabicyclo-[3.1.0]hexan-3-yl}-2-ethylpyridin-3-yl)-methyl]-1H-imidazole-4-carboxylic acid |
| 77 | 1-[(6-{5-Azaspiro[2.3]hexan-5-yl}-2-(methoxymethyl)-pyridin-3-yl)methyl]-N-[(4R)-1-methyl-1H,4H,5H,6H-cyclopenta[d]imidazol-4-yl]-1H-imidazole-4-carboxamide | 1-[(6-{5-Azaspiro[2.3]hexan-5-yl}-2-(methoxymethyl)pyridin-3-yl)methyl]-1H-imidazole-4-carboxylic acid |
| 78 | 1-[(6-{5-Azaspiro[2.3]hexan-5-yl}-2-(methoxymethyl)-pyridin-3-yl)methyl]-N-[(4R)-1-methyl-1H,4H,5H,6H-cyclopenta[d]imidazol-4-yl]-1H-pyrazole-4-carboxamide | 1-[(6-{5-Azaspiro[2.3]hexan-5-yl}-2-(methoxymethyl)pyridin-3-yl)methyl]-1H-pyrazole-4-carboxylic acid |
| 79 | 1-[(6-{5-Azaspiro[2.3]hexan-5-yl}-2-(hydroxymethyl)-pyridin-3-yl)methyl]-N-[(4R)-1-methyl-1H,4H,5H,6H-cyclopenta[d]imidazol-4-yl]-1H-pyrazole-4-carboxamide | 1-[(6-{5-Azaspiro[2.3]hexan-5-yl}-2-(hydroxymethyl)pyridin-3-yl)methyl]-1H-pyrazole-4-carboxylic acid |
| 80 | 1-[(6-{6,6-Difluoro-3-azabicyclo[3.1.0]hexan-3-yl}pyridin-3-yl)methyl]-N-[(4R)-1-methyl-1H,4H,5H,6H-cyclopenta[d]imidazol-4-yl]-1H-pyrazole-4-carboxamide | 1-[(6-{6,6-Difluoro-3-azabicyclo[3.1.0]-hexan-3-yl}pyridin-3-yl)methyl]-1H-pyrazole-4-carboxylic acid trifluoroacetate |
| 81 | 1-[(6-{3-Azabicyclo[3.1.0]hexan-3-yl}-2-(cyanomethyl)-pyridin-3-yl)methyl]-N-[(4R)-1-methyl-1H,4H,5H,6H-cyclopenta[d]imidazol-4-yl]-1H-pyrazole-4-carboxamide | 1-[(6-{3-Azabicyclo[3.1.0]hexan-3-yl}-2-(cyanomethyl)pyridin-3-yl)methyl]-1H-pyrazole-4-carboxylic acid |
| 82 | 1-[(6-{3-Azabicyclo[3.1.0]hexan-3-yl}-2-[(1R)-1-hydroxy-ethyl]pyridin-3-yl)methyl]-N-[(4R)-1-methyl-1H,4H,5H,6H-cyclopenta[d]imidazol-4-yl]-1H-pyrazole-4-carboxamide | 1-[(6-{3-Azabicyclo[3.1.0]hexan-3-yl}-2-[(1R)-1-hydroxyethyl]pyridin-3-yl)-methyl]-1H-pyrazole-4-carboxylic acid |
| 83 | 1-[(6-{3-Azabicyclo[3.1.0]hexan-3-yl}-2-[(1S)-1-hydroxy-ethyl]pyridin-3-yl)methyl]-N-[(4R)-1-methyl-1H,4H,5H,6H-cyclopenta[d]imidazol-4-yl]-1H-pyrazole-4-carboxamide | 1-[(6-{3-Azabicyclo[3.1.0]hexan-3-yl}-2-[(1S)-1-hydroxyethyl]pyridin-3-yl)-methyl]-1H-pyrazole-4-carboxylic acid |
| 84 | 1-[(6-{3-Azabicyclo[3.1.0]hexan-3-yl}-2-(2-hydroxypropan-2-yl)pyridin-3-yl)methyl]-N-[(4R)-1-methyl-1H,4H,5H,6H-cyclopenta[d]imidazol-4-yl]-1H-pyrazole-4-carboxamide | 1-[(6-{3-Azabicyclo[3.1.0]hexan-3-yl}-2-(2-hydroxypropan-2-yl)pyridin-3-yl)-methyl]-1H-pyrazole-4-carboxylic acid |
| 85 | 1-[(6-{3-Azabicyclo[3.1.0]hexan-3-yl}-2-(2-hydroxyethyl)-pyridin-3-yl)methyl]-N-[(4R)-1-methyl-1H,4H,5H,6H-cyclopenta[d]imidazol-4-yl]-1H-pyrazole-4-carboxamide | 1-[(6-{3-Azabicyclo[3.1.0]hexan-3-yl}-2-(2-hydroxyethyl)pyridin-3-yl)methyl]-1H-pyrazole-4-carboxylic acid |
| 86 | 1-[(6-{3-Azabicyclo[3.1.0]hexan-3-yl}-2-(hydroxymethyl)-pyridin-3-yl)methyl]-N-[(4R)-1-methyl-1H,4H,5H,6H-cyclopenta[d]imidazol-4-yl]-1H-pyrazole-4-carboxamide | 1-[(6-{3-Azabicyclo[3.1.0]hexan-3-yl}-2-(hydroxymethyl)pyridin-3-yl)methyl]-1H-pyrazole-4-carboxylic acid |
| 87 | 1-[(6-{5-Azaspiro[2.3]hexan-5-yl}-2-(hydroxymethyl)-pyridin-3-yl)methyl]-N-[(4R)-1-methyl-1H,4H,5H,6H-cyclopenta[d]imidazol-4-yl]-1H-imidazole-4-carboxamide | 1-[(6-{5-Azaspiro[2.3]hexan-5-yl}-2-(hydroxymethyl)pyridin-3-yl)methyl]-1H-imidazole-4-carboxylic acid |
| 88 | 1-[(6-{3-Azabicyclo[3.1.0]hexan-3-yl}-2-(1-hydroxyethyl)-pyridin-3-yl)methyl]-N-[(4R)-1-methyl-1H,4H,5H,6H-cyclopenta[d]imidazol-4-yl]-1H-pyrazole-4-carboxamide | 1-[(6-{3-Azabicyclo[3.1.0]hexan-3-yl}-2-(1-hydroxyethyl)pyridin-3-yl)methyl]-1H-pyrazole-4-carboxylic acid |
| 89 | 1-[(5-{3-Azabicyclo[3.1.0]hexan-3-yl}-3-(hydroxymethyl)-pyrazin-2-yl)methyl]-N-[(4R)-1-methyl-1H,4H,5H,6H-cyclopenta[d]imidazol-4-yl]-1H-pyrazole-4-carboxamide | 1-[(5-{3-Azabicyclo[3.1.0]hexan-3-yl}-3-(hydroxymethyl)pyrazin-2-yl)methyl]-1H-pyrazole-4-carboxylic acid |
| 90 | 1-[(6-{6,6-Difluoro-3-azabicyclo[3.1.0]hexan-3-yl}-2-methylpyridin-3-yl)methyl]-N-[(4R)-1-methyl-1H,4H,5H,6H-cyclopenta[d]imidazol-4-yl]-1H-pyrazole-4-carboxamide | 1-[(6-{6,6-Difluoro-3-azabicyclo[3.1.0]-hexan-3-yl}-2-methylpyridin-3-yl)-methyl]-1H-pyrazole-4-carboxylic acid |
| 91 | 1-[(6-{3-Azabicyclo[3.1.0]hexan-3-yl}-2-(hydroxymethyl)-pyridin-3-yl)methyl]-N-[(4R)-1-methyl-1H,4H,5H,6H-cyclo-penta[d]imidazol-4-yl]-1H-1,2,3-triazole-4-carboxamide | 1-[(6-{3-Azabicyclo[3.1.0]hexan-3-yl}-2-(hydroxymethyl)pyridin-3-yl)methyl]-1H-1,2,3-triazole-4-carboxylic acid |
| 92 | 1-[(6-{3-Azabicyclo[3.1.0]hexan-3-yl}-2-(methoxymethyl)-pyridin-3-yl)methyl]-N-[(4R)-1-methyl-1H,4H,5H,6H-cyclo-penta[d]imidazol-4-yl]-1H-1,2,3-triazole-4-carboxamide | 1-[(6-{3-Azabicyclo[3.1.0]hexan-3-yl}-2-(methoxymethyl)pyridin-3-yl)methyl]-1H-1,2,3-triazole-4-carboxylic acid |
| 93 | 1-[(6-{6,6-Difluoro-3-azabicyclo[3.1.0]hexan-3-yl}-2-(hydroxymethyl)pyridin-3-yl)methyl]-N-[(4R)-1-methyl-1H,4H,5H,6H-cyclopenta-[d]imidazol-4-yl]-1H-pyrazole-4-carboxamide | 1-[(6-{6,6-Difluoro-3-azabicyclo[3.1.0]hexan-3-yl}-2-(hydroxymethyl)pyridin-3-yl)methyl]-1H-pyrazole-4-carboxylic acid |

-continued

| Example | Name | Name of Starting Material |
|---|---|---|
| 94 | 1-[(5-{6,6-Difluoro-3-azabicyclo[3.1.0]hexan-3-yl}-3-methylpyrazin-2-yl)methyl]-N-[(4R)-1-methyl-1H,4H,5H,6H-cyclopenta[d]imidazol-4-yl]-1H-1,2,3-triazole-4-carboxamide | 1-[(5-{6,6-Difluoro-3-azabicyclo[3.1.0]hexan-3-yl}-3-methylpyrazin-2-yl)methyl]-1H-1,2,3-triazole-4-carboxylic acid |
| 95 | 1-[(6-{6,6-Difluoro-3-azabicyclo[3.1.0]hexan-3-yl}-2-(methoxymethyl)pyridin-3-yl)methyl]-N-[(4R)-1-methyl-1H,4H,5H,6H-cyclopenta-[d]imidazol-4-yl]-1H-imidazole-4-carboxamide | 1-[(6-{6,6-Difluoro-3-azabicyclo[3.1.0]hexan-3-yl}-2-(methoxymethyl)pyridin-3-yl)methyl]-1H-imidazole-4-carboxylic acid |
| 96 | 1-[(6-{6,6-Difluoro-3-azabicyclo[3.1.0]hexan-3-yl}-2-(hydroxymethyl)pyridin-3-yl)methyl]-N-[(4R)-1-methyl-1H,4H,5H,6H-cyclopenta-[d]imidazol-4-yl]-1H-imidazole-4-carboxamide | 1-[(6-{6,6-Difluoro-3-azabicyclo[3.1.0]hexan-3-yl}-2-(hydroxymethyl)pyridin-3-yl)methyl]-1H-imidazole-4-carboxylic acid |
| 97 | 1-[(6-{6,6-Difluoro-3-azabicyclo[3.1.0]hexan-3-yl}-2-methoxypyridin-3-yl)methyl]-N-[(4R)-1-methyl-1H,4H,5H,6H-cyclopenta[d]imidazol-4-yl]-1H-imidazole-4-carboxamide | 1-[(6-{6,6-Difluoro-3-azabicyclo[3.1.0]hexan-3-yl}-2-methoxypyridin-3-yl)methyl]-1H-imidazole-4-carboxylic acid |
| 98 | 1-[(6-{3-Azabicyclo[3.1.0]hexan-3-yl}-2-(hydroxymethyl)-pyridin-3-yl)methyl]-N-[(4R)-1-methyl-1H,4H,5H,6H-cyclopenta[d]imidazol-4-yl]-1H-imidazole-4-carboxamide | 1-[(6-{3-Azabicyclo[3.1.0]hexan-3-yl}-2-(hydroxymethyl)pyridin-3-yl)methyl]-1H-imidazole-4-carboxylic acid |
| 99 | 1-[(6-{3-Azabicyclo[3.1.0]hexan-3-yl}-4-chloropyridin-3-yl)methyl]-N-[(4R)-1-methyl-1H,4H,5H,6H-cyclopenta[d]imidazol-4-yl]-1H-pyrazole-4-carboxamide | 1-[(6-{3-Azabicyclo[3.1.0]hexan-3-yl}-4-chloropyridin-3-yl)methyl]-1H-pyrazole-4-carboxylic acid |
| 100 | 1-[(6-{3-Azabicyclo[3.1.0]hexan-3-yl}-2-(2-methylpropyl)-pyridin-3-yl)methyl]-N-[(4R)-1-methyl-1H,4H,5H,6H-cyclopenta[d]imidazol-4-yl]-1H-imidazole-4-carboxamide | 1-[(6-{3-Azabicyclo[3.1.0]hexan-3-yl}-2-(2-methylpropyl)pyridin-3-yl)methyl]-1H-imidazole-4-carboxylic acid |
| 101 | 1-[(6-{3-Azabicyclo[3.1.0]hexan-3-yl}-2-ethylpyridin-3-yl)methyl]-N-[(4R)-1-methyl-1H,4H,5H,6H-cyclo-penta[d]imidazol-4-yl]-1H-1,2,3-triazole-4-carboxamide | 1-[(6-{3-Azabicyclo[3.1.0]hexan-3-yl}-2-ethylpyridin-3-yl)methyl]-1H-1,2,3-triazole-4-carboxylic acid |
| 102 | 1-[(6-{6,6-Difluoro-3-azabicyclo[3.1.0]hexan-3-yl}-2-ethoxypyridin-3-yl)methyl]-N-[(4R)-1-methyl-1H,4H,5H,6H-cyclopenta[d]imidazol-4-yl]-1H-imidazole-4-carboxamide | 1-[(6-{6,6-Difluoro-3-azabicyclo[3.1.0]-hexan-3-yl}-2-ethoxypyridin-3-yl)-methyl]-1H-imidazole-4-carboxylic acid |
| 103 | 1-[(5-Cyano-6-{6,6-difluoro-3-azabicyclo[3.1.0]-hexan-3-yl}-4-methylpyridin-3-yl)methyl]-N-[(4R)-1-methyl-1H,4H,5H,6H-cyclopenta-[d]imidazol-4-yl]-1H-pyrazole-4-carboxamide | 1-[(5-Cyano-6-{6,6-difluoro-3-azabicyclo[3.1.0]hexan-3-yl}-4-methylpyridin-3-yl)methyl]-1H-pyrazole-4-carboxylic acid |
| 104 | 1-[(6-{3-Azabicyclo[3.1.0]hexan-3-yl}-2-fluoropyridin-3-yl)-methyl]-N-[(4R)-1-methyl-1H,4H,5H,6H-cyclopenta[d]imidazol-4-yl]-1H-pyrazole-4-carboxamide | 1-[(6-{3-Azabicyclo[3.1.0]hexan-3-yl}-2-fluoropyridin-3-yl)methyl]-1H-pyrazole-4-carboxylic acid |
| 105 | 1-[(5-Cyano-6-{6,6-difluoro-3-azabicyclo[3.1.0]-hexan-3-yl}-4-methylpyridin-3-yl)methyl]-N-[(4R)-1-methyl-1H,4H,5H,6H-cyclopenta-[d]imidazol-4-yl]-1H-imidazole-4-carboxamide | 1-[(5-Cyano-6-{6,6-difluoro-3-azabicyclo[3.1.0]hexan-3-yl}-4-methylpyridin-3-yl)methyl]-1H-imidazole-4-carboxylic acid |
| 106 | 1-[(6-{3-Azabicyclo[3.1.0]hexan-3-yl}-4-methylpyridin-3-yl)methyl]-N-[(4R)-1-methyl-1H,4H,5H,6H-cyclopenta[d]imidazol-4-yl]-1H-imidazole-4-carboxamide | 1-[(6-{3-Azabicyclo[3.1.0]hexan-3-yl}-4-methylpyridin-3-yl)methyl]-1H-imidazole-4-carboxylic acid |
| 107 | 1-[(6-{6,6-Difluoro-3-azabicyclo[3.1.0]hexan-3-yl}-2-methylpyridin-3-yl)methyl]-3-(hydroxymethyl)-N-[(4R)-1-methyl-1H,4H,5H,6H-cyclopenta[d]imidazol-4-yl]-1H-pyrazole-4-carboxamide | 1-[(6-{6,6-Difluoro-3-azabicyclo[3.1.0]-hexan-3-yl}-2-methylpyridin-3-yl)methyl]-3-(hydroxymethyl)-1H-pyrazole-4-carboxylic acid |
| 108 | 1-[(6-{3-Azabicyclo[3.1.0]hexan-3-yl}-2-fluoropyridin-3-yl)methyl]-N-[(4R)-1-methyl-1H,4H,5H,6H-cyclopenta[d]imidazol-4-yl]-1H-imidazole-4-carboxamide | 1-[(6-{3-Azabicyclo[3.1.0]hexan-3-yl}-2-fluoropyridin-3-yl)methyl]-1H-imidazole-4-carboxylic acid |
| 109 | 1-[(6-{6,6-Difluoro-3-azabicyclo[3.1.0]hexan-3-yl}-2-ethyl-pyridin-3-yl)methyl]-N-[(4R)-1-methyl-1H,4H,5H,6H-cyclo-penta[d]imidazol-4-yl]-1H-1,2,3-triazole-4-carboxamide | 1-[(6-{6,6-Difluoro-3-azabicyclo[3.1.0]-hexan-3-yl}-2-ethylpyridin-3-yl)methyl]-1H-1,2,3-triazole-4-carboxylic acid |
| 110 | 1-[(6-{3-Azabicyclo[3.1.0]hexan-3-yl}-2-propylpyridin-3-yl)methyl]-N-[(4R)-1-methyl-1H,4H,5H,6H-cyclopenta[d]imidazol-4-yl]-1H-imidazole-4-carboxamide | 1-[(6-{3-Azabicyclo[3.1.0]hexan-3-yl}-2-propylpyridin-3-yl)methyl]-1H-imidazole-4-carboxylic acid |
| 111 | 1-[(6-{6,6-Difluoro-3-azabicyclo[3.1.0]hexan-3-yl}-2,4-di-methylpyridin-3-yl)methyl]-N-[(4R)-1-methyl-1H,4H,5H,6H-cyclopenta[d]imidazol-4-yl]-1H-imidazole-4-carboxamide | 1-[(6-{6,6-Difluoro-3-azabicyclo[3.1.0]-hexan-3-yl}-2,4-dimethylpyridin-3-yl)-methyl]-1H-imidazole-4-carboxylic acid |
| 112 | 1-[(6-{6,6-Difluoro-3-azabicyclo[3.1.0]hexan-3-yl}-2,4-di-methylpyridin-3-yl)methyl]-N-[(4R)-1-methyl-1H,4H,5H,6H-cyclopenta[d]imidazol-4-yl]-1H-pyrazole-4-carboxamide | 1-[(6-{6,6-Difluoro-3-azabicyclo[3.1.0]-hexan-3-yl}-2,4-dimethylpyridin-3-yl)-methyl]-1H-pyrazole-4-carboxylic acid |
| 113 | 1-[(6-{3-Azabicyclo[3.1.0]hexan-3-yl}-4-methylpyridin-3-yl)methyl]-N-[(4R)-1-methyl-1H,4H,5H,6H-cyclopenta[d]imidazol-4-yl]-1H-pyrazole-4-carboxamide | 1-[(6-{3-Azabicyclo[3.1.0]hexan-3-yl}-4-methylpyridin-3-yl)methyl]-1H-pyrazole-4-carboxylic acid |
| 114 | 1-[(6-{3-Azabicyclo[3.1.0]hexan-3-yl}-5-cyanopyridin-3-yl)methyl]-N-[(4R)-1-methyl-1H,4H,5H,6H-cyclopenta[d]imidazol-4-yl]-1H-pyrazole-4-carboxamide | 1-[(6-{3-Azabicyclo[3.1.0]hexan-3-yl}-5-cyanopyridin-3-yl)methyl]-1H-pyrazole-4-carboxylic acid |
| 115 | 1-[(6-{3-Azabicyclo[3.1.0]hexan-3-yl}-4-(trifluoromethyl)-pyridin-3-yl)methyl]-N-[(4R)-1-methyl-1H,4H,5H,6H-cyclopenta[d]imidazol-4-yl]-1H-pyrazole-4-carboxamide | 1-[(6-{3-Azabicyclo[3.1.0]hexan-3-yl}-4-(trifluoromethyl)pyridin-3-yl)methyl]-1H-pyrazole-4-carboxylic acid, lithium salt |
| 116 | 1-[(6-{3-Azabicyclo[3.1.0]hexan-3-yl}-5-cyano-4-methyl-pyridin-3-yl)methyl]-N-[(4R)-1-methyl-1H,4H,5H,6H-cyclopenta[d]imidazol-4-yl]-1H-pyrazole-4-carboxamide | 1-[(6-{3-Azabicyclo[3.1.0]hexan-3-yl}-5-cyano-4-methylpyridin-3-yl)methyl]-1H-pyrazole-4-carboxylic acid |

-continued

| Example | Name | Name of Starting Material |
|---|---|---|
| 117 | 1-[(6-{3-Azabicyclo[3.1.0]hexan-3-yl}-2-cyclopropyl-pyridin-3-yl)methyl]-N-[(4R)-1-methyl-1H,4H,5H,6H-cyclopenta[d]imidazol-4-yl]-1H-pyrazole-4-carboxamide | 1-[(6-{3-Azabicyclo[3.1.0]hexan-3-yl}-2-cyclopropylpyridin-3-yl)methyl]-1H-pyrazole-4-carboxylic acid |
| 118 | 1-[(6-{3-Azabicyclo[3.1.0]hexan-3-yl}-5-cyano-4-methyl-pyridin-3-yl)methyl]-N-[(4R)-1-methyl-1H,4H,5H,6H-cyclopenta[d]imidazol-4-yl]-1H-imidazole-4-carboxamide | 1-[(6-{3-Azabicyclo[3.1.0]hexan-3-yl}-5-cyano-4-methylpyridin-3-yl)methyl]-1H-imidazole-4-carboxylic acid |
| 119 | 1-[(6-{3-Azabicyclo[3.1.0]hexan-3-yl}-2-methylpyridin-3-yl)methyl]-N-[(4R)-1-methyl-1H,4H,5H,6H-cyclopenta[d]imidazol-4-yl]-3-(trifluoromethyl)-1H-pyrazole-4-carboxamide | 1-[(6-{3-Azabicyclo[3.1.0]hexan-3-yl}-2-methylpyridin-3-yl)methyl]-3-(trifluoromethyl)-1H-pyrazole-4-carboxylic acid |
| 120 | 1-[(6-{3-Azabicyclo[3.1.0]hexan-3-yl}-4-chloropyridin-3-yl)methyl]-N-[(4R)-1-methyl-1H,4H,5H,6H-cyclopenta[d]imidazol-4-yl]-1H-imidazole-4-carboxamide | 1-[(6-{3-Azabicyclo[3.1.0]hexan-3-yl}-4-chloropyridin-3-yl)methyl]-1H-imidazole-4-carboxylic acid |
| 121 | 1-[(6-{3-Azabicyclo[3.1.0]hexan-3-yl}-4-(trifluoromethyl)-pyridin-3-yl)methyl]-N-[(4R)-1-methyl-1H,4H,5H,6H-cyclopenta[d]imidazol-4-yl]-1H-imidazole-4-carboxamide | 1-[(6-{3-Azabicyclo[3.1.0]hexan-3-yl}-4-(trifluoromethyl)pyridin-3-yl)methyl]-1H-imidazole-4-carboxylic acid |
| 122 | 1-[(6-{3-Azabicyclo[3.1.0]hexan-3-yl}-2-chloropyridin-3-yl)methyl]-N-[(4R)-1-methyl-1H,4H,5H,6H-cyclopenta[d]imidazol-4-yl]-1H-imidazole-4-carboxamide | 1-[(6-{3-Azabicyclo[3.1.0]hexan-3-yl}-2-chloropyridin-3-yl)methyl]-1H-imidazole-4-carboxylic acid |
| 123 | 1-[(6-{3-Azabicyclo[3.1.0]hexan-3-yl}-2-methylpyridin-3-yl)methyl]-3-(methoxymethyl)-N-[(4R)-1-methyl-1H,4H,5H,6H-cyclopenta-[d]imidazol-4-yl]-1H-pyrazole-4-carboxamide | 1-[(6-{3-Azabicyclo[3.1.0]hexan-3-yl}-2-methylpyridin-3-yl)methyl]-3-(methoxy-methyl)-1H-pyrazole-4-carboxylic acid |
| 124 | 1-[(6-{3-Azabicyclo[3.1.0]hexan-3-yl}-5-cyano-2-methyl-pyridin-3-yl)methyl]-N-[(4R)-1-methyl-1H,4H,5H,6H-cyclopenta[d]imidazol-4-yl]-1H-imidazole-4-carboxamide | 1-[(6-{3-Azabicyclo[3.1.0]hexan-3-yl}-5-cyano-2-methylpyridin-3-yl)methyl]-1H-imidazole-4-carboxylic acid |
| 125 | 1-[(6-{3-Azabicyclo[3.1.0]hexan-3-yl}-2-methylpyridin-3-yl)methyl]-3-(2-hydroxypropan-2-yl)-N-[(4R)-1-methyl-1H,4H,5H,6H-cyclopenta-[d]imidazol-4-yl]-1H-pyrazole-4-carboxamide | 1-[(6-{3-Azabicyclo[3.1.0]hexan-3-yl}-2-methylpyridin-3-yl)methyl]-3-(2-hydroxypropan-2-yl)-1H-pyrazole-4-carboxylic acid |
| 126 | 1-[(6-{6,6-Difluoro-3-azabicyclo[3.1.0]hexan-3-yl}-2-methylpyridin-3-yl)methyl]-3-(methoxymethyl)-N-[(4R)-1-methyl-1H,4H,5H,6H-cyclopenta[d]imidazol-4-yl]-1H-pyrazole-4-carboxamide | 1-[(6-{6,6-Difluoro-3-azabicyclo[3.1.0]-hexan-3-yl}-2-methylpyridin-3-yl)methyl]-3-(methoxymethyl)-1H-pyrazole-4-carboxylic acid |
| 127 | 1-[(6-{3-Azabicyclo[3.1.0]hexan-3-yl}-2-chloropyridin-3-yl)methyl]-N-[(4R)-1-methyl-1H,4H,5H,6H-cyclopenta[d]imidazol-4-yl]-1H-pyrazole-4-carboxamide | 1-[(6-{3-Azabicyclo[3.1.0]hexan-3-yl}-2-chloropyridin-3-yl)methyl]-1H-pyrazole-4-carboxylic acid |
| 128 | 1-[(6-{3-Azabicyclo[3.1.0]hexan-3-yl}-5-cyano-2-methyl-pyridin-3-yl)methyl]-N-[(4R)-1-methyl-1H,4H,5H,6H-cyclopenta[d]imidazol-4-yl]-1H-pyrazole-4-carboxamide | 1-[(6-{3-Azabicyclo[3.1.0]hexan-3-yl}-5-cyano-2-methylpyridin-3-yl)methyl]-1H-pyrazole-4-carboxylic acid |
| 129 | 1-[(6-{3-Azabicyclo[3.1.0]hexan-3-yl}-2,5-dimethylpyridin-3-yl)methyl]-N-[(4R)-1-methyl-1H,4H,5H,6H-cyclopenta[d]imidazol-4-yl]-1H-imidazole-4-carboxamide | 1-[(6-{3-Azabicyclo[3.1.0]hexan-3-yl}-2,5-dimethylpyridin-3-yl)methyl]-1H-imidazole-4-carboxylic acid |
| 130 | 1-[(6-{3-Azabicyclo[3.1.0]hexan-3-yl}-2,5-dimethylpyridin-3-yl)methyl]-N-[(4R)-1-methyl-1H,4H,5H,6H-cyclopenta[d]imidazol-4-yl]-1H-pyrazole-4-carboxamide | 1-[(6-{3-Azabicyclo[3.1.0]hexan-3-yl}-2,5-dimethylpyridin-3-yl)methyl]-1H-pyrazole-4-carboxylic acid |
| 131 | 1-[(6-{3-Azabicyclo[3.1.0]hexan-3-yl}pyridin-3-yl)methyl]-N-[(4R)-1-methyl-1H,4H,5H,6H-cyclopenta[d]imidazol-4-yl]-1H-pyrazole-4-carboxamide | 1-[(6-{3-Azabicyclo[3.1.0]hexan-3-yl}pyridin-3-yl)methyl]-1H-pyrazole-4-carboxylic acid |
| 132 | 1-[(6-{3-Azabicyclo[3.1.0]hexan-3-yl}-2-cyanopyridin-3-yl)methyl]-N-[(4R)-1-methyl-1H,4H,5H,6H-cyclopenta[d]imidazol-4-yl]-1H-pyrazole-4-carboxamide | 1-[(6-{3-Azabicyclo[3.1.0]hexan-3-yl}-2-cyanopyridin-3-yl)methyl]-1H-pyrazole-4-carboxylic acid |
| 133 | 1-[(6-{3-Azabicyclo[3.1.0]hexan-3-yl}-2-methylpyridin-3-yl)methyl]-N-[(4R)-1-methyl-1H,4H,5H,6H-cyclopenta[d]imidazol-4-yl]-1H-pyrazole-4-carboxamide | 1-[(6-{3-Azabicyclo[3.1.0]hexan-3-yl}-2-methylpyridin-3-yl)methyl]-1H-pyrazole-4-carboxylic acid |
| 134 | 1-[(6-{3-Azabicyclo[3.1.0]hexan-3-yl}-2-(trifluoromethyl)-pyridin-3-yl)methyl]-N-[(4R)-1-methyl-1H,4H,5H,6H-cyclopenta[d]imidazol-4-yl]-1H-pyrazole-4-carboxamide | 1-[(6-{3-Azabicyclo[3.1.0]hexan-3-yl}-2-(trifluoromethyl)pyridin-3-yl)methyl]-1H-pyrazole-4-carboxylic acid |
| 135 | 1-[(6-{3-Azabicyclo[3.1.0]hexan-3-yl}pyridin-3-yl)methyl]-N-[(4R)-1-methyl-1H,4H,5H,6H-cyclopenta[d]imidazol-4-yl]-1H-1,2,3-triazole-4-carboxamide | 1-[(6-{3-Azabicyclo[3.1.0]hexan-3-yl}pyridin-3-yl)methyl]-1H-1,2,3-triazole-4-carboxylic acid |
| 136 | 1-[(2-{6,6-Difluoro-3-azabicyclo[3.1.0]hexan-3-yl}-4-methylpyrimidin-5-yl)methyl]-N-[(4R)-1-methyl-1H,4H,5H,6H-cyclopenta[d]imidazol-4-yl]-1H-imidazole-4-carboxamide | 1-[(2-{6,6-Difluoro-3-azabicyclo[3.1.0]-hexan-3-yl}-4-methylpyrimidin-5-yl)-methyl]-1H-imidazole-4-carboxylic acid |
| 137 | 1-[(2-{3-Azabicyclo[3.1.0]hexan-3-yl}-4-methylpyrimidin-5-yl)methyl]-N-[(4R)-1-methyl-1H,4H,5H,6H-cyclo-penta[d]imidazol-4-yl]-1H-1,2,3-triazole-4-carboxamide | 1-[(2-{3-Azabicyclo[3.1.0]hexan-3-yl}-4-methylpyrimidin-5-yl)methyl]-1H-1,2,3-triazole-4-carboxylic acid |
| 138 | 1-[(5-{6,6-Difluoro-3-azabicyclo[3.1.0]hexan-3-yl}pyridin-2-yl)methyl]-N-[(4R)-1-methyl-1H,4H,5H,6H-cyclo-penta[d]imidazol-4-yl]-1H-1,2,3-triazole-4-carboxamide | 1-[(5-{6,6-Difluoro-3-azabicyclo[3.1.0]-hexan-3-yl}pyridin-2-yl)methyl]-1H-1,2,3-triazole-4-carboxylic acid |
| 139 | 5-[(6-{6,6-Difluoro-3-azabicyclo[3.1.0]hexan-3-yl}pyridin-3-yl)methyl]-N-[(4R)-1-methyl-1H,4H,5H,6H-cyclopenta[d]imidazol-4-yl]-1H-pyrrole-3-carboxamide | 5-[(6-{6,6-Difluoro-3-azabicyclo[3.1.0]hexan-3-yl}pyridin-3-yl)methyl]-1H-pyrrole-3-carboxylic acid |
| 140 | 1-[(6-{6,6-Difluoro-3-azabicyclo[3.1.0]hexan-3-yl}pyridin-3-yl)methyl]-N-[(4R)-1-methyl-1H,4H,5H,6H-cyclopenta[d]imidazol-4-yl]-1H-pyrrole-3-carboxamide | 1-[(6-{6,6-Difluoro-3-azabicyclo[3.1.0]hexan-3-yl}pyridin-3-yl)methyl]-1H-pyrrole-3-carboxylic acid |

-continued

| Example | Name | Name of Starting Material |
|---|---|---|
| 141 | 1-[(6-{6,6-Difluoro-3-azabicyclo[3.1.0]hexan-3-yl}-2-methylpyridin-3-yl)methyl]-N-[(4R)-1-methyl-1H,4H,5H,6H-cyclopenta[d]imidazol-4-yl]-1H-pyrrole-3-carboxamide | 1-[(6-{6,6-Difluoro-3-azabicyclo[3.1.0]-hexan-3-yl}-2-methylpyridin-3-yl)-methyl]-1H-pyrrole-3-carboxylic acid |
| 142 | 5-[(6-{6,6-Difluoro-3-azabicyclo[3.1.0]hexan-3-yl}-2-methylpyridin-3-yl)methyl]-N-[(4R)-1-methyl-1H,4H,5H,6H-cyclopenta[d]imidazol-4-yl]-1H-pyrrole-3-carboxamide | 5-[(6-{6,6-Difluoro-3-azabicyclo[3.1.0]-hexan-3-yl}-2-methylpyridin-3-yl)methyl]-1H-pyrrole-3-carboxylic acid |
| 143 | 1-({2-Ethyl-6-[(1R,5S,6R)-6-methyl-3-azabicyclo[3.1.0]-hexan-3-yl]pyridin-3-yl}methyl)-N-[(4R)-1-methyl-1H,4H,5H,6H-cyclopenta-[d]imidazol-4-yl]-1H-imidazole-4-carboxamide | 1-({2-Ethyl-6-[(1R,5S,6R)-6-methyl-3-azabicyclo[3.1.0]hexan-3-yl]pyridin-3-yl}methyl)-1H-imidazole-4-carboxylic acid |
| 144 | 3-[(6-{3-Azabicyclo[3.1.0]hexan-3-yl}-2-(difluoromethyl)-pyridin-3-yl)methyl]-N-[(4R)-1-methyl-1H,4H,5H,6H-cyclopenta[d]imidazol-4-yl]-1,2-oxazole-5-carboxamide | 3-[(6-{3-Azabicyclo[3.1.0]hexan-3-yl}-2-(difluoromethyl)pyridin-3-yl)methyl]-1,2-oxazole-5-carboxylic acid |
| 145 | 3-[(6-{6,6-Difluoro-3-azabicyclo[3.1.0]hexan-3-yl}-2-(difluoromethyl)pyridin-3-yl)methyl]-N-[(4R)-1-methyl-1H,4H,5H,6H-cyclopenta-[d]imidazol-4-yl]-1,2-oxazole-5-carboxamide | 3-[(6-{6,6-Difluoro-3-azabicyclo[3.1.0]hexan-3-yl}-2-(difluoromethyl)pyridin-3-yl)methyl]-1,2-oxazole-5-carboxylic acid |
| 146 | 3-[(6-{3-Azabicyclo[3.1.0]hexan-3-yl}-2-ethylpyridin-3-yl)methyl]-N-[(4R)-1-methyl-1H,4H,5H,6H-cyclopenta[d]imidazol-4-yl]-1,2-oxazole-5-carboxamide | 3-[(6-{3-Azabicyclo[3.1.0]hexan-3-yl}-2-ethylpyridin-3-yl)methyl]-1,2-oxazole-5-carboxylic acid |
| 147 | 3-[(6-{6,6-Difluoro-3-azabicyclo[3.1.0]hexan-3-yl}-2-(hydroxymethyl)pyridin-3-yl)methyl]-N-[(4R)-1-methyl-1H,4H,5H,6H-cyclopenta-[d]imidazol-4-yl]-1,2-oxazole-5-carboxamide | 3-[(6-{6,6-Difluoro-3-azabicyclo[3.1.0]-hexan-3-yl}-2-(hydroxymethyl)pyridin-3-yl)methyl]-1,2-oxazole-5-carboxylic acid |
| 148 | 3-[(6-{3-Azabicyclo[3.1.0]hexan-3-yl}-2-chloropyridin-3-yl)methyl]-N-[(4R)-1-methyl-1H,4H,5H,6H-cyclopenta[d]imidazol-4-yl]-1,2-oxazole-5-carboxamide | 3-[(6-{3-Azabicyclo[3.1.0]hexan-3-yl}-2-chloropyridin-3-yl)methyl]-1,2-oxazole-5-carboxylic acid |
| 149 | 3-[(6-{3-Azabicyclo[3.1.0]hexan-3-yl}-2-(hydroxymethyl)-pyridin-3-yl)methyl]-N-[(4R)-1-methyl-1H,4H,5H,6H-cyclopenta[d]imidazol-4-yl]-1,2-oxazole-5-carboxamide | 3-[(6-{3-Azabicyclo[3.1.0]hexan-3-yl}-2-(hydroxymethyl)pyridin-3-yl)methyl]-1,2-oxazole-5-carboxylic acid |
| 150 | 3-[(2-Chloro-6-{6,6-difluoro-3-azabicyclo[3.1.0]hexan-3-yl}pyridin-3-yl)methyl]-N-[(4R)-1-methyl-1H,4H,5H,6H-cyclopenta-[d]imidazol-4-yl]-1,2-oxazole-5-carboxamide | 3-[(2-Chloro-6-{6,6-difluoro-3-azabicyclo[3.1.0]hexan-3-yl}pyridin-3-yl)methyl]-1,2-oxazole-5-carboxylic acid |
| 151 | 3-[(6-{3-Azabicyclo[3.1.0]hexan-3-yl}pyridin-3-yl)methyl]-N-[(4R)-1-methyl-1H,4H,5H,6H-cyclopenta[d]imidazol-4-yl]-1,2-oxazole-5-carboxamide | 3-[(6-{3-Azabicyclo[3.1.0]hexan-3-yl}pyridin-3-yl)methyl]-1,2-oxazole-5-carboxylic acid |
| 152 | 3-[(6-{6,6-Difluoro-3-azabicyclo[3.1.0]hexan-3-yl}-2-methylpyridin-3-yl)methyl]-N-[(4R)-1-methyl-1H,4H,5H,6H-cyclopenta[d]imidazol-4-yl]-1,2-oxazole-5-carboxamide | 3-[(6-{6,6-Difluoro-3-azabicyclo[3.1.0]-hexan-3-yl}-2-methylpyridin-3-yl)methyl]-1,2-oxazole-5-carboxylic acid |
| 153 | 3-[(6-{6,6-Difluoro-3-azabicyclo[3.1.0]hexan-3-yl}-2-ethylpyridin-3-yl)methyl]-N-[(4R)-1-methyl-1H,4H,5H,6H-cyclopenta[d]imidazol-4-yl]-1,2-oxazole-5-carboxamide | 3-[(6-{6,6-Difluoro-3-azabicyclo[3.1.0]-hexan-3-yl}-2-ethylpyridin-3-yl)methyl]-1,2-oxazole-5-carboxylic acid |
| 154 | 2-[(6-{3-Azabicyclo[3.1.0]hexan-3-yl}-2-methylpyridin-3-yl)methyl]-N-[(4R)-1-methyl-1H,4H,5H,6H-cyclopenta[d]imidazol-4-yl]-1,3-oxazole-5-carboxamide | 2-[(6-{3-Azabicyclo[3.1.0]hexan-3-yl}-2-methylpyridin-3-yl)methyl]-1,3-oxazole-5-carboxylic acid |
| 155 | 2-[(6-{6,6-Difluoro-3-azabicyclo[3.1.0]hexan-3-yl}-2-methylpyridin-3-yl)methyl]-N-[(4R)-1-methyl-1H,4H,5H,6H-cyclopenta[d]imidazol-4-yl]-1,3-oxazole-5-carboxamide | 2-[(6-{6,6-Difluoro-3-azabicyclo[3.1.0]-hexan-3-yl}-2-methylpyridin-3-yl)methyl]-1,3-oxazole-5-carboxylic acid |
| 156 | 3-[(6-{5-Azaspiro[2.3]hexan-5-yl}-2-ethylpyridin-3-yl)methyl]-N-[(4R)-1-methyl-1H,4H,5H,6H-cyclopenta[d]imidazol-4-yl]-1,2-oxazole-5-carboxamidef | 3-[(6-{5-Azaspiro[2.3]hexan-5-yl}-2-ethylpyridin-3-yl)methyl]-1,2-oxazole-5-carboxylic acid |
| 157 | 3-[(6-{5-Azaspiro[2.3]hexan-5-yl}-2-chloropyridin-3-yl)methyl]-N-[(4R)-1-methyl-1H,4H,5H,6H-cyclopenta[d]imidazol-4-yl]-1,2-oxazole-5-carboxamide | 3-[(6-{5-Azaspiro[2.3]hexan-5-yl}-2-chloropyridin-3-yl)methyl]-1,2-oxazole-5-carboxylic acid |
| 158 | 2-[(6-{3-Azabicyclo[3.1.0]hexan-3-yl}-2-ethylpyridin-3-yl)methyl]-N-[(4R)-1-methyl-1H,4H,5H,6H-cyclopenta[d]imidazol-4-yl]-1,3-oxazole-5-carboxamide | 2-[(6-{3-Azabicyclo[3.1.0]hexan-3-yl}-2-ethylpyridin-3-yl)methyl]-1,3-oxazole-5-carboxylic acid |
| 159 | 5-[(2-Chloro-6-{6,6-difluoro-3-azabicyclo-[3.1.0]hexan-3-yl}pyridin-3-yl)methyl]-N-[(4R)-1-methyl-1H,4H,5H,6H-cyclopenta[d]imidazol-4-yl]-1H-pyrrole-3-carboxamide | 5-[(2-Chloro-6-{6,6-difluoro-3-azabicyclo[3.1.0]hexan-3-yl}pyridin-3-yl)methyl]-1H-pyrrole-3-carboxylic acid |
| 160 | 3-[(6-{6,6-Difluoro-3-azabicyclo[3.1.0]hexan-3-yl}-2-ethylpyridin-3-yl)methyl]-N-[(4R)-1-methyl-1H,4H,5H,6H-cyclopenta[d]imidazol-4-yl]-1-(propan-2-yl)-1H-pyrazole-5-carboxamide | 3-[(6-{6,6-Difluoro-3-azabicyclo[3.1.0]-hexan-3-yl}-2-ethylpyridin-3-yl)methyl]-1-(propan-2-yl)-1H-pyrazole-5-carboxylic acid |
| 161 | 3-[(6-{6,6-Difluoro-3-azabicyclo[3.1.0]hexan-3-yl}-2-ethylpyridin-3-yl)methyl]-1-ethyl-N-[(4R)-1-methyl-1H,4H,5H,6H-cyclopenta[d]imidazol-4-yl]-1H-pyrazole-5-carboxamide | 3-[(6-{6,6-Difluoro-3-azabicyclo[3.1.0]-hexan-3-yl}-2-ethylpyridin-3-yl)methyl]-1-ethyl-1H-pyrazole-5-carboxylic acid |
| 162 | 3-[(6-{3-Azabicyclo[3.1.0]hexan-3-yl}-2-ethylpyridin-3-yl)methyl]-1-ethyl-N-[(4R)-1-methyl-1H,4H,5H,6H-cyclopenta[d]imidazol-4-yl]-1H-pyrazole-5-carboxamide | 3-[(6-{3-Azabicyclo[3.1.0]hexan-3-yl}-2-ethylpyridin-3-yl)methyl]-1-ethyl-1H-pyrazole-5-carboxylic acid |
| 163 | 3-[(6-{6,6-Difluoro-3-azabicyclo[3.1.0]hexan-3-yl}-2-methylpyridin-3-yl)methyl]-1-ethyl-N-[(4R)-1-methyl-1H,4H,5H,6H-cyclopenta[d]imidazol-4-yl]-1H-pyrazole-5-carboxamide | 3-[(6-{6,6-Difluoro-3-azabicyclo[3.1.0]-hexan-3-yl}-2-methylpyridin-3-yl)methyl]-1-ethyl-1H-pyrazole-5-carboxylic acid |

-continued

| Example | Name | Name of Starting Material |
| --- | --- | --- |
| 164 | 3-[(6-{3-Azabicyclo[3.1.0]hexan-3-yl}-2-methylpyridin-3-yl)methyl]-1-ethyl-N-[(4R)-1-methyl-1H,4H,5H,6H-cyclopenta[d]imidazol-4-yl]-1H-pyrazole-5-carboxamide | 3-[(6-{3-Azabicyclo[3.1.0]hexan-3-yl}-2-methylpyridin-3-yl)methyl]-1-ethyl-1H-pyrazole-5-carboxylic acid |
| 165 | 3-[(6-{3-Azabicyclo[3.1.0]hexan-3-yl}-2-ethylpyridin-3-yl)methyl]-N-[(4R)-1-methyl-1H,4H,5H,6H-cyclopenta[d]imidazol-4-yl]-1H-pyrazole-5-carboxamide | 3-[(6-{3-Azabicyclo[3.1.0]hexan-3-yl}-2-ethylpyridin-3-yl)methyl]-1H-pyrazole-5-carboxylic acid |
| 166 | 3-[(6-{3-Azabicyclo[3.1.0]hexan-3-yl}-2-ethylpyridin-3-yl)methyl]-1-methyl-N-[(4R)-1-methyl-1H,4H,5H,6H-cyclopenta[d]imidazol-4-yl]-1H-pyrazole-5-carboxamide | 3-[(6-{3-Azabicyclo[3.1.0]hexan-3-yl}-2-ethylpyridin-3-yl)methyl]-1-methyl-1H-pyrazole-5-carboxylic acid |
| 167 | 3-[(6-{6,6-Difluoro-3-azabicyclo[3.1.0]hexan-3-yl}-2-methylpyridin-3-yl)methyl]-1-methyl-N-[(4R)-1-methyl-1H,4H,5H,6H-cyclopenta-[d]imidazol-4-yl]-1H-pyrazole-5-carboxamide | 3-[(6-{6,6-Difluoro-3-azabicyclo[3.1.0]-hexan-3-yl}-2-methylpyridin-3-yl)-methyl]-1-methyl-1H-pyrazole-5-carboxylic acid |
| 168 | 3-[(6-{3-Azabicyclo[3.1.0]hexan-3-yl}-2-methylpyridin-3-yl)methyl]-1-methyl-N-[(4R)-1-methyl-1H,4H,5H,6H-cyclopenta[d]imidazol-4-yl]-1H-pyrazole-5-carboxamide | 3-[(6-{3-Azabicyclo[3.1.0]hexan-3-yl}-2-methylpyridin-3-yl)methyl]-1-methyl-1H-pyrazole-5-carboxylic acid |
| 169 | 1-[(6-{5-Azaspiro[2.3]hexan-5-yl}-2-methylpyridin-3-yl)methyl]-N-[(4R)-1-methyl-1H,4H,5H,6H-cyclopenta[d]imidazol-4-yl]-1H-pyrazole-4-carboxamide | 1-[(6-{5-Azaspiro[2.3]hexan-5-yl}-2-methylpyridin-3-yl)methyl]-1H-pyrazole-4-carboxylic acid |
| 170 | 1-[(6-{5-Azaspiro[2.3]hexan-5-yl}-2-methylpyridin-3-yl)methyl]-N-[(4R)-1-methyl-1H,4H,5H,6H-cyclopenta[d]imidazol-4-yl]-1H-imidazole-4-carboxamide | 1-[(6-{5-Azaspiro[2.3]hexan-5-yl}-2-methylpyridin-3-yl)methyl]-1H-imidazole-4-carboxylic acid |
| 171 | 1-[(2-{3-Azabicyclo[3.1.0]hexan-3-yl}-4-methylpyrimidin-5-yl)methyl]-N-[(4R)-1-methyl-1H,4H,5H,6H-cyclopenta[d]imidazol-4-yl]-1H-imidazole-4-carboxamide | 1-[(2-{3-Azabicyclo[3.1.0]hexan-3-yl}-4-methylpyrimidin-5-yl)methyl]-1H-imidazole-4-carboxylic acid |
| 172 | 1-[(2-{5-Azaspiro[2.3]hexan-5-yl}-4-methylpyrimidin-5-yl)methyl]-N-[(4R)-1-methyl-1H,4H,5H,6H-cyclopenta[d]imidazol-4-yl]-1H-imidazole-4-carboxamide | 1-[(2-{5-Azaspiro[2.3]hexan-5-yl}-4-methylpyrimidin-5-yl)methyl]-1H-imidazole-4-carboxylic acid |
| 173 | 7-[(6-{3-Azabicyclo[3.1.0]hexan-3-yl]-2-methylpyridin-3-yl)methyl]-N-[(4R)-1-methyl-1H,4H,5H,6H-cyclopenta[d]-imidazol-4-yl]-7H-pyrrolo[2,3-d]pyrimidine-5-carboxamide | 7-[(6-{3-Azabicyclo[3.1.0]hexan-3-yl}-2-methylpyridin-3-yl)methyl]-7H-pyrrolo-[2,3-d]pyrimidine-5-carboxylic acid |
| 174 | 7-[(2-{3-Azabicyclo[3.1.0]hexan-3-yl}-4-methylpyrimidin-5-yl)methyl]-N-[(4R)-1-methyl-1H,4H,5H,6H-cyclopenta[d]-imidazol-4-yl]-7H-pyrrolo[2,3-d]pyrimidine-5-carboxamide | 7-[(2-{3-Azabicyclo[3.1.0]hexan-3-yl}-4-methylpyrimidin-5-yl)methyl]-7H-pyrrolo-[2,3-d]pyrimidine-5-carboxylic acid |
| 175 | 7-[(2-{6,6-Difluoro-3-azabicyclo[3.1.0]hexan-3-yl}-4-methylpyrimidin-5-yl)methyl]-N-[(4R)-1-methyl-1H,4H,5H,6H-cyclopenta[d]imidazol-4-yl]-7H-pyrrolo[2,3-d]pyrimidine-5-carboxamide | 7-[(2-{6,6-Difluoro-3-azabicyclo[3.1.0]-hexan-3-yl}-4-methylpyrimidin-5-yl)-methyl]-7H-pyrrolo[2,3-d]pyrimidine-5-carboxylic acid |
| 176 | 2-Chloro-1-[(6-{6,6-difluoro-3-azabicyclo-[3.1.0]hexan-3-yl}pyridin-3-yl)methyl]-N-[(4R)-1-methyl-1H,4H,5H,6H-cyclopenta[d]imidazol-4-yl]-1H-imidazole-4-carboxamide | 2-Chloro-1-[(6-{6,6-difluoro-3-aza-bicyclo[3.1.0]hexan-3-yl}pyridin-3-yl)-methyl]-1H-imidazole-4-carboxylic acid |
| 177 | 1-[(2-{3-Azabicyclo[3.1.0]hexan-3-yl}-4-methylpyrimidin-5-yl)methyl]-N-[(4R)-1-methyl-1H,4H,5H,6H-cyclopenta[d]imidazol-4-yl]-1H-pyrazole-4-carboxamide | 1-[(2-{3-Azabicyclo[3.1.0]hexan-3-yl}-4-methylpyrimidin-5-yl)methyl]-1H-pyrazole-4-carboxylic acid |
| 178 | 1-[(2-{6,6-Difluoro-3-azabicyclo[3.1.0]hexan-3-yl}-4-methylpyrimidin-5-yl)methyl]-N-[(4R)-1-methyl-1H,4H,5H,6H-cyclopenta[d]imidazol-4-yl]-1H-1,2,3-triazole-4-carboxamide | 1-[(2-{6,6-Difluoro-3-azabicyclo[3.1.0]-hexan-3-yl}-4-methylpyrimidin-5-yl)-methyl]-1H-1,2,3-triazole-4-carboxylic acid |
| 179 | 1-[(6-{6,6-Difluoro-3-azabicyclo[3.1.0]hexan-3-yl}-2-(ethoxymethyl)pyridin-3-yl)methyl]-N-[(4R)-1-methyl-1H,4H,5H,6H-cyclopenta[d]imidazol-4-yl]-1H-pyrazole-4-carboxamide | 1-[(6-{6,6-Difluoro-3-azabicyclo[3.1.0]-hexan-3-yl}-2-(ethoxymethyl)pyridin-3-yl)methyl]-1H-pyrazole-4-carboxylic acid |
| 180 | 1-[(6-{3-Azabicyclo[3.1.0]hexan-3-yl}-2-(methoxymethyl)-pyridin-3-yl)methyl]-N-[(4R)-1-methyl-1H,4H,5H,6H-cyclopenta[d]imidazol-4-yl]-1H-imidazole-4-carboxamide | 1-[(6-{3-Azabicyclo[3.1.0]hexan-3-yl}-2-(methoxymethyl)pyridin-3-yl)methyl]-1H-imidazole-4-carboxylic acid |
| 181 | 5-[(6-{3-Azabicyclo[3.1.0]hexan-3-yl}-2-methylpyridin-3-yl)methyl]-N-[(4R)-1-methyl-1H,4H,5H,6H-cyclopenta[d]imidazol-4-yl]furan-2-carboxamide | 5-[(6-{3-Azabicyclo[3.1.0]hexan-3-yl}-2-methylpyridin-3-yl)methyl]furan-2-carboxylic |
| 182 | 5-[(6-{3-Azabicyclo[3.1.0]hexan-3-yl}-2-methylpyridin-3-yl)methyl]-N-[(4R)-1-methyl-1H,4H,5H,6H-cyclopenta[d]imidazol-4-yl]furan-3-carboxamide | 5-[(6-{3-Azabicyclo[3.1.0]hexan-3-yl}-2-methylpyridin-3-yl)methyl]furan-3-carboxylic acid |
| 183 | 5-[(6-{3-Azabicyclo[3.1.0]hexan-3-yl}-2-ethylpyridin-3-yl)methyl]-N-[(4R)-1-methyl-1H,4H,5H,6H-cyclopenta[d]imidazol-4-yl]thiophene-2-carboxamide | 5-[(6-{3-Azabicyclo[3.1.0]hexan-3-yl}-2-ethylpyridin-3-yl)methyl]thiophene-2-carboxylic acid |
| 184 | 5-[(6-{6,6-Difluoro-3-azabicyclo[3.1.0]hexan-3-yl}-2-ethylpyridin-3-yl)methyl]-N-[(4R)-1-methyl-1H,4H,5H,6H-cyclopenta[d]imidazol-4-yl]thiophene-2-carboxamide | 5-[(6-{6,6-Difluoro-3-azabicyclo[3.1.0]-hexan-3-yl}-2-ethylpyridin-3-yl)-methyl]thiophene-2-carboxylic acid |
| 185 | 5-[(6-{6,6-Difluoro-3-azabicyclo[3.1.0]hexan-3-yl}-2-(hydroxymethyl)pyridin-3-yl)methyl]-N-[(4R)-1-methyl-1H,4H,5H,6H-cyclopenta-[d]imidazol-4-yl]thiophene-2-carboxamide | 5-[(6-{6,6-Difluoro-3-azabicyclo-[3.1.0]hexan-3-yl}-2-(hydroxymethyl)-pyridin-3-yl)-methyl]thiophene-2-carboxylic acid |
| 186 | 5-[(6-{6,6-difluoro-3-azabicyclo[3.1.0]hexan-3-yl}-2-ethylpyridin-3-yl)methyl]-N-[(4R)-1-methyl-1H,4H,5H,6H-cyclopenta[d]imidazol-4-yl]furan-2-carboxamide | 5-[(6-{6,6-Difluoro-3-azabicyclo-[3.1.0]hexan-3-yl}-2-ethylpyridin-3-yl)methyl]furan-2-carboxylic acid |
| 187 | 5-[(6-{6,6-Difluoro-3-azabicyclo[3.1.0]hexan-3-yl}-2-methylpyridin-3-yl)methyl]-N-[(4R)-1-methyl-1H,4H,5H,6H-cyclopenta[d]imidazol-4-yl]thiophene-2-carboxamide | 5-[(6-{6,6-Difluoro-3-azabicyclo[3.1.0]-hexan-3-yl}-2-methylpyridin-3-yl)-methyl]thiophene-2-carboxylic acid |

-continued

| Example | Name | Name of Starting Material |
|---|---|---|
| 188 | 2-[(6-{6,6-Difluoro-3-azabicyclo[3.1.0]hexan-3-yl}-2-methylpyridin-3-yl)methyl]-N-[(4R)-1-methyl-1H,4H,5H,6H-cyclopenta[d]imidazol-4-yl]-1,3-thiazole-5-carboxamide | 2-[(6-{6,6-Difluoro-3-azabicyclo[3.1.0]-hexan-3-yl}-2-methylpyridin-3-yl)-methyl]-1,3-thiazole-5-carboxylic acid |
| 189 | 5-[(6-{6,6-Difluoro-3-azabicyclo[3.1.0]hexan-3-yl}-2-methylpyridin-3-yl)methyl]-N-[(4R)-1-methyl-1H,4H,5H,6H-cyclopenta[d]imidazol-4-yl]furan-2-carboxamide | 5-[(6-{6,6-Difluoro-3-azabicyclo[3.1.0]-hexan-3-yl}-2-methylpyridin-3-yl)-methyl]furan-2-carboxylic acid |
| 190 | 1-[(4-{3-Azabicyclo[3.1.0]hexan-3-yl}-3-cyanophenyl)methyl]-N-[(4R)-1-methyl-1H,4H,5H,6H-cyclopenta[d]imidazol-4-yl]-1H-pyrazole-4-carboxamide | 1-[(4-{3-Azabicyclo[3.1.0]hexan-3-yl}-3-cyanophenyl)methyl]-1H-pyrazole-4-carboxylic acid |
| 191 | 1-[(4-{3-Azabicyclo[3.1.0]hexan-3-yl}-3,5-difluorophenyl)methyl]-N-[(4R)-1-methyl-1H,4H,5H,6H-cyclopenta[d]imidazol-4-yl]-1H-pyrazole-4-carboxamide | 1-[(4-{3-Azabicyclo[3.1.0]hexan-3-yl}-3,5-difluorophenyl)methyl]-1H-pyrazole-4-carboxylic acid |
| 192 | 2-[(4-{3-azabicyclo[3.1.0]hexan-3-yl}-3,5-difluorophenyl)methyl]-N-[(4R)-1-methyl-1H,4H,5H,6H-cyclopenta[d]imidazol-4-yl]-1H-imidazole-4-carboxamide | 2-[(4-{3-azabicyclo[3.1.0]hexan-3-yl}-3,5-difluorophenyl)methyl]-1H-imidazole-4-carboxylic acid |
| 193 | 1-[(4-{3-azabicyclo[3.1.0]hexan-3-yl}-3-cyano-2-methylphenyl)methyl]-N-[(4R)-1-methyl-1H,4H,5H,6H-cyclopenta[d]imidazol-4-yl]-1H-pyrazole-4-carboxamide | 1-[(4-{3-azabicyclo[3.1.0]hexan-3-yl}-3-cyano-2-methylphenyl)methyl]-1H-pyrazole-4-carboxylic acid |
| 194 | 1-[(4-{3-azabicyclo[3.1.0]hexan-3-yl}-3-cyano-2-methylphenyl)methyl]-N-[(4R)-1-methyl-1H,4H,5H,6H-cyclopenta[d]imidazol-4-yl]-1H-imidazole-4-carboxamide | 1-[(4-{3-azabicyclo[3.1.0]hexan-3-yl}-3-cyano-2-methylphenyl)methyl]-1H-imidazole-4-carboxylic acid |
| 195 | 1-[(4-{3-azabicyclo[3.1.0]hexan-3-yl}-3-cyano-5-fluorophenyl)methyl]-N-[(4R)-1-methyl-1H,4H,5H,6H-cyclopenta[d]imidazol-4-yl]-1H-pyrazole-4-carboxamide | 1-[(4-{3-azabicyclo[3.1.0]hexan-3-yl}-3-cyano-5-fluorophenyl)methyl]-1H-pyrazole-4-carboxylic acid |
| 196 | 1-[(4-{3-azabicyclo[3.1.0]hexan-3-yl}-3-cyanophenyl)methyl]-N-[(4R)-1-methyl-1H,4H,5H,6H-cyclopenta[d]imidazol-4-yl]-1H-imidazole-4-carboxamide | 1-[(4-{3-azabicyclo[3.1.0]hexan-3-yl}-3-cyanophenyl)methyl]-1H-imidazole-4-carboxylic acid |
| 197 | 1-[(4-{3-azabicyclo[3.1.0]hexan-3-yl}-3,5-dicyanophenyl)methyl]-N-[(4R)-1-methyl-1H,4H,5H,6H-cyclopenta[d]imidazol-4-yl]-1H-pyrazole-4-carboxamide | 1-[(4-{3-azabicyclo[3.1.0]hexan-3-yl}-3,5-dicyanophenyl)methyl]-1H-pyrazole-4-carboxylic acid |
| 198 | 1-[(4-{3-azabicyclo[3.1.0]hexan-3-yl}-3-cyano-2-fluorophenyl)methyl]-N-[(4R)-1-methyl-1H,4H,5H,6H-cyclopenta[d]imidazol-4-yl]-1H-pyrazole-4-carboxamide | 1-[(4-{3-azabicyclo[3.1.0]hexan-3-yl}-3-cyano-2-fluorophenyl)methyl]-1H-pyrazole-4-carboxylic acid |
| 199 | 1-[(4-{6,6-difluoro-3-azabicyclo[3.1.0]hexan-3-yl}-2-methylphenyl)methyl]-N-[(4R)-1-methyl-1H,4H,5H,6H-cyclopenta[d]imidazol-4-yl]-1H-pyrazole-4-carboxamide | 1-[(4-{6,6-difluoro-3-azabicyclo[3.1.0]-hexan-3-yl}-2-methylphenyl)methyl]-1H-pyrazole-4-carboxylic acid |
| 200 | 1-[(4-{3-azabicyclo[3.1.0]hexan-3-yl}-5-cyano-2-methylphenyl)methyl]-N-[(4R)-1-methyl-1H,4H,5H,6H-cyclopenta[d]imidazol-4-yl]-1H-pyrazole-4-carboxamide | 1-[(4-{3-azabicyclo[3.1.0]hexan-3-yl}-5-cyano-2-methylphenyl)methyl]-1H-pyrazole-4-carboxylic acid |
| 201 | 1-[(4-{3-azabicyclo[3.1.0]hexan-3-yl}-3-cyano-2-fluorophenyl)methyl]-N-[(4R)-1-methyl-1H,4H,5H,6H-cyclopenta[d]imidazol-4-yl]-1H-imidazole-4-carboxamide | 1-[(4-{3-azabicyclo[3.1.0]hexan-3-yl}-3-cyano-2-fluorophenyl)methyl]-1H-imidazole-4-carboxylic acid |
| 202 | 1-[(4-{3-azabicyclo[3.1.0]hexan-3-yl}-2-chloro-3-cyanophenyl)methyl]-N-[(4R)-1-methyl-1H,4H,5H,6H-cyclopenta[d]imidazol-4-yl]-1H-pyrazole-4-carboxamide | 1-[(4-{3-azabicyclo[3.1.0]hexan-3-yl}-2-chloro-3-cyanophenyl)methyl]-1H-pyrazole-4-carboxylic acid |
| 203 | 1-[(4-{3-azabicyclo[3.1.0]hexan-3-yl}-2-chloro-3-cyanophenyl)methyl]-N-[(4R)-1-methyl-1H,4H,5H,6H-cyclopenta[d]imidazol-4-yl]-1H-imidazole-4-carboxamide | 1-[(4-{3-azabicyclo[3.1.0]hexan-3-yl}-2-chloro-3-cyanophenyl)methyl]-1H-imidazole-4-carboxylic acid |
| 204 | 1-[(4-{3-azabicyclo[3.1.0]hexan-3-yl}-2-bromophenyl)methyl]-N-[(4R)-1-methyl-1H,4H,5H,6H-cyclopenta[d]imidazol-4-yl]-1H-imidazole-4-carboxamide | 1-[(4-{3-azabicyclo[3.1.0]hexan-3-yl}-2-bromophenyl)methyl]-1H-imidazole-4-carboxylic acid |
| 205 | 1-[(4-{3-azabicyclo[3.1.0]hexan-3-yl}-2-methylphenyl)methyl]-N-[(4R)-1-methyl-1H,4H,5H,6H-cyclopenta[d]imidazol-4-yl]-1H-imidazole-4-carboxamide | 1-[(4-{3-azabicyclo[3.1.0]hexan-3-yl}-2-methylphenyl)methyl]-1H-imidazole-4-carboxylic acid |
| 206 | 1-[(4-{3-azabicyclo[3.1.0]hexan-3-yl}-2-cyanophenyl)methyl]-N-[(4R)-1-methyl-1H,4H,5H,6H-cyclopenta[d]imidazol-4-yl]-1H-imidazole-4-carboxamide | 1-[(4-{3-azabicyclo[3.1.0]hexan-3-yl}-2-cyanophenyl)methyl]-1H-imidazole-4-carboxylic acid |
| 207 | 1-[(4-{3-azabicyclo[3.1.0]hexan-3-yl}-2-(hydroxymethyl)-phenyl)methyl]-N-[(4R)-1-methyl-1H,4H,5H,6H-cyclopenta[d]imidazol-4-yl]-1H-imidazole-4-carboxamide | 1-[(4-{3-azabicyclo[3.1.0]hexan-3-yl}-2-(hydroxymethyl)phenyl)methyl]-1H-imidazole-4-carboxylic acid |
| 208 | 1-[(2-cyano-4-{6,6-difluoro-3-azabicyclo-[3.1.0]hexan-3-yl}phenyl)methyl]-N-[(4R)-1-methyl-1H,4H,5H,6H-cyclopenta[d]imidazol-4-yl]-1H-pyrazole-4-carboxamide | 1-[(2-cyano-4-{6,6-difluoro-3-aza-bicyclo[3.1.0]hexan-3-yl}phenyl)methyl]-1H-pyrazole-4-carboxylic acid |
| 209 | 1-[(2-bromo-4-{6,6-difluoro-3-azabicyclo-[3.1.0]hexan-3-yl}phenyl)methyl]-N-[(4R)-1-methyl-1H,4H,5H,6H-cyclopenta[d]imidazol-4-yl]-1H-pyrazole-4-carboxamide | 1-[(2-bromo-4-{6,6-difluoro-3-aza-bicyclo[3.1.0]hexan-3-yl}phenyl)methyl]-1H-pyrazole-4-carboxylic acid |
| 210 | 1-[(2-cyano-4-{6,6-difluoro-3-azabicyclo-[3.1.0]hexan-3-yl}phenyl)methyl]-N-[(4R)-1-methyl-1H,4H,5H,6H-cyclopenta[d]imidazol-4-yl]-1H-imidazole-4-carboxamide | 1-[(2-cyano-4-{6,6-difluoro-3-aza-bicyclo[3.1.0]hexan-3-yl}phenyl)methyl]-1H-imidazole-4-carboxylic acid |
| 211 | 1-[(2-chloro-4-{6,6-difluoro-3-azabicyclo-[3.1.0]hexan-3-yl}phenyl)methyl]-N-[(4R)-1-methyl-1H,4H,5H,6H-cyclopenta[d]imidazol-4-yl]-1H-imidazole-4-carboxamide | 1-[(2-chloro-4-{6,6-difluoro-3-aza-bicyclo[3.1.0]hexan-3-yl}phenyl)methyl]-1H-imidazole-4-carboxylic acid |
| 212 | 1-[(4-{6,6-difluoro-3-azabicyclo[3.1.0]hexan-3-yl}-2-fluorophenyl)methyl]-N-[(4R)-1-methyl-1H,4H,5H,6H-cyclopenta[d]imidazol-4-yl]-1H-imidazole-4-carboxamide | 1-[(4-{6,6-difluoro-3-azabicyclo[3.1.0]-hexan-3-yl}-2-fluorophenyl)methyl]-1H-imidazole-4-carboxylic acid |

-continued

| Example | Name | Name of Starting Material |
|---|---|---|
| 213 | 1-[(4-{6,6-difluoro-3-azabicyclo[3.1.0]hexan-3-yl}-2-fluorophenyl)methyl]-N-[(4R)-1-methyl-1H,4H,5H,6H-cyclopenta[d]imidazol-4-yl]-1H-pyrazole-4-carboxamide | 1-[(4-{6,6-difluoro-3-azabicyclo[3.1.0]-hexan-3-yl}-2-fluorophenyl)methyl]-1H-pyrazole-4-carboxylic acid |

Example 214

1-[(2-{3-Azabicyclo[3.1.0]hexan-3-yl}-4-(hydroxymethyl)pyrimidin-5-yl)methyl]-N-[(4R)-1-methyl-1H,4H,5H,6H-cyclopenta[d]imidazol-4-yl]-1H-imidazole-4-carboxamide

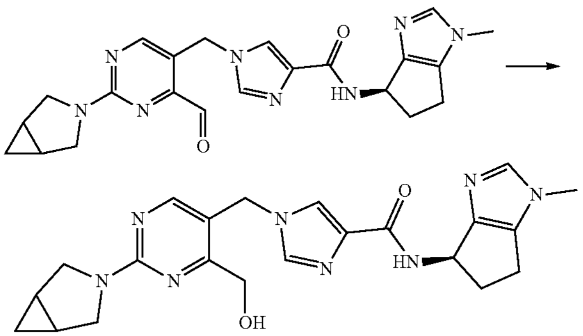

To a mixture of 1-[(2-{3-azabicyclo[3.1.0]hexan-3-yl}-4-formylpyrimidin-5-yl)methyl]-N-[(4R)-1-methyl-1H,4H,5H,6H-cyclopenta[d]imidazol-4-yl]-1H-imidazole-4-carboxamide (24 mg) in THF (2 mL) is added $NaBH_4$. The mixture is stirred for 12 h at rt and then treated with aqueous HCl (1 M, 500 μL). After stirring for 10 minutes aqueous NaOH (1 M, 500 μL) is added. The mixture is diluted with MeOH and purified by HPLC on reversed phase (ACN, water) to give the title compound. LC (Method 1): $t_R$=0.78 min; Mass spectrum ($ESI^+$): m/z=435 $[M+H]^+$.

Example 215

1-[(6-{6,6-Difluoro-3-azabicyclo[3.1.0]hexan-3-yl}-2-(1-hydroxyethyl)pyridin-3-yl)methyl]-N-[(4R)-1-methyl-1H,4H,5H,6H-cyclopenta[d]imidazol-4-yl]-1H-1,2,3-triazole-4-carboxamide

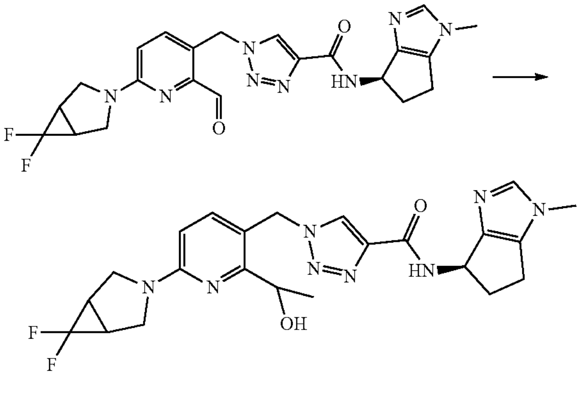

$CH_3MgBr$ (3 M in THF, 92 μL) is added dropwise under argon atmosphere to an ice-cooled mixture of 1-[(6-{6,6-difluoro-3-azabicyclo[3.1.0]hexan-3-yl}-2-formylpyridin-3-yl)methyl]-N-[(4R)-1-methyl-1H,4H,5H,6H-cyclopenta[d]imidazol-4-yl]-1H-1,2,3-triazole-4-carboxamide (13 mg) in THF (5 mL). The mixture is stirred for 12 h while warming to rt. Then the mixture is partitioned between saturated aqueous $NH_4Cl$ and EtOAc. The aqueous phase is extracted with EtOAc. The combined organic phases are dried ($Na_2SO_4$), concentrated in vacuo and the residue is purified by HPLC on reversed phase (ACN, water) to give the title compound.

LC (Method 1): $t_R$=0.88 min; Mass spectrum ($ESI^+$): m/z=485 $[M+H]^+$.

Example 216

1-[(6-{3-Azabicyclo[3.1.0]hexan-3-yl}-2-methylpyridin-3-yl)methyl]-3-(2-hydroxyethyl)-N-[(4R)-1-methyl-1H,4H,5H,6H-cyclopenta[d]imidazol-4-yl]-1H-pyrazole-4-carboxamide

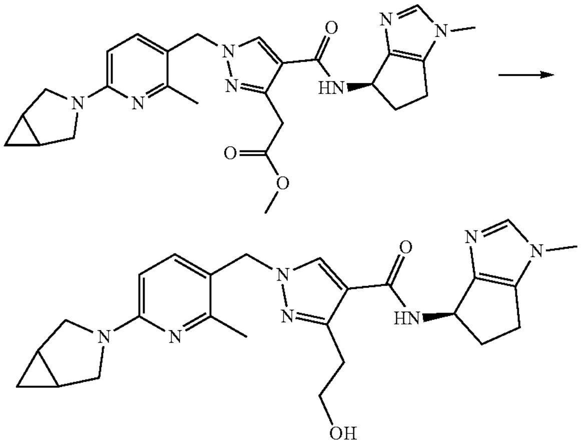

$LiAlH_4$ (1 M in THF, 200 μL) is added dropwise under argon atmosphere to a −78° C. cold mixture of methyl 2-{1-[(6-{3-azabicyclo[3.1.0]hexan-3-yl}-2-methylpyridin-3-yl)methyl]-4-{[(4R)-1-methyl-1H,4H,5H,6H-cyclopenta[d]imidazol-4-yl]carbamoyl}-1H-pyrazol-3-yl}acetate (90 mg) in THF (1 mL). The mixture is stirred for 12 h while warming to rt. To the mixture are successively added water (14 μL), aqueous NaOH (4 M, 14 μL) and again water (14 μL). After vigorous stirring for 15 minutes the mixture is filtered over celite and the filter cake is washed with THF. The combined filtrates are concentrated in vacuo and the residue is purified by HPLC on reversed phase (ACN, water) to give the title compound. LC (Method 2): $t_R$=0.66 min; Mass spectrum ($ESI^+$): m/z=462 $[M+H]^+$.

Example 217

1-[(6-{3-Azabicyclo[3.1.0]hexan-3-yl}-2-methylpyridin-3-yl)methyl]-3-(hydroxymethyl)-N-[(4R)-1-methyl-1H,4H,5H,6H-cyclopenta[d]imidazol-4-yl]-1H-pyrazole-4-carboxamide

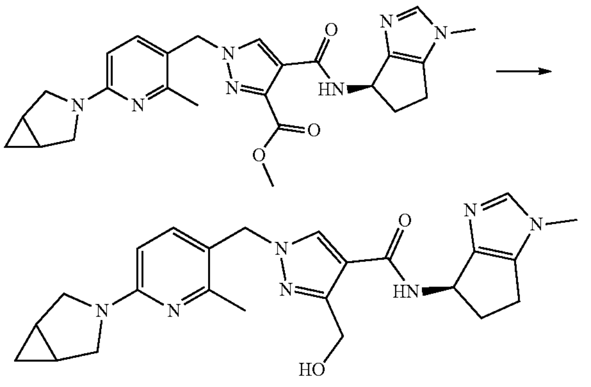

$LiAlH_4$ (1 M in THF, 200 μL) is added dropwise under argon atmosphere to an ice-cooled mixture of methyl 1-[(6-{3-azabicyclo[3.1.0]hexan-3-yl}-2-methylpyridin-3-yl)methyl]-4-{[(4R)-1-methyl-1H,4H,5H,6H-cyclopenta[d]imidazol-4-yl]carbamoyl}-1H-pyrazole-3-carboxylate (25 mg) in THF (2 mL). The mixture is stirred for 30 minutes. To the mixture are successively added water (50 NL) and aqueous NaOH (4 M, 25 μL). After vigorous stirring for 15 minutes the mixture is filtered over celite and the filter cake is washed with THF. The combined filtrates are concentrated in vacuo and the residue is purified by HPLC on reversed phase (ACN, water) to give the title compound. LC (Method 1): $t_R$=0.89 min; Mass spectrum ($ESI^+$): m/z=448 $[M+H]^+$.

Example 218

1-[(2-{6,6-Difluoro-3-azabicyclo[3.1.0]hexan-3-yl}-4-methylpyrimidin-5-yl)methyl]-N-[(4R)-1-methyl-1H,4H,5H,6H-cyclopenta[d]imidazol-4-yl]-1H-pyrazole-4-carboxamide

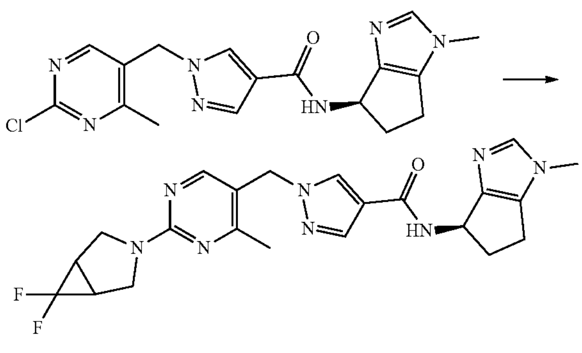

A mixture of 1-[(2-chloro-4-methylpyrimidin-5-yl)methyl]-N-[(4R)-1-methyl-1H,4H,5H,6H-cyclopenta[d]imidazol-4-yl]-1H-pyrazole-4-carboxamide (33 mg), 6,6-difluoro-3-azabicyclo[3.1.0]hexane hydrochloride (27 mg) and DIPEA (75 μL) in DMSO (1 mL) is stirred for 8 h at 60° C. After cooling to rt the mixture is diluted with DMSO and purified by HPLC on reversed phase (ACN, water) to give the title compound.

LC (Method 1): $t_R$=0.86 min; Mass spectrum (ESI+): m/z=454 $[M+H]^+$.

Example 219

3-[(6-{3-Azabicyclo[3.1.0]hexan-3-yl}-2-(methoxymethyl)pyridin-3-yl)methyl]-N-[(4R)-1-methyl-1H,4H,5H,6H-cyclopenta[d]imidazol-4-yl]-1H-pyrazole-5-carboxamide

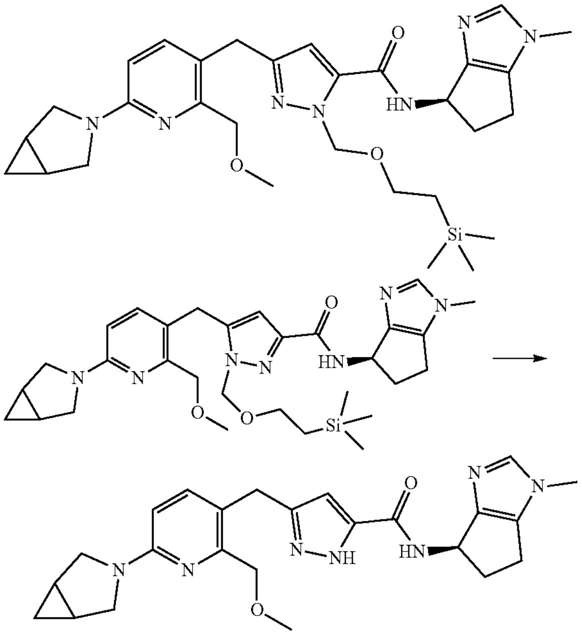

3-[(6-{3-Azabicyclo[3.1.0]hexan-3-yl}-2-(methoxymethyl)pyridin-3-yl)methyl]-N-[(4R)-1-methyl-1H,4H,5H,6H-cyclopenta[d]imidazol-4-yl]-1-{[2-(trimethylsilyl)ethoxy]methyl}-1H-pyrazole-5-carboxamide and 5-[(6-{3-azabicyclo[3.1.0]hexan-3-yl}-2-(methoxymethyl)pyridin-3-yl)methyl]-N-[(4R)-1-methyl-1H,4H,5H,6H-cyclopenta[d]imidazol-4-yl]-1-{[2-(trimethylsilyl)ethoxy]methyl}-1H-pyrazole-3-carboxamide (mixture of isomers) (20 mg) are dissolved in DCM (3 mL). Trifluoroacetic acid (1 mL) is added and the mixture is stirred for 12 h at rt. The mixture is then concentrated in vacuo, dissolved in MeOH (1 mL) and treated with $NH_3$ (7 M in MeOH, 3 mL). The mixture is heated for 12 h to 80° C. in a sealed microwave vial. After cooling to rt the mixture is concentrated in vacuo and the residue is purified by HPLC on reversed phase (ACN, water) to give the title compound.

LC (Method 1): $t_R$=0.91 min; Mass spectrum (ESI+): m/z=448 $[M+H]^+$.

Example 220 is prepared in analogy to Intermediate 219:

| Example | Structure | $t_R$ | Mass spectrum (ESI+): m/z $[M + H]^+$ | LC Method |
|---|---|---|---|---|
| 220 | 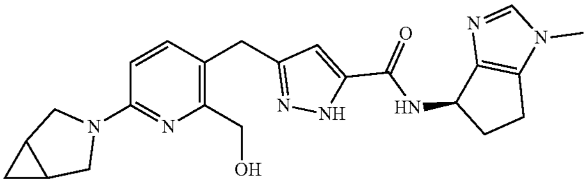 [SMILES: Cn1cnc2c1CC[C@H]2NC(=O)c1cc(Cc2ccc(N3CC4CC4C3)nc2CO)n[nH]1] | 0.87 | 434 | Method 1 |

| Example | Name | Name of Starting Material |
|---|---|---|
| 220 | 3-[(6-{3-Azabicyclo[3.1.0]hexan-3-yl}-2-(hydroxymethyl)pyridin-3-yl)methyl]-N-[(4R)-1-methyl-1H,4H,5H,6H-cyclopenta[d]imidazol-4-yl]-1H-pyrazole-5-carboxamide | 3-[(6-{3-Azabicyclo[3.1.0]hexan-3-yl}-2-(hydroxymethyl)pyridin-3-yl)methyl]-N-[(4R)-1-methyl-1H,4H,5H,6H-cyclopenta[d]imidazol-4-yl]-1-{[2-(trimethylsilyl)ethoxy]methyl}-1H-pyrazole-5-carboxamide and 5-[(6-{3-Azabicyclo[3.1.0]hexan-3-yl}-2-(hydroxymethyl)pyridin-3-yl)methyl]-N-[(4R)-1-methyl-1H,4H,5H,6H-cyclopenta[d]imidazol-4-yl]-1-{[2-(trimethylsilyl)ethoxy]methyl}-1H-pyrazole-3-carboxamide (mixture of isomers) |

Example 221

1-[(6-{6,6-Difluoro-3-azabicyclo[3.1.0]hexan-3-yl}-2-methoxypyridin-3-yl)methyl]-N-[(4R)-1-methyl-1H,4H,5H,6H-cyclopenta[d]imidazol-4-yl]-1H-pyrazole-4-carboxamide

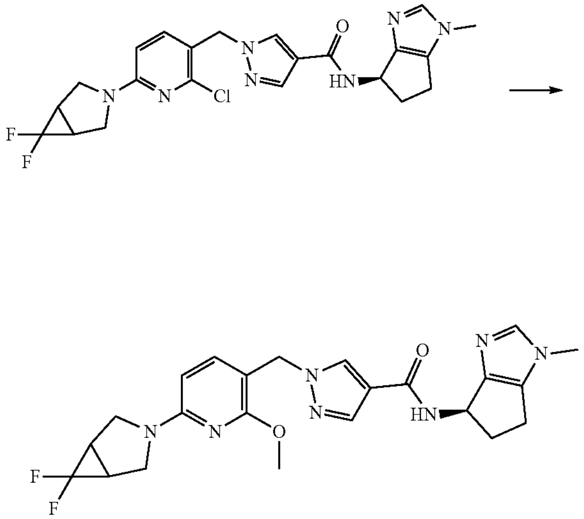 [SMILES: Cn1cnc2c1CC[C@H]2NC(=O)c1cnn(Cc2ccc(N3CC4C(C3)C4(F)F)nc2Cl)c1 ; COc1nc(N2CC3C(C2)C3(F)F)ccc1Cn1cc(C(=O)N[C@@H]2CCc3c2ncn3C)cn1]

A mixture of 1-[(2-chloro-6-{6,6-difluoro-3-azabicyclo[3.1.0]hexan-3-yl}pyridin-3-yl)methyl]-N-[(4R)-1-methyl-1H,4H,5H,6H-cyclopenta[d]imidazol-4-yl]-1H-pyrazole-4-carboxamide (50 mg) and $NaOCH_3$ (1 M in MeOH, 2 mL) is heated in a sealed microwave vial to 165° C. for 6 h. After cooling to rt the mixture is purified by HPLC on reversed phase (ACN, water) to give the title compound. LC (Method 2): $t_R$=0.86 min; Mass spectrum (ESI+): m/z=470 $[M+H]^+$.

Example 222

1-[(2-{5-Azaspiro[2.3]hexan-5-yl}-4-methylpyrimidin-5-yl)methyl]-N-[(4R)-1-methyl-1H,4H,5H,6H-cyclopenta[d]imidazol-4-yl]-1H-pyrazole-4-carboxamide

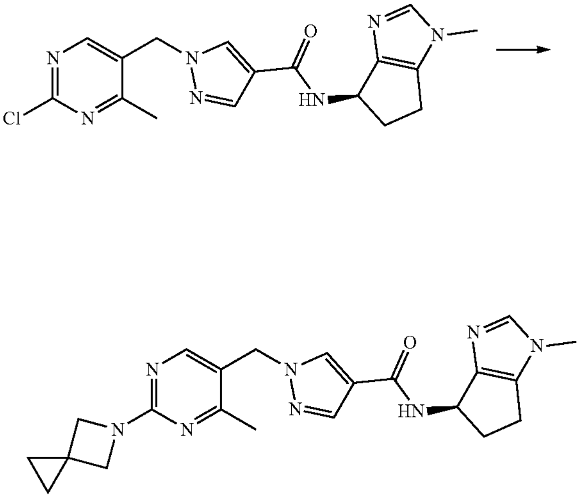

A mixture of 1-[(2-chloro-4-methylpyrimidin-5-yl)methyl]-N-[(4R)-1-methyl-1H,4H,5H,6H-cyclopenta[d]imidazol-4-yl]-1H-pyrazole-4-carboxamide (40 mg), DIPEA (100 μL) and 5-azaspiro[2.3]hexane; trifluoroacetate (32 mg) in DMSO (2 mL) is stirred at 60° C. for 16 h. The mixture is purified by HPLC on reversed phase (ACN, water) to give the title compound. LC (Method 5): $t_R$=0.56 min; Mass spectrum ($ESI^+$): m/z=419 $[M+H]^+$.

Examples 223 to 240 are prepared in analogy to example 222:

| Example | Structure | $t_R$ | Mass spectrum (ESI+): m/z $[M + H]^+$ | LC Method |
| --- | --- | --- | --- | --- |
| 223 | 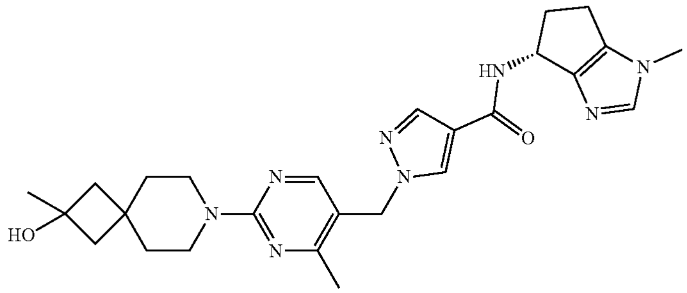 [SMILES: Cc1nc(N2CCC3(CC2)CC(C)(O)C3)ncc1Cn1cc(C(=O)N[C@@H]2CCc3c2ncn3C)cn1] | 0.58 | 491 | Method 5 |
| 224 | 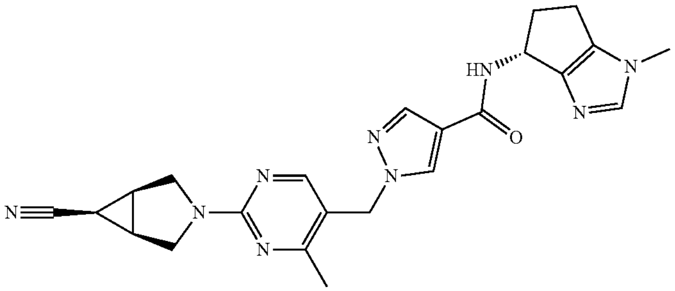 [SMILES: Cc1nc(N2C[C@@H]3[C@H](C#N)[C@@H]3C2)ncc1Cn1cc(C(=O)N[C@@H]2CCc3c2ncn3C)cn1] | 0.51 | 444 | Method 5 |
| 225 | 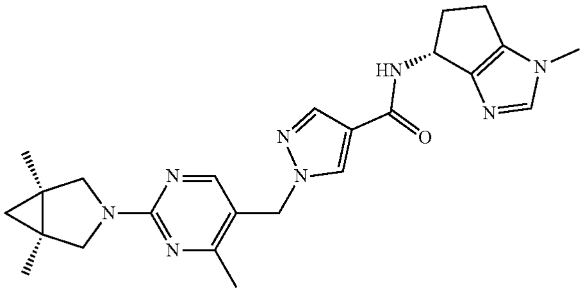 [SMILES: Cc1nc(N2C[C@@]3(C)C[C@@]3(C)C2)ncc1Cn1cc(C(=O)N[C@@H]2CCc3c2ncn3C)cn1] | 0.73 | 447 | Method 5 |
| 226 | 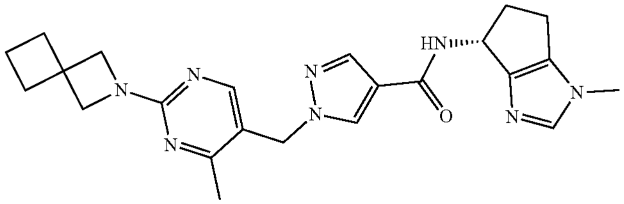 [SMILES: Cc1nc(N2CC3(CCC3)C2)ncc1Cn1cc(C(=O)N[C@@H]2CCc3c2ncn3C)cn1] | 0.62 | 433 | Method 5 |
| 227 | 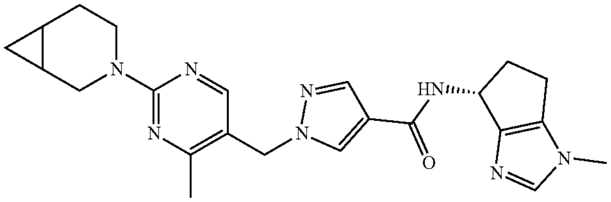 [SMILES: Cc1nc(N2CCC3CC3C2)ncc1Cn1cc(C(=O)N[C@@H]2CCc3c2ncn3C)cn1] | 0.69 | 433 | Method 5 |

-continued
| Example | Structure | $t_R$ | Mass spectrum (ESI+): m/z $[M + H]^+$ | LC Method |
|---|---|---|---|---|
| 228 | 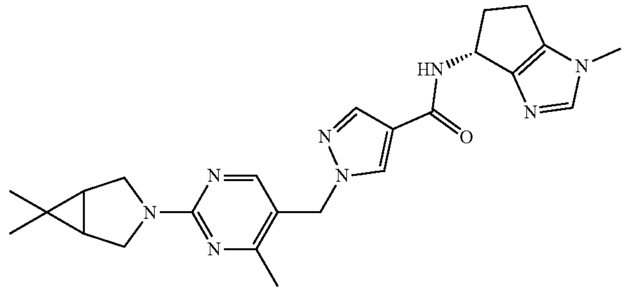 | 0.72 | 447 | Method 5 |
| 229 | 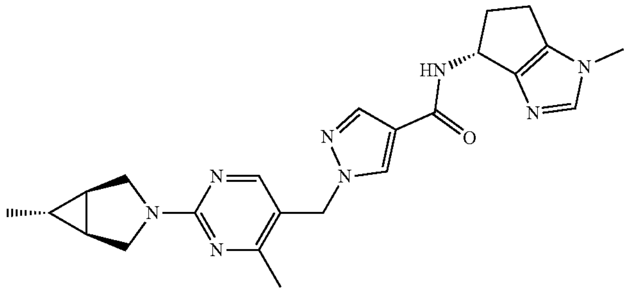 | 0.67 | 433 | Method 5 |
| 230 | 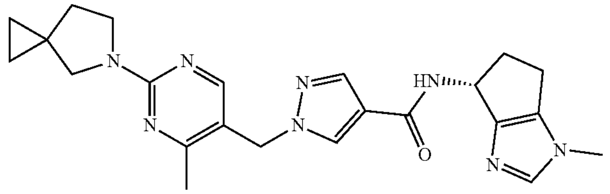 [SMILES: Cc1nc(N2CCC3(CC3)C2)ncc1Cn1cc(C(=O)N[C@@H]2CCc3c2ncn3C)cn1] | 0.65 | 433 | Method 5 |
| 231 | 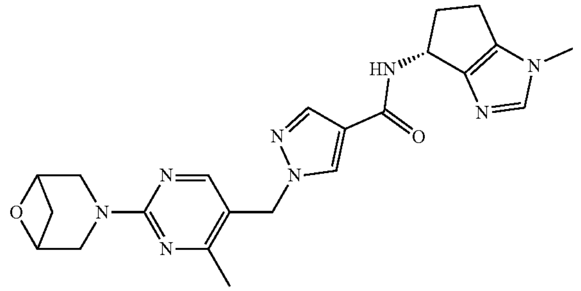 [SMILES: Cc1nc(N2CC3CC(C2)O3)ncc1Cn1cc(C(=O)N[C@@H]2CCc3c2ncn3C)cn1] | 0.46 | 435 | Method 5 |
| 232 | 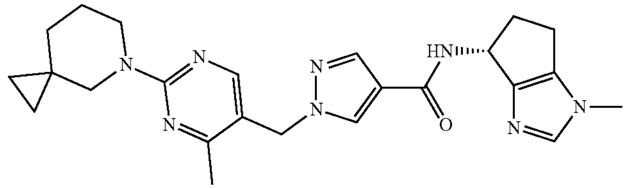 [SMILES: Cc1nc(N2CCCC3(CC3)C2)ncc1Cn1cc(C(=O)N[C@@H]2CCc3c2ncn3C)cn1] | 0.75 | 447 | Method 5 |

-continued
| Example | Structure | $t_R$ | Mass spectrum (ESI+): m/z $[M + H]^+$ | LC Method |
|---|---|---|---|---|
| 233 | 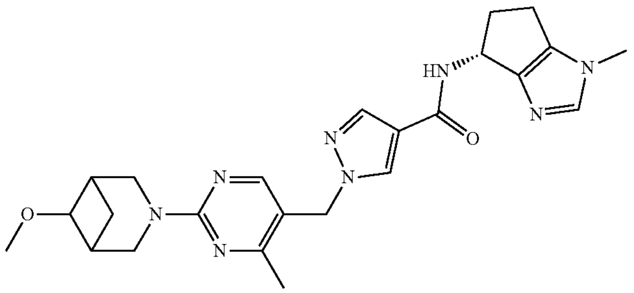 | 0.61 | 463 | Method 5 |
| 234 | 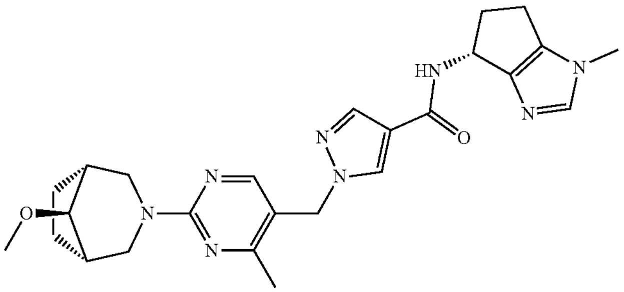 | 0.67 | 477 | Method 5 |
| 235 | 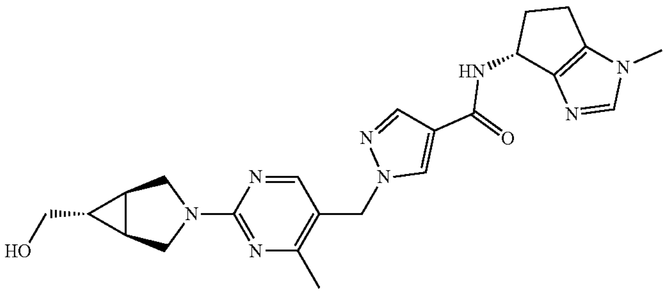 [SMILES: Cc1nc(N2C[C@@H]3[C@@H](CO)[C@@H]3C2)ncc1Cn1cc(C(=O)N[C@@H]2CCc3c2ncn3C)cn1] | 0.44 | 449 | Method 5 |
| 236 | 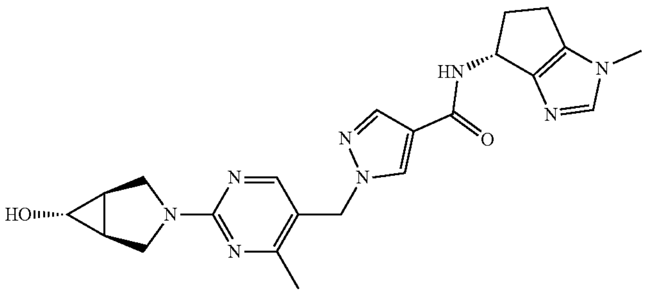 [SMILES: Cc1nc(N2C[C@@H]3[C@@H](O)[C@@H]3C2)ncc1Cn1cc(C(=O)N[C@@H]2CCc3c2ncn3C)cn1] | 0.42 | 435 | Method 5 |
| 237 | 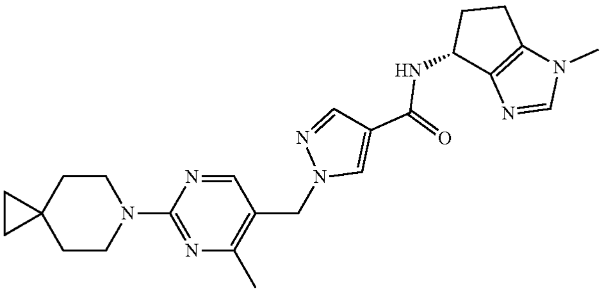 [SMILES: Cc1nc(N2CCC3(CC2)CC3)ncc1Cn1cc(C(=O)N[C@@H]2CCc3c2ncn3C)cn1] | 0.76 | 447 | Method 5 |

-continued

| Example | Structure | $t_R$ | Mass spectrum (ESI+): m/z [M + H]+ | LC Method |
|---|---|---|---|---|
| 238 | 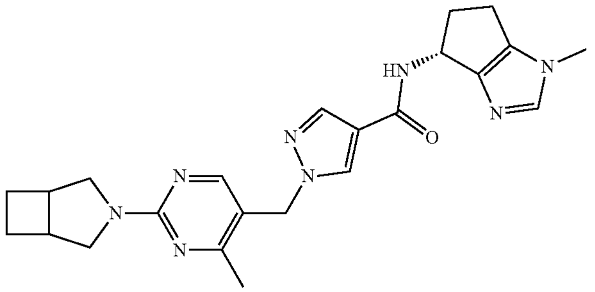 [SMILES: Cc1nc(N2CC3CCC3C2)ncc1Cn1cc(C(=O)N[C@@H]2CCc3c2ncn3C)cn1] | 0.67 | 433 | Method 5 |
| 239 | 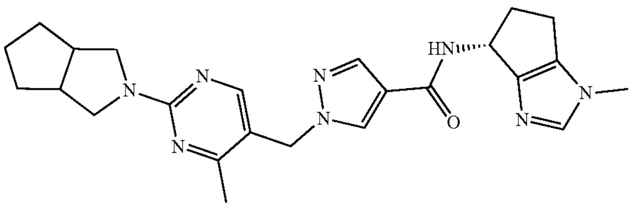 [SMILES: Cc1nc(N2CC3CCCC3C2)ncc1Cn1cc(C(=O)N[C@@H]2CCc3c2ncn3C)cn1] | 0.71 | 447 | Method 5 |
| 240 | 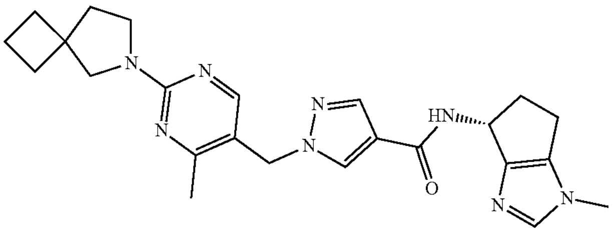 [SMILES: Cc1nc(N2CCC3(CCC3)C2)ncc1Cn1cc(C(=O)N[C@@H]2CCc3c2ncn3C)cn1] | 0.71 | 447 | Method 5 |

| Example | Name | Name of Starting Material |
|---|---|---|
| 223 | 1-[(2-{2-Hydroxy-2-methyl-7-azaspiro[3.5]nonan-7-yl}-4-methylpyrimidin-5-yl)methyl]-N-[(4R)-1-methyl-1H,4H,5H,6H-cyclopenta[d]imidazol-4-yl]-1H-pyrazole-4-carboxamide | 2-Methyl-7-azaspiro[3.5]nonan-2-ol hydrochloride |
| 224 | 1-({2-[(1R,5S,6S)-6-Cyano-3-azabicyclo[3.1.0]Lhexan-3-yl]-4-methylpyrimidin-5-yl}methyl)-N-[(4R)-1-methyl-1H,4H,5H,6H-cyclopenta[d]imidazol-4-yl]-1H-pyrazole-4-carboxamide | (1R,5S,6S)-3-Azabicyclo[3.1.0] hexane-6-carbonitrile hydrochloride |
| 225 | 1-({2-[(1R,5S)-1,5-Dimethyl-3-azabicyclo[3.1.0]hexan-3-yl]-4-methylpyrimidin-5-yl}methyl)-N-[(4R)-1-methyl-1H,4H,5H,6H-cyclopenta[d]imidazol-4-yl]-1H-pyrazole-4-carboxamide | (1R,5S)-1,5-Dimethyl-3-azabicyclo[3.1.0]hexane hydrochloride |
| 226 | 1-[(2-{2-Azaspiro[3.3]heptan-2-yl}-4-methylpyrimidin-5-yl)methyl]-N-[(4R)-1-methyl-1H,4H,5H,6H-cyclopenta[d]imidazol-4-yl]-1H-pyrazole-4-carboxamide | Bis(2-azaspiro[3.3]heptane) oxalic acid |
| 227 | 1-[(2-{3-Azabicyclo[4.1.0]heptan-3-yl]-4-methylpyrimidin-5-yl)methyl]-N-[(4R)-1-methyl-1H,4H,5H,6H-cyclopenta[d]imidazol-4-yl]-1H-pyrazole-4-carboxamide | 3-Azabicyclo[4.1.0]heptane hydrochloride |
| 228 | 1-[(2-{6,6-Dimethyl-3-azabicyclo[3.1.0]hexan-3-yl}-4-methylpyrimidin-5-yl)methyl]-N-[(4R)-1-methyl-1H,4H,5H,6H-cyclopenta[d]imidazol-4-yl]-1H-pyrazole-4-carboxamide | 6,6-Dimethyl-3-azabicyclo[3.1.0]hexane |
| 229 | N-[(4R)-1-Methyl-1H,4H,5H,6H-cyclopenta[d]imidazol-4-yl]-1-({4-methyl-2-[(1R,5S,6R)-6-methyl-3-azabicyclo[3.1.0]hexan-3-yl]pyrimidin-5-yl}methyl)-1H-pyrazole-4-carboxamide | (1R,5S,6R)-6-Methyl-3-azabicyclo-[3.1.0]hexanehydrochloride (Obtained by separation of the diastereomers of tert-butyl 6-methyl-3-azabicyclo[3.1.0]hexane-3-carboxylate by standard RP chromatography and cleavage of the protecting group with HCl in EtOAc) |
| 230 | 1-[(2-{5-Azaspiro[2.4]heptan-5-yl}-4-methylpyrimidin-5-yl)methyl]-N-[(4R)-1-methyl-1H,4H,5H,6H-cyclopenta[d]imidazol-4-yl]-1H-pyrazole-4-carboxamide | 5-Azaspiro[2.4]heptane hydrochloride |
| 231 | N-[(4R)-1-Methyl-1H,4H,5H,6H-cyclopenta[d]imidazol-4-yl]-1-[(4-methyl-2-{6-oxa-3-azabicyclo[3.1.1]heptan-3-yl}pyrimidin-5-yl)methyl]-1H-pyrazole-4-carboxamide | 6-Oxa-3-azabicyclo[3.1.1]heptane; 4-methylbenzene-1-sulfonic acid |

-continued

| Example | Name | Name of Starting Material |
|---|---|---|
| 232 | 1-[(2-{5-Azaspiro[2.5]octan-5-yl}-4-methylpyrimidin-5-yl)methyl]-N-[(4R)-1-methyl-1H,4H,5H,6H-cyclopenta[d]imidazol-4-yl]-1H-pyrazole-4-carboxamide | 5-Azaspiro[2.5]octane |
| 233 | 1-[(2-{6-Methoxy-3-azabicyclo[3.1.1]heptan-3-yl}-4-methylpyrimidin-5-yl)methyl]-N-[(4R)-1-methyl-1H,4H,5H,6H-cyclopenta[d]imidazol-4-yl]-1H-pyrazole-4-carboxamide | 6-Methoxy-3-azabicyclo [3.1.1]heptane hydrochloride |
| 234 | 1-({2-[(1R,5S,8R)-8-Methoxy-3-azabicyclo[3.2.1]octan-3-yl]-4-methylpyrimidin-5-yl}methyl)-N-[(4R)-1-methyl-1H,4H,5H,6H-cyclopenta[d]imidazol-4-yl]-1H-pyrazole-4-carboxamide | (1R,5S,8S)-8-Methoxy-3-azabicyclo[3.2.1]octane hydrochloride |
| 235 | 1-({2-[(1R,5S,6S)-6-(Hydroxymethyl)-3-azabicyclo[3.1.0]-hexan-3-yl]-4-methylpyrimidin-5-yl}methyl)-N-[(4R)-1-methyl-1H,4H,5H,6H-cyclopenta[d]imidazol-4-yl]-1H-pyrazole-4-carboxamide | [(1R,5S,6S)-3-Azabicyclo[3.1.0]hexan-6-yl]methanol |
| 236 | 1-({2-[(1R,5S,6S)-6-Hydroxy-3-azabicyclo[3.1.0]hexan-3-yl]-4-methylpyrimidin-5-yl}methyl)-N-[(4R)-1-methyl-1H,4H,5H,6H-cyclopenta[d]imidazol-4-yl]-1H-pyrazole-4-carboxamide | (1R,5S,6S)-3-Azabicyclo[3.1.0]hexan-6-ol hydrochloride |
| 237 | 1-[(2-{6-Azaspiro[2.5]octan-6-yl}-4-methylpyrimidin-5-yl)-methyl]-N-[(4R)-1-methyl-1H,4H,5H,6H-cyclopenta[d]imidazol-4-yl]-1H-pyrazole-4-carboxamide | 6-Azaspiro[2.5]octane hydrochloride |
| 238 | 1-[(2-{3-Azabicyclo[3.2.0]heptan-3-yl}-4-methylpyrimidin-5-yl)-methyl]-N-[(4R)-1-methyl-1H,4H,5H,6H-cyclopenta[d]imidazol-4-yl]-1H-pyrazole-4-carboxamide | 3-Azabicyclo[3.2.0]heptane hydrochloride |
| 239 | N-[(4R)-1-Methyl-1H,4H,5H,6H-cyclopenta[d]imidazol-4-yl]-1-[(4-methyl-2-{octahydrocyclopenta[c]pyrrol-2-yl}pyrimidin-5-yl)methyl]-1H-pyrazole-4-carboxamide | Octahydrocyclopenta[c]pyrrole |
| 240 | 1-[(2-{6-Azaspiro[3.4]octan-6-yl}-4-methylpyrimidin-5-yl)-methyl]-N-[(4R)-1-methyl-1H,4H,5H,6H-cyclopenta[d]imidazol-4-yl]-1H-pyrazole-4-carboxamide | 6-Azaspiro[3.4]octane |

The invention claimed is:

1. A compound of formula (I)

(I)

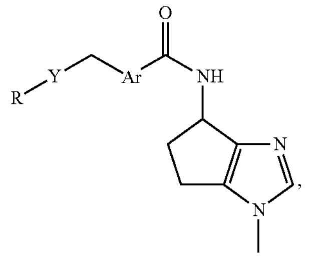

wherein

Y is selected from the group consisting of

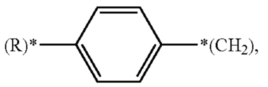

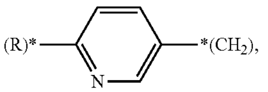

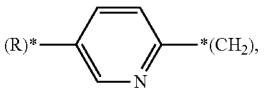

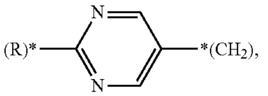

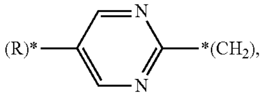

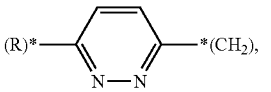 and

-continued

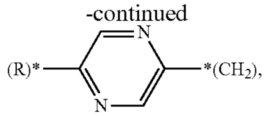

each of which is substituted with 1 or 2 independent substituents $R^1$, and wherein the bonds with asterisk and parentheses indicate the sites of attachment of R and the $CH_2$ group of formula (I);

R is selected from the group consisting of 5-azaspiro[2.3]hexane, 2-azaspiro[3.3]heptane, 5-azaspiro[2.4]heptane, 6-azaspiro[3.4]octane, 3-azabicyclo[3.1.0]hexane, 3-azabicyclo[3.2.0]heptane, octahydrocyclopenta[c]pyrrole, 6-azaspiro[2.5]octane, 5-azaspiro[2.5]octane, 7-azaspiro[3.5]nonane, 3-azabicyclo[4.1.0]heptane, 3-azabicyclo[3.1.1]heptane, 6-oxa-3-azabicyclo[3.1.1]heptane, and 3-azabicyclo[3.2.1]octane, each of which is attached via the N atom to the group Y in formula (I) and each of which is optionally substituted with one substituent selected from the group consisting of F, $CH_3$, CN, $CH_2OH$, OH, and $OCH_3$, and each of which is optionally substituted with one additional substituent selected from the group consisting of F and $CH_3$;

Ar is selected from the group consisting of

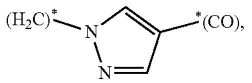

which is optionally substituted with 1 substituent $R^3$ and wherein the bonds with asterisk and parentheses indicate the sites of attachment of the groups C═O and $CH_2$ of formula (I);

$R^1$ is selected from the group consisting of

H, halogen, $C_{1-4}$-alkyl optionally substituted with 1 to 5 F, $C_{3-4}$-cycloalkyl optionally substituted with 1 $CH_3$, CN or OH group, CN, O—$C_{1-3}$-alkyl optionally substituted with 1 to 5 F, $C_{1-3}$-alkyl optionally substituted with 1 substituent selected from the group consisting of CN, OH, and O—$C_{1-3}$-alkyl; and $R^3$ is selected from the group consisting of F, Cl, Br, CN, $C_{1-4}$-alkyl optionally substituted with 1 to 5 F, $C_{3-4}$-cycloalkyl, HO—$C_{1-4}$-alkylene, $C_{1-3}$-alkyl-O—$C_{1-3}$-alkylene, and O—$C_{1-4}$-alkyl optionally substituted with 1 to 5 F;

or a salt thereof.

2. The compound according to claim 1, wherein Y is selected from the group consisting of

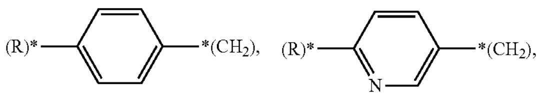

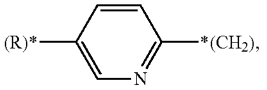

and

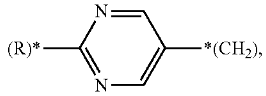

each of which is optionally substituted with 1 or 2 independent substituents $R^1$ and wherein the bonds with asterisk and parentheses indicate the sites of attachment of R and the $CH_2$ group of formula (I);

or a salt thereof.

3. The compound according to claim 1, wherein Y is selected from the group consisting of

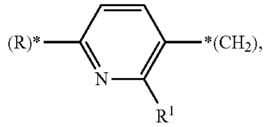

wherein the bonds with asterisk and parentheses indicate the sites of attachment of R and the $CH_2$ group of formula (I);

or a salt thereof.

4. The compound according to claim 1, wherein R is selected from the group consisting of

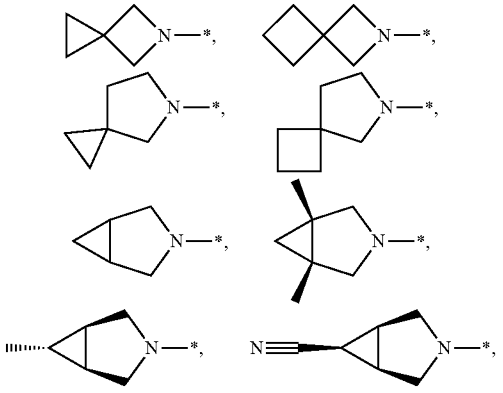

-continued

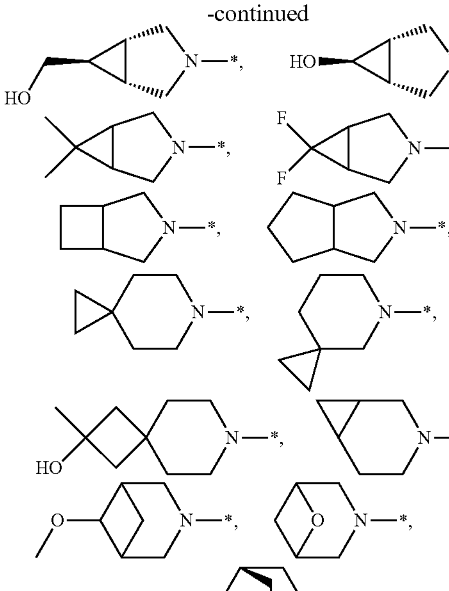

and

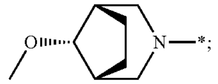

or a salt thereof.

5. The compound according to claim 1, wherein R is selected from the group consisting of

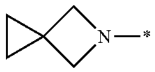

and

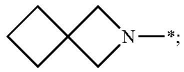

or a salt thereof.

6. The compound according to claim 1, wherein R is selected from the group consisting of

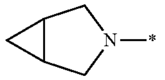

and

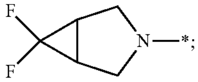

or a salt thereof.

7. The compound according to claim 1, wherein $R^1$ is selected from the group consisting of H, F, Cl, Br, $C_{1-2}$-alkyl optionally substituted with 1 to 5 F or with 1 CN, OH or O—$C_{1-2}$-alkyl group, $C_{3-4}$-alkyl optionally substituted with 1 CN or OH group, $C_{3-4}$-cycloalkyl optionally substituted with 1 $CH_3$, CN or OH group, O—$C_{1-2}$-alkyl optionally substituted with 1 to 5 F;

or a salt thereof.

8. The compound according to claim 1, wherein $R^1$ is selected from the group consisting of H, F, Cl, Br, $CH_3$, $CH_2CH_3$, $CH_2CH_2CH_3$, $CH_2CH(CH_3)_2$, cyclopropyl, cyclobutyl, $CHF_2$, $CF_3$, CN, 1-cyanocycloprop-1-yl, $CH_2CN$, $C(CH_3)_2CN$, $CH_2OH$, $CH_2CH_2OH$, $CH(OH)CH_3$, $CH_2CH_2CH_2OH$, $CH(CH_3)CH_2OH$, $C(OH)(CH_3)_2$, $CH_2OCH_3$, $CH_2OCH_2CH_3$, O—$CH_3$, O—$CH_2CH_3$, and O—$CF_3$;

or a salt thereof.

9. The compound according to claim 1, wherein $R^3$ is selected from the group consisting of Cl, CN, $CH_3$, $CF_3$, $CH_2CH_3$, $CH(CH_3)_2$, $CH_2OH$, $CH_2CH_2OH$, $C(CH_3)_2OH$, and $CH_2OCH_3$;

or a salt thereof.

10. The compound according to claim 1, wherein

Y is selected from the group consisting of

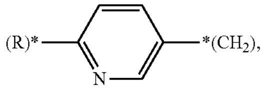

which is substituted with one additional substituent $R^1$ and wherein the bonds with asterisk and parentheses indicate the sites of attachment of R and the $CH_2$ group of formula (I);

R is selected from the group consisting of

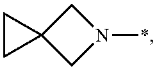, 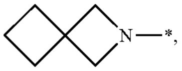,
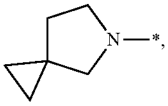, 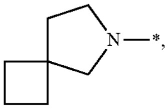,
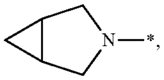, 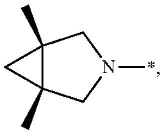,
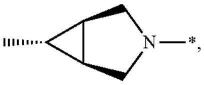, 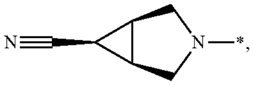,
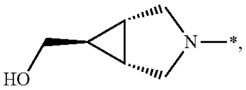, 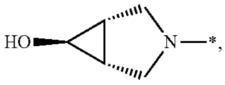,
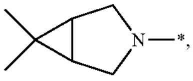, 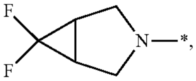,
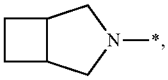, 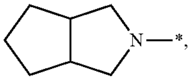,
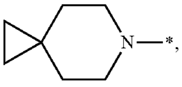, 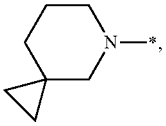,
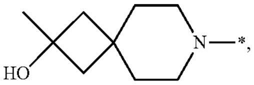, 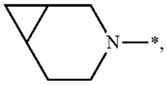,
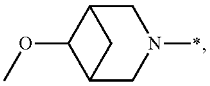, 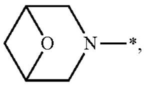, and
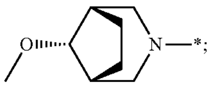;

Ar is selected from the group consisting of

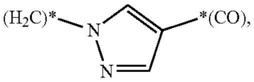

which is optionally substituted with 1 substituent $R^3$ and wherein the bonds with asterisk and parentheses indicate the sites of attachment of the groups C═O and $CH_2$ of formula (I);

$R^1$ is selected from the group consisting of

H, F, Cl, Br, $CH_3$, $CH_2CH_3$, $CH_2CH_2CH_3$, $CH_2CH(CH_3)_2$, cyclopropyl, cyclobutyl, $CHF_2$, $CF_3$, CN, 1-cyanocycloprop-1-yl, $CH_2CN$, $C(CH_3)_2CN$, $CH_2OH$, $CH_2CH_2OH$, $CH(OH)CH_3$, $CH_2CH_2CH_2OH$, $CH(CH_3)CH_2OH$, $C(OH)(CH_3)_2$, $CH_2OCH_3$, $CH_2OCH_2CH_3$, O—$CH_3$, O—$CH_2CH_3$, and O—$CF_3$; and $R^3$ is selected from the group consisting of Cl, CN, $CH_3$, $CF_3$, $CH_2CH_3$, $CH(CH_3)_2$, $CH_2OH$, $CH_2CH_2OH$, $C(CH_3)_2OH$, and $CH_2OCH_3$;

or a salt thereof.

11. The compound according to claim 1, wherein the stereochemistry of the compound is according to formula (I.1)

(I.1)

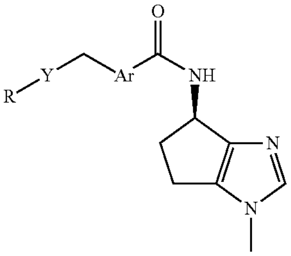

or a salt thereof.

12. A compound selected from:

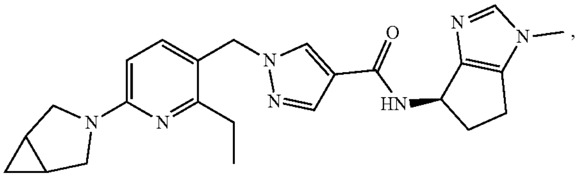,

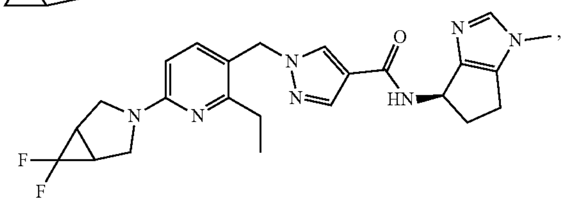,

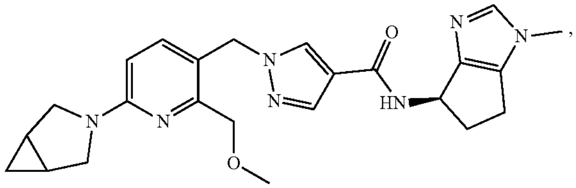,

-continued

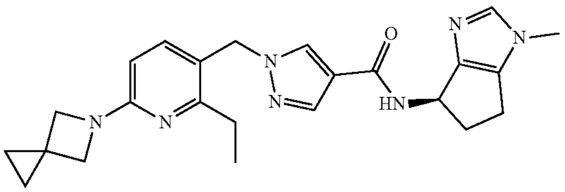

,

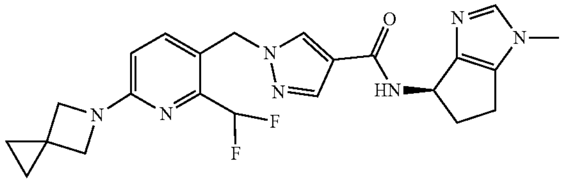

,

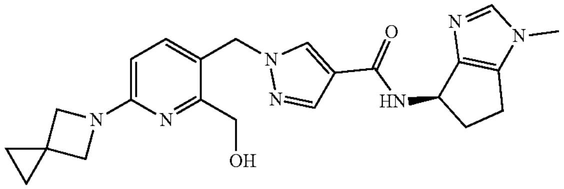

,

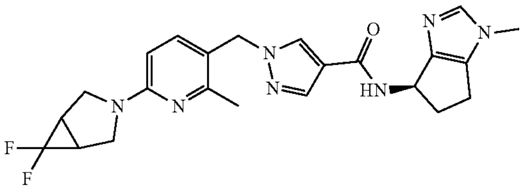

, and

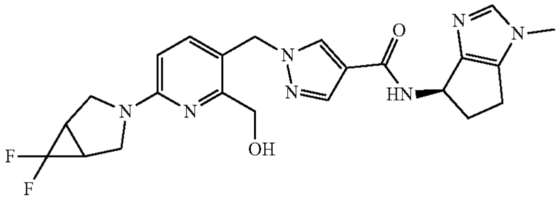

;

or a pharmaceutically acceptable salt thereof.

13. A compound of formula:

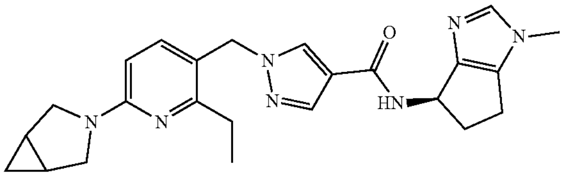

.

14. A compound of formula:

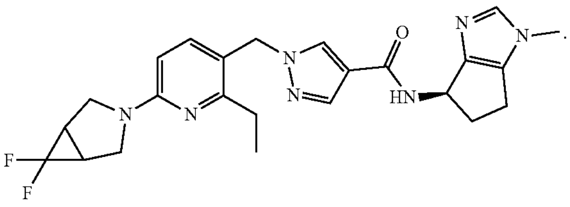 [SMILES: CCc1nc(N2CC3C(C2)C3(F)F)ccc1Cn1cc(C(=O)N[C@@H]2CCc3c2ncn3C)cn1]

.

15. A compound of formula:

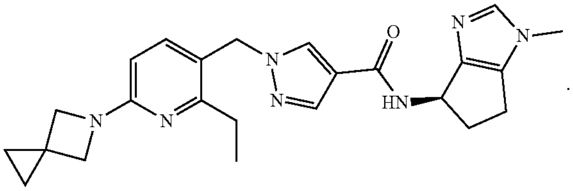

.

16. A compound of formula:

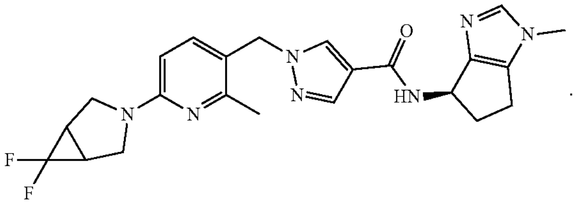 [SMILES: Cc1nc(N2CC3C(C2)C3(F)F)ccc1Cn1cc(C(=O)N[C@@H]2CCc3c2ncn3C)cn1]

.

17. A pharmaceutically acceptable salt of a compound of formula:

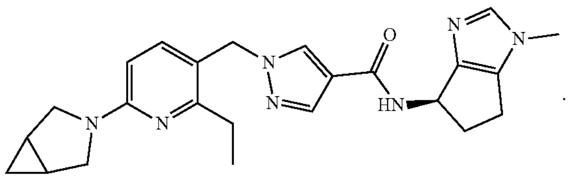 [SMILES: CCc1nc(N2CC3CC3C2)ccc1Cn1cc(C(=O)N[C@@H]2CCc3c2ncn3C)cn1]

.

18. A pharmaceutically acceptable salt of a compound of formula:

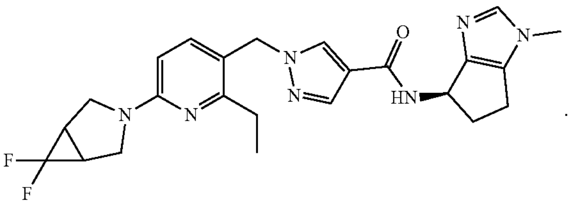 [SMILES: CCc1nc(N2CC3C(C2)C3(F)F)ccc1Cn1cc(C(=O)N[C@@H]2CCc3c2ncn3C)cn1]

.

19. A pharmaceutically acceptable salt of a compound of formula:

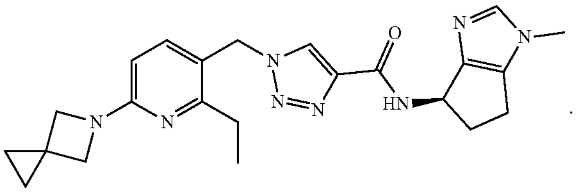 [SMILES: CCc1nc(N2CC3(CC3)C2)ccc1Cn1cc(C(=O)N[C@@H]2CCc3c2ncn3C)nn1]

.

20. A pharmaceutically acceptable salt of a compound of formula:

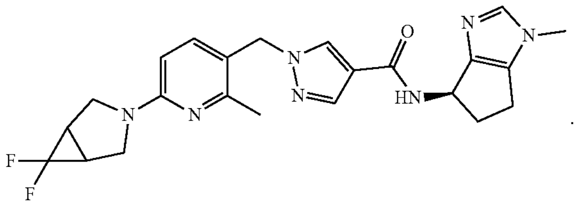 [SMILES: Cc1nc(N2CC3C(C2)C3(F)F)ccc1Cn1cc(C(=O)N[C@@H]2CCc3c2ncn3C)cn1]
.
21. A pharmaceutical composition comprising a compound according to claim 1, or a pharmaceutically acceptable salt thereof, optionally together with one or more inert carriers and/or diluents.
* * * * *